US012637467B2

(12) United States Patent
Chen

(10) Patent No.: US 12,637,467 B2
(45) Date of Patent: *May 26, 2026

(54) INHIBITOR OF BTK AND MUTANTS THEREOF

(71) Applicant: Newave Pharmaceutical Inc., Pleasanton, CA (US)

(72) Inventor: Yi Chen, Pleasanton, CA (US)

(73) Assignee: Newave Pharmaceutical Inc., Pleasanton, CA (US)

( * ) Notice: Subject to any disclaimer, the term of this patent is extended or adjusted under 35 U.S.C. 154(b) by 1249 days.

This patent is subject to a terminal disclaimer.

(21) Appl. No.: 17/431,460

(22) PCT Filed: Feb. 24, 2020

(86) PCT No.: PCT/US2020/019478

§ 371 (c)(1),
(2) Date: Aug. 17, 2021

(87) PCT Pub. No.: WO2020/176403

PCT Pub. Date: Sep. 3, 2020

(65) Prior Publication Data

US 2022/0135569 A1 May 5, 2022

Related U.S. Application Data

(60) Provisional application No. 62/911,212, filed on Oct. 5, 2019, provisional application No. 62/837,535, filed on Apr. 23, 2019, provisional application No. 62/810,169, filed on Feb. 25, 2019.

(51) Int. Cl.
*C07D 487/04* (2006.01)
*A61P 35/00* (2006.01)
*A61P 37/06* (2006.01)

(52) U.S. Cl.
CPC ............ *C07D 487/04* (2013.01); *A61P 35/00* (2018.01); *A61P 37/06* (2018.01)

(58) Field of Classification Search
CPC ........ A61P 35/00; A61P 37/06; C07D 487/04; C07D 495/04
See application file for complete search history.

(56) References Cited

U.S. PATENT DOCUMENTS

| | | | |
|---|---|---|---|
| 9,260,415 B2 | 2/2016 | Crawford et al. | |
| 2015/0005279 A1 | 1/2015 | Bonafoux et al. | |
| 2017/0224688 A1 | 8/2017 | Krejsa | |
| 2020/0377478 A1 | 12/2020 | Chen | |
| 2021/0100908 A1 | 4/2021 | Gray et al. | |
| 2022/0363689 A1 | 11/2022 | Chen | |
| 2023/0140433 A1 | 5/2023 | Chen | |
| 2023/0346779 A1 | 11/2023 | Chen | |
| 2023/0382900 A1 | 11/2023 | Chen | |
| 2024/0058457 A1 | 2/2024 | Chen | |
| 2024/0390368 A1* | 11/2024 | Chen | C07D 405/14 |
| 2025/0045728 A1* | 2/2025 | Chen | A61P 35/00 |
| 2025/0136620 A1 | 5/2025 | Chen | |

FOREIGN PATENT DOCUMENTS

| | | |
|---|---|---|
| WO | 2008/121742 A2 | 10/2008 |
| WO | 2009/158571 A1 | 12/2009 |
| WO | 2011/140488 A1 | 11/2011 |
| WO | 2013/067274 A1 | 5/2013 |
| WO | 2014/135474 A1 | 9/2014 |
| WO | 2015/050703 A1 | 4/2015 |

(Continued)

OTHER PUBLICATIONS

Sandoval et al., Two-Step Synthesis of 3,4-Dihydropyrrolopyrazinones from Ketones and Piperazin-2-ones. Org Lett. 2018;20(4):1252-1255.
International Search Report and Written Opinion for Application No. PCT/US2019/018139, dated Apr. 23, 2019, 11 pages.
International Search Report and Written Opinion for Application No. PCT/US2020/019478, dated Jun. 22, 2020, 12 pages.
International Search Report and Written Opinion for Application No. PCT/US2020/047196, dated Sep. 25, 2020, 10 pages.

(Continued)

*Primary Examiner* — Kara R. Mcmillian
(74) *Attorney, Agent, or Firm* — McCarter & English, LLP; Yu Lu; Zhongyu "Alex" Wang

(57) ABSTRACT

The disclosure includes compounds of Formula (I) (1) wherein $Q_0$, $Q_1$, $Q_2$, $Q_3$, $Q_4$, Z, W, i, j, m, n, Warhead, $R_0$, $R_1$, $R_3$, $R_4$, $R_5$, $R_6$, and $R_7$, are defined herein. Also disclosed is a method for treating a neoplastic disease, autoimmune disease, and inflammatory disorder with these compounds.

Formula (I)

(I)

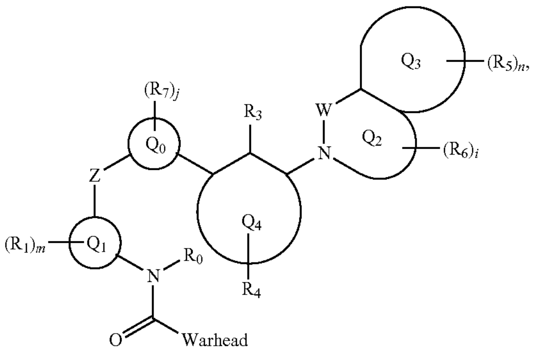

4 Claims, No Drawings

Specification includes a Sequence Listing.

(56) References Cited

FOREIGN PATENT DOCUMENTS

| | | | |
|---|---|---|---|
| WO | 2015/082583 | A1 | 6/2015 |
| WO | 2018/109050 | A1 | 6/2018 |
| WO | 2019/148150 | A1 | 8/2019 |
| WO | 2019/161152 | A1 | 8/2019 |
| WO | 2020/176403 | A1 | 9/2020 |
| WO | 2021/066958 | A1 | 4/2021 |
| WO | 2021/091575 | A1 | 5/2021 |
| WO | 2022/133184 | A1 | 6/2022 |

OTHER PUBLICATIONS

Hackam et al., Translation of research evidence from animals to humans. JAMA. Oct. 11, 2006;296(14):1731-2.
U.S. Appl. No. 16/996,516, filed Aug. 18, 2020, 2020-0377478, published.
U.S. Appl. No. 17/764,329, filed Mar. 28, 2022, Pending.
Dorwald, Side Reactions in Organic Synthesis, A Guide to Successful Synthesis Desing. Wiley-VCH Verlag GmbH & Co. KGaA, Weinheim. p. IX, (2005).
Jordan, Tamoxifen: a most unlikely pioneering medicine. Nat Rev Drug Discov. Mar. 2003;2(3):205-13.
Vippagunta et al., Crystalline solids. Adv Drug Deliv Rev. May 16, 2001;48(1):3-26.
Wolff, Burger's Medicinal Chemistry and Drug Discovery, Fifth Edition, vol. I: Principles and Practice. John Wiley & Sons, Inc., New York. pp. 975-977, (1995).
U.S. Appl. No. 17/962,798, filed Oct. 10, 2022, Pending.
Arthur et al., Development of PROTACs to address clinical limitations associated with BTK-targeted kinase inhibitors. Explor Target Antitumor Ther. Jun. 29, 2020;1:131-152.
Huang et al., A Chemoproteomic Approach to Query the Degradable Kinome Using a Multi-kinase Degrader. Cell Chem Biol. Jan. 18, 2018;25(1):88-99.e6.
International Search Report and Written Opinion for Application No. PCT/US2021/045867, dated Nov. 25, 2021, 14 pages.
International Search Report and Written Opinion for Application No. PCT/US2021/057187, dated Mar. 21, 2022, 20 pages.
International Search Report and Written Opinion for Application No. PCT/US2021/063984, dated Mar. 22, 2022, 11 pages.
U.S. Appl. No. 16/996,516, filed Aug. 18, 2020, U.S. Pat. No. 11,501,284, Issued.
U.S. Appl. No. 17/962,798, filed Oct. 10, 2022, U.S. Pat. No. 12,086,788, Issued.
U.S. Appl. No. 18/798,308, filed Aug. 8, 2024, 2025-0045728, Published.
U.S. Appl. No. 17/764,329, filed Mar. 28, 2022, 2022-0363689, Published.
U.S. Appl. No. 18/020,980, filed Feb. 13, 2023, 2023-0346779, Published.
U.S. Appl. No. 18/033,481, filed Apr. 24, 2023, 2023-0382900, Published.
U.S. Appl. No. 18/268,359, filed Jun. 20, 2023, 2024-0058457, Published.
U.S. Appl. No. 18/704,243, filed Apr. 24, 2024, 2024-0390368, Published.
U.S. Appl. No. 18/729,223, filed Jul. 16, 2024, 2025-0136620, Published.
Dobrovolsky et al., Bruton tyrosine kinase degradation as a therapeutic strategy for cancer. Blood. Feb. 28, 2019;133(9):952-961.
STN RN 2374918-45-1. 1 page, Sep. 10, 2019.
International Search Report and Written Opinion for Application No. PCT/US2022/047580, dated Jan. 25, 2023, 7 pages.
International Search Report and Written Opinion for Application No. PCT/US2023/010944, dated Apr. 14, 2023, 8 pages.
Rowe et al., Water. Handbook of Pharmaceutical Excipients, Sixth Edition. Pharmaceutical Press. pp. 766-770, (2009).
STN RN 2374918-39-3, 1 page, Sep. 10, 2019.
STN RN 2374918-41-7, 3 pages, Sep. 10, 2019.

* cited by examiner

SEQUENCE LISTING

<160> NUMBER OF SEQ ID NOS: 1

<210> SEQ ID NO 1
<211> LENGTH: 14
<212> TYPE: PRT
<213> ORGANISM: Unknown
<220> FEATURE:
<221> NAME/KEY: MOD_RES
<222> LOCATION: 1
<223> OTHER INFORMATION: /note="Description of Unknown: N-terminal 5-FAM-labeled kinase substrate peptide"

<400> SEQUENCE: 1

Gly Glu Glu Pro Leu Tyr Trp Ser Phe Pro Ala Lys Lys Lys
1 5 10

INHIBITOR OF BTK AND MUTANTS THEREOF

REFERENCE TO RELATED APPLICATIONS

This application is a U.S. national stage application, filed under 35 U.S.C. § 371(c), of International Application No. PCT/US2020/019478, filed on Feb. 24, 2020, which claims the benefit of the filing date of U.S. Provisional Patent Application Nos. 62/810,169, filed on Feb. 25, 2019; 62/837,535, filed on Apr. 23, 2019; and 62/911,212, filed on Oct. 5, 2019. The entire contents of each of the above applications are incorporated herein by reference.

SEQUENCE LISTING

The instant application contains a Sequence Listing which has been submitted electronically in ASCII format and is hereby incorporated by reference in its entirety. Said ASCII copy, created on May 20, 2020, is named SL_125569_11020.txt and is 641 bytes in size.

BACKGROUND OF THE INVENTION

Bruton tyrosine kinase (Btk) is a Tec family non-receptor protein kinase, expressed in most hematopoietic cells such as B cells, mast cells, and macrophages but not in T cells, natural killer cells, and plasma cells [Smith, C. I. et al. Journal of Immunology (1994), 152 (2), 557-65]. Btk is a crucial part of the BCR and FcR signaling pathway, and the targeted inhibition of Btk is a novel approach for treating many different human diseases such as B-cell malignancies, autoimmune disease, and inflammatory disorders [Uckun, Fatih M. et al, Anti-Cancer Agents in Medicinal Chemistry (2007), Shinohara et al, Cell 132 (2008) pp 794-806; Pan, Zhengying, Drug News & Perspectives (2008), 21 (7); 7 (6), 624-632; Gilfillan et al, Immunological Reviews 288 (2009) pp 149-169; Davis et al, Nature, 463 (2010) pp 88-94].

Covalent Bruton's tyrosine kinase (BTK) inhibitors including ibrutinib and acalabrutinib have transformed the treatment landscape of several BTK dependent B-cell malignancies, including chronic lymphocytic leukemia, Waldenstrom's macroglobulinemia, mantle cell lymphoma and marginal zone lymphoma. Despite impressive clinical response of ibrutinib in B-cell malignancies, cases of primary and secondary resistance have emerged with poor outcomes and limited treatment options. The majority of CLL patients who become resistant to irreversible BTK inhibitors such as ibrutinib develop the BTK-C481S mutation. It was reported that 80% of patients relapsing CLL will have the C481S mutation [Maddocks K J, et al. JAMA Oncol. 2015; 1:80-87]. Another research group in the Ohio State University reported in *Journal of Clinical Oncology* [Vol 35, number 13, 2017, page 1437] that at year four, roughly 20% of patients on ibrutinib clinically progressed. Of these patients who relapsed, 85% had acquired the C481S mutation. Additionally, these mutations were detected, on average, over nine months before a relapse.

Although BTK inhibitors such as Ibrutinib, and ACP-196, have made a significant contribution to the art, there is a strong need for continuing search in this field of art for highly potent and selective BTK inhibitors that can not only irreversibly inhibiting WT BTK but also reversibly inhibiting C481S mutant BTK.

SUMMARY OF THE INVENTION

The present invention relates to a class of potent and selective Btk inhibitors which are rationally designed to not only irreversibly inhibit the WT BTK but also reversibly inhibit the C481S mutant BTK. Thus, the compounds of the present invention may be useful in treating the patients resistant/refractory to the first generation BTK inhibitors such as Ibrutinib and ACP-196 (Acalabrutinib), particularly with BTK C481S mutation. The compounds of the present invention may be useful in treating the patients with diseases such as autoimmune disease, or inflammatory disorders.

In one aspect, this invention relates to a compound of Formula (I), or an N-oxide thereof, or a pharmaceutically acceptable salt, solvate, polymorph, tautomer, stereoisomer, an isotopic form, or a prodrug of said compound of Formula (I) or N-oxide thereof:

Formula (I)

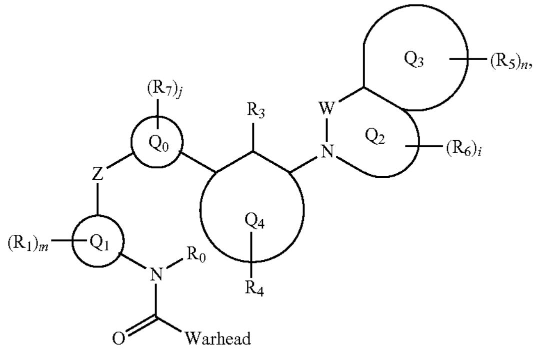

wherein $Q_0$ is a 5-9 membered aryl or 5-9 membered heterocyclic;

$Q_1$ is a 5-9 membered aryl or 5-9 membered heterocyclic;

$Q_2$ is a 5-8 membered heterocycloalkyl or 5-8 membered heteroaryl;

$Q_3$ is a 5-6 membered heteroaryl, or 6 membered aryl;

$Q_4$ is a 5-6 membered heteroaryl, or 6 membered aryl;

W is —C(O)— or —$S(O_2)$—;

Z is NH or O;

Warhead is

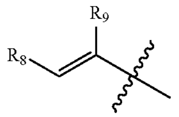

or

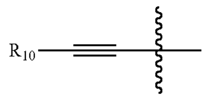

;

each of $R_0$, $R_1$, $R_5$, $R_6$, $R_7$, $R_8$, $R_9$, and $R_{10}$, independently, is H, D, alkyl, spiroalkyl, alkenyl, alkynyl, cycloalkyl, cycloalkenyl, heterocycloalkyl, spiroheterocycloalkyl, heterocycloalkenyl, aryl, heteroaryl, halo, nitro, oxo, cyano, $OR_a$, $SR_a$, alkyl-$R_a$, $NH(CH_2)_pR_a$, $C(O)R_a$, $S(O)R_a$, $SO_2R_a$, $C(O)OR_a$, $OC(O)R_a$, $NR_bR_c$, $C(O)N(R_b)R_c$, $N(R_b)C(O)R_c$, $—P(O)R_bR_c$, -alkyl-$P(O)R_bR_c$, $—S(O)(=N(R_b))R_c$, $—N=S(O)R_bR_c$, $=NR_b$, $SO_2N(R_b)R_c$, or $N(R_b)SO_2R_c$, in which said cycloalkyl, cycloalkenyl, heterocycloalkyl, heterocycloalkenyl, aryl, heteroaryl is optionally substituted with one or more $R_d$;

$R_3$ is H, halo, alkyl, haloalkyl, or hydroxyalkyl;

$R_4$ is H, halo, or low alkyl;

$R_0$ and $R_1$ groups, taken together with the atom to which they are attached, may optionally form a cycloalkyl or heterocycloalkyl optionally substituted with one or more $R_d$;

two of $R_1$ groups, taken together with the atom to which they are attached, may optionally form a cycloalkyl or heterocycloalkyl optionally substituted with one or more $R_d$;

two of $R_5$ groups, taken together with the atom to which they are attached, may optionally form a cycloalkyl or heterocycloalkyl optionally substituted with one or more $R_d$;

two of $R_6$ groups, taken together with the atom to which they are attached, may optionally form a cycloalkyl or heterocycloalkyl optionally substituted with one or more $R_d$;

two of $R_7$ groups, taken together with the atom to which they are attached, may optionally form a cycloalkyl or heterocycloalkyl optionally substituted with one or more $R_d$;

$R_a$, $R_b$, $R_c$ and $R_d$, independently, is H, D, alkyl, spiroalkyl, alkenyl, alkynyl, halo, cyano, amine, nitro, hydroxy, =O, —P(O)$R_bR_c$, -alkyl-P(O)$R_bR_c$, —S(O)(=N($R_b$))$R_c$, —N=S(O)$R_bR_c$, =N$R_b$, C(O)NHOH, C(O)OH, C(O)$NH_2$, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, spiroheterocycloalkyl, heterocycloalkenyl, aryl, or heteroaryl, in which said alkyl, cycloalkyl, cycloalkenyl, heterocycloalkyl, heterocycloalkenyl, aryl, heteroaryl is optionally substituted with one or more $R_e$;

$R_e$ is H, D, alkyl, spiroalkyl, alkenyl, alkynyl, halo, cyano, amine, nitro, hydroxy, =O, C(O)NHOH, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, spiroheterocycloalkyl, heterocycloalkenyl, aryl, or heteroaryl;

two of $R_d$ groups, taken together with the atom to which they are attached, may optionally form a cycloalkyl or heterocycloalkyl optionally substituted with one or more $R_e$; and each of i, j, m, n, p, and q, independently, is 0, 1, 2, 3, or 4.

In preferred embodiments, the compound is represented by Formula (II):

Formula (II)

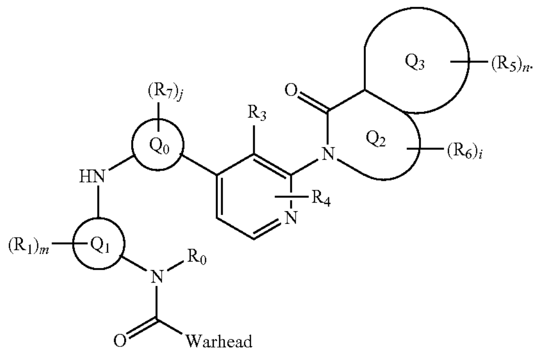

In a more preferred embodiment, the compound is represented by Formula (III)

Formula (III)

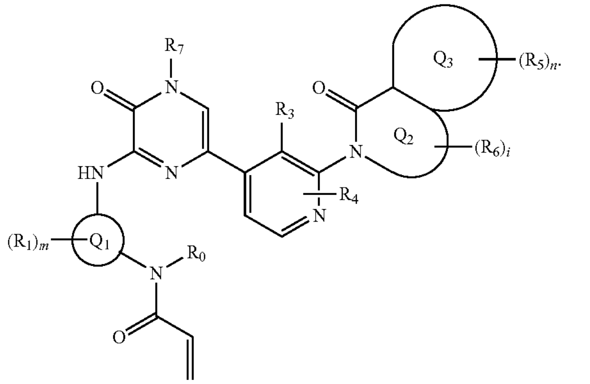

In a more preferred embodiment, the compound is represented by Formula (IV):

Formula (IV)

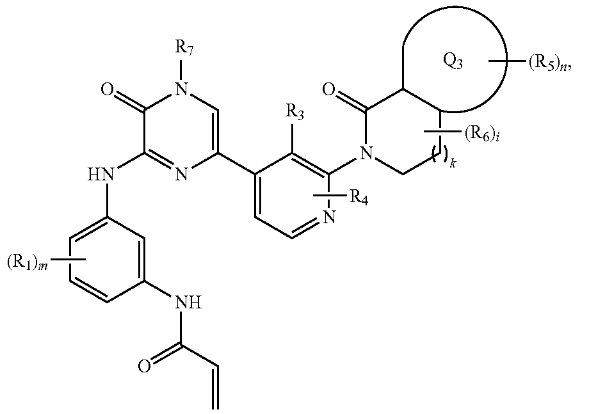

wherein k is 0, 1 or 2.

Compounds of the invention may contain one or more asymmetric carbon atoms. Accordingly, the compounds may exist as diastereomers, enantiomers, or mixtures thereof. Each of the asymmetric carbon atoms may be in the R or S configuration, and both of these configurations are within the scope of the invention.

A modified compound of any one of such compounds including a modification having an improved (e.g., enhanced, greater) pharmaceutical solubility, stability, bioavailability, and/or therapeutic index as compared to the unmodified compound is also contemplated. Exemplary modifications include (but are not limited to) applicable prodrug derivatives, and deuterium-enriched compounds.

It should be recognized that the compounds of the present invention may be present and optionally administered in the form of salts or solvates. The invention encompasses any pharmaceutically acceptable salts and solvates of any one of the above-described compounds and modifications thereof.

Also within the scope of this invention is a pharmaceutical composition containing one or more of the compounds, modifications, and/or salts and thereof described above for use in treating a neoplastic disease, autoimmune disease, and inflammatory disorders, therapeutic uses thereof, and use of the compounds for the manufacture of a medicament for treating the disease/disorder.

This invention also relates to a method of treating a neoplastic disease, particularly the B-cell malignancy including but not limited to B-cell lymphoma, lymphoma (including Hodgkin's and non-Hodgkin's lymphoma), hairy cell lymphoma, small lymphocytic lymphoma (SLL), mantle cell lymphoma (MCL), and diffuse large B-cell lymphoma (DLBCL), multiple myeloma, chronic and acute myelogenous leukemia and chronic and acute lymphocytic leukemia, by administering to a subject in need thereof an effective amount of one or more of the compounds, modifications, and/or salts, and compositions thereof described above.

Autoimmune and/or inflammatory diseases that can be affected using compounds and compositions according to the invention include, but are not limited to: psoriasis, allergy, Crohn's disease, irritable bowel syndrome, Sjogren's disease, tissue graft rejection, and hyperacute rejection of transplanted organs, asthma, systemic lupus erythematosus (and associated glomerulonephritis), dermatomyositis, multiple sclerosis, scleroderma, vasculitis (ANCA-associated and other vasculitides), autoimmune hemolytic and thrombocytopenic states, Goodpasture's syndrome (and associated glomerulonephritis and pulmonary hemorrhage), atherosclerosis, rheumatoid arthritis, chronic Idiopathic thrombocytopenic purpura (ITP), Addison's disease, Parkinson's disease, Alzheimer's disease, diabetes, septic shock, and myasthenia gravis.

The details of one or more embodiments of the invention are set forth in the description below. Other features, objects, and advantages of the invention will be apparent from the description and from the claims. It should be understood that all embodiments/features of the invention (compounds, pharmaceutical compositions, methods of make/use, etc) described herein, including any specific features described in the examples and original claims, can combine with one another unless not applicable or explicitly disclaimed.

DETAILED DESCRIPTION OF THE INVENTION

Exemplary compounds described herein include, but are not limited to, the following:

Part 1: CH3-OH

N-(5-((6-(3-(7,7-dimethyl-1-oxo-1,3,4,6,7,8-hexahydro-2H-cyclopenta[4,5]pyrrolo[1,2-a]pyrazin-2-yl)-2-(hydroxymethyl)phenyl)-4-methyl-3-oxo-3,4-dihydropyrazin-2-yl)amino)-2-(4-methylpiperazin-1-yl)phenyl)acrylamide, N-(5-((6-(3-(7,7-dimethyl-1-oxo-1,3,4,6,7,8-hexahydro-2H-cyclopenta[4,5]pyrrolo[1,2-a]pyrazin-2-yl)-2-(hydroxymethyl)phenyl)-4-methyl-3-oxo-3,4-dihydropyrazin-2-yl)amino)-2-(4-(oxetan-3-yl)piperazin-1-yl)phenyl)acrylamide, (S)—N-(5-((6-(3-(7,7-dimethyl-1-oxo-1,3,4,6,7,8-hexahydro-2H-cyclopenta[4,5]pyrrolo[1,2-a]pyrazin-2-yl)-2-(hydroxymethyl)phenyl)-4-methyl-3-oxo-3,4-dihydropyrazin-2-yl)amino)-2-(2-methyl-4-(oxetan-3-yl)piperazin-1-yl)phenyl)acrylamide, N-(5-((6-(3-(7,7-dimethyl-1-oxo-1,3,4,6,7,8-hexahydro-2H-cyclopenta[4,5]pyrrolo[1,2-a]pyrazin-2-yl)-2-(hydroxymethyl)phenyl)-4-methyl-3-oxo-3,4-dihydropyrazin-2-yl)amino)-2-(1-(oxetan-3-yl)piperidin-4-yl)phenyl)acrylamide, N-(5-((6-(3-(7,7-dimethyl-1-oxo-1,3,4,6,7,8-hexahydro-2H-cyclopenta[4,5]pyrrolo[1,2-a]pyrazin-2-yl)-2-(hydroxymethyl)phenyl)-4-methyl-3-oxo-3,4-dihydropyrazin-2-yl)amino)-2-(4-methylpiperazin-1-yl)phenyl)but-2-ynamide, N-(5-((6-(3-(7,7-dimethyl-1-oxo-1,3,4,6,7,8-hexahydro-2H-cyclopenta[4,5]pyrrolo[1,2-a]pyrazin-2-yl)-2-(hydroxymethyl)phenyl)-4-methyl-3-oxo-3,4-dihydropyrazin-2-yl)amino)-2-(4-(oxetan-3-yl)piperazin-1-yl)phenyl)but-2-ynamide, (S)—N-(5-((6-(3-(7,7-dimethyl-1-oxo-1,3,4,6,7,8-hexahydro-2H-cyclopenta[4,5]pyrrolo[1,2-a]pyrazin-2-yl)-2-(hydroxymethyl)phenyl)-4-methyl-3-oxo-3,4-dihydropyrazin-2-yl)amino)-2-(2-methyl-4-(oxetan-3-yl)piperazin-1-yl)phenyl)but-2-ynamide, N-(3-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)phenyl)acrylamide, (E)-N-(3-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)phenyl)-4-(dimethylamino)but-2-enamide, (R)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(3-(dimethylamino)pyrrolidin-1-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(1-(oxetan-3-yl)piperidin-4-yl)phenyl)acrylamide, N-(3-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-5-(4-methylpiperazin-1-yl)phenyl)acrylamide, N-(3-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-5-((4-methylpiperazin-1-yl)methyl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(4-methylpiperazin-1-yl)phenyl)but-2-ynamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(4-(oxetan-3-yl)piperazin-1-yl)phenyl)but-2-ynamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(2-methyl-4-(oxetan-3-yl)piperazin-1-yl)phenyl)but-2-ynamide, (Z)-2-cyano-N-(3-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)phenyl)-4-methyl-4-(4-(oxetan-3-yl)piperazin-1-yl)pent-2-enamide, (Z)-2-cyano-N-(3-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4- dihydropyrazin-2-yl)amino)phenyl)-4-methyl-4-(4-methylpiperazin-1-yl)pent-2-enamide, (Z)-2-cyano-N-(3-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)phenyl)-4-methyl-4-(methyl(oxetan-3-yl)amino)pent-2-enamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(2-(4-methylpiperazin-1-yl)propan-2-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(2-morpholinopropan-2-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(2-(methyl(oxetan-3-yl)amino)propan-2-yl)phenyl)acrylamide, N-(2-(2-(4,4-difluoropiperidin-1-yl)propan-2-yl)-5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)phenyl)acrylamide, N-(2-(2-(3,3-difluoropyrrolidin-1-yl)propan-2-yl)-5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(2-(4-(oxetan-3-yl)piperazin-1-yl)propan-2-yl)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-3-fluoro-2-(2-methyl-4-(oxetan-3-yl)piperazin-1-yl)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-3-methyl-2-(2-methyl-4-(oxetan-3-yl)piperazin-1-yl)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(2-methyl-4-(oxetan-3-yl)piperazin-1-yl)-3-(trifluoromethyl)phenyl)acrylamide, (S)—N-(3-cyano-5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(2-methyl-4-(oxetan-3-yl)piperazin-1-yl)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-3-(isopropylsulfonyl)-2-(2-methyl-4-(oxetan-3-yl)piperazin-1-yl)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(2-methyl-4-(oxetan-3-yl)piperazin-1-yl)-3-((trifluoromethyl)sulfonyl)phenyl)acrylamide, (S)—N-(5-((6-(2-(8,8-dimethyl-1-oxo-1,4,5,7,8,9-hexahydrocyclopenta[4,5]pyrrolo[1,2-a][1,4]diazepin-2(3H)-yl)-3-(hydroxymethyl)pyridin-4-yl)-4-methyl-3-oxo-3,4-dihydropyrazin-2-yl)amino)-2-(2-methyl-4-(oxetan-3-yl)piperazin-1-yl)phenyl)acrylamide, (S)—N-(5-((6-(2-(8,8-dimethyl-1-oxo-1,4,5,7,8,9-hexahydrocyclopenta[4,5]pyrrolo[1,2-a][1,4]diazepin-2(3H)-yl)-3-(hydroxymethyl)pyridin-4-yl)-4-methyl-3-oxo-3,4-dihydropyrazin-2-yl)amino)-3-fluoro-2-(2-methyl-4-(oxetan-3-yl)piperazin-1-yl)phenyl)acrylamide, (S)—N-(5-((6-(2-(8,8-dimethyl-1-oxo-1,4,5,7,8,9-hexahydrocyclopenta[4,5]pyrrolo[1,2-a][1,4]diazepin-2(3H)-yl)-3-(hydroxymethyl)pyridin-4-yl)-4-methyl-3-oxo-3,4-dihydropyrazin-2-yl)amino)-3-methyl-2-(2-methyl-4-(oxetan-3-yl)piperazin-1-yl)phenyl)acrylamide, (S)—N-(5-((6-(2-(8,8-dimethyl-1-oxo-1,4,5,7,8,9-hexahydrocyclopenta[4,5]pyrrolo[1,2-a][1,4]diazepin-2(3H)-yl)-3-(hydroxymethyl)pyridin-4-yl)-4-methyl-3-oxo-3,4-dihydropyrazin-2-yl)amino)-2-(2-methyl-4-(oxetan-3-yl)piperazin-1-yl)-3-(trifluoromethyl)phenyl)acrylamide, (S)—N-(3-cyano-5-((6-(2-(8,8-dimethyl-1-oxo-1,4,5,7,8,9-hexahydrocyclopenta[4,5]pyrrolo[1,2-a][1,4]diazepin-2(3H)-yl)-3-(hydroxymethyl)pyridin-4-yl)-4-methyl-3-oxo-3,4-dihydropyrazin-2-yl)amino)-2-(2-methyl-4-(oxetan-3-yl)piperazin-1-yl)phenyl)acrylamide, (S)—N-(5-((6-(2-(8,8-dimethyl-1-oxo-1,4,5,7,8,9-hexahydrocyclopenta[4,5]pyrrolo[1,2-a][1,4]diazepin-2(3H)-yl)-3-(hydroxymethyl)pyridin-4-yl)-4-methyl-3-oxo-3,4-dihydropyrazin-2-yl)amino)-3-(isopropylsulfonyl)-2-(2-methyl-4-(oxetan-3-yl)piperazin-1-yl)phenyl)acrylamide, (S)—N-(5-((6-(2-(8,8-dimethyl-1-oxo-1,4,5,7,8,9-hexahydrocyclopenta[4,5]pyrrolo[1,2-a][1,4]diazepin-2(3H)-yl)-3-(hydroxymethyl)pyridin-4-yl)-4-methyl-3-oxo-3,4-dihydropyrazin-2-yl)amino)-2-(2-methyl-4-(oxetan-3-yl)piperazin-1-yl)-3-((trifluoromethyl)sulfonyl)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(2-methyl-4-(oxetan-3-yl)piperazin-1-yl)pyridin-3-yl)acrylamide, (S)—N-(5-((6-(2-(8,8-dimethyl-1-oxo-1,4,5,7,8,9-hexahydrocyclopenta[4,5]pyrrolo[1,2-a][1,4]diazepin-2(3H)-yl)-3-(hydroxymethyl)pyridin-4-yl)-4-methyl-3-oxo-3,4-dihydropyrazin-2-yl)amino)-2-(2-methyl-4-(oxetan-3-yl)piperazin-1-yl)pyridin-3-yl)acrylamide, (S)—N-(5-((6-(2-(7,7-bis(methyl-d3)-1-oxo-1,3,4,6,7,8-hexahydro-2H-cyclopenta[4,5]pyrrolo[1,2-a]pyrazin-2-yl)-3-(hydroxymethyl)pyridin-4-yl)-4-(methyl-d3)-3-oxo-3,4-dihydropyrazin-2-yl)amino)-2-(2-methyl-4-(oxetan-3-yl)piperazin-1-yl)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)oxy)-2-(2-methyl-4-(oxetan-3-yl)piperazin-1-yl)phenyl)acrylamide, (S)—N-(6-((2'-(7,7-dimethyl-1-oxo-1,3,4,6,7,8-hexahydro-2H-cyclopenta[4,5]pyrrolo[1,2-a]pyrazin-2-yl)-3'-(hydroxymethyl)-1-methyl-6-oxo-1,6-dihydro-[3,4'-bipyridin]-5-yl)amino)-3-(2-methyl-4-(oxetan-3-yl)piperazin-1-yl)pyridin-2-yl)acrylamide, (S)—N-(5-((6-(5-(7,7-dimethyl-1-oxo-1,3,4,6,7,8-hexahydro-2H-cyclopenta[4,5]pyrrolo[1,2-a]pyrazin-2-yl)-4-(hydroxymethyl)pyridin-3-yl)-4-methyl-3-oxo-3,4-dihydropyrazin-2-yl)amino)-2-(2-methyl-4-(oxetan-3-yl)piperazin-1-yl)phenyl)acrylamide, (S)—N-(5-((6-(4-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-2-yl)-4-methyl-3-oxo-3,4-dihydropyrazin-2-yl)amino)-2-(2-methyl-4-(oxetan-3-yl)piperazin-1-yl)phenyl)acrylamide, (S)—N-(54(6-(3-(hydroxymethyl)-2-(4-oxo-1,4,7,8,9,10-hexahydrobenzo[f]isoquinolin-3(2H)-yl)pyridin-4-yl)-4-methyl-3-oxo-3,4-dihydropyrazin-2-yl)amino)-2-(2-methyl-4-(oxetan-3-yl)piperazin-1-yl)phenyl)acrylamide, (S)—N-(5-((6-(2-(8,8-dimethyl-4-oxo-1,2,4,7,8,9-hexahydro-3H-cyclopenta[f]isoquinolin-3-yl)-3-(hydroxymethyl)pyridin-4-yl)-4-methyl-3-oxo-3,4-dihydropyrazin-2-yl)amino)-2-(2-methyl-4-(oxetan-3-yl)piperazin-1-yl)phenyl)acrylamide, (S)—N-(5-((6-(2-(7,7-dimethyl-1,1-dioxido-3,4,7,8-tetrahydro-2H,6H-cyclopenta[4,5]pyrrolo[1,2-e][1,2,5]thiadiazin-2-yl)-3-(hydroxymethyl)pyridin-4-yl)-4-methyl-3-oxo-3,4-dihydropyrazin-2-yl)amino)-2-(2-methyl-4-(oxetan-3-yl)piperazin-1-yl)phenyl)acrylamide, (R)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(2-methyl-4-(oxetan-3-yl)piperazin-1-yl)thiophen-3-yl)acrylamide, 2-(4-(6-((5-acryloyl-4,5,6,7-tetrahydrothieno[3,2-c]pyridin-2-yl)amino)-4-methyl-5-oxo-4,5-dihydropyrazin-2-yl)-3-(hydroxymethyl)pyridin-2-yl)-7,7-dimethyl-3,4,7,8-tetrahydro-2H-cyclopenta[4,5]pyrrolo[1,2-a]pyrazin-1(6H)-one, 2-(4-(6-((1-(1-acryloyl-4-methyl-1,4-diazepan-6-yl)-1H-indol-5-yl)amino)-4-methyl-5-oxo-4,5-dihydropyrazin-2-yl)-3-(hydroxymethyl)pyridin-2-yl)-7,7-dimethyl-3,4,7,8-tetrahydro-2H-cyclopenta[4,5]pyrrolo[1,2-a]pyrazin-1(6H)-one, N-(5-((6-(2-(8,8-dimethyl-4-oxo-1,2,4,7,8,9-hexahydro-3H-cyclopenta[c][2,7]naphthyridin-3-yl)-3-(hydroxymethyl)pyridin-4-yl)-4-methyl-3-oxo-3,4-dihydropyrazin-2-yl)amino)-2-((2S)-4-((2R,6S)-2,6-dimethyltetrahydro-2H-pyran-4-yl)-2-methylpiperazin-1-yl)phenyl)acrylamide, N-(5-((6-(2-(8,8-dimethyl-4-oxo-1,2,4,7,8,9-hexahydro-3H-cyclopenta[c][1,7]naphthyridin-3-yl)-3-(hydroxymethyl)pyridin-4-yl)-4-methyl-3-oxo-3,4-dihydropyrazin-2-yl)amino)-2-((2S)-4-((2R,6S)-2,6-dimethyltetrahydro-2H-pyran-4-yl)-2-methylpiperazin-1-yl)phenyl)acrylamide, N-(5-((6-(2-(7,7-dimethyl-1-oxo-1,3,4,6,7,8-hexahydro-2H-cyclopenta[4,5]imidazo[1,2-a]pyrazin-2-yl)-3-(hydroxymethyl)pyridin-4-yl)-4-methyl-3-oxo-3,4-dihydropyrazin-2-yl)amino)-24(2S)-44(2R,6S)-2,6-dimethyltetrahydro-2H-pyran-4-yl)-2-methylpiperazin-1-yl)phenyl)acrylamide, (S)—N-(54(6-(3-(hydroxymethyl)-2-(1-oxo-3,4,5,6,7,8-hexahydrobenzofuro[2,3-c]pyridin-2(1H)-yl)pyridin-4-yl)-4-methyl-3-oxo-3,4-dihydropyrazin-2-yl)amino)-2-(2-methyl-4-(oxetan-3-yl)piperazin-1-yl)phenyl)acrylamide, (S)—N-(54(6-(3-(hydroxymethyl)-2-(1-oxo-1,3,4,5,6,7,8,9-octahydro-2H-pyrido [3,4-b]indol-2-yl)pyridin-4-yl)-4-methyl-3-oxo-3,4-dihydropyrazin-2-yl)amino)-2-(2-methyl-4-(oxetan-3-yl)piperazin-1-yl)phenyl)acrylamide, N-(5-((6-(2-(7,7-dimethyl-1,1-dioxido-3,4,7,8-tetrahydro-2H,6H-cyclopenta[4,5]pyrrolo[1,2-e][1,2,5]thiadiazin-2-yl)-3-(hydroxymethyl)pyridin-4-yl)-4-methyl-3-oxo-3,4-dihydropyrazin-2-yl)amino)-24(2S)-44(2R,6S)-2,6-dimethyltetrahydro-2H-pyran-4-yl)-2-methylpiperazin-1-yl)phenyl)acrylamide, N-(2-((2S)-4-((2S,6R)-2,6-dimethylmorpholino)-2-methylpiperidin-1-yl)-5-((6-(3-(hydroxymethyl)-2-((S)-1-oxo-7-(trifluoromethyl)-1,3,4,6,7,8-hexahydro-2H-cyclopenta[4,5]pyrrolo[1,2-a]pyrazin-2-yl)pyridin-4-yl)-4-methyl-3-oxo-3,4-dihydropyrazin-2-yl)amino)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(2-methyl-4-(oxetan-3-yl)piperazin-1-yl)pyridin-3-yl)acrylamide, (S)—N-(5-((6-(2-(8,8-dimethyl-1-oxo-1,4,5,7,8,9-hexahydrocyclopenta[4,5]pyrrolo[1,2-a][1,4]diazepin-2(3H)-yl)-3-(hydroxymethyl)pyridin-4-yl)-4-methyl-3-oxo-3,4-dihydropyrazin-2-yl)amino)-2-(2-methyl-4-(oxetan-3-yl)piperazin-1-yl)phenyl)acrylamide, N-(5-((6-(2-(8,8-dimethyl-1-oxo-1,4,5,7,8,9-hexahydrocyclopenta[4,5]pyrrolo[1,2-a][1,4]diazepin-2(3H)-yl)-3-(hydroxymethyl)pyridin-4-yl)-4-methyl-3-oxo-3,4-dihydropyrazin-2-yl)amino)-2-((2S)-4-((2R,6S)-2,6-dimethyltetrahydro-2H-pyran-4-yl)-2-methylpiperazin-1-yl)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-3-fluoro-2-(2-methyl-4-(oxetan-3-yl)piperazin-1-yl)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-3-methyl-2-(2-methyl-4-(oxetan-3-yl)piperazin-1-yl)phenyl)acrylamide, (S)—N-(5-((6-(3-(hydroxymethyl)-2-(5-oxo-7,8-dihydro-1,6-naphthyridin-6(5H)-yl)pyridin-4-yl)-4-methyl-3-oxo-3,4-dihydropyrazin-2-yl)amino)-2-(2-methyl-4-(oxetan-3-yl)piperazin-1-yl)phenyl)acrylamide, (S)—N-(54(6-(3-(hydroxymethyl)-2-(1-oxo-3,4-dihydro-2,7-naphthyridin-2(1H)-yl)pyridin-4-yl)-4-methyl-3-oxo-3,4-dihydropyrazin-2-yl)amino)-2-(2-methyl-4-(oxetan-3-yl)piperazin-1-yl)phenyl)acrylamide, (S)—N-(5-((6-(3-(hydroxymethyl)-2-(8-oxo-5,8-dihydro-1,7-naphthyridin-7(6H)-yl)pyridin-4-yl)-4-methyl-3-oxo-3,4-dihydropyrazin-2-yl)amino)-2-(2-methyl-4-(oxetan-3-yl)piperazin-1-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(4-morpholinopiperidin-1-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(4-(4-methylpiperazin-1-yl)piperidin-1-yl)phenyl)acrylamide, N-(2-(4,4-difluoro-[1,4'-bipiperidin]-1'-yl)-5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(2-methyl-4-morpholinopiperidin-1-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-((2S)-2-methyl-4-morpholinopiperidin-1-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-((2S)-4-((2S,6R)-2,6-dimethylmorpholino)-2-methylpiperidin-1-yl)phenyl)acrylamide, N-(2-((2'S)-4,4-difluoro-2'-methyl-[1,4'-bipiperidin]-1'-yl)-5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)phenyl)acrylamide, N-(2-((2S)-4-(3,3-difluoropyrrolidin-1-yl)-2-methylpiperidin-1-yl)-5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-((2S)-2-methyl-4-(4-methylpiperazin-1-yl)piperidin-1-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-((2S)-4-(dimethylamino)-2-methylpiperidin-1-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(2-methyl-4-(methyl(oxetan-3-yl)amino)piperidin-1-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(4-methylpiperazin-1-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(4-(oxetan-3-yl)piperazin-1-yl)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(2-methyl-4-(oxetan-3-yl)piperazin-1-yl)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(2-methyl-4-(tetrahydro-2H-pyran-4-yl)piperazin-1-yl)phenyl)acrylamide, (S)—N-(2-(4-(4,4-difluorocyclohexyl)-2-methylpiperazin-1-yl)-5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-((2S)-4-(2,6-dimethyltetrahydro-2H-pyran-4-yl)-2-methylpiperazin-1-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-((S)-4-((2R,6R)-2,6-dimethyltetrahydro-2H-pyran-4-yl)-2-methylpiperazin-1-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-((S)-4-((2S,6S)-2,6-dimethyltetrahydro-2H-pyran-4-yl)-2-methylpiperazin-1-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-((2S)-4-((2R,6S)-2,6-dimethyltetrahydro-2H-pyran-4-yl)-2-methylpiperazin-1-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-((S)-4-((2R,4s,6S)-2,6-dimethyltetrahydro-2H-pyran-4-yl)-2-methylpiperazin-1-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-((S)-2-methyl-4-((2S,4S)-2-methyltetrahydro-2H-pyran-4-yl)piperazin-1-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-((S)-2-methyl-4-((2S,4R)-2-methyltetrahydro-2H-pyran-4-yl)piperazin-1-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-((S)-2-methyl-4-((R)-tetrahydrofuran-3-yl)piperazin-1-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-((S)-2-methyl-4-((R)-oxepan-4-yl)piperazin-1-yl)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(2-methylpiperazin-1-yl)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(2,4-dimethylpiperazin-1-yl)phenyl)acrylamide, (S)—N-(2-(4-cyclopropyl-2-methylpiperazin-1-yl)-5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)phenyl)acrylamide, (S)—N-(2-(4-cyclopentyl-2-methylpiperazin-1-yl)-5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)phenyl)acrylamide, (S)—N-(2-(4-(cyclopropylmethyl)-2-methylpiperazin-1-yl)-5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(2-methyl-4-(pyridin-2-ylmethyl)piperazin-1-yl)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(2-methyl-4-((tetrahydro-2H-pyran-4-yl)methyl)piperazin-1-yl)phenyl)acrylamide, N-(2-((S)-4-(((S)-1,4-dioxan-2-yl)methyl)-2-methylpiperazin-1-yl)-5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(2-methyl-4-(1,4-dithiaspiro[4.5]decan-8-yl)piperazin-1-yl)phenyl)acrylamide, N-(2-((2S)-4-(2-oxabicyclo[2.2.2]octan-5-yl)-2-methylpiperazin-1-yl)-5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)phenyl)acrylamide, N-(2-((2S)-4-((1S,4R)-2-oxabicyclo[2.2.1]heptan-5-yl)-2-methylpiperazin-1-yl)-5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-((2S)-2-methyl-4-((3S)-3-methyltetrahydro-2H-pyran-4-yl)piperazin-1-yl)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(7-methyl-4-(tetrahydro-2H-pyran-4-yl)-1,4-diazepan-1-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-((2S)-2-methyl-4-((3R)-3-methyltetrahydro-2H-pyran-4-yl)piperazin-1-yl)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(2-methyl-4-(tetrahydro-2H-pyran-4-yl)-1,4-diazepan-1-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(2-oxo-4-(tetrahydro-2H-pyran-4-yl)piperazin-1-yl)phenyl)acrylamide, (R)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(1,4-dimethyl-6-oxopiperazin-2-yl)phenyl)acrylamide, (R)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(1,4-dimethyl-3-oxopiperazin-2-yl)phenyl)acrylamide, (R)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(4-methyl-3-oxo-1-(tetrahydro-2H-pyran-4-yl)piperazin-2-yl)phenyl)acrylamide, (R)—N-(2-(1,4-diisopropyl-5-oxopiperazin-2-yl)-5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-((2R)-1,4-dimethyl-3-oxo-5-(tetrahydro-2H-pyran-4-yl)piperazin-2-yl)phenyl)acrylamide, (R)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(1-methyl-6-oxo-4-(tetrahydro-2H-pyran-4-yl)piperazin-2-yl)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(4-methyl-1-(oxetan-3-yl)-3-oxo-1,4-diazepan-5-yl)phenyl)acrylamide, (R)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(1-methyl-4-(oxetan-3-yl)-7-oxo-1,4-diazepan-2-yl)phenyl)acrylamide, N-(54(6-(2-(8-fluoro-1-oxo-6-(1,1,1-trifluoro-2-methylpropan-2-yl)-3,4-dihydroisoquinolin-2(1H)-yl)-3-(hydroxymethyl)pyridin-4-yl)-4-methyl-3-oxo-3,4-dihydropyrazin-2-yl)amino)-2-(4-methyl-1-(oxetan-3-yl)-3-oxopiperazin-2-yl)phenyl)acrylamide, N-(5-((6-(2-(6-(tert-butyl)-8-fluoro-1-oxo-3,4-dihydroisoquinolin-2(1H)-yl)-3-(hydroxymethyl)pyridin-4-yl)-4-methyl-3-oxo-3,4-dihydropyrazin-2-yl)amino)-2-(4-methyl-1-(oxetan-3-yl)-3-oxopiperazin-2-yl)phenyl)acrylamide, (R)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(1-isopropyl-5,5-dimethyl-4-(oxetan-3-yl)-6-oxopiperazin-2-yl)phenyl)acrylamide, (R)—N-(2-(1-cyclopropyl-5,5-dimethyl-4-(oxetan-3-yl)-6-oxopiperazin-2-yl)-5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)phenyl)acrylamide, (S)—N-(5-((6-(2-(6,6-dimethyl-1-oxo-1,3,4,5,6,7-hexahydro-2H-cyclopenta[4,5]thieno[2,3-c]pyridin-2-yl)-3-(hydroxymethyl)pyridin-4-yl)-4-methyl-3-oxo-3,4-dihydropyrazin-2-yl)amino)-2-(2-methyl-4-(oxetan-3-yl)piperazin-1-yl)phenyl)acrylamide, (S)—N-(54(6-(3-(hydroxymethyl)-2-(1-oxo-3,4,5,6,7,8-hexahydrobenzo [4,5]thieno[2,3-c]pyridin-2(1H)-yl)pyridin-4-yl)-4-methyl-3-oxo-3,4-dihydropyrazin-2-yl)amino)-2-(2-methyl-4-(oxetan-3-yl)piperazin-1-yl)phenyl)acrylamide, (S)—N-(5-((6-(2-(7,7-dimethyl-1-oxo-1,3,4,5,6,7-hexahydro-2H-cyclopenta[4,5]thieno[2,3-c]pyridin-2-yl)-3-(hydroxymethyl)pyridin-4-yl)-4-methyl-3-oxo-3,4-dihydropyrazin-2-yl)amino)-2-(2-methyl-4-(oxetan-3-yl)piperazin-1-yl)phenyl)acrylamide, (S)—N-(5-((6-(2-(2-(tert-butyl)-7-oxo-4,7-dihydrothieno[2,3-c]pyridin-6(5H)-yl)-3-(hydroxymethyl)pyridin-4-yl)-4-methyl-3-oxo-3,4-dihydropyrazin-2-yl)amino)-2-(2-methyl-4-(oxetan-3-yl)piperazin-1-yl)phenyl)acrylamide, (S)—N-(54(6-(2-(6-(tert-butyl)-8-fluoro-1-oxo-3,4-dihydroisoquinolin-2(1H)-yl)-3-(hydroxymethyl)pyridin-4-yl)-4-methyl-3-oxo-3,4-dihydropyrazin-2-yl)amino)-2-(2-methyl-4-(oxetan-3-yl)piperazin-1-yl)phenyl)acrylamide, (R)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(4-methyl-1-(oxetan-3-yl)-3-oxopiperazin-2-yl)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(4-methyl-1-(oxetan-3-yl)-3-oxopiperazin-2-yl)phenyl)acrylamide, (R)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(4-methyl-1-(oxetan-3-yl)-5-oxopiperazin-2-yl)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(4-methyl-1-(oxetan-3-yl)-5-oxopiperazin-2-yl)phenyl)acrylamide, (R)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(1-methyl-4-(oxetan-3-yl)-6-oxopiperazin-2-yl)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(1-methyl-4-(oxetan-3-yl)-6-oxopiperazin-2-yl)phenyl)acrylamide, (R)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(1-isopropyl-4-(oxetan-3-yl)-6-oxopiperazin-2-yl)phenyl)acrylamide, (R)—N-(2-(1-cyclopropyl-4-(oxetan-3-yl)-6-oxopiperazin-2-yl)-54(6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)phenyl)acrylamide, N-(5-((6-(2-(2-(tert-butyl)-7-oxo-4,7-dihydrothieno[2,3-c]pyridin-6(5H)-yl)-3-(hydroxymethyl)pyridin-4-yl)-4-methyl-3-oxo-3,4-dihydropyrazin-2-yl)amino)-2-(4-methyl-1-(oxetan-3-yl)-3-oxopiperazin-2-yl)phenyl)acrylamide, N-(5-((6-(2-(7,7-dimethyl-1-oxo-1,3,4,5,6,7-hexahydro-2H-cyclopenta[4,5]thieno[2,3-c]pyridin-2-yl)-3-(hydroxymethyl)pyridin-4-yl)-4-methyl-3-oxo-3,4-dihydropyrazin-2-yl)amino)-2-(4-methyl-1-(oxetan-3-yl)-3-oxopiperazin-2-yl)phenyl)acrylamide, (R)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(4-(tetrahydro-2H-pyran-4-yl)-2-(trifluoromethyl)piperazin-1-yl)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(4-(tetrahydro-2H-pyran-4-yl)-2-(trifluoromethyl)piperazin-1-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(2,2-dimethyl-4-(tetrahydro-2H-pyran-4-yl)piperazin-1-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(7-(tetrahydro-2H-pyran-4-yl)-4,7-diazaspiro[2.5]octan-4-yl)phenyl)acrylamide, (R)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(4-(oxetan-3-yl)-2-(trifluoromethyl)piperazin-1-yl)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(4-(oxetan-3-yl)-2-(trifluoromethyl)piperazin-1-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(2,2-dimethyl-4-(oxetan-3-yl)piperazin-1-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(7-(oxetan-3-yl)-4,7-diazaspiro[2.5]octan-4-yl)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(6-methyl-2-(oxetan-3-yl)-2,7-diazaspiro[3.5]nonan-7-yl)phenyl)acrylamide, (R)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(2-(oxetan-3-yl)-6-(trifluoromethyl)-2,7-diazaspiro[3.5]nonan-7-yl)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(2-(oxetan-3-yl)-6-(trifluoromethyl)-2,7-diazaspiro[3.5]nonan-7-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(1,1-dioxido-5-(tetrahydro-2H-pyran-4-yl)-1,2,5-thiadiazinan-2-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(5-(oxetan-3-yl)-1,1-dioxido-1,2,5-thiadiazinan-2-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(4-(oxetan-3-yl)-2-oxopiperazin-1-yl)phenyl)acrylamide, Part 2: CH3

N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(piperidin-3-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(2-methyl-1-morpholinopropan-2-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(2-methyl-1-(4-methylpiperazin-1-yl)propan-2-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(4-methylpiperazine-1-carbonyl)phenyl)acrylamide, (S)—N-(5-((6-(2-(8,8-dimethyl-1-oxo-1,4,5,7,8,9-hexahydrocyclopenta[4,5]pyrrolo[1,2-a][1,4]diazepin-2(3H)-yl)-3-methylpyridin-4-yl)-4-methyl-3-oxo-3,4-dihydropyrazin-2-yl)amino)-2-(2-methyl-4-(oxetan-3-yl)piperazin-1-yl)phenyl)acrylamide, (S)—N-(5-((6-(2-(7,7-difluoro-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(2-methyl-4-(oxetan-3-yl)piperazin-1-yl)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-3-fluoro-2-(2-methyl-4-(oxetan-3-yl)piperazin-1-yl)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-3-methyl-2-(2-methyl-4-(oxetan-3-yl)piperazin-1-yl)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(2-methyl-4-(oxetan-3-yl)piperazin-1-yl)-3-(trifluoromethyl)phenyl)acrylamide, (S)—N-(3-cyano-5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(2-methyl-4-(oxetan-3-yl)piperazin-1-yl)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-3-(isopropylsulfonyl)-2-(2-methyl-4-(oxetan-3-yl)piperazin-1-yl)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(2-methyl-4-(oxetan-3-yl)piperazin-1-yl)-3-((trifluoromethyl)sulfonyl)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(2-methyl-4-(oxetan-3-yl)piperazin-1-yl)pyridin-3-yl)acrylamide, (S)—N-(5-((6-(2-(8,8-dimethyl-1-oxo-1,4,5,7,8,9-hexahydrocyclopenta[4,5]pyrrolo[1,2-a][1,4]diazepin-2(3H)-yl)-3-methylpyridin-4-yl)-4-methyl-3-oxo-3,4-dihydropyrazin-2-yl)amino)-2-(2-methyl-4-(oxetan-3-yl)piperazin-1-yl)pyridin-3-yl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(4-morpholinopiperidin-1-yl)phenyl)acrylamide, N-(2-(4,4-difluoro-[1,4'-bipiperidin]-1'-yl)-5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(4-(4-methylpiperazin-1-yl)piperidin-1-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(2-methyl-4-morpholinopiperidin-1-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-((2S)-2-methyl-4-morpholinopiperidin-1-yl)phenyl)acrylamide, N-(2-((2'S)-4,4-difluoro-2'-methyl-[1,4'-bipiperidin]-1'-yl)-5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-((2S)-2-methyl-4-(4-methylpiperazin-1-yl)piperidin-1-yl)phenyl)acrylamide.

(S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(2-methyl-4-(oxetan-3-yl)piperazin-1-yl)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(2-methyl-4-(tetrahydro-2H-pyran-4-yl)piperazin-1-yl)phenyl)acrylamide, (S)—N-(2-(4-(4,4-difluorocyclohexyl)-2-methylpiperazin-1-yl)-5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-((S)-2-methyl-4-((S)-tetrahydrofuran-3-yl)piperazin-1-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl) amino)-2-((S)-2-methyl-4-((R)-tetrahydrofuran-3-yl) piperazin-1-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl) amino)-2-((S)-2-methyl-4-((S)-oxepan-4-yl)piperazin-1-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl) amino)-2-((S)-2-methyl-4-((R)-oxepan-4-yl)piperazin-1-yl)phenyl)acrylamide, (S)—N-(5-((6-(2-(7,7-dimethyl-1-oxo-1,3,4,5,6,7-hexahydro-2H-cyclopenta[4,5]thieno[2,3-c]pyridin-2-yl)-3-methylpyridin-4-yl)-4-methyl-3-oxo-3,4-dihydropyrazin-2-yl)amino)-2-(2-methyl-4-(oxetan-3-yl)piperazin-1-yl) phenyl)acrylamide, (S)—N-(5-((6-(2-(6,6-dimethyl-1-oxo-1,3,4,5,6,7-hexahydro-2H-cyclopenta[4,5]thieno[2,3-c]pyridin-2-yl)-3-methylpyridin-4-yl)-4-methyl-3-oxo-3,4-dihydropyrazin-2-yl)amino)-2-(2-methyl-4-(oxetan-3-yl)piperazin-1-yl) phenyl)acrylamide, (S)—N-(5-((6-(2-(2-(tert-butyl)-7-oxo-4,7-dihydrothieno[2,3-c]pyridin-6(5H)-yl)-3-methylpyridin-4-yl)-4-methyl-3-oxo-3,4-dihydropyrazin-2-yl)amino)-2-(2-methyl-4-(oxetan-3-yl)piperazin-1-yl)phenyl)acrylamide, (S)—N-(2-(2-methyl-4-(oxetan-3-yl)piperazin-1-yl)-5-((4-methyl-6-(3-methyl-2-(1-oxo-3,4,5,6,7,8-hexahydrobenzo[4,5]thieno[2,3-c]pyridin-2(1H)-yl)pyridin-4-yl)-3-oxo-3,4-dihydropyrazin-2-yl)amino)phenyl) acrylamide, (R)—N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(1,4-dimethyl-6-oxopiperazin-2-yl) phenyl)acrylamide, (R)—N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(1,4-dimethyl-3-oxopiperazin-2-yl) phenyl)acrylamide, (R)—N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(4-methyl-3-oxo-1-(tetrahydro-2H-pyran-4-yl)piperazin-2-yl)phenyl)acrylamide, (R)—N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(4-methyl-1-(oxetan-3-yl)-3-oxopiperazin-2-yl)phenyl)acrylamide, N-(5-((6-(2-(2-(tert-butyl)-7-oxo-4,7-dihydrothieno[2,3-c]pyridin-6(5H)-yl)-3-methylpyridin-4-yl)-4-methyl-3-oxo-3,4-dihydropyrazin-2-yl)amino)-2-(4-methyl-1-(oxetan-3-yl)-3-oxopiperazin-2-yl)phenyl)acrylamide, N-(5-((6-(2-(7,7-dimethyl-1-oxo-1,3,4,5,6,7-hexahydro-2H-cyclopenta[4,5]thieno[2,3-c]pyridin-2-yl)-3-methylpyridin-4-yl)-4-methyl-3-oxo-3,4-dihydropyrazin-2-yl) amino)-2-(4-methyl-1-(oxetan-3-yl)-3-oxopiperazin-2-yl)phenyl)acrylamide, N-(2-(4-methyl-1-(oxetan-3-yl)-3-oxopiperazin-2-yl)-5-((4-methyl-6-(3-methyl-2-(1-oxo-3,4,5,6,7,8-hexahydrobenzo[4,5]thieno[2,3-c]pyridin-2(1H)-yl)pyridin-4-yl)-3-oxo-3,4-dihydropyrazin-2-yl)amino)phenyl) acrylamide, N-(5-((6-(2-(6,6-dimethyl-1-oxo-1,3,4,5,6,7-hexahydro-2H-cyclopenta[4,5]thieno[2,3-c]pyridin-2-yl)-3-methylpyridin-4-yl)-4-methyl-3-oxo-3,4-dihydropyrazin-2-yl) amino)-2-(4-methyl-1-(oxetan-3-yl)-3-oxopiperazin-2-yl)phenyl)acrylamide, N-(5-((6-(2-(6-(tert-butyl)-8-fluoro-1-oxo-3,4-dihydroisoquinolin-2(1H)-yl)-3-methylpyridin-4-yl)-4-methyl-3-oxo-3,4-dihydropyrazin-2-yl)amino)-2-(4-methyl-1-(oxetan-3-yl)-3-oxopiperazin-2-yl)phenyl)acrylamide, (R)—N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(4-(tetrahydro-2H-pyran-4-yl)-2-(trifluoromethyl)piperazin-1-yl)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(4-(tetrahydro-2H-pyran-4-yl)-2-(trifluoromethyl)piperazin-1-yl)phenyl)acrylamide, (S)—N-(2-(2-methyl-4-(tetrahydro-2H-pyran-4-yl)piperazin-1-yl)-5-((4-methyl-6-(3-methyl-2-(1-oxo-3,4,5,6,7,8-hexahydrobenzo[4,5]thieno[2,3-c]pyridin-2(1H)-yl) pyridin-4-yl)-3-oxo-3,4-dihydropyrazin-2-yl)amino) phenyl)acrylamide, (R)—N-(5-((4-methyl-6-(3-methyl-2-(1-oxo-3,4,5,6,7,8-hexahydrobenzo[4,5]thieno[2,3-c]pyridin-2(1H)-yl)pyridin-4-yl)-3-oxo-3,4-dihydropyrazin-2-yl)amino)-2-(4-(tetrahydro-2H-pyran-4-yl)-2-(trifluoromethyl)piperazin-1-yl)phenyl)acrylamide, (S)—N-(5-((4-methyl-6-(3-methyl-2-(1-oxo-3,4,5,6,7,8-hexahydrobenzo[4,5]thieno[2,3-c]pyridin-2(1H)-yl)pyridin-4-yl)-3-oxo-3,4-dihydropyrazin-2-yl)amino)-2-(4-(tetrahydro-2H-pyran-4-yl)-2-(trifluoromethyl)piperazin-1-yl)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)oxy)-2-(2-methyl-4-(tetrahydro-2H-pyran-4-yl) piperazin-1-yl)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)oxy)-2-(4-(tetrahydro-2H-pyran-4-yl)-2-(trifluoromethyl)piperazin-1-yl)phenyl)acrylamide, (R)—N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)oxy)-2-(4-(tetrahydro-2H-pyran-4-yl)-2-(trifluoromethyl)piperazin-1-yl)phenyl)acrylamide N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl) amino)-2-(1-isopropyl-6-oxo-4-(tetrahydro-2H-pyran-4-yl)piperazin-2-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl) amino)-2-(1-methyl-4-(tetrahydro-2H-pyran-4-yl)-6-(trifluoromethyl)piperazin-2-yl)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(2-methyl-4-(oxetan-3-yl)piperazin-1-yl) phenyl)-N-methylacrylamide, (S)—N-(5-((6-(2-(7,7-dimethyl-1,1-dioxido-3,4,7,8-tetrahydro-2H,6H-cyclopenta[4,5]pyrrolo[1,2-e][1,2,5]thiadiazin-2-yl)-3-methylpyridin-4-yl)-4-methyl-3-oxo-3,4-dihydropyrazin-2-yl)amino)-2-(2-methyl-4-(oxetan-3-yl)piperazin-1-yl)phenyl)acrylamide, N-(2-((S)-2-methyl-4-(oxetan-3-yl)piperazin-1-yl)-5-((4-methyl-6-(3-methyl-2-(1-oxo-7-(trifluoromethyl)-1,3,4,6,7,8-hexahydro-2H-cyclopenta[4,5]pyrrolo[1,2-a]pyrazin-2-yl)pyridin-4-yl)-3-oxo-3,4-dihydropyrazin-2-yl)amino)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(4-(oxetan-3-yl)-2-oxopiperazin-1-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(5-(oxetan-3-yl)-1,1-dioxido-1,2,5-thiadiazinan-2-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(2-oxo-4-(tetrahydro-2H-pyran-4-yl)piperazin-1-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(1,1-dioxido-5-(tetrahydro-2H-pyran-4-yl)-1,2,5-thiadiazinan-2-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(7-(tetrahydro-2H-pyran-4-yl)-4,7-diazaspiro[2.5]octan-4-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(2,2-dimethyl-4-(tetrahydro-2H-pyran-4-yl)piperazin-1-yl)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(2-methyl-4-(tetrahydro-2H-pyran-4-yl)piperazin-1-yl)pyridin-3-yl)acrylamide, (R)—N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(4-(oxetan-3-yl)-2-(trifluoromethyl)piperazin-1-yl)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(4-(oxetan-3-yl)-2-(trifluoromethyl)piperazin-1-yl)phenyl)acrylamide, N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(7-(oxetan-3-yl)-4,7-diazaspiro[2.5]octan-4-yl)phenyl)acrylamide, Part 3: CF3

N-(5-((6-(2-(7,7-dimethyl-1-oxo-1,3,4,6,7,8-hexahydro-2H-cyclopenta[4,5]pyrrolo[1,2-a]pyrazin-2-yl)-3-(trifluoromethyl)pyridin-4-yl)-4-methyl-3-oxo-3,4-dihydropyrazin-2-yl)amino)-2-((2S)-2-methyl-4-morpholinopiperidin-1-yl)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(trifluoromethyl)pyridin-4-yl)-4-methyl-3-oxo-3,4-dihydropyrazin-2-yl)amino)-2-(2-methyl-4-(oxetan-3-yl)piperazin-1-yl)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(trifluoromethyl)pyridin-4-yl)-4-methyl-3-oxo-3,4-dihydropyrazin-2-yl)amino)-3-fluoro-2-(2-methyl-4-(oxetan-3-yl)piperazin-1-yl)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(trifluoromethyl)pyridin-4-yl)-4-methyl-3-oxo-3,4-dihydropyrazin-2-yl)amino)-3-methyl-2-(2-methyl-4-(oxetan-3-yl)piperazin-1-yl)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(trifluoromethyl)pyridin-4-yl)-4-methyl-3-oxo-3,4-dihydropyrazin-2-yl)amino)-2-(2-methyl-4-(oxetan-3-yl)piperazin-1-yl)-3-(trifluoromethyl)phenyl)acrylamide, (S)—N-(3-cyano-5-((6-(2-(7,7-dimethyl-1-oxo-1,3,4,6,7,8-hexahydro-2H-cyclopenta[4,5]pyrrolo[1,2-a]pyrazin-2-yl)-3-(trifluoromethyl)pyridin-4-yl)-4-methyl-3-oxo-3,4-dihydropyrazin-2-yl)amino)-2-(2-methyl-4-(oxetan-3-yl)piperazin-1-yl)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(trifluoromethyl)pyridin-4-yl)-4-methyl-3-oxo-3,4-dihydropyrazin-2-yl)amino)-3-(isopropylsulfonyl)-2-(2-methyl-4-(oxetan-3-yl)piperazin-1-yl)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(trifluoromethyl)pyridin-4-yl)-4-methyl-3-oxo-3,4-dihydropyrazin-2-yl)amino)-2-(2-methyl-4-(oxetan-3-yl)piperazin-1-yl)-3-((trifluoromethyl)sulfonyl)phenyl)acrylamide, (S)—N-(5-((6-(2-(8,8-dimethyl-1-oxo-1,4,5,7,8,9-hexahydrocyclopenta[4,5]pyrrolo[1,2-a][1,4]diazepin-2(3H)-yl)-3-(trifluoromethyl)pyridin-4-yl)-4-methyl-3-oxo-3,4-dihydropyrazin-2-yl)amino)-2-(2-methyl-4-(oxetan-3-yl)piperazin-1-yl)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(trifluoromethyl)pyridin-4-yl)-4-methyl-3-oxo-3,4-dihydropyrazin-2-yl)amino)-2-(2-methyl-4-(oxetan-3-yl)piperazin-1-yl)pyridin-3-yl)acrylamide, (S)—N-(5-((6-(2-(8,8-dimethyl-1-oxo-1,4,5,7,8,9-hexahydrocyclopenta[4,5]pyrrolo[1,2-a][1,4]diazepin-2(3H)-yl)-3-(trifluoromethyl)pyridin-4-yl)-4-methyl-3-oxo-3,4-dihydropyrazin-2-yl)amino)-2-(2-methyl-4-(oxetan-3-yl)piperazin-1-yl)pyridin-3-yl)acrylamide, Compounds of the invention may contain one or more asymmetric carbon atoms. Accordingly, the compounds may exist as diastereomers, enantiomers or mixtures thereof. The syntheses of the compounds may employ racemates, diastereomers or enantiomers as starting materials or as intermediates. Diastereomeric compounds may be separated by chromatographic or crystallization methods. Similarly, enantiomeric mixtures may be separated using the same techniques or others known in the art. Each of the asymmetric carbon atoms may be in the R or S configuration and both of these configurations are within the scope of the invention.

A modified compound of any one of such compounds including a modification having an improved (e.g., enhanced, greater) pharmaceutical solubility, stability, bioavailability and/or therapeutic index as compared to the unmodified compound is also contemplated. The examples of modifications include but not limited to the prodrug derivatives, and the deuterium-enriched compounds. For example:

Prodrug derivatives: prodrugs, upon administration to a subject, will converted in vivo into active compounds of the present invention [*Nature Reviews of Drug Discovery,* 2008, Volume 7, p 255]. It is noted that in many instances, the prodrugs themselves also fall within the scope of the range of compounds according to the present invention. The prodrugs of the compounds of the present invention can be prepared by standard organic reaction, for example, by reacting with a carbamylating agent (e.g., 1,1-acyloxyalkylcarbonochloridate, para-nitrophenyl carbonate, or the like) or an acylating agent. Further examples of methods and strategies of making prodrugs are described in *Bioorganic and Medicinal Chemistry Letters,* 1994, Vol. 4, p. 1985.

Deuterium-enriched compounds: deuterium (D or $^2H$) is a stable, non-radioactive isotope of hydrogen and has an atomic weight of 2.0144. Hydrogen naturally occurs as a mixture of the isotopes $^XH$ (hydrogen or protium), D ($^2H$ or deuterium), and T ($^3H$ or tritium). The natural abundance of deuterium is 0.015%. One of ordinary skill in the art recognizes that in all chemical compounds with a H atom, the H atom actually represents a mixture of H and D, with about 0.015% being D. Thus, compounds with a level of deuterium that has been enriched to be greater than its natural abundance of 0.015%, should be considered unnatural and, as a result, novel over their nonenriched counterparts.

It should be recognized that the compounds of the present invention may be present and optionally administered in the form of salts, and solvates. For example, it is within the scope of the present invention to convert the compounds of the present invention into and use them in the form of their pharmaceutically acceptable salts derived from various organic and inorganic acids and bases in accordance with procedures well known in the art.

When the compounds of the present invention possess a free base form, the compounds can be prepared as a pharmaceutically acceptable acid addition salt by reacting the free base form of the compound with a pharmaceutically acceptable inorganic or organic acid, e.g., hydrohalides such as hydrochloride, hydrobromide, hydroiodide; other mineral acids such as sulfate, nitrate, phosphate, etc.; and alkyl and monoarylsulfonates such as ethanesulfonate, toluenesulfonate and benzenesulfonate; and other organic acids and their corresponding salts such as acetate, tartrate, maleate, succinate, citrate, benzoate, salicylate and ascorbate. Further acid addition salts of the present invention include, but are not limited to: adipate, alginate, arginate, aspartate, bisulfate, bisulfite, bromide, butyrate, camphorate, camphorsulfonate, caprylate, chloride, chlorobenzoate, cyclopentanepropionate, digluconate, dihydrogenphosphate, dinitrobenzoate, dodecylsulfate, fumarate, galacterate (from mucic acid), galacturonate, glucoheptaoate, gluconate, glutamate, glycerophosphate, hemisuccinate, hemisulfate, heptanoate, hexanoate, hippurate, 2-hydroxyethanesulfonate, iodide, isethionate, iso-butyrate, lactate, lactobionate, malonate, mandelate, metaphosphate, methanesulfonate, methylbenzoate, monohydrogenphosphate, 2-naphthalenesulfonate, nicotinate, oxalate, oleate, pamoate, pectinate, persulfate, phenylacetate, 3-phenylpropionate, phosphonate and phthalate. It should be recognized that the free base forms will typically differ from their respective salt forms somewhat in physical properties such as solubility in polar solvents, but otherwise the salts are equivalent to their respective free base forms for the purposes of the present invention.

When the compounds of the present invention possess a free acid form, a pharmaceutically acceptable base addition salt can be prepared by reacting the free acid form of the compound with a pharmaceutically acceptable inorganic or organic base. Examples of such bases are alkali metal hydroxides including potassium, sodium and lithium hydroxides; alkaline earth metal hydroxides such as barium and calcium hydroxides; alkali metal alkoxides, e.g., potassium ethanolate and sodium propanolate; and various organic bases such as ammonium hydroxide, piperidine, diethanolamine and N-methylglutamine. Also included are the aluminum salts of the compounds of the present invention. Further base salts of the present invention include, but are not limited to: copper, ferric, ferrous, lithium, magnesium, manganic, manganous, potassium, sodium and zinc salts. Organic base salts include, but are not limited to, salts of primary, secondary and tertiary amines, substituted amines including naturally occurring substituted amines, cyclic amines and basic ion exchange resins, e.g., arginine, betaine, caffeine, chloroprocaine, choline, N,N'-dibenzylethylenediamine (benzathine), dicyclohexylamine, diethanolamine, 2-diethylaminoethanol, 2-dimethylaminoethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris-(hydroxymethyl)-methylamine (tromethamine). It should be recognized that the free acid forms will typically differ from their respective salt forms somewhat in physical properties such as solubility in polar solvents, but otherwise the salts are equivalent to their respective free acid forms for the purposes of the present invention.

In one aspect, a pharmaceutically acceptable salt is a hydrochloride salt, hydrobromide salt, methanesulfonate, toluenesulfonate, acetate, fumarate, sulfate, bisulfate, succinate, citrate, phosphate, maleate, nitrate, tartrate, benzoate, biocarbonate, carbonate, sodium hydroxide salt, calcium hydroxide salt, potassium hydroxide salt, tromethamine salt, or mixtures thereof.

Compounds of the present invention that comprise tertiary nitrogen-containing groups may be quaternized with such agents as ($C_{1-4}$) alkyl halides, e.g., methyl, ethyl, iso-propyl and tert-butyl chlorides, bromides and iodides; di-($C_{1-4}$) alkyl sulfates, e.g., dimethyl, diethyl and diamyl sulfates; alkyl halides, e.g., decyl, dodecyl, lauryl, myristyl and stearyl chlorides, bromides and iodides; and aryl ($C_{1-4}$) alkyl halides, e.g., benzyl chloride and phenethyl bromide. Such salts permit the preparation of both water- and oil-soluble compounds of the invention.

Amine oxides, also known as amine-N-oxide and N-oxide, of anti-cancer agents with tertiary nitrogen atoms have been developed as prodrugs [Mol Cancer Therapy. 2004 March; 3(3):233-44]. Compounds of the present invention that comprise tertiary nitrogen atoms may be oxidized by such agents as hydrogen peroxide ($H_2O_2$), Caro's acid or peracids like meta-Chloroperoxybenzoic acid (mCPBA) to from amine oxide.

The invention encompasses pharmaceutical compositions comprising the compound of the present invention and pharmaceutical excipients, as well as other conventional pharmaceutically inactive agents. Any inert excipient that is commonly used as a carrier or diluent may be used in compositions of the present invention, such as sugars, polyalcohols, soluble polymers, salts and lipids. Sugars and polyalcohols which may be employed include, without limitation, lactose, sucrose, mannitol, and sorbitol. Illustrative of the soluble polymers which may be employed are polyoxyethylene, poloxamers, polyvinylpyrrolidone, and dextran. Useful salts include, without limitation, sodium chloride, magnesium chloride, and calcium chloride. Lipids which may be employed include, without limitation, fatty acids, glycerol fatty acid esters, glycolipids, and phospholipids.

In addition, the pharmaceutical compositions may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmellose sodium, crospovidone, guar gum, sodium starch glycolate, Primogel), buffers (e.g., tris-HCL, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol, cyclodextrins), a glidant (e.g., colloidal silicon dioxide), anti-oxidants (e.g., ascorbic acid, sodium metabisulfite, butylated hydroxyanisole), stabilizers (e.g., hydroxypropyl cellulose, hydroxypropylmethyl cellulose), viscosity increasing agents (e.g., carbomer, colloidal silicon dioxide, ethyl cellulose, guar gum), sweeteners (e.g., sucrose, aspartame, citric acid), flavoring agents (e.g., peppermint, methyl salicylate, or orange flavoring), preservatives (e.g., Thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate, methyl cellulose, hydroxyethyl cellulose, carboxymethylcellulose sodium), polymer coatings (e.g., poloxamers or poloxamines), coating and film forming agents (e.g., ethyl cellulose, acrylates, polymethacrylates) and/or adjuvants.

In one embodiment, the pharmaceutical compositions are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Additionally, the invention encompasses pharmaceutical compositions comprising any solid or liquid physical form of the compound of the invention. For example, the compounds can be in a crystalline form, in amorphous form, and have any particle size. The particles may be micronized, or may be agglomerated, particulate granules, powders, oils, oily suspensions or any other form of solid or liquid physical form.

When compounds according to the present invention exhibit insufficient solubility, methods for solubilizing the compounds may be used. Such methods are known to those of skill in this art, and include, but are not limited to, pH adjustment and salt formation, using co-solvents, such as ethanol, propylene glycol, polyethylene glycol (PEG) 300, PEG 400, DMA (10-30%), DMSO (10-20%), NMP (10-20%), using surfactants, such as polysorbate 80, polysorbate 20 (1-10%), cremophor EL, Cremophor RH40, Cremophor RH60 (5-10%), Pluronic F68/Poloxamer 188 (20-50%), Solutol HS15 (20-50%), Vitamin E TPGS, and d-α-tocopheryl PEG 1000 succinate (20-50%), using complexation such as HPβCD and SBEβCD (10-40%), and using advanced approaches such as micelle, addition of a polymer, nanoparticle suspensions, and liposome formation.

A wide variety of administration methods may be used in conjunction with the compounds of the present invention. Compounds of the present invention may be administered or coadministered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compounds according to the invention may also be administered or coadministered in slow release dosage forms. Compounds may be in gaseous, liquid, semi-liquid or solid form, formulated in a manner suitable for the route of administration to be used. For oral administration, suitable solid oral formulations include tablets, capsules, pills, granules, pellets, sachets and effervescent, powders, and the like. Suitable liquid oral formulations include solutions, suspensions, dispersions, emulsions, oils and the like. For parenteral administration, reconstitution of a lyophilized powder is typically used.

As used herein, "Acyl" means a carbonyl containing substituent represented by the formula —C(O)—R in which R is H, alkyl, a carbocycle, a heterocycle, carbocycle-substituted alkyl or heterocycle-substituted alkyl wherein the alkyl, alkoxy, carbocycle and heterocycle are as defined herein. Acyl groups include alkanoyl (e.g. acetyl), aroyl (e.g. benzoyl), and heteroaroyl.

"Aliphatic" means a moiety characterized by a straight or branched chain arrangement of constituent carbon atoms and may be saturated or partially unsaturated with one or more double or triple bonds.

The term "alkyl" refers to a straight or branched hydrocarbon containing 1-20 carbon atoms (e.g., $C_1$-$C_{10}$). Examples of alkyl include, but are not limited to, methyl, methylene, ethyl, ethylene, n-propyl, i-propyl, n-butyl, i-butyl, and t-butyl. Preferably, the alkyl group has one to ten carbon atoms. More preferably, the alkyl group has one to four carbon atoms.

The term "alkenyl" refers to a straight or branched hydrocarbon containing 2-20 carbon atoms (e.g., $C_2$-$C_{10}$) and one or more double bonds. Examples of alkenyl include, but are not limited to, ethenyl, propenyl, and allyl. Preferably, the alkylene group has two to ten carbon atoms. More preferably, the alkylene group has two to four carbon atoms.

The term "alkynyl" refers to a straight or branched hydrocarbon containing 2-20 carbon atoms (e.g., $C_2$-$C_{10}$) and one or more triple bonds. Examples of alkynyl include, but are not limited to, ethynyl, 1-propynyl, 1- and 2-butynyl, and 1-methyl-2-butynyl. Preferably, the alkynyl group has two to ten carbon atoms. More preferably, the alkynyl group has two to four carbon atoms.

The term "alkylamino" refers to an —N(R)-alkyl in which R can be H, alkyl, alkenyl, alkynyl, cycloalkyl, cycloalkenyl, heterocycloalkyl, heterocycloalkenyl, aryl, or heteroaryl.

"Alkoxy" means an oxygen moiety having a further alkyl substituent.

"Alkoxycarbonyl" means an alkoxy group attached to a carbonyl group.

"Oxoalkyl" means an alkyl, further substituted with a carbonyl group. The carbonyl group may be an aldehyde, ketone, ester, amide, acid or acid chloride.

The term "cycloalkyl" refers to a saturated hydrocarbon ring system having 3 to 30 carbon atoms (e.g., $C_3$-$C_{12}$, $C_3$-$C_8$, $C_3$-$C_6$). Examples of cycloalkyl include, but are not limited to, cyclopropyl, cyclobutyl, cyclopentyl, cyclohexyl, cycloheptyl, and cyclooctyl. The term "cycloalkenyl" refers to a non-aromatic hydrocarbon ring system having 3 to 30 carbons (e.g., $C_3$-$C_{12}$) and one or more double bonds. Examples include cyclopentenyl, cyclohexenyl, and cycloheptenyl.

The term "heterocycloalkyl" refers to a nonaromatic 5-8 membered monocyclic, 8-12 membered bicyclic, or 11-14 membered tricyclic ring system having one or more heteroatoms (such as O, N, S, P, or Se). Examples of heterocycloalkyl groups include, but are not limited to, piperazinyl, pyrrolidinyl, dioxanyl, morpholinyl, and tetrahydrofuranyl.

The term "heterocycloalkenyl" refers to a nonaromatic 5-8 membered monocyclic, 8-12 membered bicyclic, or 11-14 membered tricyclic ring system having one or more heteroatoms (such as O, N, S, P, or Se) and one or more double bonds.

The term "aryl" refers to a 6-carbon monocyclic, 10-carbon bicyclic, 14-carbon tricyclic aromatic ring system. Examples of aryl groups include, but are not limited to, phenyl, naphthyl, and anthracenyl. The term "heteroaryl" refers to an aromatic 5-8 membered monocyclic, 8-12 membered bicyclic, or 11-14 membered tricyclic ring system having one or more heteroatoms (such as O, N, S, P, or Se). Examples of heteroaryl groups include pyridyl, furyl, imidazolyl, benzimidazolyl, pyrimidinyl, thienyl, quinolinyl, indolyl, and thiazolyl.

Alkyl, alkenyl, alkynyl, cycloalkyl, heterocycloalkyl, cycloalkenyl, heterocycloalkenyl, alkylamino, aryl, and heteroaryl mentioned above include both substituted and unsubstituted moieties. Possible substituents on alkylamino, cycloalkyl, heterocycloalkyl, cycloalkenyl, heterocycloalkenyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, arylamino, hydroxy, halo, oxo (O═), thioxo (S═), thio, silyl, $C_1$-$C_{10}$ alkylthio, arylthio, $C_1$-$C_{10}$ alkylsulfonyl, arylsulfonyl, acylamino, aminoacyl, aminothioacyl, amidino, mercapto, amido, thioureido, thiocyanato, sulfonamido, guanidine, ureido, cyano, nitro, acyl, thioacyl, acyloxy, carbamido, carbamyl, carboxyl, and carboxylic ester. On the other hand, possible substituents on alkyl, alkenyl, or alkynyl include all of the above-recited substituents except $C_1$-$C_{10}$ alkyl. Cycloalkyl, cycloalkenyl, heterocycloalkyl, heterocycloalkenyl, aryl, and heteroaryl can also be fused with each other.

"Amino" means a nitrogen moiety having two further substituents where each substituent has a hydrogen or carbon atom alpha bonded to the nitrogen. Unless indicated otherwise, the compounds of the invention containing amino moieties may include protected derivatives thereof. Suitable protecting groups for amino moieties include acetyl, tert-butoxycarbonyl, benzyloxycarbonyl, and the like.

"Aromatic" means a moiety wherein the constituent atoms make up an unsaturated ring system, all atoms in the ring system are sp2 hybridized and the total number of pi electrons is equal to 4n+2. An aromatic ring may be such that the ring atoms are only carbon atoms or may include carbon and non-carbon atoms (see Heteroaryl).

"Carbamoyl" means the radical —OC(O)$NR_aR_b$ where $R_a$ and $R_b$ are each independently two further substituents where a hydrogen or carbon atom is alpha to the nitrogen. It is noted that carbamoyl moieties may include protected derivatives thereof. Examples of suitable protecting groups for carbamoyl moieties include acetyl, tert-butoxycarbonyl, benzyloxycarbonyl, and the like. It is noted that both the unprotected and protected derivatives fall within the scope of the invention.

"Carbonyl" means the radical —C(O)—. It is noted that the carbonyl radical may be further substituted with a variety of substituents to form different carbonyl groups including acids, acid halides, amides, esters, and ketones.

"Carboxy" means the radical —C(O)O—. It is noted that compounds of the invention containing carboxy moieties may include protected derivatives thereof, i.e., where the oxygen is substituted with a protecting group. Suitable protecting groups for carboxy moieties include benzyl, tert-butyl, and the like.

"Cyano" means the radical —CN.

"Formyl" means the radical —CH═O.

"Formimino" means the radical —HC═NH.

"Halo" means fluoro, chloro, bromo or iodo.

"Halo-substituted alkyl", as an isolated group or part of a larger group, means "alkyl" substituted by one or more "halo" atoms, as such terms are defined in this Application. Halo-substituted alkyl includes haloalkyl, dihaloalkyl, trihaloalkyl, perhaloalkyl and the like.

"Hydroxy" means the radical —OH.

"Imine derivative" means a derivative comprising the moiety —C(═NR)—, wherein R comprises a hydrogen or carbon atom alpha to the nitrogen.

"Isomers" mean any compound having identical molecular formulae but differing in the nature or sequence of bonding of their atoms or in the arrangement of their atoms in space. Isomers that differ in the arrangement of their atoms in space are termed "stereoisomers." Stereoisomers that are not mirror images of one another are termed "diastereomers" and stereoisomers that are nonsuperimposable mirror images are termed "enantiomers" or sometimes "optical isomers." A carbon atom bonded to four nonidentical substituents is termed a "chiral center." A compound with one chiral center has two enantiomeric forms of opposite chirality. A mixture of the two enantiomeric forms is termed a "racemic mixture."

"Nitro" means the radical $—NO_2$.

"Protected derivatives" means derivatives of compounds in which a reactive site are blocked with protecting groups. Protected derivatives are useful in the preparation of pharmaceuticals or in themselves may be active as inhibitors. A comprehensive list of suitable protecting groups can be found in T. W. Greene, Protecting Groups in Organic Synthesis, 3rd edition, Wiley & Sons, 1999.

The term "substituted" means that an atom or group of atoms has replaced hydrogen as the substituent attached to another group. For aryl and heteroaryl groups, the term "substituted" refers to any level of substitution, namely mono-, di-, tri-, tetra-, or penta-substitution, where such substitution is permitted. The substituents are independently selected, and substitution may be at any chemically accessible position. The term "unsubstituted" means that a given moiety may consist of only hydrogen substituents through available valencies (unsubstituted).

If a functional group is described as being "optionally substituted," the function group may be either (1) not substituted, or (2) substituted. If a carbon of a functional group is described as being optionally substituted with one or more of a list of substituents, one or more of the hydrogen atoms on the carbon (to the extent there are any) may separately and/or together be replaced with an independently selected optional substituent.

"Sulfide" means —S—R wherein R is H, alkyl, carbocycle, heterocycle, carbocycloalkyl or heterocycloalkyl. Particular sulfide groups are mercapto, alkylsulfide, for example methylsulfide (—S-Me); arylsulfide, e.g., phenylsulfide; aralkylsulfide, e.g., benzylsulfide.

"Sulfinyl" means the radical —S(O)—. It is noted that the sulfinyl radical may be further substituted with a variety of substituents to form different sulfinyl groups including sulfinic acids, sulfinamides, sulfinyl esters, and sulfoxides.

"Sulfonyl" means the radical —S(O)(O)—. It is noted that the sulfonyl radical may be further substituted with a variety of substituents to form different sulfonyl groups including sulfonic acids, sulfonamides, sulfonate esters, and sulfones.

"Thiocarbonyl" means the radical —C(S)—. It is noted that the thiocarbonyl radical may be further substituted with a variety of substituents to form different thiocarbonyl groups including thioacids, thioamides, thioesters, and thioketones.

"Animal" includes humans, non-human mammals (e.g., non-human primates, rodents, mice, rats, hamsters, dogs, cats, rabbits, cattle, horses, sheep, goats, swine, deer, and the like) and non-mammals (e.g., birds, and the like).

"Bioavailability" as used herein is the fraction or percentage of an administered dose of a drug or pharmaceutical composition that reaches the systemic circulation intact. In general, when a medication is administered intravenously, its bioavailability is 100%. However, when a medication is administered via other routes (e.g., orally), its bioavailability decreases (e.g., due to incomplete absorption and first-pass metabolism). Methods to improve the bioavailability include prodrug approach, salt synthesis, particle size reduction, complexation, change in physical form, solid dispersions, spray drying, and hot-melt extrusion.

"Disease" specifically includes any unhealthy condition of an animal or part thereof and includes an unhealthy condition that may be caused by, or incident to, medical or veterinary therapy applied to that animal, i.e., the "side effects" of such therapy.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means organic or inorganic salts of compounds of the present invention which are pharmaceutically acceptable, as defined above, and which possess the desired pharmacological activity. Such salts include acid addition salts formed with inorganic acids, or with organic acids. Pharmaceutically acceptable salts also include base addition salts which may be formed when acidic protons present are capable of reacting with inorganic or organic bases. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate," ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

"Pharmaceutically acceptable carrier" means a non-toxic solvent, dispersant, excipient, adjuvant, or other material which is mixed with the compounds of the present invention in order to form a pharmaceutical composition, i.e., a dose form capable of administration to the patient. Examples of pharmaceutically acceptable carrier includes suitable polyethylene glycol (e.g., PEG400), surfactant (e.g., Cremophor), or cyclopolysaccharide (e.g., hydroxypropyl-β-cyclodextrin or sulfobutyl ether β-cyclodextrins), polymer, liposome, micelle, nanosphere, etc.

"Pharmacophore," as defined by The International Union of Pure and Applied Chemistry, is an ensemble of steric and electronic features that is necessary to ensure the optimal supramolecular interactions with a specific biological target and to trigger (or block) its biological response. For example, Camptothecin is the pharmacophore of the well known drug topotecan and irinotecan. Mechlorethamine is the pharmacophore of a list of widely used nitrogen mustard drugs like Melphalan, Cyclophosphamide, Bendamustine, and so on.

"Prodrug" means a compound that is convertible in vivo metabolically into an active pharmaceutical according to the present invention. For example, an inhibitor comprising a hydroxyl group may be administered as an ester that is converted by hydrolysis in vivo to the hydroxyl compound.

"Stability" in general refers to the length of time a drug retains its properties without loss of potency. Sometimes this is referred to as shelf life. Factors affecting drug stability include, among other things, the chemical structure of the drug, impurity in the formulation, pH, moisture content, as well as environmental factors such as temperature, oxidization, light, and relative humidity. Stability can be improved by providing suitable chemical and/or crystal modifications (e.g., surface modifications that can change hydration kinetics; different crystals that can have different properties), excipients (e.g., anything other than the active substance in the dosage form), packaging conditions, storage conditions, etc.

"Therapeutically effective amount" of a composition described herein is meant an amount of the composition which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the composition described above may range from about 0.1 mg/kg to about 500 mg/kg, preferably from about 0.2 to about 50 mg/kg. Effective doses will also vary depending on route of administration, as well as the possibility of co-usage with other agents. It will be understood, however, that the total daily usage of the compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

As used herein, the term "treating" refers to administering a compound to a subject that has a neoplastic or immune disorder, or has a symptom of or a predisposition toward it, with the purpose to cure, heal, alleviate, relieve, alter, remedy, ameliorate, improve, or affect the disorder, the symptoms of or the predisposition toward the disorder. The term "an effective amount" refers to the amount of the active agent that is required to confer the intended therapeutic effect in the subject. Effective amounts may vary, as recognized by those skilled in the art, depending on route of administration, excipient usage, and the possibility of co-usage with other agents.

A "subject" refers to a human and a non-human animal. Examples of a non-human animal include all vertebrates, e.g., mammals, such as non-human primates (particularly higher primates), dog, rodent (e.g., mouse or rat), guinea pig, cat, and non-mammals, such as birds, amphibians, reptiles, etc. In a preferred embodiment, the subject is a human. In another embodiment, the subject is an experimental animal or animal suitable as a disease model.

"Combination therapy" includes the administration of the subject compounds of the present invention in further combination with other biologically active ingredients (such as, but not limited to, a second and different antineoplastic agent) and non-drug therapies (such as, but not limited to, surgery or radiation treatment). For instance, the compounds of the invention can be used in combination with other pharmaceutically active compounds, or non-drug therapies, preferably compounds that are able to enhance the effect of the compounds of the invention. The compounds of the invention can be administered simultaneously (as a single preparation or separate preparation) or sequentially to the other therapies. In general, a combination therapy envisions administration of two or more drugs/treatments during a single cycle or course of therapy.

In one embodiment, the compounds of the invention are administered in combination with one or more of traditional chemotherapeutic agents. The traditional chemotherapeutic agents encompass a wide range of therapeutic treatments in the field of oncology. These agents are administered at various stages of the disease for the purposes of shrinking tumors, destroying remaining cancer cells left over after surgery, inducing remission, maintaining remission and/or alleviating symptoms relating to the cancer or its treatment. Examples of such agents include, but are not limited to, alkylating agents such as Nitrogen Mustards (e.g., Bendamustine, Cyclophosphamide, Melphalan, Chlorambucil, Isofosfamide), Nitrosureas (e.g., Carmustine, Lomustine and Streptozocin), ethylenimines (e.g., thiotepa, hexamethylmelanine), Alkylsulfonates (e.g., Busulfan), Hydrazines and Triazines (e.g., Altretamine, Procarbazine, Dacarbazine and Temozolomide), and platinum based agents (e.g., Carboplatin, Cisplatin, and Oxaliplatin); plant alkaloids such as Podophyllotoxins (e.g., Etoposide and Tenisopide), Taxanes (e.g., Paclitaxel and Docetaxel), Vinca alkaloids (e.g., Vincristine, Vinblastine and Vinorelbine); anti-tumor antibiotics such as Chromomycins (e.g., Dactinomycin and Plicamycin), Anthracyclines (e.g., Doxorubicin, Daunorubicin, Epirubicin, Mitoxantrone, and Idarubicin), and miscellaneous antibiotics such as Mitomycin and Bleomycin; anti-metabolites such as folic acid antagonists (e.g., Methotrexate), pyrimidine antagonists (e.g., 5-Fluorouracil, Foxuridine, Cytarabine, Capecitabine, and Gemcitabine), purine antagonists (e.g., 6-Mercaptopurine and 6-Thioguanine) and adenosine deaminase inhibitors (e.g., Cladribine, Fludarabine, Nelarabine and Pentostatin); topoisomerase inhibitors such as topoisomerase I inhibitors (Topotecan, Irinotecan), topoisomerase II inhibitors (e.g., Amsacrine, Etoposide, Etoposide phosphate, Teniposide), and miscellaneous antineoplastics such as ribonucleotide reductase inhibitors (Hydroxyurea), adrenocortical steroid inhibitor (Mitotane), anti-microtubule agents (Estramustine), and retinoids (Bexarotene, Isotretinoin, Tretinoin (ATRA).

In one aspect of the invention, the compounds may be administered in combination with one or more targeted anti-cancer agents that modulate protein kinases involved in various disease states. Examples of such kinases may include, but are not limited ABL1, ABL2/ARG, ACK1, AKT1, AKT2, AKT3, ALK, ALK1/ACVRL1, ALK2/ACVR1, ALK4/ACVR1B, ALK5/TGFBR1, ALK6/BMPR1B, AMPK(A1/B1/G1), AMPK(A1/B1/G2), AMPK(A1/B1/G3), AMPK(A1/B2/G1), AMPK(A2/B1/G1), AMPK(A2/B2/G1), AMPK(A2/B2/G2), ARAF, ARK5/NUAK1, ASK1/MAP3K5, ATM, Aurora A, Aurora B, Aurora C, AXL, BLK, BMPR2, BMX/ETK, BRAF, BRK, BRSK1, BRSK2, BTK, CAMK1a, CAMK1b, CAMK1d, CAMK1g, CAMKIIa, CAMKIIb, CAMKIId, CAMKIIg, CAMK4, CAMKK1, CAMKK2, $CDCl_7$-DBF4, CDK1-cyclin A, CDK1-cyclin B, CDK1-cyclin E, CDK2-cyclin A, CDK2-cyclin A1, CDK2-cyclin E, CDK3-cyclin E, CDK4-cyclin D1, CDK4-cyclin D3, CDK5-p25, CDK5-p35, CDK6-cyclin D1, CDK6-cyclin D3, CDK7-cyclin H, CDK9-cyclin K, CDK9-cyclin Tl, CHK1, CHK2, CK1a1, CK1d, CK1epsilon, CK1g1, CK1g2, CK1g3, CK2a, CK2a2, c-KIT, CLK1, CLK2, CLK3, CLK4, c-MER, c-MET, COT1/MAP3K8, CSK, c-SRC, CTK/MATK, DAPK1, DAPK2, DCAMKL1, DCAMKL2, DDR1, DDR2, DLK/MAP3K12, DMPK, DMPK2/CDC42BPG, DNA-PK, DRAK1/STK17A, DYRK1/DYRK1A, DYRK1B, DYRK2, DYRK3, DYRK4, EEF2K, EGFR, EIF2AK1, EIF2AK2, EIF2AK3, EIF2AK4/GCN2, EPHA1, EPHA2, EPHA3, EPHA4, EPHA5, EPHA6, EPHA7, EPHA8, EPHB1, EPHB2, EPHB3, EPHB4, ERBB2/HER2, ERBB4/HER4, ERK1/MAPK3, ERK2/MAPK1, ERK5/MAPK7, FAK/PTK2, FER, FES/FPS, FGFR1, FGFR2, FGFR3, FGFR4, FGR, FLT1/VEGFR1, FLT3, FLT4/VEGFR3, FMS, FRK/PTK5, FYN, GCK/MAP4K2, GRK1, GRK2, GRK3, GRK4, GRK5, GRK6, GRK7, GSK3a, GSK3b, Haspin, HCK, HGK/MAP4K4, HIPK1, HIPK2, HIPK3, HIPK4, HPK1/MAP4K1, IGF1R, IKKa/CHUK, IKKb/IKBKB, IKKe/IKBKE, IR, IRAK1, IRAK4, IRR/INSRR, ITK, JAK1, JAK2, JAK3, JNK1, JNK2, JNK3, KDR/VEGFR2, KHS/MAP4K5, LATS1, LATS2, LCK, LCK2/ICK, LKB1, LIMK1, LOK/STK10, LRRK2, LYN, LYNB, MAPKAPK2, MAPKAPK3, MAPKAPK5/PRAK, MARK1, MARK2/PAR-1Ba, MARK3, MARK4, MEK1, MEK2, MEKK1, MEKK2, MEKK3, MELK, MINK/MINK1, MKK4, MKK6, MLCK/MYLK, MLCK2/MYLK2, MLK1/MAP3K9, MLK2/MAP3K10, MLK3/MAP3K11, MNK1, MNK2, MRCKa/, CDCl42BPA, MRCKb/, CDCl42BPB, MSK1/RPS6KA5, MSK2/RPS6KA4, MSSK1/STK23, MST1/STK4, MST2/STK3, MST3/STK24, MST4, mTOR/FRAP1, MUSK, MYLK3, MYO3b, NEK1, NEK2, NEK3, NEK4, NEK6, NEK7, NEK9, NEK11, NIK/MAP3K14, NLK, OSR1/OXSR1, P38a/MAPK14, P38b/MAPK11, P38d/MAPK13, P38g/MAPK12, P70S6K/RPS6KB1, p70S6Kb/, RPS6KB2, PAK1, PAK2, PAK3, PAK4, PAK5, PAK6, PASK, PBK/TOPK, PDGFRa, PDGFRb, PDK1/PDPK1, PDK1/PDHK1, PDK2/PDHK2, PDK3/PDHK3, PDK4/PDHK4, PHKg1, PHKg2, PI3Ka, (p110a/p85a), PI3Kb, (p110b/p85a), PI3Kd, (p110d/p85a), PI3 Kg(p120g), PIM1, PIM2, PIM3, PKA, PKAcb, PKAcg, PKCa, PKCb1, PKCb2, PKCd, PKCepsilon, PKCeta, PKCg, PKCiota, PKCmu/PRKD1, PKCnu/PRKD3, PKCtheta, PKCzeta, PKD2/PRKD2, PKG1a, PKG1b, PKG2/PRKG2, PKN1/PRK1, PKN2/PRK2, PKN3/PRK3, PLK1, PLK2, PLK3, PLK4/SAK, PRKX, PYK2, RAF1, RET, RIPK2, RIPK3, RIPK5, ROCK1, ROCK2, RON/MST1R, ROS/ROS1, RSK1, RSK2, RSK3, RSK4, SGK1, SGK2, SGK3/SGKL, SIK1, SIK2, SLK/STK2, SNARK/NUAK2, SRMS, SSTK/TSSK6, STK16, STK22D/TSSK1, STK25/YSK1, STK32b/YANK2, STK32c/YANK3, STK33, STK38/NDR1, STK38L/NDR2, STK39/STLK3, SRPK1, SRPK2, SYK, TAK1, TAOK1, TAOK2/TAO1, TAOK3/JIK, TBK1, TEC, TESK1, TGFBR2, TIE2/TEK, TLK1, TLK2, TNIK, TNK1, TRKA, TRKB, TRKC, TRPM7/CHAK1, TSSK2, TSSK3/STK22C, TTBK1, TTBK2, TTK, TXK, TYK1/LTK, TYK2, TYRO3/SKY, ULK1, ULK2, ULK3, VRK1, VRK2, WEE1, WNK1, WNK2, WNK3, YES/YES1, ZAK/MLTK, ZAP70, ZIPK/DAPK3, KINASE, MUTANTS, ABL1(E255K), ABL1(F317I), ABL1(G250E), ABL1(H396P), ABL1(M351T), ABL1(Q252H), ABL1(T315I), ABL1(Y253F), ALK (C1156Y), ALK(L1196M), ALK (F1174L), ALK (R1275Q), BRAF(V599E), BTK(E41K), CHK2(I157T), c-Kit(A829P), c-KIT(D816H), c-KIT(D816V), c-Kit (D820E), c-Kit(N822K), C-Kit (T670I), c-Kit(V559D), c-Kit(V559D/V654A), c-Kit(V559D/T670I), C-Kit (V560G), c-KIT(V654A), C-MET(D1228H), C-MET (D1228N), C-MET(F1200I), c-MET(M1250T), C-MET (Y1230A), C-MET(Y1230C), C-MET(Y1230D), C-MET (Y1230H), c-Src(T341M), EGFR(G719C), EGFR(G719S), EGFR(L858R), EGFR(L861Q), EGFR(T790M), EGFR, (L858R,T790M), EGFR(d746-750/T790M), EGFR(d746-750), EGFR(d747-749/A750P), EGFR(d747-752/P753S), EGFR(d752-759), FGFR1(V561M), FGFR2(N549H), FGFR3(G697C), FGFR3(K650E), FGFR3(K650M), FGFR4(N535K), FGFR4(V550E), FGFR4(V550L), FLT3 (D835Y), FLT3(ITD), JAK2 (V617F), LRRK2 (G2019S), LRRK2 (12020T), LRRK2 (R1441C), p38a(T106M), PDGFRa(D842V), PDGFRa(T674I), PDGFRa(V561D), RET (E762Q), RET(G691S), RET(M918T), RET(R749T), RET (R813Q), RET(V804L), RET(V804M), RET(Y791F), TIF2 (R849W), TIF2(Y897S), and TIF2(Y1108F).

In another aspect of the invention, the subject compounds may be administered in combination with one or more targeted anti-cancer agents that modulate non-kinase biological targets, pathway, or processes. Such targets pathways, or processes include but not limited to heat shock proteins (e.g. HSP90), poly-ADP (adenosine diphosphate)-ribose polymerase (PARP), hypoxia-inducible factors (HIF), proteasome, Wnt/Hedgehog/Notch signaling proteins, TNF-alpha, matrix metalloproteinase, farnesyl transferase, apoptosis pathway (e.g Bcl-xL, Bcl-2, Bcl-w), histone deacetylases (HDAC), histone acetyltransferases (HAT), and methyltransferase (e.g histone lysine methyltransferases, histone arginine methyltransferase, DNA methyltransferase, etc).

In another aspect of the invention, the compounds of the invention are administered in combination with one or more of other anti-cancer agents that include, but are not limited to, gene therapy, RNAi cancer therapy, chemoprotective agents (e.g., amfostine, mesna, and dexrazoxane), drug-antibody conjugate(e.g brentuximab vedotin, ibritumomab tioxetan), cancer immunotherapy such as Interleukin-2, cancer vaccines(e.g., sipuleucel-T) or monoclonal antibodies (e.g., Bevacizumab, Alemtuzumab, Rituximab, Trastuzumab, etc).

In another aspect of the invention, the subject compounds are administered in combination with radiation therapy or surgeries. Radiation is commonly delivered internally (implantation of radioactive material near cancer site) or externally from a machine that employs photon (x-ray or gamma-ray) or particle radiation. Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

In certain embodiments, the compounds of the invention are administered in combination with one or more of radiation therapy, surgery, or anti-cancer agents that include, but are not limited to, DNA damaging agents, antimetabolites, topoisomerase inhibitors, anti-microtubule agents, kinase inhibitors, epigenetic agents, HSP90 inhibitors, PARP inhibitors, BCL-2 inhibitor, drug-antibody conjugate, and antibodies targeting VEGF, HER2, EGFR, LD50, CD20, CD30, CD33, etc.

In certain embodiments, the compounds of the invention are administered in combination with one or more of abarelix, abiraterone acetate, aldesleukin, alemtuzumab, altretamine, anastrozole, asparaginase, bendamustine, bevacizumab, bexarotene, bicalutamide, bleomycin, bortezombi, brentuximab vedotin, busulfan, capecitabine, carboplatin, carmustine, cetuximab, chlorambucil, cisplatin, cladribine, clofarabine, clomifene, crizotinib, cyclophosphamide, dasatinib, daunorubicin liposomal, decitabine, degarelix, denileukin diftitox, denileukin diftitox, denosumab, docetaxel, doxorubicin, doxorubicin liposomal, epirubicin, eribulin mesylate, erlotinib, estramustine, etoposide phosphate, everolimus, exemestane, fludarabine, fluorouracil, fotemustine, fulvestrant, gefitinib, gemcitabine, gemtuzumab ozogamicin, goserelin acetate, histrelin acetate, hydroxyurea, ibritumomab tiuxetan, idarubicin, ifosfamide, imatinib mesylate, interferon alfa 2a, ipilimumab, ixabepilone, lapatinib ditosylate, lenalidomide, letrozole, leucovorin, leuprolide acetate, levamisole, lomustine, mechlorethamine, melphalan, methotrexate, mitomycin C, mitoxantrone, nelarabine, nilotinib, oxaliplatin, paclitaxel, paclitaxel protein-bound particle, pamidronate, panitumumab, pegaspargase, peginterferon alfa-2b, pemetrexed disodium, pentostatin, raloxifene, rituximab, sorafenib, streptozocin, sunitinib maleate, tamoxifen, temsirolimus, teniposide, thalidomide, toremifene, tositumomab, trastuzumab, tretinoin, uramustine, vandetanib, vemurafenib, vinorelbine, zoledronate, radiation therapy, or surgery.

In certain embodiments, the compounds of the invention are administered in combination with one or more anti-inflammatory agent. Anti-inflammatory agents include but are not limited to NSAIDs, non-specific and COX-2 specific cyclooxygenase enzyme inhibitors, gold compounds, corticosteroids, methotrexate, tumor necrosis factor receptor (TNF) receptors antagonists, immunosuppressants and methotrexate. Examples of NSAIDs include, but are not limited to, ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors such as celecoxib, valdecoxib, lumiracoxib and/or etoricoxib.

In some embodiments, the anti-inflammatory agent is a salicylate. Salicylates include by are not limited to acetylsalicylic acid or aspirin, sodium salicylate, and choline and magnesium salicylates. The anti-inflammatory agent may also be a corticosteroid. For example, the corticosteroid may be cortisone, dexamethasone, methylprednisolone, prednisolone, prednisolone sodium phosphate, or prednisone.

In additional embodiments the anti-inflammatory agent is a gold compound such as gold sodium thiomalate or auranofin.

The invention also includes embodiments in which the anti-inflammatory agent is a metabolic inhibitor such as a dihydrofolate reductase inhibitor, such as methotrexate or a dihydroorotate dehydrogenase inhibitor, such as leflunomide.

Other embodiments of the invention pertain to combinations in which at least one anti-inflammatory compound is an anti-05 monoclonal antibody (such as eculizumab or pexelizumab), a TNF antagonist, such as entanercept, or infliximab, which is an anti-TNF alpha monoclonal antibody.

In certain embodiments, the compounds of the invention are administered in combination with one or more immunosuppressant agents.

In some embodiments, the immunosuppressant agent is glucocorticoid, methotrexate, cyclophosphamide, azathioprine, mercaptopurine, leflunomide, cyclosporine, tacrolimus, and mycophenolate mofetil, dactinomycin, anthracyclines, mitomycin C, bleomycin, or mithramycin, or fingolimod.

The invention further provides methods for the prevention or treatment of a neoplastic disease, autoimmune and/or inflammatory disease. In one embodiment, the invention relates to a method of treating a neoplastic disease, autoimmune and/or inflammatory disease in a subject in need of treatment comprising administering to said subject a therapeutically effective amount of a compound of the invention. In one embodiment, the invention further provides for the use of a compound of the invention in the manufacture of a medicament for halting or decreasing a neoplastic disease, autoimmune and/or inflammatory disease.

In one embodiment, the neoplastic disease is a B-cell malignancy includes but not limited to B-cell lymphoma, lymphoma (including Hodgkin's lymphoma and non-Hodgkin's lymphoma), hairy cell lymphoma, small lymphocytic lymphoma (SLL), mantle cell lymphoma (MCL), and diffuse large B-cell lymphoma (DLBCL), multiple myeloma, chronic and acute myelogenous leukemia and chronic and acute lymphocytic leukemia.

The autoimmune and/or inflammatory diseases that can be affected using compounds and compositions according to the invention include, but are not limited to, allergy, Alzheimer's disease, acute disseminated encephalomyelitis, Addison's disease, ankylosing spondylitis, antiphospholipid antibody syndrome, asthma, atherosclerosis, autoimmune hemolytic anemia, autoimmune hemolytic and thrombocytopenic states, autoimmune hepatitis, autoimmune inner ear disease, bullous pemphigoid, coeliac disease, chagas disease, chronic obstructive pulmonary disease, chronic Idiopathic thrombocytopenic purpura (ITP), churg-strauss syndrome, Crohn's disease, dermatomyositis, diabetes mellitus type 1, endometriosis, Goodpasture's syndrome (and associated glomerulonephritis and pulmonary hemorrhage), graves' disease, guillain-barré syndrome, hashimoto's disease, hidradenitis suppurativa, idiopathic thrombocytopenic purpura, interstitial cystitis, irritable bowel syndrome, lupus erythematosus, morphea, multiple sclerosis, myasthenia gravis, narcolepsy, neuromyotonia, Parkinson's disease, pemphigus vulgaris, pernicious anaemia, polymyositis, primary biliary cirrhosis, psoriasis, psoriatic arthritis, rheumatoid arthritis, schizophrenia, septic shock, scleroderma, Sjogren's disease, systemic lupus erythematosus (and associated glomerulonephritis), temporal arteritis, tissue graft rejection and hyperacute rejection of transplanted organs, vasculitis (ANCA-associated and other vasculitides), vitiligo, and wegener's granulomatosis.

It should be understood that the invention is not limited to the particular embodiments shown and described herein, but that various changes and modifications may be made without departing from the spirit and scope of the invention as defined by the claims.

The compounds according to the present invention may be synthesized according to a variety of reaction schemes. Necessary starting materials may be obtained by standard procedures of organic chemistry. The compounds and processes of the present invention will be better understood in connection with the following representative synthetic schemes and examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims.

In scheme A, the reactant 5 can be prepared by the reaction of 3,5-dibromo-1-methylpyrazin-2(1H)-one with appropriate aniline. The nitro group in the reactant 5 can be other group such as a protected amine group, or —NHC(O)—Warhead.

The typical starting material

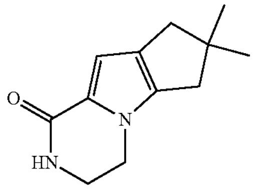

(CAS 1346674-23-4) is commercially available. However, the reported route, e.g. in WO 2013067274, to this intermediate entails at least 7 synthetic steps. The synthesis not only is long, it also includes several reagents and solvents that are toxic or hazardous and present environmental liabilities. We describe herein in Scheme I a new, more efficient, and cost-effective route (three synthetic steps) focused on the use of sustainable chemistry:

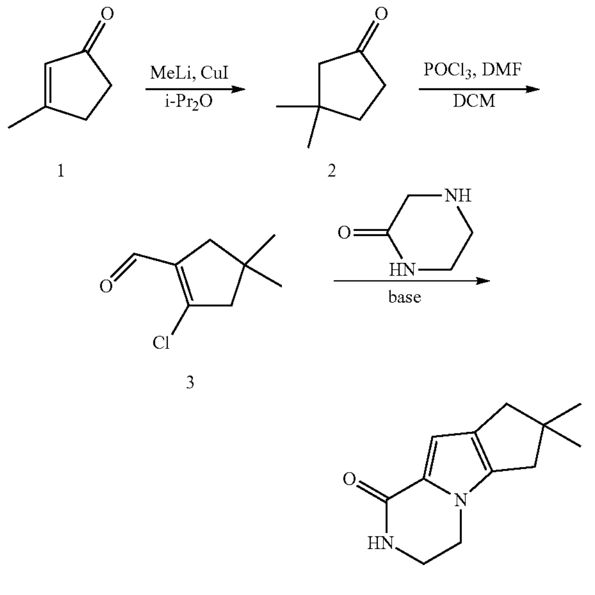

1

2

3

CAS 1346674-23-4

In Scheme I, the starting material 3-methylcyclopent-2-en-1-one was converted to 3,3-dimethylcyclopentan-1-one by standard organic reaction with high yield, which can further be converted to intermediate 3. Finally, intermediate 3 can react with piperazin-2-one to yield the target molecule of CAS 1346674-23-4.

The intermediate

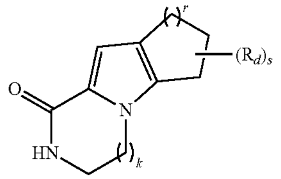

in which each of k, r, and s, independently, is 0, 1, 2, or 3, can be made by the method similar to Scheme I, by using different starting material and reagents.

The intermediate

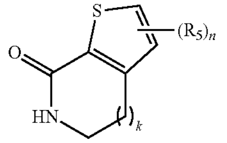

and

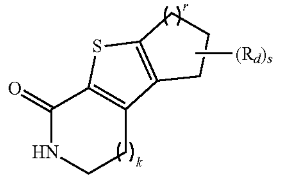

in which each of k, r, and s, independently, is 0, 1, 2, or 3, can be made by the method similar to those disclosure in the WO/2013/067260, WO/2013/067274, WO/2013/067277, WO/2015/000949.

The intermediate

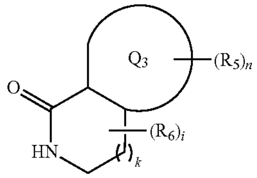

can be made by the method similar to Scheme I, by using different starting material and reagents, or by the standard organic reactions.

The intermediate

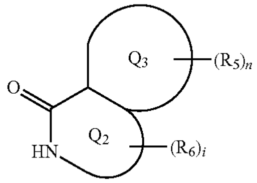

can be made by the method similar to Scheme 1 by using different starting material and reagents, or by the standard organic reactions.

The intermediate

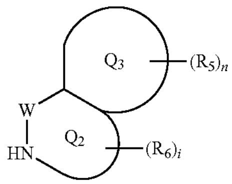

in which W is C(O) or S(O2) can be made by the method similar to Scheme 1 by using different starting material and reagents, or by the standard organic reactions.

The intermediate

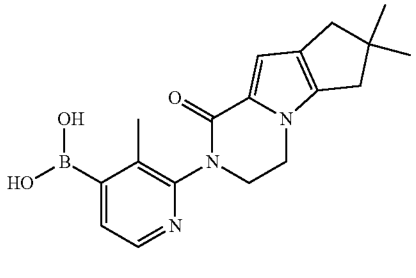 [SMILES: Cc1c(B(O)O)ccnc1N1CCn2c(cc3c2CC(C)(C)C3)C1=O]

can be made by the Scheme 1 described below.

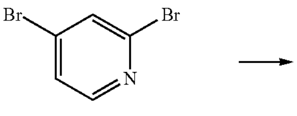

1-1

-continued

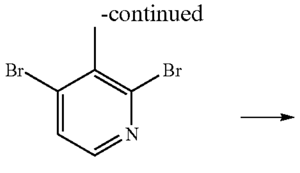

1-2

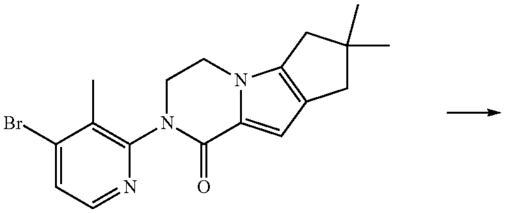

1-3

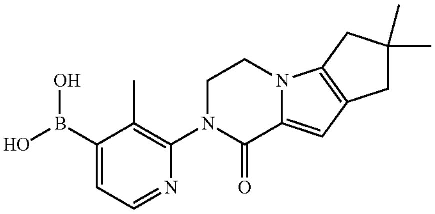

1-4

In Scheme 1, the starting material 2,4-dibromopyridine was converted to intermediate 1-2 by standard organic reaction with high yield, which can further react with 7,7-dimethyl-3,4,7,8-tetrahydro-2H-cyclopenta[4,5]pyrrolo[1,2-a]pyrazin-1(6H)-one (CAS 1346674-23-4) to afford the intermediate 1-3. Finally, 1-3 can be converted to target borate intermediate 1-4 by standard organic reaction.

The intermediate

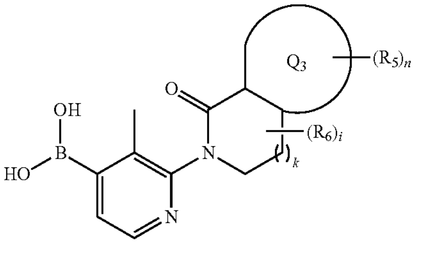

can be made by the method similar to Scheme 1, by using different starting material and reagents, or by the standard organic reactions.

The intermediate

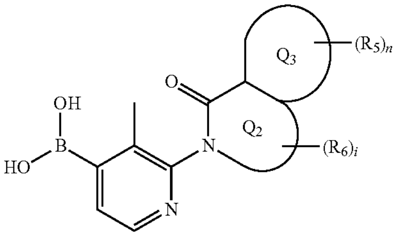

can be made by the method similar to Scheme 1 by using appropriate starting material and reagents, or by the standard organic reactions.

The intermediate

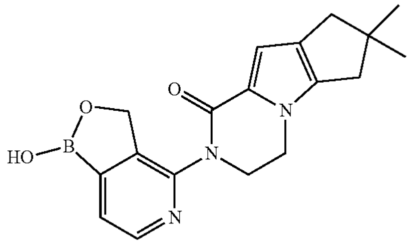 [SMILES: CC1(C)Cc2cc3n(c2C1)CCN(c1nccc2c1COB2O)C3=O]

can be made by the Scheme 2 described below.

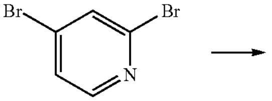

2-1

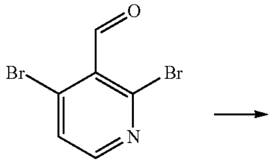

2-2

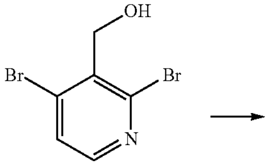

2-3

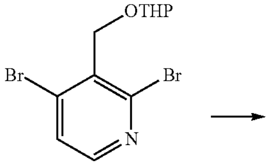

2-4

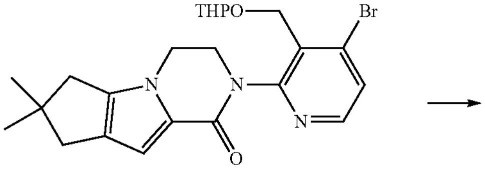

2-5

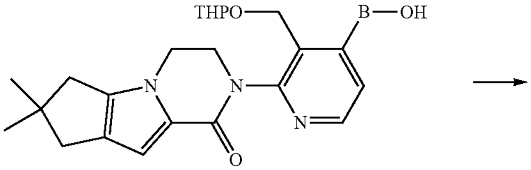

2-6

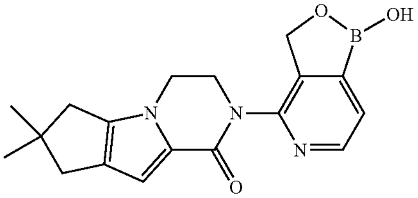

2-7

In Scheme 2, the starting material 2,4-dibromopyridine was converted to 2,4-dibromonicotinaldehyde by standard organic reaction with high yield, which can further be reduced to the alcohol intermediate 2-3. After that, the OH group of intermediate 2-3 can be protected by the THP to form the intermediate 2-4, which can react with 7,7-dimethyl-3,4,7,8-tetrahydro-2H-cyclopenta[4,5]pyrrolo[1,2-a]pyrazin-1(6H)-one (CAS 1346674-23-4) to afford the intermediate 2-5. Next, intermediate 2-5 can be converted to the intermediate 2-6, which can undergo a ring closure reaction to yield the intermediate 2-7.

The intermediate

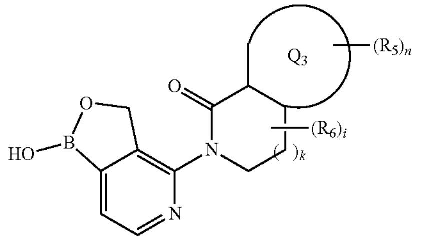

can be made by the method similar to Scheme 1, by using different starting material and reagents, or by the standard organic reactions.

The intermediate

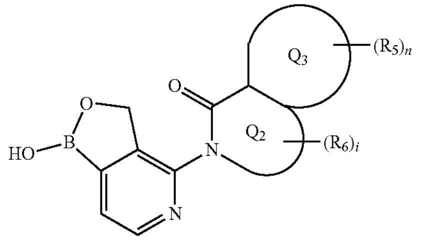

can be made by the method similar to Scheme 2 by using appropriate starting material and reagents, or by the standard organic reactions.

An improved approach to synthesize compounds of

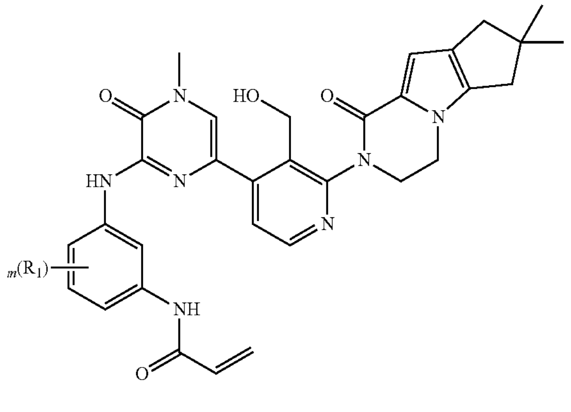

($R_3$ is —$CH_2OH$) is described in Scheme A. $R_1$, and m in general Scheme A are the same as those described in the Summary section above.

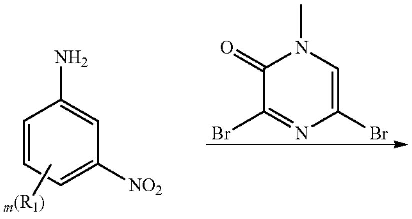

A-1

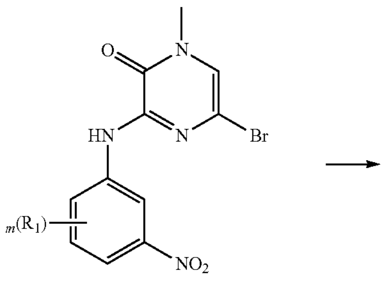

A-2

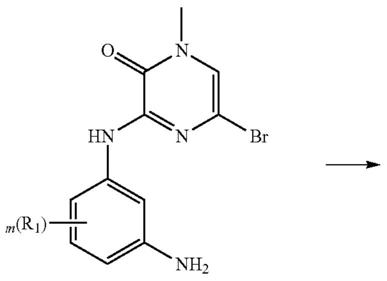

A-3

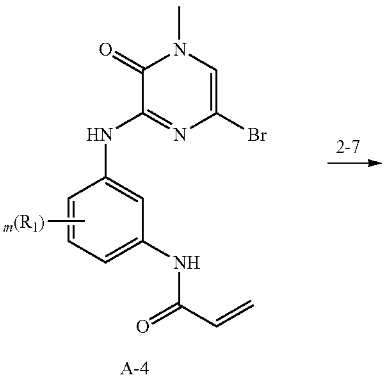

A-4

-continued

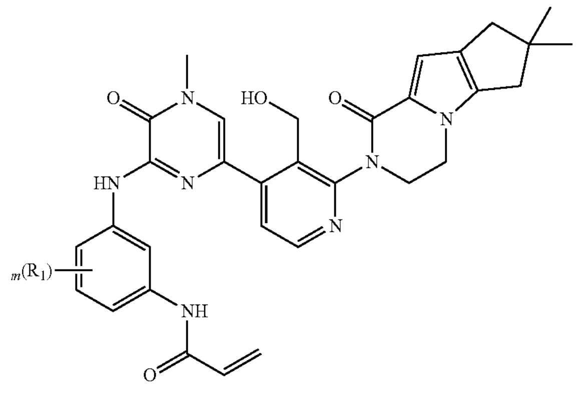

A-5

In Scheme A, the appropriate starting material 3-nitroaniline A-1 can react with 3,5-dibromo-1-methylpyrazin-2(1H)-one will yield the nitro intermediate A-2, which can be reduced to the amine intermediate A-3. A-3 can react appropriate acryloyl chloride to afford A-4 which can react with 2-7 to form the target compounds.

An improved approach to synthesize compounds of

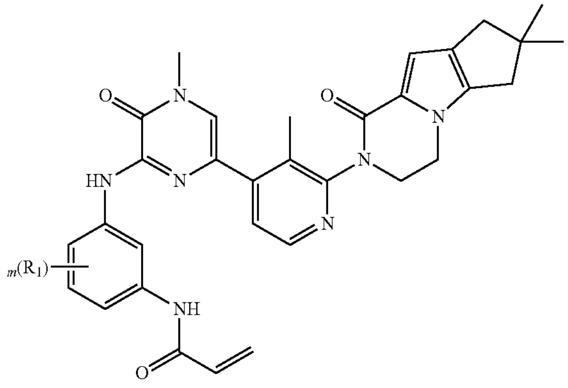

($R_3$ is —$CH_3$) is described in Scheme B. $R_1$, and m in general Scheme B are the same as those described in the Summary section above.

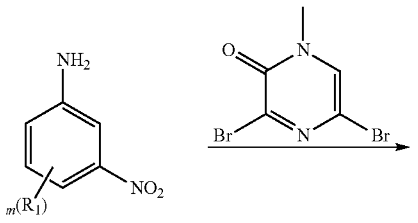

B-1

-continued

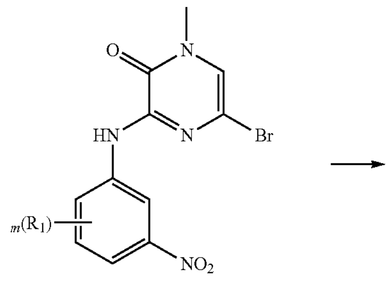

B-2

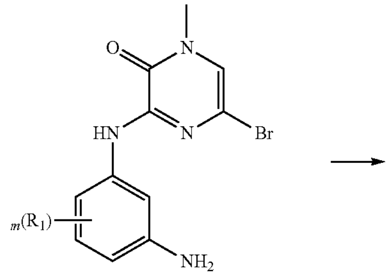

B-3

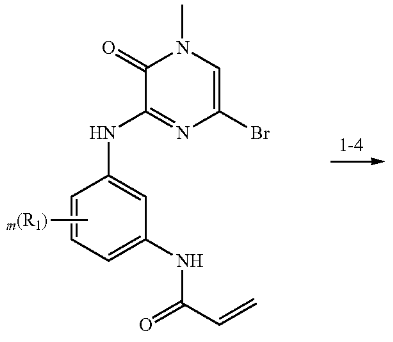

B-4

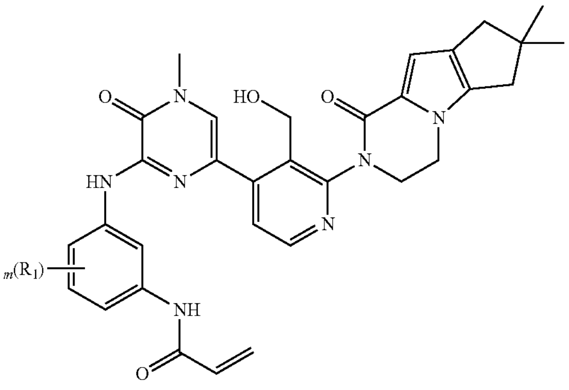

B-5

In Scheme B, the appropriate starting material 3-nitroaniline B-1 can react with 3,5-dibromo-1-methylpyrazin-2(1H)-one will yield the nitro intermediate B-2, which can be reduced to the amine intermediate B-3. B-3 can react appropriate acryloyl chloride to afford B-4 which can react with 1-4 to form the target compounds.

The Formula (IV) compounds

Formula (IV)

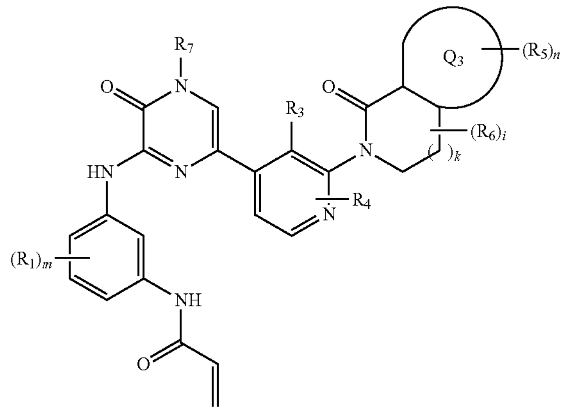

can be made by the method similar to Scheme A and B, by using different starting material, intermediates, and reagents.

The Formula (III) compounds

Formula (III)

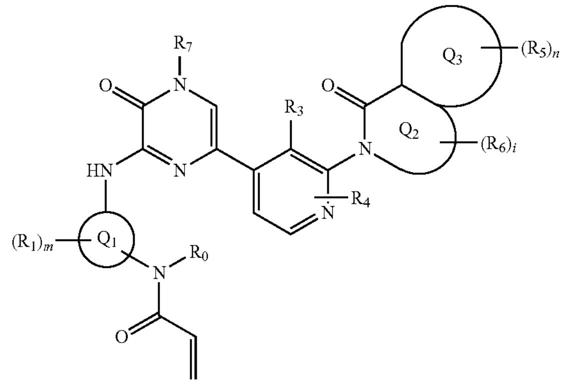

can be made by the method similar to Scheme A and B, by using different starting material, intermediates, and reagents.

The Formula (II) compounds

Formula (II)

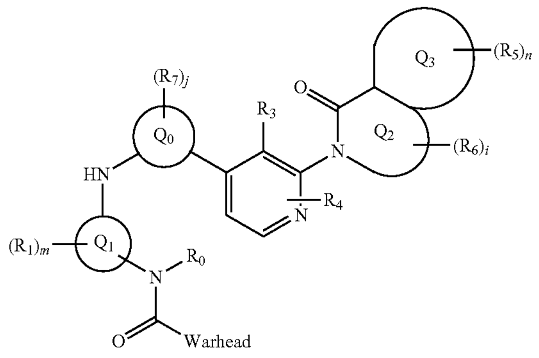

can be made by the method similar to Scheme A and B, by using different starting material, intermediates, and reagents.

The Formula (I) compounds

Formula (I)

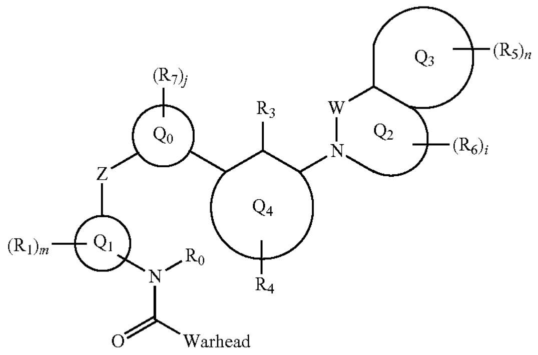

can be made by the method similar to Scheme A and B, by using different starting material, intermediates, and reagents.

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Where NMR data are presented, $^{1}H$ spectra were obtained on XL400 (400 MHz) and are reported as ppm down field from $Me_4Si$ with number of protons, multiplicities, and coupling constants in Hertz indicated parenthetically. Where HPLC data are presented, analyses were performed using an Agilent 1100 system. Where LC/MS data are presented, analyses were performed using an Applied Biosystems API-100 mass spectrometer and Shimadzu SCL-10A LC column:

Example 1: Preparation of 7,7-dimethyl-3,4,7,8-tetrahydro-2H-cyclopenta[4,5]pyrrolo[1,2-a]pyrazin-1(6H)-one Into a 1000-mL round-bottom flask purged and maintained with an inert atmosphere of nitrogen, was placed a solution of CuI (47.6 g, 249.93 mmol, 1.20 equiv) in ether (500 mL). To the solution was added MeLi (286 mL/2M, 2.20 equiv) at 0° C. and the mixture was stirred at the same temperature for 2 hours. To the solution was added 3-methylcyclopent-2-en-1-one (20 g, 208.06 mmol, 1.00 equiv) at the same temperature. The resulting solution was stirred for 2 h at 0° C. in a water/ice bath. The reaction was then quenched by the addition of 500 mL of $NH_4Cl$ (aq.), when TLC showed that SM have vanished (PE:EA=1:1). The resulting solution was extracted with 3×200 ml of ether and the organic layers combined and dried over anhydrous sodium sulfate and concentrated under vacuum. This resulted in 21 g (90%) of 3,3-dimethylcyclopentan-1-one as colorless oil.

Into a 500-mL round-bottom flask purged and maintained with an inert atmosphere of nitrogen, was placed a solution of N,N-dimethylformamide (41.6 g, 569.16 mmol, 3.00 equiv) in dichloromethane (200 mL). To the solution was added $POCl_3$ (57.3 g, 373.70 mmol, 2.00 equiv) at 0° C. and then the reaction mixture was stirred at room temperature for 1.5 hour. To the solution was added 3,3-dimethylcyclopentan-1-one (21.0 g, 187.22 mmol, 1.00 equiv) at the same temperature. The resulting solution was stirred overnight at 55° C. in an oil bath. The reaction was then quenched by the addition of 200 mL of aqueous NaAcO when TLC showed that the reaction have been finished (PE:EA=1:1). The resulting solution was extracted with 3×200 of dichloromethane and the organic layers combined and dried over anhydrous sodium sulfate and concentrated under vacuum. This resulted in 30 g (crude) of 2-chloro-4,4-dimethylcyclopent-1-ene-1-carbaldehyde as brown oil.

Into a 250-mL round-bottom flask purged and maintained with an inert atmosphere of nitrogen, was placed a solution of piperazin-2-one (18.7 g, 186.78 mmol, 1.00 equiv) and DIEA (24.2 g, 187.25 mmol, 1.00 equiv) in NMP (45 mL) and then to the solution was added 2-chloro-4,4-dimethylcyclopent-1-ene-1-carbaldehyde (29.7 g, 187.23 mmol, 1.00 equiv) at 100° C. dropwise. The resulting solution was stirred for 30 min at 100° C. in an oil bath. The reaction was then quenched by the addition of 200 mL of water when TLC showed that the reaction have been finished (EA). The solids were collected by filtration. This resulted in 20 g (52%) of 4,4-dimethyl-1,10-diazatricyclo[6.4.0.0^[2,6]]dodeca-2(6),7-dien-9-one as a off-white solid. LC-MS: (ES, m/z): 205[M+H]$^+$. $^1$H-NMR: (300 MHz, $d_6$-DMSO, ppm): δ7.38 (s, 1H), 6.36 (s, 1H), 3.92 (t, J=5.9 Hz, 2H), 3.45 (m, 2H), 2.50 (s, 2H), 2.38 (s, 2H), 1.19 (s, 6H).

Example 2: Preparation of N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(4-methylpiperazin-1-yl)phenyl)acrylamide A mixture of 4-fluoro-3-nitroaniline (100g, 0.64 mol), and N-methylpiperazine (256g, 2.56 mol) are dissolved in ethanol, The mixture was maintained at reflux for 24 h, and then the mixture was allowed to cool to room temperature, the reaction was concentrated in vacuum and filtered to give 4-(4-methylpiperazin-1-yl)-3-nitroaniline as a red solid (131g, 86%) 1H-NMR (300MHZ, $CDCl_3$) 7.11 (d, 1H), 7.02 (d, 1H), 6.807-6.845 (m, 1H), 3.76 (s, 2H), 2.98 (m, 4H), 2.557 (m, 4H), 2.35 (s, 3H).

A mixture of 4-(4-methylpiperazin-1-yl)-3-nitroaniline (14.53 g, 0.0615 mol), 3,5-dibromo-1-methylpyrazin-2(1H)-one (16.5 g, 0.0615 mol)cesium carbonate (40.1g, 0.123 mol), DMF (14 ml) and 1,4-dioxane(200 ml), after bubbling nitrogen through the resulting suspension for 30 min, Xantphons (3.5 g, 0.00615 mol) and tris(dibenzylideneacetone) dipalladium(O) (6.3g, 0.00615 mol) were added. And the reaction mixture was heated at 100° C. for 2 h, after this time, the mixture was cooled to room temperature and diluted with 90:10 methylene chloride/methanol(500 ml) and water (300 ml), and the layers were separated, the aqueous layers were extracted with 90:10 methylene chloride/methanol(500 ml), and the combined organic layers were washed with brine and dried over sodium sulfate. The drying agent was removed by filtration, the filtrate was concentrated under reduced pressure, and the resulting residue was purified by flash column chromatography (90:10 methylene chloride/methanol) to afford D (12 g, 46%) 1H-NMR (300MHZ, $CDCl_3$), 8.31 (d, 2H), 7.85 (m, 1H), 7.23 (d, 1H), 6.82 (s, 1H), 3.55 (s, 3H), 3.08 (m, 4H), 2.59 (m, 4H), 2.38 (s, 3H).

A mixture of the commerically available starting material 4-chloro-2-(7,7-dimethyl-1-oxo-1,3,4,6,7,8-hexahydro-2H-cyclopenta[4,5]pyrrolo[1,2-a]pyrazin-2-yl)nicotinaldehyde (CAS #1434050-55-1, 1.5 g, 4.37 mmol, 1.0 eq), $Pin_2B_2$ (2.8 g, 11 mmol, 2.5 eq), Pd(dppf)$Cl_2$ (356 mg, 0.44 mmol, 0.1 eq) and KOAc (1.3 g, 13 moral, 3.0 eq) in 1,4-dioxane (150 mL) was refluxed for 4h under $N_2$ atmosphere. The mixture was cooled to rt and filtered. The filtrate was concentrated to give (2-(7,7-dimethyl-1-oxo-1,3,4,6,7,8-hexahydro-2H-cyclopenta[4,5]pyrrolo[1,2-a]pyrazin-2-yl)-3-formylpyridin-4-yl)boronic acid (3.0 g) as brown oil which was used to the next step without further purification. ESI-MS (M+H)$^+$: 354.2.

A mixture of (2-(7,7-dimethyl-1-oxo-1,3,4,6,7,8-hexahydro-2H-cyclopenta[4,5]pyrrolo[1,2-a]pyrazin-2-yl)-3-formylpyridin-4-yl)boronic acid (crude from previous step, 4.37 mmol, 1.0 eq), 5-bromo-1-methyl-3-((4-(4-methylpiperazin-1-yl)-3-nitrophenyl)amino)pyrazin-2(1H)-one (Example 1, 900 mg, 2.2 mmol, 0.5 eq), Pd(dppf)$Cl_2$ (360 mg, 0.44 mmol, 0.1 eq) and $K_2CO_3$ (1.5 g, 13 moral, 3.0 eq) in dioxane (50 mL) and $H_2O$ (5 mL) was stirred at 90° C. for 4 h under $N_2$ atmosphere. The mixture was cooled to rt and concentrated and the residue was purified by column chromatography on silica gel (DCM:MeOH=30:1) to give 2-(7,7-dimethyl-1-oxo-1,3,4,6,7,8-hexahydro-2H-cyclopenta[4,5]pyrrolo[1,2-a]pyrazin-2-yl)-4-(4-methyl-6-((4-(4-methylpiperazin-1-yl)-3-nitrophenyl)amino)-5-oxo-4,5-dihydropyrazin-2-yl)nicotinaldehyde as brown solid (600 mg, two step Y: 40%). ESI-MS (M+H)$^+$: 652.1.

A mixture of 2-(7,7-dimethyl-1-oxo-1,3,4,6,7,8-hexahydro-2H-cyclopenta[4,5]pyrrolo[1,2-a]pyrazin-2-yl)-4-(4-methyl-6-((4-(4-methylpiperazin-1-yl)-3-nitrophenyl)amino)-5-oxo-4,5-dihydropyrazin-2-yl)nicotinaldehyde (600 mg, 0.92 mmol, 1.0 eq) and Pd/C (120 mg, 20% wt) in MeOH (20 mL) was hydrogenated at rt for 16 h under one atmosphere of $H_2$ pressure. The catalyst was filtered off through a Celite pad and the filtrate was concentrated to give 4-(6-((3-amino-4-(4-methylpiperazin-1-yl)phenyl)amino)-4-methyl-5-oxo-4,5-dihydropyrazin-2-yl)-2-(7,7-dimethyl-1-oxo-1,3,4,6,7,8-hexahydro-2H-cyclopenta[4,5]pyrrolo[1,2-a]pyrazin-2-yl)nicotinaldehyde as brown solid (600 mg). ESI-MS (M+H)$^+$: 622.1.

To a solution of 4-(6-((3-amino-4-(4-methylpiperazin-1-yl)phenyl)amino)-4-methyl-5-oxo-4,5-dihydropyrazin-2-yl)-2-(7,7-dimethyl-1-oxo-1,3,4,6,7,8-hexahydro-2H-cyclopenta[4,5]pyrrolo[1,2-a]pyrazin-2-yl)nicotinaldehyde (crude from previous step, 0.92 mmol, 1.0 eq) in MeOH (10 mL) was added a solution of $NaBH_4$ (70 mg, 1.8 mmol, 2.0 eq) in MeOH (10 mL) at 0° C. The solution was stirred at rt for 16 h. Concentrated and the residue was purified by Pre-HPLC (A: $H_2O$, 0.05% $NH_3 \cdot H_2O$, B: MeCN) to give 2-(4-(6-((3-amino-4-(4-methylpiperazin-1-yl)phenyl)amino)-4-methyl-5-oxo-4,5-dihydropyrazin-2-yl)-3-(hydroxymethyl)pyridin-2-yl)-7,7-dimethyl-3,4,7,8-tetrahydro-2H-cyclopenta[4,5]pyrrolo[1,2-a]pyrazin-1(6H)-one as a brown solid (150 mg, two step Y: 56%). ESI-MS (M+H)$^+$: 624.1

To a mixture of 2-(4-(6-((3-amino-4-(4-methylpiperazin-1-yl)phenyl)amino)-4-methyl-5-oxo-4,5-dihydropyrazin-2-yl)-3-(hydroxymethyl)pyridin-2-yl)-7,7-dimethyl-3,4,7,8-tetrahydro-2H-cyclopenta[4,5]pyrrolo[1,2-a]pyrazin-1(6H)-one (150 mg, 0.24 mmol, 1.0 eq), acrylic acid (26 mg, 0.36 mmol, 1.5 eq) and HATU (123 mg, 0.36 mmol, 1.5 eq) in DMF (5 mL) was added TEA (73 mg, 0.72 mmol, 3.0 eq). The mixture was stirred for 4 h at rt. The reaction mixture was purified by Pre-HPLC (A: $H_2O$, 0.05% $NH_3 \cdot H_2O$; B: MeCN) to give N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(4-methylpiperazin-1-yl) phenyl)acrylamide as a brown solid (38 mg, Y: 23%). ESI-MS $(M+H)^+$: 678.1. $^1H$ NMR (400 MHz, DMSO-$d_6$) δ: 9.24 (s, 1H), 9.06 (s, 1H), 8.88 (s, 1H), 8.46 (d, J=5.2 Hz, 1H), 7.88 (d, J=4.8 Hz, 1H), 7.75 (s, 1H), 7.63 (dd, J=2.0 Hz, 4.4 Hz, 1H), 7.12 (d, J=8.4 Hz, 1H), 6.66-6.56 (m, 1H), 6.57 (s, 1H), 6.33-6.28 (m, 1H), 5.79-5.76 (m, 1H), 5.04 (br s, 1H), 4.60-4.46 (m, 2H), 4.26-4.18 (m, 3H), 3.86-3.83 (m, 1H), 3.55 (s, 3H), 2.79-2.75 (m, 4H), 2.67-2.57 (m, 6H), 2.43 (s, 2H), 2.24 (s, 3H), 1.22 (s, 6H), Example 3: Preparation of (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(2-methyl-4-(oxetan-3-yl)piperazin-1-yl)phenyl)acrylamide Into a 1000-mL round-bottom flask purged and maintained with an inert atmosphere of nitrogen, was placed 4-fluoro-3-nitroaniline (50 g, 320.28 mmol, 1.00 equiv), $CH_3CN$ (500 mL), NMM (64.7 g, 639.64 mmol, 2.00 equiv), Cbz-Cl (87.4 g, 512.34 mmol, 1.60 equiv). The resulting solution was stirred overnight at room temperature. The resulting mixture was concentrated under vacuum. The residue was applied onto a silica gel column with ethyl acetate/petroleum ether (1:1). This resulted in 45 g (48%) of benzyl N-(4-fluoro-3-nitrophenyl)carbamate as a yellow solid. LC-MS: (ES, m/z): $[M+H]^+$=291, $^1H$-NMR: (300 MHz, $CDCl_3$, ppm): δ8.15 (m, 1H), 7.65 (m, 1H), 7.42-7.32 (m, 5H), 7.22 (m, 1H), 6.80 (s, 2H), 5.22 (s, 2H).

Into a 250-mL round-bottom flask purged and maintained with an inert atmosphere of nitrogen, was placed a solution of benzyl N-(4-fluoro-3-nitrophenyl)carbamate (10 g, 34.45 mmol, 1.00 equiv) in DMSO (100 mL), tert-butyl (3S)-3-methylpiperazine-1-carboxylate (7.58 g, 37.85 mmol), DIEA (6.67 g, 51.61 mmol, 1.50 equiv). The resulting solution was stirred overnight at 110° C. in an oil bath. The resulting solution was diluted with of water. The resulting solution was extracted with of ethyl acetate and the organic layers combined and concentrated under vacuum. The residue was applied onto a silica gel column with ethyl acetate/petroleum ether (1:1). This resulted in 10 g (62%) of tert-butyl (3S)-4-(4-[[(benzyloxy)carbonyl]amino]-2-nitrophenyl)-3-methylpiperazine-1-carboxylate as brown oil. LC-MS: (ES, m/z): $[M+H]^+$=471. $^1H$-NMR: (300 MHz, $CDCl_3$, ppm): δ7.86 (s, 1H), 7.60 (m, 1H), 7.44-7.31 (m, 7H), 5.21 (s, 2H), 3.90 (t, J=11.4 Hz, 2H), 3.21-3.02 (m, 3H), 2.79-2.72 (m, 2H), 1.49 (s, 9H), 0.80 (d, J=6.3 Hz, 3H).

Into a 250-mL round-bottom flask purged and maintained with an inert atmosphere of nitrogen, was placed a solution of tert-butyl (3S)-4-(4-[[(benzyloxy)carbonyl]amino]-2-nitrophenyl)-3-methylpiperazine-1-carboxylate (12.5 g, 26.57 mmol, 1.00 equiv) in dioxane (100 mL), hydrogen chloride dioxane (25 mL). The resulting solution was stirred for 30 min at room temperature. The resulting mixture was concentrated under vacuum. This resulted in 12.5 g (crude) of benzyl N-[4-[(2S)-2-methylpiperazin-1-yl]-3-nitrophenyl] carbamate as brown oil. LC-MS: (ES, m/z): 371 $[M+H]^+$.

Into a 250-mL round-bottom flask purged and maintained with an inert atmosphere of nitrogen, was placed a solution of benzyl N-[4-[(2S)-2-methylpiperazin-1-yl]-3-nitrophenyl]carbamate (12.5 g, 33.75 mmol, 1.00 equiv) in ethanol (100 ml), oxetan-3-one (2.2 g, 30.53 mmol, 1.20 equiv), $NaBH_3CN$ (1.67 g, 26.58 mmol, 1.00 equiv). The resulting solution was stirred for 2 h at room temperature. The resulting mixture was concentrated under vacuum. The residue was applied onto a silica gel column with ethyl acetate/petroleum ether (1:1). This resulted in 5 g (35%) of benzyl N-[4-[(2S)-2-methyl-4-(oxetan-3-yl)piperazin-1-yl]-3-nitrophenyl]carbamate as brown oil. LC-MS: (ES, m/z): $427[M+H]^+$. $^1H$-NMR (300 MHz, $CD_3OD$, ppm): δ7.86 (s, 1H), 7.60 (m, 1H), 7.48-7.31 (m, 6H), 5.21 (s, 2H), 4.75-4.55 (m, 5H), 3.55 (m, 1H), 3.26-3.10 (m, 2H), 2.97-2.72 (m, 3H), 2.30-2.11 (m, 3H), 1.80 (t, J=4.7 Hz, 1H), 1.49 (s, 9H), 0.80 (d, J=6.3 Hz, 3H).

Into a 100-mL round-bottom flask purged and maintained with an inert atmosphere of nitrogen, was placed a solution of benzyl N-[4-[(2S)-2-methyl-4-(oxetan-3-yl)piperazin-1-yl]-3-nitrophenyl]carbamate (5.0 g, 11.72 mmol, 1.00 equiv) in ethanol (50 ml), AcOH (7.0 g, 116.57 mmol, 10.00 equiv). This was followed by the addition of dust Zn (4.6 g, 6.00 equiv). The resulting solution was stirred for 1 h at room temperature. The solids were filtrated out. The resulting mixture was concentrated under vacuum and applied on a silica gel column. This resulted in 1.0 g (22%) of benzyl N-[3-amino-4-[(2S)-2-methyl-4-(oxetan-3-yl)piperazin-1-yl]phenyl]carbamate as brown oil. LC-MS: (ES, m/z): 397 $[M+H]^+$. $^1H$-NMR (300 MHz, $CD_3OD$, ppm): δ7.46-7.31 (m, 5H), 7.02 (m, 2H), 6.75 (d, J=8.4, 1H), 5.20 (s, 2H), 4.85-4.64 (m, 4H), 3.67-3.55 (m, 3H), 3.17 (m, 1H), 2.92-2.78 (m, 4H), 2.25 (m, 1H), 1.95 (m, 1H), 0.80 (d, J=6.0 Hz, 3H).

Into a 25-mL round-bottom flask purged and maintained with an inert atmosphere of nitrogen, was placed a solution of benzyl N-[3-amino-4-[(2S)-2-methyl-4-(oxetan-3-yl)piperazin-1-yl]phenyl]carbamate (1.0 g, 2.52 mmol, 1.00 equiv) in tetrahydrofuran (10 mL), NMM (510 mg, 5.04 mmol, 2.00 equiv), $(Boc)_2O$ (820 mg, 3.76 mmol, 1.50 equiv). The resulting solution was stirred overnight at room temperature. The resulting mixture was concentrated under vacuum. The residue was applied onto a silica gel column with ethyl acetate/petroleum ether (1:1). This resulted in 0.9 g (72%) of benzyl N-(3-[[(tert-butoxy)carbonyl]amino]-4-[(2S)-2-methyl-4-(oxetan-3-yl)piperazin-1-yl]phenyl)carbamate as brown oil. LC-MS: (ES, m/z): $497[M+H]^+$ Into a 50-mL round-bottom flask purged and maintained with an inert atmosphere of $H_2$, was placed a solution of benzyl N-(3-[[(tert-butoxy)carbonyl]amino]-4-[(2S)-2-methyl-4-(oxetan-3-yl)piperazin-1-yl]phenyl)carbamate (900 mg, 1.81 mmol, 1.00 equiv) in methanol (10 mL), Palladium carbon (0.1 g, 0.10 equiv). The resulting solution was stirred for 1 h at room temperature. The solids were filtered out. The resulting mixture was concentrated under vacuum. This resulted in 0.6 g (91%) of tert-butyl N-[5-amino-2-[(2S)-2-methyl-4-(oxetan-3-yl)piperazin-1-yl]phenyl]carbamate as brown oil. LC-MS: (ES, m/z): 363 $[M+H]^-$ $_1$H-NMR-PH—: (300 MHz, $CD_3OD$, ppm): δ7.46-7.31 (m, 5H), 7.02 (m, 2H), 6.75 (d, J=8.4, 1H), 4.78-4.64 (m, 4H), 3.60 (m, 1H), 3.10-2.70 (m, 5H), 2.22 (m, 1H), 1.95 (m, 1H), 0.77 (d, J=6.0 Hz, 3H).

Into a 50-mL round-bottom flask purged and maintained with an inert atmosphere of nitrogen, was placed a solution of tert-butyl N-[5-amino-2-[(2S)-2-methyl-4-(oxetan-3-yl) piperazin-1-yl]phenyl]carbamate (1.2 g, 3.31 mmol, 1.00 equiv) in IPA (10 mL), 3,5-dibromo-1-methyl-1,2-dihydropyrazin-2-one (980 mg, 3.66 mmol, 1.00 equiv), DIEA (640 mg, 4.95 mmol, 1.50 equiv). The resulting solution was stirred overnight at 80° C. in an oil bath. The resulting mixture was concentrated under vacuum. The residue was applied onto a silica gel column with ethyl acetate/petroleum ether (1:1). This resulted in 1.2 g (66%) of tert-butyl N-[5-[(6-bromo-4-methyl-3-oxo-3,4-dihydropyrazin-2-yl) amino]-2-[(2S)-2-methyl-4-(oxetan-3-yl)piperazin-1-yl]

phenyl]carbamate as brown oil. LC-MS: (ES, m/z): 551 $[M+H]^+$ $^1$H-NMR: (300 MHz, $CDCl_3$, ppm): δ8.31 (s, 1H), 8.20 (s, 1H), 7.99 (s, 1H), 7.20 (d, J=8.7, 1H), 6.95 (d, J=8.7, 1H), 6.75 (s, 1H), 4.78-4.64 (m, 5H), 3.60 (m, 1H), 3.20-2.72 (m, 7H), 2.22 (m, 1H), 1.95 (m, 1H), 0.79 (d, J=6.0 Hz, 3H).

Into a 50-mL round-bottom flask purged and maintained with an inert atmosphere of nitrogen, was placed a solution of tert-butyl N-[5-[(6-bromo-4-methyl-3-oxo-3,4-dihydropyrazin-2-yl)amino]-2-[(2S)-2-methyl-4-(oxetan-3-yl)piperazin-1-yl]phenyl]carbamate (600 mg, 1.09 mmol, 1.00 equiv) in dichloromethane (6 ml), trifluoroacetic acid (1.2 mL). The resulting solution was stirred for 1 h at room temperature. The resulting mixture was concentrated under vacuum. This resulted in 500 mg (crude) of 3-([3-amino-4-[(2S)-2-methyl-4-(oxetan-3-yl)piperazin-1-yl]phenyl]amino)-5-bromo-1-methyl-1,2-dihydropyrazin-2-one as brown oil. LC-MS: (ES, m/z): 451 $[M+H]^+$.

Into a 25-mL round-bottom flask purged and maintained with an inert atmosphere of nitrogen, was placed a solution of 3-([3-amino-4-[(2S)-2-methyl-4-(oxetan-3-yl)piperazin-1-yl]phenyl]amino)-5-bromo-1-methyl-1,2-dihydropyrazin-2-one (500 mg, 1.11 mmol, 1.00 equiv) in dioxane (15 mL)/$H_2O$ (1 mL), (2-[4,4-dimethyl-9-oxo-1,10-diazatricyclo[6.4.0.0^[2,6]]dodeca-2(6),7-dien-10-yl]-3-[(oxan-2-yloxy)methyl]pyridin-4-yl)boronic acid (431 mg, 0.98 mmol, 1.10 equiv), Pd(dppf)$Cl_2$ (50 mg, 0.07 mmol, 0.10 equiv), potassium carbonate (307 mg, 2.22 mmol, 2.00 equiv). The resulting solution was stirred for 1 h at 100° C. in an oil bath. The resulting mixture was concentrated under vacuum, dilute with $H_2O$ and extract With EA. This resulted in 500 mg (59%) of 10-[4-[6-([3-amino-4-[(2S)-2-methyl-4-(oxetan-3-yl)piperazin-1-yl]phenyl]amino)-4-methyl-5-oxo-4,5-dihydropyrazin-2-yl]-3-[(oxan-2-yloxy)methyl]pyridin-2-yl]-4,4-dimethyl-1,10-diazatricyclo[6.4.0.0^[2,6]]dodeca-2(6),7-dien-9-one(crude) as brown oil. LC-MS: (ES, m/z):764 $[M+H]^+$.

Into a 50-mL round-bottom flask purged and maintained with an inert atmosphere of nitrogen, was placed a solution of 10-[4-[6-([3-amino-4-[(2S)-2-methyl-4-(oxetan-3-yl)piperazin-1-yl]phenyl]amino)-4-methyl-5-oxo-4,5-dihydropyrazin-2-yl]-3-[(oxan-2-yloxy)methyl]pyridin-2-yl]-4,4-dimethyl-1,10-diazatricyclo[6.4.0.0^[2,6]]dodeca-2(6),7-dien-9-one (500 mg, 0.65 mmol, 1.00 equiv) in dichloromethane (5 mL), trifluoroacetic acid (1 mL). The resulting solution was stirred for 15 min at 40° C. in an oil bath. The resulting mixture was concentrated under vacuum. The crude product was purified by Prep-HPLC. This resulted in 80 mg (18%) of 10-[4-[6-([3-amino-4-[(2S)-2-methyl-4-(oxetan-3-yl)piperazin-1-yl]phenyl]amino)-4-methyl-5-oxo-4,5-dihydropyrazin-2-yl]-3-(hydroxymethyl)pyridin-2-yl]-4,4-dimethyl-1,10-diazatricyclo[6.4.0.0^[2,6]]dodeca-2(6),7-dien-9-one as a brown solid. LC-MS: (ES, m/z): 680$[M+H]^+$.

Into a 25-mL round-bottom flask purged and maintained with an inert atmosphere of nitrogen, was placed a solution of 10-[4-[6-([3-amino-4-[(2S)-2-methyl-4-(oxetan-3-yl)piperazin-1-yl]phenyl]amino)-4-methyl-5-oxo-4,5-dihydropyrazin-2-yl]-3-(hydroxymethyl)pyridin-2-yl]-4,4-dimethyl-1,10-diazatricyclo[6.4.0.0^[2,6]]dodeca-2(6),7-dien-9-one (80 mg, 0.12 mmol, 1.00 equiv) in $CH_3CN$ (1 mL), prop-2-enoic acid (10 mg, 0.14 mmol, 1.20 equiv), HATU (49.2 mg, 0.13 mmol, 1.10 equiv), NMM (17.7 mg, 0.17 mmol, 1.50 equiv). The resulting solution was stirred for 1 h at room temperature. The crude product was purified by Prep-HPLC. This resulted in 27 mg (31%) of N-(5-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxo-3,4-dihydropyrazin-2-yl]amino]-2-[(2S)-2-methyl-4-(oxetan-3-yl)piperazin-1-yl]phenyl)prop-2-enamide as a off-white solid. LC-MS: (ES, m/z): 734$[M+H]^+$. $^1$H-NMR: (300 MHz, $d_6$-DMSO, ppm): δ9.25 (s, 1H), 9.19 (s, 1H), 9.11 (s, 1H), 8.49 (d, J=5.1 Hz, 1H), 7.95 (d, J=5.1 Hz, 1H), 7.77 (s, 1H), 7.60 (d, J=8.7, 1H), 7.25 (d, J=8.7, 1H), 6.63-6.57 (m, 2H), 6.30 (m, 1H), 5.80 (d, J=3.9 Hz, 1H), 5.02 (m, 1H), 4.65-4.41 (m, 6H), 4.35-4.15 (m, 3H), 3.85 (m, 1H), 3.60-3.43 (m, 4H), 3.10 (m, 1H), 2.85-2.54 (m, 6H), 2.45 (m, 2H), 2.22 (m, 1H), 1.95 (t, J=6.6 Hz, 1H), 1.25 (s, 6H), 0.76 (d, J=6.0 Hz, 3H).

Example 4: Preparation of (S)—N-(5-((6-(3-(7,7-dimethyl-1-oxo-1,3,4,6,7,8-hexahydro-2H-cyclopenta[4,5]pyrrolo[1,2-a]pyrazin-2-yl)-2-(hydroxymethyl)phenyl)-4-methyl-3-oxo-3,4-dihydropyrazin-2-yl)amino)-2-(2-methyl-4-(oxetan-3-yl)piperazin-1-yl)phenyl)acrylamide Into a 50-mL round-bottom flask purged and maintained with an inert atmosphere of nitrogen, was placed a solution of 4,4-dimethyl-1,10-diazatricyclo[6.4.0.0^[2,6]]dodeca-2(6),7-dien-9-one (3.0 g, 14.69 mmol, 1.00 equiv) in dioxane (30 mL), 2,6-dibromobenzaldehyde (4.65 g, 17.62 mmol, 1.20 equiv), $Cs_2CO_3$ (9.6 g, 29.46 mmol, 2.00 equiv), $Pd_2(dba)_3$ (300 mg, 0.33 mmol, 0.10 equiv), Xantphos (300 mg, 0.52 mmol, 0.10 equiv). The resulting solution was stirred for 1 h at 100° C. in an oil bath. The reaction mixture was cooled to RT. The solids were filtered out. The resulting mixture was concentrated under vacuum. The residue was applied onto a silica gel column with ethyl acetate/petroleum ether (1:1). This resulted in 4.0 g (70%) of 2-bromo-6-[4,4-dimethyl-9-oxo-1,10-diazatricyclo[6.4.0.0^[2,6]]dodeca-2(6),7-dien-10-yl]benzaldehyde as a off-white solid. (ES, m/z):387$[M+H]^+$. $^1$H-NMR: (300 MHz, $CD_3OD$, ppm): δ10.36 (s, 1H), 7.43 (d, J=7.8 Hz, 1H), 7.25 (m, 2H), 6.60 (s, 1H), 3.99 (t, J=6.0 Hz, 2H), 3.63 (t, J=6.0 Hz, 3H), 2.55 (s, 2H), 2.45 (s, 2H), 1.24 (s, 6H).

Into a 50-mL round-bottom flask purged and maintained with an inert atmosphere of nitrogen, was placed a solution of 2-bromo-6-[4,4-dimethyl-9-oxo-1,10-diazatricyclo[6.4.0.0^[2,6]]dodeca-2(6),7-dien-10-yl]benzaldehyde (1.0 g, 2.58 mmol, 1.00 equiv) in dioxane (10 mL), $Pin_2B_2$ (1.64 g, 2.50 equiv), Pd(dppf)$Cl_2$ (100 mg, 0.14 mmol, 0.10 equiv), KOAc (760 mg, 7.74 mmol, 3.00 equiv). The resulting solution was stirred for 30 min at 100° C. in an oil bath. The reaction mixture was cooled to RT. The solids were filtered out. The resulting mixture was concentrated under vacuum. This resulted in 400 mg (44%) of (3-[4,4-dimethyl-9-oxo-1,10-diazatricyclo[6.4.0.0^[2,6]]dodeca-2(6),7-dien-10-yl]-2-formylphenyl)boronic acid as a brown solid. LC-MS: (ES, m/z): 353$[M+H]^+$ Into a 50-mL round-bottom flask purged and maintained with an inert atmosphere of nitrogen, was placed (3-[4,4-dimethyl-9-oxo-1,10-diazatricyclo[6.4.0.0^[2,6]]dodeca-2(6),7-dien-10-yl]-2-formylphenyl)boronic acid (346 mg, 0.98 mmol, 1.00 equiv) a solution of 3-([3-amino-4-[(2S)-2-methyl-4-(oxetan-3-yl)piperazin-1-yl]phenyl]amino)-5-bromo-1-methyl-1,2-dihydropyrazin-2-one (441 mg, 0.98 mmol, 1.00 equiv) in dioxane (10 mL)/$H_2O$ (1 mL), Pd(dppf)$Cl_2$ (30 mg, 0.04 mmol, 0.10 equiv), potassium carbonate (271 mg, 1.96 mmol, 2.00 equiv). The resulting solution was stirred for 1 h at 100° C. in an oil bath. The solids were filtered out. The resulting mixture was concentrated under vacuum. This resulted in 500 mg (75%) of 2-[6-([3-amino-4-[(2S)-2-methyl-4-(oxetan-3-yl)piperazin-1-yl]phenyl]amino)-4-methyl-5-oxo-4,5-dihydropyrazin-2- yl]-6-[4,4-dimethyl-9-oxo-1,10-diazatricyclo[6.4.0.0^[2,6]]dodeca-2(6),7-dien-10-yl]benzaldehyde as brown oil. LC-MS: (ES, m/z): 677[M+H]$^+$ Into a 25-mL round-bottom flask purged and maintained with an inert atmosphere of nitrogen was placed a solution of 2-[6-([3-amino-4-[(2S)-2-methyl-4-(oxetan-3-yl)piperazin-1-yl]phenyl]amino)-4-methyl-5-oxo-4,5-dihydropyrazin-2-yl]-6-[4,4-dimethyl-9-oxo-1,10-diazatricyclo[6.4.0.0^[2,6]]dodeca-2(6),7-dien-10-yl]benzaldehyde (500 mg, 0.74 mmol, 1.00 equiv) in ethanol (10 mL), $NaBH_4$ (16.8 mg, 0.44 mmol, 0.60 equiv). The resulting solution was stirred for 30 min at room temperature. The resulting mixture was concentrated under vacuum. The crude product was purified by Prep-HPLC. This resulted in 240 mg (48%) of 10-[3-[6-([3-amino-4-[(2S)-2-methyl-4-(oxetan-3-yl)piperazin-1-yl]phenyl]amino)-4-methyl-5-oxo-4,5-dihydropyrazin-2-yl]-2-(hydroxymethyl)phenyl]-4,4-dimethyl-1,10-diazatricyclo[6.4.0.0^[2,6]]dodeca-2(6),7-dien-9-one as a light brown solid. LC-MS: (ES, m/z): 679 [M+1-1]$^+$.

Into a 10-mL round-bottom flask purged and maintained with an inert atmosphere of nitrogen, was placed a solution of 10-[3-[6-([3-amino-4-[(2S)-2-methyl-4-(oxetan-3-yl)piperazin-1-yl]phenyl]amino)-4-methyl-5-oxo-4,5-dihydropyrazin-2-yl]-2-(hydroxymethyl)phenyl]-4,4-dimethyl-1,10-diazatricyclo[6.4.0.0^[2,6]]dodeca-2(6),7-dien-9-one (240 mg, 0.35 mmol, 1.00 equiv) in $CH_3CN$ (10 mL), prop-2-enoic acid (30.5 mg, 0.42 mmol, 1.20 equiv), HATU (147.7 mg, 0.39 mmol, 1.10 equiv), NMM (71.4 mg, 0.71 mmol, 2.00 equiv). The resulting solution was stirred for 1 h at room temperature. The crude product was purified by Prep-HPLC. This resulted in 60 mg (23%) of N-(5-[[6-(3-[4,4-dimethyl-9-oxo-1,10-diazatricyclo[6.4.0.0^[2,6]]dodeca-2(6),7-dien-10-yl]-2-(hydroxymethyl)phenyl)-4-methyl-3-oxo-3,4-dihydropyrazin-2-yl]amino]-2-[(2S)-2-methyl-4-(oxetan-3-yl)piperazin-1-yl]phenyl)prop-2-enamide as a off-white solid. LC-MS: (ES, m/z): 733[M+1-1]$^+$. $^1$H-NMR: (300 MHz, $d_6$-DMSO, ppm): δ9.17 (m, 2H), 8.91 (s, 1H), 7.82-7.63 (m, 2H), 7.49-7.42 (m, 2H), 7.40-7.23 (m, 2H), 6.67-6.49 (m, 2H), 6.25 (m, 1H), 5.80 (d, J=10.5 Hz, 1H), 4.81 (m, 1H), 4.62-4.40 (m, 6H), 4.25-4.02 (m, 3H), 3.93 (m, 1H), 3.60-3.40 (m, 4H), 3.10 (m, 1H), 2.80-2.60 (m, 4H), 2.55 (s, 2H), 2.45 (s, 2H), 2.22 (m, 1H), 1.95 (t, J=6.8 Hz, 1H), 1.22 (s, 6H), 0.73 (d, J=6.0 Hz, 3H).

Example 5: Preparation of N-(3-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)phenyl)acrylamide Into a 250-mL round-bottom flask, was placed tert-butyl N-(3-aminophenyl)carbamate (5 g, 24.01 mmol, 1.00 equiv), 3,5-dibromo-1-methyl-1,2-dihydropyrazin-2-one (5.8 g, 21.65 mmol, 1.50 equiv), DIEA (4.9 g, 37.98 mmol, 2.00 equiv), i-propanol (50 mL). The resulting solution was stirred overnight at 80° C. The resulting mixture was concentrated under vacuum. The crude product was purified by Flash PE:EA=100/20 increasing to PE:EA=100/50 within 30 min. This resulted in 7.4 g (78%) of tert-butyl N-[3-[(6-bromo-4-methyl-3-oxo-3,4-dihydropyrazin-2-yl)amino]phenyl]carbamate as a light yellow solid. LC-MS: (ES, m/z): [M+H]$^+$=395. $^1$H-NMR-: (300 MHz, $CDCl_3$, ppm): δ9.32 (s, 1H), 9.28 (s, 1H), 7.91 (s, 1H), 7.52 (d, J=5.4 Hz, 1H), 7.16-7.09 (m, 2H), 3.45 (s, 3H), 1.47 (s, 9H).

Into a 25-mL round-bottom flask, was placed tert-butyl N-[3-[(6-bromo-4-methyl-3-oxo-3,4-dihydropyrazin-2-yl)amino]phenyl]carbamate (400 mg, 0.51 mmol, 1.00 equiv), hydrogen chloride/Dioxane (10 mL). The resulting solution was stirred for 30 min at room temperature. The resulting mixture was concentrated under vacuum. This resulted in 300 mg (90%) of 3-[(3-aminophenyl)amino]-5-bromo-1-methyl-1,2-dihydropyrazin-2-one as a yellow solid. LC-MS: (ES, m/z): [M+H]$^+$=295.

Into a 50-mL round-bottom flask purged and maintained with an inert atmosphere of nitrogen, was placed 3-[(3-aminophenyl)amino]-5-bromo-1-methyl-1,2-dihydropyrazin-2-one (200 mg, 0.68 mmol, 1.00 equiv), (2-4,4-dimethyl-9-oxo-1,10-diazatricyclo[6.4.0.0^2,6]dodeca-2(6),7-dien-10-yl-3-[(oxan-2-yloxy)methyl]pyridin-4-yl)boronic acid (298 mg, 0.68 mmol, 1.00 equiv), $Pd(dppf)Cl_2$ (58 mg, 0.07 mmol, 0.10 equiv), potassium carbonate (281 mg, 2.04 mmol, 3.00 equiv), Dioxane (12 mL), water(2 mL). The resulting solution was stirred for 30 min at 100° C. The resulting mixture was concentrated under vacuum after cooled. The resulting solution was diluted with of methanol. The crude product was purified by Flash MeCN:$H_2O$=25/75 increasing to MeCN:$H_2O$=50/50 within 13 min. This resulted in 280 mg (68%) of 10-(4-[6-[(3-aminophenyl)amino]-4-methyl-5-oxo-4,5-dihydropyrazin-2-yl]-3-[(oxan-2-yloxy)methyl]pyridin-2-yl)-4,4-dimethyl-1,10-diazatricyclo[6.4.0.0^[2,6]]dodeca-2(6),7-dien-9-one as a brown solid. LC-MS (ES, m/z): [M+H]$^+$=610.

Into a 50-mL round-bottom flask, was placed 10-(4-[6-[(3-aminophenyl)amino]-4-methyl-5-oxo-4,5-dihydropyrazin-2-yl]-3-[(oxan-2-yloxy)methyl]pyridin-2-yl)-4,4-dimethyl-1,10-diazatricyclo[6.4.0.0^[2,6]]dodeca-2(6),7-dien-9-one (230 mg, 0.38 mmol, 1.00 equiv), trifluoroacetic acid (1 mL), dichloromethane (20 mL). The resulting solution was stirred for 30 min at room temperature. The resulting mixture was concentrated under vacuum. The resulting solution was diluted with of ethyl acetate. The pH value of the solution was adjusted to 8 with saturate solution of sodium bicarbonate. The solids were filtered out. The resulting mixture was concentrated under vacuum. This resulted in 150 mg (76%) of 10-(4-[6-[(3-aminophenyl)amino]-4-methyl-5-oxo-4,5-dihydropyrazin-2-yl]-3-(hydroxymethyl)pyridin-2-yl)-4,4-dimethyl-1,10-diazatricyclo[6.4.0.0^[2,6]]dodeca-2(6),7-dien-9-one as colorless oil. LC-MS-714-4: (ES, m/z): [M+H]$^+$=526.

Into a 25-mL round-bottom flask, was placed 10-(4-[6-[(3-aminophenyl)amino]-4-methyl-5-oxo-4,5-dihydropyrazin-2-yl]-3-(hydroxymethyl)pyridin-2-yl)-4,4-dimethyl-1,10-diazatricyclo[6.4.0.0^[2,6]]dodeca-2(6),7-dien-9-one (150 mg, 0.28 mmol, 1.00 equiv), prop-2-enoic acid (20.1 mg, 0.28 mmol, 1.00 equiv), NMM (58 mg, 0.38 mmol, 2.00 equiv), HATU (141 mg, 0.25 mmol, 1.30 equiv), MeCN (5 mL). The resulting solution was stirred for 30 min at room temperature. The crude product was purified by Prep-HPLC. This resulted in 32.4 mg (18%) of N-(3-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxo-3,4-dihydropyrazin-2-yl]amino]phenyl)prop-2-enamide as a off-white solid. LC-MS: (ES, m/z): [M+H]$^+$=580. $^1$H-NMR: (300 MHz, $CDCl_3$, ppm): δ9.99 (s, 1H), 9.24 (s, 1H), 8.47 (m, 2H), 7.84-7.73 (m, 2H), 7.60 (d, J=7.5 Hz, 1H), 7.30-7.20 (m, 2H), 6.58 (s, 1H), 6.55-6.25 (m, 2H), 5.76 (d, J=9.9 Hz, 1H), 4.97 (m, 1H), 4.64-4.45 (m, 2H), 4.33-4.15 (m, 3H), 3.88 (m, 1H), 3.57 (s, 3H), 2.59 (d, J=5.1 Hz, 2H), 2.42 (d, J=5.1 Hz, 2H), 1.22 (s, 6H).

Example 7: Preparation of N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(1-(oxetan-3-yl)piperidin-4-yl)phenyl)acrylamide Into a 250-mL round-bottom flask purged and maintained with an inert atmosphere of nitrogen, was placed 4-bromo-3-nitroaniline (5 g, 23.04 mmol, 1.00 equiv), tert-butyl 4-(tetramethyl-1,3,2-dioxaborolan-2-yl)-1,2,3,6-tetrahydropyridine-1-carboxylate (14 g, 45.28 mmol, 2.00 equiv), Pd(dppf)$Cl_2$(2 g, 2.33 mmol, 0.10 equiv), potassium carbonate (19 g, 137.47 mmol, 6.00 equiv), Dioxane (80 mL), water(20 mL). The resulting solution was stirred overnight at 90° C. The solids were filtrated out. The resulting mixture was concentrated under vacuum. The crude product was purified by Flash PE:EA=50/50 increasing to PE:EA=20/80 within 30 min. This resulted in 5.7 g (77%) of tert-butyl 4-(4-amino-2-nitrophenyl)-1,2,3,6-tetrahydropyridine-1-carboxylate as light yellow oil. LC-MS-1: (ES, m/z): $[M+H]^+=320$. $^1$H-NMR-PH-1: (300 MHz, $d_6$-DMSO, ppm): δ7.05 (m, 2H), 6.80 (d, J=8.1 Hz, 1H), 5.74 (s, 2H), 5.49 (s, 1H), 3.88 (m, 2H), 3.46 (t, J=10.8 Hz, 2H), 2.17 (s, 2H).

Into a 250-mL round-bottom flask, was placed tert-butyl 4-(4-amino-2-nitrophenyl)-1,2,3,6-tetrahydropyridine-1-carboxylate (7 g, 21.92 mmol, 1.00 equiv), water (10 mL), sodium carbonate (4.6 g, 43.40 mmol, 2.00 equiv), dichloromethane (50 mL). The resulting mixture was stirred 30 min at 0° C. This was followed by the addition of Cbz-Cl (4.5 g, 26.47 mmol, 1.20 equiv) dropwise with stirring in 5 min at 0° C. The resulting solution was stirred overnight at room temperature. The resulting mixture was washed with 2×100 mL of brine. The resulting mixture was concentrated under vacuum. This resulted in 7 g (70%) of tert-butyl 4-(4-[[(benzyloxy)carbonyl]amino]-2-nitrophenyl)-1,2,3,6-tetrahydropyridine-1-carboxylate as yellow oil. LC-MS-2: (ES, m/z): $[M+H]^+=454$. $^1$H-NMR-PH-2: (300 MHz, $d_6$-DMSO, ppm): δ10.27 (s, 1H), 8.13 (s, 1H), 7.68 (d, J=8.4 Hz, 1H), 7.46-7.32 (m, 7H), 5.62 (s, 1H), 5.19 (s, 2H), 3.92 (m, 2H), 3.53 (t, J=10.8 Hz, 2H), 2.24 (s, 2H).

Into a 250-mL round-bottom flask, was placed tert-butyl 4-(4-[[(benzyloxy)carbonyl]amino]-2-nitrophenyl)-1,2,3,6-tetrahydropyridine-1-carboxylate (5 g, 11.03 mmol, 1.00 equiv), hydrogen chloride/dioxane (40 mL). The resulting solution was stirred for 1.5 h at room temperature. The resulting mixture was concentrated under vacuum. This resulted in 4.5 g (crude) of benzyl N-[3-nitro-4-(1,2,3,6-tetrahydropyridin-4-yl)phenyl]carbamate as a light yellow solid. LC-MS-3: (ES, m/z): $[M+H]^+=354$.

Into a 250-mL round-bottom flask, was placed benzyl N-[3-nitro-4-(1,2,3,6-tetrahydropyridin-4-yl)phenyl]carbamate (4.5g, 25.47 mmol, 1.00 equiv), oxetan-3-one (1.35 g, 37.47 mmol, 1.50 equiv), $NaCNBH_3$ (1.6 g, 50.79 mmol, 2.00 equiv), methanol (30 mL). The resulting solution was stirred for 4 h at 50° C. The resulting solution was extracted with of ethyl acetate and the organic layers combined. The resulting mixture was washed with 2×100 mL of sodium chloride. The solid was dried in an oven under reduced pressure and concentrated under vacuum. This resulted in 3.6 g (61%) of benzyl N-[3-nitro-4-[1-(oxetan-3-yl)-1,2,3,6-tetrahydropyridin-4-yl]phenyl]carbamate as a white solid. LC-MS-4: (ES, m/z): $[M+H]^+=410$. $^1$H-NMR-PH-4: (300 MHz, $d_6$-DMSO, ppm): δ10.27 (s, 1H), 8.09 (s, 1H), 7.67 (d, J=8.4 Hz, 1H), 7.46-7.32 (m, 6H), 5.59 (s, 1H), 5.19 (s, 2H), 4.56 (t, J=9 Hz, 2H), 4.49 (t, J=9 Hz, 2H), 3.60 (m, 1H), 2.92 (s, 2H), 2.48 (m, 2H), 2.26 (s, 2H).

Into a 50-mL round-bottom flask, was placed benzyl N-[3-nitro-4-[1-(oxetan-3-yl)-1,2,3,6-tetrahydropyridin-4-yl]phenyl]carbamate (3.6 g, 8.79 mmol, 1.00 equiv), acetic acid (5.25 g, 87.42 mmol, 10.00 equiv), ethanol (25 mL), zinc (2.8 g, 42.81 mmol, 5.00 equiv). The resulting solution was stirred for 30 min at room temperature. The solids were filtered out. The resulting mixture was concentrated under vacuum. The resulting solution was diluted with ethyl acetate. The pH was adjusted to 8 with sodium carbonate (1 mol/L). The resulting mixture was washed with 2×200 mL of H2O. The mixture was dried over anhydrous sodium sulfate and concentrated under vacuum. The crude product was purified by Flash PE:EA=100/30 increasing to PE:EA=100/50 within 45 min. This resulted in 2.5g (75%) of benzyl N-[3-amino-4-[1-(oxetan-3-yl)-1,2,3,6-tetrahydropyridin-4-yl]phenyl]carbamate as yellow oil. LC-MS-5: (ES, m/z): $[M+H]^+=380$. $^1$H-NMR-PH-5: (300 MHz, $d_6$-DMSO, ppm): δ9.61 (s, 1H), 7.52-7.28 (m, 5H), 6.87 (s, 1H), 6.77 (d, J=7.8 Hz, 1H), 6.61 (d, J=8.1 Hz, 1H), 5.60 (s, 1H), 5.13 (s, 2H), 4.74 (s, 2H), 4.57 (t, J=9 Hz, 2H), 4.50 (t, J=9 Hz, 2H), 3.52 (m, 1H), 2.92 (s, 2H), 2.48 (m, 2H), 2.28 (s, 2H).

Into a 250-mL round-bottom flask, was placed benzyl N-[3-amino-4-[1-(oxetan-3-yl)-1,2,3,6-tetrahydropyridin-4-yl]phenyl]carbamate (2.5 g, 13.18 mmol, 1.00 equiv), TEA (2 g, 39.53 mmol, 3.00 equiv), di-tert-butyl dicarbonate (1.75 g, 16.04 mmol, 1.30 equiv), tetrahydrofuran (30 mL). The resulting solution was stirred overnight at 65° C. The resulting mixture was concentrated under vacuum. The crude product was purified by Flash PE:EA=100/30 increasing to PE:EA=100/50 within 25 min. This resulted in 2 g (63%) of benzyl N-(3-[[(tert-butoxy)carbonyl]amino]-4-[1-(oxetan-3-yl)-1,2,3,6-tetrahydropyridin-4-yl]phenyl)carbamate as yellow oil. LC-MS-6: (ES, m/z): $[M+H]^+=480$. $^1$H-NMR-PH-6: (300 MHz, $d_6$-DMSO, ppm): δ9.74 (s, 1H), 8.20 (s, 1H), 7.47-7.28 (m, 6H), 7.24 (d, J=8.1 Hz, 1H), 7.05 (d, J=8.4 Hz, 1H), 5.75 (s, 1H), 5.14 (s, 2H), 4.57 (s, 2H), 4.57 (t, J=9 Hz, 2H), 4.50 (t, J=9 Hz, 2H), 3.54 (m, 1H), 2.92 (s, 2H), 2.48 (m, 2H), 2.28 (s, 2H), 1.22 (s, 9H)

Into a 250-mL round-bottom flask purged and maintained with an inert atmosphere of $H_2$, was placed benzyl N-(3-[[(tert-butoxy)carbonyl]amino]-4-[1-(oxetan-3-yl)-1,2,3,6-tetrahydropyridin-4-yl]phenyl)carbamate (1.4 g, 2.92 mmol, 1.00 equiv), Palladium carbon (140 mg, 0.10 equiv), ethyl acetate (40 mL). The resulting solution was stirred overnight at room temperature. The solids were filtered out. The resulting mixture was concentrated under vacuum. This resulted in 610 mg (60%) of tert-butyl N-[5-amino-2-[1-(oxetan-3-yl)piperidin-4-yl]phenyl]carbamate as a light yellow solid. LC-MS-7: (ES, m/z): $[M+H]^+=348$. $^1$H-NMR-PH-7: (300 MHz, $d_6$-DMSO, ppm): δ8.26 (s, 1H), 6.90 (d, J=7.8 Hz, 1H), 6.40 (m, 2H), 4.87 (s, 2H), 4.54 (t, J=7.2 Hz, 2H), 4.46 (t, J=7.2 Hz, 2H), 3.37 (m, 1H), 2.78 (d, J=10.8 Hz, 2H), 2.60 (m, 1H), 1.80-1.45 (m, 6H), 1.21 (s, 9H).

Into a 50-mL round-bottom flask purged and maintained with an inert atmosphere of nitrogen, was placed tert-butyl N-[5-amino-2-[1-(oxetan-3-yl)piperidin-4-yl]phenyl]carbamate (600 mg, 2.30 mmol, 1.00 equiv), 3,5-dibromo-1-methyl-1,2-dihydropyrazin-2-one (550 mg, 2.74 mmol, 1.20 equiv), DIEA (435 mg, 4.50 mmol, 2.50 equiv), i-propanol (25 mL). The resulting solution was stirred overnight at 80° C. The resulting mixture was concentrated under vacuum. The crude product was purified by Flash PE:EA=100/85. This resulted in 600 mg (65%) of tert-butyl N-[5-[(6-bromo-4-methyl-3-oxo-3,4-dihydropyrazin-2-yl)amino]-2-[1-(oxetan-3-yl)piperidin-4-yl]phenyl]carbamate as a light yellow solid. LC-MS-8: (ES, m/z): $[M+H]^+=534$. $^1$H-NMR- PH-8: (300 MHz, $d_6$-DMSO, ppm): δ9.40 (s, 1H), 8.57 (s, 1H), 7.79 (s, 1H), 7.72 (d, J=8.4 Hz, 1H), 7.32 (s, 1H), 7.23 (d, J=8.4 Hz, 1H), 4.54 (t, J=6.3 Hz, 2H), 4.46 (t, J=6.3 Hz, 2H), 3.45-3.37 (m, 5H), 2.83-2.70 (m, 3H), 1.83-1.52 (m, 6H), 1.38 (s, 9H)

Into a 250-mL round-bottom flask, was placed tert-butyl N-[5-[(6-bromo-4-methyl-3-oxo-3,4-dihydropyrazin-2-yl) amino]-2-[1-(oxetan-3-yl)piperidin-4-yl]phenyl]carbamate (600 mg, 1.12 mmol, 1.00 equiv), trifluoroacetic acid (2 mL), dichloromethane (20 mL). The resulting solution was stirred for 3 h at room temperature. The resulting mixture was concentrated under vacuum. The resulting solution was diluted with methanol and pH was adjusted to 8 with potassium carbonate. The solids were filtered out. The resulting mixture was concentrated under vacuum. This resulted in 410 mg (84%) of 3-([3-amino-4-[1-(oxetan-3-yl) piperidin-4-yl]phenyl]amino)-5-bromo-1-methyl-1,2-dihydropyrazin-2-one as a light yellow solid. LC-MS-9: (ES, m/z): $[M+H]^+$=434.

Into a 50-mL round-bottom flask purged and maintained with an inert atmosphere of nitrogen, was placed 3-([3-amino-4-[1-(oxetan-3-yl)piperidin-4-yl]phenyl]amino)-5-bromo-1-methyl-1,2-dihydropyrazin-2-one (300 mg, 0.7 mmol, 1.00 equiv), (2-[4,4-dimethyl-9-oxo-1,10-diazatricyclo[6.4.0.0^[2,6]]dodeca-2(6),7-dien-10-yl]-3-[(oxan-2-yloxy)methyl]pyridin-4-yl)boronic acid (350 mg, 0.8 mmol, 1.10 equiv), Pd(dppf)$Cl_2$ (60 mg, 0.03 mmol, 0.10 equiv), $K_2CO_3$ (286 mg, 2.03 mmol, 3.00 equiv), Dioxane (20 mL), water(2 mL). The resulting solution was stirred for 30 min at 100° C. The resulting mixture was concentrated under vacuum. The resulting solution was diluted with of methanol. The crude product was purified by Flash MeCN: $H_2O$=20/80 increasing to MeCN:$H_2O$=55/45 within 12 min. This resulted in 210 mg (81%) of 10-[4-[6-([3-amino-4-[1-(oxetan-3-yl)piperidin-4-yl]phenyl]amino)-4-methyl-5-oxo-4,5-dihydropyrazin-2-yl]-3-[(oxan-2-yloxy)methyl]pyridin-2-yl]-4,4-dimethyl-1,10-diazatricyclo[6.4.0.0^[2,6]]dodeca-2(6),7-dien-9-one as a light yellow solid. LC-MS-10: (ES, m/z): $[M+H]^+$=749.

Into a 25-mL round-bottom flask, was placed 10-[4-[6-([3-amino-4-[1-(oxetan-3-yl)piperidin-4-yl]phenyl]amino)-4-methyl-5-oxo-4,5-dihydropyrazin-2-yl]-3-[(oxan-2-yloxy)methyl]pyridin-2-yl]-4,4-dimethyl-1,10-diazatricyclo [6.4.0.0^[2,6]]dodeca-2(6),7-dien-9-one (210 mg, 0.28 mmol, 1.00 equiv), dichloromethane (10 mL), trifluoroacetic acid (1 mL). The resulting solution was stirred for 1 h at room temperature. The resulting mixture was concentrated under vacuum and pH was adjusted to 8 with sodium bicarbonate solution. The resulting mixture was extracted with EA and washed with brine. The mixture was dried over anhydrous sodium sulfate and concentrated under vacuum. This resulted in 135 mg (72%) of 10-[4-[6-([3-amino-4-[1-(oxetan-3-yl)piperidin-4-yl]phenyl]amino)-4-methyl-5-oxo-4,5-dihydropyrazin-2-yl]-3-(hydroxymethyl)pyridin-2-yl]-4,4-dimethyl-1,10-diazatricyclo[6.4.0.0^[2,6]]dodeca-2(6), 7-dien-9-one as a light yellow solid. LC-MS-11: (ES, m/z): $[M+H]^+$=665. $^1$H-NMR-PH-11: (300 MHz, $CDCl_3$, ppm): δ8.55 (d, J=5.1 Hz, 1H), 8.20 (s, 1H), 8.00 (s, 1H), 7.76 (d, J=5.1 Hz, 1H), 7.29 (s, 1H), 7.23 (d, J=5.7 Hz, 1H), 7.23 (d, J=5.4 Hz, 1H), 6.85 (s, 1H), 5.02 (m, 1H), 4.82-4.37 (m, 7H), 4.20 (m, 2H), 3.92 (m, 1H), 3.70-3.50 (m, 5H), 2.98 (m, 2H), 2.62-2.47 (m, 5H), 2.07-1.82 (m, 6H), 1.73-1.45 (m, 5H), 1.28 (s, 6H).

Into a 25-mL round-bottom flask, was placed 10-[4-[6-([3-amino-4-[1-(oxetan-3-yl)piperidin-4-yl]phenyl]amino)-4-methyl-5-oxo-4,5-dihydropyrazin-2-yl]-3-(hydroxymethyl)pyridin-2-yl]-4,4-dimethyl-1,10-diazatricyclo[6.4.0.0^

[2,6]]dodeca-2(6),7-dien-9-one (135 mg, 0.23 mmol, 1.00 equiv), prop-2-enoic acid (17 mg, 0.23 mmol, 1.00 equiv), HATU (94 mg, 0.25 mmol, 1.10 equiv), NMM (54 mg, 0.53 mmol, 2.50 equiv), MeCN (5 mL). The resulting solution was stirred for 30 min at room temperature. The crude product was purified by Prep-HPLC. This resulted in 15.2 mg (11%) of N-(5-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxo-3,4-dihydropyrazin-2-yl]amino]-2-[1-(oxetan-3-yl)piperidin-4-yl]phenyl) prop-2-enamide as a white solid. LC-MS-0: (ES, m/z): $[M+H]^+$=719. $^1$H-NMR-PH-0: (300 MHz, $CDCl_3$, ppm): δ9.54 (s, 1H), 9.32 (s, 1H), 8.45 (d, J=4.8 Hz, 1H), 8.32 (m, 1H), 7.79-7.70 (m, 3H), 7.25 (d, J=8.7 Hz, 1H), 6.61-6.44 (m, 2H), 6.27 (m, 1H), 5.75 (d, J=10.8 Hz, 1H), 5.01 (m, 1H), 4.67-4.42 (m, 6H), 4.35-4.15 (m, 3H), 3.87 (m, 1H), 3.57 (s, 3H), 3.40 (m, 1H), 2.85-2.57 (m, 5H), 2.45 (m, 2H), 1.84-1.55 (m, 6H), 1.23 (s, 6H).

Example 8: Preparation of N-(5-((6-(3-(7,7-dimethyl-1-oxo-1,3,4,6,7,8-hexahydro-2H-cyclopenta[4,5]pyrrolo[1,2-a]pyrazin-2-yl)-2-(hydroxymethyl)phenyl)-4-methyl-3-oxo-3,4-dihydropyrazin-2-yl)amino)-2-(1-(oxetan-3-yl)piperidin-4-yl)phenyl)acrylamide Into a 25-mL round-bottom flask purged and maintained with an inert atmosphere of nitrogen, was placed 3-([3-amino-4-[1-(oxetan-3-yl)piperidin-4-yl]phenyl]amino)-5-bromo-1-methyl-1,2-dihydropyrazin-2-one (300 mg, 0.69 mmol, 1.00 equiv), (3-[4,4-dimethyl-9-oxo-1,10-diazatricyclo[6.4.0.0^[2,6]]dodeca-2(6),7-dien-10-yl]-2-formylphenyl)boronic acid (260 mg, 0.74 mmol, 1.10 equiv), Pd(dppf) $Cl_2$ (35 mg, 0.05 mmol, 0.10 equiv), potassium carbonate (286 mg, 2.07 mmol, 3.00 equiv), Dioxane (15 mL), water(2 mL). The resulting solution was stirred for 40 min at 100° C. for 2h. The resulting mixture was concentrated under vacuum. The resulting solution was extracted with of methanol and the organic layers combined. The crude product was purified by Flash MeCN:H2O=30/70 increasing to MeCN: H2O=65/35 within 12 min. This resulted in 268 mg (59%) of 2-[6-([3-amino-4-[1-(oxetan-3-yl)piperidin-4-yl]phenyl] amino)-4-methyl-5-oxo-4,5-dihydropyrazin-2-yl]-6-[4,4-dimethyl-9-oxo-1,10-diazatricyclo[6.4.0.0^[2,6]]dodeca-2(6), 7-dien-10-yl]benzaldehyde as a light yellow solid. LC-MS-1: (ES, m/z): $662[M+1-1]^+$ Into a 25-mL round-bottom flask, was placed 2-[6-(3-amino-4-[1-(oxetan-3-yl)piperidin-4-yl]phenylamino)-4-methyl-5-oxo-4,5-dihydropyrazin-2-yl]-6-4,4-dimethyl-9-oxo-1,10-diazatricyclo[6.4.0.0^2,6]dodeca-2(6),7-dien-10-ylbenzaldehyde (240 mg, 0.36 mmol, 1.00 equiv), $NaBH_4$ (7 mg, 0.18 mmol, 0.50 equiv), ethanol (8 mL). The resulting solution was stirred for 30 min at room temperature. The resulting solution was concentrated and diluted with methanol. The pH was adjusted to 8 with potassium carbonate. The solids were filtered out and the filtrate was concentrated under vacuum. This resulted in 132 mg (55%) of 10-[3-[6-([3-amino-4-[1-(oxetan-3-yl)piperidin-4-yl]phenyl]amino)-4-methyl-5-oxo-4,5-dihydropyrazin-2-yl]-2-(hydroxymethyl)phenyl]-4,4-dimethyl-1,10-diazatricyclo[6.4.0.0^[2,6]]dodeca-2(6),7-dien-9-one as light yellow oil. LC-MS-2: (ES, m/z): $664[M+H]^+$. $^1$H-NMR-PH-2: (300 MHz, $d_6$-DMSO, ppm): δ8.71 (s, 1H), 7.53-7.25 (m, 5H), 7.04 (d, J=8.4 Hz, 1H), 6.90 (d, J=8.4 Hz, 1H), 6.53 (s, 1H), 4.81 (m, 3H), 4.62-4.40 (m, 6H), 4.25-4.02 (m, 3H), 3.93 (m, 1H), 3.55 (s, 1H), 3.35 (m, 1H), 2.80 (m, 2H), 2.55 (s, 2H), 2.45 (s, 2H), 1.95-1.4 (m, 7H), 1.22 (s, 6H).

Into a 25-mL round-bottom flask, was placed 10-[3-[6-([3-amino-4-[1-(oxetan-3-yl)piperidin-4-yl]phenyl]amino)-4-methyl-5-oxo-4,5-dihydropyrazin-2-yl]-2-(hydroxymethyl)phenyl]-4,4-dimethyl-1,10-diazatricyclo[6.4.0.0^[2,6]]dodeca-2(6),7-dien-9-one (100 mg, 0.15 mmol, 1.00 equiv), prop-2-enoic acid (12 mg, 0.17 mmol, 1.10 equiv), HATU (68 mg, 0.18 mmol, 1.20 equiv), NMM (30 mg, 0.30 mmol, 2.00 equiv), MeCN (4 mL). The resulting solution was stirred for 30 min at room temperature. The crude product was purified by Prep-HPLC. This resulted in 20.5 mg (20%) of N-(5-[[6-(3-[4,4-dimethyl-9-oxo-1,10-diazatricyclo[6.4.0.0^[2,6]]dodeca-2(6),7-dien-10-yl]-2-(hydroxymethyl)phenyl)-4-methyl-3-oxo-3,4-dihydropyrazin-2-yl]amino]-2-[1-(oxetan-3-yl)piperidin-4-yl]phenyl)prop-2-enamide as a white solid. LC-MS-0: (ES, m/z): 718 $[M+H]^+$ $^1$H-NMR-PH-0: (300 MHz, $CDCl_3$, ppm): δ8.28 (s, 1H), 7.95 (s, 1H), 7.70-7.20 (m, 7H), 6.80 (s, 1H), 6.45-6.25 (m, 2H), 5.73 (s, 1H), 4.70 (m, 4H), 4.62-4.37 (m, 3H), 4.25-4.10 (m, 3H), 3.95 (m, 1H), 3.65 (s, 3H), 3.55 (m, 1H), 2.90 (m, 2H), 2.70-2.45 (m, 6H), 2.04-1.80 (m, 5H), 1.26 (s, 6H).

Example 9: Preparation of N-(3-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-5-(4-methylpiperazin-1-yl)phenyl)acrylamide Into a 250-mL round-bottom flask purged and maintained with an inert atmosphere of nitrogen, was placed a solution of 1-bromo-3,5-dinitrobenzene (5.5 g, 22.27 mmol, 1.00 equiv) in dioxane (50 mL), 1-methylpiperazine (2.64 g, 26.36 mmol, 1.20 equiv), $Cs_2CO_3$ (14.5 g, 44.50 mmol, 2.00 equiv). This was followed by the addition of $Pd_2(dba)_3$ (550 mg, 0.60 mmol, 0.10 equiv), BINAP (770 mg, 1.24 mmol, 0.15 equiv). The resulting solution was stirred overnight at 100° C. in an oil bath. The reaction mixture was cooled to 25° C. The solids were filtered out. The resulting mixture was concentrated under vacuum. The residue was applied onto a silica gel column with ethyl acetate/hexane (1:1). This resulted in 4.0 g (67%) of 1-(3,5-dinitrophenyl)-4-methylpiperazine as a yellow solid. LC-MS-1: (ES, m/z): 267 $[M+H]^+$.

Into a 25-mL round-bottom flask purged and maintained with an inert atmosphere of $H_2$, was placed a solution of 1-(3,5-dinitrophenyl)-4-methylpiperazine (1.3 g, 4.88 mmol, 1.00 equiv) in methanol (10 mL), Palladium carbon (0.1 g, 0.10 equiv). The resulting solution was stirred for 2 h at room temperature. The solids were filtered out. The resulting mixture was concentrated under vacuum. This resulted in 1.0 g (99%) of 5-(4-methylpiperazin-1-yl)benzene-1,3-diamine as brown oil. LC-MS-2: (ES, m/z): 207 $[M+H]^+$. $^1$H-NMR-PH-1: (300 MHz, $d_6$-DMSO, ppm): δ5.44 (s, 2H), 5.38 (s, 1H), 4.49 (s, 4H), 2.95 (t, J=6.5 Hz, 4H), 2.38 (t, J=6.5 Hz, 4H), 2.19 (s, 3H).

Into a 50-mL round-bottom flask purged and maintained with an inert atmosphere of nitrogen, was placed a solution of 3,5-dibromo-1-methyl-1,2-dihydropyrazin-2-one (1.0 g, 3.73 mmol, 1.00 equiv) in IPA (10 mL), 5-(4-methylpiperazin-1-yl)benzene-1,3-diamine (1.0 g, 4.85 mmol, 1.00 equiv), DIEA (530 mg, 4.10 mmol, 1.10 equiv). The resulting solution was stirred for 1 h at 40° C. in an oil bath. The reaction mixture was cooled to 25° C. The solids were collected by filtration. This resulted in 0.5 g (34%) of 3-[[3-amino-5-(4-methylpiperazin-1-yl)phenyl]amino]-5-bromo-1-methyl-1,2-dihydropyrazin-2-one as a brown solid. LC-MS-3: (ES, m/z): 392$[M+M]^+$.

Into a 25-mL round-bottom flask purged and maintained with an inert atmosphere of nitrogen, was placed a solution of 3-[[3-amino-5-(4-methylpiperazin-1-yl)phenyl]amino]-5-bromo-1-methyl-1,2-dihydropyrazin-2-one (300 mg, 0.76 mmol, 1.00 equiv) in dioxane (10 mL)/$H_2O$ (1 mL), (2-[4,4-dimethyl-9-oxo-1,10-diazatricyclo[6.4.0.0^[2,6]]dodeca-2(6),7-dien-10-yl]-3-[(oxan-2-yloxy)methyl]pyridin-4-yl)boronic acid (300 mg, 0.68 mmol, 1.00 equiv), potassium carbonate (240 mg, 1.74 mmol, 2.00 equiv). This was followed by the addition of $Pd(dppf)Cl_2$ (30 mg, 0.04 mmol, 0.10 equiv). The resulting solution was stirred for 1 h at 100° C. in an oil bath. The resulting mixture was concentrated under vacuum. The residue was applied onto column with $CH_3CN$:$H_2O$ (1:1). This resulted in 190 mg (35%) of 10-[4-(6-[[3-amino-5-(4-methylpiperazin-1-yl)phenyl]amino]-4-methyl-5-oxo-4,5-dihydropyrazin-2-yl)-3-[(oxan-2-yloxy)methyl]pyridin-2-yl]-4,4-dimethyl-1,10-diazatricyclo[6.4.0.0^[2,6]]dodeca-2(6),7-dien-9-one as a brown solid. LC-MS-4: (ES, m/z): 708$[M+H]^+$.

Into a 25-mL round-bottom flask purged and maintained with an inert atmosphere of nitrogen, was placed a solution of 10-[4-(6-[[3-amino-5-(4-methylpiperazin-1-yl)phenyl]amino]-4-methyl-5-oxo-4,5-dihydropyrazin-2-yl)-3-[(oxan-2-yloxy)methyl]pyridin-2-yl]-4,4-dimethyl-1,10-diazatricyclo[6.4.0.0^[2,6]]dodeca-2(6),7-dien-9-one (190 mg, 0.27 mmol, 1.00 equiv) in dichloromethane (5 mL), trifluoroacetic acid (1 mL). The resulting solution was stirred for 20 mins at 40° C. in an oil bath. The resulting mixture was concentrated under vacuum. This resulted in 190 mg (crude) of 10-[4-(6-[[3-amino-5-(4-methylpiperazin-1-yl)phenyl]amino]-4-methyl-5-oxo-4,5-dihydropyrazin-2-yl)-3-(hydroxymethyl)pyridin-2-yl]-4,4-dimethyl-1,10-diazatricyclo[6.4.0.0^[2,6]]dodeca-2(6),7-dien-9-one as brown oil. LC-MS-5: (ES, m/z): 624$[M+1-1]^+$.

Into a 25-mL round-bottom flask purged and maintained with an inert atmosphere of nitrogen, was placed prop-2-enoic acid (21 mg, 0.29 mmol, 1.10 equiv), HATU (122.5 mg, 0.32 mmol, 1.20 equiv), NMM (54 mg, 0.53 mmol, 2.00 equiv). The resulting mixture was stirred 10 min. To the mixture was added 10-[4-(6-[[3-amino-5-(4-methylpiperazin-1-yl)phenyl]amino]-4-methyl-5-oxo-4,5-dihydropyrazin-2-yl)-3-(hydroxymethyl)pyridin-2-yl]-4,4-dimethyl-1,10-diazatricyclo[6.4.0.0^[2,6]]dodeca-2(6),7-dien-9-one (190 mg, 0.30 mmol, 1.00 equiv). The resulting solution was stirred for 1 h at room temperature. The crude product was purified by Flash-Prep-HPLC. This resulted in 23 mg (11%) of N-(3-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxo-3,4-dihydropyrazin-2-yl]amino]-5-(4-methylpiperazin-1-yl)phenyl)prop-2-enamide as a light brown solid. LC-MS-0: (ES, m/z): 678 $[M+H]^+$. $^1$H-NMR-PH-1: (300 MHz, $d_6$-DMSO, ppm): δ9.88 (s, 1H), 9.02 (s, 1H), 8.49 (d, J=5.1 Hz, 1H), 7.80-7.74 (m, 3H), 7.50 (s, 1H), 6.97 (s, 1H), 6.57 (s, 1H), 6.52-6.25 (m, 2H), 5.75 (d, J=9.6H, 1H), 5.02 (m, 1H), 4.67-4.49 (m, 2H), 4.32-4.15 (m, 3H), 3.90 (m, 1H), 3.55 (s, 3H), 3.13 (m, 4H), 2.60 (m, 2H), 2.45 (m, 6H), 2.25 (s, 3H), 1.23 (s, 3H).

Example 10: Preparation of N-(3-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-5-((4-methylpiperazin-1-yl)methyl)phenyl)acrylamide Synthesis of 1-[(3,5-dinitrophenyl)methyl]-4-methylpiperazine: Into a 250-mL round-bottom flask, was placed 1-(chloromethyl)-3,5-dinitrobenzene (3 g, 13.85 mmol, 1.00 equiv), 1-methylpiperazine (1.38 g, 13.78 mmol, 1.00 equiv), potassium carbonate (4.8 g, 34.73 mmol, 2.50 equiv), tetrahydrofuran (30 mL). The resulting solution was stirred overnight at 70° C. The reaction mixture was cooled to room temperature. The solids were filtered out. The filtrate was concentrated under vacuum. The crude product was purified by re-crystallization from ether. This resulted in 3 g (77%) of 1-[(3,5-dinitrophenyl)methyl]-4-methylpiperazine as a yellow solid. LC-MS-718-1: (ES, m/z): 281 $[M+H]^+$ $^1$H-NMR-PH-718-1: (300 MHz, $d_6$-DMSO, ppm): δ8.73 (s, 1H), 8.56 (s, 2H), 3.74 (s, 2H), 2.44 (br s, 4H), 2.34 (br s, 4H), 2.16 (s, 3H).

Synthesis of 5-[(4-methylpiperazin-1-yl)methyl]benzene-1,3-diamine: Into a 250-mL round-bottom flask purged and maintained with an inert atmosphere of $H_2$, was placed 1-[(3,5-dinitrophenyl)methyl]-4-methylpiperazine (2.0 g, 7.14 mmol, 1.00 equiv), Palladium carbon (0.2 g, 0.10 equiv), methanol (40 mL). The resulting solution was stirred for 3 h at room temperature. The solids were filtered out. The filtrate was concentrated under vacuum. This resulted in 1.1 g (70%) of 5-[(4-methylpiperazin-1-yl)methyl]benzene-1,3-diamine as colorless oil. LC-MS-718-2: (ES, m/z): 221 $[M+H]^+$. $^1$H-NMR-PH-718-2: (300 MHz, $d_6$-DMSO, ppm): δ5.76 (s, 2H), 5.70 (s, 1H), 4.61 (s, 4H), 3.12 (s, 2H), 2.30 (br s, 8H), 2.15 (s, 3H).

Synthesis of 3-([3-amino-5-[(4-methylpiperazin-1-yl) methyl]phenyl]amino)-5-bromo-1-methyl-1,2-dihydropyrazin-2-one: Into a 50-mL round-bottom flask, was placed 3,5-dibromo-1-methyl-1,2-dihydropyrazin-2-one (1.0 g, 1.00 equiv), 5-[(4-methylpiperazin-1-yl)methyl]benzene-1,3-diamine (0.7 g, 1.00 equiv), DIEA (1.0 g, 7.74 mmol, 2.50 equiv), i-propanol (15 mL). The resulting solution was stirred overnight at 80° C. The reaction mixture was cooled to room temperature. The resulting mixture was concentrated under vacuum. The crude product was purified by Prep-HPLC. This resulted in 153 mg (14%) of 3-([3-amino-5-[(4-methylpiperazin-1-yl)methyl]phenyl]amino)-5-bromo-1-methyl-1,2-dihydropyrazin-2-one as a light yellow solid. LC-MS-718-3: (ES, m/z): 407 $[M+H]^+$. $^1$H-NMR-PH-718-3: (300 MHz, $d_6$-DMSO, ppm): δ8.92 (s, 1H), 7.28 (s, 1H), 6.95-6.93 (m, 2H), 6.28 (s, 1H), 5.01 (s, 2H), 3.44 (s, 3H), 3.27 (s, 2H), 2.39-2.36 (m, 8H), 2.15 (s, 3H).

Synthesis of 10-[4-[6-([3-amino-5-[(4-methylpiperazin-1-yl)methyl]phenyl]amino)-4-methyl-5-oxo-4,5-dihydropyrazin-2-yl]-3-[(oxan-2-yloxy)methyl]pyridin-2-yl]-4,4-dimethyl-1,10-diazatricyclo[6.4.0.0^[2,6]]dodeca-2(6),7-dien-9-one: Into a 50-mL round-bottom flask purged and maintained with an inert atmosphere of nitrogen, was placed 3-([3-amino-5-[(4-methylpiperazin-1-yl)methyl]phenyl] amino)-5-bromo-1-methyl-1,2-dihydropyrazin-2-one (100 mg, 0.25 mmol, 1.00 equiv), (2-[4,4-dimethyl-9-oxo-1,10-diazatricyclo[6.4.0.0^[2,6]]dodeca-2(6),7-dien-10-yl]-3-[(oxan-2-yloxy)methyl]pyridin-4-yl)boronic acid (120 mg, 0.27 mmol, 1.10 equiv), Pd(dppf)$Cl_2$ (20 mg, 0.03 mmol, 0.10 equiv), potassium carbonate (68 mg, 0.49 mmol, 2.00 equiv), dioxane (10 mL), water (1 mL). The resulting solution was stirred for 30 min at 80° C. The reaction mixture was cooled to room temperature. The solids were filtered out. The filtrate was concentrated under vacuum. The crude product was purified by Prep-HPLC. This resulted in 30 mg (17%) of 10-[4-[6-([3-amino-5-[(4-methylpiperazin-1-yl)methyl]phenyl]amino)-4-methyl-5-oxo-4,5-dihydropyrazin-2-yl]-3-[(oxan-2-yloxy)methyl]pyridin-2-yl]-4,4-dimethyl-1,10-diazatricyclo[6.4.0.0^[2,6]]dodeca-2(6),7-dien-9-one as a brown solid. LC-MS-718-4: (ES, m/z): 722 $[M+1-1]^+$ Synthesis of 10-[4-[6-([3-amino-5-[(4-methylpiperazin-1-yl)methyl]phenyl]amino)-4-methyl-5-oxo-4,5-dihydropyrazin-2-yl]-3-(hydroxymethyl)pyridin-2-yl]-4,4-dimethyl-1,10-diazatricyclo[6.4.0.0^[2,6]]dodeca-2(6),7-dien-9-one: Into a 25-mL round-bottom flask, was placed dichloromethane (2 mL), trifluoroacetic acid (0.2 mL), 10-4-[6-(3-amino-5-[(4-methylpiperazin-1-yl)methyl]phenylamino)-4-methyl-5-oxo-4,5-dihydropyrazin-2-yl]-3-[(oxan-2-yloxy) methyl]pyridin-2-yl-4,4-dimethyl-1,10-diazatricyclo [6.4.0.0^2,6]dodeca-2(6),7-dien-9-one (30 mg, 0.03 mmol, 1.00 equiv). The resulting solution was stirred for 30 min at room temperature. The resulting mixture was concentrated under vacuum. This resulted in 20 mg (74%) of 10-[4-[6-([3-amino-5-[(4-methylpiperazin-1-yl)methyl]phenyl] amino)-4-methyl-5-oxo-4,5-dihydropyrazin-2-yl](hydroxymethyl)pyridin-2-yl]-4,4-dimethyl-1,10-diazatricyclo [6.4.0.0^[2,6]]dodeca-2(6),7-dien-9-one as yellow oil. LC-MS-718-5: (ES, m/z): 638 $[M+H]^+$ Synthesis of N-(3-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxo-3,4-dihydropyrazin-2-yl]amino]-5-[(4-methylpiperazin-1-yl)methyl] phenyl)prop-2-enamide: Into a 25-mL round-bottom flask, was placed prop-2-enoic acid (20 mg, 0.28 mmol, 1.00 equiv), 10-4-[6-(3-amino-5-[(4-methylpiperazin-1-yl) methyl]phenylamino)-4-methyl-5-oxo-4,5-dihydropyrazin-2-yl]-3-(hydroxymethyl)pyridin-2-yl-4,4-dimethyl-1,10-diazatricyclo[6.4.0.0"2,6]dodeca-2(6),7-dien-9-one (2.7 mg, 1.20 equiv), HATU (14 mg, 1.20 equiv), NMM (8 mg, 2.50 equiv), MeCN (2 mL). The resulting solution was stirred for 30 min at room temperature. The crude product was purified by Prep-HPLC. This resulted in 5 mg (3%) of N-(3-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxo-3,4-dihydropyrazin-2-yl]amino]-5-[(4-methylpiperazin-1-yl)methyl]phenyl)prop-2-enamide as a brown solid. LC-MS-718-0: (ES, m/z): 692 $[M+H]^+$. $^1$H-NMR-PH-718-0: (300 MHz, $d_6$-DMSO, ppm): δ8.56-8.52 (m, 2H), 8.33 (s, 1H), 7.83-7.78 (m, 3H), 7.30 (s, 2H), 6.82 (s, 1H), 6.44 (d, J=15.3 Hz, 1H), 6.30 (dd, J=17.1, 9.9 Hz, 1H), 5.74 (dd, J=9.9, 1.5 Hz, 1H), 4.84-4.79 (m, 1H), 4.54-4.50 (m, 2H), 4.16-4.12 (m, 2H), 3.93-3.90 (m, 1H), 3.65 (s, 3H), 3.49 (s, 2H), 2.56-2.51 (m, 13H), 2.32 (s, 3H), 1.27 (s, 6H).

Example 11: Preparation of (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl) amino)-2-(2-methyl-4-(oxetan-3-yl)piperazin-1-yl) phenyl)acrylamide Synthesis of 2,4-dibromo-3-methylpyridine: Into a 250-mL 3-necked round-bottom flask purged and maintained with an inert atmosphere of nitrogen, was placed a solution of $(i\text{-}Pr)_2NH$ (3.19 g, 1.50 equiv) in tetrahydrofuran (50 mL). This was followed by the addition of n-$C_4H_9Li$ (10 ml, 1.5 equiv) at −30° C. and the mixture was stirred at the same temperature for 30 min. This was followed by the addition of 2,4-dibromopyridine (5 g, 21.11 mmol, 1.00 equiv) at −70° C. and the mixture was stirred at the same temperature for 30 min. To the above solution was added iodomethane (4.5 g, 1.50 equiv) at −70° C. The resulting solution was stirred for 30 min at −70° C. The reaction was then quenched by the addition of 100 mL aqueous $NH_4Cl$. The resulting solution was extracted with 3×50 mL of ethyl acetate and the organic layers combined and dried with Na2SO4. The solids were filtered out. The filtrate was concentrated under vacuum. The residue was applied onto a silica gel column with ethyl acetate/petroleum ether (1:1). This resulted in 3.0 g (57%) of 2,4-dibromo-3-methylpyridine as a white solid. LC-MS-727-1: (ES, m/z): 252 $[M+H]^+$ $^1$H-NMR-PH-727-1: (300 MHz, $CDCl_3$, ppm): δ7.99 (d, J=5.1 Hz, 1H), 7.45 (d, J=5.1 Hz, 1H), 2.58 (s, 3H).

Synthesis of 10-(4-bromo-3-methylpyridin-2-yl)-4,4-dimethyl-1,10-diazatricyclo[6.4.0.0^[2,6]]dodeca-2(6),7-dien-9-one: Into a 50-mL round-bottom flask purged and maintained with an inert atmosphere of nitrogen, was placed a solution of 4,4-dimethyl-1,10-diazatricyclo[6.4.0.0^[2,6]]dodeca-2(6),7-dien-9-one (1.0 g, 4.90 mmol, 1.00 equiv) in dioxane (10 mL). Then 2,4-dibromo-3-methylpyridine (1.59 g, 6.34 mmol, 1.30 equiv), $Pd_2(dba)_3$ (100 mg, 0.11 mmol, 0.10 equiv), Xantphos (100 mg, 0.17 mmol, 0.10 equiv), $Cs_2CO_3$ (3.19 g, 9.79 mmol, 2.00 equiv) were added to the mixture. The resulting solution was stirred for 1.5 h at 100° C. in an oil bath. The reaction mixture was cooled to room temperature. The solids were filtered out. The filtrate was concentrated under vacuum. The residue was applied onto a silica gel column with ethyl acetate/petroleum ether (1:1). This resulted in 1.0 g (55%) of 10-(4-bromo-3-methylpyridin-2-yl)-4,4-dimethyl-1,10-diazatricyclo[6.4.0.0^[2,6]]dodeca-2(6),7-dien-9-one as a brown solid. LC-MS-727-2 (ES, m/z): 374 $[M+H]^+$. $^1$H-NMR-PH-727-1: (300 MHz, $CDCl_3$, ppm): δ8.10 (d, J=5.4 Hz, 1H), 7.41 (d, J=5.1 Hz, 1H), 6.79 (s, 1H), 4.44-4.41 (m, 1H), 4.15-4.09 (m, 2H), 3.90-3.86 (m, 1H), 2.54 (s, 2H), 2.49 (s, 2H), 2.34 (s, 3H), 1.25 (s, 6H).

Synthesis of (2-[4,4-dimethyl-9-oxo-1,10-diazatricyclo[6.4.0.0^[2,6]]dodeca-2(6),7-dien-10-yl]-3-methylpyridin-4-yl)boronic acid: Into a 25-mL round-bottom flask purged and maintained with an inert atmosphere of nitrogen, was placed a solution of 10-(4-bromo-3-methylpyridin-2-yl)-4,4-dimethyl-1,10-diazatricyclo[6.4.0.0^[2,6]]dodeca-2(6),7-dien-9-one (500 mg, 1.34 mmol, 1.00 equiv) in dioxane (5 mL) and then to the solution was added $Pin_2B_2$ (850 mg, 2.50 equiv), KOAc (400 mg, 4.08 mmol, 3.00 equiv), $Pd(dppf)Cl_2$ (50 mg, 0.07 mmol, 0.10 equiv). The resulting solution was stirred for 1 h at 100° C. in an oil bath. The reaction mixture was cooled to room temperature. The solids were filtered out. The filtrate was concentrated under vacuum. The residue was purified by Flash-Prep-HPLC with $CH_3CN:H_2O$ (1:1). This resulted in 150 mg (33%) of (2-[4,4-dimethyl-9-oxo-1,10-diazatricyclo[6.4.0.0^[2,6]]dodeca-2(6),7-dien-10-yl]-3-methylpyridin-4-yl)boronic acid as a brown solid. LC-MS-727-3: (ES, m/z): 340 $[M+H]^+$.

Synthesis of 10-[4-[6-([3-amino-4-[(2S)-2-methyl-4-(oxetan-3-yl)piperazin-1-yl]phenyl]amino)-4-methyl-5-oxo-4,5-dihydropyrazin-2-yl]-3-methylpyridin-2-yl]-4,4-dimethyl-1,10-diazatricyclo[6.4.0.0^[2,6]]dodeca-2(6),7-dien-9-one: Into a 25-mL round-bottom flask purged and maintained with an inert atmosphere of nitrogen, was placed a solution of (2-[4,4-dimethyl-9-oxo-1,10-diazatricyclo[6.4.0.0^[2,6]]dodeca-2(6),7-dien-10-yl]-3-methylpyridin-4-yl)boronic acid (120 mg, 0.35 mmol, 1.00 equiv) in dioxane (1 mL), then to the solution was added 3-([3-amino-4-[(2S)-2-methyl-4-(oxetan-3-yl)piperazin-1-yl]phenyl]amino)-5-bromo-1-methyl-1,2-dihydropyrazin-2-one (100 mg, 0.22 mmol, 1.10 equiv), $Pd(dppf)Cl_2$ (10 mg, 0.01 mmol, 1.00 equiv), potassium carbonate (73 mg, 0.53 mmol, 2.00 equiv). The resulting solution was stirred for 1 h at 100° C. in an oil bath. The reaction mixture was cooled to room temperature. The resulting mixture was concentrated under vacuum. The residue was purified by Flash-Prep-HPLC. This resulted in 120 mg (51%) of 10-[4-[6-([3-amino-4-[(2S)-2-methyl-4-(oxetan-3-yl)piperazin-1-yl]phenyl]amino)-4-methyl-5-oxo-4,5-dihydropyrazin-2-yl]-3-methylpyridin-2-yl]-4,4-dimethyl-1,10-diazatricyclo[6.4.0.0^[2,6]]dodeca-2(6),7-dien-9-one as a brown solid. LC-MS-727-4: (ES, m/z): 664 $[M+H]^+$.

Synthesis of N-(5-[[6-(2-[4,4-dimethyl-9-oxo-1,10-diazatricyclo[6.4.0.0^[2,6]]dodeca-2(6),7-dien-10-yl]-3-methylpyridin-4-yl)-4-methyl-3-oxo-3,4-dihydropyrazin-2-yl]amino]-2-[(2S)-2-methyl-4-(oxetan-3-yl)piperazin-1-yl]phenyl)prop-2-enamide: Into a 25-mL round-bottom flask purged and maintained with an inert atmosphere of nitrogen, was placed a solution of 10-[4-[6-([3-amino-4-[(2S)-2-methyl-4-(oxetan-3-yl)piperazin-1-yl]phenyl]amino)-4-methyl-5-oxo-4,5-dihydropyrazin-2-yl]-3-methylpyridin-2-yl]-4,4-dimethyl-1,10-diazatricyclo[6.4.0.0^[2,6]]dodeca-2(6),7-dien-9-one (200 mg, 0.30 mmol, 1.00 equiv) in $CH_3CN$ (1 mL) and then to the solution was added prop-2-enoic acid (21.7 mg, 0.30 mmol, 1.00 equiv), HATU (115 mg, 0.30 mmol, 1.00 equiv), NMM (61 mg, 0.60 mmol, 2.00 equiv). The resulting solution was stirred for 4 h at room temperature. The resulting mixture was concentrated under vacuum. The crude product was purified by Flash-Prep-HPLC. This resulted in 21.1 mg (10%) of N-(5-[[6-(2-[4,4-dimethyl-9-oxo-1,10-diazatricyclo[6.4.0.0^[2,6]]dodeca-2(6),7-dien-10-yl]-3-methylpyridin-4-yl)-4-methyl-3-oxo-3,4-dihydropyrazin-2-yl]amino]-2-[(2S)-2-methyl-4-(oxetan-3-yl)piperazin-1-yl]phenyl)prop-2-enamide as a light yellow solid. LC-MS-727-0: (ES, m/z): 718 $[M+1-1]^+$. $^1$H-NMR-PH-727-1: (300 MHz, $d_6$-$DMSO_3$, ppm): δ8.88 (d, J=5.7 Hz, 1H), 8.32 (d, J=5.7 Hz, 1H), 7.67-7.59 (m, 2H), 7.33-7.27 (m, 2H), 6.64-6.55 (m, 2H), 6.24 (d, J=16.5 Hz, 1H), 5.76 (d, J=11.4 Hz, 1H), 4.72-4.65 (m, 4H), 4.19-4.09 (m, 4H), 3.90-3.83 (m, 2H), 3.54 (s, 3H), 3.30-3.12 (m, 3H), 3.00-2.83 (m, 3H), 2.51 (s, 2H), 2.40 (s, 2H), 2.26 (s, 3H), 1.18 (s, 6H), 0.74-0.71 (m, 3H).

Example 12: Preparation of N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(2-methyl-4-morpholinopiperidin-1-yl)phenyl)acrylamide Synthesis of tert-butyl 2-methyl-4-(morpholin-4-yl)piperidine-1-carboxylate: Into a 500-mL round-bottom flask, was placed tert-butyl 2-methyl-4-oxopiperidine-1-carboxylate (18 g, 84.40 mmol, 1.00 equiv), morpholine (8 g, 91.83 mmol, 1.10 equiv), $NaCNBH_3$ (10 g, 2.00 equiv), ethanol (200 mL). The resulting solution was stirred overnight at 50° C. The resulting mixture was concentrated under vacuum. The crude product was purified by Flash-Prep-HPLC. This resulted in 9.4 g (39%) of tert-butyl 2-methyl-4-(morpholin-4-yl)piperidine-1-carboxylate as colorless oil. LC-MS-729-1: (ES, m/z): 285 $[M+H]^+$. $^1$H-NMR-PH-729-1: (300 MHz, $CDCl_3$, ppm): δ4.01-3.94 (m, 1H), 3.75-3.72 (m, 4H), 3.17-3.07 (m, 1H), 2.56-2.51 (m, 4H), 2.42-2.37 (m, 1H), 1.89-1.83 (m, 2H), 1.68-1.53 (m, 3H), 1.48 (s, 9H), 1.27 (d, J=6.3 Hz, 3H).

Synthesis of 4-(2-methylpiperidin-4-yl)morpholine: Into a 250-mL round-bottom flask, was placed tert-butyl 2-methyl-4-(morpholin-4-yl)piperidine-1-carboxylate (5 g, 17.58 mmol, 1.00 equiv), hydrogen chloride/Dioxane (50 mL). The resulting solution was stirred for 30 min at room temperature. The resulting mixture was concentrated under vacuum. The resulting mixture was diluted with MeCN and based with potassium carbonate. The mixture was filtered and the filtrate was concentrated. This resulted in 3 g (93%)

of 4-(2-methylpiperidin-4-yl)morpholine as a white solid. LC-MS-729-2: (ES, m/z): 185 $[M+H]^+$ Synthesis of benzyl N-[4-[2-methyl-4-(morpholin-4-yl) piperidin-1-yl]-3-nitrophenyl]carbamate, Into a 250-mL round-bottom flask, was placed 4-(2-methylpiperidin-4-yl) morpholine (3 g, 16.28 mmol, 1.00 equiv), benzyl N-(4-fluoro-3-nitrophenyl)carbamate (5.6 g, 19.29 mmol, 1.20 equiv), potassium carbonate (6.75 g, 48.91 mmol, 3.00 equiv), MeCN (60 mL). The resulting solution was stirred overnight at 90° C. The solids were collected by filtration. The resulting mixture was concentrated under vacuum and applied onto a silica gel column with ethyl acetate/petroleum ether (75:25). The crude product was purified by Flash-Prep-HPLC with MeCN:0.1% TFA/$H_2O$=20/80 increasing to MeCN:0.1% TFA/$H_2O$=45/55 within 12 min. This resulted in 1.5 g (21%) of benzyl N-[4-[2-methyl-4-(morpholin-4-yl)piperidin-1-yl]-3-nitrophenyl]carbamate as a yellow solid. LC-MS-729-3: (ES, m/z): 455 $[M+H]^+$. $^1$H-NMR-PH-729-3: (300 MHz, $d_6$-DMSO, ppm): δ10.21 (s, 1H), 9.90 (br s, 1H), 7.87 (s, 1H), 7.64-7.52 (m, 2H), 7.50-7.30 (m, 5H), 5.18 (s, 2H), 4.10-3.96 (m, 2H), 3.80-3.60 (m, 2H), 3.55-3.30 (m, 3H), 3.20-2.97 (m, 4H), 2.69 (t, J=11.1 Hz, 1H), 2.25-2.10 (m, 2H), 1.75-1.55 (m, 1H), 1.40-1.30 (m, 1H), 0.74 (d, J=6.0 Hz, 3H).

Synthesis of benzyl N-[3-amino-4-[2-methyl-4-(morpholin-4-yl)piperidin-1-yl]phenyl]carbamate: Into a 100-mL round-bottom flask, was placed benzyl N-[4-[2-methyl-4-(morpholin-4-yl)piperidin-1-yl]-3-nitrophenyl]carbamate (1.2 g, 2.64 mmol, 1.00 equiv), Zn (1.0 g, 15.38 mmol, 6.00 equiv), $NH_4Cl$ (1.7 g, 31.78 mmol, 12.00 equiv), MeOH (15 mL). The resulting solution was stirred for 1 h at room temperature. The solids were collected by filtration. The filtrate was concentrated under vacuum. The residue was applied onto a silica gel column with dichloromethane/methanol (15:1). This resulted in 0.84 g (75%) of benzyl N-[3-amino-4-[2-methyl-4-(morpholin-4-yl)piperidin-1-yl] phenyl]carbamate as a brown solid. LC-MS-729-4: (ES, m/z): 425 $[M+H]^+$ Synthesis of benzyl N-(3-[[(tert-butoxy)carbonyl]amino]-4-[2-methyl-4-(morpholin-4-yl)piperidin-1-yl]phenyl)carbamate Into a 250-mL round-bottom flask, was placed benzyl N-[3-amino-4-[2-methyl-4-(morpholin-4-yl)piperidin-1-yl]phenyl]carbamate (0.5 g, 3.53 mmol, 1.00 equiv), $Boc_2O$ (0.38 g, 5.28 mmol, 1.50 equiv), DIEA (0.38 g, 8.84 mmol, 2.50 equiv), tetrahydrofuran (15 mL). The resulting solution was stirred overnight at 75° C. The reaction mixture was cooled to room temperature. The resulting mixture was concentrated under vacuum. The residue was applied onto a silica gel column with ethyl acetate/petroleum ether (75:25). This resulted in 0.5 g (80%) of benzyl N-(3-[[(tert-butoxy) carbonyl]amino]-4-[2-methyl-4-(morpholin-4-yl)piperidin-1-yl]phenyl)carbamate as a light yellow solid. LC-MS-729-5: (ES, m/z): 252 $[M+H]^+$. $^1$H-NMR-PH-729-5: (300 MHz, $d_6$-DMSO, ppm): δ9.69 (s, 1H), 8.19 (s, 1H), 8.05 (s, 1H), 7.46-7.30 (m, 5H), 7.18-7.15 (m, 1H), 7.10-7.06 (m, 1H), 5.14 (s, 2H), 3.59 (br s, 4H), 2.90-2.47 (m, 4H), 2.42-2.25 (m, 2H), 2.0-1.82 (m, 2H), 1.72-1.60 (m, 1H), 1.50-1.32 (m, 12H), 0.71 (d, J=6.0 Hz, 3H).

Synthesis of tert-butyl N-[5-amino-2-[2-methyl-4-(morpholin-4-yl)piperidin-1-yl]phenyl]carbamate: Into a 250-mL round-bottom flask purged and maintained with an inert atmosphere of $H_2$, was placed benzyl N-(3-[[(tert-butoxy) carbonyl]amino]-4-[2-methyl-4-(morpholin-4-yl)piperidin-1-yl]phenyl)carbamate (500 mg, 1.52 mmol, 1.00 equiv), Palladium carbon (50 mg), methanol (30 mL). The resulting solution was stirred for 3 h at 25° C. The mixture was concentrated under vacuum. This resulted in 381 mg (crude) of tert-butyl N-[5-amino-2-[2-methyl-4-(morpholin-4-yl)piperidin-1-yl]phenyl]carbamate as colorless oil. LC-MS-729-6: (ES, m/z): 391 $[M+H]^+$ Synthesis of tert-butyl N-[5-[(6-bromo-4-methyl-3-oxo-3,4-dihydropyrazin-2-yl)amino]-2-[2-methyl-4-(morpholin-4-yl)piperidin-1-yl]phenyl]carbamate: Into a 100-mL round-bottom flask, was placed tert-butyl N-[5-amino-2-[2-methyl-4-(morpholin-4-yl)piperidin-1-yl]phenyl]carbamate (300 mg, 1.54 mmol, 1 equiv), 3,5-dibromo-1-methyl-1,2-dihydropyrazin-2-one (250 mg, 1.87 mmol, 1.21 equiv), DIEA (250 mg, 3.87 mmol, 2.52 equiv), i-PrOH (10 mL). The resulting solution was stirred overnight at 80° C. The reaction mixture was cooled to room temperature. The resulting mixture was concentrated. The residue was applied onto a silica gel column with ethyl acetate. This resulted in 265 mg (59.73%) of tert-butyl N-[5-[(6-bromo-4-methyl-3-oxo-3,4-dihydropyrazin-2-yl)amino]-2-[2-methyl-4-(morpholin-4-yl)piperidin-1-yl]phenyl]carbamate as a yellow solid. LC-MS-729-7: (ES, m/z): 577 $[M+H]^+$. $^1$H-NMR-PH-729-7: (300 MHz, $d_6$-DMSO, ppm): δ9.38 (s, 1H), 8.41 (s, 1H), 8.04 (s, 1H), 7.59-7.55 (m, 1H), 7.32 (s, 1H), 7.23 (d, J=0.9 Hz, 1H), 3.65-3.55 (m, 4H), 3.44 (s, 3H), 2.92-2.52 (m, 4H), 2.42-2.28 (m, 2H), 2.00-1.82 (m, 2H), 1.50-1.30 (m, 13H), 0.73-0.69 (m, 3H).

Synthesis of 3-([3-amino-4-[2-methyl-4-(morpholin-4-yl) piperidin-1-yl]phenyl]amino)-5-bromo-1-methyl-1,2-dihydropyrazin-2-one: Into a 25-mL round-bottom flask, was placed tert-butyl N-[5-[(6-bromo-4-methyl-3-oxo-3,4-dihydropyrazin-2-yl)amino]-2-[2-methyl-4-(morpholin-4-yl)piperidin-1-yl]phenyl]carbamate (200 mg, 0.31 mmol, 1 equiv), HCl/Dioxane (5 mL). The resulting solution was stirred for 4 hr at room temperature. The resulting mixture was concentrated. This resulted in 160 mg (96.45%) of 3-([3-amino-4-[2-methyl-4-(morpholin-4-yl)piperidin-1-yl] phenyl]amino)-5-bromo-1-methyl-1,2-dihydropyrazin-2-one as a light yellow solid. LC-MS-729-8: (ES, m/z): 477 $[M+H]^+$ Synthesis of 10-(4-[6-[(3-aminophenyl)amino]-4-methyl-5-oxo-4,5-dihydropyrazin-2-yl]-3-[(oxan-2-yloxy)methyl] pyridin-2-yl)-4,4-dimethyl-1,10-diazatricyclo[6.4.0.0^[2,6]] dodeca-2(6),7-dien-9-one: Into a 25-mL round-bottom flask purged and maintained with an inert atmosphere of nitrogen, was placed 3-([3-amino-4-[2-methyl-4-(morpholin-4-yl)piperidin-1-yl]phenyl]amino)-5-bromo-1-methyl-1,2-dihydropyrazin-2-one (160 mg, 0.34 mmol, 1 equiv), (2-[4,4-dimethyl-9-oxo-1,10-diazatricyclo[6.4.0.0^[2,6]]dodeca-2(6),7-dien-10-yl]-3-[(oxan-2-yloxy)methyl]pyridin-4-yl) boronic acid (147 mg, 0.33 mmol, 1.00 equiv), $Pd(dppf)Cl_2$ (30 mg, 0.03 mmol, 0.10 equiv), $K_2CO_3$ (116 mg, 0.84 mmol, 2.50 equiv), dioxane (5 mL, Infinity mmol, Infinity equiv), $H_2O$ (0.5 mL). The resulting solution was stirred for 40 min at 90° C. The reaction mixture was cooled to room temperature. The resulting mixture was concentrated and purified by Flash-Prep-HPLC. This resulted in 210 mg (79.12%) of 10-(4-[6-[(3-aminophenyl)amino]-4-methyl-5-oxo-4,5-dihydropyrazin-2-yl]-3-[(oxan-2-yloxy)methyl] pyridin-2-yl)-4,4-dimethyl-1,10-diazatricyclo[6.4.0.0^[2,6]] dodeca-2(6),7-dien-9-one as a solid. LC-MS-729-9: (ES, m/z): 792 $[M+H]^+$ Synthesis of 10-(4-[6-[(3-aminophenyl)amino]-4-methyl-5-oxo-4,5-dihydropyrazin-2-yl]-3-(hydroxymethyl)pyridin-2-yl)-4,4-dimethyl-1,10-diazatricyclo[6.4.0.0^[2,6]]dodeca-2(6),7-dien-9-one: Into a 50-mL round-bottom flask, was placed 10-(4-[6-[(3-aminophenyl)amino]-4-methyl-5-oxo-4,5-dihydropyrazin-2-yl]-3-[(oxan-2-yloxy)methyl]pyridin-2-yl)-4,4-dimethyl-1,10-diazatricyclo[6.4.0.0^[2,6]]dodeca-2(6),7-dien-9-one (200 mg, 0.38 mmol, 1.00 equiv), trifluoroacetic acid (1 mL), dichloromethane (20 mL). The resulting solution was stirred for 30 min at room temperature. The resulting mixture was concentrated under vacuum. The resulting solution was diluted with ethyl acetate and based with aq. sodium bicarbonate. The solids were filtered out and the filtrate was concentrated under vacuum. This resulted in 130 mg (76%) of 10-(4-[6-[(3-aminophenyl) amino]-4-methyl-5-oxo-4,5-dihydropyrazin-2-yl]-3-(hydroxymethyl)pyridin-2-yl)-4,4-dimethyl-1,10-diazatricyclo [6.4.0.0^[2,6]]dodeca-2(6),7-dien-9-one as colorless oil. LC-MS-729-10: (ES, m/z): 708 $[M+H]^+$ Synthesis of N-(3-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxo-3,4-dihydropyrazin-2-yl]amino]phenyl)prop-2-enamide: Into a 25-mL round-bottom flask, was placed 10-(4-[6-[(3-aminophenyl) amino]-4-methyl-5-oxo-4,5-dihydropyrazin-2-yl]-3-(hydroxymethyl)pyridin-2-yl)-4,4-dimethyl-1,10-diazatricyclo [6.4.0.0^[2,6]]dodeca-2(6),7-dien-9-one (100 mg, 0.19 mmol, 1.00 equiv), prop-2-enoic acid (13.7 mg, 0.19 mmol, 1.00 equiv), NMM (38.5 mg, 0.38 mmol, 2.00 equiv), HATU (94 mg, 0.25 mmol, 1.30 equiv), MeCN (5 mL). The resulting solution was stirred for 30 min at room temperature. The crude product was purified by Prep-HPLC. This resulted in 19.7 mg (18%) of N-(3-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxo-3,4-dihydropyrazin-2-yl]amino]phenyl)prop-2-enamide as off-white solid. LC-MS-729-0: (ES, m/z): 762 $[M+I-1]^+$. $^1$H-NMR-PH-729-0: (300 MHz, DMSO, ppm): δ9.23 (s, 2H), 9.14 (s, 1H), 8.49 (d, J=5.1 Hz, 1H), 7.96-7.95 (m, 1H), 7.77 (s, 1H), 7.61 (d, J=8.1 Hz, 1H), 7.23 (d, J=8.7 Hz, 1H), 6.68-6.62 (m, 1H), 6.57 (s, 1H), 6.30 (d, J=17.1 Hz, 1H), 5.80 (d, J=11.7 Hz, 1H), 5.03-5.00 (m, 1H), 4.65-4.40 (m, 2H), 4.32-4.16 (m, 4H), 3.85-3.83 (m, 1H), 3.68-3.55 (m, 7H), 3.01-2.72 (m, 2H), 2.71-2.52 (m, 4H), 2.48-2.25 (m, 4H), 1.98-1.78 (m, 2H), 1.72-1.52 (m, 1H), 1.46-1.30 (m, 1H), 1.23 (s, 6H), 0.76 (d, J=5.7 Hz, 3H).

Example 13: Preparation of (R)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(3-(dimethylamino) pyrrolidin-1-yl)phenyl)acrylamide Synthesis of benzyl N-[4-[(3R)-3-(dimethylamino)pyrrolidin-1-yl]-3-nitrophenyl]carbamate as a yellow solid Into a 250-mL round-bottom flask, was placed (3R)—N,N-dimethylpyrrolidin-3-amine dihydrochloride (5 g, 26.72 mmol, 1 equiv), benzyl N-(4-fluoro-3-nitrophenyl)carbamate (9.3 g, 32.07 mmol, 1.20 equiv), TEA (10.8 g, 106.89 mmol, 4.00 equiv), DMF (80 mL). The resulting solution was stirred overnight at 100° C. The reaction mixture was cooled to room temperature. The reaction was then quenched by the addition of 200 mL of water. The resulting solution was extracted with 2×200 ml of ethyl acetate. The organic mixture was washed with 2×200 ml of brine. The organic phase was dried over anhydrous sodium sulfate. The solids were filtered out. The filtrate was concentrated under vacuum. The crude product was purified by re-crystallization from MeCN. This resulted in 5.2 g (50.62%) of benzyl N-[4-[(3R)-3-(dimethylamino)pyrrolidin-1-yl]-3-nitrophenyl]carbamate as a yellow solid. LC-MS-729-C-1: (ES, m/z): 385 $[M+H]^+$. $^1$H-NMR-PH-729-C-1: (300 MHz, $d_6$-DMSO, ppm): δ9.78 (s, 1H), 7.96 (s, 1H), 7.52-7.37 (m, 6H), 7.06 (d, J=9.3 Hz, 1H), 5.15 (s, 2H), 3.30-3.27 (m, 1H), 3.13-3.01 (m, 3H), 2.71-2.68 (m, 1H), 2.17 (s, 6H), 1.83-1.71 (m, 1H).

Synthesis of benzyl N-[3-amino-4-[3-(dimethylamino) pyrrolidin-1-yl]phenyl]carbamate: Into a 250-mL round-bottom flask, was placed benzyl N-[4-[3-(dimethylamino)pyrrolidin-1-yl]-3-nitrophenyl]carbamate (5 g, 13.01 mmol, 1 equiv), zinc (5.1 g, 78.04 mmol, 6.00 equiv), $NH_4Cl$ (8.3 g, 156.07 mmol, 12.00 equiv), MeOH (100 mL). The resulting solution was stirred for 1 hr at room temperature. The resulting mixture was concentrated. This resulted in 3.9 g (84.60%) of benzyl N-[3-amino-4-[3-(dimethylamino)pyrrolidin-1-yl]phenyl]carbamate as a grey solid. LC-MS-729-C-2: (ES, m/z): 365 $[M+H]^+$ Synthesis of benzyl N-(3-[[(tert-butoxy)carbonyl]amino]-4-[3-(dimethylamino)pyrrolidin-1-yl]phenyl)carbamate: Into a 250-mL round-bottom flask, was placed benzyl N-[3-amino-4-[3-(dimethylamino)pyrrolidin-1-yl]phenyl]carbamate (3 g, 16.93 mmol, 1 equiv), di-tert-butyl dicarbonate (2.2 mg, 20 mmol), DIEA (2.73 g, 40 mmol), THF (50 mL). The resulting solution was stirred overnight at 75° C. The reaction mixture was cooled to room temperature. The resulting mixture was concentrated. The residue was applied onto a silica gel column with ethyl acetate/petroleum ether (50:50). This resulted in 2.6 g (68%) of benzyl N-(3-[[(tert-butoxy)carbonyl]amino]-4-[3-(dimethylamino)pyrrolidin-1-yl]phenyl)carbamate as a yellow solid. LC-MS-729-C-3: (ES, m/z): 465 $[M+H]^+$. $^1$H-NMR-PH-729-C-3: (300 MHz, DMSO, ppm): δ9.51 (s, 1H), 8.06 (s, 1H), 7.54 (s, 1H), 7.41-7.33 (m, 5H), 7.14-7.11 (m, 1H), 6.89 (d, J=9.0 Hz, 1H), 5.13 (s, 2H), 3.21-3.12 (m, 1H), 3.09-2.99 (m, 3H), 2.79-2.69 (m, 1H), 2.17 (s, 6H), 2.09-2.00 (m, 1H), 1.78-1.65 (m, 1H),1.44 (s, 9H).

Synthesis of tert-butyl N-[5-amino-2-[(3S)-3-(dimethylamino)pyrrolidin-1-yl]phenyl]carbamate: Into a 250-mL round-bottom flask purged and maintained with an inert atmosphere of $H_2$, was placed benzyl N-(3-[[(tert-butoxy) carbonyl]amino]-4-[(3S)-3-(dimethylamino)pyrrolidin-1-yl]phenyl)carbamate (2 g, 0.44 mmol, 1 equiv), Pd/C (200 mg), MeOH (50 mL). The resulting solution was stirred for 2 hr at room temperature. The solids were filtered out. The filtrate was concentrated under vacuum. The resulting mixture was concentrated. This resulted in 1.15 g of tert-butyl N-[5-amino-2-[(3S)-3-(dimethylamino)pyrrolidin-1-yl]phenyl]carbamate as brown oil. LC-MS-729-C-4: (ES, m/z): 321 $[M+H]^+$ Synthesis of tert-butyl N-[5-[(6-bromo-4-methyl-3-oxo-3,4-dihydropyrazin-2-yl)amino]-2-[(3S)-3-(dimethylamino) pyrrolidin-1-yl]phenyl]carbamate: Into a 250-mL round-bottom flask, was placed tert-butyl N-[5-amino-2-[(3S)-3-(dimethylamino)pyrrolidin-1-yl]phenyl]carbamate (1 g, 1 equiv), 3,5-dibromo-1-methyl-1,2-dihydropyrazin-2-one (1 g, 1.20 equiv), DIEA (1 g, 2.49 equiv), i-PrOH (10 mL). The resulting solution was stirred overnight at 80° C. The reaction mixture was cooled to room temperature. The resulting mixture was concentrated. The residue was applied onto a silica gel column with EA/PE (50:50). This resulted in 1 g (60.62%) of tert-butyl N-[5-[(6-bromo-4-methyl-3-oxo-3,4-dihydropyrazin-2-yl)amino]-2-[(3S)-3-(dimethylamino) pyrrolidin-1-yl]phenyl]carbamate as a yellow solid. LC-MS-729-C-5: (ES, m/z): 507 $[M+1-1]^+$ Synthesis of 3-([3-amino-4-[(3S)-3-(dimethylamino)pyrrolidin-1-yl]phenyl]amino)-5-bromo-1-methyl-1,2-dihydropyrazin-2-one: Into a 25-mL round-bottom flask, was placed tert-butyl N-[5-[(6-bromo-4-methyl-3-oxo-3,4-dihydropyrazin-2-yl)amino]-2-[(3S)-3-(dimethylamino)pyrrolidin-1-yl]phenyl]carbamate (1 g, 0.39 mmol, 1 equiv), HCl/Dioxane (10 mL). The resulting solution was stirred for 30 min at room temperature. The resulting mixture was concentrated. This resulted in 750 mg (93.43%) of 3-([3-amino-4-[(3S)-3-(dimethylamino)pyrrolidin-1-yl]phenyl]amino)-5-bromo-1-methyl-1,2-dihydropyrazin-2-one as a light yellow solid. LC-MS-729-C-6: (ES, m/z): 407 $[M+1-1]^+$ Synthesis of N-[5-[(6-bromo-4-methyl-3-oxo-3,4-dihydropyrazin-2-yl)amino]-2-[3-(dimethylamino)pyrrolidin-1-yl]phenyl]prop-2-enamide: Into a 50-mL round-bottom flask, was placed 3-([3-amino-4-[3-(dimethylamino)pyrrolidin-1-yl]phenyl]amino)-5-bromo-1-methyl-1,2-dihydropyrazin-2-one (600 mg, 1.96 mmol, 1 equiv), prop-2-enoic acid (127.2 mg, 2.36 mmol, 1.2 equiv), HATU (672 mg, 2.36 mmol, 1.2 equiv), NMM (596 mg, 7.86 mmol, 4.0 equiv), MeCN (15 mL). The resulting solution was stirred for 30 min at room temperature. The resulting mixture was concentrated. The crude product was purified by Prep-HPLC. This resulted in 307 mg (45.25%) of N-[5-[(6-bromo-4-methyl-3-oxo-3,4-dihydropyrazin-2-yl)amino]-2-[3-(dimethylamino)pyrrolidin-1-yl]phenyl]prop-2-enamide as a light yellow solid. LC-MS-729-C-1: (ES, m/z): 461 $[M+H]^+$ Synthesis of N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(3-(dimethylamino)pyrrolidin-1-yl)phenyl)acrylamide: Into a 25-mL round-bottom flask purged and maintained with an inert atmosphere of nitrogen, was placed N-[5-[(6-bromo-4-methyl-3-oxo-3,4-dihydropyrazin-2-yl)amino]-2-[(3S)-3-(dimethylamino) pyrrolidin-1-yl]phenyl]prop-2-enamide (50 mg, 0.11 mmol, 1 equiv), (2-[4,4-dimethyl-9-oxo-1,10-diazatricyclo[6.4.0.0^[2,6]]dodeca-2(6),7-dien-10-yl]-3-(hydroxymethyl)pyridin-4-yl)boronic acid (50.0 mg, 0.14 mmol, 1.3 equiv), $Pd(dppf)Cl_2$ (9.3 mg, 0.01 mmol, 0.1 equiv), $K_2CO_3$ (37.4 mg, 0.27 mmol, 2.5 equiv), dioxane (5 mL), $H_2O$ (0.5 mL). The resulting solution was stirred for 1 hr at 90° C. The reaction mixture was cooled to room temperature. The solids were filtered out. The filtrate was concentrated. The crude product was purified by Prep-HPLC. This resulted in 14 mg (18.67%) of N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(3-(dimethylamino)pyrrolidin-1-yl) phenyl)acrylamide as a white solid. LC-MS-729-C-0: (ES, m/z): 692 $[M+H]^+$. $^1$H-NMR-PH-729-C-0: (300 MHz, DMSO, ppm): δ9.38 (d, J=5.1 Hz, 1H), 9.17 (s, 1H), 8.44 (d, J=5.1 Hz, 1H), 8.34-8.32 (m, 1H), 7.76-7.63 (m, 3H), 6.86 (d, J=8.7 Hz, 1H), 6.62-6.48 (m, 2H), 6.27 (d, J=16.2 Hz, 1H), 5.73 (d, J=11.4 Hz, 1H), 5.05-4.95 (m, 1H), 4.70-4.38 (m, 2H), 4.29-4.20 (m, 3H), 3.89-3.84 (m, 1H), 3.55 (s, 3H), 3.14-3.07 (m, 3H), 2.74-2.49 (m, 6H), 2.15 (s, 6H), 2.05 (m, 1H), 1.75-1.69 (m, 1H), 1.23 (s, 6H).

Example 14: Preparation of N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(piperidin-3-yl)phenyl)acrylamide Synthesis of tert-butyl 3-(4-amino-2-nitrophenyl)-5,6-dihydro-2H-pyridine-1-carboxylate: Into a 500-mL round-bottom flask purged and maintained with an inert atmosphere of nitrogen, was placed tert-butyl 3-(4,4,5,5-tetramethyl-1,3,2-dioxaborolan-2-yl)-5,6-dihydro-2H-pyridine-1-carboxylate (8.55 g, 27.647 mmol, 1.20 equiv), 4-bromo-3-nitroaniline (5.00 g, 23.039 mmol, 1.00 equiv), $Pd(dppf)Cl_2CH_2Cl_2$(1.88 g, 2.304 mmol, 0.10 equiv), $K_2CO_3$ (6.37 g, 46.091 mmol, 2.00 equiv), dioxane (80.00 mL), $H_2O$ (20.00 mL). The resulting solution was stirred for 2 h at 100° C. The solids were filtered out. The combined organic layer was concentrated. The residue was applied onto a silica gel column with ethyl acetate/petroleum ether (60:40). This resulted in 7 g (95.14%) of tert-butyl 3-(4-amino-2-nitrophenyl)-5,6-dihydro-2H-pyridine-1-carboxylate as a white solid. LC-MS-751-1: (ES, m/z): 320 $[M+H]^+$ Synthesis of tert-butyl 3-(4-[[(benzyloxy)carbonyl]amino]-2-nitrophenyl)-5,6-dihydro-2H-pyridine-1-carboxylate: Into a 250-mL 3-necked round-bottom flask, was placed tert-butyl 3-(4-amino-2-nitrophenyl)-5,6-dihydro-2H-pyridine-1-carboxylate (7.00 g, 21.919 mmol, 1.00 equiv), $Na_2CO_3$ (4.65 g, 43.838 mmol, 2.00 equiv), DCM (50.00 mL). This was followed by the addition of $H_2O$ (10.00 mL) stirred at 0° C. To this was added benzyl chloroformate (4.49 g, 26.303 mmol, 1.20 equiv) at 0° C. The resulting solution was stirred for overnight at room temperature. The reaction was then quenched by the addition of water. The mixture was dried over anhydrous sodium sulfate and concentrated. This resulted in 9 g of tert-butyl 3-(4-[[(benzyloxy)carbonyl]amino]-2-nitrophenyl)-5,6-dihydro-2H-pyridine-1-carboxylate as a light yellow oil. LC-MS-751-2: (ES, m/z): 454 $[M+H]^+$ Synthesis of tert-butyl 3-(2-amino-4-[[(benzyloxy)carbonyl]amino]phenyl)-5,6-dihydro-2H-pyridine-1-carboxylate: Into a 100-mL round-bottom flask, was placed tert-butyl 3-(4-[[(benzyloxy)carbonyl]amino]-2-nitrophenyl)-5,6-dihydro-2H-pyridine-1-carboxylate (5.00 g, 11.025 mmol, 1.00 equiv), Fe (3.08 g, 55.127 mmol, 5.00 equiv), $CH_3COOH$ (20.00 mL), $H_2O$ (2.00 mL). The resulting solution was stirred for 1 h at 60° C. The resulting mixture was concentrated. The resulting solution was extracted with ethyl acetate The pH value of the solution was adjusted to 7 with $NaHCO_3$. The resulting mixture was washed with brine. The mixture was dried over anhydrous sodium sulfate and concentrated. The residue was applied onto a silica gel column with ethyl acetate/petroleum ether (60:40). This resulted in 4 g (85.66%) of tert-butyl 3-(2-amino-4-[[(benzyloxy)carbonyl]amino]phenyl)-5,6-dihydro-2H-pyridine-1-carboxylate as a yellow solid. LC-MS-751-3: (ES, m/z): 424 $[M+H]^+$. $^1$H NMR-751-3: (300 MHz, DMSO-$d_6$, ppm): δ9.49 (s, 1H), 7.49-7.32 (m, 5H), 6.88 (d, J=2.0 Hz, 1H), 6.76 (d, J=8.2 Hz, 1H), 6.61 (dd, J=8.2, 2.1 Hz, 1H), 5.78-5.70 (s, 1H), 5.13 (s, 2H), 4.84 (s, 2H), 3.89 (d, J=2.7 Hz, 2H), 3.48 (t, J=5.6 Hz, 2H), 2.25-2.13 (s, 2H), 1.42 (s, 9H).

Synthesis of tert-butyl 3-(4-[[(benzyloxy)carbonyl]amino]-2-[(tert-butoxycarbonyl)amino]phenyl)-5,6-dihydro-2H-pyridine-1-carboxylate: Into a 250-mL round-bottom flask, was placed tert-butyl 3-(2-amino-4-[[(benzyloxy)carbonyl]amino]phenyl)-5,6-dihydro-2H-pyridine-1-carboxylate (4.00 g, 9.445 mmol, 1.00 equiv), di-tert-butyl dicarbonate (4.12 g, 18.890 mmol, 2.00 equiv), $K_2CO_3$ (2.61 g, 18.885 mmol, 2.00 equiv), dioxane (80.00 mL), $H_2O$ (40.00 mL). The resulting solution was stirred for overnight at room temperature. The reaction was then quenched by the addition of water. The resulting solution was extracted with ethyl acetate. The resulting mixture was washed with brine. The mixture was dried over anhydrous sodium sulfate and concentrated. The residue was applied onto a silica gel column with ethyl acetate/petroleum ether (40:60). This resulted in 5 g (101.10%) of tert-butyl 3-(4-[[(benzyloxy)carbonyl]amino]-2-[(tert-butoxycarbonyl)amino]phenyl)-5,6-dihydro-2H-pyridine-1-carboxylate as a white solid. LC-MS-751-4: (ES, m/z): 524 $[M+H]^+$. $^1$H NMR-751-4: (300 MHz, DMSO-$d_6$, ppm): δ9.79 (s, 1H), 8.31 (s, 1H), 7.51 (d, J=2.1 Hz, 1H), 7.50-7.31 (m, 5H), 7.25 (dd, J=8.4, 2.2 Hz, 1H), 7.07 (d, J=8.4 Hz, 1H), 5.69 (s, 1H), 5.16 (s, 2H), 3.97 (s, 2H), 3.45 (t, J=5.7 Hz, 2H), 2.18 (s, 2H), 1.42 (s, 18H).

Synthesis of tert-butyl 3-[4-amino-2-[(tert-butoxycarbonyl)amino]phenyl]piperidine-1-carboxylate: Into a 250-mL round-bottom flask purged and maintained with an inert atmosphere of nitrogen, was placed tert-butyl3-(4-[[(benzyloxy)carbonyl]amino]-2-[(tert-butoxycarbonyl)amino]phenyl)-5,6-dihydro-2H-pyridine-carboxylate (5.00 g, 9.549 mmol, 1.00 equiv), Pd/C (500.00 mg), MeOH (100 mL), EA (50.00 mL). The resulting solution was stirred for overnight at rt. The solids were collected by filtration. The combined organic layer was concentrated. This resulted in 3.4 g (90.95%) of tert-butyl 3-[4-amino-2-[(tert-butoxycarbonyl)amino]phenyl]piperidine-1-carboxylate as colorless oil. LC-MS-751-5: (ES, m/z): 392 $[M+H]^+$ Synthesis of tert-butyl 3-[4-[(6-bromo-4-methyl-3-oxopyrazin-2-yl)amino]-2-[(tert-butoxycarbonyl)amino]phenyl]piperidine-1-carboxylate: Into a 250-mL round-bottom flask, was placed tert-butyl 3-[4-amino-2-[(tert-butoxycarbonyl)amino]phenyl]piperidine-1-carboxylate (3.40 g, 8.684 mmol, 1.00 equiv), 3,5-dibromo-1-methylpyrazin-2-one (2.56 g, 9.553 mmol, 1.1 equiv), i-PrOH (50.00 mL), DIEA (2.24 g, 17.369 mmol, 2.0 equiv). The resulting solution was stirred for overnight at 90° C. The resulting mixture was concentrated. The residue was applied onto a silica gel column with ethyl acetate/petroleum ether (40:60). This resulted in 4 g (79.62%) of tert-butyl 3-[4-[(6-bromo-4-methyl-3-oxopyrazin-2-yl)amino]-2-[(tert-butoxycarbonyl)amino]phenyl]piperidine-1-carboxylate as a light yellow solid.

LC-MS-751-6: (ES, m/z): 578 $[M+H]^+$.

Synthesis of 3-[[3-amino-4-(piperidin-3-yl)phenyl]amino]-5-bromo-1-methylpyrazin-2-one: Into a 250-mL round-bottom flask, was placed tert-butyl 3-[4-[(6-bromo-4-methyl-3-oxopyrazin-2-yl)amino]-2-[(tert-butoxycarbonyl)amino]phenyl]piperidine-1-carboxylate (4.00 g). To the above HCl(g)/MeOH (80.00 mL) was added. The resulting solution was stirred for 2 hr at room temperature. The resulting mixture was concentrated. This resulted in 2.9 g of 3-[[3-amino-4-(piperidin-3-yl)phenyl]amino]-5-bromo-1-methylpyrazin-2-one as a white solid. LC-MS-751-7: (ES, m/z): 378 $[M+H]^+$ Synthesis of tert-butyl 3-[2-amino-4-[(6-bromo-4-methyl-3-oxopyrazin-2-yl)amino]phenyl]piperidine-1-carboxylate: Into a 250-mL round-bottom flask, was placed 3-[[3-amino-4-(piperidin-3-yl)phenyl]amino]-5-bromo-1-methylpyrazin-2-one (2.90 g, 7.666 mmol, 1.00 equiv), $Boc_2O$ (1.84 g, 8.431 mmol, 1.10 equiv), TEA (1.55 g, 15.333 mmol, 2.00 equiv), DCM (50 ml). The resulting solution was stirred for 1 overnight at room temperature. The resulting mixture was concentrated. The crude product was purified by re-crystallization from ethyl ether. This resulted in 2.5 g (68.17%) of tert-butyl 3-[2-amino-4-[(6-bromo-4-methyl-3-oxopyrazin-2-yl)amino]phenyl]piperidine-1-carboxylate as a white solid. LC-MS-751-8: (ES, m/z): 478 $[M+H]^+$. $^1H$ NMR-751-8: (300 MHz, DMSO-$d_6$, ppm): δ 8.99 (s, 1H), 7.27 (s, 1H), 7.11-7.01 (m, 2H), 6.92 (d, J=9.0 Hz, 1H), 4.90 (s, 2H), 3.98 (s, 2H), 3.43 (s, 3H), 2.84-2.54 (m, 3H), 1.90-1.82 (m, 1H), 1.73-1.64 (m, 1H), 1.60-1.46 (m, 2H), 1.42 (s, 9H).

Synthesis of tert-butyl 3-[4-[(6-bromo-4-methyl-3-oxopyrazin-2-yl)amino]-2-(prop-2-enamido)phenyl]piperidine-1-carboxylate: Into a 25-mL round-bottom flask, was placed tert-butyl 3-[2-amino-4-[(6-bromo-4-methyl-3-oxopyrazin-2-yl)amino]phenyl]piperidine-1-carboxylate (500.00 mg, 1.045 mmol, 1.00 equiv), acryloyl chloride (141.90 mg, 1.568 mmol, 1.5 equiv), NMM (211.43 mg, 2.090 mmol, 2.00 equiv), DCM (10 mL). The resulting solution was stirred for 2 hr at room temperature. The resulting mixture was concentrated. The residue was applied onto a silica gel column with ethyl acetate/petroleum ether (70:30). This resulted in 300 mg (53.91%) of tert-butyl 3-[4-[(6-bromo-4-methyl-3-oxopyrazin-2-yl)amino]-2-(prop-2-enamido)phenyl]piperidine-1-carboxylate as a yellow solid. LC-MS-751-9: (ES, m/z): 532 $[M+H]^+$. $^1H$ NMR-751-9: (300 MHz, DMSO-$d_6$, ppm): δ9.67 (s, 1H), 9.47 (s, 1H), 7.86-7.75 (m, 2H), 7.36-7.25 (m, 2H), 6.58-6.43 (m, 1H), 6.24 (dd, J=17.0, 2.1 Hz, 1H), 5.75 (d, J=7.6 Hz, 1H), 4.10-3.81 (m, 2H), 3.44 (s, 3H), 2.83-2.62 (m, 3H), 1.87-1.76 (m, 1H), 1.70 (d, J=13.4 Hz, 1H), 1.65-1.50 (m, 1H), 1.37 (s, 9H).

Synthesis of tert-butyl 3-(4-[[6-(2-[4,4-dimethyl-9-oxo-1,10-diazatricyclo[6.4.0.0^[2,6]]dodeca-2(6),7-dien-10-yl]-3-methylpyridin-4-yl)-4-methyl-3-oxopyrazin-2-yl]amino]-2-(prop-2-enamido)phenyl)piperidine-1-carboxylate: Into a 40-mL microwave tube and maintained with an inert atmosphere of nitrogen, was placed tert-butyl 3-[4-[(6-bromo-4-methyl-3-oxopyrazin-2-yl)amino]-2-(prop-2-enamido)phenyl]piperidine-1-carboxylate (300.00 mg, 0.563 mmol, 1.00 equiv), 2-[4,4-dimethyl-9-oxo-1,10-diazatricyclo[6.4.0.0^[2,6]]dodeca-2(6),7-dien-10-yl]-3-methylpyridin-4-ylboronic acid (248.46 mg, 0.732 mmol, 1.30 equiv), Pd(dppf)$Cl_2CH_2Cl_2$ (46.01 mg, 0.056 mmol, 0.10 equiv), $K_2CO_3$ (155.51 mg, 1.127 mmol, 2.00 equiv), DME (10.00 mL), $H_2O$ (2.00 mL). The resulting solution was stirred for 1 hr at 90° C. The resulting mixture was concentrated. The residue was applied onto a silica gel column with ethyl acetate/petroleum ether (40:60). This resulted in 240 mg (57.03%) of tert-butyl 3-(4-[[6-(2-[4,4-dimethyl-9-oxo-1,10-diazatricyclo[6.4.0.0^[2,6]]dodeca-2(6),7-dien-10-yl]-3-methylpyridin-4-yl)-4-methyl-3-oxopyrazin-2-yl]amino]-2-(prop-2-enamido)phenyl)piperidine-1-carboxylate as a yellow solid. LC-MS-751-10: (ES, m/z): 747 $[M+H]^+$ Synthesis of N-(5-[[6-(2-[4,4-dimethyl-9-oxo-1,10-diazatricyclo[6.4.0.0^[2,6]]dodeca-2(6),7-dien-10-yl]-3-methylpyridin-4-yl)-4-methyl-3-oxopyrazin-2-yl]amino]-2-(piperidin-3-yl)phenyl)prop-2-enamide-: Into a 25-mL round-bottom flask, was placed tert-butyl 3-(4-[[6-(2-[4,4-dimethyl-9-oxo-1,10-diazatricyclo [6.4.0.0^[2,6]]dodeca-2(6),7-dien-10-yl]-3-methylpyridin-4-yl)-4-methyl-3-oxopyrazin-2-yl]amino]-2-(prop-2-enamido)phenyl)piperidine-1-carboxylate (150.00 mg, 0.201 mmol, 1.00 equiv), DCM (8.00 mL), TFA (1.5. mL). The resulting solution was stirred for 2.5 hr at room temperature. The resulting mixture was concentrated. The reaction was then quenched by the addition of $NaHCO_3$. The resulting solution was extracted with dichloromethane. The resulting mixture was washed with brine. The mixture was dried over anhydrous sodium sulfate and concentrated. The crude product was purified by Prep-HPLC. This resulted in 80 mg (61.59%) of N-(5-[[6-(2-[4,4-dimethyl-9-oxo-1,10-diazatricyclo[6.4.0.0^[2,6]]dodeca-2(6),7-dien-10-yl]-3-methylpyridin-4-yl)-4-methyl-3-oxopyrazin-2-yl]amino]-2-(piperidin-3-yl)phenyl)prop-2-enamide as a white solid. LC-MS-751-0: (ES, m/z): 647 $[M+H]^+$. $^1H$ NMR-751-0: (300 MHz, DMSO-$d_6$, ppm): δ9.61 (s, 1H), 9.29 (s, 1H), 8.32 (d, J=5.0 Hz, 1H), 8.16 (d, J=7.2 Hz, 1H), 7.77 (d, J=8.5 Hz, 1H), 7.49 (d, J=4.8 Hz, 1H), 7.43 (s, 1H), 7.21 (d, J=8.6 Hz, 1H), 6.60-6.47 (m, 2H), 6.23 (d, J=16.6 Hz, 1H), 5.70 (d, J=10.2 Hz, 1H), 4.30-4.11 (m, 3H), 3.84 (d, J=12.5 Hz, 1H), 3.57 (s, 3H), 2.99-2.73 (m, 3H), 2.58 (d, J=5.5 Hz, 2H), 2.43 (s, 3H), 2.29 (s, 3H), 1.83-1.69 (m, 1H), 1.69-1.58 (m, 1H), 1.58-1.37 (m, 2H), 1.23 (s, 7H).

Example 15: Preparation of N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(4-methylpiperazine-1-carbonyl)phenyl)acrylamide Synthesis of methyl 2-amino-4-nitrobenzoate. Into a 100-mL round-bottom flask, was placed 2-amino-4-nitrobenzoic acid (2.00 g), $SOCl_2$ (4.00 mL), MeOH (20.00 mL). The resulting solution was stirred for 3 hr at 55° C. The reaction mixture was cooled. The crude product was purified by re-crystallization from a ether. The solids were collected by filtration. This resulted in 1 g of methyl 2-amino-4-nitrobenzoate as a yellow solid. LC-MS-752-1: (ES, m/z): 197 $[M+H]^+$. $^1H$ NMR-752-1: (300 MHz, $CDCl_3$, ppm): δ8.02 (d, J=8.8 Hz, 1H), 7.53 (d, J=2.2 Hz, 1H), 7.42 (dd, J=8.8, 2.2 Hz, 1H), 6.05 (brs, 2H), 3.94 (s, 3H).

Synthesis of methyl 2-[bis(tert-butoxycarbonyl)amino]-4-nitrobenzoate: Into a 100-mL round-bottom flask, was placed methyl 2-amino-4-nitrobenzoate (1.00 g, 5.098 mmol, 1.00 equiv), $Boc_2O$ (3.34 g, 15.293 mmol, 3.00 equiv), TEA (1.03 g, 10.196 mmol, 2.00 equiv), DMAP (0.06 g, 0.510 mmol, 0.10 equiv), THF (20.00 mL). The resulting solution was stirred for 4 hr at room temperature. The reaction was then quenched by the addition of water. The resulting solution was extracted with ethyl acetate dried over anhydrous sodium sulfate and concentrated. This resulted in 1.8 g (89.08%) of methyl 2-[bis(tert-butoxycarbonyl)amino]-4-nitrobenzoate as a yellow solid. LC-MS-752-2: (ES, m/z): 397 $[M+H]^+$. $^1H$ NMR-752-2: (300 MHz, $CDCl_3$, ppm): δ8.26 (dd, J=8.6, 2.2 Hz, 1H), 8.17 (d, J=8.6 Hz, 1H), 8.10 (d, J=2.2 Hz, 1H), 3.94 (s, 3H), 1.42 (s, 18H).

Synthesis of 2-[bis(tert-butoxycarbonyl)amino]-4-nitrobenzoic acid: Into a 100-mL round-bottom flask, was placed methyl 2-[bis(tert-butoxycarbonyl)amino]-4-nitrobenzoate (1.80 g, 1 equiv), LiOH (300.00 mg), $H_2O$ (4.00 mL), THF (20.00 mL). The resulting solution was stirred for 1 overnight at room temperature. The reaction was then quenched by the addition of 1N hydrochloric acid aqueous solution was added to the reaction solution and extracted with ethyl acetate. The organic layer was dried over anhydrous $Na_2SO_4$, concentrated. This resulted in 1 g (57.59%) of 2-[bis(tert-butoxycarbonyl)amino]-4-nitrobenzoic acid as a yellow solid.

LC-MS-752-3: (ES, m/z): 383 $[M+H]^+$.

Synthesis of tert-butyl N-(tert-butoxycarbonyl)-N-[2-(4-methylpiperazine-1-carbonyl)-5-nitrophenyl]carbamate-: Into a 50-mL round-bottom flask, was placed 2-[bis(tert-butoxycarbonyl)amino]-4-nitrobenzoic acid (1.00 g, 2.615 mmol, 1.00 equiv), piperazine, 1-methyl-(0.31 g, 3.138 mmol, 1.20 equiv), HATU (1.49 g, 3.923 mmol, 1.50 equiv), NMM (0.53 g, 5.231 mmol, 2.00 equiv), DCM (15.00 mL). The resulting solution was stirred for 4 hr at room temperature. The resulting mixture was concentrated. The residue was applied onto a silica gel column with ethyl acetate/petroleum ether (100:1). This resulted in 500 mg (41.16%) of tert-butyl N-(tert-butoxycarbonyl)-N-[2-(4-methylpiperazine-1-carbonyl)-5-nitrophenyl]carbamate as a light yellow solid. LC-MS-752-4: (ES, m/z): 465 $[M+H]^+$ Synthesis of tert-butyl N-[5-amino-2-(4-methylpiperazine-1-carbonyl)phenyl]-N-(tert-butoxycarbonyl)carbamate: Into a 100-mL round-bottom flask purged and maintained with an inert atmosphere of $H_2$, was placed tert-butyl N-(tert-butoxycarbonyl)-N-[2-(4-methylpiperazine-1-carbonyl)-5-nitrophenyl]carbamate (500.00 mg), MeOH (20.00 ml), Pd/C (500.00 mg). The resulting solution was stirred for 6 hr at room temperature. The solids were collected by filtration. The combined organic layer was concentrated. This resulted in 400 mg of tert-butyl N-[5-amino-2-(4-methylpiperazine-1-carbonyl)phenyl]-N-(tert-butoxycarbonyl)carbamate as colorless oil. LC-MS-752-5: (ES, m/z): 435 $[M+H]^+$.

Synthesis of tert-butyl N-[5-[(6-bromo-4-methyl-3-oxopyrazin-2-yl)amino]-2-(4-methylpiperazine-1-carbonyl)phenyl]-N-(tert-butoxycarbonyl)carbamate: Into a 250-mL round-bottom flask purged and maintained with an inert atmosphere of nitrogen, was placed tert-butyl N-[5-amino-2-(4-methylpiperazine-1-carbonyl)phenyl]-N-(tert-butoxycarbonyl)carbamate (400.00 mg, 0.921 mmol, 1.00 equiv), 3,5-dibromo-1-methylpyrazin-2-one (369.92 mg, 1.381 mmol, 1.5 equiv), $Pd_2(dba)_3$ (168.59 mg, 0.184 mmol, 0.2 equiv), XantPhos (213.05 mg, 0.368 mmol, 0.4 equiv), $Cs_2CO_3$ (599.85 mg, 1.841 mmol, 2.0 equiv), Toluene (25.00 mL). The resulting solution was stirred for 4 hr at 100° C. The resulting mixture was concentrated. The residue was applied onto a silica gel column with ethyl acetate/petroleum ether (70:30). This resulted in 200 mg (34.96%) of tert-butyl N-[5-[(6-bromo-4-methyl-3-oxopyrazin-2-yl)amino]-2-(4-methylpiperazine-1-carbonyl)phenyl]-N-(tert-butoxycarbonyl)carbamate as a light yellow solid. LC-MS-752-6: (ES, m/z): 621 $[M+H]^+$ Synthesis of 3-[[3-amino-4-(4-methylpiperazine-1-carbonyl)phenyl]amino]-5-bromo-1-methylpyrazin-2-one: Into a 50-mL round-bottom flask, was placed tert-butyl N-[5-[(6-bromo-4-methyl-3-oxopyrazin-2-yl)amino]-2-(4-methylpiperazine-1-carbonyl)phenyl]-N-(tert-butoxycarbonyl)carbamate (200.00 mg), HCl(gas) in 1,4-dioxane (10.00 mL). The resulting solution was stirred for 2 hr at room temperature. The resulting mixture was concentrated. This resulted in 120 mg of 3-[[3-amino-4-(4-methylpiperazine-1-carbonyl)phenyl]amino]-5-bromo-1-methylpyrazin-2-one as a white solid. LC-MS-752-7: (ES, m/z): 421 $[M+H]^+$.

Synthesis of N-[5-[(6-bromo-4-methyl-3-oxopyrazin-2-yl)amino]-2-(4-methylpiperazine-1-carbonyl)phenyl]prop-2-enamide: Into a 50-mL round-bottom flask, was placed 3-[[3-amino-4-(4-methylpiperazine-1-carbonyl)phenyl]amino]-5-bromo-1-methylpyrazin-2-one (120.00 mg, 0.285 mmol, 1.00 equiv), acryloyl chloride (28.36 mg, 0.313 mmol, 1.10 equiv), NMM (57.62 mg, 0.570 mmol, 2.00 equiv), DCM (10.00 mL). The resulting solution was stirred for 30 min at room temperature. The resulting mixture was concentrated. The crude product was purified by Flash-Prep-HPLC 0.1% $NH_3 \cdot H_2O$:MeCN=30% increasing to 0.1% $NH_3 \cdot H_2O$:MeCN=58% within 9 min. This resulted in 80 mg (59.09%) of N-[5-[(6-bromo-4-methyl-3-oxopyrazin-2-yl)amino]-2-(4-methylpiperazine-1-carbonyl)phenyl]prop-2-enamide as a white solid. LC-MS-752-8: (ES, m/z): 475 $[M+H]^+$.

Synthesis of –752-0: Into a 8-mL vial purged and maintained with an inert atmosphere of nitrogen, was placed N-[5-[(6-bromo-4-methyl-3-oxopyrazin-2-yl)amino]-2-(4-methylpiperazine-1-carbonyl)phenyl]prop-2-enamide (80.00 mg, 0.168 mmol, 1.00 equiv), 2-[4,4-dimethyl-9-oxo-1,10-diazatricyclo[6.4.0.0^[2,6]]dodeca-2(6),7-dien-10-yl]-3-methylpyridin-4-ylboronic acid (73.00 mg, 0.219 mmol, 1.30 equiv), $Pd(dppf)Cl_2CH_2Cl_2$ (13.74 mg, 0.017 mmol, 0.10 equiv), $K_2CO_3$ (46.52 mg, 0.337 mmol, 2.00 equiv), DME (8.00 mL), $H_2O$ (2.00 mL). The resulting solution was stirred for 1 hr at 90° C. The crude product was purified by Prep-HPLC. This resulted in 20 mg (17.23%) of N-(5-[[6-(2-[4,4-dimethyl-9-oxo-1,10-diazatricyclo[6.4.0.0^[2,6]]dodeca-2(6),7-dien-10-yl]-3-methylpyridin-4-yl)-4-methyl-3-oxopyrazin-2-yl]amino]-2-(4-methylpiperazine-1-carbonyl) phenyl)prop-2-enamide as a white solid. LC-MS-752-0: (ES, m/z): 690 $[M+H]^+$. $^1$H NMR-752-0: (300 MHz, DMSO-$d_6$, ppm): δ9.76 (s, 1H), 9.52 (s, 1H), 8.48 (s, 1H), 8.34 (d, J=5.0 Hz, 1H), 7.81 (dd, J=8.8, 1.8 Hz, 1H), 7.58-7.47 (m, 2H), 7.20 (d, J=8.5 Hz, 1H), 6.59-6.44 (m, 2H), 6.24 (dd, J=17.1, 1.8 Hz, 1H), 5.74 (dd, J=12.2, 2.4 Hz, 1H), 4.29-4.10 (m, 3H), 3.86 (d, J=11.9 Hz, 1H), 3.59 (s, 3H), 2.68-2.54 (m, 2H), 2.43 (s, 2H), 2.29 (s, 7H), 2.16 (s, 3H), 1.23 (s, 6H).

Example 16: Preparation of N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(2-methyl-1-morpholinopropan-2-yl)phenyl) acrylamide Synthesis of 5-bromo-1-methyl-3-([4-[2-methyl-1-(morpholin-4-yl)propan-2-yl]-3-nitrophenyl]amino)pyrazin-2-one: Into a 100-mL round-bottom flask purged and maintained with an inert atmosphere of nitrogen, was placed 4-[2-methyl-1-(morpholin-4-yl)propan-2-yl]-3-nitroaniline (400.00 mg, 1.432 mmol, 1.00 equiv), 3,5-dibromo-1-methylpyrazin-2-one (498.72 mg, 1.862 mmol, 1.30 equiv), $Pd_2(dba)_3$ (131.13 mg, 0.143 mmol, 0.10 equiv), XantPhos (165.71 mg, 0.286 mmol, 0.20 equiv), $Cs_2CO_3$ (933.11 mg, 2.864 mmol, 2.00 equiv), dioxane (20.00 mL). The resulting solution was stirred for 4 hr at 100° C. The solids were collected by filtration. The combined organic layer was concentrated. The crude product was purified by re-crystallization from MeCN. This resulted in 350 mg (52.41%) of 5-bromo-1-methyl-3-([4-[2-methyl-1-(morpholin-4-yl)propan-2-yl]-3-nitrophenyl]amino)pyrazin-2-one as a brown solid. LC-MS-753-1: (ES, m/z): 466 $[M+H]^+$. $^1$H NMR-753-1: (300 MHz, DMSO-$d_6$, ppm): δ9.90 (s, 1H), 8.19 (d, J=2.4 Hz, 1H), 8.08 (dd, J=8.9, 2.5 Hz, 1H), 7.62 (d, J=9.0 Hz, 1H), 7.43 (s, 1H), 3.53-3.39 (m, 7H), 2.53-2.47 (m, 2H), 2.23 (t, J=4.6 Hz, 4H), 1.29 (s, 6H).

Synthesis of 3-([3-amino-4-[2-methyl-1-(morpholin-4-yl) propan-2-yl]phenyl]amino)-5-bromo-1-methylpyrazin-2-one: Into a 100-mL round-bottom flask, was placed 5-bromo-1-methyl-3-([4-[2-methyl-1-(morpholin-4-yl)propan-2-yl]-3-nitrophenyl]amino)pyrazin-2-one (350.00 mg, 0.751 mmol, 1.00 equiv), $CH_3COOH$ (1352.13 mg, 22.516 mmol, 30.00 equiv), Zn (736.37 mg, 11.258 mmol, 15.00 equiv), EtOH (30.00 mL). The resulting solution was stirred for 2 hr at room temperature. The solids were collected by filtration. The combined organic layer was concentrated. The resulting solution was extracted with ethyl acetate The resulting mixture was washed with brine. The mixture was dried over anhydrous sodium sulfate and concentrated. This resulted in 300 mg (91.60%) of 3-([3-amino-4-[2-methyl-1-(morpholin-4-yl)propan-2-yl]phenyl]amino)-5-bromo-1-methylpyrazin-2-one as brown oil. LC-MS-753-2: (ES, m/z): 436 $[M+H]^+$.

Synthesis of N-[5-[(6-bromo-4-methyl-3-oxopyrazin-2-yl)amino]-2-[2-methyl-1-(morpholin-4-yl)propan-2-yl]phenyl]prop-2-enamide: Into a 100-mL round-bottom flask, was placed 3-([3-amino-4-[2-methyl-1-(morpholin-4-yl)propan-2-yl]phenyl]amino)-5-bromo-1-methylpyrazin-2-one (300.00 mg, 0.688 mmol, 1.00 equiv), acryloyl chloride (74.67 mg, 0.825 mmol, 1.20 equiv), NMM (139.08 mg, 1.375 mmol, 2.00 equiv), DCM (10.00 mL). The resulting solution was stirred for 30 min at room temperature. The resulting mixture was concentrated. The crude product was purified by Flash-Prep-HPLC 0.1% $NH_4HCO_3$:MeCN=30% increasing to 0.1% $NH_4HCO_3$:MeCN=70% within 9 min. This resulted in 260 mg (77.11%) of N-[5-[(6-bromo-4-methyl-3-oxopyrazin-2-yl)amino]-2-[2-methyl-1-(morpholin-4-yl)propan-2-yl]phenyl]prop-2-enamide as a white solid. LC-MS-753-3: (ES, m/z): 490 $[M+H]^+$. $^1$H NMR-753-3: (300 MHz, DMSO-$d_6$, ppm): δ10.75 (s, 1H), 9.40 (s, 1H), 7.95 (s, 1H), 7.77 (d, J=8.5 Hz, 1H), 7.39-7.25 (m, 2H), 6.61-6.44 (m, 1H), 6.27 (dd, J=16.9, 2.1 Hz, 1H), 5.81 (d, J=11.0 Hz, 1H), 3.54 (s, 4H), 3.44 (s, 3H), 2.36 (s, 4H), 1.35 (s, 6H).

Synthesis of N-(5-[[6-(2-[4,4-dimethyl-9-oxo-1,10-diazatricyclo[6.4.0.0^[2,6]]dodeca-2(6),7-dien-10-yl]-3-methylpyridin-4-yl)-4-methyl-3-oxopyrazin-2-yl]amino]-2-[2-methyl-1-(morpholin-4-yl)propan-2-yl]phenyl)prop-2-enamide: Into a 40-mL microwave and maintained with an inert atmosphere of nitrogen, was placed N-[5-[(6-bromo-4-methyl-3-oxopyrazin-2-yl)amino]-2-[2-methyl-1-(morpholin-4-yl)propan-2-yl]phenyl]prop-2-enamide (200.00 mg, 0.408 mmol, 1.00 equiv), 2-[4,4-dimethyl-9-oxo-1,10-diazatricyclo[6.4.0.0^[2,6]]dodeca-2(6),7-dien-10-yl]-3-methylpyridin-4-ylboronic acid (193.67 mg, 0.571 mmol, 1.40 equiv), $Pd(dppf)Cl_2CH_2Cl_2$ (33.30 mg, 0.041 mmol, 0.10 equiv), $K_2CO_3$ (112.73 mg, 0.816 mmol, 2.00 equiv), DME (10.00 mL), $H_2O$ (2.00 mL). The resulting solution was stirred for 2 hr at 95° C. The crude product was purified by Prep-HPLC. This resulted in 150 mg (52.18%) of N-(5-[[6-(2-[4,4-dimethyl-9-oxo-1,10-diazatricyclo[6.4.0.0^[2,6]]dodeca-2(6),7-dien-10-yl]-3-methylpyridin-4-yl)-4-methyl-3-oxopyrazin-2-yl]amino]-2-[2-methyl-1-(morpholin-4-yl)propan-2-yl]phenyl)prop-2-enamide as a light brown solid. LC-MS-753-0: (ES, m/z): 705 $[M+H]^+$. $^1$H NMR-753-0: (300 MHz, DMSO-d6, ppm): δ10.78 (s, 1H), 9.26 (s, 1H), 8.38-8.29 (m, 2H), 7.69 (d, J=8.6 Hz, 1H), 7.54 (d, J=5.2 Hz, 1H), 7.43 (s, 1H), 7.28 (d, J=8.8 Hz, 1H), 6.58-6.45 (m, 2H), 6.27 (d, J=16.8 Hz, 1H), 5.76 (d, J=10.2 Hz, 1H), 4.31-4.10 (m, 3H), 3.84 (d, J=12.4 Hz, 1H), 3.57 (s, 3H), 3.57-3.47 (m, 4H), 2.58 (d, J=5.8 Hz, 2H), 2.43 (s, 2H), 2.34 (d, J=4.7 Hz, 4H), 2.29 (s, 3H), 1.34 (d, J=4.2 Hz, 6H), 1.23 (s, 6H).

Example 17: Preparation of N-(5-[[6-(2-[4,4-dimethyl-9-oxo-1,10-diazatricyclo[6.4.0.0^[2,6]]dodeca-2(6),7-dien-10-yl]-3-methylpyridin-4-yl)-4-methyl-3-oxopyrazin-2-yl]amino]-2-[(2S)-2-methyl-4-(morpholin-4-yl)piperidin-1-yl]phenyl)prop-2-enamide Synthesis of tert-butyl (2S)-2-methyl-4-(morpholin-4-yl) piperidine-1-carboxylate: Into a 250-mL round-bottom flask, was placed tert-butyl (2S)-2-methyl-4-oxopiperidine-1-carboxylate (4.50 g, 21.099 mmol, 1.00 equiv), THF (70 mL), AcOH (1 mL), morpholine (3.68 g, 42.240 mmol, 2.00 equiv) and stirred for 10 min. This was followed by the addition of $NaBH(AcO)_3$ (8.94 g, 42.199 mmol, 2.00 equiv), in portions at room temperature. The resulting solution was stirred for 14 hr at 30 degrees C. in an oil bath. The reaction was then quenched by the addition of 3 mL of MeOH. The resulting mixture was concentrated. The residue was applied onto a silica gel column and eluted with PE/EA (1:4). This resulted in 4.5 g (74.99%) of tert-butyl (2S)-2-methyl-4-(morpholin-4-yl)piperidine-1-carboxylate as a white solid. LCMS-1 (ES, m/z): M+1: 285

Synthesis of 4-[(2S)-2-methylpiperidin-4-yl]morpholine: Into a 100-mL round-bottom flask, was placed tert-butyl (2S)-2-methyl-4-(morpholin-4-yl)piperidine-1-carboxylate (3.50 g), HCl in dioxane (40 mL, 2M). The resulting solution was stirred for 14 hr at room temperature. The resulting mixture was concentrated. This resulted in 2.3 g of 4-[(2S)-2-methylpiperidin-4-yl]morpholine as a white solid. LCMS-2 (ES, m/z): M+1: 185

Synthesis of 5-bromo-1-methyl-3-([4-[(2S)-2-methyl-4-(morpholin-4-yl)piperidin-1-yl]-3-nitrophenyl]amino) pyrazin-2-one: Into a 250-mL round-bottom flask, was placed 5-bromo-3-[(4-fluoro-3-nitrophenyl)amino]-1-methylpyrazin-2-one (3.91 g, 11.396 mmol, 1.00 equiv), 4-[(2S)-2-methylpiperidin-4-yl]morpholine (2.10 g, 11.396 mmol, 1.00 equiv), NMP (50.00 ml), DIEA (4.42 g, 34.199 mmol, 3.00 equiv). The resulting solution was stirred for 72 hr at 110 degrees C. in an oil bath. The resulting solution was diluted with 250 mL of $H_2O$. The resulting solution was extracted with 3×50 mL of dichloromethane. The resulting mixture was washed with 3×20 ml of $H_2O$. The mixture was dried over anhydrous sodium sulfate and concentrated. The residue was applied onto a silica gel column and eluted with dichloromethane/methanol (10:1). This resulted in 2.6 g (31.48%) of 5-bromo-1-methyl-3-([4-[(2S)-2-methyl-4-(morpholin-4-yl)piperidin-1-yl]-3-nitrophenyl]amino) pyrazin-2-one as a brown solid. LCMS-3 (ES, m/z): M+1: 507

Synthesis of 4-methyl-6-([4-[(2S)-2-methyl-4-(morpholin-4-yl)piperidin-1-yl]-3-nitrophenyl]amino)-5-oxopyrazin-2-ylboronic acid: Into a 50-mL round-bottom flask purged and maintained with an inert atmosphere of nitrogen, was placed 5-bromo-1-methyl-3-([4-[(2S)-2-methyl-4-(morpholin-4-yl) piperidin-1-yl]-3-nitrophenyl]amino) pyrazin-2-one (2.60 g, 5.124 mmol, 1.00 equiv), bis(pinacolato)diboron (2.60 g, 10.239 mmol, 2.00 equiv), XPhos Pd G3 (216.87 mg, 0.256 mmol, 0.05 equiv), KOAc (1.01 g, 10.291 mmol, 2.01 equiv), THF (30.00 mL, 0.416 mmol, 0.08 equiv). The resulting solution was stirred for 14 hr at 70 degrees C. in an oil bath. The solids were filtered out. The resulting mixture was concentrated. This resulted in 5 g(crude) of 4-methyl-6-([4-[(2S)-2-methyl-4-(morpholin-4-yl)piperidin-1-yl]-3-nitrophenyl]amino)-5-oxopyrazin-2-ylboronic acid as a brown solid. LCMS-4 (ES, m/z): M+1: 473

Synthesis of 4,4-dimethyl-10-[3-methyl-4-[4-methyl-6-([4-[(2S)-2-methyl-4-(oxan-4-yl) piperidin-1-yl]-3-nitrophenyl]amino)-5-oxopyrazin-2-yl]pyridin-2-yl]-1,10-diazatricyclo[6.4.0.0^[2,6]]dodeca-2(6),7-dien-9-one: Into a 8-mL vial purged and maintained with an inert atmosphere of nitrogen, was placed 4-methyl-6-([4-[(2S)-2-methyl-4-(morpholin-4-yl)piperidin-1-yl]-3-nitrophenyl]amino)-5-oxopyrazin-2-ylboronic acid (450.00 mg, crude), 10-(4-iodo-3-methylpyridin-2-yl)-4,4-dimethyl-1,10-diazatricyclo [6.4.0.0^[2,6]]dodeca-2(6),7-dien-9-one (100.00 mg, 0.237 mmol, 1.00 equiv), $Pd(dppf)Cl_2$ (19.38 mg, 0.024 mmol, 0.10 equiv), THF (2.00 mL, Infinity mmol, Infinity equiv), $H_2O$ (0.50 mL, 0.028 mmol, 0.12 equiv), $K_3PO_4$ (201.54 mg, 0.949 mmol, 4.00 equiv). The resulting solution was stirred for 14 hr at 50 degrees C. in an oil bath. The resulting mixture was concentrated. The residue was applied onto a silica gel column and eluted with dichloromethane/methanol (10:1). This resulted in 120 mg (70.13%) of 4,4-dimethyl-10-[3-methyl-4-[4-methyl-6-([4-[(2S)-2-methyl-4-(oxan-4-yl)piperidin-1-yl]-3-nitrophenyl]amino)-5-oxopyrazin-2-yl] pyridin-2-yl]-1,10-diazatricyclo[6.4.0.0^[2,6]]dodeca-2(6), 7-dien-9-one as a yellow solid. LCMS-1 (ES, m/z): M+1: 722

Synthesis of 10-[4-[6-([3-amino-4-[(2S)-2-methyl-4-(morpholin-4-yl)piperidin-1-yl]phenyl]amino)-4-methyl-5-oxopyrazin-2-yl]-3-methylpyridin-2-yl]-4,4-dimethyl-1,10-diazatricyclo[6.4.0.0^[2,6]]dodeca-2(6),7-dien-9-one: Into a 50-mL round-bottom flask, was placed 4,4-dimethyl-10-[3-methyl-4-[4-methyl-6-([4-[(2S)-2-methyl-4-(oxan-4-yl)piperidin-1-yl]-3-nitrophenyl]amino)-5-oxopyrazin-2-yl]pyridin-2-yl]-1,10-diazatricyclo[6.4.0.0^[2,6]]dodeca-2(6),7-dien-9-one (100.00 mg), THF (10.00 mL), Pd/C (10.00 mg). To the above $H_2$ (gas) was introduced in. The resulting solution was stirred for 6 hr at room temperature. The solids were filtered out. The residue was purified by Prep-TLC with dichloromethane/methanol (10:1). This resulted in 30 mg of 10-[4-[6-([3-amino-4-[(2S)-2-methyl-4-(morpholin-4-yl)piperidin-1-yl]phenyl]amino)-4-methyl-5-oxopyrazin-2-yl]-3-methylpyridin-2-yl]-4,4-dimethyl-1,10-diazatricyclo[6.4.0.0^[2,6]]dodeca-2(6),7-dien-9-one as a light yellow solid. LCMS-2 (ES, m/z): M+1: 692

Synthesis of N-(5-[[6-(2-[4,4-dimethyl-9-oxo-1,10-diazatricyclo[6.4.0.0^[2,6]]dodeca-2 (6),7-dien-10-yl]-3-methylpyridin-4-yl)-4-methyl-3-oxopyrazin-2-yl]amino]-2-[(2S)-2-methyl-4-(morpholin-4-yl]piperidin-1-yl]phenyl) prop-2-enamide: Into a 2-mL vial, was placed 10-[4-[6-([3-amino-4-[(2S)-2-methyl-4-(morpholin-4-yl)piperidin-1-yl] phenyl]amino)-4-methyl-5-oxopyrazin-2-yl]-3-methylpyridin-2-yl]-4,4-dimethyl-1,10-diazatricyclo [6.4.0.0^[2,6]]dodeca-2(6),7-dien-9-one (25.00 mg, 0.036 mmol, 1.00 equiv), DCM (0.50 mL), DIEA (9.34 mg, 0.072 mmol, 2.00 equiv). This was followed by the addition of acryloyl chloride (4.91 mg, 0.054 mmol, 1.50 equiv) dropwise with stirring at 0 degrees C. The resulting solution was stirred for 30 min at 0 degrees C. in a water/ice bath. The reaction was then quenched by the addition of 0.1 mL of MeOH. The crude product was purified by Prep-HPLC with the following conditions (Waters 2767): Column, X Bridge Prep C18 OBD 19*150 mm 5 urn; Mobile phase, A: 0.1% $NH_3$—$H_2O$ in water; B: ACN; Gradient: 37-52% B in 7.9 min; Flow rate: 20 ml/min; Detector, 220 nm. This resulted in 7 mg (25.97%) of N-(5-[[6-(2-[4,4-dimethyl-9-oxo-1,10-diazatricyclo[6.4.0.0^[2,6]]dodeca-2(6),7-dien-10-yl]-3-methylpyridin-4-yl)-4-methyl-3-oxopyrazin-2-yl]amino]-2-[(2S)-2-methyl-4-(morpholin-4-yl)piperidin-1-yl]phenyl) prop-2-enamide as a white solid. LCMS-0 (ES, m/z): M+1: 746. H-NMR-0: (300 MHz, DMSO-$d_6$) δ 9.20 (d, J=9.9 Hz, 2H), 9.05-8.94 (m, 1H), 8.35 (d, J=5.1 Hz, 1H), 7.66 (dt, J=10.1, 5.4 Hz, 2H), 7.41 (s, 1H), 7.22 (d, J=8.7 Hz, 1H), 6.65 (dd, J=16.8, 10.2 Hz, 1H), 6.55 (s, 1H), 6.25 (dd, J=16.8, 3.9 Hz, 1H), 5.78 (d, J=10.5 Hz, 1H), 4.40-4.05 (m, 3H), 3.85 (d, J=12.0 Hz, 1H), 3.59 (d, J=7.8 Hz, 7H), 2.92 (s, 1H), 2.80-2.75 (m, 1H), 2.61-2.59 (s, 1H), 2.43 (s, 2H), 2.35-2.25 (m, 4H), 1.89 (dd, J=29.1, 12.0 Hz, 2H), 1.70-1.50 (m, 1H), 1.46-1.33 (m, 1H), 1.23 (s, 6H), 0.75 (dd, J=6.3, 2.1 Hz, 3H).

Example 18: Preparation of N-(5-[[6-(2-[4,4-dimethyl-9-oxo-1,10-diazatricyclo[6.4.0.0^[2,6]]dodeca-2(6),7-dien-10-yl]-3-methylpyridin-4-yl)-4-methyl-3-oxopyrazin-2-yl]amino]-2-[4-(morpholin-4-yl) piperidin-1-yl]phenyl)prop-2-enamide hydrochloride Synthesis of 5-bromo-3-[(4-fluoro-3-nitrophenyl)amino]-1-methylpyrazin-2-one Into a 250-mL round-bottom flask, was placed 4-fluoro-3-nitroaniline (10.00 g, 64.055 mmol, 1.00 equiv), 3,5-dibromo-1-methylpyrazin-2-one (17.16 g, 64.052 mmol, 1.00 equiv), NMP (30 ml). The resulting solution was stirred for 1 h at 140 degrees C. in an oil bath. The resulting solution was diluted with 300 mL of EA. The solids were collected by filtration. This resulted in 13 g (59.15%) of 5-bromo-3-[(4-fluoro-3-nitrophenyl)amino]-1-methylpyrazin-2-one as a brown solid. LCMS-1 (ES, m/z): M+1: 343/345

Synthesis of 5-bromo-1-methyl-3-([4-[4-(morpholin-4-yl)piperidin-1-yl]-3-nitrophenyl]amino) pyrazin-2-one Into a 50-mL round-bottom flask, was placed 5-bromo-3-[(4-fluoro-3-nitrophenyl)amino]-1-methylpyrazin-2-one (1.00 g, 2.915 mmol, 1.00 equiv), 4-(piperidin-4-yl)morpholine (0.50 g, 2.915 mmol, 1.00 equiv), NMP (10.00 mL), DIEA (1.13 g, 8.743 mmol, 3.00 equiv). The resulting solution was stirred for 14 h at 110 degrees C. in an oil bath. The resulting solution was diluted with 30 mL of $H_2O$. The resulting solution was extracted with 3×10 mL of dichloromethane. The resulting mixture was washed with 3×5 of $H_2O$. The resulting mixture was washed with 1×10 mL of aq. NaCl and dried with sodium sulfate. The resulting mixture was concentrated. The residue was applied onto a silica gel column and purified with dichloromethane/methanol (10:1). This resulted in 800 mg (55.64%) of 5-bromo-1-methyl-3-([4-[4-(morpholin-4-yl)piperidin-1-yl]-3-nitrophenyl]amino) pyrazin-2-one as a brown solid. LCMS-2 (ES, m/z): M+1: 493/495

Synthesis of 4-methyl-6-([4-[4-(morpholin-4-yl)piperidin-1-yl]-3-nitrophenyl]amino)-5-oxopyrazin-2-ylboronic acid Into a 50-mL round-bottom flask and maintained with an inert atmosphere of nitrogen, was placed 5-bromo-1-methyl-3-([4-[4-(morpholin-4-yl)piperidin-1-yl]-3-nitrophenyl]amino)pyrazin-2-one (400.00 mg, 0.811 mmol, 1.00 equiv), bis(pinacolato)diboron (411.77 mg, 1.622 mmol, 2.00 equiv), 3G Xphos Pd (33.11 mg, 0.041 mmol, 0.05 equiv), KOAc (159.14 mg, 1.622 mmol, 2.00 equiv), THF (10.00 mL). The resulting solution was stirred for 14 h at 65 degrees C. in an oil bath. The solids were filtered out. The resulting mixture was concentrated. The resulting solution was diluted with 1 mL of $Et_2O$. The solids were collected by filtration. This resulted in 250 mg (67.28%) of 4-methyl-6-([4-[4-(morpholin-4-yl)piperidin-1-yl]-3-nitrophenyl] amino)-5-oxopyrazin-2-ylboronic acid as a orange solid. LCMS-7-3 (ES, m/z): M+1: 459

Synthesis of 4,4-dimethyl-10-[3-methyl-4-[4-methyl-6-([4-[4-(morpholin-4-yl)piperidin-1-yl]-3-nitrophenyl] amino)-5-oxopyrazin-2-yl]pyridin-2-yl]-1,10-diazatricyclo [6.4.0.0^[2,6]]dodeca-2(6),7-dien-9-one Into a 8-mL vial purged and maintained with an inert atmosphere of nitrogen, was placed 4-methyl-6-([4-[4-(morpholin-4-yl)piperidin-1-yl]-3-nitrophenyl]amino)-5-oxopyrazin-2-ylboronic acid (100.00 mg, 0.218 mmol, 1.00 equiv), 10-(4-iodo-3-methylpyridin-2-yl)-4,4-dimethyl-1,10-diazatricyclo [6.4.0.0^[2,6]]dodeca-2(6),7-dien-9-one (91.93 mg, 0.218 mmol, 1.00 equiv), Pd(dppf)$Cl_2$ (17.82 mg, 0.022 mmol, 0.10 equiv), $K_3PO_4$(138.95 mg, 0.655 mmol, 3.00 equiv), THF (0.80 mL), $H_2O$ (0.20 mL). The resulting solution was stirred for 14 h at 50 degrees C. in an oil bath. The residue was applied onto a silica gel column and purified with dichloromethane/methanol (10:1). This resulted in 110 mg (71.22%) of 4,4-dimethyl-10-[3-methyl-4-[4-methyl-6-([4-[4-(morpholin-4-yl)piperidin-1-yl]-3-nitrophenyl]amino)-5-oxopyrazin-2-yl]pyridin-2-yl]-1,10-diazatricyclo[6.4.0.0^[2,6]] dodeca-2(6),7-dien-9-one as a brown solid. LCMS-4 (ES, m/z): M+1: 708

Synthesis of 0-[4-[6-([3-amino-4-[4-(morpholin-4-yl)piperidin-1-yl]phenyl]amino)-4-methyl-5-oxopyrazin-2-yl]-3-methylpyridin-2-yl]-4,4-dimethyl-1,10-diazatricyclo [6.4.0.0^[2,6]]dodeca-2(6),7-dien-9-one Into a 50-mL round-bottom flask, was placed 4,4-dimethyl-10-[3-methyl-4-[4-methyl-6-([4-[4-(morpholin-4-yl)piperidin-1-yl]-3-nitrophenyl]amino)-5-oxopyrazin-2-yl]pyridin-2-yl]-1,10-diazatricyclo[6.4.0.0^[2,6]]dodeca-2(6),7-dien-9-one (100.00 mg, 0.141 mmol, 1.00 equiv), Pd/C (15.94 mg, 0.042 mmol, 0.30 equiv), THF (5.00 mL). To the above $H_2$(g) was introduced in. The resulting solution was stirred for 14 h at room temperature. The solids were filtered out. The resulting mixture was concentrated. This resulted in 70 mg (73.10%) of 10-[4-[6-([3-amino-4-[4-(morpholin-4-yl)piperidin-1-yl] phenyl]amino)-4-methyl-5-oxopyrazin-2-yl]-3-methylpyridin-2-yl]-4,4-dimethyl-1,10-diazatricyclo[6.4.0.0^[2,6]]dodeca-2(6),7-dien-9-one as a brown solid. LCMS-5 (ES, m/z): M+1: 678

Synthesis of N-(5-[[6-(2-[4,4-dimethyl-9-oxo-1,10-diazatricyclo[6.4.0.0^[2,6]]dodeca-2(6),7-dien-10-yl]-3-methylpyridin-4-yl)-4-methyl-3-oxopyrazin-2-yl]amino]-2-[4-(morpholin-4-yl)piperidin-1-yl]phenyl)prop-2-enamide hydrochloride Into a 8-mL vial, was placed 10-[4-[6-([3-amino-4-[4-(morpholin-4-yl)piperidin-1-yl]phenyl]amino)-4-methyl-5-oxopyrazin-2-yl]-3-methylpyridin-2-yl]-4,4-dimethyl-1,10-diazatricyclo[6.4.0.0^[2,6]]dodeca-2(6),7-dien-9-one (60 mg, 0.089 mmol, 1.00 equiv), DCM (1.00 mL), TEA (17.91 mg, 0.177 mmol, 2.00 equiv). Acryloyl chloride (12.02 mg, 0.133 mmol, 1.50 equiv) was added at 0 degrees C. in a water/ice bath. The resulting solution was stirred for 1 hr at 0 degrees C. in a water/ice bath. The reaction was then quenched by the addition of 0.1 mL of MeOH. The resulting mixture was concentrated. The crude product was purified by Prep-HPLC with the following conditions (Waters 2767): Column, X Bridge Prep C18 OBD 19*150 mm 5 um; Mobile phase, A: 0.1% HCl in water; B: ACN; Gradient: 30-80% B in 7.9 min; Flow rate: 20 ml/min; Detector, 220 nm. This resulted in 9 mg (13.23%) of N-(5-[[6-(2-[4,4-dimethyl-9-oxo-1,10-diazatricyclo [6.4.0.0^[2,6]]dodeca-2(6),7-dien-10-yl]-3-methylpyridin-4-yl)-4-methyl-3-oxopyrazin-2-yl]amino]-2-[4-(morpholin-4-yl)piperidin-1-yl]phenyl)prop-2-enamide hydrochloride as a yellow solid. LCMS-0 (ES, m/z): M+HCl+1: 768 H-NMR-0: $^1$H NMR (300 MHz, DMSO-$d_6$) δ 10.15 (s, 1H), 9.22 (s, 1H), 9.10 (s, 1H), 8.72 (s, 1H), 8.35 (d, J=5.1 Hz, 1H), 7.73-7.56 (m, 2H), 7.41 (s, 1H), 7.13 (d, J=8.7 Hz, 1H), 6.69-6.48 (m, 2H), 6.34-6.24 (m, 1H), 5.77 (d, J=10.8 Hz, 1H), 4.31-4.12 (s, 3H), 4.03 (d, J=12.0 Hz, 2H), 3.90-3.70 (m, 3H), 3.58 (s, 3H), 3.50-3.48 (m, 2H), 3.23-3.02 (m, 4H), 2.70-2.52 (m, 5H), 2.43 (s, 2H), 2.30 (s, 3H), 2.20-2.15 (m, 2H), 2.00-1.85 (m, 2H), 1.23 (s, 6H).

Example 19: Preparation of N-(5-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxopyrazin-2-yl]amino]-2-[4-(morpholin-4-yl)piperidin-1-yl]phenyl)prop-2-enamide Synthesis of 4,4-dimethyl-10-[4-[4-methyl-6-([4-[4-(morpholin-4-yl)piperidin-1-yl]-3-nitrophenyl]amino)-5-oxopyrazin-2-yl]-3-[(oxan-2-yloxy)methyl]pyridin-2-yl]-1,10-diazatricyclo[6.4.0.0^[2,6]]dodeca-2(6),7-dien-9-one Into a 8-mL round-bottom flask purged and maintained with an inert atmosphere of nitrogen, was placed 4-methyl-6-([4-[4-(morpholin-4-yl)piperidin-1-yl]-3-nitrophenyl]amino)-5-oxopyrazin-2-ylboronic acid (100.00 mg, 0.218 mmol, 1.00 equiv), 10-[4-iodo-3-[(oxan-2-yloxy)methyl]pyridin-2-yl]-4,4-dimethyl-1,10-diazatricyclo[6.4.0.0^[2,6]]dodeca-2(6), 7-dien-9-one (113.77 mg, 0.218 mmol, 1.00 equiv), THF (4.00 mL), $H_2O$ (1.00 mL, 0.056 mmol, 0.25 equiv), Pd(dppf)$Cl_2$ (17.82 mg, 0.022 mmol, 0.10 equiv), $K_3PO_4$ (138.95 mg, 0.655 mmol, 3.00 equiv). The resulting solution was stirred for 3 hr at 50 degrees C. in an oil bath. The resulting mixture was concentrated. The residue was applied onto a silica gel column and eluted with dichloromethane/methanol (10:1). This resulted in 90 mg (51.05%) of 4,4- dimethyl-10-[4-[4-methyl-6-([4-[4-(morpholin-4-yl)piperidin-1-yl]-3-nitrophenyl]amino)-5-oxopyrazin-2-yl]-3-[(oxan-2-yloxy)methyl]pyridin-2-yl]-1,10-diazatricyclo[6.4.0.0^[2,6]]dodeca-2(6),7-dien-9-one as a brown solid. LCMS-1 (ES, m/z): M+1: 808

Synthesis of 10-[4-[6-([3-amino-4-[4-(morpholin-4-yl)piperidin-1-yl]phenyl]amino)-4-methyl-5-oxopyrazin-2-yl]-3-[(oxan-2-yloxy)methyl]pyridin-2-yl]-4,4-dimethyl-1,10-diazatricyclo[6.4.0.0^[2,6]]dodeca-2(6),7-dien-9-one: Into a 50-mL round-bottom flask, was placed 4,4-dimethyl-10-[4-[4-methyl-6-([4-[4-(morpholin-4-yl)piperidin-1-yl]-3-nitrophenyl]amino)-5-oxopyrazin-2-yl]-3-[(oxan-2-yloxy)methyl]pyridin-2-yl]-1,10-diazatricyclo[6.4.0.0^[2,6]]dodeca-2(6),7-dien-9-one (80.00 mg, 0.099 mmol, 1.00 equiv), $PtO_2$ (11.24 mg, 0.049 mmol, 0.50 equiv), THF (10.00 mL). To the above $H_2$ (gas) was introduced in The resulting solution was stirred for 2 hr at room temperature. The solids were filtered out. The resulting mixture was concentrated. The residue was applied onto a silica gel column and eluted with dichloromethane/methanol (10:1). This resulted in 50 mg (64.91%) of 10-[4-[6-([3-amino-4-[4-(morpholin-4-yl)piperidin-1-yl]phenyl]amino)-4-methyl-5-oxopyrazin-2-yl]-3-[(oxan-2-yloxy)methyl]pyridin-2-yl]-4,4-dimethyl-1,10-diazatricyclo[6.4.0.0^[2,6]]dodeca-2(6),7-dien-9-one as a brown solid. LCMS-2 (ES, m/z): M+1: 778

Synthesis of N-(5-[[6-(2-[4,4-dimethyl-9-oxo-1,10-diazatricyclo[6.4.0.0^[2,6]]dodeca-2(6),7-dien-10-yl]-3-[(oxan-2-yloxy)methyl]pyridin-4-yl)-4-methyl-3-oxopyrazin-2-yl]amino]-2-[4-(morpholin-4-yl)piperidin-1-yl]phenyl)prop-2-enamide: Into a 8-mL vial, was placed 10-[4-[6-([3-amino-4-[4-(morpholin-4-yl)piperidin-1-yl]phenyl]amino)-4-methyl-5-oxopyrazin-2-yl]-3-[(oxan-2-yloxy)methyl]pyridin-2-yl]-4,4-dimethyl-1,10-diazatricyclo[6.4.0.0^[2,6]]dodeca-2(6),7-dien-9-one (40.00 mg, 0.051 mmol, 1.00 equiv), DCM (1.00 mL), DIEA (13.2 mg, 0.103 mmol, 2.00 equiv). This was followed by the addition of acryloyl chloride (6.98 mg, 0.077 mmol, 1.50 equiv) at 0 degrees C. The resulting solution was stirred for 30 min at 0 degrees C. in a water/ice bath. The reaction was then quenched by the addition of 0.2 mL of MeOH. The resulting mixture was concentrated. The residue was purified by Prep-TLC with dichloromethane/methanol (10:1). This resulted in 35 mg (81.82%) of N-(5-[[6-(2-[4,4-dimethyl-9-oxo-1,10-diazatricyclo[6.4.0.0^[2,6]]dodeca-2(6),7-dien-10-yl]-3-[(oxan-2-yloxy)methyl]pyridin-4-yl)-4-methyl-3-oxopyrazin-2-yl]amino]-2-[4-(morpholin-4-yl)piperidin-1-yl]phenyl)prop-2-enamide as a brown solid. LCMS-3 (ES, m/z): M+1: 832

Synthesis of N-(5-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxopyrazin-2-yl]amino]-2-[4-(morpholin-4-yl)piperidin-1-yl]phenyl)prop-2-enamide hydrochloride: Into a 8-mL vial, was placed N-(5-[[6-(2-[4,4-dimethyl-9-oxo-1,10-diazatricyclo[6.4.0.0^[2,6]]dodeca-2(6),7-dien-10-yl]-3-[(oxan-2-yloxy)methyl]pyridin-4-yl)-4-methyl-3-oxopyrazin-2-yl]amino]-2-[4-(morpholin-4-yl)piperidin-1-yl]phenyl)prop-2-enamide (30.00 mg, 0.036 mmol, 1.00 equiv), DCM (1.00 mL), TFA (0.10 mL). The resulting solution was stirred for 2 hr at 0 degrees C. in a water/ice bath. The pH value of the solution was adjusted to 7 with TEA. The crude product was purified by Prep-HPLC with the following conditions (Waters 2767): Column, X Bridge Prep C18 OBD 19*150 mm 5 um; mobile phase, A: 0.1% HCl in water; B: ACN; Gradient: 45-75% B in 7.9 min; Flow rate: 20 ml/min; Detector, 220 nm. This resulted in 14.5 mg (51.27%) of N-(5-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxopyrazin-2-yl]amino]-2-[4-(morpholin-4-yl)piperidin-1-yl]phenyl)prop-2-enamide hydrochloride as a yellow solid. LCMS-0 (ES, m/z): M+HCl+1: 784. H-NMR-0: (300 MHz, Methanol-$d_4$) δ 8.84 (s, 1H), 8.62 (d, J=5.7 Hz, 1H), 8.16 (d, J=5.7 Hz, 1H), 7.85 (s, 1H), 7.54 (d, J=9.6 Hz, 1H), 7.39 (d, J=9.0 Hz, 1H), 6.78 (s, 1H), 6.63 (dd, J=16.8, 10.2 Hz, 1H), 6.50-6.40 (m, 1H), 5.88 (d, J=11.1 Hz, 1H), 4.78 (s, 2H), 4.45-4.02 (m, 6H), 4.04-3.72 (m, 4H), 3.69 (s, 3H), 3.60 (d, J=11.4 Hz, 2H), 3.50-3.40 (m, 2H), 3.01-3.00 (m, 2H), 2.64 (s, 2H), 2.51 (s, 2H), 2.42-2.30 (m, 2H), 2.02-2.01 (m, 2H), 1.29 (s, 6H).

Example 20: Preparation of N-(2-[4,4-difluoro-[1,4'-bipiperidin]-1'-yl]-5-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxopyrazin-2-yl]amino]phenyl)prop-2-enamide Synthesis of 5-bromo-3-[(4-fluoro-3-nitrophenyl)amino]-1-methylpyrazin-2-one Into a 250-mL round-bottom flask, was placed 4-fluoro-3-nitroaniline (10.00 g, 64.055 mmol, 1.00 equiv), 3,5-dibromo-1-methylpyrazin-2-one (17.16 g, 64.052 mmol, 1.00 equiv), NMP (30 ml). The resulting solution was stirred for 1 h at 140 degrees C. in an oil bath. The resulting solution was diluted with 300 mL of EA. The solids were collected by filtration. This resulted in 13 g (59.15%) of 5-bromo-3-[(4-fluoro-3-nitrophenyl)amino]-1-methylpyrazin-2-one as a brown solid. LCMS-1 (ES, m/z): M+1: 343/345

Synthesis of [(3,3-dimethylcyclopent-1-en-1-yl)oxy]trimethylsilane Into a 10-L 4-necked round-bottom flask purged and maintained with an inert atmosphere of nitrogen, was placed CuCl (20.60 g, 208.083 mmol, 0.05 equiv), LiCl (17.64 g, 416.108 mmol, 0.10 equiv), THF (2.50 L). This was followed by the addition of 2-cyclopenten-1-one, 3-methyl-(400.00 g, 4161.075 mmol, 1.00 equiv) at −5 to 5 degrees C. To this was added TMSCl (474.67 g, 4369.129 mmol, 1.05 equiv) dropwise with stirring at −5 to 5 degrees C. To the mixture was added MeMgCl (1670.00 mL, 14495.069 mmol, 3.48 equiv) dropwise with stirring at −5 to 10 degrees C. The resulting solution was stirred for 2 h at −5 to 10 degrees C. in an ice/salt bath. The reaction was then quenched by the addition of 34 g of MeOH. The resulting solution was diluted with 5 L of $NH_4Cl$. The solids were filtered out. The resulting solution was extracted with 3×5 L of petroleum ether dried over anhydrous sodium sulfate and concentrated. This resulted in 780 g (crude) of [(3,3-dimethylcyclopent-1-en-1-yl)oxy]trimethylsilane as yellow oil. GC-MS-2: (ES, m/z): M: 184

Synthesis of 3,3-dimethylcyclopentanone Into a 20-L 4-necked round-bottom flask, was placed [(3,3-dimethylcyclopent-1-en-1-yl)oxy]trimethylsilane (780.00 g, 4230.990 mmol, 1.00 equiv), DCM (7.8 L), $H_2O$ (30.49 g, 1692.396 mmol, 0.4 equiv). This was followed by the addition of $POCl_3$ (214.09 g, 1396.251 mmol, 0.33 equiv) dropwise with stirring at 25 to 30 degrees C. The resulting solution was stirred for 0.5 hr at 25 degrees C. This solvent straight used for next step. GC-MS-3: (ES, m/z): M: 112

Synthesis of 3,3-dimethylcyclopentanone Into a 20-L 4-necked round-bottom flask, was placed 3,3-dimethylcyclopentan-1-one in DCM (7.80 L). This was followed by the addition of DMF (619 g, 2.0 equiv) dropwise with stirring at 25 degrees C. To this was added $POCl_3$ (1362 g, 2.1 equiv) dropwise with stirring at 40 degrees C. The resulting solution was stirred for overnight at 40 degrees C. in an oil bath. The reaction was then quenched by the addition of 2000 g of $K_3PO_4$. The resulting solution was extracted with 3×10 L of dichloromethane dried over anhydrous sodium sulfate and concentrated. This resulted in 530 g (4804.86%) of 2-chloro-4,4-dimethylcyclopent-1-ene-1-carbaldehyde as a brown solid. GC-MS-4: (ES, m/z): M: 158

Synthesis of 4,4-dimethyl-1,10-diazatricyclo[6.4.0.0^[2,6]]dodeca-2(6),7-dien-9-one Into a 5-L 4-necked round-bottom flask, was placed 2-chloro-4,4-dimethylcyclopent-1-ene-1-carbaldehyde (474.00 g, 2988.085 mmol, 1.00 equiv), DMF (3 L), piperazin-2-one (299.17 g, 2988.084 mmol, 1.00 equiv), DIEA (463.43 g, 3585.703 mmol, 1.2 equiv). The resulting solution was stirred for overnight at 115 degrees C. in an oil bath. The reaction mixture was cooled to room temperature with a water/ice bath. The solids were collected by filtration. The resulting mixture was washed with 3×2 L of $H_2O$ and 3×2 L of PE. The solid was dried in an oven under reduced pressure. This resulted in 230 g (37.68%) of 4,4-dimethyl-1,10-diazatricyclo[6.4.0.0^[2,6]]dodeca-2(6),7-dien-9-one as a grey solid. LCMS-5: (ES, m/z): M+1: 205

Synthesis of 2-[4,4-dimethyl-9-oxo-1,10-diazatricyclo[6.4.0.0^[2,6]]dodeca-2(6),7-dien-10-yl]-4-iodopyridine-3-carbaldehyde Into a 2-L 4-necked round-bottom flask purged and maintained with an inert atmosphere of nitrogen, was placed 4,4-dimethyl-1,10-diazatricyclo[6.4.0.0^[2,6]]dodeca-2(6),7-dien-9-one (38.00 g, 1.00 equiv), THF (500.00 mL). This was followed by the addition of LiHMDS (558.80 mL, 3.00 equiv) dropwise with stirring at 0 degrees C. To this was added 2-fluoro-4-iodopyridine-3-carbaldehyde (93.50 g, 2.00 equiv), in portions at degrees C. The resulting solution was stirred for overnight at room temperature. The reaction was then quenched by the addition of 1 L of water. The pH value of the solution was adjusted to 7 with HCl (2 mol/L). The solids were filtered out. The resulting solution was extracted with 3×1 L of ethyl acetate concentrated. The residue was applied onto a silica gel column and eluted with ethyl acetate/petroleum ether (2:3). The collected fractions were combined and concentrated. This resulted in 12 g of 2-[4,4-dimethyl-9-oxo-1,10-diazatricyclo[6.4.0.0^[2,6]]dodeca-2(6),7-dien-10-yl]-4-iodopyridine-3-carbaldehyde as a light yellow solid. LCMS-6 (ES, m/z): M+1: 436

Synthesis of 10-[3-(hydroxymethyl)-4-iodopyridin-2-yl]-4,4-dimethyl-1,10-diazatricyclo[6.4.0.0^[2,6]]dodeca-2(6),7-dien-9-one Into a 250-mL round-bottom flask, was placed 2-[4,4-dimethyl-9-oxo-1,10-diazatricyclo[6.4.0.0^[2,6]]dodeca-2(6),7-dien-10-yl]-4-iodopyridine-3-carbaldehyde (10.00 g, 22.975 mmol, 1.00 equiv), EtOH (100.00 mL). This was followed by the addition of $NaBH_4$ (2.61 g, 68.987 mmol, 3.00 equiv), in portions at 0 degrees C. The resulting solution was stirred for 3 hr at room temperature. The reaction was then quenched by the addition of 100 mL of water. The resulting solution was extracted with 3×200 mL of ethyl acetate concentrated. The residue was applied onto a silica gel column and eluted with ethyl acetate/petroleum ether (1:1). The collected fractions were combined and concentrated. This resulted in 8.24 g (82.02%) of 10-[3-(hydroxymethyl)-4-iodopyridin-2-yl]-4,4-dimethyl-1,10-diazatricyclo[6.4.0.0^[2,6]]dodeca-2(6),7-dien-9-one as a white solid. LCMS-7: (ES, m/z): M+1: 438

Synthesis of 10-[4-iodo-3-[(oxan-2-yloxy)methyl]pyridin-2-yl]-4,4-dimethyl-1,10-diazatricyclo[6.4.0.0^[2,6]]dodeca-2(6),7-dien-9-one Into a 500-mL round-bottom flask, was placed 10-[3-(hydroxymethyl)-4-iodopyridin-2-yl]-4,4-dimethyl-1,10-diazatricyclo[6.4.0.0^[2,6]]dodeca-2(6),7-dien-9-one (7.30 g, 16.694 mmol, 1.00 equiv), DCM (200.00 mL), DHP (2.11 g, 0.025 mmol, 1.5 equiv), PPTS (0.42 g, 0.002 mmol, 0.1 equiv). The resulting solution was stirred for overnight at 45 degrees C. in an oil bath. The resulting mixture was concentrated. The residue was applied onto a silica gel column and eluted with ethyl acetate/petroleum ether (1:1). The collected fractions were combined and concentrated. This resulted in 8 g (91.91%) of 10-[4-iodo-3-[(oxan-2-yloxy)methyl]pyridin-2-yl]-4,4-dimethyl-1,10-diazatricyclo[6.4.0.0^[2,6]]dodeca-2(6),7-dien-9-one as a light yellow solid. LCMS-8: (ES, m/z): M+1: 522

Synthesis of tert-butyl 4,4-difluoro-[1,4'-bipiperidine]-1'-carboxylate Into a 25-mL round-bottom flask, was placed tert-butyl 4-oxopiperidine-1-carboxylate (1.00 g, 5.019 mmol, 1.00 equiv), 4,4-difluoropiperidine (0.73 g, 6.027 mmol, 1.20 equiv), THF (5.00 mL), AcOH (0.50 mL, 0.008 mmol), $NaBH(OAc)_3$ (2.13 g, 10.050 mmol, 2.00 equiv). The resulting solution was stirred for 14 hr at 30 degrees C. in a water/ice bath. The reaction was then quenched by the addition of 1 mL of MeOH. The resulting mixture was concentrated. The residue was applied onto a silica gel column and eluted with dichloromethane/methanol (10:1). This resulted in 1.5 g (98.19%) of tert-butyl 4,4-difluoro-[1,4'-bipiperidine]-1'-carboxylate as a white solid. LCMS-9 (ES, m/z): M+1: 305

Synthesis of 4,4-difluoro-1,4'-bipiperidine Into a 50-mL round-bottom flask, was placed tert-butyl 4,4-difluoro-[1,4'-bipiperidine]-r-carboxylate (1.50 g), HCl (2M) in dioxane (15.00 mL). The resulting solution was stirred for 14 hr at room temperature. The resulting mixture was concentrated. The residue was applied onto a silica gel column and eluted with dichloromethane/methanol (10:1). This resulted in 1 g (crude) of 4,4-difluoro-1,4'-bipiperidine as a white solid. LCMS-10 (ES, m/z): M+1: 205

Synthesis of 5-bromo-3-[(4-[4,4-difluoro-[1,4'-bipiperidin]-1'-yl]-3-nitrophenyl)amino]-1-methylpyrazin-2-one Into a 50-mL round-bottom flask, was placed 5-bromo-3-[(4-fluoro-3-nitrophenyl)amino]-1-methylpyrazin-2-one (1.00 g, 2.915 mmol, 1.00 equiv), 4,4-difluoro-1,4'-bipiperidine (0.60 g, 2.937 mmol, 1.01 equiv), NMP (15.00 mL), DIEA (1.13 g, 8.743 mmol, 3.00 equiv). The resulting solution was stirred for 14 hr at 110 degrees C. in an oil bath. The resulting solution was diluted with 50 mL of $H_2O$. The resulting solution was extracted with 3×20 mL of dichloromethane. The residue was applied onto a silica gel column and eluted with dichloromethane/methanol (10:1). This resulted in 250 mg (16.27%) of 5-bromo-3-[(4-[4,4-difluoro-[1,4'-bipiperidin]-1'-yl]-3-nitrophenyl)amino]-1-methylpyrazin-2-one as a yellow solid. LCMS-11 (ES, m/z): M+1: 527/529

Synthesis of 6-[(4-[4,4-difluoro-[1,4'-bipiperidin]-1'-yl]-3-nitrophenyl)amino]-4-methyl-5-oxopyrazin-2-ylboronic acid Into a 8-mL vial purged and maintained with an inert atmosphere of nitrogen, was placed 5-bromo-3-[(4-[4,4-difluoro-[1,4'-bipiperidin]-1'-yl]-3-nitrophenyl)amino]-1-methylpyrazin-2-one (100 mg, 0.190 mmol, 1.00 equiv), bis(pinacolato)diboron (96.30 mg, 0.379 mmol, 2.00 equiv), THF (3.00 mL), KOAc (37.22 mg, 0.379 mmol, 2 equiv), XPhos Pd G3 (16.05 mg, 0.019 mmol, 0.1 equiv). The resulting solution was stirred for 6 hr at 70 degrees C. in an oil bath. The solids were filtered out. The resulting mixture was concentrated. This resulted in 120 mg (crude) of 6-[(4-[4,4-difluoro-[1,4'-bipiperidin]-1'-yl]-3-nitrophenyl)amino]-4-methyl-5-oxopyrazin-2-ylboronic acid as a black solid. LCMS-12 (ES, m/z): M+1: 493

Synthesis of 10-(4-[6-[(4-[4,4-difluoro-[1,4'-bipiperidin]-1'-yl]-3-nitrophenyl)amino]-4-methyl-5-oxopyrazin-2-yl]-3-[(oxan-2-yloxy)methyl]pyridin-2-yl)-4,4-dimethyl-1,10-diazatricyclo[6.4.0.0^[2,6]]dodeca-2(6),7-dien-9-one Into a 8-mL round-bottom flask purged and maintained with an inert atmosphere of nitrogen, was placed 6-[(4-[4,4-difluoro-[1,4'-bipiperidin]-1'-yl]-3-nitrophenyl)amino]-4-methyl-5-oxopyrazin-2-ylboronic acid (110.00 mg, crude), 10-[4-iodo-3-[(oxan-2-yloxy)methyl]pyridin-2-yl]-4,4-dimethyl-1,10-diazatricyclo[6.4.0.0^[2,6]]dodeca-2(6),7-dien-9-one (116.50 mg), THF (3.00 mL), $H_2O$ (0.30 mL), $Pd(dppf)Cl_2$ (9.12 mg, 0.011 mmol, 0.05 equiv), $K_3PO_4$ (142.29 mg, 0.670 mmol, 3.00 equiv). The resulting solution was stirred for 14 hr at 50 degrees C. in an oil bath. The resulting mixture was concentrated. The residue was purified by Prep-TLC with dichloromethane/methanol (10:1). This resulted in 100 mg (38.80%) of 10-(4-[6-[(4-[4,4-difluoro-[1,4'-bipiperidin]-1'-yl]-3-nitrophenyl)amino]-4-methyl-5-oxopyrazin-2-yl]-3-[(oxan-2-yloxy)methyl]pyridin-2-yl)-4,4-dimethyl-1,10-diazatricyclo[6.4.0.0^[2,6]]dodeca-2(6),7-dien-9-one as a brown solid. LCMS-13: M+1: 842

Synthesis of 10-(4-[6-[(4-[4,4-difluoro-[1,4'-bipiperidin]-1'-yl]-3-nitrophenyl)amino]-4-methyl-5-oxopyrazin-2-yl]-3-[(oxan-2-yloxy)methyl]pyridin-2-yl)-4,4-dimethyl-1,10-diazatricyclo[6.4.0.0^[2,6]]dodeca-2(6),7-dien-9-one Into a 30-mL sealed tube, was placed 10-(4-[6-[(4-[4,4-difluoro-[1,4 (90.00 mg, 0.107 mmol, 1.00 equiv), THF (10.00 mL), $PtO_2$ (12.14 mg, 0.053 mmol, 0.50 equiv). To the above $H_2$ (gas) was introduced in at degrees C. The resulting solution was stirred for 1 hr at room temperature. The solids were filtered out. The residue was purified by Prep-TLC with dichloromethane/methanol (10:1). This resulted in 35 mg (40.32%) of 10-(4464(3-amino-4-[4,4-difluoro-[1,4'-bipiperidin]-1'-yl]phenyl)amino]-4-methyl-5-oxopyrazin-2-yl]-3-[(oxan-2-yloxy)methyl]pyridin-2-yl)-4,4-dimethyl-1,10-diazatricyclo[6.4.0.0^[2,6]]dodeca-2(6),7-dien-9-one as a brown solid. LCMS-14: (ES, m/z): M+1: 812

Synthesis of N-(2-[4,4-difluoro-[1,4'-bipiperidin]-1'-yl]-5-[[6-(2-[4,4-dimethyl-9-oxo-1,10-diazatricyclo[6.4.0.0^[2,6]]dodeca-2(6),7-dien-10-yl]-3-[(oxan-2-yloxy)methyl]pyridin-4-yl)-4-methyl-3-oxopyrazin-2-yl]amino)phenyl)prop-2-enamide Into a 8-mL vial, was placed 10-(4-[6-[(3-amino-4-[4,4-difluoro-[1,4'-bipiperidin]-1'-yl]phenyl)amino]-4-methyl-5-oxopyrazin-2-yl]-3-[(oxan-2-yloxy)methyl]pyridin-2-yl)-4,4-dimethyl-1,10-diazatricyclo[6.4.0.0^[2,6]]dodeca-2(6),7-dien-9-one (30.00 mg, 0.037 mmol, 1.00 equiv), DCM (1.00 mL), DIEA (9.55 mg, 0.074 mmol, 2.00 equiv). This was followed by the addition of acryloyl chloride (5.02 mg, 0.055 mmol, 1.50 equiv) at 0 degrees C. The resulting solution was stirred for 30 min at 0 degrees C. in a water/ice bath. The reaction was then quenched by the addition of 0.2 mL of MeOH. The resulting mixture was concentrated. The residue was purified by Prep-TLC with dichloromethane/methanol (10:1). This resulted in 25 mg (78.13%) of N-(2-[4,4-difluoro-[1,4'-bipiperidin]-1'-yl]-5-[[6-(2-[4,4-dimethyl-9-oxo-1,10-diazatricyclo[6.4.0.0^[2,6]]dodeca-2(6),7-dien-10-yl]-3-[(oxan-2-yloxy)methyl]pyridin-4-yl)-4-methyl-3-oxopyrazin-2-yl]amino]phenyl)prop-2-enamide as a brown solid. LCMS-15 (ES, m/z): M+1: 866

Synthesis of N-(2-[4,4-difluoro-[1,4'-bipiperidin]-1'-yl]-5-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxopyrazin-2-yl]amino]phenyl)prop-2-enamide Into a 8-mL vial, was placed N-(2-[4,4-difluoro-[1,4'-bipiperidin]-1'-yl]-5-[[6-(2-[4,4-dimethyl-9-oxo-1,10-diazatricyclo[6.4.0.0^[2,6]]dodeca-2(6),7-dien-10-yl]-3-[(oxan-2-yloxy)methyl]pyridin-4-yl)-4-methyl-3-oxopyrazin-2-yl]amino]phenyl)prop-2-enamide (20 mg), DCM (1 mL), TFA (0.1 mL). The resulting solution was stirred for 2 hr at 0 degrees C. in a water/ice bath. The pH value of the solution was adjusted to 7 with TEA at 0 degrees C. in a water/ice bath. The resulting mixture was concentrated. The crude product was purified by Prep-HPLC with the following conditions (Waters 2767): Column, X Bridge Prep C18 OBD 19*150 mm 5 um; mobile phase, A: 0.1% $NH_3$—$H_2O$ in water; B: ACN; Gradient: 35%-75% B in 7.9 min; Flow rate: 20 ml/min; Detector, 220 nm. This resulted in 7 mg (38.77%) of N-(2-[4,4-difluoro-[1,4'-bipiperidin]-1'-yl]-5-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxopyrazin-2-yl]amino]phenyl)prop-2-enamide as a light yellow solid. LCMS-0: (ES, m/z): M+1: 782 $^1$H NMR (300 MHz, Methanol-$d_4$) δ 8.78 (s, 1H), 8.52 (d, J=5.1 Hz, 1H), 7.90 (d, J=5.1 Hz, 1H), 7.68 (s, 1H), 7.55 (dd, J=8.7, 2.7 Hz, 1H), 7.22 (d, J=8.7 Hz, 1H), 6.74 (s, 1H), 6.55 (dd, J=16.8, 10.2 Hz, 1H), 6.38 (dd, J=16.8, 1.8 Hz, 1H), 5.82 (d, J=10.8 Hz, 1H), 4.85-4.72 (m, 1H), 4.60 (d, J=12.3 Hz, 1H), 4.42-4.20 (m, 3H), 3.96 (d, J=12.0 Hz, 1H), 3.66 (s, 3H), 3.11-3.01 (m, 2H), 2.90-2.40 (m, 11H), 2.15-1.93 (m, 6H), 1.81 (t, J=10.2 Hz, 2H), 1.28 (s, 6H).

Example 21: Preparation of N-(5-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxopyrazin-2-yl]amino]-2-[4-(4-methylpiperazin-1-yl)piperidin-1-yl]phenyl)prop-2-enamide Synthesis of 2,4-dibromopyridine-3-carbaldehyde: Into a 1000-mL 3-necked round-bottom flask, was placed 2,4-dibromopyridine (40.00 g, 168.852 mmol, 1.00 equiv), THF (400.00 mL). This was followed by the addition of LDA (2M in hexane, 126.60 mL, 1.5 equiv) dropwise with stirring at −78 degrees C. The resulting solution was stirred for 1 hr at −78 degrees C. Then, DMF (16.04, 219.507, 1.3 equiv) was added by dropwise with stirring at −78 degrees C. The resulting solution was stirred for 0.5 hr at −78 degrees C. The reaction was then quenched by the addition of 500 mL of $NH_4Cl$. The resulting solution was extracted with 3×500 mL of ethyl acetate concentrated. The residue was applied onto a silica gel column and eluted with ethyl acetate/petroleum ether (0:1-1:1). This resulted in 24.4 g (54.55%) of 2,4-dibromopyridine-3-carbaldehyde as a white solid. LCMS-1: (ES, m/z): M+1: 264

Synthesis of (2,4-dibromopyridin-3-yl)methanol: Into a 100-mL round-bottom flask, was placed 2,4-dibromopyridine-3-carbaldehyde (2.00 g, 7.550 mmol, 1.00 equiv), EtOH (30.00 mL). This was followed by the addition of $NaBH_4$ (285.64 mg, 7.550 mmol, 1 equiv), in portions at 0 degrees C. The resulting solution was stirred for 3 h at room temperature. The reaction was then quenched by the addition of 30 mL of water. The resulting solution was extracted with 3×30 mL of ethyl acetate concentrated. The residue was applied onto a silica gel column and eluted with ethyl acetate/petroleum ether (1:1). The collected fractions were combined and concentrated. This resulted in 1.4 g (69.47%) of (2,4-dibromopyridin-3-yl)methanol as a light yellow solid. LCMS-2: (ES, m/z): M+1: 266

Synthesis of 2,4-dibromo-3-[(oxan-2-yloxy)methyl]pyridine: Into a 100-mL round-bottom flask, was placed (2,4-dibromopyridin-3-yl)methanol (1.40 g, 5.245 mmol, 1.00 equiv), DCM (30.00 mL, 0.353 mmol, 0.07 equiv), PPTS (131.81 mg, 0.525 mmol, 0.10 equiv), DHP (661.79 mg, 7.868 mmol, 1.50 equiv). The resulting solution was stirred for overnight at 45 degrees C. in an oil bath. The reaction was then quenched by the addition of 30 mL of water. The resulting solution was extracted with 3×30 mL of dichloromethane concentrated. The residue was applied onto a silica gel column and eluted with ethyl acetate/petroleum ether (1:1). The collected fractions were combined and concentrated. This resulted in 1.5 mg (0.08%) of 2,4-dibromo-3-[(oxan-2-yloxy)methyl]pyridine as colorless oil. LCMS-3: (ES, m/z): M+1: 350

Synthesis of 10-[4-bromo-3-[(oxan-2-yloxy)methyl]pyridin-2-yl]-4,4-dimethyl-1,10-diazatricyclo[6.4.0.0^[2,6]]dodeca-2(6),7-dien-9-one: Into a 100-mL round-bottom flask purged and maintained with an inert atmosphere of nitrogen, was placed 4,4-dimethyl-1,10-diazatricyclo[6.4.0.0^[2,6]]dodeca-2(6),7-dien-9-one (1.00 g, 4.895 mmol, 1.00 equiv), dioxane (40.00 mL, 0.454 mmol, 0.09 equiv), $Cs_2CO_3$ (3.19 g, 9.791 mmol, 2 equiv), 2,4-dibromo-3-[(oxan-2-yloxy)methyl]pyridine (1.72 g, 4.900 mmol, 1.00 equiv), $Pd_2(dba)_3$ (448.28 mg, 0.490 mmol, 0.1 equiv), XantPhos (283.26 mg, 0.490 mmol, 0.1 equiv). The resulting solution was stirred for 1 h at 100 degrees C. in an oil bath. The reaction was then quenched by the addition of 40 mL of water. The resulting solution was extracted with 3×40 mL of ethyl acetate concentrated. The residue was applied onto a silica gel column and eluted with ethyl acetate/petroleum ether (1:1). The collected fractions were combined and concentrated. This resulted in 900 mg (38.75%) of 10-[4-bromo-3-[(oxan-2-yloxy)methyl]pyridin-2-yl]-4,4-dimethyl-1,10-diazatricyclo[6.4.0.0^[2,6]]dodeca-2(6),7-dien-9-one as a brown solid. LCMS-4 (ES, m/z): M+1: 474

Synthesis of 2-[4,4-dimethyl-9-oxo-1,10-diazatricyclo[6.4.0.0^[2,6]]dodeca-2(6),7-dien-10-yl]-3-[(oxan-2-yloxy)methyl]pyridin-4-ylboronic acid: Into a 100-mL round-bottom flask purged and maintained with an inert atmosphere of nitrogen, was placed 10-[4-bromo-3-[(oxan-2-yloxy)methyl]pyridin-2-yl]-4,4-dimethyl-1,10-diazatricyclo[6.4.0.0^[2,6]]dodeca-2(6),7-dien-9-one (1.00 g, 2.108 mmol, 1.00 equiv), dioxane (10.00 mL), bis(pinacolato)diboron (1.34 g, 5.277 mmol, 2.50 equiv), KOAc (620.00 mg, 6.317 mmol, 3.00 equiv), $Pd(dppf)Cl_2$ (172.00 mg, 0.211 mmol, 0.10 equiv). The resulting solution was stirred for 2 h at 100 degrees C. in an oil bath. The reaction mixture was cooled to room temperature. The solids were filtered out. The resulting mixture was concentrated under vacuum. This resulted in 920 mg (crude) of 2-[4,4-dimethyl-9-oxo-1,10-diazatricyclo[6.4.0.0^[2,6]]dodeca-2(6),7-dien-10-yl]-3-[(oxan-2-yloxy)methyl]pyridin-4-ylboronic acid as brown oil. LCMS-5 (ES, m/z): M+1: 436

Synthesis of 10-[1-hydroxy-3H-[1,2]oxaborolo[4,3-c]pyridin-4-yl]-4,4-dimethyl-1,10-diazatricyclo[6.4.0.0^[2,6]]dodeca-2(6),7-dien-9-one: Into a 100-mL round-bottom flask, was placed 2-[4,4-dimethyl-9-oxo-1,10-diazatricyclo[6.4.0.0^[2,6]]dodeca-2(6),7-dien-10-yl]-3-[(oxan-2-yloxy)methyl]pyridin-4-ylboronic acid (920 mg, 1.00 equiv, crude), dioxane (10 mL), HCl (6N, 10 mL). The resulting solution was stirred for 1 h at 25 degrees C. The resulting mixture was concentrated under vacuum. The crude product was purified by Flash-Prep-HPLC with the following conditions: Column, C18 reversed phase column; mobile phase, $H_2O$ (0.05% $NH_3$—$H_2O$) and $CH_3CN$ (5% $CH_3CN$ up to 30% in 15 min); Flow rate: 60 mL/min; Detector, 254/220 nm. This resulted in 350 mg of 10-[1-hydroxy-3H-[1,2]oxaborolo[4,3-c]pyridin-4-yl]-4,4-dimethyl-1,10-diazatricyclo[6.4.0.0^[2,6]]dodeca-2(6),7-dien-9-one as a light yellow solid. LCMS-6 (ES, m/z): M+1: 338

Synthesis of 5-bromo-3-[(4-fluoro-3-nitrophenyl)amino]-1-methylpyrazin-2-one: Into a 250-mL round-bottom flask, was placed 4-fluoro-3-nitroaniline (10.00 g, 64.055 mmol, 1.00 equiv), 3,5-dibromo-1-methylpyrazin-2-one (17.16 g, 64.052 mmol, 1.00 equiv), NMP (30 ml). The resulting solution was stirred for 1 h at 140 degrees C. in an oil bath. The resulting solution was diluted with 300 mL of EA. The solids were collected by filtration. This resulted in 13 g (59.15%) of 5-bromo-3-[(4-fluoro-3-nitrophenyl)amino]-1-methylpyrazin-2-one as a brown solid. LCMS-7 (ES, m/z): M+1: 343/345

Synthesis of 5-bromo-1-methyl-3-([4-[4-(4-methylpiperazin-1-yl)piperidin-1-yl]-3-nitrophenyl]amino)pyrazin-2-one: Into a 50-mL round-bottom flask, was placed 5-bromo-3-[(4-fluoro-3-nitrophenyl)amino]-1-methylpyrazin-2-one (3.00 g, 8.744 mmol, 1.00 equiv), 1-methyl-4-(piperidin-4-yl)piperazine (1.60 g, 8.729 mmol, 1.00 equiv), NMP (30.00 mL), DIEA (3.39 g, 26.230 mmol, 3.00 equiv). The resulting solution was stirred for 14 hr at 110 degrees C. in an oil bath. The resulting solution was diluted with 150 mL of $H_2O$. The resulting solution was extracted with 3×50 mL of dichloromethane. The resulting mixture was washed with 3×30 ml of $H_2O$. The resulting mixture was concentrated. The residue was applied onto a silica gel column and eluted with dichloromethane/methanol (10:1). This resulted in 1.2 g (27.10%) of 5-bromo-1-methyl-3-([4-[4-(4-methylpiperazin-1-yl)piperidin-1-yl]-3-nitrophenyl]amino)pyrazin-2-one as a red solid. LCMS-8 (ES, m/z): M+1: 506/508

Synthesis of 3-([3-amino-4-[4-(4-methylpiperazin-1-yl)piperidin-1-yl]phenyl]amino)-5-bromo-1-methylpyrazin-2-one: Into a 50-mL round-bottom flask, was placed 5-bromo-1-methyl-3-([4-[4-(4-methylpiperazin-1-yl) piperidin-1-yl]-3-nitrophenyl]amino)pyrazin-2-one (1.20 g, 2.370 mmol, 1.00 equiv), EtOH (10.00 m), $H_2O$ (10.00 mL), Fe (0.53 g, 9.491 mmol, 4.01 equiv), $NH_4Cl$ (0.76 g, 14.208 mmol, 6.00 equiv). The resulting solution was stirred for 2 hr at 80 degrees C. in an oil bath. The solids were filtered out. The resulting mixture was concentrated. The residue was applied onto a silica gel column and eluted with dichloromethane/methanol (5:1). This resulted in 200 mg (17.72%) of 3-([3-amino-4-[4-(4-methylpiperazin-1-yl)piperidin-1-yl]phenyl]amino)-5-bromo-1-methylpyrazin-2-one as a brown solid. LCMS-9 (ES, m/z): M+1: 476/478

Synthesis of N-[5-[(6-bromo-4-methyl-3-oxopyrazin-2-yl)amino]-2-[4-(4-methylpiperazin-1-yl) piperidin-1-yl]phenyl]prop-2-enamide: Into a 8-mL vial, was placed 3-([3-amino-4-[4-(4-methylpiperazin-1-yl)piperidin-1-yl]phenyl]amino)-5-bromo-1-methylpyrazin-2-one (160.00 mg, 0.336 mmol, 1.00 equiv), acrylic acid (36.30 mg, 0.504 mmol, 1.50 equiv), DMF (4.00 mL), DIEA (86.81 mg, 0.672 mmol, 2.00 equiv), HATU (153.23 mg, 0.403 mmol, 1.20 equiv). The resulting solution was stirred for 14 hr at room temperature. The resulting solution was diluted with 20 mL of $H_2O$. The resulting solution was extracted with 3×15 mL of dichloromethane. The resulting mixture was washed with 2×10 ml of $H_2O$. The residue was applied onto a silica gel column and eluted with dichloromethane/methanol (10:1). This resulted in 40 mg (22.45%) of N-[5-[(6-bromo-4-methyl-3-oxopyrazin-2-yl)amino]-2-[4-(4-methylpiperazin-1-yl)piperidin-1-yl]phenyl]prop-2-enamide as a brown solid. LCMS-10 (ES, m/z): M+1: 530/532

Synthesis of N-(5-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxopyrazin-2-yl]amino]-2-[4-(4-methylpiperazin-1-yl)piperidin-1-yl]phenyl)prop-2-enamide: Into a 8-mL vial purged and maintained with an inert atmosphere of nitrogen, was placed N-[5-[(6-bromo-4-methyl-3-oxopyrazin-2-yl)amino]-2-[4-(4-methylpiperazin-1-yl) piperidin-1-yl]phenyl]prop-2-enamide (35.00 mg, 0.066 mmol, 1.00 equiv), 10-[1-hydroxy-3H-[1,2]oxaborolo[4,3-c]pyridin-4-yl]-4,4-dimethyl-1,10- diazatricyclo[6.4.0.0^[2,6]]dodeca-2(6),7-dien-9-one (22.25 mg, 0.066 mmol, 1.00 equiv), dioxane (3.00 mL), $H_2O$ (0.30 mL), Pd(dppf)$Cl_2$ (2.69 mg, 0.003 mmol, 0.05 equiv), $K_2CO_3$ (27.36 mg, 0.198 mmol, 3.00 equiv). The resulting solution was stirred for 1 hr at 90 degrees C. in an oil bath. The resulting mixture was concentrated. The residue was purified by Prep-TLC with dichloromethane/methanol (10:1). The crude product was purified by Prep-HPLC with the following conditions (Waters 2767): Column, X Bridge Prep C18 OBD 19*150 mm 5 um; mobile phase, A: 0.1% $NH_3$—$H_2O$ in water; B: ACN; Gradient: 40%-75% B in 7.9 min; Flow rate: 20 ml/min; Detector, 220 nm. This resulted in 13 mg (25.89%) of N-(5-[[6-(2-[4,4-dimethyl-9-oxo-1,10-diazatricyclo[6.4.0.0-[2,6]]dodeca-2(6),7-dien-10-yl]-3-(hydroxymethyl)pyridin-4-yl)-4-methyl-3-oxopyrazin-2-yl]amino]-2-[4-(4-methylpiperazin-1-yl)piperidin-1-yl]phenyl)prop-2-enamide as a white solid. LCMS-0 (ES, m/z): M+1: 761 H-NMR-0: $^1$H NMR (300 MHz, Methanol-$d_4$) δ 8.79 (s, 1H), 8.52 (d, J=5.1 Hz, 1H), 7.90 (d, J=5.1 Hz, 1H), 7.68 (s, 1H), 7.56 (dd, J=8.7, 2.7 Hz, 1H), 7.22 (d, J=8.7 Hz, 1H), 6.74 (s, 1H), 6.65-6.60 (m, 1H), 6.42-6.31 (m, 1H), 5.82 (d, J=10.2 Hz, 1H), 4.80-4.72 (m, 1H), 4.70-4.50 (m, 1H), 4.40-4.21 (m, 3H), 3.96 (d, J=11.8 Hz, 1H), 3.67 (s, 3H), 3.15-3.01 (m, 2H), 2.90-2.67 (m, 5H), 2.66-2.46 (m, 6H), 2.46-2.39 (m, 1H), 2.33 (s, 3H), 2.05 (d, J=12.0 Hz, 2H), 1.76 (t, J=10.8 Hz, 2H), 1.28 (s, 6H).

Example 22: Preparation of N-(5-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxopyrazin-2-yl]amino]-2-[(2S)-2-methyl-4-(oxan-4-yl)piperazin-1-yl]phenyl)prop-2-enamide Synthesis of [(3,3-dimethylcyclopent-1-en-1-yl)oxy]trimethylsilane: Into a 10-L 4-necked round-bottom flask purged and maintained with an inert atmosphere of nitrogen, was placed CuCl (20.60 g, 208.083 mmol, 0.05 equiv), LiCl (17.64 g, 416.108 mmol, 0.10 equiv), THF (2.50 L). This was followed by the addition of 2-cyclopenten-1-one, 3-methyl-(400.00 g, 4161.075 mmol, 1.00 equiv) at −5 to 5 degrees C. To this was added TMSCl (474.67 g, 4369.129 mmol, 1.05 equiv) dropwise with stirring at −5 to 5 degrees C. To the mixture was added MeMgCl (1670.00 mL, 14495.069 mmol, 3.48 equiv) dropwise with stirring at −5 to 10 degrees C. The resulting solution was stirred for 2 h at −5 to 10 degrees C. in an ice/salt bath. The reaction was then quenched by the addition of 34 g of MeOH. The resulting solution was diluted with 5 L of $NH_4Cl$. The solids were filtered out. The resulting solution was extracted with 3×5 L of petroleum ether dried over anhydrous sodium sulfate and concentrated. This resulted in 780 g (crude) of [(3,3-dimethylcyclopent-1-en-1-yl)oxy]trimethylsilane as yellow oil. GC-MS: (ES, m/z): M: 184

Synthesis of 3,3-dimethylcyclopentanone: Into a 20-L 4-necked round-bottom flask, was placed [(3,3-dimethylcyclopent-1-en-1-yl)oxy]trimethylsilane (780.00 g, 4230.990 mmol, 1.00 equiv), DCM (7.8 L), $H_2O$ (30.49 g, 1692.396 mmol, 0.4 equiv). This was followed by the addition of $POCl_3$ (214.09 g, 1396.251 mmol, 0.33 equiv) dropwise with stirring at 25 to 30 degrees C. The resulting solution was stirred for 0.5 hr at 25 degrees C. This solvent straight used for next step. GC-MS: (ES, m/z): M: 112

Synthesis of 3,3-dimethylcyclopentanon: Into a 20-L 4-necked round-bottom flask, was placed 3,3-dimethylcyclopentan-1-one in DCM (7.80 L). This was followed by the addition of DMF (619 g, 2.0 equiv) dropwise with stirring at 25 degrees C. To this was added $POCl_3$ (1362 g, 2.1 equiv) dropwise with stirring at 40 degrees C. The resulting solution was stirred for overnight at 40 degrees C. in an oil bath. The reaction was then quenched by the addition of 2000 g of $K_3PO_4$. The resulting solution was extracted with 3×10 L of dichloromethane dried over anhydrous sodium sulfate and concentrated. This resulted in 530 g (4804.86%) of 2-chloro-4,4-dimethylcyclopent-1-ene-1-carbaldehyde as a brown solid. GC-MS: (ES, m/z): M: 158

Synthesis of 4,4-dimethyl-1,10-diazatricyclo[6.4.0.0^[2,6]]dodeca-2(6),7-dien-9-one: Into a 5-L 4-necked round-bottom flask, was placed 2-chloro-4,4-dimethylcyclopent-1-ene-1-carbaldehyde (474.00 g, 2988.085 mmol, 1.00 equiv), DMF (3 L), piperazin-2-one (299.17 g, 2988.084 mmol, 1.00 equiv), DIEA (463.43 g, 3585.703 mmol, 1.2 equiv). The resulting solution was stirred for overnight at 115 degrees C. in an oil bath. The reaction mixture was cooled to room temperature with a water/ice bath. The solids were collected by filtration. The resulting mixture was washed with 3×2 L of $H_2O$ and 3×2 L of PE. The solid was dried in an oven under reduced pressure. This resulted in 230 g (37.68%) of 4,4-dimethyl-1,10-diazatricyclo[6.4.0.0^[2,6]]dodeca-2(6),7-dien-9-one as a grey solid. LC-MS: (ES, m/z): M+1: 205

Synthesis of 2-[4,4-dimethyl-9-oxo-1,10-diazatricyclo[6.4.0.0^[2,6]]dodeca-2(6),7-dien-10-yl]-4-iodopyridine-3-carbaldehyde: Into a 2-L 4-necked round-bottom flask purged and maintained with an inert atmosphere of nitrogen, was placed 4,4-dimethyl-1,10-diazatricyclo[6.4.0.0^[2,6]]dodeca-2(6),7-dien-9-one (38.00 g, 1.00 equiv), THF (500.00 mL). This was followed by the addition of LiHMDS (558.80 mL, 3.00 equiv) dropwise with stirring at 0 degrees C. To this was added 2-fluoro-4-iodopyridine-3-carbaldehyde (93.50 g, 2.00 equiv), in portions at degrees C. The resulting solution was stirred for overnight at room temperature. The reaction was then quenched by the addition of 1 L of water. The pH value of the solution was adjusted to 7 with HCl (2 mol/L). The solids were filtered out. The resulting solution was extracted with 3×1 L of ethyl acetate concentrated. The residue was applied onto a silica gel column and eluted with ethyl acetate/petroleum ether (2:3). The collected fractions were combined and concentrated. This resulted in 12 g of 2-[4,4-dimethyl-9-oxo-1,10-diazatricyclo[6.4.0.0^[2,6]]dodeca-2(6),7-dien-10-yl]-4-iodopyridine-3-carbaldehyde as a light yellow solid. LC-MS: (ES, m/z): M+1: 436

Synthesis of tert-butyl (3S)-4-[4-[(6-bromo-4-methyl-3-oxopyrazin-2-yl)amino]-2-nitrophenyl]-3-methylpiperazine-1-carboxylate: Into a 50-mL round-bottom flask, was placed 5-bromo-3-[(4-fluoro-3-nitrophenyl)amino]-1-methylpyrazin-2-one (2.00 g, 5.829 mmol, 1.00 equiv), NMP (20.00 mL), tert-butyl (3S)-3-methylpiperazine-1-carboxylate (1.17 g, 5.842 mmol, 1.00 equiv), DIEA (2.26 g, 17.487 mmol, 3.00 equiv). The resulting solution was stirred for 48 h at 110° C. in an oil bath. The resulting solution was diluted with 100 mL of $H_2O$. The resulting solution was extracted with 3×50 mL of dichloromethane/methanol (10:1). The resulting mixture was washed with 3×20 ml of NaCl. The resulting mixture was concentrated. The residue was applied onto a silica gel column with dichloromethane/methanol (10:1). This resulted in 3 g (59.00%) of tert-butyl (3S)-4-[4-[(6-bromo-4-methyl-3-oxopyrazin-2-yl)amino]-2-nitrophenyl]-3-methylpiperazine-1-carboxylate as a brown solid. LC-MS: (ES, m/z): M+1: 523

Synthesis of 5-bromo-1-methyl-3-([4-[(2S)-2-methylpiperazin-1-yl]-3-nitrophenyl]amino)pyrazin-2-one: Into a 100-mL round-bottom flask, was placed tert-butyl (3S)-4-

[4-[(6-bromo-4-methyl-3-oxopyrazin-2-yl)amino]-2-nitrophenyl]-3-methylpiperazine-1-carboxylate (3.00 g, 1 equiv, 60%), HCl (2M) in 1,4-dioxane (30.00 mL). The resulting solution was stirred for 13 h at room temperature. The resulting mixture was concentrated. The resulting solution was diluted with 30 mL of $H_2O$. The pH value of the solution was adjusted to 8 with $NH_3$—$H_2O$. The resulting solution was extracted with 3×15 mL of dichloromethane concentrated. The residue was applied onto a silica gel column with dichloromethane/methanol (10:1). This resulted in 700 mg (48.09%) of 5-bromo-1-methyl-3-([4-[(2S)-2-methylpiperazin-1-yl]-3-nitrophenyl]amino)pyrazin-2-one as a red solid. LC-MS: (ES, m/z): M+1: 423

Synthesis of 5-bromo-1-methyl-3-([4-[(2S)-2-methyl-4-(oxan-4-yl)piperazin-1-yl]-3-nitrophenyl]amino)pyrazin-2-one: Into a 50-mL round-bottom flask, was placed 5-bromo-1-methyl-3-([4-[(2S)-2-methylpiperazin-1-yl]-3-nitrophenyl]amino)pyrazin-2-one (250 mg, 0.591 mmol, 1.00 equiv), 4H-pyran-4-one, tetrahydro-(70.96 mg, 0.709 mmol, 1.20 equiv), THF (5 ml), AcOH (5 drops), NaBH $(AcO)_3$ (250.36 mg, 1.181 mmol, 2.00 equiv). The resulting solution was stirred for 14 h at 30° C. in an oil bath. The resulting mixture was concentrated. The residue was applied onto a silica gel column with dichloromethane/methanol (10:1). This resulted in 220 mg (73.41%) of 5-bromo-1-methyl-3-([4-[(2S)-2-methyl-4-(oxan-4-yl)piperazin-1-yl]-3-nitrophenyl]amino)pyrazin-2-one as a white solid. LC-MS: (ES, m/z): M+1: 507

Synthesis of 4-methyl-6-([4-[(2S)-2-methyl-4-(oxan-4-yl)piperazin-1-yl]-3-nitrophenyl]amino)-5-oxopyrazin-2-ylboronic acid: Into a 25-mL round-bottom flask purged and maintained with an inert atmosphere of nitrogen, was placed 5-bromo-1-methyl-3-([4-[(2S)-2-methyl-4-(oxan-4-yl)piperazin-1-yl]-3-nitrophenyl]amino)pyrazin-2-one (200.00 mg, 0.394 mmol, 1.00 equiv), bis(pinacolato)diboron (200.19 mg, 0.788 mmol, 2.00 equiv), THF (5.00 mL, 0.069 mmol, 0.1 equiv), XPhos Pd G3 (16.68 mg, 0.020 mmol, 0.05 equiv), KOAc (77.37 mg, 0.788 mmol, 2.00 equiv). The resulting solution was stirred for 4 h at 70° C. in an oil bath. The solids were filtered out. This resulted in 150 mg (53.98%) of 4-methyl-6-([4-[(2S)-2-methyl-4-(oxan-4-yl)piperazin-1-yl]-3-nitrophenyl]amino)-5-oxopyrazin-2-ylboronic acid as a black solid. LC-MS: (ES, m/z): M+1: 473

Synthesis of 2-[4,4-dimethyl-9-oxo-1,10-diazatricyclo[6.4.0.0^[2,6]]dodeca-2(6),7-dien-10-yl]-4-[4-methyl-6-([4-[(2S)-2-methyl-4-(oxan-4-yl)piperazin-1-yl]-3-nitrophenyl]amino)-5-oxopyrazin-2-yl]pyridine-3-carbaldehyde: Into a 40-mL vial purged and maintained with an inert atmosphere of nitrogen, was placed 2-[4,4-dimethyl-9-oxo-1,10-diazatricyclo[6.4.0.0^[2,6]]dodeca-2(6),7-dien-10-yl]-4-iodopyridine-3-carbaldehyde (200.00 mg, 0.459 mmol, 1.00 equiv), 4-methyl-6-([4-[(2S)-2-methyl-4-(oxan-4-yl)piperazin-1-yl]-3-nitrophenyl]amino)-5-oxopyrazin-2-ylboronic acid (651.07 mg, 1.378 mmol, 3.00 equiv), THF (8.00 mL), H2O (2.00 mL), $K_3PO_4$ (292.60 mg, 1.378 mmol, 3.00 equiv), Pd(dppf)$Cl_2$ (33.62 mg, 0.046 mmol, 0.10 equiv). The resulting solution was stirred for 2 h at 50 degrees C. in an oil bath. The solids were filtered out. The resulting solution was extracted with 3×10 mL of ethyl acetate concentrated. The residue was applied onto a silica gel column and eluted with dichloromethane/methanol (10:1). The collected fractions were combined and concentrated. This resulted in 130 mg (38.45%) of 2-[4,4-dimethyl-9-oxo-1,10-diazatricyclo[6.4.0.0^[2,6]]dodeca-2(6),7-dien-10-yl]-4-[4-methyl-6-([4-[(2S)-2-methyl-4-(oxan-4-yl)piperazin-1-yl]-3-nitrophenyl]amino)-5-oxopyrazin-2-yl]pyridine-3-carbaldehyde as a brown solid. LC-MS: (ES, m/z): M+1: 736

Synthesis of 10-[3-(hydroxymethyl)-4-[4-methyl-6-([4-[(2S)-2-methyl-4-(oxan-4-yl)piperazin-1-yl]-3-nitrophenyl]amino)-5-oxopyrazin-2-yl]pyridin-2-yl]-4,4-dimethyl-1,10-diazatricyclo[6.4.0.0^[2,6]]dodeca-2(6),7-dien-9-one: Into a 8-mL vial, was placed 2-[4,4-dimethyl-9-oxo-1,10-diazatricyclo[6.4.0.0^[2,6]]dodeca-2(6),7-dien-10-yl]-4-[4-methyl-6-([4-[(2S)-2-methyl-4-(oxan-4-yl)piperazin-1-yl]-3-nitrophenyl]amino)-5-oxopyrazin-2-yl]pyridine-3-carbaldehyde (100.00 mg, 0.136 mmol, 1.00 equiv), THF (2.00 mL), $H_2O$ (200.00 uL), $K_2HPO_4$ (59.18 mg, 0.340 mmol, 2.50 equiv). This was followed by the addition of NaOH (1M) (300.00 uL, 7.501 mmol, 55.19 equiv) dropwise with stirring at 0 degrees C. To this was added $NaBH_4$ (5.14 mg, 0.136 mmol, 1.00 equiv), in portions at 0 degrees C. The resulting solution was stirred for 20 min at room temperature. The reaction was then quenched by the addition of 2 mL of water. The resulting solution was extracted with 3×5 mL of ethyl acetate concentrated. The residue was applied onto a silica gel column and eluted with dichloromethane/methanol (10:1). The collected fractions were combined and concentrated. This resulted in 50 mg (49.86%) of 10-[3-(hydroxymethyl)-4-[4-methyl-6-([4-[(2S)-2-methyl-4-(oxan-4-yl)piperazin-1-yl]-3-nitrophenyl]amino)-5-oxopyrazin-2-yl]pyridin-2-yl]-4,4-dimethyl-1,10-diazatricyclo[6.4.0.0^[2,6]]dodeca-2(6),7-dien-9-one as a yellow solid. LC-MS: (ES, m/z): M+1: 738

Synthesis of 10-[4-[6-([3-amino-4-[(2S)-2-methyl-4-(oxan-4-yl)piperazin-1-yl]phenyl]amino)-4-methyl-5-oxopyrazin-2-yl]-3-(hydroxymethyl)pyridin-2-yl]-4,4-dimethyl-1,10-diazatricyclo[6.4.0.0^[2,6]]dodeca-2(6),7-dien-9-one: Into a 30-mL pressure tank reactor, was placed 10-[3-(hydroxymethyl)-4-[4-methyl-6-([4-[(2S)-2-methyl-4-(oxan-4-yl)piperazin-1-yl]-3-nitrophenyl]amino)-5-oxopyrazin-2-yl]pyridin-2-yl]-4,4-dimethyl-1,10-diazatricyclo[6.4.0.0^[2,6]]dodeca-2(6),7-dien-9-one (50.00 mg, 0.068 mmol, 1.00 equiv), THF (5.00 mL, 0.069 mmol, 1.02 equiv), $PtO_2$ (4.62 mg, 0.020 mmol, 0.30 equiv). To the above $H_2(g)$ was introduced in at room temperature. The resulting solution was stirred for 2 h at room temperature. The solids were filtered out. The resulting mixture was concentrated. This resulted in 30 mg (crude) of 10-[4-[6-([3-amino-4-[(2S)-2-methyl-4-(oxan-4-yl)piperazin-1-yl]phenyl]amino)-4-methyl-5-oxopyrazin-2-yl]-3-(hydroxymethyl)pyridin-2-yl]-4,4-dimethyl-1,10-diazatricyclo[6.4.0.0^[2,6]]dodeca-2(6),7-dien-9-one as a yellow solid. LC-MS: (ES, m/z): M+1: 708

Synthesis of N-(5-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxopyrazin-2-yl]amino]-2-[(2S)-2-methyl-4-(oxan-4-yl)piperazin-1-yl]phenyl)prop-2-enamide hydrochloride: Into a 8-mL vial, was placed 10-[4-[6-([3-amino-4-[(2S)-2-methyl-4-(oxan-4-yl)piperazin-1-yl]phenyl]amino)-4-methyl-5-oxopyrazin-2-yl]-3-(hydroxymethyl)pyridin-2-yl]-4,4-dimethyl-1,10-diazatricyclo[6.4.0.0^[2,6]]dodeca-2(6),7-dien-9-one (20.00 mg, 0.028 mmol, 1.00 equiv), DCM (4.00 mL), DIEA (7.30 mg, 0.057 mmol, 2 equiv). This was followed by the addition of acryloyl chloride (2.56 mg, 0.028 mmol, 1.00 equiv) dropwise with stirring at 0 degrees C. The resulting solution was stirred for 2 h at room temperature. The resulting mixture was concentrated. The crude product was purified by Prep-HPLC with the following conditions: Column, X-bridge RP18; mobile phase, 0.05% FA in water and $CH_3CN$ (45% $CH_3CN$ up to 60% in 5 min); Detector, UV 254 nm. The collected solution was concentrated under vacuum to remove $CH_3CN$ and the resulting solution was dried by lyophilization(added with con.HCl (1 drop)). This resulted in 3.3 mg (14.63%) of N-(5-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxopyrazin-2-yl]amino]-2-[(2S)-2-methyl-4-(oxan-4-yl) piperazin-1-yl]phenyl)prop-2-enamide hydrochloride as a light yellow solid. LC-MS: (ES, m/z): M+1-HCl: 762. $^1$H NMR ((300 MHz, DMSO-$d_6$, ppm) δ 10.38 (s, 1H), 9.32 (s, 1H), 9.19 (s, 2H), 8.49 (d, J=5.1 Hz, 1H), 7.95 (d, J=5.1 Hz, 1H), 7.78 (s, 1H), 7.69 (d, J=9.0 Hz, 1H), 7.21 (d, J=8.7 Hz, 1H), 6.75 (dd, J=17.1, 10.2 Hz, 1H), 6.57 (s, 1H), 6.46-6.28 (m, 1H), 5.89-5.77 (m, 1H), 4.54 (d, J=17.1 Hz, 2H), 4.22 (s, 3H), 4.02 (d, J=11.4 Hz, 2H), 3.85 (s, 1H), 3.57 (s, 3H), 3.36 (t, J=11.4 Hz, 2H), 3.16 (d, J=12.9 Hz, 1H), 2.97 (t, J=15.0 Hz, 2H), 2.59 (d, J=4.5 Hz, 3H), 2.44 (s, 2H), 2.09 (s, 2H), 1.77 (s, 2H), 1.23 (s, 6H), 0.80 (d, J=6.0 Hz, 3H).

Example 23: Preparation of N-[2-[(2S)-4-(4,4-difluorocyclohexyl)-2-methylpiperazin-1-yl]-5-[[6-(2-[4,4-dimethyl-9-oxo-1,10-diazatricyclo[6.4.0.0^[2,6]]dodeca-2(6),7-dien-10-yl]-3-(hydroxymethyl) pyridin-4-yl)-4-methyl-3-oxopyrazin-2-yl]amino] phenyl]prop-2-enamide Synthesis of 2,4-dibromopyridine-3-carbaldehyde, Into a 1000-mL 3-necked round-bottom flask, was placed 2,4-dibromopyridine (40.00 g, 168.852 mmol, 1.00 equiv), THF (400.00 mL). This was followed by the addition of LDA (2M in hexane, 126.60 mL, 1.5 equiv) dropwise with stirring at −78 degrees C. The resulting solution was stirred for 1 h at −78 degrees C. Then DMF (16,04,219.507, 1.3 equiv) dropwise with stirring at −78 degrees C. The resulting solution was stirred for 0.5 hr at −78 degrees C. The reaction was then quenched by the addition of 500 mL of NH4Cl. The resulting solution was extracted with 3×500 mL of ethyl acetate concentrated. The residue was applied onto a silica gel column and eluted with ethyl acetate/petroleum ether (0:1-1:1). This resulted in 24.4 g (54.55%) of 2,4-dibromopyridine-3-carbaldehyde as a white solid. LC-MS: (ES, m/z): M+1: 264

Synthesis of (2,4-dibromopyridin-3-yl)methanol, Into a 100-mL round-bottom flask, was placed 2,4-dibromopyridine-3-carbaldehyde (2.00 g, 7.550 mmol, 1.00 equiv), EtOH (30.00 mL). This was followed by the addition of $NaBH_4$ (285.64 mg, 7.550 mmol, 1 equiv), in portions at 0 degrees C. The resulting solution was stirred for 3 h at room temperature. The reaction was then quenched by the addition of 30 mL of water. The resulting solution was extracted with 3×30 mL of ethyl acetate concentrated. The residue was applied onto a silica gel column and eluted with ethyl acetate/petroleum ether (1:1). The collected fractions were combined and concentrated. This resulted in 1.4 g (69.47%) of (2,4-dibromopyridin-3-yl)methanol as a light yellow solid. LC-MS: (ES, m/z): M+1: 266

Synthesis of 2,4-dibromo-3-[(oxan-2-yloxy)methyl]pyridine, Into a 100-mL round-bottom flask, was placed (2,4-dibromopyridin-3-yl)methanol (1.40 g, 5.245 mmol, 1.00 equiv), DCM (30.00 mL, 0.353 mmol, 0.07 equiv), PPTS (131.81 mg, 0.525 mmol, 0.10 equiv), DHP (661.79 mg, 7.868 mmol, 1.50 equiv). The resulting solution was stirred for overnight at 45 degrees C. in an oil bath. The reaction was then quenched by the addition of 30 mL of water. The resulting solution was extracted with 3×30 mL of dichloromethane concentrated. The residue was applied onto a silica gel column and eluted with ethyl acetate/petroleum ether (1:1). The collected fractions were combined and concentrated. This resulted in 1.5 mg (0.08%) of 2,4-dibromo-3-[(oxan-2-yloxy)methyl]pyridine as colorless oil. LC-MS: (ES, m/z): M+1: 350

Synthesis of 10-[4-bromo-3-[(oxan-2-yloxy)methyl]pyridin-2-yl]-4,4-dimethyl-1,10-diazatricyclo[6.4.0.0^[2,6]]dodeca-2(6),7-dien-9-one, Into a 100-mL round-bottom flask purged and maintained with an inert atmosphere of nitrogen, was placed 4,4-dimethyl-1,10-diazatricyclo[6.4.0.0^[2,6]] dodeca-2(6),7-dien-9-one (1.00 g, 4.895 mmol, 1.00 equiv), dioxane (40.00 mL, 0.454 mmol, 0.09 equiv), Cs2CO3 (3.19 g, 9.791 mmol, 2 equiv), 2,4-dibromo-3-[(oxan-2-yloxy) methyl]pyridine (1.72 g, 4.900 mmol, 1.00 equiv), Pd2 (dba)3 (448.28 mg, 0.490 mmol, 0.1 equiv), XantPhos (283.26 mg, 0.490 mmol, 0.1 equiv). The resulting solution was stirred for 1 h at 100 degrees C. in an oil bath. The reaction was then quenched by the addition of 40 mL of water. The resulting solution was extracted with 3×40 mL of ethyl acetate concentrated. The residue was applied onto a silica gel column and eluted with ethyl acetate/petroleum ether (1:1). The collected fractions were combined and concentrated. This resulted in 900 mg (38.75%) of 10-[4-bromo-3-[(oxan-2-yloxy)methyl]pyridin-2-yl]-4,4-dimethyl-1,10-diazatricyclo[6.4.0.0^[2,6]]dodeca-2(6),7-dien-9-one as a brown solid. LC-MS: (ES, m/z): M+1: 474

Synthesis of 2-[4,4-dimethyl-9-oxo-1,10-diazatricyclo [6.4.0.0^[2,6]]dodeca-2(6),7-dien-10-yl]-3-[(oxan-2-yloxy) methyl]pyridin-4-ylboronic acid, Into a 100-mL round-bottom flask purged and maintained with an inert atmosphere of nitrogen, was placed 10-[4-bromo-3-[(oxan-2-yloxy) methyl]pyridin-2-yl]-4,4-dimethyl-1,10-diazatricyclo [6.4.0.0^[2,6]]dodeca-2(6),7-dien-9-one (1.00 g, 2.108 mmol, 1.00 equiv), dioxane (10.00 mL), bis(pinacolato) diboron (1.34 g, 5.277 mmol, 2.50 equiv), KOAc (620.00 mg, 6.317 mmol, 3.00 equiv), Pd(dppf)$Cl_2$ (172.00 mg, 0.211 mmol, 0.10 equiv). The resulting solution was stirred for 2 h at 100 degrees C. in an oil bath. The reaction mixture was cooled to room temperature. The solids were filtered out. The resulting mixture was concentrated under vacuum. This resulted in 920 mg (crude) of 2-[4,4-dimethyl-9-oxo-1,10-diazatricyclo[6.4.0.0^[2,6]]dodeca-2(6),7-dien-10-yl]-3-[(oxan-2-yloxy)methyl]pyridin-4-ylboronic acid as brown oil. LC-MS: (ES, m/z): M+1: 436

Synthesis of 10-[1-hydroxy-3H-[1,2]oxaborolo[4,3-c] pyridin-4-yl]-4,4-dimethyl-1,10-diazatricyclo[6.4.0.0^[2,6]] dodeca-2(6),7-dien-9-one, Into a 100-mL round-bottom flask, was placed 2-[4,4-dimethyl-9-oxo-1,10-diazatricyclo [6.4.0.0^[2,6]]dodeca-2(6),7-dien-10-yl]-3-[(oxan-2-yloxy) methyl]pyridin-4-ylboronic acid (920 mg, 1.00 equiv, crude), dioxane (10 mL), HCl (6N, 10 mL). The resulting solution was stirred for 1 h at 25 degrees C. The resulting mixture was concentrated under vacuum. The crude product was purified by Flash-Prep-HPLC with the following conditions: Column, C18 reversed phase column; mobile phase, $H_2O$ (0.05% $NH_3 \cdot H_2O$) and $CH_3CN$ (5% $CH_3CN$ up to 30% in 15 min); Flow rate: 60 mL/min; Detector, 254/220 nm. This resulted in 350 mg of 10-[1-hydroxy-3H-[1,2]oxaborolo[4,3-c]pyridin-4-yl]-4,4-dimethyl-1,10-diazatricyclo [6.4.0.0^[2,6]]dodeca-2(6),7-dien-9-one as a light yellow solid. LC-MS: (ES, m/z): M+1: 338

Synthesis of 5-bromo-3-([4-[(2S)-4-(4,4-difluorocyclohexyl)-2-methylpiperazin-1-yl]-3-nitrophenyl]amino)-1-methylpyrazin-2-one, Into a 40-mL round-bottom flask, was placed 5-bromo-1-methyl-3-([4-[(2S)-2-methylpiperazin-1-yl]-3-nitrophenyl]amino)pyrazin-2-one (253.20 mg, 0.598 mmol, 1.00 equiv), 4,4-difluorocyclohexan-1-one (160.47 mg, 1.196 mmol, 2.00 equiv), THF (10.00 mL), HOAc (0.20 mL), $NaBH(OAc)_3$ (316.96 mg, 1.495 mmol, 2.5 equiv). The resulting solution was stirred for overnight at room temperature. The reaction was then quenched by the addition of 20 mL of water. The resulting solution was extracted with 3×20 mL of ethyl acetate concentrated. The residue was applied onto a silica gel column and eluted with dichloromethane/methanol (10:1). The collected fractions were combined and concentrated. This resulted in 154 mg (47.55%) of 5-bromo-3-([4-[(2S)-4-(4,4-difluorocyclohexyl)-2-methylpiperazin-1-yl]-3-nitrophenyl]amino)-1-methylpyrazin-2-one as a brown solid. LC-MS: (ES, m/z): M+1: 541

Synthesis of 3-([3-amino-4-[(2S)-4-(4,4-difluorocyclohexyl)-2-methylpiperazin-1-yl]phenyl]amino)-5-bromo-1-methylpyrazin-2-one, Into a 50-mL round-bottom flask, was placed 5-bromo-3-([4-[(2S)-4-(4,4-difluorocyclohexyl)-2-methylpiperazin-1-yl]-3-nitrophenyl]amino)-1-methylpyrazin-2-one (154.00 mg, 0.284 mmol, 1.00 equiv), EtOH (9.00 mL), H2O (3.00 mL), Fe (63.54 mg, 1.138 mmol, 4.00 equiv), $NH_4Cl$ (121.72 mg, 2.276 mmol, 8 equiv). The resulting solution was stirred for 2 h at 80 degrees C. in an oil bath. The solids were filtered out. The resulting mixture was concentrated. The residue was applied onto a silica gel column and eluted with dichloromethane/methanol (5:1). The collected fractions were combined and concentrated. This resulted in 145 mg (99.68%) of 3-([3-amino-4-[(2S)-4-(4,4-difluorocyclohexyl)-2-methylpiperazin-1-yl]phenyl]amino)-5-bromo-1-methylpyrazin-2-one as a yellow solid. LC-MS: (ES, m/z): M+1: 511

Synthesis of N-[5-[(6-bromo-4-methyl-3-oxopyrazin-2-yl)amino]-2-[(2S)-4-(4,4-difluorocyclohexyl)-2-methylpiperazin-1-yl]phenyl]prop-2-enamide, Into a 40-mL vial, was placed 3-([3-amino-4-[(2S)-4-(4,4-difluorocyclohexyl)-2-methylpiperazin-1-yl]phenyl]amino)-5-bromo-1-methylpyrazin-2-one (145.00 mg, 0.284 mmol, 1.00 equiv), DCM (10.00 mL), DIEA (73.29 mg, 0.567 mmol, 2 equiv). This was followed by the addition of acryloyl chloride (25.66 mg, 0.284 mmol, 1.00 equiv) dropwise with stirring at 0 degrees C. The resulting solution was stirred for 2 h at room temperature. The reaction was then quenched by the addition of 20 mL of water. The resulting solution was extracted with 3×20 mL of dichloromethane concentrated. The residue was applied onto a silica gel column and eluted with dichloromethane/methanol (10:1). The collected fractions were combined and concentrated. This resulted in 82 mg (51.15%) of N-[5-[(6-bromo-4-methyl-3-oxopyrazin-2-yl)amino]-2-[(2S)-4-(4,4-difluorocyclohexyl)-2-methylpiperazin-1-yl]phenyl]prop-2-enamide as a light yellow solid. LC-MS: (ES, m/z): M+1: 565

Synthesis of N-[2-[(2S)-4-(4,4-difluorocyclohexyl)-2-methylpiperazin-1-yl]-5-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxopyrazin-2-yl]amino]phenyl]prop-2-enamide: Into a 8-mL vial purged and maintained with an inert atmosphere of nitrogen, was placed N-[5-[(6-bromo-4-methyl-3-oxopyrazin-2-yl)amino]-2-[(2S)-4-(4,4-difluorocyclohexyl)-2-methylpiperazin-1-yl]phenyl]prop-2-enamide (82.00 mg, 0.145 mmol, 1.00 equiv), 10-[1-hydroxy-3H-[1,2]oxaborolo[4,3-c]pyridin-4-yl]-4,4-dimethyl-1,10-diazatricyclo[6.4.0.0^[2,6]]dodeca-2(6),7-dien-9-one (48.90 mg, 0.145 mmol, 1.00 equiv), dioxane (4.00 mL), $H_2O$ (0.40 mL), $K_2CO_3$ (50.10 mg, 0.363 mmol, 2.50 equiv), $Pd(dppf)Cl_2$ (10.61 mg, 0.015 mmol, 0.1 equiv). The resulting solution was stirred for 1 h at 90 degrees C. in an oil bath. The solids were filtered out. The resulting mixture was concentrated. The crude product was purified by Prep-HPLC with the following conditions: Column, X-bridge RP18; mobile phase, 0.05% ammonia in water and $CH_3CN$ (45% $CH_3CN$ up to 60% in 5 min); Detector, UV 254 nm. This resulted in 25 mg (21.66%) of N4-[4(2S)-4-(4,4-difluorocyclohexyl)-2-methylpiperazin-1-yl]-5-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxopyrazin-2-yl]amino]phenyl]prop-2-enamide as a white solid. LC-MS: (ES, m/z): M+1: 796. $^1H$ NMR (300 MHz, DMSO-$d_6$, ppm) δ 9.03 (s, 1H), 8.46 (d, J=5.1 Hz, 1H), 7.90 (d, J=5.1 Hz, 1H), 7.70 (s, 1H), 7.57 (d, J=8.7 Hz, 1H), 7.24 (d, J=8.7 Hz, 1H), 6.66-6.48 (m, 2H), 6.27 (d, J=17.1 Hz, 1H), 5.80 (d, J=10.4 Hz, 1H), 4.65-4.52 (m, 1H), 4.46 (dd, J=12.0, 5.4 Hz, 1H), 4.19 (s, 3H), 3.82 (s, 1H), 3.55 (s, 3H), 3.01 (s, 1H), 2.93-2.65 (m, 4H), 2.56 (d, J=5.1 Hz, 2H), 2.43-2.42 (m, 1H), 2.41 (s, 2H), 2.28 (s, 1H), 2.17 (t, J=10.2 Hz, 1H), 2.04 (s, 1H), 1.83 (d, J=13.5 Hz, 4H), 1.54 (d, J=11.7 Hz, 2H), 1.20 (s, 6H), 0.70 (d, J=6.0 Hz, 3H).

Example 24: Preparation of N-(2-((2'S, 4'S or 4'R)-4,4-difluoro-2'-methyl-[1,4'-bipiperidin]-1'-yl)-5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)phenyl)acrylamide Synthesis of 5-bromo-3-[(4-fluoro-3-nitrophenyl)amino]-1-methylpyrazin-2-one: Into a 250-mL round-bottom flask, was placed 4-fluoro-3-nitroaniline (10.00 g, 64.055 mmol, 1.00 equiv), 3,5-dibromo-1-methylpyrazin-2-one (17.16 g, 64.052 mmol, 1.00 equiv), NMP (30 ml). The resulting solution was stirred for 1 h at 140 degrees C. in an oil bath. The resulting solution was diluted with 300 mL of EA. The solids were collected by filtration. This resulted in 13 g (59.15%) of 5-bromo-3-[(4-fluoro-3-nitrophenyl) amino]-1-methylpyrazin-2-one as a brown solid. LCMS-1 (ES, m/z): M+1: 343

Synthesis of 2, 4-dibromopyridine-3-carbaldehyde: Into a 1000-mL 3-necked round-bottom flask, was placed 2, 4-dibromopyridine (40.00 g, 168.852 mmol, 1.00 equiv), THF (400.00 mL). This was followed by the addition of LDA (2M in hexane, 126.60 mL, 1.50 equiv) dropwise with stirring at −78 degrees C. The resulting solution was stirred for 1 h at −78 degrees C. Then DMF (16.04 ml, 219.507 mmol, 1.30 equiv) dropwise with stirring at −78 degrees C. The resulting solution was stirred for 0.5 h at −78 degrees C. The reaction was then quenched by the addition of 500 mL of $NH_4Cl$. The resulting solution was extracted with 3×500 mL of ethyl acetate concentrated. The residue was applied onto a silica gel column and eluted with ethyl acetate/petroleum ether (0:1-1:1). This resulted in 24.4 g (54.55%) of 2, 4-dibromopyridine-3-carbaldehyde as a white solid. LCMS-2 (ES, m/z): M+1: 264

Synthesis of (2, 4-dibromopyridin-3-yl) methanol: Into a 100-mL round-bottom flask, was placed 2, 4-dibromopyridine-3-carbaldehyde (2.00 g, 7.550 mmol, 1.00 equiv), EtOH (30.00 mL). This was followed by the addition of $NaBH_4$ (285.64 mg, 7.550 mmol, 1 equiv), in portions at 0 degrees C. The resulting solution was stirred for 3 h at room temperature. The reaction was then quenched by the addition of 30 mL of water. The resulting solution was extracted with 3×30 mL of ethyl acetate concentrated. The residue was applied onto a silica gel column and eluted with ethyl acetate/petroleum ether (1:1). The collected fractions were combined and concentrated. This resulted in 1.4 g (69.47%) of (2, 4-dibromopyridin-3-yl) methanol as a light yellow solid. LCMS-3 (ES, m/z): M+1: 266

Synthesis of 2,4-dibromo-3-[(oxan-2-yloxy) methyl]pyridine: Into a 100-mL round-bottom flask, was placed (2, 4-dibromopyridin-3-yl) methanol (1.40 g, 5.245 mmol, 1.00 equiv), DCM (30.00 mL, 0.353 mmol, 0.07 equiv), PPTS (131.81 mg, 0.525 mmol, 0.10 equiv), DHP (661.79 mg, 7.868 mmol, 1.50 equiv). The resulting solution was stirred for overnight at 45 degrees C. in an oil bath. The reaction was then quenched by the addition of 30 mL of water. The resulting solution was extracted with 3×30 mL of dichloromethane concentrated. The residue was applied onto a silica gel column and eluted with ethyl acetate/petroleum ether (1:1). The collected fractions were combined and concentrated. This resulted in 1.5 g (80%) of 2,4-dibromo-3-[(oxan-2-yloxy) methyl]pyridine as colorless oil. LCMS-4 (ES, m/z): M+1: 350

Synthesis of 10-[4-bromo-3-[(oxan-2-yloxy) methyl]pyridin-2-yl]-4, 4-dimethyl-1, 10-diazatricyclo[6.4.0.0^[2, 6]]dodeca-2(6), 7-dien-9-one: Into a 100-mL round-bottom flask purged and maintained with an inert atmosphere of nitrogen, was placed 4,4-dimethyl-1,10-diazatricyclo [6.4.0.0^[2,6]]dodeca-2(6),7-dien-9-one (1.00 g, 4.895 mmol, 1.00 equiv), dioxane (40.00 mL, 0.454 mmol, 0.09 equiv), $Cs_2CO_3$ (3.19 g, 9.791 mmol, 2.00 equiv), 2,4-dibromo-3-[(oxan-2-yloxy)methyl]pyridine (1.72 g, 4.900 mmol, 1.00 equiv), $Pd_2(dba)_3$ (448.28 mg, 0.490 mmol, 0.10 equiv), XantPhos (283.26 mg, 0.490 mmol, 0.10 equiv). The resulting solution was stirred for 1 h at 100 degrees C. in an oil bath. The reaction was then quenched by the addition of 40 mL of water. The resulting solution was extracted with 3×40 mL of ethyl acetate concentrated. The residue was applied onto a silica gel column and eluted with ethyl acetate/petroleum ether (1:1). The collected fractions were combined and concentrated. This resulted in 900 mg (38.75%) of 10-[4-bromo-3-[(oxan-2-yloxy)methyl]pyridin-2-yl]-4,4-dimethyl-1,10-diazatricyclo[6.4.0.0^[2,6]]dodeca-2(6),7-dien-9-one as a brown solid. LCMS-5 (ES, m/z): M+1: 474

Synthesis of 2-[4, 4-dimethyl-9-oxo-1, 10-diazatricyclo [6.4.0.0^[2, 6]]dodeca-2(6), 7-dien-10-yl]-3-[(oxan-2-yloxy) methyl]pyridin-4-ylboronic acid: Into a 100-mL round-bottom flask purged and maintained with an inert atmosphere of nitrogen, was placed 10-[4-bromo-3-[(oxan-2-yloxy)methyl]pyridin-2-yl]-4, 4-dimethyl-1, 10-diazatricyclo [6.4.0.0^[2, 6]]dodeca-2(6), 7-dien-9-one (1.00 g, 2.108 mmol, 1.00 equiv), Dioxane (10.00 mL), bis(pinacolato)diboron (1.34 g, 5.277 mmol, 2.50 equiv), KOAc (620.00 mg, 6.317 mmol, 3.00 equiv), $Pd(dppf)Cl_2$ (172.00 mg, 0.211 mmol, 0.10 equiv). The resulting solution was stirred for 2 h at 100 degrees C. in an oil bath. The reaction mixture was cooled to room temperature. The solids were filtered out. The resulting mixture was concentrated under vacuum. This resulted in 920 mg (crude) of 2-[4,4-dimethyl-9-oxo-1,10-diazatricyclo[6.4.0.0^[2,6]]dodeca-2(6),7-dien-10-yl]-3-[(oxan-2-yloxy)methyl]pyridin-4-ylboronic acid as brown oil. LCMS-6 (ES, m/z): M+1: 436

Synthesis of 10-[1-hydroxy-3H-[1, 2]oxaborolo[4, 3-c] pyridin-4-yl]-4, 4-dimethyl-1, 10-diazatricyclo[6.4.0.0^[2, 6]]dodeca-2(6), 7-dien-9-one: Into a 100-mL round-bottom flask, was placed 2-[4,4-dimethyl-9-oxo-1,10-diazatricyclo [6.4.0.0^[2,6]]dodeca-2(6),7-dien-10-yl]-3-[(oxan-2-yloxy) methyl]pyridin-4-ylboronic acid (920 mg, 1.00 equiv, crude), dioxane (10 mL), HCl (6N, 10 mL). The resulting solution was stirred for 1 h at 25 degrees C. The resulting mixture was concentrated under vacuum. The crude product was purified by Flash-Prep-HPLC with the following conditions: Column, C18 reversed phase column; mobile phase, $H_2O$ (0.05% $NH_3 \cdot H_2O$) and $CH_3CN$ (5% $CH_3CN$ up to 30% in 15 min); Flow rate: 60 mL/min; Detector, 254/220 nm. This resulted in 350 mg of 10-[1-hydroxy-3H-[1,2]oxaborolo[4,3-c]pyridin-4-yl]-4,4-dimethyl-1,10-diazatricyclo [6.4.0.0^[2,6]]dodeca-2(6),7-dien-9-one as a light yellow solid. LCMS-7 (ES, m/z): M+1: 338

Synthesis of (E)-N-methoxy-N-methylbut-2-enamide: Into a 3-L 4-necked round-bottom flask, was placed N, O-dimethylhydroxylamine (150.00 g, 1544.231 mmol, 1.10 equiv), DCM (1500.00 mL). This was followed by the addition of TEA (298.00 g, 2948.077 mmol, 2.10 equiv) dropwise with stirring at 0 degrees C. The solution was stirred for 20 min. To this was added acryloyl chloride (146.00 g, 1403.846 mmol, 1.00 equiv) dropwise with stirring at 0 degrees C. The resulting solution was stirred for 3 h at room temperature in a water bath. The resulting mixture was washed with 3×400 ml of 1N HCl and 3×400 mL of $NaHCO_3$. The resulting mixture was washed with 1×500 mL of brine. The mixture was dried over anhydrous sodium sulfate and concentrated. This resulted in 110 g of (E)-N-methoxy-N-methylprop-2-enamide as light yellow oil. LCMS-8 (ES, m/z): M+1: 130

Synthesis of (S)-2-methyl-14(S)-1-phenylethyl) piperidin-4-one: Into a 1000-mL 3-necked round-bottom flask, was placed (2E)-N-methoxy-N-methylbut-2-enamide (50.00 g, 390.625 mmol, 1.00 equiv), THF (500.00 mL). This was followed by the addition of bromo (ethenyl) magnesium (76.00 g, 585.938 mmol, 1.50 equiv) dropwise with stirring at 0 degrees C. The solution was stirred for 1 h at R.T degree C. To this was added (S)-1-phenylethanamine (95.00 g, 781.250 mmol, 2.00 equiv) dropwise with stirring at R.T. To the mixture was added $H_2O$ (50.00 mL) dropwise with stirring at R.T. The resulting solution was stirred for 2 h at room temperature in a water bath. The resulting mixture was concentrated. The resulting solution was diluted with 300 mL of water. The resulting solution was extracted with 3×400 mL of dichloromethane and the organic layers combined. The resulting mixture was washed with 1×300 mL of brine. The solid was dried in an oven under reduced pressure. The residue was applied onto a silica gel column with ethyl acetate/petroleum ether (1:5). This resulted in 4.5 g of (S)-2-methyl-1-((S)-1-phenylethyl) piperidin-4-one as a yellow solid. LCMS-9 (ES, m/z): M+1: 218

Synthesis of (S)-4, 4-difluoro-2'-methyl-1'4(S)-1-phenylethyl)-1, 4'-bipiperidine(cis and trans mixture): Into a 50-mL round-bottom flask, was placed 4, 4-difluoropiperidine (602.00 mg, 4.980 mmol, 2.00 equiv), (S)-2-methyl-1-((S)-1-phenylethyl) piperidin-4-one (540.00 mg, 2.490 mmol, 1.00 equiv), $NaBH(OAc)_3$ (1.05 g, 4.980 mmol, 2.00 equiv), AcOH (200.00 uL), THF (20.00 mL). The resulting solution was stirred for 6 h at room temperature. The resulting mixture was concentrated. The resulting solution was diluted with 20 mL of water. The resulting solution was extracted with 3×30 mL of ethyl acetate and the organic layers combined. The resulting mixture was washed with 2×20 ml of $NaHCO_3$ and 1×20 mL of brine. The mixture was dried over anhydrous sodium sulfate and concentrated. The residue was applied onto a silica gel column with ethyl acetate/petroleum ether (1:3). This resulted in 1.0 g of (S)-4, 4-difluoro-2'-methyl-1'-((S)-1-phenylethyl)-1, 4'-bipiperidine(cis and trans mixture) as light yellow oil. LCMS-10 (ES, m/z): M+1: 323

Synthesis of (S)-4, 4-difluoro-2'-methyl-1, 4'-bipiperidine (cis and trans mixture): Into a 50-mL pressure tank reactor purged and maintained with an inert atmosphere of hydric (10 atm), was placed (S)-4, 4-difluoro-2'-methyl-1'-((S)-1-phenylethyl)-1, 4'-bipiperidine(cis and trans mixture) (1.00 g, 3.106 mmol, 1.00 equiv), $Pd(OH)_2/C$ (43.00 mg, 0.311 mmol, 0.10 equiv), THF (6.00 mL). The resulting solution was stirred for 18 h at room temperature. The solids were filtered out. The resulting mixture was concentrated. The residue was applied onto a silica gel column with dichloromethane/methanol (3:1). This resulted in 900 mg of (S)-4,4-difluoro-2'-methyl-1,4'-bipiperidine(cis and trans mixture) as light green oil. LCMS-11 (ES, m/z): M+1: 219

Synthesis of 5-bromo-3-(4-((2'S, 4'S or 4'R)-4, 4-difluoro-2'-methyl-1, 4'-bipiperidin-1'-yl)-3-nitrophenylamino)-1-methylpyrazin-2(1H)-one(Assumed): Into a 50-mL round-bottom flask, was placed (S)-4,4-difluoro-2'-methyl-1,4'-bipiperidine (cis and trans mixture) (900.00 mg, 4.128 mmol, 1.00 equiv), 5-bromo-3-[(4-fluoro-3-nitrophenyl) amino]-1-methylpyrazin-2-one (1.40 g, 4.128 mmol, 1.00 equiv), DIEA (1.60 g, 12.385 mmol, 3.00 equiv), NMP (20.00 mL). The resulting solution was stirred for 72 h at 110 degrees C. in an oil bath. The reaction mixture was cooled to room temperature with a water/ice bath. The resulting solution was diluted with 150 mL of DCM. The resulting mixture was washed with 5×30 of water and 1×30 mL of brine. The mixture was dried over anhydrous sodium sulfate and concentrated. The residue was applied onto a silica gel column with dichloromethane/methanol (3:1). This resulted in 340 mg of 5-bromo-3-(4-((2'S, 4'S or 4'R)-4, 4-difluoro-2'-methyl-1, 4'-bipiperidin-1'-yl)-3-nitrophenylamino)-1-methylpyrazin-2(1H)-one(Assumed) as brown oil. LCMS-12 (ES, m/z): M+1: 541

Synthesis of 5-bromo-3-(4-((2'S, 4'R or 4'S)-4, 4-difluoro-2'-methyl-1, 4'-bipiperidin-1'-yl)-3-nitrophenylamino)-1-methylpyrazin-2(1H)-one(Assumed): Into a 50-mL round-bottom flask, was placed (S)-4,4-difluoro-2'-methyl-1,4'-bipiperidine (900.00 mg, 4.128 mmol, 1.00 equiv), 5-bromo-3-[(4-fluoro-3-nitrophenyl) amino]-1-methylpyrazin-2-one (1.40 g, 4.128 mmol, 1.00 equiv), DIEA (1.60 g, 12.385 mmol, 3.00 equiv), NMP (20.00 mL). The resulting solution was stirred for 72 h at 110 degrees C. in an oil bath. The reaction mixture was cooled to room temperature with a water/ice bath. The resulting solution was diluted with 150 mL of DCM. The resulting mixture was washed with 5×30 of water and 1×30 mL of brine. The mixture was dried over anhydrous sodium sulfate and concentrated. The residue was applied onto a silica gel column with dichloromethane/methanol (3:1). This resulted in 340 mg of 5-bromo-3-(4-((2'S, 4'R or 4'S)-4, 4-difluoro-2'-methyl-1, 4'-bipiperidin-1'-yl)-3-nitrophenylamino)-1-methylpyrazin-2(1H)-one(Assumed) as brown oil. LCMS-13 (ES, m/z): M+1: 541

Synthesis of 3-(3-amino-4-((2'S, 4'S or 4'R)-4, 4-difluoro-2'-methyl-1, 4'-bipiperidin-1'-yl) phenylamino)-5-bromo-1-methylpyrazin-2(1H)-one(Assumed): Into a 50-mL round-bottom flask, was placed 5-bromo-3-(4-((2'S, 4'S or 4'R)-4, 4-difluoro-2'-methyl-1, 4'-bipiperidin-1'-yl)-3-nitrophenylamino)-1-methylpyrazin-2(1H)-one(Assumed) (180.00 mg, 0.333 mmol, 1.00 equiv), Fe (75.00 mg, 1.333 mmol, 4.00 equiv), $NH_4Cl$ (144.00 mg, 2.667 mmol, 8.00 equiv), EtOH (9.00 mL), $H_2O$ (3.00 mL). The resulting solution was stirred for 2 h at 80 degrees C. in an oil bath. The reaction mixture was cooled to room temperature with a water/ice bath. The solids were filtered out. The resulting mixture was concentrated. The resulting solution was diluted with 50 mL of water. The resulting solution was extracted with 5×40 mL of dichloromethane and the organic layers combined. The resulting mixture was washed with 1×40 ml of brine. The mixture was dried over anhydrous sodium sulfate and concentrated. This resulted in 120 mg of 3-(3-amino-4-((2'S, 4'S or 4'R)-4, 4-difluoro-2'-methyl-1, 4'-bipiperidin-1'-yl) phenylamino)-5-bromo-1-methylpyrazin-2(1H)-one(Assumed) as light yellow oil. LCMS-14 (ES, m/z): M+1: 511

Synthesis of 3-(3-amino-4-((2'S, 4'R or 4'S)-4, 4-difluoro-2'-methyl-1, 4'-bipiperidin-1'-yl) phenylamino)-5-bromo-1-methylpyrazin-2(1H)-one(Assumed): Into a 50-mL round-bottom flask, was placed 5-bromo-3-(4-((2'S, 4'R or 4'S)-4, 4-difluoro-2'-methyl-1, 4'-bipiperidin-1'-yl)-3-nitrophenylamino)-1-methylpyrazin-2(1H)-one(Assumed) (180.00 mg, 0.333 mmol, 1.00 equiv), Fe (75.00 mg, 1.333 mmol, 4.00 equiv), $NH_4Cl$ (144.00 mg, 2.667 mmol, 8.00 equiv), EtOH (9.00 mL), $H_2O$ (3.00 mL). The resulting solution was stirred for 2 h at 80 degrees C. in an oil bath. The reaction mixture was cooled to room temperature with a water/ice bath. The solids were filtered out. The resulting mixture was concentrated. The resulting solution was diluted with 50 mL of water. The resulting solution was extracted with 5×40 mL of dichloromethane and the organic layers combined. The resulting mixture was washed with 1×40 ml of brine. The mixture was dried over anhydrous sodium sulfate and concentrated. This resulted in 120 mg of 3-(3-amino-4-((2'S, 4'R or 4'S)-4, 4-difluoro-2'-methyl-1, 4'-bipiperidin-1'-yl) phenylamino)-5-bromo-1-methylpyrazin-2(1H)-one(Assumed) as light yellow oil. LCMS-15 (ES, m/z): M+1: 511

Synthesis of N-(5-(6-bromo-4-methyl-3-oxo-3, 4-dihydropyrazin-2-ylamino)-2-((2'S, 4'S or 4'R)-4, 4-difluoro-2'-methyl-1, 4'-bipiperidin-1'-yl) phenyl) acrylamide(Assumed): Into a 50-mL round-bottom flask, was placed 3-(3-amino-4-((2'S, 4'S or 4'R)-4, 4-difluoro-2'-methyl-1, 4'-bipiperidin-1'-yl) phenylamino)-5-bromo-1-methylpyrazin-2(1H)-one(Assumed) (120.00 mg, 0.235 mmol, 1.00 equiv), DIEA (61.00 mg, 0.471 mmol, 2.00 equiv), DCM (5.00 mL). This solution was stirred for 15 min at 0 degree C. This was followed by the addition of acryloyl chloride (26.00 mg, 0.282 mmol, 1.20 equiv) dropwise with stirring at 0 degrees C. The resulting solution was stirred for 1 h at room temperature. The resulting mixture was concentrated. The residue was applied onto a silica gel column with dichloromethane/methanol (3:1). This resulted in 80 mg of N-(5-(6-bromo-4-methyl-3-oxo-3, 4-dihydropyrazin-2-ylamino)-2-((2'S, 4'S or 4'R)-4, 4-difluoro-2'-methyl-1, 4'-bipiperidin-1'-yl) phenyl) acrylamide(Assumed) as a brown solid. LCMS-16 (ES, m/z): M+1: 565

Synthesis of N-(5-(6-bromo-4-methyl-3-oxo-3, 4-dihydropyrazin-2-ylamino)-2-((2'S, 4'R or 4'S)-4, 4-difluoro-2'-methyl-1, 4'-bipiperidin-1'-yl) phenyl) acrylamide(Assumed): Into a 50-mL round-bottom flask, was placed 3-(3-amino-4-((2'S, 4'R or 4'S)-4, 4-difluoro-2'-methyl-1, 4'-bipiperidin-1'-yl) phenylamino)-5-bromo-1-methylpyrazin-2(1H)-one(Assumed) (120.00 mg, 0.235 mmol, 1.00 equiv), DIEA (61.00 mg, 0.471 mmol, 2.00 equiv), DCM (5.00 mL). This solution was stirred for 15 min at 0 degree C. This was followed by the addition of acryloyl chloride (26.00 mg, 0.282 mmol, 1.20 equiv) dropwise with stirring at 0 degrees C. The resulting solution was stirred for 1 h at room temperature. The resulting mixture was concentrated. The residue was applied onto a silica gel column with dichloromethane/methanol (3:1). This resulted in 80 mg of N-(5-(6-bromo-4-methyl-3-oxo-3, 4-dihydropyrazin-2-ylamino)-2-((2'S, 4'R or 4'S)-4, 4-difluoro-2'-methyl-1, 4'-bipiperidin-1'-yl) phenyl) acrylamide(Assumed) as a brown solid. LCMS-17 (ES, m/z): M+1: 565

Synthesis of N-(2-((2'S,4'S or 4'R)-4,4-difluoro-2'-methyl-[1,4'-bipiperidin]-1'-yl)-5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)phenyl)acrylamide: Into a 50-mL round-bottom flask purged and maintained with an inert atmosphere of nitrogen, was placed N-(5-(6-bromo-4-methyl-3-oxo-3, 4-dihydropyrazin-2-ylamino)-2-((2'S, 4'S or 4'R)-4, 4-difluoro-2'-methyl-1, 4'-bipiperidin-1'-yl) phenyl) acrylamide(Assumed) (140.00 mg, 0.248 mmol, 1.00 equiv), 10-[1-hydroxy-3H-[1,2]oxaborolo[4,3-c]pyridin-4-yl]-4,4-dimethyl-1,10-diazatricyclo[6.4.0.0^[2,6]]dodeca-2(6),7-dien-9-one (81.00 mg, 0.248 mmol, 1.00 equiv), Pd(dppf)$Cl_2$ (12.00 mg, 0.025 mmol, 0.10 equiv), Dioxane (5.00 mL), $K_3PO_4$ (86.00 mg, 0.621 mmol, 2.50 equiv). The resulting solution was stirred for 2 h at 90 degrees C. in an oil bath. The reaction mixture was cooled to room temperature with a water/ice bath. The resulting solution was diluted with 10 mL of DCM. The solids were filtered out. The resulting mixture was concentrated. The crude product was purified by Prep-HPLC with the following conditions: column, X-Bridge Prep C18 19*150 mm 5 um; mobile phase, A: water (it contains 10 mM $NH_4HCO_3$ 0.05% ammonia); B: ACN; Gradient: 20-45% B in 8 min; Flow rate: 20 mL/min; detector, UV 220 nm. The collected solution was concentrated under vacuum to remove $CH_3CN$ and the resulting solution was dried by lyophilization. This resulted in 20 mg of N-(2-((2'S,4'S or 4'R)-4,4-difluoro-2'-methyl-[1,4'-bipiperidin]-1'-yl)-5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)phenyl)acrylamide (Assumed) as a light yellow solid. LCMS-18 (ES, m/z): M+1: 796. $^1$H NMR (300 MHz, DMSO-$d_6$, ppm) δ 9.22 (s, 2H), 9.13 (s, 1H), 8.47-8.49 (d, J=6.0 Hz, 1H), 7.94-7.96 (d, J=6.0 Hz, 1H), 7.77 (s, 1H), 7.60-7.63 (d, J=9.0 Hz, 1H), 7.21-7.24 (d, J=9.0 Hz, 1H), 6.63-6.67 (m, 1H), 6.57 (s, 1H), 6.27-6.33 (d, J=18.0 Hz, 1H), 5.79-5.83 (d, J=12.0 Hz, 1H), 5.02 (s, 1H), 4.57 (s, 1H), 4.51 (s, 1H), 4.22 (s, 3H), 3.84 (s, 1H), 3.57 (s, 3H), 2.93 (s, 1H), 2.51-2.80 (m, 9H), 2.44 (s, 2H), 1.86-2.00 (m, 5H), 1.67-1.79 (m, 2H), 1.40-1.47 (m, 1H), 1.23 (s, 6H), 0.75-0.77 (d, J=6.0 Hz, 3H).

Synthesis of N-(2-((2'S,4'R or 4'S)-4,4-difluoro-2'-methyl-[1,4'-bipiperidin]-1'-yl)-5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)phenyl)acrylamide (Assumed): Into a 50-mL round-bottom flask purged and maintained with an inert atmosphere of nitrogen, was placed N-(5-(6-bromo-4-methyl-3-oxo-3, 4-dihydropyrazin-2-ylamino)-2-((2'S, 4'R or 4'S)-4, 4-difluoro-2'-methyl-1, 4'-bipiperidin-1'-yl) phenyl) acrylamide(Assumed) (140.00 mg, 0.248 mmol, 1.00 equiv), 10-[1-hydroxy-3H-[1,2]oxaborolo[4,3-c]pyridin-4-yl]-4,4-dimethyl-1,10-diazatricyclo [6.4.0.0^[2,6]]dodeca-2(6),7-dien-9-one (81.00 mg, 0.248 mmol, 1.00 equiv), Pd(dppf)$Cl_2$ (12.00 mg, 0.025 mmol, 0.10 equiv), $K_3PO_4$ (86.00 mg, 0.621 mmol, 2.50 equiv), Dioxane (5.00 mL). The resulting solution was stirred for 2 h at 90 degrees C. in an oil bath. The reaction mixture was cooled to room temperature with a water/ice bath. The resulting solution was diluted with 10 mL of DCM. The solids were filtered out. The resulting mixture was concentrated. The crude product was purified by Prep-HPLC with the following conditions: column, X-Bridge Prep C18 19*150 mm 5 um; mobile phase, A: water (it contains 10 mM $NH_4HCO_3$ 0.05% ammonia); B: ACN; Gradient: 20-45% B in 8 min; Flow rate: 20 mL/min; detector, UV 220 nm. The collected solution was concentrated under vacuum to remove $CH_3CN$ and the resulting solution was dried by lyophilization. This resulted in 15 mg of N-(2-((2'S,4'R or 4'S)-4,4-difluoro-2'-methyl-[1,4'-bipiperidin]-1'-yl)-5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)phenyl)acrylamide(Assumed) as a light yellow solid. LCMS-19 (ES, m/z): M+1: 796. $^1$H NMR (300 MHz, DMSO-$d_6$, ppm) δ 9.19 (s, 1H), 9.05 (s, 1H), 8.91 (s, 1H), 8.46-8.48 (d, J=6.0 Hz, 1H), 7.89-7.91 (d, J=6.0 Hz, 1H), 7.75 (s, 1H), 7.60-7.63 (d, J=9.0 Hz, 1H), 7.05-7.08 (d, J=9.0 Hz, 1H), 6.64-6.73 (m, 1H), 6.56-6.58 (d, J=6.0 Hz, 1H), 6.28-6.34 (d, J=18.0 Hz, 1H), 5.76-5.80 (d, J=12.0 Hz, 1H), 4.99-5.04 (m, 1H), 4.43-4.63 (m, 2H), 4.22 (s, 3H), 3.83-3.86 (m, 1H), 3.56 (s, 3H), 3.02-3.05 (m, 1H), 2.80-2.83 (m, 1H), 2.52-2.64 (m, 8H), 2.44 (s, 2H), 1.92-2.08 (m, 5H), 1.81 (s, 2H), 1.58-1.64 (m, 1H), 1.23 (s, 6H), 0.83-0.85 (d, J=6.0 Hz, 3H).

Example 25: Preparation of N-(54(6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-((2S,4'S or 4'R)-2-methyl-4-(4-methylpiperazin-1-yl)piperidin-1-yl)phenyl)acrylamide(Assumed)

Synthesis of 5-bromo-3-[(4-fluoro-3-nitrophenyl)amino]-1-methylpyrazin-2-one: Into a 250-mL round-bottom flask, was placed 4-fluoro-3-nitroaniline (10.00 g, 64.055 mmol, 1.00 equiv), 3, 5-dibromo-1-methylpyrazin-2-one (17.16 g, 64.052 mmol, 1.00 equiv), NMP (30 ml). The resulting solution was stirred for 1 h at 140 degrees C. in an oil bath. The resulting solution was diluted with 300 mL of EA. The solids were collected by filtration. This resulted in 13 g (59.15%) of 5-bromo-3-[(4-fluoro-3-nitrophenyl) amino]-1-methylpyrazin-2-one as a brown solid. LCMS-1 (ES, m/z): M+1: 343

Synthesis of 2, 4-dibromopyridine-3-carbaldehyde: Into a 1000-mL 3-necked round-bottom flask, was placed 2, 4-dibromopyridine (40.00 g, 168.852 mmol, 1.00 equiv), THF (400.00 mL). This was followed by the addition of LDA (2M in hexane, 126.60 mL, 1.50 equiv) dropwise with stirring at −78 degrees C. The resulting solution was stirred for 1 h at −78 degrees C. Then DMF (16.04 ml, 219.507 mmol, 1.30 equiv) dropwise with stirring at −78 degrees C. The resulting solution was stirred for 0.5 h at −78 degrees C. The reaction was then quenched by the addition of 500 mL of $NH_4Cl$. The resulting solution was extracted with 3×500 mL of ethyl acetate concentrated. The residue was applied onto a silica gel column and eluted with ethyl acetate/petroleum ether (0:1-1:1). This resulted in 24.4 g (54.55%) of 2, 4-dibromopyridine-3-carbaldehyde as a white solid. LCMS-2 (ES, m/z): M+1: 264

Synthesis of (2, 4-dibromopyridin-3-yl) methanol: Into a 100-mL round-bottom flask, was placed 2, 4-dibromopyridine-3-carbaldehyde (2.00 g, 7.550 mmol, 1.00 equiv), EtOH (30.00 mL). This was followed by the addition of $NaBH_4$ (285.64 mg, 7.550 mmol, 1 equiv), in portions at 0 degrees C. The resulting solution was stirred for 3 h at room temperature. The reaction was then quenched by the addition of 30 mL of water. The resulting solution was extracted with 3×30 mL of ethyl acetate concentrated. The residue was applied onto a silica gel column and eluted with ethyl acetate/petroleum ether (1:1). The collected fractions were combined and concentrated. This resulted in 1.4 g (69.47%) of (2, 4-dibromopyridin-3-yl) methanol as a light yellow solid. LCMS-3 (ES, m/z): M+1: 266

Synthesis of 2,4-dibromo-3-[(oxan-2-yloxy) methyl]pyridine: Into a 100-mL round-bottom flask, was placed (2, 4-dibromopyridin-3-yl) methanol (1.40 g, 5.245 mmol, 1.00 equiv), DCM (30.00 mL, 0.353 mmol, 0.07 equiv), PPTS (131.81 mg, 0.525 mmol, 0.10 equiv), DHP (661.79 mg, 7.868 mmol, 1.50 equiv). The resulting solution was stirred for overnight at 45 degrees C. in an oil bath. The reaction was then quenched by the addition of 30 mL of water. The resulting solution was extracted with 3×30 mL of dichloromethane concentrated. The residue was applied onto a silica gel column and eluted with ethyl acetate/petroleum ether (1:1). The collected fractions were combined and concentrated. This resulted in 1.5 g (80%) of 2,4-dibromo-3-[(oxan-2-yloxy) methyl]pyridine as colorless oil. LCMS-4 (ES, m/z): M+1: 350

Synthesis of 10-[4-bromo-3-[(oxan-2-yloxy) methyl]pyridin-2-yl]-4, 4-dimethyl-1, 10-diazatricyclo[6.4.0.0^[2, 6]]dodeca-2(6), 7-dien-9-one: Into a 100-mL round-bottom flask purged and maintained with an inert atmosphere of nitrogen, was placed 4,4-dimethyl-1,10-diazatricyclo [6.4.0.0^[2,6]]dodeca-2(6),7-dien-9-one (1.00 g, 4.895 mmol, 1.00 equiv), dioxane (40.00 mL, 0.454 mmol, 0.09 equiv), $Cs_2CO_3$ (3.19 g, 9.791 mmol, 2.00 equiv), 2,4-dibromo-3-[(oxan-2-yloxy)methyl]pyridine (1.72 g, 4.900 mmol, 1.00 equiv), $Pd_2(dba)_3$ (448.28 mg, 0.490 mmol, 0.10 equiv), XantPhos (283.26 mg, 0.490 mmol, 0.10 equiv). The resulting solution was stirred for 1 h at 100 degrees C. in an oil bath. The reaction was then quenched by the addition of 40 mL of water. The resulting solution was extracted with 3×40 mL of ethyl acetate concentrated. The residue was applied onto a silica gel column and eluted with ethyl acetate/petroleum ether (1:1). The collected fractions were combined and concentrated. This resulted in 900 mg (38.75%) of 10-[4-bromo-3-[(oxan-2-yloxy)methyl]pyridin-2-yl]-4,4-dimethyl-1,10-diazatricyclo[6.4.0.0^[2,6]]dodeca-2(6),7-dien-9-one as a brown solid. LCMS-5 (ES, m/z): M+1: 474

Synthesis of 2-[4, 4-dimethyl-9-oxo-1, 10-diazatricyclo [6.4.0.0^[2, 6]]dodeca-2(6), 7-dien-10-yl]-3-[(oxan-2-yloxy) methyl]pyridin-4-ylboronic acid: Into a 100-mL round-bottom flask purged and maintained with an inert atmosphere of nitrogen, was placed 10-[4-bromo-3-[(oxan-2-yloxy)methyl]pyridin-2-yl]-4, 4-dimethyl-1, 10-diazatricyclo [6.4.0.0^[2, 6]]dodeca-2(6), 7-dien-9-one (1.00 g, 2.108 mmol, 1.00 equiv), Dioxane (10.00 mL), bis(pinacolato)diboron (1.34 g, 5.277 mmol, 2.50 equiv), KOAc (620.00 mg, 6.317 mmol, 3.00 equiv), $Pd(dppf)Cl_2$ (172.00 mg, 0.211 mmol, 0.10 equiv). The resulting solution was stirred for 2 h at 100 degrees C. in an oil bath. The reaction mixture was cooled to room temperature. The solids were filtered out. The resulting mixture was concentrated under vacuum. This resulted in 920 mg (crude) of 2-[4,4-dimethyl-9-oxo-1,10-diazatricyclo[6.4.0.0^[2,6]]dodeca-2(6),7-dien-10-yl]-3-[(oxan-2-yloxy)methyl]pyridin-4-ylboronic acid as brown oil. LCMS-6 (ES, m/z): M+1: 436

Synthesis of 10-[1-hydroxy-3H-[1, 2]oxaborolo[4, 3-c] pyridin-4-yl]-4, 4-dimethyl-1, 10-diazatricyclo[6.4.0.0^[2, 6]]dodeca-2(6), 7-dien-9-one: Into a 100-mL round-bottom flask, was placed 2-[4,4-dimethyl-9-oxo-1,10-diazatricyclo [6.4.0.0^[2,6]]dodeca-2(6),7-dien-10-yl]-3-[(oxan-2-yloxy) methyl]pyridin-4-ylboronic acid (920 mg, 1.00 equiv, crude), dioxane (10 mL), HCl (6N, 10 mL). The resulting solution was stirred for 1 h at 25 degrees C. The resulting mixture was concentrated under vacuum. The crude product was purified by Flash-Prep-HPLC with the following conditions: Column, C18 reversed phase column; mobile phase, $H_2O$ (0.05% $NH_3 \cdot H_2O$) and $CH_3CN$ (5% $CH_3CN$ up to 30% in 15 min); Flow rate: 60 mL/min; Detector, 254/220 nm. This resulted in 350 mg of 10-[1-hydroxy-3H-[1,2]oxaborolo[4,3-c]pyridin-4-yl]-4,4-dimethyl-1,10-diazatricyclo [6.4.0.0^[2,6]]dodeca-2(6),7-dien-9-one as a light yellow solid. LCMS-7 (ES, m/z): M+1: 338

Synthesis of (E)-N-methoxy-N-methylbut-2-enamide: Into a 3-L 4-necked round-bottom flask, was placed N, O-dimethylhydroxylamine (150.00 g, 1544.231 mmol, 1.10 equiv), DCM (1500.00 mL). This was followed by the addition of TEA (298.00 g, 2948.077 mmol, 2.10 equiv) dropwise with stirring at 0 degrees C. The solution was stirred for 20 min. To this was added acryloyl chloride (146.00 g, 1403.846 mmol, 1.00 equiv) dropwise with stirring at 0 degrees C. The resulting solution was stirred for 3 h at room temperature in a water bath. The resulting mixture was washed with 3×400 ml of 1N HCl and 3×400 mL of $NaHCO_3$. The resulting mixture was washed with 1×500 mL of brine. The mixture was dried over anhydrous sodium sulfate and concentrated. This resulted in 110 g of (E)-N-methoxy-N-methylprop-2-enamide as light yellow oil. LCMS-8 (ES, m/z): M+1: 130

Synthesis of (S)-2-methyl-14(S)-1-phenylethyl) piperidin-4-one: Into a 1000-mL 3-necked round-bottom flask, was placed (2E)-N-methoxy-N-methylbut-2-enamide (50.00 g, 390.625 mmol, 1.00 equiv), THF (500.00 mL). This was followed by the addition of bromo (ethenyl) magnesium (76.00 g, 585.938 mmol, 1.50 equiv) dropwise with stirring at 0 degrees C. The solution was stirred for 1 h at R.T degree C. To this was added (S)-1-phenylethanamine (95.00 g, 781.250 mmol, 2.00 equiv) dropwise with stirring at R.T. To the mixture was added $H_2O$ (50.00 mL) dropwise with stirring at R.T. The resulting solution was stirred for 2 h at room temperature in a water bath. The resulting mixture was concentrated. The resulting solution was diluted with 300 mL of water. The resulting solution was extracted with 3×400 mL of dichloromethane and the organic layers combined. The resulting mixture was washed with 1×300 mL of brine. The solid was dried in an oven under reduced pressure. The residue was applied onto a silica gel column with ethyl acetate/petroleum ether (1:5). This resulted in 4.5 g of (S)-2-methyl-1-((S)-1-phenylethyl) piperidin-4-one as a yellow solid. LCMS-9 (ES, m/z): M+1: 218

Synthesis of 1-methyl-4-((S)-2-methyl-1-((S)-1-phenylethyl) piperidin-4-yl) piperazine(cis and trans mixture): Into a 50-mL round-bottom flask, was placed 1-methylpiperazine (461.00 mg, 4.600 mmol, 2.00 equiv), (S)-2-methyl-1-((S)-1-phenylethyl) piperidin-4-one (500.00 mg, 2.300 mmol, 1.00 equiv), $NaBH(OAc)_3$ (977.00 mg, 4.600 mmol, 2.00 equiv), AcOH (200.00 uL), THF (20.00 mL). The resulting solution was stirred for 6 h at room temperature. The resulting mixture was concentrated. The resulting solution was diluted with 20 mL of water. The resulting solution was extracted with 3×30 mL of ethyl acetate and the organic layers combined. The resulting mixture was washed with 2×20 ml of $NaHCO_3$ and 1×20 mL of brine. The mixture was dried over anhydrous sodium sulfate. The residue was applied onto a silica gel column with ethyl acetate/petroleum ether (1:3). This resulted in 900 mg of 1-methyl-4-((S)-2-methyl-1-((S)-1-phenylethyl) piperidin-4-yl) piperazine(cis and trans mixture) as light yellow oil. LCMS-10 (ES, m/z): M+1: 302

Synthesis of (5)-1-methyl-4-(2-methylpiperidin-4-yl) piperazine(cis and trans mixture): Into a 50-mL pressure tank reactor purged and maintained with an inert atmosphere of hydric(10 atm), was placed 1-methyl-4-((S)-2-methyl-1-((S)-1-phenylethyl) piperidin-4-yl) piperazine(cis and trans mixture) (900.00 mg, 2.990 mmol, 1.00 equiv), THF (5.00 mL), $Pd(OH)_2/C$ (42.00 mg, 0.299 mmol, 0.10 equiv). The resulting solution was stirred for 18 h at room temperature.

The solids were filtered out. The resulting mixture was concentrated. The residue was applied onto a silica gel column with dichloromethane/methanol (3:1). This resulted in 1.0 g of (S)-1-methyl-4-(2-methylpiperidin-4-yl) piperazine(cis and trans mixture) as light green oil. LCMS-11 (ES, m/z): M+1: 198

Synthesis of (S)-5-bromo-1-methyl-3-(4-(2-methyl-4-(4-methylpiperazin-1-yl) piperidin-1-yl)-3-nitrophenylamino) pyrazin-2(1H)-one(cis and trans mixture): Into a 50-mL round-bottom flask, was placed (S)-1-methyl-4-(2-methylpiperidin-4-yl) piperazine(cis and trans mixture) (1.00 g, 5.076 mmol, 1.00 equiv), 5-bromo-3-[(4-fluoro-3-nitrophenyl) amino]-1-methylpyrazin-2-one (1.70 g, 5.076 mmol, 1.00 equiv), DIEA (1.96 g, 15.228 mmol, 3.00 equiv), NMP (20.00 mL). The resulting solution was stirred for 72 h at 110 degrees C. in an oil bath. The reaction mixture was cooled. The resulting solution was diluted with 150 mL of DCM. The resulting mixture was washed with 5×30 of water and 1×30 mL of brine. The mixture was dried over anhydrous sodium sulfate and concentrated. The residue was applied onto a silica gel column with dichloromethane/methanol (3:1). This resulted in 350 mg of (S)-5-bromo-1-methyl-3-(4-(2-methyl-4-(4-methylpiperazin-1-yl) piperidin-1-yl)-3-nitrophenylamino) pyrazin-2(1H)-one(cis and trans mixture) as brown oil. LCMS-12 (ES, m/z): M+1: 520

Synthesis of (S)-3-(3-amino-4-(2-methyl-4-(4-methylpiperazin-1-yl) piperidin-1-yl) phenylamino)-5-bromo-1-methylpyrazin-2(1H)-one(cis and trans mixture): Into a 50-mL round-bottom flask, was placed (S)-5-bromo-1-methyl-3-(4-(2-methyl-4-(4-methylpiperazin-1-yl) piperidin-1-yl)-3-nitrophenylamino) pyrazin-2(1H)-one(cis and trans mixture) (356.00 mg, 0.686 mmol, 1.00 equiv), Fe (154.00 mg, 2.744 mmol, 4.00 equiv), $NH_4Cl$ (296.00 mg, 5.487 mmol, 8.00 equiv), EtOH (9.00 mL), $H_2O$ (3.00 mL). The resulting solution was stirred for 2 h at 80 degrees C. in an oil bath. The reaction mixture was cooled to room temperature with a water/ice bath. The solids were filtered out. The resulting mixture was concentrated. The resulting solution was diluted with 50 mL of water. The resulting solution was extracted with 5×40 mL of dichloromethane and the organic layers combined. The resulting mixture was washed with 1×40 of brine. The mixture was dried over anhydrous sodium sulfate and concentrated. This resulted in 320 mg of (S)-3-(3-amino-4-(2-methyl-4-(4-methylpiperazin-1-yl) piperidin-1-yl) phenylamino)-5-bromo-1-methylpyrazin-2 (1H)-one(cis and trans mixture) as light yellow oil. LCMS-13 (ES, m/z): M+1: 490

Synthesis of (S)—N-(5-(6-bromo-4-methyl-3-oxo-3, 4-dihydropyrazin-2-ylamino)-2-(2-methyl-4-(4-methylpiperazin-1-yl) piperidin-1-yl) phenyl) acrylamide(cis and trans mixture): Into a 50-mL round-bottom flask purged and maintained with an inert atmosphere of nitrogen, was placed (S)-3-(3-amino-4-(2-methyl-4-(4-methylpiperazin-1-yl) piperidin-1-yl) phenylamino)-5-bromo-1-methylpyrazin-2(1H)-one(cis and trans mixture) (350.00 mg, 0.716 mmol, 1.00 equiv), DIEA (184.00 mg, 1.431 mmol, 2.00 equiv), DCM (10.00 mL). This solution was stirred for 15 min at 0 degree C. This was followed by the addition of acryloyl chloride (71.00 mg, 0.787 mmol, 1.10 equiv) dropwise with stirring at 0 degrees C. The resulting solution was stirred for 1 h at room temperature in a water/ice bath. The resulting mixture was concentrated. The residue was applied onto a silica gel column with dichloromethane/methanol (3:1). This resulted in 120 mg of (S)—N-(5-(6-bromo-4-methyl-3-oxo-3, 4-dihydropyrazin-2-ylamino)-2-(2-methyl-4-(4-methylpiperazin-1-yl) piperidin-1-yl) phenyl) acrylamide(cis and trans mixture) as brown oil. LCMS-14 (ES, m/z): M+1: 544

Synthesis of N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-((2S,4'S or 4'R)-2-methyl-4-(4-methylpiperazin-1-yl)piperidin-1-yl)phenyl)acrylamide (Assumed): Into a 50-mL round-bottom flask purged and maintained with an inert atmosphere of nitrogen, was placed (S)—N-(5-(6-bromo-4-methyl-3-oxo-3, 4-dihydropyrazin-2-ylamino)-2-(2-methyl-4-(4-methylpiperazin-1-yl) piperidin-1-yl) phenyl) acrylamide(cis and trans mixture) (100.00 mg, 0.184 mmol, 1.00 equiv), 10-[1-hydroxy-3H-[1,2]oxaborolo[4,3-c]pyridin-4-yl]-4,4-dimethyl-1,10-diazatricyclo[6.4.0.0^[2,6]]dodeca-2(6),7-dien-9-one (62.00 mg, 0.184 mmol, 1.00 equiv), $Pd(dppf)Cl_2$ (13.00 mg, 0.018 mmol, 0.10 equiv), $K_3PO_4$ (98.00 mg, 0.460 mmol, 2.50 equiv), Dioxane (10.00 mL). The resulting solution was stirred for 2 h at 90 degrees C. in an oil bath. The reaction mixture was cooled to room temperature with a water/ice bath. The resulting solution was diluted with 10 mL of DCM. The solids were filtered out. The resulting mixture was concentrated. The crude product was purified by Prep-HPLC with the following conditions: column, X-Bridge Prep C18 19*150 mm 5 um; mobile phase, A: water (it contains 10 mM $NH_4HCO_3$ 0.05% ammonia); B: ACN; Gradient: 20-45% B in 8 min; Flow rate: 20 mL/min; detector, UV 220 nm. The collected solution was concentrated under vacuum to remove $CH_3CN$ and the resulting solution was dried by lyophilization. This resulted in 10 mg of N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-((2S, 4'S or 4'R)-2-methyl-4-(4-methylpiperazin-1-yl)piperidin-1-yl)phenyl)acrylamide (Assumed) as a white solid. LCMS-15 (ES, m/z): M+1: 775. 1H NMR (300 MHz, $CDCl_3$-d, ppm) δ 9.28-9.18 (m, 2H), 8.62-8.65 (d, J=9.0 Hz, 1H), 8.36 (s, 1H), 8.17 (s, 2H), 7.43-7.52 (m, 1H), 7.16-7.19 (d, J=9.0 Hz, 1H), 6.86 (s, 1H), 6.41-6.46 (m, 1H), 6.23-6.32 (m, 1H), 5.77-5.80 (d, J=9.0 Hz, 1H), 5.15-5.18 (d, J=9.0 Hz, 1H), 4.70-4.72 (m, 1H), 4.37-4.60 (m, 2H), 4.15-4.19 (m, 2H), 3.83-3.90 (m, 1H), 3.69 (s, 3H), 2.92-2.94 (m, 2H), 2.64-2.74 (m, 5H), 2.54-2.60 (m, 4H), 2.54 (s, 3H), 2.37 (s, 3H), 2.03-2.15 (m, 3H), 1.37-1.41 (m, 3H), 1.30 (s, 6H), 0.84-0.86 (d, J=6.0 Hz, 3H).

Synthesis of N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-((25, 4'R or 4'S)-2-methyl-4-(4-methylpiperazin-1-yl)piperidin-1-yl)phenyl)acrylamide (Assumed): Into a 50-mL round-bottom flask purged and maintained with an inert atmosphere of nitrogen, was placed (S)—N-(5-(6-bromo-4-methyl-3-oxo-3, 4-dihydropyrazin-2-ylamino)-2-(2-methyl-4-(4-methylpiperazin-1-yl) piperidin-1-yl) phenyl) acrylamide(cis and trans mixture) (100.00 mg, 0.184 mmol, 1.00 equiv), 10-[1-hydroxy-3H-[1,2]oxaborolo[4,3-c]pyridin-4-yl]-4,4-dimethyl-1,10-diazatricyclo[6.4.0.0^[2,6]]dodeca-2(6),7-dien-9-one (62.00 mg, 0.184 mmol, 1.00 equiv), $Pd(dppf)Cl_2$(13.00 mg, 0.018 mmol, 0.10 equiv), $K_3PO_4$ (97.00 mg, 0.460 mmol, 2.50 equiv), Dioxane (10.00 mL). The resulting solution was stirred for 2 h at 90 degrees C. in an oil bath. The reaction mixture was cooled to room temperature with a water/ice bath. The resulting solution was diluted with 10 mL of DCM. The solids were filtered out. The resulting mixture was concentrated. The crude product was purified by Prep-HPLC with the following conditions: column, X-Bridge Prep C18 19*150 mm Sum; mobile phase, A: water (it contains 10 mM $NH_4HCO_3$ 0.05% ammonia); B: ACN;

Gradient: 20-45% B in 8 min; Flow rate: 20 mL/min; detector, UV 220 nm. The collected solution was concentrated under vacuum to remove CH3CN and the resulting solution was dried by lyophilization. This resulted in 5.5 mg of N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-((2S, 4'R or 4'S)-2-methyl-4-(4-methylpiperazin-1-yl)piperidin-1-yl)phenyl)acrylamide (Assumed) as a light yellow solid. LCMS-16 (ES, m/z): M+1: 775. 1H NMR (300 MHz, $CD_3OD$-$d_4$, ppm) δ 8.54-8.56 (d, J=6.0 Hz, 1H), 8.46 (s, 1H), 7.86-7.90 (m, 2H), 7.63 (s, 2H), 6.73 (s, 1H), 6.57-6.68 (m, 2H), 5.97-6.00 (m, 1H), 4.21-4.28 (m, 5H), 3.89-3.93 (m, 1H), 3.69 (s, 3H), 3.56-3.61 (m, 4H), 2.97 (s, 3H), 2.70-2.73 (m, 1H), 2.63 (s, 2H), 2.51 (s, 3H), 2.28-2.40 (m, 4H), 2.03-2.11 (m, 3H), 1.31 (s, 2H), 1.28 (s, 6H), 1.21-1.13 (m, 3H), 0.90-0.93 (m, 1H).

Example 27: Preparation of N-(5-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxopyrazin-2-yl]amino]-2-[(2S)-2-methyl-4-[(2R,4r,6S)-2,6-dimethyloxan-4-yl]piperazin-1-yl]phenyl)prop-2-enamide (cis) and N-(5-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxopyrazin-2-yl]amino]-2-[(2S)-2-methyl-4-[(2R,4s,6S)-2,6-dimethyloxan-4-yl]piperazin-1-yl]phenyl)prop-2-enamide (trans)

Synthesis of [(3,3-dimethylcyclopent-1-en-1-yl)oxy]trimethylsilane: Into a 10-L 4-necked round-bottom flask purged and maintained with an inert atmosphere of nitrogen, was placed CuCl (20.60 g, 208.083 mmol, 0.05 equiv), LiCl (17.64 g, 416.108 mmol, 0.10 equiv), THF (2.50 L). This was followed by the addition of 2-cyclopenten-1-one, 3-methyl-(400.00 g, 4161.075 mmol, 1.00 equiv) at −5 to 5 degrees C. To this was added TMSCl (474.67 g, 4369.129 mmol, 1.05 equiv) dropwise with stirring at −5 to 5 degrees C. To the mixture was added MeMgCl (1670.00 mL, 14495.069 mmol, 3.48 equiv) dropwise with stirring at −5 to 10 degrees C. The resulting solution was stirred for 2 h at −5 to 10 degrees C. in an ice/salt bath. The reaction was then quenched by the addition of 34 g of MeOH. The resulting solution was diluted with 5 L of $NH_4Cl$. The solids were filtered out. The resulting solution was extracted with 3×5 L of petroleum ether dried over anhydrous sodium sulfate and concentrated. This resulted in 780 g (crude) of [(3,3-dimethylcyclopent-1-en-1-yl)oxy]trimethylsilane as yellow oil. GC-MS: (ES, m/z): M 184

Synthesis of 3,3-dimethylcyclopentanone: Into a 20-L 4-necked round-bottom flask, was placed [(3,3-dimethylcyclopent-1-en-1-yl)oxy]trimethylsilane (780.00 g, 4230.990 mmol, 1.00 equiv), DCM (7.8 L), $H_2O$ (30.49 g, 1692.396 mmol, 0.4 equiv). This was followed by the addition of $POCl_3$ (214.09 g, 1396.251 mmol, 0.33 equiv) dropwise with stirring at 25 to 30 degrees C. The resulting solution was stirred for 0.5 hr at 25 degrees C. This solvent straight used for next step. GC-MS (ES, m/z): M 112

Synthesis of 3,3-dimethylcyclopentanone: Into a 20-L 4-necked round-bottom flask, was placed 3,3-dimethylcyclopentan-1-one (crude) in DCM (7.80 L). This was followed by the addition of DMF (619 g, 2.0 equiv) dropwise with stirring at 25 degrees C. To this was added $POCl_3$ (1362 g, 2.1 equiv) dropwise with stirring at 40 degrees C. The resulting solution was stirred for overnight at 40 degrees C. in an oil bath. The reaction was then quenched by the addition of 2000 g of $K_3PO_4$. The resulting solution was extracted with 3×10 L of dichloromethane dried over anhydrous sodium sulfate and concentrated. This resulted in 530 g of 2-chloro-4,4-dimethylcyclopent-1-ene-1-carbaldehyde as a brown solid. GC-MS: (ES, m/z): M: 158

Synthesis of 4,4-dimethyl-1,10-diazatricyclo[6.4.0.0^[2,6]]dodeca-2(6),7-dien-9-one: Into a 5-L 4-necked round-bottom flask, was placed 2-chloro-4,4-dimethylcyclopent-1-ene-1-carbaldehyde (474.00 g, 2988.085 mmol, 1.00 equiv), DMF (3 L), piperazin-2-one (299.17 g, 2988.084 mmol, 1.00 equiv), DIEA (463.43 g, 3585.703 mmol, 1.2 equiv). The resulting solution was stirred overnight at 115 degrees C. in an oil bath. The reaction mixture was cooled to room temperature with a water/ice bath. The solids were collected by filtration and washed with 3×2 L of $H_2O$ and 3×2 L of PE. The solid was dried in an oven under reduced pressure. This resulted in 230 g (37.68%) of 4,4-dimethyl-1,10-diazatricyclo[6.4.0.0^[2,6]]dodeca-2(6),7-dien-9-one as a grey solid. LC-MS: (ES, m/z): M+1: 205

Synthesis of 2,4-dibromopyridine-3-carbaldehyde: Into a 1000-mL 3-necked round-bottom flask, was placed 2,4-dibromopyridine (40.00 g, 168.852 mmol, 1.00 equiv), THF (400.00 mL). This was followed by the addition of LDA (2M in hexane, 126.60 mL, 1.5 equiv) dropwise with stirring at −78 degrees C. The resulting solution was stirred for 1 hr at −78 degrees C. Then DMF (16.04 g, 219.507 mmol, 1.3 equiv) was added dropwise with stirring at −78 degrees C. The resulting solution was stirred for 0.5 hr at −78 degrees C. The reaction was then quenched by the addition of 500 mL of $NH_4Cl$. The resulting solution was extracted with 3×500 mL of ethyl acetate and concentrated. The residue was applied onto a silica gel column and eluted with ethyl acetate/petroleum ether (0:1-1:1). This resulted in 24.4 g (54.55%) of 2,4-dibromopyridine-3-carbaldehyde as a white solid. LC-MS: (ES, m/z): M+1: 264

Synthesis of (2,4-dibromopyridin-3-yl)methanol: Into a 100-mL round-bottom flask, was placed 2,4-dibromopyridine-3-carbaldehyde (20.00 g, 75.50 mmol, 1.00 equiv), EtOH (300.00 mL). This was followed by the addition of $NaBH_4$ (2.86 g, 75.50 mmol, 1.00 equiv), in portions at 0 degrees C. The resulting solution was stirred for 3 h at room temperature. The reaction was then quenched by the addition of 300 mL of water. The resulting solution was extracted with 3×300 mL of ethyl acetate and concentrated. The residue was applied onto a silica gel column and eluted with ethyl acetate/petroleum ether (1:1). The collected fractions were combined and concentrated. This resulted in 14 g (69.47%) of (2,4-dibromopyridin-3-yl)methanol as a light yellow solid. LC-MS: (ES, m/z): M+1: 266

Synthesis of 2,4-dibromo-3-[(oxan-2-yloxy)methyl]pyridine: Into a 100-mL round-bottom flask, was placed (2,4-dibromopyridin-3-yl)methanol (14.0 g, 52.45 mmol, 1.00 equiv), DCM (300.00 mL), PPTS (1.32 g, 5.25 mmol, 0.10 equiv), DHP (6.62 g, 78.68 mmol, 1.50 equiv). The resulting solution was stirred overnight at 45 degrees C. in an oil bath. The reaction was then quenched by the addition of 300 mL of water. The resulting solution was extracted with 3×300 mL of dichloromethane and concentrated. The residue was applied onto a silica gel column and eluted with ethyl acetate/petroleum ether (1:1). The collected fractions were combined and concentrated. This resulted in 15 g (80%) of 2,4-dibromo-3-[(oxan-2-yloxy)methyl]pyridine as colorless oil. LC-MS: (ES, m/z): M+1: 350

Synthesis of 10-[4-bromo-3-[(oxan-2-yloxy)methyl]pyridin-2-yl]-4,4-dimethyl-1,10-diazatricyclo[6.4.0.0^[2,6]]dodeca-2(6),7-dien-9-one: Into a 100-mL round-bottom flask purged and maintained with an inert atmosphere of nitrogen, was placed 4,4-dimethyl-1,10-diazatricyclo[6.4.0.0^[2,6]]dodeca-2(6),7-dien-9-one (10.00 g, 48.95 mmol, 1.00 equiv), dioxane (400.00 mL), $Cs_2CO_3$ (31.9 g, 97.91 mmol, 2.00 equiv), 2,4-dibromo-3-[(oxan-2-yloxy)methyl]pyridine (17.2 g, 49.0 mmol, 1.00 equiv), $Pd_2(dba)_3$ (4.48 g, 4.90 mmol, 0.1 equiv), XantPhos (2.83 g, 4.90 mmol, 0.1 equiv). The resulting solution was stirred for 1 h at 100 degrees C. in an oil bath. The reaction was then quenched by the addition of 400 mL of water. The resulting solution was extracted with 3×400 mL of ethyl acetate and concentrated. The residue was applied onto a silica gel column and eluted with ethyl acetate/petroleum ether (1:1). The collected fractions were combined and concentrated. This resulted in 9 g (38.75%) of 10-[4-bromo-3-[(oxan-2-yloxy)methyl]pyridin-2-yl]-4,4-dimethyl-1,10-diazatricyclo[6.4.0.0^[2,6]]dodeca-2(6),7-dien-9-one as a brown solid. LC-MS: (ES, m/z): M+1: 474

Synthesis of 2-[4,4-dimethyl-9-oxo-1,10-diazatricyclo[6.4.0.0^[2,6]]dodeca-2(6),7-dien-10-yl]-3-[(oxan-2-yloxy)methyl]pyridin-4-ylboronic acid: Into a 100-mL round-bottom flask purged and maintained with an inert atmosphere of nitrogen, was placed 10-[4-bromo-3-[(oxan-2-yloxy)methyl]pyridin-2-yl]-4,4-dimethyl-1,10-diazatricyclo[6.4.0.0^[2,6]]dodeca-2(6),7-dien-9-one (10.00 g, 21.08 mmol, 1.00 equiv), dioxane (100.00 mL), bis(pinacolato)diboron (13.4 g, 52.77 mmol, 2.50 equiv), KOAc (6.20 g, 63.17 mmol, 3.00 equiv), $Pd(dppf)Cl_2$ (1.72 g, 2.11 mmol, 0.10 equiv). The resulting solution was stirred for 2 h at 100 degrees C. in an oil bath. The reaction mixture was cooled to room temperature. The solids were filtered out. The resulting mixture was concentrated under vacuum. This resulted in 9.2 g (crude) of 2-[4,4-dimethyl-9-oxo-1,10-diazatricyclo[6.4.0.0^[2,6]]dodeca-2(6),7-dien-10-yl]-3-[(oxan-2-yloxy)methyl]pyridin-4-ylboronic acid as brown oil. LC-MS: (ES, m/z): M+1: 436

Synthesis of 10-[1-hydroxy-3H-[1,2]oxaborolo[4,3-c]pyridin-4-yl]-4,4-dimethyl-1,10-diazatricyclo[6.4.0.0^[2,6]]dodeca-2(6),7-dien-9-one: Into a 100-mL round-bottom flask, was placed 2-[4,4-dimethyl-9-oxo-1,10-diazatricyclo[6.4.0.0^[2,6]]dodeca-2(6),7-dien-10-yl]-3-[(oxan-2-yloxy)methyl]pyridin-4-ylboronic acid (9.2 g, 1.00 equiv, crude), dioxane (100 mL), HCl (6N, 100 mL). The resulting solution was stirred for 1 h at 25 degrees C. The resulting mixture was concentrated under vacuum. The crude product was purified by Flash-Prep-HPLC with the following conditions: Column, C18 reversed phase column; mobile phase, $H_2O$ (0.05% $NH_3 \cdot H_2O$) and $CH_3CN$ (5% $CH_3CN$ up to 30% in 15 min); Flow rate: 60 mL/min; Detector, 254/220 nm. This resulted in 3.5 g of 10-[1-hydroxy-3H-[1,2]oxaborolo[4,3-c]pyridin-4-yl]-4,4-dimethyl-1,10-diazatricyclo[6.4.0.0^[2,6]]dodeca-2(6),7-dien-9-one as a light yellow solid. LC-MS: (ES, m/z): M+1: 338

Synthesis of tert-butyl (3S)-4-[4-[(6-bromo-4-methyl-3-oxopyrazin-2-yl)amino]-2-nitrophenyl]-3-methylpiperazine-1-carboxylate: Into a 50-mL round-bottom flask, was placed 5-bromo-3-[(4-fluoro-3-nitrophenyl)amino]-1-methylpyrazin-2-one (20.00 g, 58.29 mmol, 1.00 equiv), NMP (200.00 mL), tert-butyl (3S)-3-methylpiperazine-1-carboxylate (11.7 g, 58.42 mmol, 1.00 equiv), DIEA (22.6 g, 174.87 mmol, 3.00 equiv). The resulting solution was stirred for 48 h at 110° C. in an oil bath. The resulting solution was diluted with 1000 mL of $H_2O$. The resulting solution was extracted with 3×500 mL of dichloromethane/methanol (10:1). The resulting mixture was washed with 3×200 mL of brine. The resulting mixture was concentrated. The residue was applied onto a silica gel column with dichloromethane/methanol (10:1). This resulted in 30 g (59.00%) of tert-butyl (3S)-4-[4-[(6-bromo-4-methyl-3-oxopyrazin-2-yl)amino]-2-nitrophenyl]-3-methylpiperazine-1-carboxylate as a brown solid. LC-MS: (ES, m/z): M+1: 523

Synthesis of 5-bromo-1-methyl-3-([4-[(2S)-2-methylpiperazin-1-yl]-3-nitrophenyl]amino)pyrazin-2-one: Into a 100-mL round-bottom flask, was placed tert-butyl (3S)-4-[4-[(6-bromo-4-methyl-3-oxopyrazin-2-yl)amino]-2-nitrophenyl]-3-methylpiperazine-1-carboxylate (30.00 g, 1.00 equiv, 60%), HCl (2M) in 1,4-dioxane (300.00 mL). The resulting solution was stirred for 13 h at room temperature. The resulting mixture was concentrated. The resulting solution was diluted with 300 mL of $H_2O$. The pH value of the solution was adjusted to 8 with $NH_3 \cdot H_2O$. The resulting solution was extracted with 3×150 mL of dichloromethane and concentrated. The residue was applied onto a silica gel column with dichloromethane/methanol (10:1). This resulted in 7.0 g (48.09%) of 5-bromo-1-methyl-3-([4-[(2S)-2-methylpiperazin-1-yl]-3-nitrophenyl]amino)pyrazin-2-one as a red solid. LC-MS: (ES, m/z): M+1: 423

Synthesis of (cis)-2,6-dimethyloxan-4-ol: Into a 2000-mL pressure tank reactor (10 atm), was placed gamma-2,6-dimethylpyrone (50.00 g, 402.774 mmol, 1.00 equiv), EtOH (800.00 mL), 10% Pd/C (4.00 g, 37.587 mmol, 0.09 equiv), to the above $H_2$ was introduced in. The resulting solution was stirred overnight at 35 degrees C. in an oil bath. The solids were filtered out. The resulting mixture was concentrated under vacuum. This resulted in 49.4 g (94.21%) of (cis)-2,6-dimethyloxan-4-ol as yellow oil. GC-MS: (ES, m/z): M: 130

Synthesis of (cis)-2,6-dimethyloxan-4-one: Into a 1000-mL round-bottom flask, was placed (cis)-2,6-dimethyloxan-4-ol (40.00 g, 307.250 mmol, 1.00 equiv), DCM (500.00 mL), $CH_3COONa$ (21.00 g, 256.098 mmol, 0.83 equiv), PCC (140.00 g, 649.486 mmol, 2.11 equiv). The resulting solution was stirred for 2 hr at 25 degrees C. The reaction was then quenched by the addition of 1000/1000 mL of $Na_2SO_3$/DCM. The solids were filtered out. The resulting solution was extracted with 3×500 mL of dichloromethane and the organic layers combined. The resulting mixture was washed with 1×2000 ml of brine. The mixture was dried over anhydrous sodium sulfate and concentrated under vacuum. The residue was applied onto a silica gel column with ethyl acetate/petroleum ether (1:9). This resulted in 9.88 g (25.09%) of (cis)-2,6-dimethyloxan-4-one as yellow oil. GC-MS: (ES, m/z): M: 128

Synthesis of 5-bromo-3-([4-[(2S)-4-[(2R,6S)-2,6-dimethyloxan-4-yl]-2-methylpiperazin-1-yl]-3-nitrophenyl]amino)-1-methylpyrazin-2-one: Into a 250-mL round-bottom flask, was placed 5-bromo-1-methyl-3-([4-[(2S)-2-methylpiperazin-1-yl]-3-nitrophenyl]amino)pyrazin-2-one hydrochloride (10.00 g, 21.752 mmol, 1.00 equiv), THF (100 mL), (cis)-2,6-dimethyloxan-4-one (3.60 g, 28.087 mmol, 1.29 equiv), HOAc (300.00 mg, 4.996 mmol, 0.23 equiv), $NaBH(OAc)_3$ (9.26 g, 43.691 mmol, 2.01 equiv). The resulting solution was stirred overnight at 30 degrees C. in an oil bath. The resulting mixture was concentrated under vacuum. The residue was applied onto a silica gel column with dichloromethane/methanol (10:1). This resulted in 6.3 g (54.09%) of 5-bromo-3-([4-[(2S)-4-[(2R,6S)-2,6-dimethyloxan-4-yl]-2-methylpiperazin-1-yl]-3-nitrophenyl]amino)-1-methylpyrazin-2-one as a red solid(cis and trans mixtures). LC-MS: (ES, m/z): M+1: 535

Synthesis of 3-([3-amino-4-[(2S)-2-methyl-4-[(2R,4r,6S)-2,6-dimethyloxan-4-yl]piperazin-1-yl]phenyl]amino)-5-bromo-1-methylpyrazin-2-one (cis) and 3-([3-amino-4-[(2S)-2-methyl-4-[(2R,4s,6S)-2,6-dimethyloxan-4-yl]

piperazin-1-yl]phenyl]amino)-5-bromo-1-methylpyrazin-2-one (trans): Into a 250-mL round-bottom flask, was placed 5-bromo-1-methyl-3-([4-[(2S)-2-methyl-4-[(2R,4r,6S)-2,6-dimethyloxan-4-yl]piperazin-1-yl]-3-nitrophenyl]amino) pyrazin-2-one (6.30 g, 11.766 mmol, 1.00 equiv), EtOH (60.00 mL), $H_2O$ (20.00 mL), Fe (4.03 g, 72.164 mmol, 6.13 equiv), $NH_4Cl$ (3.82 g, 71.414 mmol, 6.07 equiv). The resulting solution was stirred for 2 hr at 70 degrees C. in an oil bath. The reaction mixture was cooled to room temperature. The resulting solution was diluted with 1000 mL of water. The resulting solution was extracted with 3×300 mL of dichloromethane and the organic layers combined. The resulting mixture was washed with 1×1000 ml of brine. The mixture was dried over anhydrous sodium sulfate and concentrated under vacuum. The residue was applied onto a silica gel column with dichloromethane/methanol (10:1). This resulted in 3 g (50.44%) of 3-([3-amino-4-[(2S)-2-methyl-4-[(2R,4r,6S)-2,6-dimethyloxan-4-yl]piperazin-1-yl]phenyl]amino)-5-bromo-1-methylpyrazin-2-one (cis) as a yellow solid and 150 mg (2.52%) of 3-([3-amino-4-[(2S)-2-methyl-4-[(2R,4s,6S)-2,6-dimethyloxan-4-yl]piperazin-1-yl]phenyl]amino)-5-bromo-1-methylpyrazin-2-one (trans) as a yellow solid. LC-MS: (ES, m/z): M+1: 504

Synthesis of N-[5-[(6-bromo-4-methyl-3-oxopyrazin-2-yl)amino]-2-[(2S)-2-methyl-4-[(2R,4r,6S)-2,6-dimethyloxan-4-yl]piperazin-1-yl]phenyl]prop-2-enamide (cis): Into a 250-mL round-bottom flask purged and maintained with an inert atmosphere of nitrogen, was placed 3-([3-amino-4-[(2S)-2-methyl-4-[(2R,4r,6S)-2,6-dimethyloxan-4-yl]piperazin-1-yl]phenyl]amino)-5-bromo-1-methylpyrazin-2-one (cis) (2.00 g, 3.957 mmol, 1.00 equiv), DCM (50.00 mL), DIEA (1.02 g, 7.892 mmol, 1.99 equiv), acryloyl chloride (357.00 mg, 3.944 mmol, 1.00 equiv). The resulting solution was stirred for 2 hr at 25 degrees C. The resulting mixture was concentrated under vacuum. The residue was applied onto a silica gel column with dichloromethane/methanol (20:1). This resulted in 1.8 g (81.31%) of N-[5-[(6-bromo-4-methyl-3-oxopyrazin-2-yl)amino]-2-[(2S)-2-methyl-4-[(2R,4r,6S)-2,6-dimethyloxan-4-yl]piperazin-1-yl]phenyl] prop-2-enamide (cis) as a yellow solid. LC-MS: (ES, m/z): M+1: 558

Synthesis of N-(5-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxopyrazin-2-yl] amino]-2-[(2S)-2-methyl-4-[(2R,4r,6S)-2,6-dimethyloxan-4-yl]piperazin-1-yl]phenyl)prop-2-enamide (cis): Into a 100-mL round-bottom flask purged and maintained with an inert atmosphere of nitrogen, was placed N-[5-[(6-bromo-4-methyl-3-oxopyrazin-2-yl)amino]-2-[(2S)-2-methyl-4-[(2R,4r,6S)-2,6-dimethyloxan-4-yl]piperazin-1-yl]phenyl] prop-2-enamide (cis) (1.80 g, 3.217 mmol, 1.00 equiv), dioxane (20.00 mg), $H_2O$ (2.00 mg), $K_2CO_3$ (2.23 g, 16.135 mmol, 5.02 equiv), 10-[1-hydroxy-3H-[1,2]oxaborolo[4,3-c]pyridin-4-yl]-4,4-dimethyl-1,10-diazatricyclo[6.4.0.0^[2,6]]dodeca-2(6),7-dien-9-one (1.63 g, 4.834 mmol, 1.50 equiv), Pd(DTBPF)$Cl_2$ (316.00 mg, 0.485 mmol, 0.15 equiv). The resulting solution was stirred for 1 hr at 90 degrees C. in an oil bath. The reaction mixture was cooled to room temperature. The resulting mixture was concentrated under vacuum. The residue was applied onto a silica gel column with dichloromethane/methanol (20:1). The crude product was purified by Flash-Prep-HPLC with the following conditions (IntelFlash-1): Column, C18 reversed phase column; mobile phase, $H_2O$ (0.05% $NH_3 \cdot H_2O$) and $CH_3CN$ (40% $CH_3CN$ up to 90% in 15 min); Detector, 254/220 nm. This resulted in 1.6 g (62.96%) of N-(5-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxopyrazin-2-yl]amino]-2-[(2S)-2-methyl-4-[(2R,4r,6S)-2,6-dimethyloxan-4-yl]piperazin-1-yl]phenyl)prop-2-enamide (cis) as a white solid. LC-MS: (ES, m/z): M+1: 790; H-NMR (300 MHz, DMSO-$d_6$, ppm) δ 9.23 (d, J=14.7 Hz, 2H), 9.12 (s, 1H), 8.48 (d, J=5.1 Hz, 1H), 7.95 (d, J=5.2 Hz, 1H), 7.77 (s, 1H), 7.60 (d, J=8.5 Hz, 1H), 7.24 (d, J=8.7 Hz, 1H), 6.70-6.54 (m, 2H), 6.29 (d, J=17.0 Hz, 1H), 5.81 (dd, J=10.1, 1.9 Hz, 1H), 5.06 (s, 1H), 4.63-4.44 (m, 2H), 4.22 (s, 3H), 3.84 (d, J=8.3 Hz, 1H), 3.57 (s, 3H), 3.42 (t, J=8.7 Hz, 2H), 3.02 (s, 1H), 2.87 (dd, J=26.2, 10.4 Hz, 2H), 2.73 (p, J=2.3 Hz, 2H), 2.59 (d, J=4.7 Hz, 2H), 2.44 (s, 2H), 2.17 (t, J=10.0 Hz, 1H), 1.79 (d, J=12.2 Hz, 2H), 1.23 (s, 6H), 1.13 (d, J=6.1 Hz, 6H), 1.05-0.95 (m, 2H), 0.72 (d, J=6.1 Hz, 3H).

Synthesis of N-[5-[(6-bromo-4-methyl-3-oxopyrazin-2-yl)amin]-2-[(2S)-2-methyl-4-[(2R,4s,6S)-2,6-dimethyloxan-4-yl]piperazin-1-yl]phenyl]prop-2-enamide (trans): Into a 8-mL vial, was placed 3-([3-amino-4-[(2S)-2-methyl-4-[(2R,4s,6S)-2,6-dimethyloxan-4-yl]piperazin-1-yl]phenyl]amino)-5-bromo-1-methylpyrazin-2-one (110.00 mg, 0.218 mmol, 1.00 equiv), DCM (1.00 mL), DIEA (84.38 mg, 0.653 mmol, 3.00 equiv), acryloyl chloride (23.64 mg, 0.261 mmol, 1.20 equiv). The resulting solution was stirred for 1 hr at 0 degrees C. in a water/ice bath. The resulting mixture was concentrated. The residue was applied onto a silica gel column with dichloromethane/methanol (10:1). This resulted in 110 mg of N-[5-[(6-bromo-4-methyl-3-oxopyrazin-2-yl)amin]-2-[(2S)-2-methyl-4-[(2R,4 s,6S)-2,6-dimethyloxan-4-yl]piperazin-1-yl]phenyl]prop-2-enamide as a brown solid. LC-MS: (ES, m/z): M+1: 558

Synthesis of N-(5-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxopyrazin-2-yl] amino]-2-[(2S)-2-methyl-4-[(2R,4s,6S)-2,6-dimethyloxan-4-yl]piperazin-1-yl]phenyl)prop-2-enamide(trans): Into a 8-mL round-bottom flask purged and maintained with an inert atmosphere of nitrogen, was placed N-[5-[(6-bromo-4-methyl-3-oxopyrazin-2-yl)amino]-2-[(2S)-2-methyl-4-[(2R,4s,6S)-2,6-dimethyloxan-4-yl]piperazin-1-yl]phenyl] prop-2-enamide (110.00 mg, 0.197 mmol, 1.00 equiv), 10-[1-hydroxy-3H-[1,2]oxaborolo[4,3-c]pyridin-4-yl]-4,4-dimethyl-1,10-diazatricyclo[6.4.0.0^[2,6]]dodeca-2(6),7-dien-9-one (72.92 mg, 0.216 mmol, 1.10 equiv), dioxane (2.00 mL), $H_2O$ (0.60 mL), Pd(DtBPF)$Cl_2$(12.81 mg, 0.020 mmol, 0.10 equiv), $K_2CO_3$ (81.51 mg, 0.590 mmol, 3.00 equiv). The resulting solution was stirred for 1 hr at 90 degrees C. The crude product was purified by Prep-HPLC with the following conditions (Waters 2767): Column, X Bridge Prep C18 OBD 19*150 mm 5 um; mobile phase, A: 0.1% $NH_3$—$H_2O$ in water; B: ACN; Gradient: 30%-75% B in 7.9 min; Detector, 220 nm. This resulted in 40 mg (25.75%) of N-(5-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxopyrazin-2-yl] amino]-2-[(2S)-2-methyl-4-[(2R,4s,6S)-2,6-dimethyloxan-4-yl]piperazin-1-yl]phenyl)prop-2-enamide as a light yellow solid LC-MS: (ES, m/z): M+1: 790; H-NMR (300 MHz, DMSO-$d_6$, ppm) δ 9.23 (m, 9.40-9.21 Hz, 2H), 9.10 (s, 1H), 8.48 (d, J=5.1 Hz, 1H), 8.00-7.89 (m, 1H), 7.77 (s, 1H), 7.62 (d, J=8.8 Hz, 1H), 7.25 (d, J=8.7 Hz, 1H), 6.70-6.54 (m, 2H), 6.29 (d, J=16.8 Hz, 1H), 5.80 (dd, J=10.2, 1.8 Hz, 1H), 5.02 (s, 1H), 4.65-4.45 (m, 2H), 4.35-4.10 (m, 3H), 3.90-3.72 (m, 3H), 3.57 (s, 3H), 3.22-2.91 (m, 3H), 2.85-2.71 (m, 2H), 2.60-2.58 (m, 2H), 2.51-2.35 (m, 3H), 2.30-2.15 (m, 1H), 2.05-1.93 (m, 3H), 1.23 (s, 8H), 1.05 (t, J=6.6 Hz, 6H), 0.76 (d, J=6.0 Hz, 3H).

Example 28: Preparation of (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(trifluoromethyl)pyridin-4-yl)-4-methyl-3-oxo-3,4-dihydropyrazin-2-yl)amino)-2-(2-methyl-4-(oxetan-3-yl)piperazin-1-yl)phenyl)acrylamide Synthesis of [(3,3-dimethylcyclopent-1-en-1-yl)oxy]trimethylsilane: Into a 10-L 4-necked round-bottom flask purged and maintained with an inert atmosphere of nitrogen, was placed CuCl (20.60 g, 208.083 mmol, 0.05 equiv), LiCl (17.64 g, 416.108 mmol, 0.10 equiv), THF (2.50 L). This was followed by the addition of 2-cyclopenten-1-one, 3-methyl-(400.00 g, 4161.075 mmol, 1.00 equiv) at −5 to 5 degrees C. To this was added TMSCl (474.67 g, 4369.129 mmol, 1.05 equiv) dropwise with stirring at −5 to 5 degrees C. To the mixture was added MeMgCl (1670.00 mL, 14495.069 mmol, 3.48 equiv) dropwise with stirring at −5 to 10 degrees C. The resulting solution was stirred for 2 h at −5 to 10 degrees C. in an ice/salt bath. The reaction was then quenched by the addition of 34 g of MeOH. The resulting solution was diluted with 5 L of $NH_4Cl$. The solids were filtered out. The resulting solution was extracted with 3×5 L of petroleum ether dried over anhydrous sodium sulfate and concentrated. This resulted in 780 g (crude) of [(3,3-dimethylcyclopent-1-en-1-yl)oxy]trimethylsilane as yellow oil. GC-MS: (ES, m/z): M: 184

Synthesis of 3,3-dimethylcyclopentanone: Into a 20-L 4-necked round-bottom flask, was placed [(3,3-dimethylcyclopent-1-en-1-yl)oxy]trimethylsilane (780.00 g, 4230.990 mmol, 1.00 equiv), DCM (7.8 L), $H_2O$ (30.49 g, 1692.396 mmol, 0.4 equiv). This was followed by the addition of $POCl_3$ (214.09 g, 1396.251 mmol, 0.33 equiv) dropwise with stirring at 25 to 30 degrees C. The resulting solution was stirred for 0.5 hr at 25 degrees C. This solvent straight used for next step. GC-MS: (ES, m/z): M: 112

Synthesis of 3,3-dimethylcyclopentanon: Into a 20-L 4-necked round-bottom flask, was placed 3,3-dimethylcyclopentan-1-one (crude) in DCM (7.80 L). This was followed by the addition of DMF (619 g, 2.0 equiv) dropwise with stirring at 25 degrees C. To this was added $POCl_3$ (1362 g, 2.1 equiv) dropwise with stirring at 40 degrees C. The resulting solution was stirred for overnight at 40 degrees C. in an oil bath. The reaction was then quenched by the addition of 2000 g of $K_3PO_4$. The resulting solution was extracted with 3×10 L of dichloromethane dried over anhydrous sodium sulfate and concentrated. This resulted in 530 g of 2-chloro-4,4-dimethylcyclopent-1-ene-1-carbaldehyde as a brown solid. GC-MS: (ES, m/z): M: 158

Synthesis of 4,4-dimethyl-1,10-diazatricyclo[6.4.0.0^[2,6]]dodeca-2(6),7-dien-9-one: Into a 5-L 4-necked round-bottom flask, was placed 2-chloro-4,4-dimethylcyclopent-1-ene-1-carbaldehyde (474.00 g, 2988.085 mmol, 1.00 equiv), DMF (3 L), piperazin-2-one (299.17 g, 2988.084 mmol, 1.00 equiv), DIEA (463.43 g, 3585.703 mmol, 1.2 equiv). The resulting solution was stirred for overnight at 115 degrees C. in an oil bath. The reaction mixture was cooled to room temperature with a water/ice bath. The solids were collected by filtration. The resulting mixture was washed with 3×2 L of $H_2O$ and 3×2 L of PE. The solid was dried in an oven under reduced pressure. This resulted in 230 g (37.68%) of 4,4-dimethyl-1,10-diazatricyclo[6.4.0.0^[2,6]]dodeca-2(6),7-dien-9-one as a grey solid. LC-MS: (ES, m/z): M+1: 205

Synthesis of 2,4-dichloro-3-iodopyridine: Into a 500 mL 3-necked round-bottom flask purged and maintained with an inert atmosphere of nitrogen, was placed 2,4-dichloropyridine (20.00 g, 135.14 mmol, 1.00 equiv), THF (200.00 mL). This was followed by the addition of LDA (2M in hexane, 162.16 mL, 1.2 equiv) dropwise with stirring at −78 degrees C. The resulting solution was stirred for 1 hr at −78 degrees C. Then iodine (41.20 g, 162.16 mmol, 1.2 equiv) was added dropwise with stirring at −78 degrees C. The resulting solution was stirred for 0.5 hr at −78 degrees C., then return to room temperature and continue stirring for 1 hour. The reaction was then quenched by the addition of 100 mL of saturated $Na_2SO_3$ aqueous solution. The resulting solution was extracted with 3×200 mL of DCM and concentrated. The residue was washed by $Et_2O$ (1×50 mL). This resulted in 22.0 g (60%) of 2,4-dichloro-3-iodopyridine as a light brown solid. $^1H$ NMR (300 MHz, $CDCl_3$-d, ppm) δ 8.33 (d, J=6.0 Hz, 1H), 7.63 (d, J=6.0 Hz, 1H).

Synthesis of 2,4-dichloro-3-(trifluoromethyl)pyridine: Into a 250 mL 3-necked round-bottom flask purged and maintained with an inert atmosphere of nitrogen, was placed 2,4-dichloro-3-iodopyridine (15.00 g, 54.74 mmol, 1.00 equiv), DMF (150.00 mL). This was followed by the addition of methyl 2,2-difluoro-2-(fluorosulfonyl)acetate (15.80 g, 82.12 mmol, 1.5 equiv), CuI (10.00 g, 54.74 mmol, 1.0 equiv) in portions at room temperature. The resulting solution was stirred for 5 h at 100° C. The reaction was then quenched by the addition of 50 mL of water. The resulting solution was extracted with 3×100 mL of ethyl acetate and the organic phase was washed by 3×50 mL of water. The organic phase was dried by $Na_2SO_4$, filtrated, concentrated. The residue was applied onto a silica gel column and eluted with ethyl acetate/petroleum ether (1:3). The collected fractions were combined and concentrated. This resulted in 7.0 g (59%) of 2,4-dichloro-3-(trifluoromethyl)pyridine as a light brown solid. $^1H$ NMR (300 MHz, $CDCl_3$-d, ppm) δ 8.40 (d, J=6.0 Hz, 1H), 7.42 (d, J=6.0 Hz, 1H).

Synthesis of 2,4-dibromo-3-[(oxan-2-yloxy)methyl]pyridine: Into a 100-mL round-bottom flask, was placed (2,4-dibromopyridin-3-yl)methanol (1.40 g, 5.245 mmol, 1.00 equiv), DCM (30.00 mL, 0.353 mmol, 0.07 equiv), PPTS (131.81 mg, 0.525 mmol, 0.10 equiv), DHP (661.79 mg, 7.868 mmol, 1.50 equiv). The resulting solution was stirred for overnight at 45 degrees C. in an oil bath. The reaction was then quenched by the addition of 30 mL of water. The resulting solution was extracted with 3×30 mL of dichloromethane concentrated. The residue was applied onto a silica gel column and eluted with ethyl acetate/petroleum ether (1:1). The collected fractions were combined and concentrated. This resulted in 1.5 g (80%) of 2,4-dibromo-3-[(oxan-2-yloxy)methyl]pyridine as colorless oil. LC-MS: (ES, m/z): M+1: 350.

Synthesis of 10-[4-bromo-3-[(oxan-2-yloxy)methyl]pyridin-2-yl]-4,4-dimethyl-1,10-diazatricyclo[6.4.0.0^[2,6]]dodeca-2(6),7-dien-9-one: Into a 100-mL round-bottom flask purged and maintained with an inert atmosphere of nitrogen, was placed 4,4-dimethyl-1,10-diazatricyclo[6.4.0.0^[2,6]]dodeca-2(6),7-dien-9-one (1.00 g, 4.895 mmol, 1.00 equiv), dioxane (40.00 mL, 0.454 mmol, 0.09 equiv), $Cs_2CO_3$ (3.19 g, 9.791 mmol, 2 equiv), 2,4-dibromo-3-[(oxan-2-yloxy)methyl]pyridine (1.72 g, 4.900 mmol, 1.00 equiv), $Pd_2(dba)_3$ (448.28 mg, 0.490 mmol, 0.1 equiv), XantPhos (283.26 mg, 0.490 mmol, 0.1 equiv). The resulting solution was stirred for 1 h at 100 degrees C. in an oil bath. The reaction was then quenched by the addition of 40 mL of water. The resulting solution was extracted with 3×40 mL of ethyl acetate concentrated. The residue was applied onto a silica gel column and eluted with ethyl acetate/petroleum ether (1:1). The collected fractions were combined and concentrated. This resulted in 900 mg (38.75%) of 10-[4- bromo-3-[(oxan-2-yloxy)methyl]pyridin-2-yl]-4,4-dimethyl-1,10-diazatricyclo[6.4.0.0^[2,6]]dodeca-2(6),7-dien-9-one as a brown solid. LC-MS: (ES, m/z): M+1: 474

Synthesis of 2-[4,4-dimethyl-9-oxo-1,10-diazatricyclo[6.4.0.0^[2,6]]dodeca-2(6),7-dien-10-yl]-3-[(oxan-2-yloxy)methyl]pyridin-4-ylboronic acid, Into a 100-mL round-bottom flask purged and maintained with an inert atmosphere of nitrogen, was placed 10-[4-bromo-3-[(oxan-2-yloxy)methyl]pyridin-2-yl]-4,4-dimethyl-1,10-diazatricyclo[6.4.0.0^[2,6]]dodeca-2(6),7-dien-9-one (1.00 g, 2.108 mmol, 1.00 equiv), dioxane (10.00 mL), bis(pinacolato)diboron (1.34 g, 5.277 mmol, 2.50 equiv), KOAc (620.00 mg, 6.317 mmol, 3.00 equiv), Pd(dppf)$Cl_2$ (172.00 mg, 0.211 mmol, 0.10 equiv). The resulting solution was stirred for 2 h at 100 degrees C. in an oil bath. The reaction mixture was cooled to room temperature. The solids were filtered out. The resulting mixture was concentrated under vacuum. This resulted in 920 mg (crude) of 2-[4,4-dimethyl-9-oxo-1,10-diazatricyclo[6.4.0.0^[2,6]]dodeca-2(6),7-dien-10-yl]-3-[(oxan-2-yloxy)methyl]pyridin-4-ylboronic acid as brown oil. LC-MS: (ES, m/z): M+1: 436

Synthesis of 10-[1-hydroxy-3H-[1,2]oxaborolo[4,3-c]pyridin-4-yl]-4,4-dimethyl-1,10-diazatricyclo[6.4.0.0^[2,6]]dodeca-2(6),7-dien-9-one, Into a 100-mL round-bottom flask, was placed 2-[4,4-dimethyl-9-oxo-1,10-diazatricyclo[6.4.0.0^[2,6]]dodeca-2(6),7-dien-10-yl]-3-[(oxan-2-yloxy)methyl]pyridin-4-ylboronic acid (920 mg, 1.00 equiv, crude), dioxane (10 mL), HCl (6N, 10 mL). The resulting solution was stirred for 1 h at 25 degrees C. The resulting mixture was concentrated under vacuum. The crude product was purified by Flash-Prep-HPLC with the following conditions: Column, C18 reversed phase column; mobile phase, $H_2O$ (0.05% $NH_3 \cdot H_2O$) and $CH_3CN$ (5% $CH_3CN$ up to 30% in 15 min); Flow rate: 60 mL/min; Detector, 254/220 nm. This resulted in 350 mg of 10-[1-hydroxy-3H-[1,2]oxaborolo[4,3-c]pyridin-4-yl]-4,4-dimethyl-1,10-diazatricyclo[6.4.0.0^[2,6]]dodeca-2(6),7-dien-9-one as a light yellow solid. LC-MS: (ES, m/z): M+1: 338

Synthesis of tert-butyl (3S)-4-(5-bromo-3-nitropyridin-2-yl)-3-methylpiperazine-1-carboxylat, Into a 100-mL round-bottom flask, was placed tert-butyl (3S)-3-methylpiperazine-1-carboxylate (1.69 g, 8.438 mmol, 1.00 equiv), $CH_3CN$ (30.00 mL), 5-bromo-2-chloro-3-nitropyridine (2.00 g, 8.423 mmol, 1.00 equiv), $K_2CO_3$ (2.92 g, 21.128 mmol, 2.50 equiv). The resulting solution was stirred for 1 overnight at 80 degrees C. in an oil bath. The reaction mixture was cooled to room temperature. The resulting solution was diluted with 500 mL of water. The resulting solution was extracted with 3×200 mL of ethyl acetate and the organic layers combined. The resulting mixture was washed with 1×1000 ml of brine. The mixture was dried over anhydrous sodium sulfate and concentrated under vacuum. The residue was applied onto a silica gel column with ethyl acetate/petroleum ether (1:7). This resulted in 3.2 g (94.51%) of tert-butyl (3S)-4-(5-bromo-3-nitropyridin-2-yl)-3-methylpiperazine-1-carboxylate as yellow oil. LC-MS: (ES, m/z): M+1: 401

Synthesis of (2S)-1-(5-bromo-3-nitropyridin-2-yl)-2-methylpiperazine hydrochloride, Into a 100-mL round-bottom flask, was placed tert-butyl (3S)-4-(5-bromo-3-nitropyridin-2-yl)-3-methylpiperazine-1-carboxylate (3.00 g, 7.476 mmol, 1.00 equiv), HCl/1,4-dioxane (2M, 30.00 mL). The resulting solution was stirred for 2 hr at room temperature. The resulting mixture was concentrated under vacuum. This resulted in 2.32 g (91.92%) of (2S)-1-(5-bromo-3-nitropyridin-2-yl)-2-methylpiperazine hydrochloride as a yellow solid. LC-MS: (ES, m/z): M+1: 301

Synthesis of (2S)-1-(5-bromo-3-nitropyridin-2-yl)-2-methyl-4-(oxetan-3-yl)piperazine, Into a 250-mL round-bottom flask, was placed (2S)-1-(5-bromo-3-nitropyridin-2-yl)-2-methylpiperazine hydrochloride (2.32 g, 6.872 mmol, 1.00 equiv), THF (30.00 mL), 3-oxetanone (746.00 mg, 10.352 mmol, 1.51 equiv), HOAc (100.00 mg, 1.665 mmol, 0.24 equiv), $NaBH(OAc)_3$ (2.93 g, 13.825 mmol, 2.01 equiv). The resulting solution was stirred for 1 overnight at 30 degrees C. in an oil bath. The resulting mixture was concentrated under vacuum. The residue was applied onto a silica gel column with ethyl acetate/petroleum ether (1:3). This resulted in 2.4 g (97.77%) of (2S)-1-(5-bromo-3-nitropyridin-2-yl)-2-methyl-4-(oxetan-3-yl)piperazine as yellow oil. LC-MS: (ES, m/z): M+1: 357; H-NMR (300 MHz, $CDCl_3$-d, ppm) δ 8.35 (d, J=2.3 Hz, 1H), 8.24 (d, J=2.3 Hz, 1H), 4.77-4.36 (m, 5H), 3.51 (td, J=12.2, 11.3, 3.6 Hz, 2H), 3.13 (d, J=13.3 Hz, 1H), 2.69 (d, J=10.9 Hz, 1H), 2.56 (d, J=11.1 Hz, 1H), 2.26 (d, J=11.2 Hz, 1H), 2.10 (q, J=11.6, 8.3 Hz, 1H), 1.42 (d, J=6.7 Hz, 3H).

Synthesis of N-[6-[(2S)-2-methyl-4-(oxetan-3-yl)piperazin-1-yl]-5-nitropyridin-3-yl]-1,1-diphenylmethanimine, Into a 250-mL round-bottom flask purged and maintained with an inert atmosphere of nitrogen, was placed (2S)-1-(5-bromo-3-nitropyridin-2-yl)-2-methyl-4-(oxetan-3-yl)piperazine (2.20 g, 6.159 mmol, 1.00 equiv), toluene (30.00 mL), diphenylmethanimine (1.34 g, 7.394 mmol, 1.20 equiv), $Cs_2CO_3$ (6.03 g, 18.507 mmol, 3.00 equiv), $Pd_2(dba)_3 \cdot CHCl_3$ (1.28 g, 1.237 mmol, 0.20 equiv), Xantphos (1.43 g, 2.471 mmol, 0.40 equiv). The resulting solution was stirred for 2 hr at 100 degrees C. in an oil bath. The reaction mixture was cooled to room temperature. The resulting mixture was concentrated under vacuum. The residue was applied onto a silica gel column with ethyl acetate/petroleum ether (1:1). This resulted in 2.54 g (90.14%) of N[6-[(2S)-2-methyl-4-(oxetan-3-yl)piperazin-1-yl]-5-nitropyridin-3-yl]-1,1-diphenylmethanimine as red oil. LC-MS: (ES, m/z): M+1: 458

Synthesis of 6-[(2S)-2-methyl-4-(oxetan-3-yl)piperazin-1-yl]-5-nitropyridin-3-amine, Into a 100-mL round-bottom flask, was placed N-[6-[(2S)-2-methyl-4-(oxetan-3-yl)piperazin-1-yl]-5-nitropyridin-3-yl]-1,1-diphenylmethanimine (2.00 g, 4.371 mmol, 1.00 equiv), EtOH (15.00 mL), THF (15.00 mL), HCl (3.00 mL). The resulting solution was stirred for 1.5 hr at room temperature. The pH value of the solution was adjusted to 8 with aqueous $NaHCO_3$. The resulting solution was extracted with 3×100 mL of ethyl acetate and the organic layers combined. The resulting mixture was washed with 1×500 ml of brine. The mixture was dried over anhydrous sodium sulfate and concentrated under vacuum. The residue was applied onto a silica gel column with dichloromethane/methanol (10:1). This resulted in 1.26 g (98.27%) of 6-[(2S)-2-methyl-4-(oxetan-3-yl)piperazin-1-yl]-5-nitropyridin-3-amine as a red solid. LC-MS: (ES, m/z): M+1: 294; H NMR (300 MHz, DMSO-$d_6$, ppm) δ 8.01 (d, J=2.7 Hz, 1H), 7.32 (d, J=2.8 Hz, 1H), 5.63 (s, 2H), 4.69-4.29 (m, 4H), 3.43 (ddd, J=12.7, 8.5, 4.8 Hz, 2H), 3.05 (ddd, J=11.7, 5.3, 3.0 Hz, 1H), 2.89 (ddd, J=11.6, 8.5, 2.9 Hz, 1H), 2.45 (d, J=7.6 Hz, 1H), 2.27-2.08 (m, 1H), 1.89 (dd, J=10.8, 7.7 Hz, 1H), 0.79 (d, J=6.3 Hz, 3H).

Synthesis of 5-bromo-1-methyl-3-([6-[(2S)-2-methyl-4-(oxetan-3-yl)piperazin-1-yl]-5-nitropyridin-3-yl]amino)pyrazin-2-one, Into a 40-mL vial purged and maintained with an inert atmosphere of nitrogen, was placed 6-[(2S)-2-methyl-4-(oxetan-3-yl)piperazin-1-yl]-5-nitropyridin-3-amine (600.00 mg, 2.045 mmol, 1.00 equiv), toluene (10.00 mL), 3,5-dibromo-1-methylpyrazin-2-one (545.00 mg, 2.034 mmol, 0.99 equiv), $K_2CO_3$ (424.00 mg, 3.068 mmol, 1.50 equiv), $Pd(OAc)_2$ (92.00 mg, 0.410 mmol, 0.20 equiv), Xantphos (474.00 mg, 0.819 mmol, 0.40 equiv). The resulting solution was stirred for 2 hr at 100 degrees C. in an oil bath. The reaction mixture was cooled to room temperature. The resulting mixture was concentrated under vacuum. The residue was applied onto a silica gel column with ethyl acetate. This resulted in 810 mg (82.44%) of 5-bromo-1-methyl-3-([6-[(2S)-2-methyl-4-(oxetan-3-yl)piperazin-1-yl]-5-nitropyridin-3-yl]amino)pyrazin-2-one as a red solid. LC-MS: (ES, m/z): M+1: 480; H NMR (300 MHz, DMSO-$d_6$, ppm) δ 9.98 (s, 1H), 8.94 (q, J=2.5 Hz, 2H), 7.39 (s, 1H), 4.66-4.15 (m, 6H), 3.45 (s, 3H), 3.42-3.32 (m, 2H), 3.08 (d, J=13.1 Hz, 1H), 2.64 (d, J=11.0 Hz, 1H), 2.16 (dd, J=11.0, 3.6 Hz, 1H), 2.10-1.95 (m, 1H), 1.22 (d, J=6.6 Hz, 3H).

Synthesis of 3-([5-amino-6-[(2S)-2-methyl-4-(oxetan-3-yl)piperazin-1-yl]pyridin-3-yl]amino)-5-bromo-1-methylpyrazin-2-one, Into a 100-mL round-bottom flask, was placed 5-bromo-1-methyl-3-([6-[(2S)-2-methyl-4-(oxetan-3-yl)piperazin-1-yl]-5-nitropyridin-3-yl]amino)pyrazin-2-one (600.00 mg, 1.249 mmol, 1.00 equiv), EtOH (27.00 mL), H2O (9.00 mL), Fe (700.00 mg, 12.535 mmol, 10.03 equiv), $NH_4Cl$ (663.00 mg, 12.395 mmol, 9.92 equiv). The resulting solution was stirred for 2 hr at 80 degrees C. in an oil bath. The reaction mixture was cooled to room temperature. The resulting solution was diluted with 200 mL of water. The resulting solution was extracted with 3×50 mL of dichloromethane and the organic layers combined. The resulting mixture was washed with 1×300 ml of brine. The mixture was dried over anhydrous sodium sulfate and concentrated under vacuum. The crude product was purified by Flash-Prep-HPLC with the following conditions (IntelFlash-1): Column, C18 reversed phase column; mobile phase, $H_2O$ (0.05% TFA) and $CH_3CN$ (5% $CH_3CN$ up to 40% in 15 min); Flow rate: 80 mL/min; Detector, 254/220 nm. This resulted in 150 mg (26.66%) of 3-([5-amino-6-[(2S)-2-methyl-4-(oxetan-3-yl)piperazin-1-yl]pyridin-3-yl]amino)-5-bromo-1-methylpyrazin-2-one as a brown solid. LC-MS: (ES, m/z): M+1: 450

Synthesis of N-[5-[(6-bromo-4-methyl-3-oxopyrazin-2-yl)amino]-2-[(2S)-2-methyl-4-(oxetan-3-yl)piperazin-1-yl]pyridin-3-yl]prop-2-enamide, Into a 100-mL round-bottom flask purged and maintained with an inert atmosphere of nitrogen, was placed 3-([5-amino-6-[(2S)-2-methyl-4-(oxetan-3-yl)piperazin-1-yl]pyridin-3-yl]amino)-5-bromo-1-methylpyrazin-2-one (150.00 mg, 0.333 mmol, 1.00 equiv), DCM (5.00 mL), DIEA (86.00 mg, 0.665 mmol, 2.00 equiv), acryloyl chloride (30.00 mg, 0.331 mmol, 1.00 equiv). The resulting solution was stirred for 2 hr at room temperature. The resulting mixture was concentrated under vacuum. The residue was applied onto a silica gel column with dichloromethane/methanol (10:1). This resulted in 120 mg (71.43%) of N-[5-[(6-bromo-4-methyl-3-oxopyrazin-2-yl)amino]-2-[(2S)-2-methyl-4-(oxetan-3-yl)piperazin-1-yl]pyridin-3-yl]prop-2-enamide as a light yellow solid. LC-MS: (ES, m/z): M+1: 504; H NMR (300 MHz, DMSO-$d_6$, ppm) δ 9.70 (s, 1H), 9.14 (s, 1H), 8.90 (d, J=2.5 Hz, 1H), 8.68 (d, J=2.6 Hz, 1H), 7.36 (s, 1H), 6.66 (dd, J=17.0, 10.2 Hz, 1H), 6.26 (dd, J=17.0, 1.9 Hz, 1H), 5.88-5.66 (m, 1H), 4.68-4.32 (m, 4H), 3.45 (s, 3H), 3.52-3.38 (m, 2H), 2.89 (dt, J=19.2, 11.0 Hz, 2H), 2.62 (t, J=10.3 Hz, 2H), 2.34 (t, J=9.5 Hz, 1H), 2.06 (t, J=9.5 Hz, 1H), 0.84 (d, J=6.2 Hz, 3H).

Synthesis of (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(trifluoromethyl)pyridin-4-yl)-4-methyl-3-oxo-3,4-dihydropyrazin-2-yl)amino)-2-(2-methyl-4-(oxetan-3-yl)piperazin-1-yl)phenyl)acrylamide: Into a 100-mL round-bottom flask purged and maintained with an inert atmosphere of nitrogen, was placed (S)—N-(54(6-bromo-4-methyl-3-oxo-3,4-dihydropyrazin-2-yl)amino)-2-(2-methyl-4-(oxetan-3-yl)piperazin-1-yl)pyridin-3-yl)acrylamide (300.00 mg, 0.59 mmol, 1.00 equiv), Toluene (5.00 mL), 4,4,4',4',5,5,5',5'-octamethyl-2,2'-bi(1,3,2-dioxaborolane) (224.00 mg, 0.89 mmol, 1.5 equiv), KOAc (143.00 mg, 1.48 mmol, 2.5 equiv), 3G X-phos Pd (30.00 mg, 0.059 mmol, 0.1 equiv). The resulting solution was stirred for 1 hr at 110° C. The resulting mixture was concentrated under vacuum. The residue was applied onto a silica gel column with dichloromethane/methanol (10:1). This resulted in 170 mg (60.7%) of (S)-(6-((5-acrylamido-6-(2-methyl-4-(oxetan-3-yl)piperazin-1-yl)pyridin-3-yl)amino)-4-methyl-5-oxo-4,5-dihydropyrazin-2-yl)boronic acid as a light brown solid. LC-MS-PH—PHNW-789-4: (ES, m/z): M+1: 470.

Synthesis of N-(5-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxopyrazin-2-yl]amino]-2-[(2S)-2-methyl-4-(oxetan-3-yl)piperazin-1-yl]pyridin-3-yl)prop-2-enamide: Into a 40-mL vial purged and maintained with an inert atmosphere of nitrogen, was placed (S)-(6-((5-acrylamido-6-(2-methyl-4-(oxetan-3-yl)piperazin-1-yl)pyridin-3-yl)amino)-4-methyl-5-oxo-4,5-dihydropyrazin-2-yl)boronic acid (100.00 mg, 0.213 mmol, 1.00 equiv), dioxane (1.00 mL), $H_2O$ (0.2 mL), 2-(4-chloro-3-(trifluoromethyl)pyridin-2-yl)-7,7-dimethyl-3,4,7,8-tetrahydro-2H-cyclopenta[4,5]pyrrolo[1,2-a]pyrazin-1(6H)-one (66.00 mg, 0.171 mmol, 0.8 equiv), $Pd(dppf)Cl_2$ (40.00 mg, 0.040 mmol, 0.20 equiv), $K_3PO_4$ (135.00 mg, 0.639 mmol, 3.0 equiv). The resulting solution was stirred for 1 h at 80 degrees C. in an oil bath. The reaction mixture was cooled to room temperature. The resulting mixture was concentrated under vacuum. The residue was applied onto a silica gel column with dichloromethane/methanol (10:1). The crude product was purified by Prep-HPLC with the following conditions: Column, XBridge Shield RP18 OBD Column, 5 um, 19*150 mm; mobile phase, Water (0.05% $NH_3 \cdot H_2O$) and ACN (20% Phase B up to 65% in 12 min); Detector, UV 254/220 nm. This resulted in 13 mg (10%) of (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(trifluoromethyl)pyridin-4-yl)-4-methyl-3-oxo-3,4-dihydropyrazin-2-yl)amino)-2-(2-methyl-4-(oxetan-3-yl)piperazin-1-yl)phenyl)acrylamide as a light yellow solid. LC-MS: (ES, m/z): M+1: 772. $^1$H NMR (300 MHz, $CDCL_3$, ppm) δ 9.58 (s, 1H), 9.38 (s, 1H), 9.11 (s, 1H), 8.65 (d, J=2.5 Hz, 1H), 8.49 (d, J=5.2 Hz, 1H), 7.90 (d, J=5.2 Hz, 1H), 7.80 (s, 1H), 6.69 (dd, J=17.0, 10.2 Hz, 1H), 6.58 (s, 1H), 6.33 (d, J=17.0 Hz, 1H), 5.81 (dd, J=10.1, 1.9 Hz, 1H), 5.04 (s, 1H), 4.65-4.38 (m, 6H), 4.20 (d, J=10.8 Hz, 3H), 3.85 (d, J=9.2 Hz, 1H), 3.57 (s, 3H), 3.46 (td, J=15.6, 14.1, 7.4 Hz, 2H), 2.88 (q, J=12.9, 11.7 Hz, 2H), 2.62 (dd, J=21.5, 7.2 Hz, 4H), 2.44 (s, 2H), 2.34 (q, J=8.4, 5.9 Hz, 1H), 2.04 (t, J=9.6 Hz, 1H), 1.23 (s, 6H), 0.79 (d, J=6.2 Hz, 3H).

Example 29: Preparation of N-(5-[[6-(2-[4,4-dimethyl-9-oxo-1,10-diazatricyclo[6.5.0.0^[2,6]]trideca-2(6),7-dien-10-yl]-3-(hydroxymethyl)pyridin-4-yl)-4-methyl-3-oxopyrazin-2-yl]amino]-2-[(2S)-2-methyl-4-(oxetan-3-yl)piperazin-1-yl]phenyl)prop-2-enamide Synthesis of [(3,3-dimethylcyclopent-1-en-1-yl)oxy]trimethylsilane: Into a 10-L 4-necked round-bottom flask purged and maintained with an inert atmosphere of nitrogen, was placed CuCl (20.60 g, 208.083 mmol, 0.05 equiv), LiCl (17.64 g, 416.108 mmol, 0.10 equiv), THF (2.50 L). This was followed by the addition of 2-cyclopenten-1-one, 3-methyl-(400.00 g, 4161.075 mmol, 1.00 equiv) at −5 to 5 degrees C. To this was added TMSCl (474.67 g, 4369.129 mmol, 1.05 equiv) dropwise with stirring at −5 to 5 degrees C. To the mixture was added MeMgCl (1670.00 mL, 14495.069 mmol, 3.48 equiv) dropwise with stirring at −5 to 10 degrees C. The resulting solution was stirred for 2 h at −5 to 10 degrees C. in an ice/salt bath. The reaction was then quenched by the addition of 34 g of MeOH. The resulting solution was diluted with 5 L of $NH_4Cl$. The solids were filtered out. The resulting solution was extracted with 3×5 L of petroleum ether dried over anhydrous sodium sulfate and concentrated. This resulted in 780 g (crude) of [(3,3-dimethylcyclopent-1-en-1-yl)oxy]trimethylsilane as yellow oil. GC-MS-1 (ES, m/z): M+1: 184

Synthesis of 3,3-dimethylcyclopentanone Into a 20-L 4-necked round-bottom flask, was placed [(3,3-dimethylcyclopent-1-en-1-yl)oxy]trimethylsilane (780.00 g, 4230.990 mmol, 1.00 equiv), DCM (7.8 L), $H_2O$ (30.49 g, 1692.396 mmol, 0.4 equiv). This was followed by the addition of $POCl_3$ (214.09 g, 1396.251 mmol, 0.33 equiv) dropwise with stirring at 25 to 30 degrees C. The resulting solution was stirred for 0.5 h at 25 degrees C. This solvent straight used for next step. GC-MS-2: (ES, m/z): M+1: 112

Synthesis of 3,3-dimethylcyclopentanone: Into a 20-L 4-necked round-bottom flask, was placed 3,3-dimethylcyclopentan-1-one in DCM (7.80 L). This was followed by the addition of DMF (619 g, 2.0 equiv) dropwise with stirring at 25 degrees C. To this was added $POCl_3$ (1362 g, 2.1 equiv) dropwise with stirring at 40 degrees C. The resulting solution was stirred for overnight at 40 degrees C. in an oil bath. The reaction was then quenched by the addition of 2000 g of $K_3PO_4$. The resulting solution was extracted with 3×10 L of dichloromethane dried over anhydrous sodium sulfate and concentrated. This resulted in 530 g (crude) of 2-chloro-4,4-dimethylcyclopent-1-ene-1-carbaldehyde as a brown solid. GC-MS-3: (ES, m/z): M+1: 158

Synthesis of 4,4-dimethyl-1,10-diazatricyclo[6.5.0.0^[2,6]]trideca-2(6),7-dien-9-one: Into a 250-mL round-bottom flask, was placed 2-chloro-4,4-dimethylcyclopent-1-ene-1-carbaldehyde (21.35 g, 0.135 mmol, 1.2 equiv), DMF (100.00 mL), 1,4-diazepan-2-one (12.80 g, 112.135 mmol, 1.00 equiv), DIEA (28.99 g, 0.224 mmol, 2 equiv). The resulting solution was stirred for overnight at 115 degrees C. in an oil bath. The reaction mixture was cooled to room temperature with a water/ice bath. The reaction was then quenched by the addition of 200 mL of water. The resulting solution was extracted with 3×300 mL of ethyl acetate concentrated. The residue was applied onto a silica gel column and eluted with ethyl acetate/petroleum ether (1:1). The collected fractions were combined and concentrated. This resulted in 3.35 g (13.69%) of 4,4-dimethyl-1,10-diazatricyclo[6.5.0.0^[2,6]]trideca-2(6),7-dien-9-one as a grey solid. LC-MS-4: (ES, m/z): M+1: 219

Synthesis of 2, 4-dibromopyridine-3-carbaldehyde: Into a 1000-mL 3-necked round-bottom flask, was placed 2, 4-dibromopyridine (40.00 g, 168.852 mmol, 1.00 equiv), THF (400.00 mL). This was followed by the addition of LDA (2M in hexane, 126.60 mL, 1.50 equiv) dropwise with stirring at −78 degrees C. The resulting solution was stirred for 1 h at −78 degrees C. Then DMF (16.04 ml, 219.507 mmol, 1.30 equiv) dropwise with stirring at −78 degrees C. The resulting solution was stirred for 0.5 h at −78 degrees C. The reaction was then quenched by the addition of 500 mL of $NH_4Cl$. The resulting solution was extracted with 3×500 mL of ethyl acetate concentrated. The residue was applied onto a silica gel column and eluted with ethyl acetate/petroleum ether (0:1-1:1). This resulted in 24.4 g (54.55%) of 2, 4-dibromopyridine-3-carbaldehyde as a white solid. LC-MS-5: (ES, m/z): M+1: 264

Synthesis of (2, 4-dibromopyridin-3-yl) methanol: Into a 100-mL round-bottom flask, was placed 2, 4-dibromopyridine-3-carbaldehyde (2.00 g, 7.550 mmol, 1.00 equiv), EtOH (30.00 mL). This was followed by the addition of $NaBH_4$ (285.64 mg, 7.550 mmol, 1 equiv), in portions at 0 degrees C. The resulting solution was stirred for 3 h at room temperature. The reaction was then quenched by the addition of 30 mL of water. The resulting solution was extracted with 3×30 mL of ethyl acetate concentrated. The residue was applied onto a silica gel column and eluted with ethyl acetate/petroleum ether (1:1). The collected fractions were combined and concentrated. This resulted in 1.4 g (69.47%) of (2, 4-dibromopyridin-3-yl) methanol as a light yellow solid. LC-MS-6: (ES, m/z): M+1: 266

Synthesis of 2,4-dibromo-3-[(oxan-2-yloxy) methyl]pyridine: Into a 100-mL round-bottom flask, was placed (2, 4-dibromopyridin-3-yl) methanol (1.40 g, 5.245 mmol, 1.00 equiv), DCM (30.00 mL, 0.353 mmol, 0.07 equiv), PPTS (131.81 mg, 0.525 mmol, 0.10 equiv), DHP (661.79 mg, 7.868 mmol, 1.50 equiv). The resulting solution was stirred for overnight at 45 degrees C. in an oil bath. The reaction was then quenched by the addition of 30 mL of water. The resulting solution was extracted with 3×30 mL of dichloromethane concentrated. The residue was applied onto a silica gel column and eluted with ethyl acetate/petroleum ether (1:1). The collected fractions were combined and concentrated. This resulted in 1.5 g (80%) of 2,4-dibromo-3-[(oxan-2-yloxy) methyl]pyridine as colorless oil. LC-MS-7: (ES, m/z): M+1: 350.

Synthesis of 10-[4-bromo-3-[(oxan-2-yloxy)methyl]pyridin-2-yl]-4,4-dimethyl-1,10-diazatricyclo[6.5.0.0^[2,6]]trideca-2(6),7-dien-9-one: Into a 100-mL round-bottom flask purged and maintained with an inert atmosphere of nitrogen, was placed 2,4-dibromo-3-[(oxan-2-yloxy)methyl]pyridine (5.36 g, 15.269 mmol, 1.00 equiv), 4,4-dimethyl-1,10-diazatricyclo[6.5.0.0^[2,6]]trideca-2(6),7-dien-9-one (3.33 g, 0.015 mmol, 1 equiv), dioxane (40.00 mL), $Cs_2CO_3$ (9.95 g, 0.031 mmol), $Pd_2(dba)_3$ (1.40 g, 0.002 mmol, 0.1 equiv), Xantphos (883.49 mg, 1.527 mmol, 0.10 equiv). The resulting solution was stirred for 1.5 h at 100 degrees C. in an oil bath. The solids were filtered out. The resulting mixture was concentrated. The residue was applied onto a silica gel and eluted column with ethyl acetate/petroleum ether (1:1). The collected fractions were combined and concentrated. This resulted in 3.65 g (48.94%) of 10-[4-bromo-3-[(oxan-2-yloxy)methyl]pyridin-2-yl]-4,4-dimethyl-1,10-diazatricyclo[6.5.0.0^[2,6]]trideca-2(6),7-dien-9-one as brown oil. LC-MS-8: (ES, m/z): M+1: 488/490

Synthesis of 2-[4,4-dimethyl-9-oxo-1,10-diazatricyclo[6.5.0.0^[2,6]]trideca-2(6),7-dien-10-yl]-3-[(oxan-2-yloxy)methyl]pyridin-4-ylboronic acid: Into a 100-mL round-bottom flask purged and maintained with an inert atmosphere of nitrogen, was placed 10-[4-bromo-3-[(oxan-2-yloxy)methyl]pyridin-2-yl]-4,4-dimethyl-1,10-diazatricyclo[6.5.0.0^[2,6]]trideca-2(6),7-dien-9-one (3.65 g, 7.473 mmol, 1.00 equiv), dioxane (50.00 mL), bis(pinacolato)diboron (2.85 g, 0.011 mmol, 1.5 equiv), KOAc (2.20 g, 0.022 mmol, 3 equiv), $Pd(dppf)Cl_2$ (546.80 mg, 0.747 mmol, 0.10 equiv). The resulting solution was stirred for 2 h at 100 degrees C. in an oil bath. The solids were filtered out. The resulting mixture was concentrated. The resulting solution was diluted with 30 mL of $CH_3CN$. The solids were collected by filtration. This resulted in 1.95 g (57.56%) of 2-[4,4-dimethyl-9-oxo-1,10-diazatricyclo[6.5.0.0^[2,6]]trideca-2(6),7-dien-10-yl]-3-[(oxan-2-yloxy)methyl]pyridin-4-ylboronic acid as a yellow solid. LC-MS-9: (ES, m/z): M+1: 454

Synthesis of 10-[1-hydroxy-3H-[1,2]oxaborolo[4,3-c]pyridin-4-yl]-4,4-dimethyl-1,10-diazatricyclo[6.5.0.0^[2,6]]trideca-2(6),7-dien-9-one: Into a 50-mL round-bottom flask, was placed 2-[4,4-dimethyl-9-oxo-1,10-diazatricyclo[6.5.0.0^[2,6]]trideca-2(6),7-dien-10-yl]-3-[(oxan-2-yloxy)methyl]pyridin-4-ylboronic acid (1.95 g, 4.301 mmol, 1.00 equiv), HCl(gas) in 1,4-dioxane. The resulting solution was stirred for 1 h at room temperature. The resulting mixture was concentrated. The resulting solution was diluted with 20 mL of $Et_2O$. The solids were collected by filtration. This resulted in 1.7 g (112.53%) of 10-[1-hydroxy-3H-[1,2]oxaborolo[4,3-c]pyridin-4-yl]-4,4-dimethyl-1,10-diazatricyclo[6.5.0.0^[2,6]]trideca-2(6),7-dien-9-one as a yellow solid. LC-MS-10: (ES, m/z): M+1: 352

Synthesis of 5-bromo-3-[(4-fluoro-3-nitrophenyl)amino]-1-methylpyrazin-2-one: Into a 250-mL round-bottom flask, was placed 4-fluoro-3-nitroaniline (10.00 g, 64.055 mmol, 1.00 equiv), 3,5-dibromo-1-methylpyrazin-2-one (17.16 g, 64.052 mmol, 1.00 equiv), NMP (30 ml). The resulting solution was stirred for 1 h at 140 degrees C. in an oil bath. The resulting solution was diluted with 300 mL of EA. The solids were collected by filtration. This resulted in 13 g (59.15%) of 5-bromo-3-[(4-fluoro-3-nitrophenyl)amino]-1-methylpyrazin-2-one as a brown solid. LC-MS-11 (ES, m/z): M+1: 343/345

Synthesis of tert-butyl (3S)-4-[4-[(6-bromo-4-methyl-3-oxopyrazin-2-yl)amino]-2-nitrophenyl]-3-methylpiperazine-1-carboxylate: Into a 50-mL round-bottom flask, was placed 5-bromo-3-[(4-fluoro-3-nitrophenyl)amino]-1-methylpyrazin-2-one(10 g, 29.2 mmol, 1.00 equiv), NMP (40.00 mL), tert-butyl (3S)-3-methylpiperazine-1-carboxylate (5.8 g, 5.842 mmol, 1.00 equiv), DIEA (2.26 g, 17.487 mmol, 3.00 equiv). The resulting solution was stirred for 40 h at 120° C. in an oil bath. The resulting solution was diluted with 100 mL of $H_2O$. The resulting solution was extracted with 3×50 mL of dichloromethane/methanol (10:1). The resulting mixture was washed with 3×20 ml of NaCl. The resulting mixture was concentrated. The residue was applied onto a silica gel column with dichloromethane/methanol (10:1). This resulted in 10 g (57.00%) of tert-butyl (3S)-4-[4-[(6-bromo-4-methyl-3-oxopyrazin-2-yl)amino]-2-nitrophenyl]-3-methylpiperazine-1-carboxylate as a brown solid. LC-MS-12: (ES, m/z): M+1: 523

Synthesis of 5-bromo-1-methyl-3-([4-[(2S)-2-methylpiperazin-1-yl]-3-nitrophenyl]amino)pyrazin-2-one: Into a 100-mL round-bottom flask, was placed tert-butyl (3S)-4-[4-[(6-bromo-4-methyl-3-oxopyrazin-2-yl)amino]-2-nitrophenyl]-3-methylpiperazine-1-carboxylate(10.00 g, 1 equiv, 60%), HCl (2M) in 1,4-dioxane (100 mL). The resulting solution was stirred for 14 h at room temperature. The resulting mixture was concentrated. The resulting solution was diluted with 30 mL of $H_2O$. The pH value of the solution was adjusted to 8 with $NH_3$—$H_2O$. The resulting solution was extracted with 3×15 mL of dichloromethane concentrated. The residue was applied onto a silica gel column with dichloromethane/methanol (10:1). This resulted in 5 g of 5-bromo-1-methyl-3-([4-[(2S)-2-methylpiperazin-1-yl]-3-nitrophenyl]amino)pyrazin-2-one as a red solid. LC-MS-13: (ES, m/z): M+1: 423

Synthesis of 5-bromo-1-methyl-3-([4-[(2S)-2-methyl-4-(oxetan-3-yl)piperazin-1-yl]-3-nitrophenyl]amino)pyrazin-2-one Into a 250-mL round-bottom flask, was placed 5-bromo-1-methyl-3-([4-[(2S)-2-methylpiperazin-1-yl]-3-nitrophenyl]amino)pyrazin-2-one (4.00 g, 9.450 mmol, 1.00 equiv), 3-oxetanone (0.89 g, 12.350 mmol, 1.31 equiv), THF (40.00 mL), AcOH (0.80 mL). This was followed by the addition of $NaBH(AcO)_3$ (3.00 g, 14.155 mmol, 1.50 equiv) dropwise with stirring at room temperature. The resulting solution was stirred for 4 h at room temperature. The reaction was then quenched by the addition of 10 mL of water. The resulting mixture was concentrated. The resulting solution was diluted with 40 mL of DCM. The resulting mixture was washed with 1×10 ml $Na_2CO_3$ (aq). The mixture was dried over anhydrous sodium sulfate and concentrated. The residue was applied onto a silica gel column with and eluted with dichloromethane/methanol (10:1). This resulted in 3 g (66.23%) of 5-bromo-1-methyl-3-([4-[(2S)-2-methyl-4-(oxetan-3-yl)piperazin-1-yl]-3-nitrophenyl]amino)pyrazin-2-one as a brown solid. LC-MS-14: (ES, m/z): M+1: 479/481

Synthesis of 3-([3-amino-4-[(2S)-2-methyl-4-(oxetan-3-yl)piperazin-1-yl]phenyl]amino)-5-bromo-1-methylpyrazin-2-one: Into a 250-mL round-bottom flask, was placed 5-bromo-1-methyl-3-([4-[(2S)-2-methyl-4-(oxetan-3-yl)piperazin-1-yl]-3-nitrophenyl]amino)pyrazin-2-one (3.00 g, 6.259 mmol, 1.00 equiv), Fe (1.40 g, 25.035 mmol, 4.00 equiv), $NH_4Cl$ (2.01 g, 37.576 mmol, 6.00 equiv), EtOH (30.00 mL), $H_2O$ (30.00 mL). The resulting solution was stirred for 2 h at 80 degrees C. in an oil bath. The solids were filtered out. The resulting mixture was concentrated. The resulting solution was diluted with 200 mL of DCM. The pH value of the solution was adjusted to 8 with $NH_3$—$H_2O$. The resulting mixture was washed with 1×20 ml of $H_2O$. The resulting mixture was washed with 1×20 mL of NaCl(aq). The mixture was dried over anhydrous sodium sulfate. The residue was applied onto a silica gel column and eluted with dichloromethane/methanol (10:1). This resulted in 2.5 g (88.89%) of 3-([3-amino-4-[(2S)-2-methyl-4-(oxetan-3-yl)piperazin-1-yl]phenyl]amino)-5-bromo-1-methylpyrazin-2-one as a brown solid. LC-MS-15: (ES, m/z): M+1: 449/451

Synthesis of N-[5-[(6-bromo-4-methyl-3-oxopyrazin-2-yl)amino]-2-[(2S)-2-methyl-4-(oxetan-3-yl)piperazin-1-yl]phenyl]prop-2-enamide: Into a 100-mL round-bottom flask, was placed 3-([3-amino-4-[(2S)-2-methyl-4-(oxetan-3-yl)piperazin-1-yl]phenyl]amino)-5-bromo-1-methylpyrazin-2-one (2.50 g, 5.564 mmol, 1.00 equiv), DCM (30.00 mL, 471.901 mmol, 84.82 equiv), DIEA (1.44 g, 11.142 mmol, 2.00 equiv). This was followed by the addition of acryloyl chloride (0.65 g, 7.182 mmol, 1.29 equiv), in portions at 0 degrees C. The resulting solution was stirred for 1 h at 0 degrees C. in a water/ice bath. The reaction was then quenched by the addition of 1 mL of MeOH. The resulting mixture was concentrated. The residue was applied onto a silica gel column and eluted with dichloromethane/methanol (10:1). This resulted in 2.8 g (80.98%) of N-[5-[(6-bromo-4-methyl-3-oxopyrazin-2-yl)amino]-2-[(2S)-2-methyl-4-(oxetan-3-yl)piperazin-1-yl]phenyl]prop-2-enamide as a yellow solid. LC-MS-16: (ES, m/z): M+1: 503/505

Synthesis of N-(5-[[6-(2-[4,4-dimethyl-9-oxo-1,10-diazatricyclo[6.5.0.0^[2,6]]trideca-2(6),7-dien-10-yl]-3-(hydroxymethyl)pyridin-4-yl)-4-methyl-3-oxopyrazin-2-yl]amino]-2-[(2S)-2-methyl-4-(oxetan-3-yl)piperazin-1-yl]phenyl)prop-2-enamide: Into a 40-mL vial purged and maintained with an inert atmosphere of nitrogen, was placed N-[5-[(6-bromo-4-methyl-3-oxopyrazin-2-yl)amino]-2-[(2S)-2-methyl-4-(oxetan-3-yl)piperazin-1-yl]phenyl]prop-2-enamide (103.00 mg, 0.205 mmol, 1.00 equiv), 10-[1-hydroxy-3H-[1,2]oxaborolo[4,3-c]pyridin-4-yl]-4,4-dimethyl-1,10-diazatricyclo[6.5.0.0^[2,6]]trideca-2(6),7- dien-9-one (71.86 mg, 0.205 mmol, 1.00 equiv), dioxane (10.00 mL), $H_2O$ (1.00 mL), $K_2CO_3$ (70.69 mg, 0.512 mmol, 2.5 equiv), Pd(dppf)$Cl_2$ (14.97 mg, 0.020 mmol, 0.1 equiv). The resulting solution was stirred for 2 h at 100 degrees C. in an oil bath. The solids were filtered out. The resulting mixture was concentrated. The crude product was purified by Prep-HPLC with the following conditions: Column, X-bridge RP18; mobile phase, 0.05% ammonia in water and $CH_3CN$ (50% $CH_3CN$ up to 75% in 5 min); Detector, UV 254 nm. This resulted in 9 mg (5.88%) of N-(5-[[6-(2-[4,4-dimethyl-9-oxo-1,10-diazatricyclo [6.5.0.0^[2,6]]trideca-2(6),7-dien-10-yl]-3-(hydroxymethyl) pyridin-4-yl)-4-methyl-3-oxopyrazin-2-yl]amino]-2-[(2S)-2-methyl-4-(oxetan-3-yl)piperazin-1-yl]phenyl)prop-2-enamide as a white solid. LC-MS-0: (ES, m/z): M+1: 748. H-NMR-0: $^1$H NMR (300 MHz, Methanol-$d_4$) δ 8.95 (s, 1H), 8.52 (d, J=5.1 Hz, 1H), 7.86 (d, J=5.1 Hz, 1H), 7.64 (s, 1H), 7.56 (dd, J=8.7, 2.4 Hz, 1H), 7.33 (d, J=8.7 Hz, 1H), 6.64 (s, 1H), 6.49 (dd, J=16.8, 10.2 Hz, 1H), 6.41-6.25 (m, 1H), 5.88-5.75 (m, 1H), 4.78-4.60 (m, 6H), 4.25 (t, J=6.9 Hz, 2H), 3.96 (d, J=37.8 Hz, 2H), 3.66 (s, 3H), 3.60 (q, J=7.5, 7.2 Hz, 1H), 3.13 (d, J=26.4 Hz, 1H), 2.90 (dt, J=30.3, 10.5 Hz, 4H), 2.60 (s, 2H), 2.49 (s, 2H), 2.29 (d, J=9.0 Hz, 3H), 1.97 (t, J=10.5 Hz, 1H), 1.27 (s, 6H), 0.82 (d, J=6.3 Hz, 3H)

Example 30: Preparation of N-(5-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxopyrazin-2-yl]amino]-3-fluoro-2-[(2S)-2-methyl-4-(oxetan-3-yl)piperazin-1-yl] phenyl)prop-2-enamide Synthesis of 2,4-dibromopyridine-3-carbaldehyde: Into a 1000-mL 3-necked round-bottom flask, was placed 2,4-dibromopyridine (40.00 g, 168.852 mmol, 1.00 equiv), THF (400.00 mL). This was followed by the addition of LDA (2M in hexane, 126.60 mL, 1.5 equiv) dropwise with stirring at −78 degrees C. The resulting solution was stirred for 1 hr at −78 degrees C. Then add DMF (16,04,219.507, 1.3 equiv) dropwise with stirring at −78 degrees C. The resulting solution was stirred for 0.5 hr at −78 degrees C. The reaction was then quenched by the addition of 500 mL of NH4Cl. The resulting solution was extracted with 3×500 mL of ethyl acetate concentrated. The residue was applied onto a silica gel column and eluted with ethyl acetate/petroleum ether (0:1-1:1). This resulted in 24.4 g (54.55%) of 2,4-dibromopyridine-3-carbaldehyde as a white solid. LC-MS: (ES, m/z): M+1: 264

Synthesis of (2,4-dibromopyridin-3-yl)methanol: Into a 100-mL round-bottom flask, was placed 2,4-dibromopyridine-3-carbaldehyde (2.00 g, 7.550 mmol, 1.00 equiv), EtOH (30.00 mL). This was followed by the addition of $NaBH_4$ (285.64 mg, 7.550 mmol, 1 equiv), in portions at 0 degrees C. The resulting solution was stirred for 3 h at room temperature. The reaction was then quenched by the addition of 30 mL of water. The resulting solution was extracted with 3×30 mL of ethyl acetate concentrated. The residue was applied onto a silica gel column and eluted with ethyl acetate/petroleum ether (1:1). The collected fractions were combined and concentrated. This resulted in 1.4 g (69.47%) of (2,4-dibromopyridin-3-yl)methanol as a light yellow solid. LC-MS: (ES, m/z): M+1: 266

Synthesis of 2,4-dibromo-3-[(oxan-2-yloxy)methyl]pyridine: Into a 100-mL round-bottom flask, was placed (2,4-dibromopyridin-3-yl)methanol (1.40 g, 5.245 mmol, 1.00 equiv), DCM (30.00 mL, 0.353 mmol, 0.07 equiv), PPTS (131.81 mg, 0.525 mmol, 0.10 equiv), DHP (661.79 mg, 7.868 mmol, 1.50 equiv). The resulting solution was stirred for overnight at 45 degrees C. in an oil bath. The reaction was then quenched by the addition of 30 mL of water. The resulting solution was extracted with 3×30 mL of dichloromethane concentrated. The residue was applied onto a silica gel column and eluted with ethyl acetate/petroleum ether (1:1). The collected fractions were combined and concentrated. This resulted in 1.5 g of 2,4-dibromo-3-[(oxan-2-yloxy)methyl]pyridine as colorless oil. LC-MS: (ES, m/z): M+1: 350

Synthesis of 10-[4-bromo-3-[(oxan-2-yloxy)methyl]pyridin-2-yl]-4,4-dimethyl-1,10-diazatricyclo[6.4.0.0^[2,6]]dodeca-2(6),7-dien-9-one: Into a 100-mL round-bottom flask purged and maintained with an inert atmosphere of nitrogen, was placed 4,4-dimethyl-1,10-diazatricyclo[6.4.0.0^[2,6]] dodeca-2(6),7-dien-9-one (1.00 g, 4.895 mmol, 1.00 equiv), dioxane (40.00 mL, 0.454 mmol, 0.09 equiv), $Cs_2CO_3$ (3.19 g, 9.791 mmol, 2 equiv), 2,4-dibromo-3-[(oxan-2-yloxy) methyl]pyridine (1.72 g, 4.900 mmol, 1.00 equiv), $Pd_2(dba)_3$ (448.28 mg, 0.490 mmol, 0.1 equiv), XantPhos (283.26 mg, 0.490 mmol, 0.1 equiv). The resulting solution was stirred for 1 h at 100 degrees C. in an oil bath. The reaction was then quenched by the addition of 40 mL of water. The resulting solution was extracted with 3×40 mL of ethyl acetate concentrated. The residue was applied onto a silica gel column and eluted with ethyl acetate/petroleum ether (1:1). The collected fractions were combined and concentrated. This resulted in 900 mg (38.75%) of 10-[4-bromo-3-[(oxan-2-yloxy)methyl]pyridin-2-yl]-4,4-dimethyl-1,10-diazatricyclo[6.4.0.0^[2,6]]dodeca-2(6),7-dien-9-one as a brown solid. LC-MS: (ES, m/z): M+1: 474

Synthesis of 2-[4,4-dimethyl-9-oxo-1,10-diazatricyclo [6.4.0.0^[2,6]]dodeca-2(6),7-dien-10-yl]-3-[(oxan-2-yloxy) methyl]pyridin-4-ylboronic acid: Into a 100-mL round-bottom flask purged and maintained with an inert atmosphere of nitrogen, was placed 10-[4-bromo-3-[(oxan-2-yloxy) methyl]pyridin-2-yl]-4,4-dimethyl-1,10-diazatricyclo [6.4.0.0^[2,6]]dodeca-2(6),7-dien-9-one (1.00 g, 2.108 mmol, 1.00 equiv), dioxane (10.00 mL), bis(pinacolato) diboron (1.34 g, 5.277 mmol, 2.50 equiv), KOAc (620.00 mg, 6.317 mmol, 3.00 equiv), Pd(dppf)$Cl_2$ (172.00 mg, 0.211 mmol, 0.10 equiv). The resulting solution was stirred for 2 h at 100 degrees C. in an oil bath. The reaction mixture was cooled to room temperature. The solids were filtered out. The resulting mixture was concentrated under vacuum. This resulted in 920 mg (crude) of 2-[4,4-dimethyl-9-oxo-1,10-diazatricyclo[6.4.0.0^[2,6]]dodeca-2(6),7-dien-10-yl]-3-[(oxan-2-yloxy)methyl]pyridin-4-ylboronic acid as brown oil. LC-MS: (ES, m/z): M+1: 436

Synthesis of 10-[1-hydroxy-3H-[1,2]oxaborolo[4,3-c] pyridin-4-yl]-4,4-dimethyl-1,10-diazatricyclo[6.4 0.0^2,6]] dodeca-2(6),7-dien-9-one: Into a 100-mL round-bottom flask, was placed 2-[4,4-dimethyl-9-oxo-1,10-diazatricyclo [6.4.0.0^[2,6]]dodeca-2(6),7-dien-10-yl]-3-[(oxan-2-yloxy) methyl]pyridin-4-ylboronic acid (920 mg, 1.00 equiv, crude), dioxane (10 mL), HCl (6N, 10 mL). The resulting solution was stirred for 1 h at 25 degrees C. The resulting mixture was concentrated under vacuum. The crude product was purified by Flash-Prep-HPLC with the following conditions: Column, C18 reversed phase column; mobile phase, $H_2O$ (0.05% $NH_3 \cdot H_2O$) and $CH_3CN$ (5% $CH_3CN$ up to 30% in 15 min); Flow rate: 60 mL/min; Detector, 254/220 nm. This resulted in 350 mg of 10-[1-hydroxy-3H-[1,2]oxaborolo[4,3-c]pyridin-4-yl]-4,4-dimethyl-1,10-diazatricyclo [6.4.0.0^[2,6]]dodeca-2(6),7-dien-9-one as a light yellow solid. LC-MS: (ES, m/z): M+1: 338

Synthesis of tert-butyl (3S)-3-methyl-4-(2-methyl-4-nitrophenyl)piperazine-1-carboxylate: Into a 100-mL round-bottom flask, was placed tert-butyl (3S)-3-methylpiperazine-1-carboxylate (19.37 g, 96.714 mmol, 3.00 equiv), 1-fluoro-2-methyl-4-nitrobenzene (5.00 g, 32.231 mmol, 1.00 equiv), DMSO (40 mL). The resulting solution was stirred for 72 h at 140 degrees C. The reaction was then quenched by the addition of 100 mL of water. The resulting solution was extracted with 3×50 mL of ethyl acetate. The resulting mixture was washed with 3×50 ml of Brine. The mixture was dried over anhydrous sodium sulfate and concentrated. The residue was applied onto a silica gel column with ethyl acetate/petroleum ether (0:1-1:1). This resulted in 5 g (46.25%) of tert-butyl (3S)-3-methyl-4-(2-methyl-4-nitrophenyl) piperazine-1-carboxylate as a white crude solid. LC-MS: (ES, m/z): M+1: 336

Synthesis of (2S)-2-methyl-1-(2-methyl-4-nitrophenyl) piperazine: Into a 100-mL round-bottom flask, was placed tert-butyl (3S)-3-methyl-4-(2-methyl-4-nitrophenyl) piperazine-1-carboxylate (5.00 g, 14.907 mmol, 1.00 equiv), EA (20.00 mL), HCl(gas, 2M/L) in EA (30.00 mL, 59.7 mmol, 4.0 equiv). The resulting solution was stirred for 12 h at room temperature. The solids were collected by filtration. This resulted in 3 g (85.53%) of (2S)-2-methyl-1-(2-methyl-4-nitrophenyl)piperazine as a white solid. LC-MS: (ES, m/z): M+1: 236

Synthesis of (2S)-2-methyl-1-(2-methyl-4-nitrophenyl)-4-(oxetan-3-yl)piperazine: Into a 250-mL round-bottom flask, was placed (2S)-2-methyl-1-(2-methyl-4-nitrophenyl) piperazine (3.00 g, 12.750 mmol, 1.00 equiv), 3-oxetanone (1.38 g, 19.126 mmol, 1.5 equiv), THF (30.00 mL). This was followed by the addition of $NaBH(AcO)_3$ (6.76 g, 31.876 mmol, 2.5 equiv), in portions at degrees C. The resulting solution was stirred for 12 h at room temperature. The reaction was then quenched by the addition of 100 mL of water. The resulting solution was extracted with 3×100 mL of ethyl acetate. The resulting mixture was washed with 3×100 ml of Brine. The solid was dried in an oven under reduced pressure. The residue was applied onto a silica gel column with ethyl acetate/petroleum ether (0:1-1:0). This resulted in 1.4 g (37.69%) of (2S)-2-methyl-1-(2-methyl-4-nitrophenyl)-4-(oxetan-3-yl)piperazine as a white crude solid. LC-MS: (ES, m/z): M+1: 292

Synthesis of (2S)-1-(2-bromo-6-methyl-4-nitrophenyl)-2-methyl-4-(oxetan-3-yl)piperazine: Into a 100-mL round-bottom flask, was placed (2S)-2-methyl-1-(2-methyl-4-nitrophenyl)-4-(oxetan-3-yl)piperazine (1.40 g, 4.805 mmol, 1.00 equiv), TFA (20.00 mL), NBS (1.71 g, 9.610 mmol, 2 equiv). The resulting solution was stirred for 24 h at room temperature. The resulting mixture was concentrated. The residue was applied onto a silica gel column with dichloromethane/methanol (1:0-10:1). This resulted in 1.2 g (67.45%) of (2S)-1-(2-bromo-6-methyl-4-nitrophenyl)-2-methyl-4-(oxetan-3-yl)piperazine as a brown crude solid. LC-MS: (ES, m/z): M+1: 370/372.

Synthesis of 3-methyl-4-[2-methyl-4-(oxetan-3-yl)piperazin-1-yl]-5-(prop-2-enamido)cyclohexyl azinic acid: Into a 40-mL round-bottom flask, was placed (2S)-1-(2-bromo-6-methyl-4-nitrophenyl)-2-methyl-4-(oxetan-3-yl)piperazine (600.00 mg, 1.621 mmol, 1.00 equiv), acryloyl chloride (440.03 mg, 4.862 mmol, 3 equiv), $Pd(AcO)_2$ (72.77 mg, 0.324 mmol, 0.2 equiv), BIAP (424.58 mg, 0.648 mmol, 0.4 equiv), Toluene (10.00 mL). The resulting solution was stirred for 4 h at 100 degrees C. The resulting mixture was concentrated. The residue was applied onto a silica gel column with dichloromethane/methanol (0:1-1:10). This resulted in 300 mg (50.24%) of 3-methyl-4-[2-methyl-4-(oxetan-3-yl)piperazin-1-yl]-5-(prop-2-enamido)cyclohexylazinic acid as a brown crude solid. LC-MS: (ES, m/z): M+1: 361

Synthesis of N-[5-amino-3-methyl-2-[(2S)-2-methyl-4-(oxetan-3-yl)piperazin-1-yl]phenyl]prop-2-enamide: Into a 40-mL round-bottom flask, was placed N-[3-methyl-2-[(2S)-2-methyl-4-(oxetan-3-yl)piperazin-1-yl]-5-nitrophenyl]prop-2-enamide (300.00 mg, 0.832 mmol, 1.00 equiv), Fe (464.84 mg, 8.324 mmol, 10.00 equiv), $NH_4Cl$ (445.25 mg, 8.324 mmol, 10 equiv), EtOH (5.00 mL), $H_2O$ (5.00 mL). The resulting solution was stirred for 1 h at 80 degrees C. The solids were filtered out. The resulting mixture was concentrated. The residue was applied onto a silica gel column with dichloromethane/methanol (0:1-1:10). This resulted in 200 mg (72.72%) of N-[5-amino-3-methyl-2-[(2S)-2-methyl-4-(oxetan-3-yl)piperazin-1-yl]phenyl]prop-2-enamide as a brown crude solid. LC-MS: (ES, m/z): M+1: 331

Synthesis of N-[5-[(6-bromo-4-methyl-3-oxopyrazin-2-yl)amino]-3-methyl-2-[(2S)-2-methyl-4-(oxetan-3-yl)piperazin-1-yl]phenyl]prop-2-enamide: Into a 8-mL round-bottom flask, was placed 3,5-dibromo-1-methylpyrazin-2-one (178.37 mg, 0.666 mmol, 1.1 equiv), N-[5-amino-3-methyl-2-[(2S)-2-methyl-4-(oxetan-3-yl)piperazin-1-yl]phenyl] prop-2-enamide (200.00 mg, 0.605 mmol, 1.00 equiv), isopropyl alcohol (3.00 mL), $Et_3N$ (183.74 mg, 1.816 mmol, 3 equiv). The resulting solution was stirred for 12 h at 90 degrees C. The resulting mixture was concentrated. The residue was applied onto a silica gel column with ethyl acetate/petroleum ether (0:1-1:1). This resulted in 270 mg (86.21%) of N-[5-[(6-bromo-4-methyl-3-oxopyrazin-2-yl) amino]-3-methyl-2-[(2S)-2-methyl-4-(oxetan-3-yl)piperazin-1-yl]phenyl]prop-2-enamide as a yellow solid. LC-MS: (ES, m/z): M+1: 517/519

Synthesis of N-(5-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxopyrazin-2-yl] amino]-3-fluoro-2-[(2S)-2-methyl-4-(oxetan-3-yl) piperazin-1-yl]phenyl)prop-2-enamide: Into a 8-mL round-bottom flask, was placed N-[5-[(6-bromo-4-methyl-3-oxopyrazin-2-yl)amino]-3-methyl-2-[(2S)-2-methyl-4-(oxetan-3-yl)piperazin-1-yl]phenyl]prop-2-enamide (100.00 mg, 0.193 mmol, 1.00 equiv), 10-[2-hydroxy-1H,3H-borolo [3,4-c]pyridin-4-yl]-4,4-dimethyl-1,10-diazatricyclo [6.4.0.0^[2,6]]dodeca-2(6),7-dien-9-one (77.74 mg, 0.232 mmol, 1.20 equiv), $Pd(dppf)Cl_2$ (14.14 mg, 0.019 mmol, 0.1 equiv), $K_2CO_3$ (80.13 mg, 0.580 mmol, 3 equiv), Dioxane (1 mL), $H_2O$ (1 mL). The resulting solution was stirred for 2 h at 90 degrees C. The resulting mixture was concentrated. The residue was applied onto a silica gel column with dichloromethane/methanol (1:0-10:1). This resulted in 45 mg (30.97%) of N-(5-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxopyrazin-2-yl] amino]-3-fluoro-2-[(2S)-2-methyl-4-(oxetan-3-yl) piperazin-1-yl]phenyl)prop-2-enamide as a white solid. LC-MS: (ES, m/z): M+1: 749, $^1H$ NMR ($CDCl_3$,300 ppm) δ 8.55-8.53 (s, 0.3H), 8.44 (s, 1H), 8.33-8.28 (m, 4H), 7.79-7.63 (m, 2H), 7.33-7.28 (m, 1H), 6.84-6.80 (m, 1H), 6.42-6.41 (m, 1H), 5.39-5.24 (m, 3H), 4.88-4.33 (m, 9H), 4.29-4.17 (m, 5H), 4.10-3.82 (m, 2H), 3.68 (s, 6H), 3.34-3.29 (m, 2H), 3.20-2.80 (m, 2H), 2.70-2.50 (m, 6H), 2.42 (m, 3H), 2.32 (s, 2H), 1.29 (s, 11H), 0.82 (s, 5H).

Example 31: Preparation of N-[5-([6-[3-(hydroxymethyl)-2-(5-oxo-7,8-dihydro-1,6-naphthyridin-6-yl) pyridin-4-yl]-4-methyl-3-oxopyrazin-2-yl]amino)-2-[(2S)-2-methyl-4-(oxetan-3-yl)piperazin-1-yl] phenyl]prop-2-enamide Synthesis of 5-bromo-3-[(4-fluoro-3-nitrophenyl)amino]-1-methylpyrazin-2-one: Into a 250-mL round-bottom flask, was placed 4-fluoro-3-nitroaniline (10.00 g, 64.055 mmol, 1.00 equiv), 3,5-dibromo-1-methylpyrazin-2-one (17.16 g, 64.052 mmol, 1.00 equiv), NMP (30 mL). The resulting solution was stirred for 1 h at 140 degrees C. in an oil bath. The resulting solution was diluted with 300 mL of EA. The solids were collected by filtration. This resulted in 13 g (59.15%) of 5-bromo-3-[(4-fluoro-3-nitrophenyl)amino]-1-methylpyrazin-2-one as a brown solid. LCMS (ES, m/z): M+1: 343/345

Synthesis of tert-butyl (3S)-4-[4-[(6-bromo-4-methyl-3-oxopyrazin-2-yl)amino]-2-nitrophenyl]-3-methylpiperazine-1-carboxylate: Into a 50-mL round-bottom flask, was placed 5-bromo-3-[(4-fluoro-3-nitrophenyl)amino]-1-methylpyrazin-2-one (10 g, 29.2 mmol, 1.00 equiv), NMP (40.00 mL), tert-butyl (3S)-3-methylpiperazine-1-carboxylate (5.8 g, 5.842 mmol, 1.00 equiv), DIEA (2.26 g, 17.487 mmol, 3.00 equiv). The resulting solution was stirred for 40 h at 120° C. in an oil bath. The resulting solution was diluted with 100 mL of $H_2O$. The resulting solution was extracted with 3×50 mL of dichloromethane/methanol (10:1). The resulting mixture was washed with 3×20 ml of brine. The resulting mixture was concentrated. The residue was applied onto a silica gel column with dichloromethane/methanol (10:1). This resulted in 10 g (57.00%) of tert-butyl (3S)-4-[4-[(6-bromo-4-methyl-3-oxopyrazin-2-yl)amino]-2-nitrophenyl]-3-methylpiperazine-1-carboxylate as a brown solid. LC-MS: (ES, m/z): M+1: 523

Synthesis of 5-bromo-1-methyl-3-([4-[(2S)-2-methylpiperazin-1-yl]-3-nitrophenyl]amino)pyrazin-2-one: Into a 100-mL round-bottom flask, was placed tert-butyl (3S)-4-[4-[(6-bromo-4-methyl-3-oxopyrazin-2-yl)amino]-2-nitrophenyl]-3-methylpiperazine-1-carboxylate (10.00 g, 1 equiv, 60%), HCl in 1,4-dioxane (2N, 100 mL). The resulting solution was stirred for 14 h at room temperature. The resulting mixture was concentrated. The resulting solution was diluted with 30 mL of $H_2O$. The pH value of the solution was adjusted to 8 with $NH_3 \cdot H_2O$. The resulting solution was extracted with 3×15 mL of dichloromethane and concentrated. The residue was applied onto a silica gel column with dichloromethane/methanol (10:1). This resulted in 5 g of 5-bromo-1-methyl-3-([4-[(2S)-2-methylpiperazin-1-yl]-3-nitrophenyl]amino)pyrazin-2-one as a red solid. LC-MS: (ES, m/z): M+1: 423

Synthesis of 5-bromo-1-methyl-3-([4-[(2S)-2-methyl-4-(oxetan-3-yl)piperazin-1-yl]-3-nitrophenyl]amino)pyrazin-2-one: Into a 250-mL round-bottom flask, was placed 5-bromo-1-methyl-3-([4-[(2S)-2-methylpiperazin-1-yl]-3-nitrophenyl]amino)pyrazin-2-one (4.00 g, 9.450 mmol, 1.00 equiv), 3-oxetanone (0.89 g, 12.350 mmol, 1.31 equiv), THF (40.00 mL), AcOH (0.80 mL). This was followed by the addition of $NaBH(AcO)_3$ (3.00 g, 14.155 mmol, 1.50 equiv) dropwise with stirring at room temperature. The resulting solution was stirred for 4 hr at room temperature. The reaction was then quenched by the addition of 10 mL of water. The resulting mixture was concentrated. The resulting solution was diluted with 40 mL of DCM. The resulting mixture was washed with 1×10 mL of $Na_2CO_3$ (aq). The mixture was dried over anhydrous sodium sulfate and concentrated. The residue was applied onto a silica gel column with and eluted with dichloromethane/methanol (10:1). This resulted in 3 g (66.23%) of 5-bromo-1-methyl-3-([4-[(2S)-2-methyl-4-(oxetan-3-yl)piperazin-1-yl]-3-nitrophenyl] amino)pyrazin-2-one as a brown solid. LC-MS: (ES, m/z): M+1: 479/481

Synthesis of 3-([3-amino-4-[(2S)-2-methyl-4-(oxetan-3-yl)piperazin-1-yl]phenyl]amino)-5-bromo-1-methylpyrazin-2-one: Into a 250-mL round-bottom flask, was placed 5-bromo-1-methyl-3-([4-[(2S)-2-methyl-4-(oxetan-3-yl)piperazin-1-yl]-3-nitrophenyl]amino)pyrazin-2-one (3.00 g, 6.259 mmol, 1.00 equiv), Fe (1.40 g, 25.035 mmol, 4.00 equiv), $NH_4Cl$ (2.01 g, 37.576 mmol, 6.00 equiv), EtOH (30.00 mL), $H_2O$ (30.00 mL). The resulting solution was stirred for 2 hr at 80 degrees C. in an oil bath. The solids were filtered out. The resulting mixture was concentrated. The resulting solution was diluted with 200 mL of DCM. The pH value of the solution was adjusted to 8 with $NH_3 \cdot H_2O$. The resulting mixture was washed with 1×20 mL of $H_2O$. The resulting mixture was washed with 1×20 mL of brine. The mixture was dried over anhydrous sodium sulfate and concentrated. The residue was applied onto a silica gel column and eluted with dichloromethane/methanol (10:1). This resulted in 2.5 g (88.89%) of 3-([3-amino-4-[(2S)-2-methyl-4-(oxetan-3-yl)piperazin-1-yl]phenyl]amino)-5-bromo-1-methylpyrazin-2-one as a brown solid. LC-MS: (ES, m/z): M+1: 449/451

Synthesis of N-[5-[(6-bromo-4-methyl-3-oxopyrazin-2-yl)amino]-2-[(2S)-2-methyl-4-(oxetan-3-yl)piperazin-1-yl] phenyl]prop-2-enamide: Into a 100-mL round-bottom flask, was placed 3-([3-amino-4-[(2S)-2-methyl-4-(oxetan-3-yl) piperazin-1-yl]phenyl]amino)-5-bromo-1-methylpyrazin-2-one (2.50 g, 5.564 mmol, 1.00 equiv), DCM (30.00 mL, 471.901 mmol, 84.82 equiv), DIEA (1.44 g, 11.142 mmol, 2.00 equiv). This was followed by the addition of acryloyl chloride (0.65 g, 7.182 mmol, 1.29 equiv), in portions at 0 degrees C. The resulting solution was stirred for 1 hr at 0 degrees C. in a water/ice bath. The reaction was then quenched by the addition of 1 mL of MeOH. The resulting mixture was concentrated. The residue was applied onto a silica gel column and eluted with dichloromethane/methanol (10:1). This resulted in 2.8 g (80.98%) of N-[5-[(6-bromo-4-methyl-3-oxopyrazin-2-yl)amino]-2-[(2S)-2-methyl-4-(oxetan-3-yl)piperazin-1-yl]phenyl]prop-2-enamide as a yellow solid. LC-MS: (ES, m/z): M+1: 503/505

Synthesis of 2, 4-dibromopyridine-3-carbaldehyde: Into a 1000-mL 3-necked round-bottom flask, was placed 2, 4-dibromopyridine (40.00 g, 168.852 mmol, 1.00 equiv), THF (400.00 mL). This was followed by the addition of LDA (2M in hexane, 126.60 mL, 1.50 equiv) dropwise with stirring at −78 degrees C. The resulting solution was stirred for 1 h at −78 degrees C. Then add DMF (16.04 ml, 219.507 mmol, 1.30 equiv) dropwise with stirring at −78 degrees C. The resulting solution was stirred for 0.5 h at −78 degrees C. The reaction was then quenched by the addition of 500 mL of $NH_4Cl$. The resulting solution was extracted with 3×500 mL of ethyl acetate concentrated. The residue was applied onto a silica gel column and eluted with ethyl acetate/petroleum ether (0:1-1:1). This resulted in 24.4 g (54.55%) of 2, 4-dibromopyridine-3-carbaldehyde as a white solid. LC-MS: (ES, m/z): M+1: 264

Synthesis of (2, 4-dibromopyridin-3-yl) methanol: Into a 100-mL round-bottom flask, was placed 2, 4-dibromopyridine-3-carbaldehyde (2.00 g, 7.550 mmol, 1.00 equiv), EtOH (30.00 mL). This was followed by the addition of $NaBH_4$ (285.64 mg, 7.550 mmol, 1 equiv), in portions at 0 degrees C. The resulting solution was stirred for 3 h at room temperature. The reaction was then quenched by the addition of 30 mL of water. The resulting solution was extracted with 3×30 mL of ethyl acetate and concentrated. The residue was applied onto a silica gel column and eluted with ethyl acetate/petroleum ether (1:1). The collected fractions were combined and concentrated. This resulted in 1.4 g (69.47%) of (2, 4-dibromopyridin-3-yl) methanol as a light yellow solid. LC-MS: (ES, m/z): M+1: 266

Synthesis of 2,4-dibromo-3-[(oxan-2-yloxy) methyl]pyridine: Into a 100-mL round-bottom flask, was placed (2, 4-dibromopyridin-3-yl) methanol (1.40 g, 5.245 mmol, 1.00 equiv), DCM (30.00 mL, 0.353 mmol, 0.07 equiv), PPTS (131.81 mg, 0.525 mmol, 0.10 equiv), DHP (661.79 mg, 7.868 mmol, 1.50 equiv). The resulting solution was stirred overnight at 45 degrees C. in an oil bath. The reaction was then quenched by the addition of 30 mL of water. The resulting solution was extracted with 3×30 mL of dichloromethane and concentrated. The residue was applied onto a silica gel column and eluted with ethyl acetate/petroleum ether (1:1). The collected fractions were combined and concentrated. This resulted in 1.5 g of 2,4-dibromo-3-[(oxan-2-yloxy) methyl]pyridine as colorless oil. LC-MS: (ES, m/z): M+1: 350

Synthesis of ethyl 2-ethenylpyridine-3-carboxylate: Into a 250-mL round-bottom flask purged and maintained with an inert atmosphere of nitrogen, was placed ethyl 2-chloropyridine-3-carboxylate (10.00 g, 53.876 mmol, 1.00 equiv), DMF (50.00 mL), tributyl(ethenyl)stannane (20.00 g, 63.071 mmol, 1.17 equiv), BHT (50 mg), $Pd(PPh_3)_2Cl_2$ (780.00 mg, 1.111 mmol, 0.02 equiv). The resulting solution was stirred overnight at 50 degrees C. in an oil bath. The reaction was then quenched by the addition of 500 mL of water. The resulting solution was extracted with 2×500 mL of $Et_2O$ and the organic layers combined. The resulting mixture was washed with 1×1000 ml of brine. The mixture was dried over anhydrous sodium sulfate and concentrated under vacuum. The residue was applied onto a silica gel column with ethyl acetate/petroleum ether (1:16). This resulted in 8.6 g (90.08%) of ethyl 2-ethenylpyridine-3-carboxylate as yellow oil. LC-MS: (ES, m/z): M+1: 178

Synthesis of 7,8-dihydro-6H-1,6-naphthyridin-5-one: Into a 100-mL round-bottom flask, was placed ethyl 2-ethenylpyridine-3-carboxylate (3.00 g, 16.930 mmol, 1.00 equiv), HOAc (30.00 mL), $NH_4OAc$ (13.05 g, 169.299 mmol, 10.00 equiv). The resulting solution was stirred overnight at 120 degrees C. in an oil bath. The reaction mixture was cooled to room temperature. The resulting mixture was concentrated under vacuum. The residue was applied onto a silica gel column with dichloromethane/methanol (20:1). The crude product was purified by Flash-Prep-HPLC with the following conditions (IntelFlash-1): Column, C18 reversed phase column; mobile phase, $H_2O$ (10 mm $NH_4HCO_3$) and $CH_3CN$ (5% B hold 2 min, 5% B up to 20% B in 8 min, hold 95% B 2 min); Detector, 220 nm. This resulted in 520 mg (20.73%) of 7,8-dihydro-6H-1,6-naphthyridin-5-one as a white solid. H-NMR (300 MHz, Chloroform-d, ppm) δ 8.71-8.61 (m, 1H), 8.34 (dd, J=7.8, 1.7 Hz, 1H), 7.34 (dd, J=7.8, 4.9 Hz, 1H), 6.76 (s, 1H), 3.69 (td, J=6.8, 2.5 Hz, 2H), 3.23 (t, J=6.7 Hz, 2H).

Synthesis of 6-[4-bromo-3-[(oxan-2-yloxy)methyl]pyridin-2-yl]-7,8-dihydro-1,6-naphthyridin-5-one: Into a 40-mL vial purged and maintained with an inert atmosphere of nitrogen, was placed 7,8-dihydro-6H-1,6-naphthyridin-5-one (520.00 mg, 3.510 mmol, 1.00 equiv), dioxane (10.00 mL), 2,4-dibromo-3-[(oxan-2-yloxy)methyl]pyridine (1.97 g, 5.612 mmol, 1.60 equiv), phen (253.00 mg, 1.404 mmol, 0.40 equiv), CuI (401.00 mg, 2.106 mmol, 0.60 equiv), $K_2CO_3$ (1.45 g, 10.492 mmol, 2.99 equiv). The resulting solution was stirred overnight at 110 degrees C. in an oil bath. The reaction mixture was cooled to room temperature. The resulting mixture was concentrated under vacuum. The residue was applied onto a silica gel column with ethyl acetate/petroleum ether (7:3). This resulted in 950 mg (64.71%) of 6-[4-bromo-3-[(oxan-2-yloxy)methyl]pyridin-2-yl]-7,8-dihydro-1,6-naphthyridin-5-one as a yellow solid. LC-MS: (ES, m/z): M+1: 418

Synthesis of 3-[(oxan-2-yloxy)methyl]-2-(5-oxo-7,8-dihydro-1,6-naphthyridin-6-yl)pyridin-4-ylboronic acid: Into a 100-mL round-bottom flask purged and maintained with an inert atmosphere of nitrogen, was placed 6-[4-bromo-3-[(oxan-2-yloxy)methyl]pyridin-2-yl]-7,8-dihydro-1,6-naphthyridin-5-one (950.00 mg, 2.271 mmol, 1.00 equiv), dioxane (20.00 mL), bis(pinacolato)diboron (1.44 g, 5.671 mmol, 2.50 equiv), KOAc (669.00 mg, 6.817 mmol, 3.00 equiv), $Pd(dppf)Cl_2{\cdot}CH_2Cl_2$ (185.00 mg, 0.227 mmol, 0.10 equiv). The resulting solution was stirred for 2 hr at 100 degrees C. in an oil bath. The reaction mixture was cooled to room temperature. The solids were filtered out. The resulting mixture was concentrated under vacuum. The crude product was purified by Flash-Prep-HPLC with the following conditions (IntelFlash-1): Column, C18 reversed phase column; mobile phase, $H_2O$ and $CH_3CN$ (10% B up to 40% in 15 min); Detector, 220 nm. This resulted in 500 mg (57.45%) of 3-[(oxan-2-yloxy)methyl]-2-(5-oxo-7,8-dihydro-1,6-naphthyridin-6-yl)pyridin-4-ylboronic acid as a white solid. LC-MS: (ES, m/z): M+1: 383

Synthesis of 6-[1-hydroxy-3H-[1,2]oxaborolo[4,3-c]pyridin-4-yl]-7,8-dihydro-1,6-naphthyridin-5-one: Into a 100-mL round-bottom flask, was placed 3-[(oxan-2-yloxy)methyl]-2-(5-oxo-7,8-dihydro-1,6-naphthyridin-6-yl)pyridin-4-ylboronic acid (300.00 mg, 0.783 mmol, 1.00 equiv), HCl(gas) in 1,4-dioxane (2N, 12.00 mL). The resulting solution was stirred for 1 hr at 25 degrees C. The resulting mixture was concentrated under vacuum. This resulted in 250 mg (113.61%) of 6-[1-hydroxy-3H-[1,2]oxaborolo[4,3-c]pyridin-4-yl]-7,8-dihydro-1,6-naphthyridin-5-one as a white solid. H-NMR δ 9.15 (dd, J=8.1, 1.4 Hz, 1H), 9.04 (d, J=5.8 Hz, 1H), 8.64 (d, J=4.9 Hz, 1H), 8.25-8.13 (m, 1H), 7.84 (s, 1H), 5.16 (s, 2H), 4.42 (t, J=6.2 Hz, 2H), 3.76-3.69 (m, 2H).

Synthesis of N-[5-([6-[3-(hydroxymethyl)-2-(5-oxo-7,8-dihydro-1,6-naphthyridin-6-yl)pyridin-4-yl]-4-methyl-3-oxopyrazin-2-yl]amino)-2-[(2S)-2-methyl-4-(oxetan-3-yl)piperazin-1-yl]phenyl]prop-2-enamide: Into a 40-mL vial purged and maintained with an inert atmosphere of nitrogen, was placed N-[5-[(6-bromo-4-methyl-3-oxopyrazin-2-yl)amino]-2-[(2S)-2-methyl-4-(oxetan-3-yl)piperazin-1-yl]phenyl]prop-2-enamide (135.00 mg, 0.268 mmol, 1.00 equiv), dioxane (5.00 mL), $H_2O$ (0.50 mL), 6-[1-hydroxy-3H-[1,2]oxaborolo[4,3-c]pyridin-4-yl]-7,8-dihydro-1,6-naphthyridin-5-one (153.00 mg, 0.544 mmol, 2.03 equiv), $K_2CO_3$ (186.00 mg, 1.346 mmol, 5.02 equiv), Xphos Pd G3 (45.00 mg, 0.053 mmol, 0.20 equiv). The resulting solution was stirred for 1 hr at 100 degrees C. in an oil bath. The reaction mixture was cooled to room temperature. The resulting mixture was concentrated under vacuum. The residue was applied onto a silica gel column with dichloromethane/methanol (20:1). The crude product was purified by Prep-HPLC with the following conditions: Column, XBridge Shield RP18 OBD Column, 5 um, 19*150 mm; mobile phase, Water (0.05% $NH_3{\cdot}H_2O$) and ACN (20% Phase B up to 60% in 10 min); Detector, UV 254/220 nm. This resulted in 60 mg (33.01%) of N-[5-([6-[3-(hydroxymethyl)-2-(5-oxo-7,8-dihydro-1,6-naphthyridin-6-yl)pyridin-4-yl]-4-methyl-3-oxopyrazin-2-yl]amino)-2-[(2S)-2- methyl-4-(oxetan-3-yl)piperazin-1-yl]phenyl]prop-2-enamide as a white solid. LC-MS: (ES, m/z): M+1: 678; H-NMR (300 MHz, DMSO-$d_6$, ppm) δ 9.28 (s, 1H), 9.20 (s, 1H), 9.10 (s, 1H), 8.72 (dd, J=4.9, 1.8 Hz, 1H), 8.51 (d, J=5.1 Hz, 1H), 8.28 (d, J=7.8 Hz, 1H), 7.94 (dd, J=5.2, 2.3 Hz, 1H), 7.69 (d, J=2.9 Hz, 1H), 7.62 (dd, J=8.7, 2.5 Hz, 1H), 7.49 (dd, J=7.8, 4.9 Hz, 1H), 7.27 (d, J=8.7 Hz, 1H), 6.62 (dd, J=16.9, 10.2 Hz, 1H), 6.28 (dd, J=16.9, 1.8 Hz, 1H), 5.79 (d, J=10.3 Hz, 1H), 5.05 (s, 1H), 4.53 (dq, J=28.6, 6.1 Hz, 6H), 4.22 (td, J=11.9, 4.6 Hz, 1H), 3.96-3.82 (m, 1H), 3.57 (s, 3H), 3.53-3.39 (m, 2H), 3.27-3.00 (m, 2H), 2.71 (d, J=27.3 Hz, 4H), 2.22 (s, 1H), 1.92 (t, J=10.0 Hz, 1H), 0.73 (d, J=6.1 Hz, 3H).

Example 32: Preparation of N-[5-([6-[3-(hydroxymethyl)-2-(1-oxo-3,4-dihydro-2,7-naphthyridin-2-yl)pyridin-4-yl]-4-methyl-3-oxopyrazin-2-yl]amino)-2-[(2S)-2-methyl-4-(oxetan-3-yl)piperazin-1-yl]phenyl]prop-2-enamide Synthesis of 5-bromo-3-[(4-fluoro-3-nitrophenyl)amino]-1-methylpyrazin-2-one: Into a 250-mL round-bottom flask, was placed 4-fluoro-3-nitroaniline (10.00 g, 64.055 mmol, 1.00 equiv), 3,5-dibromo-1-methylpyrazin-2-one (17.16 g, 64.052 mmol, 1.00 equiv), NMP (30 mL). The resulting solution was stirred for 1 h at 140 degrees C. in an oil bath. The resulting solution was diluted with 300 mL of EA. The solids were collected by filtration. This resulted in 13 g (59.15%) of 5-bromo-3-[(4-fluoro-3-nitrophenyl)amino]-1-methylpyrazin-2-one as a brown solid. LCMS (ES, m/z): M+1: 343/345

Synthesis of tert-butyl (3S)-4-[4-[(6-bromo-4-methyl-3-oxopyrazin-2-yl)amino]-2-nitrophenyl]-3-methylpiperazine-1-carboxylate: Into a 50-mL round-bottom flask, was placed 5-bromo-3-[(4-fluoro-3-nitrophenyl)amino]-1-methylpyrazin-2-one (10 g, 29.2 mmol, 1.00 equiv), NMP (40.00 mL), tert-butyl (3S)-3-methylpiperazine-1-carboxylate (5.8 g, 5.842 mmol, 1.00 equiv), DIEA (2.26 g, 17.487 mmol, 3.00 equiv). The resulting solution was stirred for 40 h at 120° C. in an oil bath. The resulting solution was diluted with 100 mL of $H_2O$. The resulting solution was extracted with 3×50 mL of dichloromethane/methanol (10:1). The resulting mixture was washed with 3×20 ml of brine. The resulting mixture was concentrated. The residue was applied onto a silica gel column with dichloromethane/methanol (10:1). This resulted in 10 g (57.00%) of tert-butyl (3S)-4-[4-[(6-bromo-4-methyl-3-oxopyrazin-2-yl)amino]-2-nitrophenyl]-3-methylpiperazine-1-carboxylate as a brown solid. LC-MS: (ES, m/z): M+1: 523

Synthesis of 5-bromo-1-methyl-3-([4-[(2S)-2-methylpiperazin-1-yl]-3-nitrophenyl]amino)pyrazin-2-one: Into a 100-mL round-bottom flask, was placed tert-butyl (3S)-4-[4-[(6-bromo-4-methyl-3-oxopyrazin-2-yl)amino]-2-nitrophenyl]-3-methylpiperazine-1-carboxylate (10.00 g, 1 equiv, 60%), HCl in 1,4-dioxane (2N, 100 mL). The resulting solution was stirred for 14 h at room temperature. The resulting mixture was concentrated. The resulting solution was diluted with 30 mL of $H_2O$. The pH value of the solution was adjusted to 8 with $NH_3{\cdot}H_2O$. The resulting solution was extracted with 3×15 mL of dichloromethane and concentrated. The residue was applied onto a silica gel column with dichloromethane/methanol (10:1). This resulted in 5 g of 5-bromo-1-methyl-3-([4-[(2S)-2-methylpiperazin-1-yl]-3-nitrophenyl]amino)pyrazin-2-one as a red solid. LC-MS: (ES, m/z): M+1: 423

Synthesis of 5-bromo-1-methyl-3-([4-[(2S)-2-methyl-4-(oxetan-3-yl)piperazin-1-yl]-3-nitrophenyl]amino)pyrazin-2-one: Into a 250-mL round-bottom flask, was placed 5-bromo-1-methyl-3-([4-[(2S)-2-methylpiperazin-1-yl]-3-nitrophenyl]amino)pyrazin-2-one (4.00 g, 9.450 mmol, 1.00 equiv), 3-oxetanone (0.89 g, 12.350 mmol, 1.31 equiv), THF (40.00 mL), AcOH (0.80 mL). This was followed by the addition of $NaBH(AcO)_3$ (3.00 g, 14.155 mmol, 1.50 equiv) dropwise with stirring at room temperature. The resulting solution was stirred for 4 hr at room temperature. The reaction was then quenched by the addition of 10 mL of water. The resulting mixture was concentrated. The resulting solution was diluted with 40 mL of DCM. The resulting mixture was washed with 1×10 mL of $Na_2CO_3$ (aq). The mixture was dried over anhydrous sodium sulfate and concentrated. The residue was applied onto a silica gel column with and eluted with dichloromethane/methanol (10:1). This resulted in 3 g (66.23%) of 5-bromo-1-methyl-3-([4-[(2S)-2-methyl-4-(oxetan-3-yl)piperazin-1-yl]-3-nitrophenyl]amino)pyrazin-2-one as a brown solid. LC-MS: (ES, m/z): M+1: 479/481

Synthesis of 3-([3-amino-4-[(2S)-2-methyl-4-(oxetan-3-yl)piperazin-1-yl]phenyl]amino)-5-bromo-1-methylpyrazin-2-one: Into a 250-mL round-bottom flask, was placed 5-bromo-1-methyl-3-([4-[(2S)-2-methyl-4-(oxetan-3-yl)piperazin-1-yl]-3-nitrophenyl]amino)pyrazin-2-one (3.00 g, 6.259 mmol, 1.00 equiv), Fe (1.40 g, 25.035 mmol, 4.00 equiv), $NH_4Cl$ (2.01 g, 37.576 mmol, 6.00 equiv), EtOH (30.00 mL), $H_2O$ (30.00 mL). The resulting solution was stirred for 2 hr at 80 degrees C. in an oil bath. The solids were filtered out. The resulting mixture was concentrated. The resulting solution was diluted with 200 mL of DCM. The pH value of the solution was adjusted to 8 with $NH_3{\cdot}H_2O$. The resulting mixture was washed with 1×20 mL of $H_2O$. The resulting mixture was washed with 1×20 mL of brine. The mixture was dried over anhydrous sodium sulfate and concentrated. The residue was applied onto a silica gel column and eluted with dichloromethane/methanol (10:1). This resulted in 2.5 g (88.89%) of 3-([3-amino-4-[(2S)-2-methyl-4-(oxetan-3-yl)piperazin-1-yl]phenyl]amino)-5-bromo-1-methylpyrazin-2-one as a brown solid. LC-MS: (ES, m/z): M+1: 449/451

Synthesis of N-[5-[(6-bromo-4-methyl-3-oxopyrazin-2-yl)amino]-2-[(2S)-2-methyl-4-(oxetan-3-yl)piperazin-1-yl]phenyl]prop-2-enamide: Into a 100-mL round-bottom flask, was placed 3-([3-amino-4-[(2S)-2-methyl-4-(oxetan-3-yl)piperazin-1-yl]phenyl]amino)-5-bromo-1-methylpyrazin-2-one (2.50 g, 5.564 mmol, 1.00 equiv), DCM (30.00 mL, 471.901 mmol, 84.82 equiv), DIEA (1.44 g, 11.142 mmol, 2.00 equiv). This was followed by the addition of acryloyl chloride (0.65 g, 7.182 mmol, 1.29 equiv), in portions at 0 degrees C. The resulting solution was stirred for 1 hr at 0 degrees C. in a water/ice bath. The reaction was then quenched by the addition of 1 mL of MeOH. The resulting mixture was concentrated. The residue was applied onto a silica gel column and eluted with dichloromethane/methanol (10:1). This resulted in 2.8 g (80.98%) of N-[5-[(6-bromo-4-methyl-3-oxopyrazin-2-yl)amino]-2-[(2S)-2-methyl-4-(oxetan-3-yl)piperazin-1-yl]phenyl]prop-2-enamide as a yellow solid. LC-MS: (ES, m/z): M+1: 503/505

Synthesis of 2, 4-dibromopyridine-3-carbaldehyde: Into a 1000-mL 3-necked round-bottom flask, was placed 2, 4-dibromopyridine (40.00 g, 168.852 mmol, 1.00 equiv), THF (400.00 mL). This was followed by the addition of LDA (2M in hexane, 126.60 mL, 1.50 equiv) dropwise with stirring at −78 degrees C. The resulting solution was stirred for 1 h at −78 degrees C. Then add DMF (16.04 ml, 219.507 mmol, 1.30 equiv) dropwise with stirring at −78 degrees C. The resulting solution was stirred for 0.5 h at −78 degrees C. The reaction was then quenched by the addition of 500 mL of $NH_4Cl$. The resulting solution was extracted with 3×500 mL of ethyl acetate concentrated. The residue was applied onto a silica gel column and eluted with ethyl acetate/petroleum ether (0:1-1:1). This resulted in 24.4 g (54.55%) of 2, 4-dibromopyridine-3-carbaldehyde as a white solid. LC-MS: (ES, m/z): M+1: 264

Synthesis of (2, 4-dibromopyridin-3-yl) methanol: Into a 100-mL round-bottom flask, was placed 2, 4-dibromopyridine-3-carbaldehyde (2.00 g, 7.550 mmol, 1.00 equiv), EtOH (30.00 mL). This was followed by the addition of $NaBH_4$ (285.64 mg, 7.550 mmol, 1 equiv), in portions at 0 degrees C. The resulting solution was stirred for 3 h at room temperature. The reaction was then quenched by the addition of 30 mL of water. The resulting solution was extracted with 3×30 mL of ethyl acetate and concentrated. The residue was applied onto a silica gel column and eluted with ethyl acetate/petroleum ether (1:1). The collected fractions were combined and concentrated. This resulted in 1.4 g (69.47%) of (2, 4-dibromopyridin-3-yl) methanol as a light yellow solid. LC-MS: (ES, m/z): M+1: 266

Synthesis of 2,4-dibromo-3-[(oxan-2-yloxy) methyl]pyridine: Into a 100-mL round-bottom flask, was placed (2, 4-dibromopyridin-3-yl) methanol (1.40 g, 5.245 mmol, 1.00 equiv), DCM (30.00 mL, 0.353 mmol, 0.07 equiv), PPTS (131.81 mg, 0.525 mmol, 0.10 equiv), DHP (661.79 mg, 7.868 mmol, 1.50 equiv). The resulting solution was stirred overnight at 45 degrees C. in an oil bath. The reaction was then quenched by the addition of 30 mL of water. The resulting solution was extracted with 3×30 mL of dichloromethane and concentrated. The residue was applied onto a silica gel column and eluted with ethyl acetate/petroleum ether (1:1). The collected fractions were combined and concentrated. This resulted in 1.5 g of 2,4-dibromo-3-[(oxan-2-yloxy) methyl]pyridine as colorless oil. LC-MS: (ES, m/z): M+1: 350

Synthesis of ethyl 4-chloropyridine-3-carboxylate: Into a 250-mL round-bottom flask, was placed 4-chloropyridine-3-carboxylic acid (10.00 g, 63.472 mmol, 1.00 equiv), $SOCl_2$ (100.00 mL). The resulting solution was stirred for 90 min at 80 degrees C. in an oil bath. After cooling to room temperature, the solution was concentrated to dryness and then azeotroped with toluene (2×100 mL) to afford a solid. The resultant solid was added in portions to a cooled (o degrees C.) solution of EtOH (200.00 mL) and DIEA (100.00 mL, 574.111 mmol, 9.05 equiv). The resulting solution was stirred for 4 h at room temperature. The resulting solution was diluted with 500 mL of water. The resulting solution was extracted with 3×300 mL of ethyl acetate and the organic layers combined. The resulting mixture was washed with 1×1000 ml of brine. The mixture was dried over anhydrous sodium sulfate and concentrated under vacuum. The residue was applied onto a silica gel column with ethyl acetate/petroleum ether (1:3). This resulted in 8.8 g (74.7%) of ethyl 4-chloropyridine-3-carboxylate as yellow oil. H-NMR (300 MHz, Chloroform-d, ppm) δ 9.03 (s, 1H), 8.58 (d, J=5.4 Hz, 1H), 7.41 (d, J=5.4 Hz, 1H), 4.44 (q, J=7.1 Hz, 2H), 1.42 (t, J=7.1 Hz, 3H).

Synthesis of ethyl 4-ethenylpyridine-3-carboxylate: Into a 250-mL round-bottom flask purged and maintained with an inert atmosphere of nitrogen, was placed ethyl 4-chloropyridine-3-carboxylate (8.80 g, 47.411 mmol, 1.00 equiv), DMF (100.00 mL), tributyl(ethenyl)stannane (27.00 g, 85.146 mmol, 1.80 equiv), BHT (50.00 mg), $Pd(PPh_3)_2Cl_2$ (998.00 mg, 1.422 mmol, 0.03 equiv). The resulting solution was stirred overnight at 50 degrees C. in an oil bath. The reaction mixture was cooled to room temperature. The resulting solution was diluted with 500 mL of water. The resulting solution was extracted with 3×300 mL of ethyl acetate and the organic layers combined. The resulting mixture was washed with 1×1000 ml of brine. The mixture was dried over anhydrous sodium sulfate and concentrated under vacuum. The residue was applied onto a silica gel column with ethyl acetate/petroleum ether (3:1). This resulted in 3.1 g (36.90%) of ethyl 4-ethenylpyridine-3-carboxylate as yellow oil. H-NMR (300 MHz, Chloroform-d, ppm) δ 9.11 (d, J=0.7 Hz, 1H), 8.68 (dd, J=5.3, 0.6 Hz, 1H), 7.61-7.46 (m, 2H), 5.89 (dd, J=17.4, 1.0 Hz, 1H), 5.58 (dd, J=11.0, 1.0 Hz, 1H), 4.43 (q, J=7.1 Hz, 2H), 1.44 (t, J=7.1 Hz, 3H).

Synthesis of 3,4-dihydro-2H-2,7-naphthyridin-1-one: Into a 100-mL round-bottom flask, was placed ethyl 4-ethenylpyridine-3-carboxylate (2.80 g, 15.801 mmol, 1.00 equiv), HOAc (30.00 mL), $NH_4OAc$ (12.20 g, 158.272 mmol, 10.02 equiv). The resulting solution was stirred overnight at 120 degrees C. in an oil bath. The reaction mixture was cooled to room temperature. The resulting mixture was concentrated under vacuum. The residue was applied onto a silica gel column with dichloromethane/methanol (10:1). The crude product was purified by Flash-Prep-HPLC with the following conditions (IntelFlash-1): Column, C18 reversed phase column; mobile phase, $H_2O$ (10 mm $NH_4HCO_3$) and $CH_3CN$ (5% $CH_3CN$ up to 20% in 8 min); Detector, 254/220 nm. This resulted in 430 mg (18.37%) of 3,4-dihydro-2H-2,7-naphthyridin-1-one as a white solid. H-NMR (300 MHz, Chloroform-d, ppm) δ 9.20 (d, J=0.8 Hz, 1H), 8.66 (d, J=5.0 Hz, 1H), 7.19 (dq, J=5.1, 0.9 Hz, 1H), 6.84 (s, 1H), 3.69-3.59 (m, 2H), 3.03 (t, J=6.6 Hz, 2H).

Synthesis of 2-[4-bromo-3-[(oxan-2-yloxy)methyl]pyridin-2-yl]-3,4-dihydro-2,7-naphthyridin-1-one: Into a 40-mL vial purged and maintained with an inert atmosphere of nitrogen, was placed 2,4-dibromo-3-[(oxan-2-yloxy)methyl]pyridine (1.47 g, 4.188 mmol, 1.59 equiv), dioxane (15.00 mL), 3,4-dihydro-2H-2,7-naphthyridin-1-one (390.00 mg, 2.632 mmol, 1.00 equiv), phen (190.00 mg, 1.054 mmol, 0.40 equiv), CuI (301.00 mg, 1.580 mmol, 0.60 equiv), $K_2CO_3$ (1.09 g, 7.887 mmol, 3.00 equiv). The resulting solution was stirred overnight at 110 degrees C. in an oil bath. The reaction mixture was cooled to room temperature. The resulting mixture was concentrated under vacuum. The residue was applied onto a silica gel column with dichloromethane/methanol (20:1). This resulted in 770 mg (69.93%) of 2-[4-bromo-3-[(oxan-2-yloxy)methyl]pyridin-2-yl]-3,4-dihydro-2,7-naphthyridin-1-one as a yellow solid. LC-MS: (ES, m/z): M+1: 418

Synthesis of 3-[(oxan-2-yloxy)methyl]-2-(1-oxo-3,4-dihydro-2,7-naphthyridin-2-yl)pyridin-4-ylboronic acid: Into a 100-mL round-bottom flask purged and maintained with an inert atmosphere of nitrogen, was placed 2-[4-bromo-3-[(oxan-2-yloxy)methyl]pyridin-2-yl]-3,4-dihydro-2,7-naphthyridin-1-one (550.00 mg, 1.315 mmol, 1.00 equiv), dioxane (10.00 mL), bis(pinacolato)diboron (838.00 mg, 3.300 mmol, 2.51 equiv), KOAc (388.00 mg, 3.953 mmol, 3.01 equiv), $Pd(dppf)Cl_2 \cdot CH_2Cl_2$ (108.00 mg, 0.132 mmol, 0.10 equiv). The resulting solution was stirred for 2 hr at 100 degrees C. in an oil bath. The reaction mixture was cooled to room temperature. The solids were filtered out. The resulting mixture was concentrated under vacuum. The crude product was purified by Flash-Prep-HPLC with the following conditions (IntelFlash-1): Column, C18 reversed phase column; mobile phase, $H_2O$ and $CH_3CN$ (10% $CH_3CN$ up to 40% in 15 min); Detector, 254/220 nm. This resulted in 180 mg (35.72%) of 3-[(oxan-2-yloxy)methyl]-

2-(1-oxo-3,4-dihydro-2,7-naphthyridin-2-yl)pyridin-4-ylboronic acid as a white solid. LC-MS: (ES, m/z): M+1: 383

Synthesis of 2-[1-hydroxy-3H-[1,2]oxaborolo[4,3-c]pyridin-4-yl]-3,4-dihydro-2,7-naphthyridin-1-one: Into a 100-mL round-bottom flask, was placed 3-[(oxan-2-yloxy) methyl]-2-(1-oxo-3,4-dihydro-2,7-naphthyridin-2-yl) pyridin-4-ylboronic acid (180.00 mg, 0.470 mmol, 1.00 equiv), HCl(gas) in 1,4-dioxane (2N, 12.00 mL). The resulting solution was stirred for 1 hr at room temperature. The resulting mixture was concentrated under vacuum. This resulted in 180 mg (136.33%) of 2-[1-hydroxy-3H-[1,2] oxaborolo[4,3-c]pyridin-4-yl]-3,4-dihydro-2,7-naphthyridin-1-one as a yellow solid. H-NMR (300 MHz, Methanol-4 ppm) δ 9.38 (t, J=0.8 Hz, 1H), 8.99 (dd, J=6.0, 0.9 Hz, 1H), 8.76-8.62 (m, 1H), 8.21 (dd, J=6.1, 0.8 Hz, 1H), 7.85 (d, J=5.0 Hz, 1H), 5.18 (s, 2H), 4.35 (t, J=6.4 Hz, 2H), 3.67-3.60 (m, 2H).

Synthesis of N-[5-([6-[3-(hydroxymethyl)-2-(1-oxo-3,4-dihydro-2,7-naphthyridin-2-yl)pyridin-4-yl]-4-methyl-3-oxopyrazin-2-yl]amino)-2-[(2S)-2-methyl-4-(oxetan-3-yl) piperazin-1-yl]phenyl]prop-2-enamide: Into a 40-mL vial purged and maintained with an inert atmosphere of nitrogen, was placed N-[5-[(6-bromo-4-methyl-3-oxopyrazin-2-yl) amino]-2-[(2S)-2-methyl-4-(oxetan-3-yl)piperazin-1-yl] phenyl]prop-2-enamide (135.00 mg, 0.268 mmol, 1.00 equiv), dioxane (5.00 mL), $H_2O$ (0.50 mL), 2-[1-hydroxy-3H-[1,2]oxaborolo[4,3-c]pyridin-4-yl]-3,4-dihydro-2,7-naphthyridin-1-one (151.00 mg, 0.537 mmol, 2.00 equiv), $K_2CO_3$ (186.00 mg, 1.346 mmol, 5.02 equiv), Xphos Pd G3 (45.00 mg, 0.053 mmol, 0.20 equiv). The resulting solution was stirred for 1 hr at 100 degrees C. in an oil bath. The reaction mixture was cooled to room temperature. The resulting mixture was concentrated under vacuum. The residue was applied onto a silica gel column with dichloromethane/methanol (20:1). The crude product was purified by Prep-HPLC with the following conditions: Column, XBridge Shield RP18 OBD Column, 5 um, 19*150 mm; mobile phase, Water (0.05% $NH_3 \cdot H_2O$) and ACN (20% Phase B up to 60% in 10 min); Detector, UV 254/220 nm. This resulted in 45 mg (24.76%) of N-[5-([6-[3-(hydroxymethyl)-2-(1-oxo-3,4-dihydro-2,7-naphthyridin-2-yl)pyridin-4-yl]-4-methyl-3-oxopyrazin-2-yl]amino)-2-[(2S)-2-methyl-4-(oxetan-3-yl)piperazin-1-yl]phenyl]prop-2-enamide as a white solid. LC-MS: (ES, m/z): M+1: 678; H-NMR (300 MHz, DMSO-$d_6$, ppm) δ 9.28 (s, 1H), 9.20 (s, 1H), 9.09 (s, 1H), 9.02 (s, 1H), 8.70 (d, J=5.0 Hz, 1H), 8.51 (d, J=5.1 Hz, 1H), 7.94 (dd, J=5.1, 2.3 Hz, 1H), 7.68 (d, J=3.0 Hz, 1H), 7.62 (dd, J=8.7, 2.6 Hz, 1H), 7.48 (d, J=5.0 Hz, 1H), 7.27 (d, J=8.7 Hz, 1H), 6.62 (dd, J=16.9, 10.2 Hz, 1H), 6.28 (dd, J=17.0, 1.8 Hz, 1H), 5.79 (d, J=10.3 Hz, 1H), 5.04 (s, 1H), 4.53 (dq, J=28.2, 6.4 Hz, 6H), 4.14 (dt, J=11.4, 5.8 Hz, 1H), 3.95-3.79 (m, 1H), 3.58 (s, 3H), 3.49 (d, J=7.2 Hz, 1H), 3.30 (s, 1H), 3.18-3.06 (m, 2H), 2.71 (d, J=26.9 Hz, 4H), 2.25 (d, J=14.4 Hz, 1H), 1.92 (t, J=10.0 Hz, 1H), 0.73 (d, J=6.1 Hz, 3H).

Example 33: Preparation of N-[5-([6-[3-(hydroxymethyl)-2-(8-oxo-5,6-dihydro-1,7-naphthyridin-7-yl) pyridin-4-yl]-4-methyl-3-oxopyrazin-2-yl]amino)-2-[(2S)-2-methyl-4-(oxetan-3-yl)piperazin-1-yl] phenyl]prop-2-enamide Synthesis of 2, 4-dibromopyridine-3-carbaldehyde: Into a 1000-mL 3-necked round-bottom flask, was placed 2, 4-dibromopyridine (40.00 g, 168.852 mmol, 1.00 equiv), THF (400.00 mL). This was followed by the addition of LDA (2M in hexane, 126.60 mL, 1.50 equiv) dropwise with stirring at −78 degrees C. The resulting solution was stirred for 1 h at −78° C. Then add DMF (16.04 ml, 219.507 mmol, 1.30 equiv) dropwise with stirring at −78° C. The resulting solution was stirred for 0.5 h at −78° C. The reaction was then quenched by the addition of 500 mL of $NH_4Cl$. The resulting solution was extracted with 3×500 mL of ethyl acetate concentrated. The residue was applied onto a silica gel column and eluted with ethyl acetate/petroleum ether (0:1-1:1). This resulted in 24.4 g (54.55%) of 2, 4-dibromopyridine-3-carbaldehyde as a white solid. LC-MS: (ES, m/z): M+1: 264

Synthesis of (2, 4-dibromopyridin-3-yl) methanol: Into a 100-mL round-bottom flask, was placed 2, 4-dibromopyridine-3-carbaldehyde (2.00 g, 7.550 mmol, 1.00 equiv), EtOH (30.00 mL). This was followed by the addition of $NaBH_4$ (285.64 mg, 7.550 mmol, 1 equiv), in portions at 0° C. The resulting solution was stirred for 3 h at RT. The reaction was then quenched by the addition of 30 mL of water. The resulting solution was extracted with 3×30 mL of ethyl acetate and concentrated. The residue was applied onto a silica gel column and eluted with ethyl acetate/petroleum ether (1:1). The collected fractions were combined and concentrated. This resulted in 1.4 g (69.47%) of (2, 4-dibromopyridin-3-yl) methanol as a light yellow solid. LC-MS: (ES, m/z): M+1: 266

Synthesis of 2,4-dibromo-3-[(oxan-2-yloxy) methyl]pyridine: Into a 100-mL round-bottom flask, was placed (2, 4-dibromopyridin-3-yl) methanol (1.40 g, 5.245 mmol, 1.00 equiv), DCM (30.00 mL, 0.353 mmol, 0.07 equiv), PPTS (131.81 mg, 0.525 mmol, 0.10 equiv), DHP (661.79 mg, 7.868 mmol, 1.50 equiv). The resulting solution was stirred overnight at 45° C. in an oil bath. The reaction was then quenched by the addition of 30 mL of water. The resulting solution was extracted with 3×30 mL of dichloromethane and concentrated. The residue was applied onto a silica gel column and eluted with ethyl acetate/petroleum ether (1:1). The collected fractions were combined and concentrated. This resulted in 1.5 g of 2,4-dibromo-3-[(oxan-2-yloxy) methyl]pyridine as colorless oil. LC-MS: (ES, m/z): M+1: 350

Synthesis of 7-[4-bromo-3-[(oxan-2-yloxy)methyl]pyridin-2-yl]-5,6-dihydro-1,7-naphthyridin-8-one: Into a 40-mL vial purged and maintained with an inert atmosphere of nitrogen, was added 6,7-dihydro-5H-1,7-naphthyridin-8-one (250.00 mg, 1.68 mmol, 1.00 equiv), Dioxane (10.00 mL), 2,4-dibromo-3-[(oxan-2-yloxy)methyl]pyridine (948.0 mg, 2.70 mmol, 1.6 equiv), $Cs_2CO_3$(1100 mg, 3.37 mmol, 2 equiv), copper(I) iodide (3210.5 mg, 1.68 mmol, 1 equiv), methyl[2-(methylamino)ethyl]amine (148.74 mg, 1.68 mmol, 1 equiv). The resulting solution was stirred for 4 h at 90° C. The reaction mixture was cooled to RT. The resulting solution was diluted with 20 mL of $H_2O$. The resulting solution was extracted with 4×20 mL of dichloromethane The resulting mixture was washed with 20 mL of brine. The mixture was dried over anhydrous sodium sulfate and concentrated. The residue was applied onto a silica gel column with dichloromethane/methanol (100:0-90:10). This resulted in 600 mg (42.51%) of 7-[4-bromo-3-[(oxan-2-yloxy)methyl]pyridin-2-yl]-5,6-dihydro-1,7-naphthyridin-8-one as light yellow oil. LC-MS: (ES, m/z): 418 $[M+H]^+$ Synthesis of 5-bromo-3-[(4-fluoro-3-nitrophenyl)amino]-1-methylpyrazin-2-one: Into a 250-mL round-bottom flask, was placed 4-fluoro-3-nitroaniline (10.00 g, 64.055 mmol, 1.00 equiv), 3,5-dibromo-1-methylpyrazin-2-one (17.16 g, 64.052 mmol, 1.00 equiv), NMP (30 mL). The resulting solution was stirred for 1 h at 140 degrees C. in an oil bath. The resulting solution was diluted with 300 mL of EA. The solids were collected by filtration. This resulted in 13 g (59.15%) of 5-bromo-3-[(4-fluoro-3-nitrophenyl)amino]-1-methylpyrazin-2-one as a brown solid. LC-MS (ES, m/z): M+1: 343/345

Synthesis of tert-butyl (3S)-4-[4-[(6-bromo-4-methyl-3-oxopyrazin-2-yl)amino]-2-nitrophenyl]-3-methylpiperazine-1-carboxylate: Into a 50-mL round-bottom flask, was placed 5-bromo-3-[(4-fluoro-3-nitrophenyl)amino]-1-methylpyrazin-2-one (10 g, 29.2 mmol, 1.00 equiv), NMP (40.00 mL), tert-butyl (3S)-3-methylpiperazine-1-carboxylate (5.8 g, 5.842 mmol, 1.00 equiv), DIEA (2.26 g, 17.487 mmol, 3.00 equiv). The resulting solution was stirred for 40 h at 120° C. in an oil bath. The resulting solution was diluted with 100 mL of $H_2O$. The resulting solution was extracted with 3×50 mL of dichloromethane/methanol (10:1). The resulting mixture was washed with 3×20 ml of brine. The resulting mixture was concentrated. The residue was applied onto a silica gel column with dichloromethane/methanol (10:1). This resulted in 10 g (57.00%) of tert-butyl (3S)-4-[4-[(6-bromo-4-methyl-3-oxopyrazin-2-yl)amino]-2-nitrophenyl]-3-methylpiperazine-1-carboxylate as a brown solid. LC-MS: (ES, m/z): M+1: 523

Synthesis of 5-bromo-1-methyl-3-([4-[(2S)-2-methylpiperazin-1-yl]-3-nitrophenyl]amino)pyrazin-2-one: Into a 100-mL round-bottom flask, was placed tert-butyl (3S)-4-[4-[(6-bromo-4-methyl-3-oxopyrazin-2-yl)amino]-2-nitrophenyl]-3-methylpiperazine-1-carboxylate (10.00 g, 1 equiv, 60%), HCl in 1,4-dioxane (2N, 100 mL). The resulting solution was stirred for 14 h at room temperature. The resulting mixture was concentrated. The resulting solution was diluted with 30 mL of $H_2O$. The pH value of the solution was adjusted to 8 with $NH_3 \cdot H_2O$. The resulting solution was extracted with 3×15 mL of dichloromethane and concentrated. The residue was applied onto a silica gel column with dichloromethane/methanol (10:1). This resulted in 5 g of 5-bromo-1-methyl-3-([4-[(2S)-2-methylpiperazin-1-yl]-3-nitrophenyl]amino)pyrazin-2-one as a red solid. LC-MS: (ES, m/z): M+1: 423

Synthesis of 5-bromo-1-methyl-3-([4-[(2S)-2-methyl-4-(oxetan-3-yl)piperazin-1-yl]-3-nitrophenyl]amino)pyrazin-2-one: Into a 250-mL round-bottom flask, was placed 5-bromo-1-methyl-3-([4-[(2S)-2-methylpiperazin-1-yl]-3-nitrophenyl]amino)pyrazin-2-one (4.00 g, 9.450 mmol, 1.00 equiv), 3-oxetanone (0.89 g, 12.350 mmol, 1.31 equiv), THF (40.00 mL), AcOH (0.80 mL). This was followed by the addition of $NaBH(AcO)_3$ (3.00 g, 14.155 mmol, 1.50 equiv) dropwise with stirring at room temperature. The resulting solution was stirred for 4 hr at room temperature. The reaction was then quenched by the addition of 10 mL of water. The resulting mixture was concentrated. The resulting solution was diluted with 40 mL of DCM. The resulting mixture was washed with 1×10 mL of $Na_2CO_3$ (aq). The mixture was dried over anhydrous sodium sulfate and concentrated. The residue was applied onto a silica gel column with and eluted with dichloromethane/methanol (10:1). This resulted in 3 g (66.23%) of 5-bromo-1-methyl-3-([4-[(2S)-2-methyl-4-(oxetan-3-yl)piperazin-1-yl]-3-nitrophenyl]amino)pyrazin-2-one as brown solid. LC-MS: (ES, m/z): M+1: 479/481

Synthesis of 3-([3-amino-4-[(2S)-2-methyl-4-(oxetan-3-yl)piperazin-1-yl]phenyl]amino)-5-bromo-1-methylpyrazin-2-one: Into a 250-mL round-bottom flask, was placed 5-bromo-1-methyl-3-([4-[(2S)-2-methyl-4-(oxetan-3-yl)piperazin-1-yl]-3-nitrophenyl]amino)pyrazin-2-one (3.00 g, 6.259 mmol, 1.00 equiv), Fe (1.40 g, 25.035 mmol, 4.00 equiv), $NH_4Cl$ (2.01 g, 37.576 mmol, 6.00 equiv), EtOH (30.00 mL), $H_2O$ (30.00 mL). The resulting solution was stirred for 2 hr at 80 degrees C. in an oil bath. The solids were filtered out. The resulting mixture was concentrated. The resulting solution was diluted with 200 mL of DCM. The pH value of the solution was adjusted to 8 with $NH_3 \cdot H_2O$. The resulting mixture was washed with 1×20 mL of $H_2O$. The resulting mixture was washed with 1×20 mL of brine. The mixture was dried over anhydrous sodium sulfate and concentrated. The residue was applied onto a silica gel column and eluted with dichloromethane/methanol (10:1). This resulted in 2.5 g (88.89%) of 3-([3-amino-4-[(2S)-2-methyl-4-(oxetan-3-yl)piperazin-1-yl]phenyl]amino)-5-bromo-1-methylpyrazin-2-one as brown solid. LC-MS: (ES, m/z): M+1: 449/451

Synthesis of N-[5-[(6-bromo-4-methyl-3-oxopyrazin-2-yl)amino]-2-[(2S)-2-methyl-4-(oxetan-3-yl)piperazin-1-yl]phenyl]prop-2-enamide: Into a 100-mL round-bottom flask, was placed 3-([3-amino-4-[(2S)-2-methyl-4-(oxetan-3-yl)piperazin-1-yl]phenyl]amino)-5-bromo-1-methylpyrazin-2-one (2.50 g, 5.564 mmol, 1.00 equiv), DCM (30.00 mL, 471.901 mmol, 84.82 equiv), DIEA (1.44 g, 11.142 mmol, 2.00 equiv). This was followed by the addition of acryloyl chloride (0.65 g, 7.182 mmol, 1.29 equiv), in portions at 0 degrees C. The resulting solution was stirred for 1 hr at 0 degrees C. in a water/ice bath. The reaction was then quenched by the addition of 1 mL of MeOH. The resulting mixture was concentrated. The residue was applied onto a silica gel column and eluted with dichloromethane/methanol (10:1). This resulted in 2.8 g (80.98%) of N-[5-[(6-bromo-4-methyl-3-oxopyrazin-2-yl)amino]-2-[(2S)-2-methyl-4-(oxetan-3-yl)piperazin-1-yl]phenyl]prop-2-enamide as a yellow solid. LC-MS: (ES, m/z): M+1: 503/505

Synthesis of N-(5-[[4-methyl-3-oxo-6-(trimethylstannyl)pyrazin-2-yl]amino]-2-[(2S)-2-methyl-4-(oxetan-3-yl)piperazin-1-yl]phenyl)prop-2-enamide: Into a 100-mL round-bottom flask purged and maintained with an inert atmosphere of nitrogen, was placed N-[5-[(6-bromo-4-methyl-3-oxopyrazin-2-yl)amino]-2-[(2S)-2-methyl-4-(oxetan-3-yl)piperazin-1-yl]phenyl]prop-2-enamide (1.50 g, 2.980 mmol, 1.00 equiv), hexamethyldistannane (1.46 g, 4.456 mmol, 1.50 equiv), dioxane (30 mL), $Pd(DtBPF)Cl_2$ (0.19 g, 0.000 mmol, 0.1 equiv). The resulting solution was stirred for 3 h at 100° C. in an oil bath. The resulting mixture was concentrated. The crude product was purified by Flash-Prep-HPLC with the following conditions (CombiFlash-1): Column, C18 silica gel; mobile phase, A: 0.1% $NH_3$—$H_2O$ in water; B: ACN; Gradient: 30%-70% B in 9 min; Detector, 220 nm. This resulted in 220 mg (12.57%) of N-(5-[[4-methyl-3-oxo-6-(trimethylstannyl)pyrazin-2-yl]amino]-2-[(2S)-2-methyl-4-(oxetan-3-yl)piperazin-1-yl]phenyl)prop-2-enamide as solid. LC-MS: (ES, m/z): M+1: 589

Synthesis of N-[2-[(2S)-2-methyl-4-(oxetan-3-yl)piperazin-1-yl]-5-[(4-methyl-6-[3-[(oxan-2-yloxy)methyl]-2-(8-oxo-5,6-dihydro-1,7-naphthyridin-7-yl)pyridin-4-yl]-3-oxopyrazin-2-yl)amino]phenyl]prop-2-enamide: Into a 40-mL vial purged and maintained with an inert atmosphere of nitrogen, was added 7-[4-bromo-3-[(oxan-2-yloxy)methyl]pyridin-2-yl]-5,6-dihydro-1,7-naphthyridin-8-one (157.59 mg, 0.377 mmol, 1.2 equiv), dioxane (5.00 mL), N-[2-[(2S)-2-methyl-4-(oxetan-3-yl)piperazin-1-yl]-5-[[4-methyl-6-(trimethylstannyl)-3H-pyrazin-2-yl]amino]phenyl]prop-2-enamide (180.00 mg, 0.314 mmol, 1.00 equiv), $K_2CO_3$ (87.41 mg, 0.628 mmol, 2 equiv), tetrakis(triphenylphosphine)palladium(O) (72.56 mg, 0.063 mmol, 0.2 equiv). The resulting solution was stirred for 1 h at 110° C. The reaction mixture was cooled to RT. The resulting solution was diluted with 20 mL of $H_2O$. The resulting solution was extracted with 4×20 mL of dichloromethane The resulting mixture was washed with 20 mL of brine. The mixture was dried over anhydrous sodium sulfate and concentrated. The residue was applied onto a silica gel column with dichloromethane/methanol (95:5). This resulted in 40 mg crude(16.72%) of N-[2-[(2S)-2-methyl-4-(oxetan-3-yl) piperazin-1-yl]-5-[(4-methyl-6-[3-[(oxan-2-yloxy) methyl]-2-(8-oxo-5,6-dihydro-1,7-naphthyridin-7-yl)pyridin-4-yl]-3-oxopyrazin-2-yl)amino]phenyl]prop-2-enamide as light yellow oil. LC-MS: (ES, m/z): 762 $[M+H]^+$ Synthesis of N-[5-([6-[3-(hydroxymethyl)-2-(8-oxo-5,6-dihydro-1,7-naphthyridin-7-yl)pyridin-4-yl]-4-methyl-3-oxopyrazin-2-yl]amino)-2-[(2S)-2-methyl-4-(oxetan-3-yl) piperazin-1-yl]phenyl]prop-2-enamide: Into a 40-mL vial, was added N-[2-[(2S)-2-methyl-4-(oxetan-3-yl)piperazin-1-yl]-5-[(4-methyl-6-[3-[(oxan-2-yloxy)methyl]-2-(8-oxo-5, 6-dihydro-1,7-naphthyridin-7-yl)pyridin-4-yl]-3-oxopyrazin-2-yl)amino]phenyl]prop-2-enamide (40.00 mg, 0.053 mmol, 1.00 equiv), DCM (2.50 mL), trifluoroacetaldehyde (0.50 mL). The resulting solution was stirred for 1 h at 0° C. The resulting solution was diluted with 10 mL of $H_2O$. The resulting solution was extracted with 3×10 mL of dichloromethane. The resulting mixture was washed with 10 mL of brine. The mixture was dried over anhydrous sodium sulfate and concentrated. The crude product (20 mg) was purified by Prep-HPLC with the following conditions (IntelFlash-1): Column, C18 silica gel; mobile phase, $CH_3CN$:$H_2O$=65% 0.5% $NH_3 \cdot H_2O$; Detector, UV 220 nm. 4.3 mg product was obtained. This resulted in 4.3 mg (12.08%) of N-[5-([6-[3-(hydroxymethyl)-2-(8-oxo-5,6-dihydro-1,7-naphthyridin-7-yl)pyridin-4-yl]-4-methyl-3-oxopyrazin-2-yl]amino)-2-[(2S)-2-methyl-4-(oxetan-3-yl)piperazin-1-yl]phenyl]prop-2-enamide as grey solid. LC-MS: (ES, m/z): 678 $[M+H]^+$. $^1$H NMR (300 MHz, Chloroform-d, ppm) δ 9.29 (m, 1H), 9.13 (s, 1H), 9.00 (s, 1H), 8.82 (s, 1H), 8.68 (s, 1H), 8.38 (m, 1H), 8.17 (m, 2H), 7.73 (m, 1H), 7.47 (s, 2H), 7.27-7.17 (m, 1H), 6.44 (m, 1H), 6.37-6.24 (m, 1H), 5.80 (m, 1H), 4.72 (m, 7H), 4.47 (s, 3H), 3.85 (s, 1H), 3.70 (m, 3H), 3.59 (s, 1H), 3.23 (m, 4H), 2.98 (s, 1H), 2.84 (s, 3H), 2.47 (m, 1H), 2.18 (s, 1H), 1.88 (s, 2H), 0.82 (d, J=6.1 Hz, 3H).

Example 34: Preparation of N-(5-[[6-(2-[4,4-dimethyl-9-oxo-7-thia-10-azatricyclo[6.4.0.0^[2,6]]dodeca-1(8),2(6)-dien-10-yl]-3-(hydroxymethyl)pyridin-4-yl)-4-methyl-3-oxopyrazin-2-yl]amino]-2-[(2S)-2-methyl-4-(oxetan-3-yl)piperazin-1-yl] phenyl)prop-2-enamide Synthesis of 5-bromo-3-[(4-fluoro-3-nitrophenyl)amino]-1-methylpyrazin-2-one: Into a 250-mL round-bottom flask, was placed 4-fluoro-3-nitroaniline (10.00 g, 64.055 mmol, 1.00 equiv), 3,5-dibromo-1-methylpyrazin-2-one (17.16 g, 64.052 mmol, 1.00 equiv), NMP (30 mL). The resulting solution was stirred for 1 h at 140 degrees C. in an oil bath. The resulting solution was diluted with 300 mL of EA. The solids were collected by filtration. This resulted in 13 g (59.15%) of 5-bromo-3-[(4-fluoro-3-nitrophenyl)amino]-1-methylpyrazin-2-one as a brown solid. LCMS (ES, m/z): M+1: 343/345

Synthesis of tert-butyl (3S)-4-[4-[(6-bromo-4-methyl-3-oxopyrazin-2-yl)amino]-2-nitrophenyl]-3-methylpiperazine-1-carboxylate: Into a 50-mL round-bottom flask, was placed 5-bromo-3-[(4-fluoro-3-nitrophenyl)amino]-1-methylpyrazin-2-one (10 g, 29.2 mmol, 1.00 equiv), NMP (40.00 mL), tert-butyl (3S)-3-methylpiperazine-1-carboxylate (5.8 g, 5.842 mmol, 1.00 equiv), DIEA (2.26 g, 17.487 mmol, 3.00 equiv). The resulting solution was stirred for 40 h at 120° C. in an oil bath. The resulting solution was diluted with 100 mL of $H_2O$. The resulting solution was extracted with 3×50 mL of dichloromethane/methanol (10:1). The resulting mixture was washed with 3×20 ml of brine. The resulting mixture was concentrated. The residue was applied onto a silica gel column with dichloromethane/methanol (10:1). This resulted in 10 g (57.00%) of tert-butyl (3S)-4-[4-[(6-bromo-4-methyl-3-oxopyrazin-2-yl)amino]-2-nitrophenyl]-3-methylpiperazine-1-carboxylate as a brown solid. LC-MS: (ES, m/z): M+1: 523

Synthesis of 5-bromo-1-methyl-3-([4-[(2S)-2-methylpiperazin-1-yl]-3-nitrophenyl]amino)pyrazin-2-one: Into a 100-mL round-bottom flask, was placed tert-butyl (3S)-4-[4-[(6-bromo-4-methyl-3-oxopyrazin-2-yl)amino]-2-nitrophenyl]-3-methylpiperazine-1-carboxylate (10.00 g, 1 equiv, 60%), HCl in 1,4-dioxane (2N, 100 mL). The resulting solution was stirred for 14 h at room temperature. The resulting mixture was concentrated. The resulting solution was diluted with 30 mL of $H_2O$. The pH value of the solution was adjusted to 8 with $NH_3 \cdot H_2O$. The resulting solution was extracted with 3×15 mL of dichloromethane and concentrated. The residue was applied onto a silica gel column with dichloromethane/methanol (10:1). This resulted in 5 g of 5-bromo-1-methyl-3-([4-[(2S)-2-methylpiperazin-1-yl]-3-nitrophenyl]amino)pyrazin-2-one as a red solid. LC-MS: (ES, m/z): M+1: 423

Synthesis of 5-bromo-1-methyl-3-([4-[(2S)-2-methyl-4-(oxetan-3-yl)piperazin-1-yl]-3-nitrophenyl]amino)pyrazin-2-one: Into a 250-mL round-bottom flask, was placed 5-bromo-1-methyl-3-([4-[(2S)-2-methylpiperazin-1-yl]-3-nitrophenyl]amino)pyrazin-2-one (4.00 g, 9.450 mmol, 1.00 equiv), 3-oxetanone (0.89 g, 12.350 mmol, 1.31 equiv), THF (40.00 mL), AcOH (0.80 mL). This was followed by the addition of $NaBH(AcO)_3$ (3.00 g, 14.155 mmol, 1.50 equiv) dropwise with stirring at room temperature. The resulting solution was stirred for 4 hr at room temperature. The reaction was then quenched by the addition of 10 mL of water. The resulting mixture was concentrated. The resulting solution was diluted with 40 mL of DCM. The resulting mixture was washed with 1×10 mL of $Na_2CO_3$ (aq). The mixture was dried over anhydrous sodium sulfate and concentrated. The residue was applied onto a silica gel column with and eluted with dichloromethane/methanol (10:1). This resulted in 3 g (66.23%) of 5-bromo-1-methyl-3-([4-[(2S)-2-methyl-4-(oxetan-3-yl)piperazin-1-yl]-3-nitrophenyl] amino)pyrazin-2-one as a brown solid. LC-MS: (ES, m/z): M+1: 479/481

Synthesis of 3-([3-amino-4-[(2S)-2-methyl-4-(oxetan-3-yl)piperazin-1-yl]phenyl]amino)-5-bromo-1-methylpyrazin-2-one: Into a 250-mL round-bottom flask, was placed 5-bromo-1-methyl-3-([4-[(2S)-2-methyl-4-(oxetan-3-yl)piperazin-1-yl]-3-nitrophenyl]amino)pyrazin-2-one (3.00 g, 6.259 mmol, 1.00 equiv), Fe (1.40 g, 25.035 mmol, 4.00 equiv), $NH_4Cl$ (2.01 g, 37.576 mmol, 6.00 equiv), EtOH (30.00 mL), $H_2O$ (30.00 mL). The resulting solution was stirred for 2 hr at 80 degrees C. in an oil bath. The solids were filtered out. The resulting mixture was concentrated. The resulting solution was diluted with 200 mL of DCM. The pH value of the solution was adjusted to 8 with $NH_3 \cdot H_2O$. The resulting mixture was washed with 1×20 mL of $H_2O$. The resulting mixture was washed with 1×20 mL of brine. The mixture was dried over anhydrous sodium sulfate and concentrated. The residue was applied onto a silica gel column and eluted with dichloromethane/methanol (10:1). This resulted in 2.5 g (88.89%) of 3-([3-amino-4-[(2S)-2-methyl-4-(oxetan-3-yl)piperazin-1-yl]phenyl]amino)-5-bromo-1-methylpyrazin-2-one as a brown solid. LC-MS: (ES, m/z): M+1: 449/451

Synthesis of N-[5-[(6-bromo-4-methyl-3-oxopyrazin-2-yl)amino]-2-[(2S)-2-methyl-4-(oxetan-3-yl)piperazin-1-yl]phenyl]prop-2-enamide: Into a 100-mL round-bottom flask, was placed 3-([3-amino-4-[(2S)-2-methyl-4-(oxetan-3-yl)piperazin-1-yl]phenyl]amino)-5-bromo-1-methylpyrazin-2-one (2.50 g, 5.564 mmol, 1.00 equiv), DCM (30.00 mL, 471.901 mmol, 84.82 equiv), DIEA (1.44 g, 11.142 mmol, 2.00 equiv). This was followed by the addition of acryloyl chloride (0.65 g, 7.182 mmol, 1.29 equiv), in portions at 0 degrees C. The resulting solution was stirred for 1 hr at 0 degrees C. in a water/ice bath. The reaction was then quenched by the addition of 1 mL of MeOH. The resulting mixture was concentrated. The residue was applied onto a silica gel column and eluted with dichloromethane/methanol (10:1). This resulted in 2.8 g (80.98%) of N-[5-[(6-bromo-4-methyl-3-oxopyrazin-2-yl)amino]-2-[(2S)-2-methyl-4-(oxetan-3-yl)piperazin-1-yl]phenyl]prop-2-enamide as a yellow solid. LC-MS: (ES, m/z): M+1: 503/505

Synthesis of 2, 4-dibromopyridine-3-carbaldehyde: Into a 1000-mL 3-necked round-bottom flask, was placed 2, 4-dibromopyridine (40.00 g, 168.852 mmol, 1.00 equiv), THF (400.00 mL). This was followed by the addition of LDA (2M in hexane, 126.60 mL, 1.50 equiv) dropwise with stirring at −78 degrees C. The resulting solution was stirred for 1 h at −78 degrees C. Then add DMF (16.04 ml, 219.507 mmol, 1.30 equiv) dropwise with stirring at −78 degrees C. The resulting solution was stirred for 0.5 h at −78 degrees C. The reaction was then quenched by the addition of 500 mL of $NH_4Cl$. The resulting solution was extracted with 3×500 mL of ethyl acetate concentrated. The residue was applied onto a silica gel column and eluted with ethyl acetate/petroleum ether (0:1-1:1). This resulted in 24.4 g (54.55%) of 2, 4-dibromopyridine-3-carbaldehyde as a white solid. LC-MS: (ES, m/z): M+1: 264

Synthesis of (2, 4-dibromopyridin-3-yl) methanol: Into a 100-mL round-bottom flask, was placed 2, 4-dibromopyridine-3-carbaldehyde (2.00 g, 7.550 mmol, 1.00 equiv), EtOH (30.00 mL). This was followed by the addition of $NaBH_4$ (285.64 mg, 7.550 mmol, 1 equiv), in portions at 0 degrees C. The resulting solution was stirred for 3 h at room temperature. The reaction was then quenched by the addition of 30 mL of water. The resulting solution was extracted with 3×30 mL of ethyl acetate and concentrated. The residue was applied onto a silica gel column and eluted with ethyl acetate/petroleum ether (1:1). The collected fractions were combined and concentrated. This resulted in 1.4 g (69.47%) of (2, 4-dibromopyridin-3-yl) methanol as a light yellow solid. LC-MS: (ES, m/z): M+1: 266

Synthesis of 2,4-dibromo-3-[(oxan-2-yloxy) methyl]pyridine: Into a 100-mL round-bottom flask, was placed (2, 4-dibromopyridin-3-yl) methanol (1.40 g, 5.245 mmol, 1.00 equiv), DCM (30.00 mL, 0.353 mmol, 0.07 equiv), PPTS (131.81 mg, 0.525 mmol, 0.10 equiv), DHP (661.79 mg, 7.868 mmol, 1.50 equiv). The resulting solution was stirred overnight at 45 degrees C. in an oil bath. The reaction was then quenched by the addition of 30 mL of water. The resulting solution was extracted with 3×30 mL of dichloromethane and concentrated. The residue was applied onto a silica gel column and eluted with ethyl acetate/petroleum ether (1:1). The collected fractions were combined and concentrated. This resulted in 1.5 g of 2,4-dibromo-3-[(oxan-2-yloxy) methyl]pyridine as colorless oil. LC-MS: (ES, m/z): M+1: 350

Synthesis of [(3,3-dimethylcyclopent-1-en-1-yl)oxy]trimethylsilane: Into a 10-L 4-necked round-bottom flask purged and maintained with an inert atmosphere of nitrogen, was placed CuCl (20.60 g, 208.083 mmol, 0.05 equiv), LiCl (17.64 g, 416.108 mmol, 0.10 equiv), THF (2.50 L). This was followed by the addition of 2-cyclopenten-1-one, 3-methyl-(400.00 g, 4161.075 mmol, 1.00 equiv) at −5 to 5 degrees C. To this was added TMSCl (474.67 g, 4369.129 mmol, 1.05 equiv) dropwise with stirring at −5 to 5 degrees C. To the mixture was added MeMgCl (1670.00 mL, 14495.069 mmol, 3.48 equiv) dropwise with stirring at −5 to 10 degrees C. The resulting solution was stirred for 2 h at −5 to 10 degrees C. in an ice/salt bath. The reaction was then quenched by the addition of 34 g of MeOH. The resulting solution was diluted with 5 L of $NH_4Cl$. The solids were filtered out. The resulting solution was extracted with 3×5 L of petroleum ether dried over anhydrous sodium sulfate and concentrated. This resulted in 780 g (crude) of [(3,3-dimethylcyclopent-1-en-1-yl)oxy]trimethylsilane as yellow oil. GC-MS: (ES, m/z): M 184

Synthesis of 3,3-dimethylcyclopentanone: Into a 20-L 4-necked round-bottom flask, was placed [(3,3-dimethylcyclopent-1-en-1-yl)oxy]trimethylsilane (780.00 g, 4230.990 mmol, 1.00 equiv), DCM (7.8 L), $H_2O$ (30.49 g, 1692.396 mmol, 0.4 equiv). This was followed by the addition of $POCl_3$ (214.09 g, 1396.251 mmol, 0.33 equiv) dropwise with stirring at 25 to 30 degrees C. The resulting solution was stirred for 0.5 hr at 25 degrees C. This solvent straight used for next step. GC-MS (ES, m/z): M 112

Synthesis of 3,3-dimethylcyclopentanone: Into a 20-L 4-necked round-bottom flask, was placed 3,3-dimethylcyclopentan-1-one (crude) in DCM (7.80 L). This was followed by the addition of DMF (619 g, 2.0 equiv)$_{dropwise}$ with stirring at 25 degrees C. To this was added $POCl_3$ (1362 g, 2.1 equiv) dropwise with stirring at 40 degrees C. The resulting solution was stirred for overnight at 40 degrees C. in an oil bath. The reaction was then quenched by the addition of 2000 g of $K_3PO_4$. The resulting solution was extracted with 3×10 L of dichloromethane dried over anhydrous sodium sulfate and concentrated. This resulted in 530 g of 2-chloro-4,4-dimethylcyclopent-1-ene-1-carbaldehyde as a brown solid. GC-MS: (ES, m/z): M: 158

Synthesis of ethyl 5,5-dimethyl-4H,6H-cyclopenta[b]thiophene-2-carboxylate: Into a 500-mL round-bottom flask, was placed 2-chloro-4,4-dimethylcyclopent-1-ene-1-carbaldehyde (20.00 g, 126.080 mmol, 1.00 equiv), DCM (200.00 mL), TEA (38.40 g, 379.484 mmol, 3.01 equiv), ethyl thioglycolate (15.00 g, 124.823 mmol, 0.99 equiv). The reaction mixture was stirred at reflux for 6 h. After this time the reaction was cooled to room temperature and concentrated to a thick orange residue. EtOH (200.00 mL) and TEA (38.40 g, 379.484 $_{mmol}$, 3.01 equiv) were added and the resulting solution was stirred overnight at 80 degrees C. in an oil bath. The reaction mixture was cooled to room temperature. The resulting solution was diluted with 500 mL of ether. The resulting mixture was washed with 1×200 ml of 1M HCl and 1×200 mL of brine. The mixture was dried over anhydrous sodium sulfate and concentrated under vacuum. The residue was applied onto a silica gel column with ethyl acetate/petroleum ether (1:10). This resulted in 8 g (28.29%) of ethyl 5,5-dimethyl-4H,6H-cyclopenta[b]thiophene-2-carboxylate as red oil. H-NMR (300 MHz, Chloroform-d, ppm) δ 7.68-7.45 (m, 1H), 4.34 (q, J=7.1 Hz, 2H), 2.75 (q, J=1.0 Hz, 2H), 2.59 (t, J=1.0 Hz, 2H), 1.37 (t, J=7.1 Hz, 3H), 1.25 (s, 6H).

Synthesis of 5,5-dimethyl-4H,6H-cyclopenta[b]thiophene-2-carboxylic acid: Into a 250-mL round-bottom flask, was placed ethyl 5,5-dimethyl-4H,6H-cyclopenta[b]thiophene-2-carboxylate (7.80 g, 34.772 mmol, 1.00 equiv), EtOH (30.00 mL), THF (30.00 mL), $H_2O$ (30.00 mL), $LiOH\cdot H_2O$ (2.92 g, 69.583 mmol, 2.00 equiv). The resulting solution was stirred for 4 hr at 60 degrees C. in an oil bath. The reaction mixture was cooled to room temperature. The resulting mixture was concentrated under vacuum. The pH value of the solution was adjusted to 3-4 with HCl (2 mol/L). The solids were collected by filtration. This resulted in 5.6 g (82.06%) of 5,5-dimethyl-4H,6H-cyclopenta[b]thiophene-2-carboxylic acid as a light yellow solid. H-NMR (300 MHz, Chloroform-d, ppm) δ 7.61 (s, 1H), 2.78 (d, J=1.2 Hz, 2H), 2.61 (s, 2H), 1.26 (s, 6H).

Synthesis of N-methoxy-N,5,5-trimethyl-4H,6H-cyclopenta[b]thiophene-2-carboxamide: Into a 250-mL round-bottom flask, was placed 5,5-dimethyl-4H,6H-cyclopenta[b]thiophene-2-carboxylic acid (5.50 g, 28.024 mmol, 1.00 equiv), DMF (60.00 mL), DIEA (7.24 g, 56.018 mmol, 2.00 equiv), HATU (11.73 g, 30.850 mmol, 1.10 equiv), N,O-dimethylhydroxylamine hydrochloride (5.44 g, 55.772 mmol, 1.99 equiv). The resulting solution was stirred for 1 hr at room temperature. The resulting solution was diluted with 500 mL of water. The resulting solution was extracted with 3×300 mL of ethyl acetate and the organic layers combined. The resulting mixture was washed with 2×500 ml of brine. The mixture was dried over anhydrous sodium sulfate and concentrated under vacuum. The residue was applied onto a silica gel column with ethyl acetate/petroleum ether (1:3). This resulted in 5.95 g (88.71%) of N-methoxy-N,5,5-trimethyl-4H,6H-cyclopenta[b]thiophene-2-carboxamide as a yellow solid. H-NMR (300 MHz, Chloroform-d, ppm) δ 7.68 (t, J=0.6 Hz, 1H), 3.79 (s, 3H), 3.37 (s, 3H), 2.76 (q, J=1.0 Hz, 2H), 2.60 (q, J=1.0 Hz, 2H), 1.26 (s, 6H).

Synthesis of 1-[5,5-dimethyl-4H,6H-cyclopenta[b]thiophen-2-yl]prop-2-en-1-one: Into a 500-mL 3-necked round-bottom flask purged and maintained with an inert atmosphere of nitrogen, was placed N-methoxy-N,5,5-trimethyl-4H,6H-cyclopenta[b]thiophene-2-carboxamide (5.10 g, 21.309 mmol, 1.00 equiv), THF (50.00 mL). This was followed by the addition of bromo(ethenyl)magnesium (105.00 mL, 105.000 mmol, 4.93 equiv) dropwise with stirring at −78 degrees C. The resulting solution was stirred for 1 hr at room temperature. The resulting solution was diluted with 100 mL of 2M HCl. The resulting solution was extracted with 3×200 mL of ethyl acetate and the organic layers combined. The resulting mixture was washed with 1×500 ml of $H_2O$ and 1×500 mL of brine. The mixture was dried over anhydrous sodium sulfate and concentrated under vacuum. The residue was applied onto a silica gel column with ethyl acetate/petroleum ether (1:10). This resulted in 3.13 g (71.20%) of 1-[5,5-dimethyl-4H,6H-cyclopenta[b]thiophen-2-yl]prop-2-en-1-one as a yellow solid. H-NMR (300 MHz, Chloroform-d, ppm) δ 7.57-7.47 (m, 1H), 7.04 (dd, J=17.0, 10.4 Hz, 1H), 6.48 (dd, J=17.0, 1.8 Hz, 1H), 5.84 (dd, J=10.4, 1.8 Hz, 1H), 2.78 (q, J=1.0 Hz, 2H), 2.62 (q, J=0.9 Hz, 2H), 1.26 (s, 6H).

Synthesis of 3-chloro-1-[5,5-dimethyl-4H,6H-cyclopenta[b]thiophen-2-yl]propan-1-one: Into a 250-mL round-bottom flask, was placed 1-[5,5-dimethyl-4H,6H-cyclopenta[b]thiophen-2-yl]prop-2-en-1-one (3.13 g, 1 equiv), ether (50.00 mL). This was followed by the addition of HCl(gas) in ether (2N, 50.00 mL) dropwise with stirring at 0 degrees C. The resulting solution was stirred for 30 min at 0 degrees C. The resulting mixture was concentrated under vacuum. The residue was applied onto a silica gel column with ethyl acetate/petroleum ether (1:10). This resulted in 3.5 g (95.03%) of 3-chloro-1-[5,5-dimethyl-4H,6H-cyclopenta[b]thiophen-2-yl]propan-1-one as yellow oil. H-NMR (300 MHz, Chloroform-d, ppm) δ 7.50-7.42 (m, 1H), 3.92 (t, J=6.9 Hz, 2H), 3.32 (t, J=6.9 Hz, 2H), 2.77 (q, J=0.9 Hz, 2H), 2.61 (q, J=0.9 Hz, 2H), 1.26 (s, 6H).

Synthesis of 10,10-dimethyl-7-thiatricyclo[6.3.0.0^[2,6]]undeca-1(8),2(6)-dien-5-one: Into a 100-mL round-bottom flask, was placed 3-chloro-1-[5,5-dimethyl-4H,6H-cyclopenta[b]thiophen-2-yl]propan-1-one (3.50 g, 14.418 mmol, 1.00 equiv), $H_2SO_4$ (30.00 mL). The resulting solution was stirred overnight at 90 degrees C. in an oil bath. The reaction mixture was cooled to room temperature. The resulting solution was diluted with 300 mL of ice water. The resulting solution was extracted with 3×100 mL of ethyl acetate and the organic layers combined. The resulting mixture was washed with 3×500 ml of $H_2O$. The mixture was dried over anhydrous sodium sulfate and concentrated under vacuum. The residue was applied onto a silica gel column with ethyl acetate/petroleum ether (1:5). This resulted in 790 mg (26.56%) of 10,10-dimethyl-7-thiatricyclo[6.3.0.0^[2,6]]undeca-1(8),2(6)-dien-5-one as a yellow solid. H-NMR (300 MHz, Chloroform-d, ppm) δ 2.97-2.86 (m, 4H), 2.81 (d, J=1.3 Hz, 2H), 2.55 (d, J=1.3 Hz, 2H), 1.25 (s, 6H).

Synthesis of N-[(5E)-10,10-dimethyl-7-thiatricyclo[6.3.0.0^[2,6]]undeca-1(8),2(6)-dien-5-ylidene]hydroxylamine: Into a 100-mL round-bottom flask, was placed 10,10-dimethyl-7-thiatricyclo[6.3.0.0^[2,6]]undeca-1(8),2(6)-dien-5-one (770.00 mg, 3.732 mmol, 1.00 equiv), MeOH (20.00 mL), hydroxylamine hydrochloride (1.69 g, 24.320 mmol, 6.52 equiv), sodium acetate (1.99 g, 24.258 mmol, 6.50 equiv). The resulting solution was stirred overnight at room temperature. The resulting solution was diluted with 300 mL of water. The resulting solution was extracted with 3×100 mL of dichloromethane and the organic layers combined. The resulting mixture was washed with 1×500 ml of brine. The mixture was dried over anhydrous sodium sulfate and concentrated under vacuum. This resulted in 910 mg (crude) of N-[(5E)-10,10-dimethyl-7-thiatricyclo[6.3.0.0^[2,6]]undeca-1(8),2(6)-dien-5-ylidene]hydroxylamine as a white solid. H-NMR (300 MHz, Chloroform-d, ppm) δ 3.27-3.10 (m, 2H), 2.90-2.74 (m, 4H), 2.50 (dt, J=5.0, 1.4 Hz, 2H), 1.27 (s, 6H).

Synthesis of 4,4-dimethyl-7-thia-10-azatricyclo[6.4.0.0^[2,6]]dodeca-1(8),2(6)-dien-9-one: Into a 100-mL round-bottom flask, was placed N-[(5E)-10,10-dimethyl-7-thiatricyclo[6.3.0.0^[2,6]]undeca-1(8),2(6)-dien-5-ylidene]hydroxylamine (890.00 mg, 4.021 mmol, 1.00 equiv), PPA (10.00 mL). The resulting solution was stirred overnight at 80 degrees C. in an oil bath. The reaction was then quenched by the addition of 50 mL of water at 0 degrees C. The resulting solution was extracted with 3×200 mL of DCM:MeOH=9:1 and the organic layers combined. The resulting mixture was washed with 2×500 ml of $NaHCO_3$ and 1×500 mL of brine. The mixture was dried over anhydrous sodium sulfate and concentrated under vacuum. The residue was applied onto a silica gel column with ethyl acetate/petroleum ether (1:5). This resulted in 450 mg (50.56%) of 4,4-dimethyl-7-thia-10-azatricyclo[6.4.0.0^[2,6]]dodeca-1(8),2(6)-dien-9-one as a yellow solid. H-NMR (300 MHz, Chloroform-d, ppm) δ 5.75 (s, 1H), 3.60 (td, J=7.0, 2.5 Hz, 2H), 2.83-2.72 (m, 4H), 2.52 (d, J=1.3 Hz, 2H), 1.27 (s, 6H).

Synthesis of 10-[4-bromo-3-[(oxan-2-yloxy)methyl]pyridin-2-yl]-4,4-dimethyl-7-thia-10-azatricyclo[6.4.0.0^[2,6]]dodeca-1(8),2(6)-dien-9-one: Into a 40-mL vial purged and maintained with an inert atmosphere of nitrogen, was placed 4,4-dimethyl-7-thia-10-azatricyclo[6.4.0.0^[2,6]]dodeca-1(8),2(6)-dien-9-one (450.00 mg, 2.033 mmol, 1.00 equiv), dioxane (10.00 mL), 2,4-dibromo-3-[(oxan-2-yloxy)methyl]pyridine (1.14 g, 3.248 mmol, 1.60 equiv), phen (147.00 mg, 0.816 mmol, 0.40 equiv), CuI (233.00 mg, 1.223 mmol, 0.60 equiv), $K_2CO_3$ (845.00 mg, 6.114 mmol, 3.01 equiv). The resulting solution was stirred overnight at 110 degrees C. in an oil bath. The reaction mixture was cooled to room temperature. The resulting mixture was concentrated under vacuum. The residue was applied onto a silica gel column with ethyl acetate/petroleum ether (2:3). This resulted in 860 mg (86.07%) of 10-[4-bromo-3-[(oxan-2-yloxy)methyl] pyridin-2-yl]-4,4-dimethyl-7-thia-10-azatricyclo[6.4.0.0^[2,6]]dodeca-1(8),2(6)-dien-9-one as a yellow solid. LC-MS: (ES, m/z): M+1: 491

Synthesis of 2-[4,4-dimethyl-9-oxo-7-thia-10-azatricyclo [6.4.0.0^[2,6]]dodeca-1(8),2(6)-dien-10-yl]-3-[(oxan-2-yloxy)methyl]pyridin-4-ylboronic acid: Into a 100-mL round-bottom flask purged and maintained with an inert atmosphere of nitrogen, was placed 10-[4-bromo-3-[(oxan-2-yloxy)methyl]pyridin-2-yl]-4,4-dimethyl-7-thia-10-azatricyclo[6.4.0.0^[2,6]]dodeca-1(8),2(6)-dien-9-one (603.00 mg, 1.227 mmol, 1.00 equiv), dioxane (10.00 mL), bis (pinacolato)diboron (782.00 mg, 3.079 mmol, 2.51 equiv), $Pd(dppf)Cl_2 \cdot CH_2Cl_2$ (150.00 mg, 0.184 mmol, 0.15 equiv), KOAc (362.00 mg, 3.689 mmol, 3.01 equiv). The resulting solution was stirred for 1.5 hr at 100 degrees C. in an oil bath. The reaction mixture was cooled to room temperature. The solids were filtered out. The resulting mixture was concentrated under vacuum. The crude product was purified by Flash-Prep-HPLC with the following conditions (Intel-Flash-1): Column, C18 reversed phase column; mobile phase, $H_2O$ and $CH_3CN$ (30% $CH_3CN$ up to 70% in 15 min); Detector, 254/220 nm. This resulted in 380 mg (50.90%) of 2-[4,4-dimethyl-9-oxo-7-thia-10-azatricyclo [6.4.0.0^[2,6]]dodeca-1(8),2(6)-dien-10-yl]-3-[(oxan-2-yloxy)methyl]pyridin-4-ylboronic acid as a yellow solid. LC-MS: (ES, m/z): M+1: 457

Synthesis of 10-[1-hydroxy-3H-[1,2]oxaborolo[4,3-c] pyridin-4-yl]-4,4-dimethyl-7-thia-10-azatricyclo[6.4.0.0^[2,6]]dodeca-1(8),2(6)-dien-9-one: Into a 100-mL round-bottom flask, was placed 2-[4,4-dimethyl-9-oxo-7-thia-10-azatricyclo[6.4.0.0^[2,6]]dodeca-1(8),2(6)-dien-10-yl]-3-[(oxan-2-yloxy)methyl]pyridin-4-ylboronic acid (380.00 mg, 0.833 mmol, 1.00 equiv), HCl(gas) in 1,4-dioxane (2N, 12.00 mL). The resulting solution was stirred for 1 hr at room temperature. The resulting mixture was concentrated under vacuum. This resulted in 280 mg (94.93%) of 10-[1-hydroxy-3H-[1,2]oxaborolo[4,3-c]pyridin-4-yl]-4,4-dimethyl-7-thia-10-azatricyclo[6.4.0.0^[2,6]]dodeca-1(8),2(6)-dien-9-one as a white solid. LC-MS: (ES, m/z): M+1: 355

Synthesis of N-(5-[[6-(2-[4,4-dimethyl-9-oxo-7-thia-10-azatricyclo[6.4.0.0^[2,6]]dodeca-1(8),2(6)-dien-10-yl]-3-(hydroxymethyl)pyridin-4-yl)-4-methyl-3-oxopyrazin-2-yl] amino]-2-[(2S)-2-methyl-4-(oxetan-3-yl)piperazin-1-yl] phenyl)prop-2-enamide: Into a 40-mL vial purged and maintained with an inert atmosphere of nitrogen, was placed N-[5-[(6-bromo-4-methyl-3-oxopyrazin-2-yl)amino]-2-[(2S)-2-methyl-4-(oxetan-3-yl)piperazin-1-yl]phenyl]prop-2-enamide (120.00 mg, 0.238 mmol, 1.00 equiv), dioxane (10.00 mL), H2O (1.00 mL), 10-[1-hydroxy-3H-[1,2]oxaborolo [4,3-c]pyridin-4-yl]-4,4-dimethyl-7-thia-10-azatricyclo[6.4.0.0^[2,6]]dodeca-1(8),2(6)-dien-9-one (211.00 mg, 0.596 mmol, 2.50 equiv), $K_2CO_3$ (165.00 mg, 1.194 mmol, 5.01 equiv), Xphos Pd G3 (41.00 mg, 0.048 mmol, 0.20 equiv). The resulting solution was stirred for 1 hr at 100 degrees C. in an oil bath. The reaction mixture was cooled to room temperature. The resulting mixture was concentrated under vacuum. The residue was applied onto a silica gel column with dichloromethane/methanol (20:1). The crude product was purified by Prep-HPLC with the following conditions: Column, XBridge Shield RP18 OBD Column, Sum, 19*150 mm; mobile phase, Water (0.05% $NH_3 \cdot H2O$) and ACN (20% Phase B up to 60% in 10 min); Detector, UV 254/220 nm. This resulted in 80 mg (44.69%) of N-(5-[[6-(2-[4,4-dimethyl-9-oxo-7-thia-10-azatricyclo [6.4.0.0^[2,6]]dodeca-1(8),2(6)-dien-10-yl]-3-(hydroxymethyl)pyridin-4-yl)-4-methyl-3-oxopyrazin-2-yl]amino]-2-[(2S)-2-methyl-4-(oxetan-3-yl)piperazin-1-yl]phenyl)prop-2-enamide as a white solid. LC-MS: (ES, m/z): M+1: 751; H-NMR (300 MHz, DMSO-$d_6$, ppm) δ 9.27 (s, 1H), 9.19 (s, 1H), 9.10 (d, J=2.5 Hz, 1H), 8.48 (d, J=5.1 Hz, 1H), 7.93 (d, J=5.2 Hz, 1H), 7.73 (d, J=1.4 Hz, 1H), 7.61 (dd, J=8.7, 2.6 Hz, 1H), 7.26 (d, J=8.7 Hz, 1H), 6.61 (dd, J=16.9, 10.2 Hz, 1H), 6.29 (dd, J=16.8, 1.8 Hz, 1H), 5.80 (dd, J=10.1, 1.8 Hz, 1H), 5.08-4.89 (m, 1H), 4.53 (dq, J=28.3, 6.3 Hz, 6H), 4.17 (td, J=12.2, 5.3 Hz, 1H), 3.95-3.69 (m, 1H), 3.57 (s, 3H), 3.48 (t, J=6.3 Hz, 1H), 3.21-2.96 (m, 2H), 2.95-2.65 (m, 7H), 2.56 (d, J=8.4 Hz, 2H), 2.22 (s, 1H), 2.01-1.81 (m, 1H), 1.24 (d, J=2.7 Hz, 6H), 0.73 (d, J=6.1 Hz, 3H).

Example 35: Preparation of N-(5-[[6-(2-[5,5-dimethyl-9-oxo-7-thia-10-azatricyclo[6.4.0.0^[2,6]]dodeca-1(8),2(6)-dien-10-yl]-3-(hydroxymethyl)pyridin-4-yl)-4-methyl-3-oxopyrazin-2-yl]amino]-2-[(2S)-2-methyl-4-(oxetan-3-yl)piperazin-1-yl] phenyl)prop-2-enamide Synthesis of 5-bromo-3-[(4-fluoro-3-nitrophenyl)amino]-1-methylpyrazin-2-one: Into a 250-mL round-bottom flask, was placed 4-fluoro-3-nitroaniline (10.00 g, 64.055 mmol, 1.00 equiv), 3,5-dibromo-1-methylpyrazin-2-one (17.16 g, 64.052 mmol, 1.00 equiv), NMP (30 mL). The resulting solution was stirred for 1 h at 140 degrees C. in an oil bath. The resulting solution was diluted with 300 mL of EA. The solids were collected by filtration. This resulted in 13 g (59.15%) of 5-bromo-3-[(4-fluoro-3-nitrophenyl)amino]-1-methylpyrazin-2-one as a brown solid. LCMS (ES, m/z): M+1: 343/345

Synthesis of tert-butyl (3S)-4-[4-[(6-bromo-4-methyl-3-oxopyrazin-2-yl)amino]-2-nitrophenyl]-3-methylpiperazine-1-carboxylate: Into a 50-mL round-bottom flask, was placed 5-bromo-3-[(4-fluoro-3-nitrophenyl)amino]-1-methylpyrazin-2-one (10 g, 29.2 mmol, 1.00 equiv), NMP (40.00 mL), tert-butyl (3S)-3-methylpiperazine-1-carboxylate (5.8 g, 5.842 mmol, 1.00 equiv), DIEA (2.26 g, 17.487 mmol, 3.00 equiv). The resulting solution was stirred for 40 h at 120° C. in an oil bath. The resulting solution was diluted with 100 mL of $H_2O$. The resulting solution was extracted with 3×50 mL of dichloromethane/methanol (10:1). The resulting mixture was washed with 3×20 ml of brine. The resulting mixture was concentrated. The residue was applied onto a silica gel column with dichloromethane/methanol (10:1). This resulted in 10 g (57.00%) of tert-butyl (3S)-4-[4-[(6-bromo-4-methyl-3-oxopyrazin-2-yl)amino]-2-nitrophenyl]-3-methylpiperazine-1-carboxylate as a brown solid. LC-MS: (ES, m/z): M+1: 523

Synthesis of 5-bromo-1-methyl-3-([4-[(2S)-2-methylpiperazin-1-yl]-3-nitrophenyl]amino)pyrazin-2-one: Into a 100-mL round-bottom flask, was placed tert-butyl (3S)-4-[4-[(6-bromo-4-methyl-3-oxopyrazin-2-yl)amino]-2-nitrophenyl]-3-methylpiperazine-1-carboxylate (10.00 g, 1 equiv, 60%), HCl in 1,4-dioxane (2N, 100 mL). The resulting solution was stirred for 14 h at room temperature. The resulting mixture was concentrated. The resulting solution was diluted with 30 mL of $H_2O$. The pH value of the solution was adjusted to 8 with $NH_3 \cdot H_2O$. The resulting solution was extracted with 3×15 mL of dichloromethane and concentrated. The residue was applied onto a silica gel column with dichloromethane/methanol (10:1). This resulted in 5 g of 5-bromo-1-methyl-3-([4-[(2S)-2-methylpiperazin-1-yl]-3-nitrophenyl]amino)pyrazin-2-one as a red solid. LC-MS: (ES, m/z): M+1: 423

Synthesis of 5-bromo-1-methyl-3-([4-[(2S)-2-methyl-4-(oxetan-3-yl)piperazin-1-yl]-3-nitrophenyl]amino)pyrazin-2-one: Into a 250-mL round-bottom flask, was placed 5-bromo-1-methyl-3-([4-[(2S)-2-methylpiperazin-1-yl]-3-nitrophenyl]amino)pyrazin-2-one (4.00 g, 9.450 mmol, 1.00 equiv), 3-oxetanone (0.89 g, 12.350 mmol, 1.31 equiv), THF (40.00 mL), AcOH (0.80 mL). This was followed by the addition of $NaBH(AcO)_3$ (3.00 g, 14.155 mmol, 1.50 equiv) dropwise with stirring at room temperature. The resulting solution was stirred for 4 hr at room temperature. The reaction was then quenched by the addition of 10 mL of water. The resulting mixture was concentrated. The resulting solution was diluted with 40 mL of DCM. The resulting mixture was washed with 1×10 mL of $Na_2CO_3$ (aq). The mixture was dried over anhydrous sodium sulfate and concentrated. The residue was applied onto a silica gel column with and eluted with dichloromethane/methanol (10:1). This resulted in 3 g (66.23%) of 5-bromo-1-methyl-3-([4-[(2S)-2-methyl-4-(oxetan-3-yl)piperazin-1-yl]-3-nitrophenyl]amino)pyrazin-2-one as a brown solid. LC-MS: (ES, m/z): M+1: 479/481

Synthesis of 3-([3-amino-4-[(2S)-2-methyl-4-(oxetan-3-yl)piperazin-1-yl]phenyl]amino)-5-bromo-1-methylpyrazin-2-one: Into a 250-mL round-bottom flask, was placed 5-bromo-1-methyl-3-([4-[(2S)-2-methyl-4-(oxetan-3-yl)piperazin-1-yl]-3-nitrophenyl]amino)pyrazin-2-one (3.00 g, 6.259 mmol, 1.00 equiv), Fe (1.40 g, 25.035 mmol, 4.00 equiv), $NH_4Cl$ (2.01 g, 37.576 mmol, 6.00 equiv), EtOH (30.00 mL), $H_2O$ (30.00 mL). The resulting solution was stirred for 2 hr at 80 degrees C. in an oil bath. The solids were filtered out. The resulting mixture was concentrated. The resulting solution was diluted with 200 mL of DCM. The pH value of the solution was adjusted to 8 with $NH_3 \cdot H_2O$. The resulting mixture was washed with 1×20 mL of $H_2O$. The resulting mixture was washed with 1×20 mL of brine. The mixture was dried over anhydrous sodium sulfate and concentrated. The residue was applied onto a silica gel column and eluted with dichloromethane/methanol (10:1). This resulted in 2.5 g (88.89%) of 3-([3-amino-4-[(2S)-2-methyl-4-(oxetan-3-yl)piperazin-1-yl]phenyl]amino)-5-bromo-1-methylpyrazin-2-one as a brown solid. LC-MS: (ES, m/z): M+1: 449/451

Synthesis of N-[5-[(6-bromo-4-methyl-3-oxopyrazin-2-yl)amino]-2-[(2S)-2-methyl-4-(oxetan-3-yl)piperazin-1-yl]phenyl]prop-2-enamide: Into a 100-mL round-bottom flask, was placed 3-([3-amino-4-[(2S)-2-methyl-4-(oxetan-3-yl)piperazin-1-yl]phenyl]amino)-5-bromo-1-methylpyrazin-2-one (2.50 g, 5.564 mmol, 1.00 equiv), DCM (30.00 mL, 471.901 mmol, 84.82 equiv), DIEA (1.44 g, 11.142 mmol, 2.00 equiv). This was followed by the addition of acryloyl chloride (0.65 g, 7.182 mmol, 1.29 equiv), in portions at 0 degrees C. The resulting solution was stirred for 1 hr at 0 degrees C. in a water/ice bath. The reaction was then quenched by the addition of 1 mL of MeOH. The resulting mixture was concentrated. The residue was applied onto a silica gel column and eluted with dichloromethane/methanol (10:1). This resulted in 2.8 g (80.98%) of N-[5-[(6-bromo-4-methyl-3-oxopyrazin-2-yl)amino]-2-[(2S)-2-methyl-4-(oxetan-3-yl)piperazin-1-yl]phenyl]prop-2-enamide as a yellow solid. LC-MS: (ES, m/z): M+1: 503/505

Synthesis of 2, 4-dibromopyridine-3-carbaldehyde: Into a 1000-mL 3-necked round-bottom flask, was placed 2, 4-dibromopyridine (40.00 g, 168.852 mmol, 1.00 equiv), THF (400.00 mL). This was followed by the addition of LDA (2M in hexane, 126.60 mL, 1.50 equiv) dropwise with stirring at −78 degrees C. The resulting solution was stirred for 1 h at −78 degrees C. Then add DMF (16.04 ml, 219.507 mmol, 1.30 equiv) dropwise with stirring at −78 degrees C. The resulting solution was stirred for 0.5 h at −78 degrees C. The reaction was then quenched by the addition of 500 mL of $NH_4Cl$. The resulting solution was extracted with 3×500 mL of ethyl acetate concentrated. The residue was applied onto a silica gel column and eluted with ethyl acetate/petroleum ether (0:1-1:1). This resulted in 24.4 g (54.55%) of 2, 4-dibromopyridine-3-carbaldehyde as a white solid. LC-MS: (ES, m/z): M+1: 264

Synthesis of (2, 4-dibromopyridin-3-yl) methanol: Into a 100-mL round-bottom flask, was placed 2, 4-dibromopyridine-3-carbaldehyde (2.00 g, 7.550 mmol, 1.00 equiv), EtOH (30.00 mL). This was followed by the addition of $NaBH_4$ (285.64 mg, 7.550 mmol, 1 equiv), in portions at 0 degrees C. The resulting solution was stirred for 3 h at room temperature. The reaction was then quenched by the addition of 30 mL of water. The resulting solution was extracted with 3×30 mL of ethyl acetate and concentrated. The residue was applied onto a silica gel column and eluted with ethyl acetate/petroleum ether (1:1). The collected fractions were combined and concentrated. This resulted in 1.4 g (69.47%) of (2, 4-dibromopyridin-3-yl) methanol as a light yellow solid. LC-MS: (ES, m/z): M+1: 266

Synthesis of 2,4-dibromo-3-[(oxan-2-yloxy) methyl]pyridine: Into a 100-mL round-bottom flask, was placed (2, 4-dibromopyridin-3-yl) methanol (1.40 g, 5.245 mmol, 1.00 equiv), DCM (30.00 mL, 0.353 mmol, 0.07 equiv), PPTS (131.81 mg, 0.525 mmol, 0.10 equiv), DHP (661.79 mg, 7.868 mmol, 1.50 equiv). The resulting solution was stirred overnight at 45 degrees C. in an oil bath. The reaction was then quenched by the addition of 30 mL of water. The resulting solution was extracted with 3×30 mL of dichloromethane and concentrated. The residue was applied onto a silica gel column and eluted with ethyl acetate/petroleum ether (1:1). The collected fractions were combined and concentrated. This resulted in 1.5 g of 2,4-dibromo-3-[(oxan-2-yloxy) methyl]pyridine as colorless oil. LC-MS: (ES, m/z): M+1: 350

Synthesis of 2-chloro-3,3-dimethylcyclopent-1-ene-1-carbaldehyde: To a stirred solution of DMF (16.94 g, 231.757 mmol, 1.30 equiv) in DCM (200.00 mL, 6292.018 mmol, 35.29 equiv) was added $POCl_3$ (27.34 g, 178.298 mmol, 1.00 equiv) dropwise at 0 degrees C. under nitrogen atmosphere. The resulting mixture was stirred for 1 h at room temperature under nitrogen atmosphere. To the above mixture was added 2,2-dimethylcyclopentan-1-one (20.00 g, 178.298 mmol, 1.00 equiv) in DCM (200.00 mL, 6292.018 mmol, 35.29 equiv) dropwise over 1 h at room temperature. The resulting mixture was stirred for 16 h at 40 degrees C. under nitrogen atmosphere. The mixture was allowed to cool down to room temperature. The reaction was quenched with Water/ice at 0 degrees C. and added Sodium acetate (200 g) stirred for 1 h. The resulting mixture was extracted with $CH_2Cl_2$ (3×200 mL). The combined organic layers were washed with brine (2×100 mL), dried over anhydrous $Na_2SO_4$. After filtration, the filtrate was concentrated under reduced pressure to afford 2-chloro-3,3-dimethylcyclopent-1-ene-1-carbaldehyde (26 g, 91.93%) as a brown oil.

Synthesis of ethyl 6,6-dimethyl-4H,5H-cyclopenta[b]thiophene-2-carboxylate: To a stirred solution of 2-chloro-3,3-dimethylcyclopent-1-ene-1-carbaldehyde (26.00 g, 163.903 mmol, 1.00 equiv) and TEA (49.76 g, 491.710 mmol, 3.00 equiv) in DCM (500.00 mL, 7865.023 mmol, 47.99 equiv) was added ethyl thioglycolate (19696.27 mg, 163.903 mmol, 1.00 equiv) in portions at room temperature under air atmosphere. The resulting mixture was stirred for 16 h at 40 degrees C. under air atmosphere. The mixture was allowed to cool down to room temperature. The resulting mixture was concentrated under reduced pressure. The residue was dissolved in EtOH (500 mL) and added TEA (49.76 g, 491.710 mmol, 3.00 equiv). The resulting mixture was stirred for 16 h at 40 degrees C. under air atmosphere. The resulting mixture was concentrated under reduced pressure. The residue dissolved in diethyl ether (100 mL) and washed with 1×100 mL of HCl (1 N) and brine. The resulting mixture was extracted with diethyl ether (3×200 mL). The combined organic layers dried over anhydrous $Na_2SO_4$. After filtration, the filtrate was concentrated under reduced pressure. The residue was purified by silica gel column chromatography, eluted with PE/EtOAc (10:1) to afford ethyl 6,6-dimethyl-4H,5H-cyclopenta[b]thiophene-2-carboxylate (16 g, 43.52%) as a brown oil. H-NMR (300 MHz, DMSO-$d_6$, ppm) δ 4.25 (q, J=7.1 Hz, 2H), 2.73 (dd, J=7.6, 6.4 Hz, 2H), 2.21 (dd, J=7.5, 6.5 Hz, 2H), 1.29 (s, 6H), 1.26 (t, J=7.1 Hz, 3H).

Synthesis of 6,6-dimethyl-4H,5H-cyclopenta[b]thiophene-2-carboxylic acid: To a stirred solution of ethyl 6,6-dimethyl-4H,5H-cyclopenta[b]thiophene-2-carboxylate (16.00 g, 71.327 mmol, 1.00 equiv) and LiOH·$H_2O$ (6842.19 mg, 163.049 mmol, 2.00 equiv) in THF (30.00 mL, 0.416 mmol, 0.01 equiv) and EtOH (30.00 mL, 0.651 mmol, 0.01 equiv) and $H_2O$ (30.00 mL, 1665.251 mmol, 20.43 equiv) at room temperature under air atmosphere. The resulting mixture was stirred for 4 h at 60 degrees C. under air atmosphere. The resulting mixture was concentrated under reduced pressure. The resulting mixture was diluted with 1N HCl (50 mL). The resulting mixture was filtered; the filter cake was washed with water (3×50 mL). To afford the cake was 6,6-dimethyl-4H,5H-cyclopenta[b]thiophene-2-carboxylic acid (10g, 71.44%) as a yellow solid. H-NMR (300 MHz, Chloroform-d, ppm) δ 7.58 (s, 1H), 2.79 (t, J=7.0 Hz, 2H), 2.29 (dd, J=7.5, 6.5 Hz, 2H), 1.37 (s, 6H).

Synthesis of N-methoxy-N,6,6-trimethyl-4H,5H-cyclopenta[b]thiophene-2-carboxamide: To a stirred solution of 6,6-dimethyl-4H,5H-cyclopenta[b]thiophene-2-carboxylic acid(10.00 g, 50.953 mmol, 1.00 equiv) and DIEA (13170.61 mg, 101.906 mmol, 2.00 equiv), HATU (19373.78 mg, 50.953 mmol, 1.00 equiv) in DMF (150.00 mL, 2.736 mmol, 0.05 equiv). To the above mixture was added N,O-dimethylhydroxylamine (6.22 g, 101.906 mmol, 2.00 equiv) in DMF (50.00 mL, 2584.351 mmol, 50.72 equiv) dropwise at room temperature. The resulting mixture was stirred for additional 2 h at room temperature. The reaction was quenched with Water at room temperature. The resulting mixture was extracted with EtOAc (2×200 mL). The combined organic layers were washed with brine (3×200 mL), dried over anhydrous $Na_2SO_4$. After filtration, the filtrate was concentrated under reduced pressure. The residue was purified by silica gel column chromatography, eluted with PE/EtOAc (10:1) to afford N-methoxy-N,6,6-trimethyl-4H,5H-cyclopenta[b]thiophene-2-carboxamide (9g, 73.80%) as a yellow solid. H-NMR (300 MHz, DMSO-$d_6$, ppm) δ 7.53 (s, 1H), 3.75 (s, 3H), 3.25 (s, 3H), 2.77-2.69 (m, 2H), 2.21 (dd, J=7.5, 6.5 Hz, 2H), 1.30 (s, 6H).

Synthesis of 3-chloro-1-[6,6-dimethyl-4H,5H-cyclopenta[b]thiophen-2-yl]propan-1-one: To a stirred solution of N-methoxy-N,6,6-trimethyl-4H,5H-cyclopenta[b]thiophene-2-carboxamide (5.00 g, 20.892 mmol, 1.00 equiv) in THF (100.00 mL, 1234.299 mmol, 59.08 equiv) was added bromo(ethenyl)magnesium (90.00 mL, 0.686 mmol, 5 equiv) dropwise at −78 degrees C. under nitrogen atmosphere. The resulting mixture was stirred for 2 h at −78 degrees C. under nitrogen atmosphere. To the above mixture was added HCl(g) diethyl ether (100 mL, 5 equiv) dropwise over 0.5 h at −78 degrees C. The resulting mixture was stirred for additional 2 h at −78 degrees C. The resulting mixture was concentrated under reduced pressure. The residue was dissolved in diethyl ether (100 mL) and washed with 1×100 mL of HCl (1 N). The resulting mixture was extracted with diethyl ether (2×100 mL). The combined organic layers were washed with brine (2×100 mL), dried over anhydrous $Na_2SO_4$. After filtration, the filtrate was concentrated under reduced pressure. The residue was purified by silica gel column chromatography, eluted with PE/EtOAc (10:1) to afford 3-chloro-1-[6,6-dimethyl-4H,5H-cyclopenta[b]thiophen-2-yl]propan-1-one (2 g, 39.43%) as a yellow oil. LC-MS: (ES, m/z): M+1: 243

Synthesis of 9,9-dimethyl-7-thiatricyclo[6.3.0.0^[2,6]]undeca-1(8),2(6)-dien-5-one: A solution of 3-chloro-1-[6,6-dimethyl-4H,5H-cyclopenta[b]thiophen-2-yl]propan-1-one (2.00 g, 1 equiv) in $H_2SO_4$ (20.00 mL) was stirred for 16 h at 90 degrees C. under nitrogen atmosphere. The reaction was quenched with Water/ice at room temperature. The resulting mixture was extracted with EtOAc (5×50 mL). The combined organic layers were washed with brine (2×100 mL), dried over anhydrous $Na_2SO_4$. After filtration, the filtrate was concentrated under reduced pressure to afford 9,9-dimethyl-7-thiatricyclo[6.3.0.0^[2,6]]undeca-1(8),2(6)-dien-5-one (0.2 g, 11.77%) as a brown oil. LC-MS: (ES, m/z): M+1: 207

Synthesis of N-[(5E)-9,9-dimethyl-7-thiatricyclo[6.3.0.0^[2,6]]undeca-1(8),2(6)-dien-5-ylidene]hydroxylamine: Into a 100-mL round-bottom flask, was placed 9,9-dimethyl-7-thiatricyclo[6.3.0.0^[2,6]]undeca-1(8),2(6)-dien-5-one (240.00 mg, 1.163 mmol, 1.00 equiv), MeOH (10.00 mL), hydroxylamine hydrochloride (728.00 mg, 10.476 mmol, 9.01 equiv), $CH_3COONa$ (858.56 mg, 10.470 mmol, 9.00 equiv). The resulting solution was stirred overnight at room temperature. The resulting solution was diluted with 500 mL of water. The resulting solution was extracted with 3×100 mL of dichloromethane and the organic layers combined. The resulting mixture was washed with 1×500 ml of brine. The mixture was dried over anhydrous sodium sulfate and concentrated under vacuum. This resulted in 278 mg (crude) of N-[(5E)-9,9-dimethyl-7-thiatricyclo[6.3.0.0^[2,6]]undeca-1(8),2(6)-dien-5-ylidene]hydroxylamine as a brown solid. H-NMR (300 MHz, $CDCl_3$-d, ppm) δ 3.30-3.07 (m, 2H), 2.96-2.64 (m, 4H), 2.29 (ddd, J=9.5, 6.4, 2.8 Hz, 2H), 1.35 (d, J=5.5 Hz, 6H).

Synthesis of 5,5-dimethyl-7-thia-10-azatricyclo[6.4.0.0^[2,6]]dodeca-1(8),2(6)-dien-9-one: Into a 100-mL round-bottom flask, was placed N-[(5E)-9,9-dimethyl-7-thiatricyclo[6.3.0.0^[2,6]]undeca-1(8),2(6)-dien-5-ylidene] hydroxylamine (270.00 mg, 1.220 mmol, 1.00 equiv), PPA (10.00 mL). The resulting solution was stirred overnight at 80 degrees C. in an oil bath. The reaction mixture was cooled to room temperature. The resulting solution was diluted with 200 mL of DCM:MeOH=9:1. The reaction was then quenched by the addition of 300 mL of water. The resulting solution was extracted with 3×100 mL of DCM:MeOH=9:1 and the organic layers combined. The resulting mixture was washed with 2×500 ml of brine. The mixture was dried over anhydrous sodium sulfate and concentrated under vacuum. The residue was applied onto a silica gel column with ethyl acetate/petroleum ether (1:1). This resulted in 170 mg (62.96%) of 5,5-dimethyl-7-thia-10-azatricyclo[6.4.0.0^[2,6]]dodeca-1(8),2(6)-dien-9-one as a white solid. H-NMR (300 MHz, DMSO-$d_6$, ppm) δ 3.39 (td, J=6.9, 2.6 Hz, 2H), 2.67 (td, J=6.9, 3.4 Hz, 4H), 2.21 (t, J=7.0 Hz, 2H), 1.28 (s, 6H).

Synthesis of 10-[4-bromo-3-[(oxan-2-yloxy)methyl]pyridin-2-yl]-5,5-dimethyl-7-thia-10-azatricyclo[6.4.0.0^[2,6]]dodeca-1(8),2(6)-dien-9-one: Into a 40-mL vial purged and maintained with an inert atmosphere of nitrogen, was placed 2,4-dibromo-3-[(oxan-2-yloxy)methyl]pyridine (404.00 mg, 1.151 mmol, 1.59 equiv), dioxane (5.00 mL), 5,5-dimethyl-7-thia-10-azatricyclo[6.4.0.0^[2,6]]dodeca-1(8),2(6)-dien-9-one (160.00 mg, 0.723 mmol, 1.00 equiv), phen (65.00 mg, 0.361 mmol, 0.50 equiv), CuI (110.00 mg, 0.578 mmol, 0.80 equiv), $K_2CO_3$ (300.00 mg, 2.171 mmol, 3.00 equiv). The resulting solution was stirred overnight at 110 degrees C. in an oil bath. The reaction mixture was cooled to room temperature. The resulting mixture was concentrated under vacuum. The residue was applied onto a silica gel column with ethyl acetate/petroleum ether (1:3). This resulted in 280 mg (78.81%) of 10-[4-bromo-3-[(oxan-2-yloxy)methyl]pyridin-2-yl]-5,5-dimethyl-7-thia-10-azatricyclo[6.4.0.0^[2,6]]dodeca-1(8),2(6)-dien-9-one as a yellow solid. LC-MS: (ES, m/z): M+1: 491

Synthesis of 2-[5,5-dimethyl-9-oxo-7-thia-10-azatricyclo[6.4.0.0^[2,6]]dodeca-1(8),2(6)-dien-10-yl]-3-[(oxan-2-yloxy)methyl]pyridin-4-ylboronic acid: Into a 40-mL vial purged and maintained with an inert atmosphere of nitrogen, was placed 10-[4-bromo-3-[(oxan-2-yloxy)methyl]pyridin-2-yl]-5,5-dimethyl-7-thia-10-azatricyclo[6.4.0.0^[2,6]]dodeca-1(8),2(6)-dien-9-one (260.00 mg, 0.529 mmol, 1.00 equiv), dioxane (5.00 mL), bis(pinacolato)diboron (337.00 mg, 1.327 mmol, 2.51 equiv), KOAc (156.00 mg, 1.590 mmol, 3.00 equiv), $Pd(dppf)Cl_2{\cdot}CH_2Cl_2$ (65.00 mg, 0.080 mmol, 0.15 equiv). The resulting solution was stirred for 1.5 hr at 100 degrees C. in an oil bath. The reaction mixture was cooled to room temperature. The solids were filtered out. The resulting mixture was concentrated under vacuum. The crude product was purified by Flash-Prep-HPLC with the following conditions (IntelFlash-1): Column, C18 reversed phase column; mobile phase, $H_2O$ and $CH_3CN$ (30% $CH_3CN$ up to 70% in 15 min); Detector, 254/220 nm. This resulted in 170 mg (52.81%) of 2-[5,5-dimethyl-9-oxo-7-thia-10-azatricyclo[6.4.0.0^[2,6]]dodeca-1(8),2(6)-dien-10-yl]-3-[(oxan-2-yloxy)methyl]pyridin-4-ylboronic acid as a yellow solid. LC-MS: (ES, m/z): M+1: 457

Synthesis of 10-[1-hydroxy-3H-[1,2]oxaborolo[4,3-c]pyridin-4-yl]-5,5-dimethyl-7-thia-10-azatricyclo[6.4.0.0^[2,6]]dodeca-1(8),2(6)-dien-9-one: Into a 100-mL round-bottom flask, was placed 2-[5,5-dimethyl-9-oxo-7-thia-10-azatricyclo[6.4.0.0^[2,6]]dodeca-1(8),2(6)-dien-10-yl]-3-[(oxan-2-yloxy)methyl]pyridin-4-ylboronic acid (170.00 mg, 1 equiv), HCl(gas) in 1,4-dioxane (2N, 12.00 mL). The resulting solution was stirred for 1 hr at room temperature. The resulting mixture was concentrated under vacuum. This resulted in 120 mg (90.94%) of 10-[1-hydroxy-3H-[1,2]oxaborolo[4,3-c]pyridin-4-yl]-5,5-dimethyl-7-thia-10-azatricyclo[6.4.0.0^[2,6]]dodeca-1(8),2(6)-dien-9-one as a white solid. LC-MS: (ES, m/z): M+1: 355

Synthesis of N-(5-[[6-(2-[5,5-dimethyl-9-oxo-7-thia-10-azatricyclo[6.4.0.0^[2,6]]dodeca-1(8),2(6)-dien-10-yl]-3-(hydroxymethyl)pyridin-4-yl)-4-methyl-3-oxopyrazin-2-yl]amino]-2-[(2S)-2-methyl-4-(oxetan-3-yl)piperazin-1-yl]phenyl)prop-2-enamide: Into a 40-mL vial purged and maintained with an inert atmosphere of nitrogen, was placed N-[5-[(6-bromo-4-methyl-3-oxopyrazin-2-yl)amino]-2-[(2S)-2-methyl-4-(oxetan-3-yl)piperazin-1-yl]phenyl]prop-2-enamide (85.00 mg, 0.169 mmol, 1.00 equiv), dioxane (10.00 mL), $H_2O$ (1.00 mL), 10-[1-hydroxy-3H-[1,2]oxaborolo [4,3-c]pyridin-4-yl]-5,5-dimethyl-7-thia-10-azatricyclo[6.4.0.0^[2,6]]dodeca-1(8),2(6)-dien-9-one (120.00 mg, 0.339 mmol, 2.01 equiv), Xphos Pd G3 (29.00 mg, 0.034 mmol, 0.20 equiv), $K_2CO_3$ (117.00 mg, 0.847 mmol, 5.01 equiv). The resulting solution was stirred for 1 hr at 100 degrees C. in an oil bath. The reaction mixture was cooled to room temperature. The resulting mixture was concentrated under vacuum. The residue was applied onto a silica gel column with dichloromethane/methanol (20:1). The crude product was purified by Prep-HPLC with the following conditions: Column, XBridge Shield RP18 OBD Column, Sum, 19*150 mm; mobile phase, Water (0.05% $NH_3{\cdot}H_2O$) and ACN (20% Phase B up to 60% in 10 min); Detector, UV 254/220 nm. This resulted in 70 mg (55.21%) of N-(5-[[6-(2-[5,5-dimethyl-9-oxo-7-thia-10-azatricyclo[6.4.0.0^[2,6]]dodeca-1(8),2(6)-dien-10-yl]-3-(hydroxymethyl)pyridin-4-yl)-4-methyl-3-oxopyrazin-2-yl]amino]-2-[(2S)-2-methyl-4-(oxetan-3-yl)piperazin-1-yl]phenyl)prop-2-enamide as a white solid. LC-MS: (ES, m/z): M+1: 751; H-NMR (300 MHz, DMSO-$d_6$, ppm) δ 9.27 (s, 1H), 9.19 (s, 1H), 9.10 (d, J=2.5 Hz, 1H), 8.48 (d, J=5.1 Hz, 1H), 7.92 (d, J=5.2 Hz, 1H), 7.72 (d, J=1.5 Hz, 1H), 7.62 (dd, J=8.6, 2.5 Hz, 1H), 7.27 (d, J=8.7 Hz, 1H), 6.61 (dd, J=16.9, 10.2 Hz, 1H), 6.29 (dd, J=17.1, 1.8 Hz, 1H), 5.80 (dd, J=10.2, 1.8 Hz, 1H), 4.96 (dt, J=11.2, 5.3 Hz, 1H), 4.68-4.43 (m, 6H), 4.18 (td, J=12.3, 5.3 Hz, 1H), 3.92-3.72 (m, 1H), 3.48 (t, J=6.3 Hz, 1H), 3.17-2.90 (m, 3H), 2.86-2.63 (m, 6H), 2.26 (t, J=7.0 Hz, 3H), 1.92 (t, J=10.1 Hz, 1H), 1.32 (s, 6H), 0.73 (d, J=6.1 Hz, 3H).

Example 36, Preparation of N-[5-([6-[3-(hydroxymethyl)-2-[6-oxo-8-thia-5-azatricyclo[7.4.0.0 ^[2,7]]trideca-1(9),2(7)-dien-5-yl]pyridin-4-yl]-4-methyl-3-oxopyrazin-2-yl]amino)-2-[(2S)-2-methyl-4-(oxetan-3-yl)piperazin-1-yl]phenyl]prop-2-enamide Synthesis of 2, 4-dibromopyridine-3-carbaldehyde: Into a 1000-mL 3-necked round-bottom flask, was placed 2, 4-dibromopyridine (40.00 g, 168.852 mmol, 1.00 equiv), THF (400.00 mL). This was followed by the addition of LDA (2M in hexane, 126.60 mL, 1.50 equiv) dropwise with stirring at −78 degrees C. The resulting solution was stirred for 1 h at −78 degrees C. Then add DMF (16.04 ml, 219.507 mmol, 1.30 equiv) dropwise with stirring at −78 degrees C. The resulting solution was stirred for 0.5 h at −78 degrees C. The reaction was then quenched by the addition of 500 mL of $NH_4Cl$. The resulting solution was extracted with 3×500 mL of ethyl acetate concentrated. The residue was applied onto a silica gel column and eluted with ethyl acetate/petroleum ether (0:1-1:1). This resulted in 24.4 g (54.55%) of 2, 4-dibromopyridine-3-carbaldehyde as a white solid. LCMS-1 (ES, m/z): M+1: 264

Synthesis of (2, 4-dibromopyridin-3-yl) methanol: Into a 100-mL round-bottom flask, was placed 2, 4-dibromopyridine-3-carbaldehyde (2.00 g, 7.550 mmol, 1.00 equiv), EtOH (30.00 mL). This was followed by the addition of $NaBH_4$ (285.64 mg, 7.550 mmol, 1 equiv), in portions at 0 degrees C. The resulting solution was stirred for 3 h at room temperature. The reaction was then quenched by the addition of 30 mL of water. The resulting solution was extracted with 3×30 mL of ethyl acetate concentrated. The residue was applied onto a silica gel column and eluted with ethyl acetate/petroleum ether (1:1). The collected fractions were combined and concentrated. This resulted in 1.4 g (69.47%) of (2, 4-dibromopyridin-3-yl) methanol as a light yellow solid. LCMS-2 (ES, m/z): M+1: 266

Synthesis of 2,4-dibromo-3-[(oxan-2-yloxy) methyl]pyridine: Into a 100-mL round-bottom flask, was placed (2, 4-dibromopyridin-3-yl) methanol (1.40 g, 5.245 mmol, 1.00 equiv), DCM (30.00 mL, 0.353 mmol, 0.07 equiv), PPTS (131.81 mg, 0.525 mmol, 0.10 equiv), DHP (661.79 mg, 7.868 mmol, 1.50 equiv). The resulting solution was stirred for overnight at 45 degrees C. in an oil bath. The reaction was then quenched by the addition of 30 mL of water. The resulting solution was extracted with 3×30 mL of dichloromethane concentrated. The residue was applied onto a silica gel column and eluted with ethyl acetate/petroleum ether (1:1). The collected fractions were combined and concentrated. This resulted in 1.5g of 2,4-dibromo-3-[(oxan-2-yloxy) methyl]pyridine as colorless oil. LCMS-3 (ES, m/z): M+1: 350

Synthesis of 5-bromo-3-[(4-fluoro-3-nitrophenyl)amino]-1-methylpyrazin-2-one: Into a 250-mL round-bottom flask, was placed 4-fluoro-3-nitroaniline (10.00 g, 64.055 mmol, 1.00 equiv), 3,5-dibromo-1-methylpyrazin-2-one (17.16 g, 64.052 mmol, 1.00 equiv), NMP (30 ml). The resulting solution was stirred for 1 h at 140 degrees C. in an oil bath. The resulting solution was diluted with 300 mL of EA. The solids were collected by filtration. This resulted in 13 g (59.15%) of 5-bromo-3-[(4-fluoro-3-nitrophenyl)amino]-1-methylpyrazin-2-one as a brown solid. LCMS-4 (ES, m/z): M+1: 343/345

Synthesis of tert-butyl (3S)-4-[4-[(6-bromo-4-methyl-3-oxopyrazin-2-yl)amino]-2-nitrophenyl]-3-methylpiperazine-1-carboxylate: Into a 50-mL round-bottom flask, was placed 5-bromo-3-[(4-fluoro-3-nitrophenyl)amino]-1-methylpyrazin-2-one (10 g, 29.2 mmol, 1.00 equiv), NMP (40.00 mL), tert-butyl (3S)-3-methylpiperazine-1-carboxylate (5.8 g, 5.842 mmol, 1.00 equiv), DIEA (2.26 g, 17.487 mmol, 3.00 equiv). The resulting solution was stirred for 40 h at 120° C. in an oil bath. The resulting solution was diluted with 100 mL of $H_2O$. The resulting solution was extracted with 3×50 mL of dichloromethane/methanol (10:1). The resulting mixture was washed with 3×20 ml of NaCl. The resulting mixture was concentrated. The residue was applied onto a silica gel column with dichloromethane/methanol (10:1). This resulted in 10 g (57%) of tert-butyl (3S)-4-[4-[(6-bromo-4-methyl-3-oxopyrazin-2-yl)amino]-2-nitrophenyl]-3-methylpiperazine-1-carboxylate as a brown solid. LCMS-5 (ES, m/z): M+1: 523

Synthesis of 5-bromo-1-methyl-3-([4-[(2S)-2-methylpiperazin-1-yl]-3-nitrophenyl]amino)pyrazin-2-one: Into a 100-mL round-bottom flask, was placed tert-butyl (3S)-4-[4-[(6-bromo-4-methyl-3-oxopyrazin-2-yl)amino]-2-nitrophenyl]-3-methylpiperazine-1-carboxylate (10.00 g, 1 equiv, 60%), HCl (2M) in 1,4-dioxane (100 mL). The resulting solution was stirred for 14 h at room temperature. The resulting mixture was concentrated. The resulting solution was diluted with 30 mL of $H_2O$. The pH value of the solution was adjusted to 8 with $NH_3$—$H_2O$. The resulting solution was extracted with 3×15 mL of dichloromethane concentrated. The residue was applied onto a silica gel column with dichloromethane/methanol (10:1). This resulted in 5 g of 5-bromo-1-methyl-3-([4-[(2S)-2-methylpiperazin-1-yl]-3-nitrophenyl]amino)pyrazin-2-one as a red solid. LCMS-6 (ES, m/z): M+1: 423

Synthesis of 5-bromo-1-methyl-3-([4-[(2S)-2-methyl-4-(oxetan-3-yl)piperazin-1-yl]-3-nitrophenyl]amino)pyrazin-2-one: Into a 250-mL round-bottom flask, was placed 5-bromo-1-methyl-3-[4-[(2S)-2-methylpiperazin-1-yl]-3-nitrophenyl]amino)pyrazin-2-one (4.00 g, 9.450 mmol, 1.00 equiv), 3-oxetanone (0.89 g, 12.350 mmol, 1.31 equiv), THF (40.00 mL), AcOH (0.80 mL). This was followed by the addition of $NaBH(AcO)_3$ (3.00 g, 14.155 mmol, 1.50 equiv) dropwise with stirring at room temperature. The resulting solution was stirred for 4 hr at room temperature. The reaction was then quenched by the addition of 10 mL of water. The resulting mixture was concentrated. The resulting solution was diluted with 40 mL of DCM. The resulting mixture was washed with 1×10 ml $Na_2CO_3$ (aq). The mixture was dried over anhydrous sodium sulfate and concentrated. The residue was applied onto a silica gel column with and eluted with dichloromethane/methanol (10:1). This resulted in 3 g (66.23%) of 5-bromo-1-methyl-3-([4-[(2S)-2-methyl-4-(oxetan-3-yl)piperazin-1-yl]-3-nitrophenyl]amino)pyrazin-2-one as a brown solid. LCMS-7 (ES, m/z): M+1: 479/481

Synthesis of 3-([3-amino-4-[(2S)-2-methyl-4-(oxetan-3-yl)piperazin-1-yl]phenyl]amino)-5-bromo-1-methylpyrazin-2-one: Into a 250-mL round-bottom flask, was placed 5-bromo-1-methyl-3-([4-[(2S)-2-methyl-4-(oxetan-3-yl)piperazin-1-yl]-3-nitrophenyl]amino)pyrazin-2-one (3.00 g, 6.259 mmol, 1.00 equiv), Fe (1.40 g, 25.035 mmol, 4.00 equiv), $NH_4Cl$ (2.01 g, 37.576 mmol, 6.00 equiv), EtOH (30.00 mL), $H_2O$ (30.00 mL). The resulting solution was stirred for 2 hr at 80 degrees C. in an oil bath. The solids were filtered out. The resulting mixture was concentrated. The resulting solution was diluted with 200 mL of DCM. The pH value of the solution was adjusted to 8 with NH3-H2O. The resulting mixture was washed with 1×20 ml of $H_2O$. The resulting mixture was washed with 1×20 mL of NaCl(aq). The mixture was dried over anhydrous sodium sulfate. The residue was applied onto a silica gel column and eluted with dichloromethane/methanol (10:1). This resulted in 2.5 g (88.89%) of 3-([3-amino-4-[(2S)-2-methyl-4-(oxetan-3-yl)piperazin-1-yl]phenyl]amino)-5-bromo-1-methylpyrazin-2-one as a brown solid. LCMS-8 (ES, m/z): M+1: 449/451

Synthesis of N-[5-[(6-bromo-4-methyl-3-oxopyrazin-2-yl)amino]-2-[(2S)-2-methyl-4-(oxetan-3-yl)piperazin-1-yl]phenyl]prop-2-enamide: Into a 100-mL round-bottom flask, was placed 3-([3-amino-4-[(2S)-2-methyl-4-(oxetan-3-yl)piperazin-1-yl]phenyl]amino)-5-bromo-1-methylpyrazin-2-one (2.50 g, 5.564 mmol, 1.00 equiv), DCM (30.00 mL, 471.901 mmol, 84.82 equiv), DIEA (1.44 g, 11.142 mmol, 2.00 equiv). This was followed by the addition of acryloyl chloride (0.65 g, 7.182 mmol, 1.29 equiv), in portions at 0 degrees C. The resulting solution was stirred for 1 hr at 0 degrees C. in a water/ice bath. The reaction was then quenched by the addition of 1 mL of MeOH. The resulting mixture was concentrated. The residue was applied onto a silica gel column and eluted with dichloromethane/methanol (10:1). This resulted in 2.8 g (80.98%) of N-[5-[(6-bromo-4-methyl-3-oxopyrazin-2-yl)amino]-2-[(2S)-2-methyl-4-(oxetan-3-yl)piperazin-1-yl]phenyl]prop-2-enamide as a yellow solid. LCMS-9 (ES, m/z): M+1: 503/505

Synthesis of N-(methoxymethyl)-N-methyl-4,5,6,7-tetrahydro-1-benzothiophene-2-carboxamide: Into a 250-mL 3-necked round-bottom flask purged and maintained with an inert atmosphere of nitrogen, was placed 4,5,6,7-tetrahydro-1-benzothiophene-2-carboxylic acid (8.0 g, 43.95 mmol, 1.0 equiv), DMF (193 mg, 2.197 mmol, 0.05 equiv), DCM (150 ml). This was followed by the addition of oxalyl chloride (6.1 g, 48.35 mmol, 1.1 equiv) dropwise with stirring at 0 degrees C. The resulting solution was stirred for 1 h in a water/ice bath. To this was added TEA (13.3 g, 131.85 mmol, 3.0 equiv) and N,O-dimethylhydroxylamine HCl salt (4.3 g, 43.95 mmol, 1.0 equiv) at 0 degrees C. The resulting solution was stirred for 2h at room temperature. The resulting solution was diluted with 100 mL of water. The resulting solution was extracted with 3×150 mL of dichloromethane and the organic layers combined. The resulting mixture was washed with 2×100 ml of water and 1×100 mL of brine. The mixture was dried over anhydrous sodium sulfate and concentrated. The residue was applied onto a silica gel column with ethyl acetate/petroleum ether (1:10). This resulted in 9.0 g of N-(methoxymethyl)-N-methyl-4,5,6,7-tetrahydro-1-benzothiophene-2-carboxamide as a white solid. LCMS-10 (ES, m/z): M+1: 226

Synthesis of 3-chloro-1-(4,5,6,7-tetrahydro-1-benzothiophen-2-yl)propan-1-one: Into a 250-mL 3-necked round-bottom flask purged and maintained with an inert atmosphere of nitrogen, was placed N-methoxy-N-methyl-4,5,6,7-tetrahydro-1-benzothiophene-2-carboxamide (8.00 g, 35.560 mmol, 1.00 equiv), THF (40.00 mL). This was followed by the addition of bromo(ethenyl)magnesium(1M in THF) (160.00 mL, 142.220 mmol, 4.00 equiv) dropwise with stirring at −10 degrees C. The resulting solution was stirred for 4h at 0 degrees C. in an ice/salt bath. The reaction was then quenched by the addition of 40 mL of 2M HCl. The resulting solution was extracted with 2×100 mL of ethyl acetate and the organic layers combined. The resulting mixture was washed with 2×100 ml of water and 1×100 mL of brine. The mixture was dried over anhydrous sodium sulfate and concentrated. The resulting solution was diluted with 80 mL of DCM. The residue was dissolved in 40 mL of 2M in $Et_2O$. The resulting mixture was concentrated. The residue was applied onto a silica gel column with ethyl acetate/petroleum ether (1:5). This resulted in 2.3 g of 3-chloro-1-(4,5,6,7-tetrahydro-1-benzothiophen-2-yl)propan-1-one as yellow oil. LCMS-11 (ES, m/z): M+1: 229

Synthesis of 7-thiatricyclo[6.4.0.0^[2, 6]]dodeca-1(8),2(6)-dien-5-one: Into a 100-mL round-bottom flask, was placed 3-chloro-1-(4,5,6,7-tetrahydro-1-benzothiophen-2-yl)propan-1-one (2.30 g, 10.090 mmol, 1.00 equiv), $H_2SO_4$ (20.00 mL). The resulting solution was stirred for 16 hr at 95 degrees C. in an oil bath. The reaction mixture was cooled to room temperature with a water/ice bath. The resulting solution was diluted with 50 mL of water. The resulting solution was extracted with 2×50 mL of ethyl acetate and the organic layers combined. The resulting mixture was washed with 1×50 ml of brine. The mixture was dried over anhydrous sodium sulfate and concentrated. The residue was applied onto a silica gel column with ethyl acetate/petroleum ether (1:5). This resulted in 0.8 g of 7-thiatricyclo[6.4.0.0^[2,6]]dodeca-1(8),2(6)-dien-5-one as brown oil. LCMS-12 (ES, m/z): M+1: 193

Synthesis of N-[(5E)-7-thiatricyclo[6.4.0.0^[2,6]]dodeca-1(8),2(6)-dien-5-ylidene]hydroxylamine: Into a 100-mL 3-necked round-bottom flask purged and maintained with an inert atmosphere of nitrogen, was placed $NH_2OH \cdot HCl$ (1.41 g, 20.313 mmol, 5.00 equiv), MeOH (30.00 mL). This was followed by the addition of NaOAc (1.66 g, 20.313 mmol, 5.00 equiv) at 0 degrees C. and the solution was stirred for 30 min. To this was added 7-thiatricyclo[6.4.0.0^[2,6]]dodeca-1(8),2(6)-dien-5-one (780.00 mg, 4.063 mmol, 1.00 equiv) at 0 degrees C. The resulting solution was stirred for 16h at room temperature. The resulting mixture was concentrated. This resulted in 300 mg of N-[(5E)-7-thiatricyclo[6.4.0.0^[2,6]]dodeca-1(8),2(6)-dien-5-ylidene]hydroxylamine as brown oil. LCMS-13 (ES, m/z): M+1: 208

Synthesis of 8-thia-5-azatricyclo[7.4.0.0^[2,7]]trideca-1(9),2(7)-dien-6-one: Into a 50-mL round-bottom flask purged and maintained with an inert atmosphere of nitrogen, was placed N-[(5E)-7-thiatricyclo[6.4.0.0^[2,6]]dodeca-1(8),2(6)-dien-5-ylidene]hydroxylamine (295.00 mg, 1.425 mmol, 1.00 equiv), PPA (6.00 mL). The resulting solution was stirred for 18h at 80 degrees C. in an oil bath. The reaction mixture was cooled to room temperature with a water bath. The resulting solution was diluted with 20 mL of water. The solids were collected by filtration. This resulted in 260 mg of 8-thia-5-azatricyclo[7.4.0.0^[2,7]]trideca-1(9),2(7)-dien-6-one as an off-white solid. LCMS-14 (ES, m/z): M+1: 208

Synthesis of 5-[4-bromo-3-[(oxan-2-yloxy) methyl]pyridin-2-yl]-8-thia-5-azatricyclo[7.4.0.0^[2, 7]]trideca-1(9), 2(7)-dien-6-one: Into a 50-mL round-bottom flask purged and maintained with an inert atmosphere of nitrogen, was placed 8-thia-5-azatricyclo[7.4.0.0^[2,7]]trideca-1(9),2(7)-dien-6-one (260.00 mg, 1.251 mmol, 1.00 equiv), 2,4-dibromo-3-[(oxan-2-yloxy)methyl]pyridine (873.00 mg, 1.875 mmol, 1.50 equiv), CuI (182.00 mg, 0.751 mmol, 0.60 equiv), $Cs_2CO_3$ (1.01 g, 2.502 mmol, 2.00 equiv), DMA (10.00 mL), 1,10-phenanthroline (182.00 mg, 0.751 mmol, 0.60 equiv). The resulting solution was stirred for 4h at 110 degrees C. in an oil bath. The reaction mixture was cooled to room temperature with a water bath. The solids were filtered out. The resulting solution was diluted with 20 mL of water. The resulting solution was extracted with 2×20 mL of ethyl acetate and the organic layers combined. The resulting mixture was washed with 3×20 ml of water. The resulting mixture was washed with 1×20 mL of brine. The mixture was dried over anhydrous sodium sulfate and concentrated. The residue was applied onto a silica gel column with dichloromethane/methanol (10:1). This resulted in 360 mg of 5-[4-bromo-3-[(oxan-2-yloxy)methyl]pyridin-2-yl]-8-thia-5-azatricyclo[7.4.0.0^[2,7]]trideca-1(9),2(7)-dien-6-one as dark brown oil. LCMS-15 (ES, m/z): M+1: 477

Synthesis of 3-[(oxan-2-yloxy)methyl]-2-[6-oxo-8-thia-5-azatricyclo[7.4.0.0^[2,7]]trideca-1(9),2(7)-dien-5-yl]pyridin-4-ylboronic acid: Into a 50-mL round-bottom flask purged and maintained with an inert atmosphere of nitrogen, was placed 5-[4-bromo-3-[(oxan-2-yloxy)methyl]pyridin-2-yl]-8-thia-5-azatricyclo[7.4.0.0^[2,7]]trideca-1(9),2(7)-dien-6-one (360.00 mg, 0.756 mmol, 1.00 equiv), bis(pinacolato)diboron (102.00 mg, 1.891 mmol, 2.50 equiv), KOAc (222.00 mg, 2.268 mmol, 3.00 equiv), $Pd(dppf)Cl_2$ (56.00 mg, 0.076 mmol, 0.10 equiv), Dioxane (20.00 mL). The resulting solution was stirred for 2h at 100 degrees C. in an oil bath. The reaction mixture was cooled to room temperature with a water bath. The solids were filtered out. The resulting mixture was concentrated. The crude product was purified by Flash-Prep-HPLC with the following conditions (CombiFlash-1): Column, C18 silica gel; mobile phase, $H_2O$: ACN=20% increasing to $H_2O$: ACN=65% within 10 min; Detector, 220 nm. This resulted in 180 mg of 3-[(oxan-2-yloxy)methyl]-2-[6-oxo-8-thia-5-azatricyclo[7.4.0.0^[2, 7]]trideca-1(9),2(7)-dien-5-yl]pyridin-4-ylboronic acid as an off-white solid. LCMS-16 (ES, m/z): M+1: 443

Synthesis of 5-[1-hydroxy-3H-[1, 2]oxaborolo [4, 3-c]pyridin-4-yl]-8-thia-5-azatricyclo[7.4.0.0^[2, 7]]trideca-1(9), 2(7)-dien-6-one: Into a 50-mL round-bottom flask, was placed 3-[(oxan-2-yloxy)methyl]-2-[6-oxo-8-thia-5-azatricyclo[7.4.0.0^[2,7]]trideca-1(9),2(7)-dien-5-yl]pyridin-4-ylboronic acid (160.00 mg, 0.362 mmol, 1.00 equiv), 4N HCl in Dioxane (5.00 mL). The resulting solution was stirred for 1 hr at room temperature. The solids were collected by filtration. The solids was washed by water 10 ml. This resulted in 100 mg of 5-[1-hydroxy-3H-[1,2]oxaborolo[4,3-c]pyridin-4-yl]-8-thia-5-azatricyclo[7.4.0.0^[2,7]]trideca-1(9),2(7)-dien-6-one as an off-white solid. LCMS-17 (ES, m/z): M+1: 341

Synthesis of N-[5-([6-[3-(hydroxymethyl)-2-[6-oxo-8-thia-5-azatricyclo[7.4.0.0 ^[2,7]]trideca-1(9),2(7)-dien-5-yl]

pyridin-4-yl]-4-methyl-3-oxopyrazin-2-yl]amino)-2-[(2S)-2-methyl-4-(oxetan-3-yl)piperazin-1-yl]phenyl]prop-2-enamide: Into a 50-mL round-bottom flask purged and maintained with an inert atmosphere of nitrogen, was placed 5-[1-hydroxy-3H-[1,2]oxaborolo[4,3-c]pyridin-4-yl]-8-thia-5-azatricyclo[7.4.0.0^[2,7]]trideca-1(9),2(7)-dien-6-one (80.00 mg, 0.235 mmol, 1.00 equiv), N-[5-[(6-bromo-4-methyl-3-oxopyrazin-2-yl)amino]-2-[(2S)-2-methyl-4-(oxetan-3-yl)piperazin-1-yl]phenyl]prop-2-enamide (100.00 mg, 0.235 mmol, 1.00 equiv), $K_3PO_4$ (100.00 mg, 0.471 mmol, 2.00 equiv), Toluene (5.00 mL), BrettPhos Pd G3 (21.00 mg, 0.024 mmol, 0.10 equiv). The resulting solution was stirred for 1 hr at 90 degrees C. in an oil bath. The reaction mixture was cooled to room temperature with a water bath. The solids were filtered out. The resulting mixture was concentrated. The residue was applied onto a silica gel column with dichloromethane/methanol (10:1). The crude product (100 mg) was purified by Prep-HPLC with the following conditions: column, X-Bridge Prep C18 19*150 mm 5 um; mobile phase, A: water (it contains 10 mM $NH_4HCO_3$ 0.05% ammonia); B: ACN; Gradient: 20-45% B in 8 min; Flow rate: 20 mL/min; detector, UV 220 nm. The collected solution was concentrated under vacuum to remove $CH_3CN$ and the resulting solution was dried by lyophilization. This resulted in 12 mg of N-[5-([6-[3-(hydroxymethyl)-2-[6-oxo-8-thia-5-azatricyclo[7.4.0.0^[2,7]]trideca-1(9),2(7)-dien-5-yl]pyridin-4-yl]-4-methyl-3-oxopyrazin-2-yl]amino)-2-[(2S)-2-methyl-4-(oxetan-3-yl)piperazin-1-yl]phenyl]prop-2-enamide as a white solid. LCMS-18 (ES, m/z): M+1: 737, $^1H$ NMR (300 MHz, DMSO-$d_6$, ppm) δ 9.26 (s, 1H), 9.19 (s, 1H), 9.10 (s, 1H), 8.47-8.49 (d, J=6.0 Hz, 1H), 7.91-7.93 (d, J=6.0 Hz, 1H), 7.72 (s, 1H), 7.59-7.61 (d, J=6.0 Hz, 1H), 7.25-7.27 (d, J=6.0 Hz, 1H), 6.57-6.60 (m, 1H), 6.29-6.31 (d, J=6.0 Hz, 1H), 5.78-5.81 (d, J=9.0 Hz, 1H), 4.95 (m, 1H), 4.53 (m, 6H), 4.18 (m, 1H), 3.86 (m, 1H), 3.57 (s, 3H), 3.46-3.48 (m, 1H), 3.10 (s, 1H), 3.01-2.87 (m, 2H), 2.78-2.70 (m, 6H), 2.68-2.73 (m, 2H), 2.21-2.30 (m, 1H), 1.92 (t, J=10.0 Hz, 1H), 1.81 (m, 4H), 0.72-0.74 (d, J=6.0 Hz, 3H).

Example 37: Preparation of N-(5-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxopyrazin-2-yl]amino]-2-[(2S)-2-methyl-4-[(2R,4R)-2-methyloxan-4-yl]piperazin-1-yl]phenyl)prop-2-enamide hydrochloride (cis) and N-(5-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxopyrazin-2-yl]amino]-2-[(2S)-2-methyl-4-[(2R,4S)-2-methyloxan-4-yl]piperazin-1-yl]phenyl)prop-2-enamide (trans)

Synthesis of [(3,3-dimethylcyclopent-1-en-1-yl)oxy]trimethylsilane: Into a 10-L 4-necked round-bottom flask purged and maintained with an inert atmosphere of nitrogen, was placed CuCl (20.60 g, 208.083 mmol, 0.05 equiv), LiCl (17.64 g, 416.108 mmol, 0.10 equiv), THF (2.50 L). This was followed by the addition of 2-cyclopenten-1-one, 3-methyl-(400.00 g, 4161.075 mmol, 1.00 equiv) at −5 to 5 degrees C. To this was added TMSCl (474.67 g, 4369.129 mmol, 1.05 equiv) dropwise with stirring at −5 to 5 degrees C. To the mixture was added MeMgCl (1670.00 mL, 14495.069 mmol, 3.48 equiv) dropwise with stirring at −5 to 10 degrees C. The resulting solution was stirred for 2 h at −5 to 10 degrees C. in an ice/salt bath. The reaction was then quenched by the addition of 34 g of MeOH. The resulting solution was diluted with 5 L of $NH_4Cl$. The solids were filtered out. The resulting solution was extracted with 3×5 L of petroleum ether dried over anhydrous sodium sulfate and concentrated. This resulted in 780 g (crude) of [(3,3-dimethylcyclopent-1-en-1-yl)oxy]trimethylsilane as yellow oil. GC-MS: (ES, m/z): M: 184

Synthesis of 3,3-dimethylcyclopentanone: Into a 20-L 4-necked round-bottom flask, was placed [(3,3-dimethylcyclopent-1-en-1-yl)oxy]trimethylsilane (780.00 g, 4230.990 mmol, 1.00 equiv), DCM (7.8 L), $H_2O$ (30.49 g, 1692.396 mmol, 0.4 equiv). This was followed by the addition of $POCl_3$ (214.09 g, 1396.251 mmol, 0.33 equiv) dropwise with stirring at 25 to 30 degrees C. The resulting solution was stirred for 0.5 hr at 25 degrees C. This solvent straight used for next step. GC-MS: (ES, m/z): M: 112

Synthesis of 3,3-dimethylcyclopentanon: Into a 20-L 4-necked round-bottom flask, was placed 3,3-dimethylcyclopentan-1-one (crude) in DCM (7.80 L). This was followed by the addition of DMF (619 g, 2.0 equiv) dropwise with stirring at 25 degrees C. To this was added $POCl_3$ (1362 g, 2.1 equiv) dropwise with stirring at 40 degrees C. The resulting solution was stirred for overnight at 40 degrees C. in an oil bath. The reaction was then quenched by the addition of 2000 g of $K_3PO_4$. The resulting solution was extracted with 3×10 L of dichloromethane dried over anhydrous sodium sulfate and concentrated. This resulted in 530 g of 2-chloro-4,4-dimethylcyclopent-1-ene-1-carbaldehyde as a brown solid. GC-MS: (ES, m/z): M: 158

Synthesis of 4,4-dimethyl-1,10-diazatricyclo[6.4.0.0^[2,6]]dodeca-2(6),7-dien-9-one: Into a 5-L 4-necked round-bottom flask, was placed 2-chloro-4,4-dimethylcyclopent-1-ene-1-carbaldehyde (474.00 g, 2988.085 mmol, 1.00 equiv), DMF (3 L), piperazin-2-one (299.17 g, 2988.084 mmol, 1.00 equiv), DIEA (463.43 g, 3585.703 mmol, 1.2 equiv). The resulting solution was stirred for overnight at 115 degrees C. in an oil bath. The reaction mixture was cooled to room temperature with a water/ice bath. The solids were collected by filtration. The resulting mixture was washed with 3×2 L of $H_2O$ and 3×2 L of PE. The solid was dried in an oven under reduced pressure. This resulted in 230 g (37.68%) of 4,4-dimethyl-1,10-diazatricyclo[6.4.0.0^[2,6]]dodeca-2(6),7-dien-9-one as a grey solid. LC-MS: (ES, m/z): M+1: 205

Synthesis of 2,4-dibromopyridine-3-carbaldehyde, Into a 1000-mL 3-necked round-bottom flask, was placed 2,4-dibromopyridine (40.00 g, 168.852 mmol, 1.00 equiv), THF (400.00 mL). This was followed by the addition of LDA (2M in hexane, 126.60 mL, 1.5 equiv) dropwise with stirring at −78 degrees C. The resulting solution was stirred for 1 h at −78 degrees C. Then add DMF (16.04 g, 219.507 mmol, 1.3 equiv) dropwise with stirring at −78 degrees C. The resulting solution was stirred for 0.5 hr at −78 degrees C. The reaction was then quenched by the addition of 500 mL of $NH_4Cl$. The resulting solution was extracted with 3×500 mL of ethyl acetate concentrated. The residue was applied onto a silica gel column and eluted with ethyl acetate/petroleum ether (0:1-1:1). This resulted in 24.4 g (54.55%) of 2,4-dibromopyridine-3-carbaldehyde as a white solid. LC-MS: (ES, m/z): M+1: 264

Synthesis of (2,4-dibromopyridin-3-yl)methanol, Into a 100-mL round-bottom flask, was placed 2,4-dibromopyridine-3-carbaldehyde (2.00 g, 7.550 mmol, 1.00 equiv), EtOH (30.00 mL). This was followed by the addition of $NaBH_4$ (285.64 mg, 7.550 mmol, 1 equiv), in portions at 0 degrees C. The resulting solution was stirred for 3 h at room temperature. The reaction was then quenched by the addition of 30 mL of water. The resulting solution was extracted with 3×30 mL of ethyl acetate concentrated. The residue was applied onto a silica gel column and eluted with ethyl acetate/petroleum ether (1:1). The collected fractions were combined and concentrated. This resulted in 1.4 g (69.47%) of (2,4-dibromopyridin-3-yl)methanol as a light yellow solid. LC-MS: (ES, m/z): M+1: 266

Synthesis of 2,4-dibromo-3-[(oxan-2-yloxy)methyl]pyridine, Into a 100-mL round-bottom flask, was placed (2,4-dibromopyridin-3-yl)methanol (1.40 g, 5.245 mmol, 1.00 equiv), DCM (30.00 mL, 0.353 mmol, 0.07 equiv), PPTS (131.81 mg, 0.525 mmol, 0.10 equiv), DHP (661.79 mg, 7.868 mmol, 1.50 equiv). The resulting solution was stirred for overnight at 45 degrees C. in an oil bath. The reaction was then quenched by the addition of 30 mL of water. The resulting solution was extracted with 3×30 mL of dichloromethane concentrated. The residue was applied onto a silica gel column and eluted with ethyl acetate/petroleum ether (1:1). The collected fractions were combined and concentrated. This resulted in 1.5 g (80%) of 2,4-dibromo-3-[(oxan-2-yloxy)methyl]pyridine as colorless oil. LC-MS: (ES, m/z): M+1: 350

Synthesis of 10-[4-bromo-3-[(oxan-2-yloxy)methyl]pyridin-2-yl]-4,4-dimethyl-1,10-diazatricyclo[6.4.0.0^[2,6]]dodeca-2(6),7-dien-9-one, Into a 100-mL round-bottom flask purged and maintained with an inert atmosphere of nitrogen, was placed 4,4-dimethyl-1,10-diazatricyclo[6.4.0.0^[2,6]]dodeca-2(6),7-dien-9-one (1.00 g, 4.895 mmol, 1.00 equiv), dioxane (40.00 mL, 0.454 mmol, 0.09 equiv), $Cs_2CO_3$ (3.19 g, 9.791 mmol, 2 equiv), 2,4-dibromo-3-[(oxan-2-yloxy)methyl]pyridine (1.72 g, 4.900 mmol, 1.00 equiv), $Pd_2(dba)_3$ (448.28 mg, 0.490 mmol, 0.1 equiv), XantPhos (283.26 mg, 0.490 mmol, 0.1 equiv). The resulting solution was stirred for 1 h at 100 degrees C. in an oil bath. The reaction was then quenched by the addition of 40 mL of water. The resulting solution was extracted with 3×40 mL of ethyl acetate concentrated. The residue was applied onto a silica gel column and eluted with ethyl acetate/petroleum ether (1:1). The collected fractions were combined and concentrated. This resulted in 900 mg (38.75%) of 10-[4-bromo-3-[(oxan-2-yloxy)methyl]pyridin-2-yl]-4,4-dimethyl-1,10-diazatricyclo[6.4.0.0^[2,6]]dodeca-2(6),7-dien-9-one as a brown solid. LC-MS: (ES, m/z): M+1: 474

Synthesis of 2-[4,4-dimethyl-9-oxo-1,10-diazatricyclo[6.4.0.0^[2,6]]dodeca-2(6),7-dien-10-yl]-3-[(oxan-2-yloxy)methyl]pyridin-4-ylboronic acid, Into a 100-mL round-bottom flask purged and maintained with an inert atmosphere of nitrogen, was placed 10-[4-bromo-3-[(oxan-2-yloxy)methyl]pyridin-2-yl]-4,4-dimethyl-1,10-diazatricyclo[6.4.0.0^[2,6]]dodeca-2(6),7-dien-9-one (1.00 g, 2.108 mmol, 1.00 equiv), dioxane (10.00 mL), bis(pinacolato)diboron (1.34 g, 5.277 mmol, 2.50 equiv), KOAc (620.00 mg, 6.317 mmol, 3.00 equiv), $Pd(dppf)Cl_2$ (172.00 mg, 0.211 mmol, 0.10 equiv). The resulting solution was stirred for 2 h at 100 degrees C. in an oil bath. The reaction mixture was cooled to room temperature. The solids were filtered out. The resulting mixture was concentrated under vacuum. This resulted in 920 mg (crude) of 2-[4,4-dimethyl-9-oxo-1,10-diazatricyclo[6.4.0.0^[2,6]]dodeca-2(6),7-dien-10-yl]-3-[(oxan-2-yloxy)methyl]pyridin-4-ylboronic acid as brown oil. LC-MS: (ES, m/z): M+1: 436

Synthesis of 10-[1-hydroxy-3H-[1,2]oxaborolo[4,3-c]pyridin-4-yl]-4,4-dimethyl-1,10-diazatricyclo[6.4.0.0^[2,6]]dodeca-2(6),7-dien-9-one, Into a 100-mL round-bottom flask, was placed 2-[4,4-dimethyl-9-oxo-1,10-diazatricyclo[6.4.0.0^[2,6]]dodeca-2(6),7-dien-10-yl]-3-[(oxan-2-yloxy)methyl]pyridin-4-ylboronic acid (920 mg, 1.00 equiv, crude), dioxane (10 mL), HCl (6N, 10 mL). The resulting solution was stirred for 1 h at 25 degrees C. The resulting mixture was concentrated under vacuum. The crude product was purified by Flash-Prep-HPLC with the following conditions: Column, C18 reversed phase column; mobile phase, $H_2O$ (0.05% $NH_3 \cdot H_2O$) and $CH_3CN$ (5% $CH_3CN$ up to 30% in 15 min); Flow rate: 60 mL/min; Detector, 254/220 nm. This resulted in 350 mg of 10-[1-hydroxy-3H-[1,2]oxaborolo[4,3-c]pyridin-4-yl]-4,4-dimethyl-1,10-diazatricyclo[6.4.0.0^[2,6]]dodeca-2(6),7-dien-9-one as a light yellow solid. LC-MS: (ES, m/z): M+1: 338

Synthesis of tert-butyl (3S)-4-[4-[(6-bromo-4-methyl-3-oxopyrazin-2-yl)amino]-2-nitrophenyl]-3-methylpiperazine-1-carboxylate: Into a 50-mL round-bottom flask, was placed 5-bromo-3-[(4-fluoro-3-nitrophenyl)amino]-1-methylpyrazin-2-one (2.00 g, 5.829 mmol, 1.00 equiv), NMP (20.00 mL), tert-butyl (3S)-3-methylpiperazine-1-carboxylate (1.17 g, 5.842 mmol, 1.00 equiv), DIEA (2.26 g, 17.487 mmol, 3.00 equiv). The resulting solution was stirred for 48 h at 110° C. in an oil bath. The resulting solution was diluted with 100 mL of $H_2O$. The resulting solution was extracted with 3×50 mL of dichloromethane/methanol (10:1). The resulting mixture was washed with 3×20 ml of NaCl. The resulting mixture was concentrated. The residue was applied onto a silica gel column with dichloromethane/methanol (10:1). This resulted in 3 g (59.00%) of tert-butyl (3S)-4-[4-[(6-bromo-4-methyl-3-oxopyrazin-2-yl)amino]-2-nitrophenyl]-3-methylpiperazine-1-carboxylate as a brown solid. LC-MS: (ES, m/z): M+1: 523

Synthesis of 5-bromo-1-methyl-3-([4-[(2S)-2-methylpiperazin-1-yl]-3-nitrophenyl]amino)pyrazin-2-one: Into a 100-mL round-bottom flask, was placed tert-butyl (3S)-4-[4-[(6-bromo-4-methyl-3-oxopyrazin-2-yl)amino]-2-nitrophenyl]-3-methylpiperazine-1-carboxylate (3.00 g, 1 equiv, 60%), HCl (2M) in 1,4-dioxane (30.00 mL). The resulting solution was stirred for 13 h at room temperature. The resulting mixture was concentrated. The resulting solution was diluted with 30 mL of $H_2O$. The pH value of the solution was adjusted to 8 with $NH_3$—$H_2O$. The resulting solution was extracted with 3×15 mL of dichloromethane concentrated. The residue was applied onto a silica gel column with dichloromethane/methanol (10:1). This resulted in 700 mg (48.09%) of 5-bromo-1-methyl-3-([4-[(2S)-2-methylpiperazin-1-yl]-3-nitrophenyl]amino)pyrazin-2-one as a red solid. LC-MS: (ES, m/z): M+1: 423

Synthesis of 5-bromo-1-methyl-3-([4-[(2S)-2-methyl-4-(2-methyloxan-4-yl)piperazin-1-yl]-3-nitrophenyl]amino)pyrazin-2-one: Into a 100-mL round-bottom flask, was placed 5-bromo-1-methyl-3-([4-[(2S)-2-methylpiperazin-1-yl]-3-nitrophenyl]amino)pyrazin-2-one (2.00 g, 4.725 mmol, 1.00 equiv), THF (30.00 mL), HOAc (50.00 mg, 0.833 mmol, 0.18 equiv), 2-methyloxan-4-one (500.00 mg, 4.380 mmol, 0.93 equiv), $NaBH(OAc)_3$ (1.86 g, 8.776 mmol, 1.86 equiv). The resulting solution was stirred overnight at 30 degrees C. in an oil bath. The resulting mixture was concentrated under vacuum. The residue was applied onto a silica gel column with dichloromethane/methanol (20:1). This resulted in 1.38 g (56.01%) of 5-bromo-1-methyl-3-([4-[(2S)-2-methyl-4-(2-methyloxan-4-yl)piperazin-1-yl]-3-nitrophenyl]amino)pyrazin-2-one as a red solid (cis and trans mixtures). LC-MS: (ES, m/z): M+1: 521

Synthesis of 3-([3-amino-4-[(2S)-2-methyl-4-(2-methyloxan-4-yl)piperazin-1-yl]phenyl]amino)-5-bromo-1-methylpyrazin-2-one: Into a 250-mL round-bottom flask, was placed 5-bromo-1-methyl-3-([4-[(2S)-2-methyl-4-(2-methyloxan-4-yl)piperazin-1-yl]-3-nitrophenyl]amino)pyrazin-2-one (1.38 g, 2.647 mmol, 1.00 equiv), EtOH (30.00 mL), $H_2O$ (10.00 mL), Fe (892.00 mg, 15.973 mmol, 6.04 equiv), $NH_4Cl$ (848.00 mg, 15.853 mmol, 5.99 equiv). The resulting solution was stirred for 2 hr at 70 degrees C. in an oil bath. The reaction mixture was cooled to room temperature. The resulting solution was diluted with 300 mL of water. The resulting solution was extracted with 3×100 mL of dichloromethane and the organic layers combined. The resulting mixture was washed with 1×500 ml of brine. The mixture was dried over anhydrous sodium sulfate and concentrated under vacuum. The residue was applied onto a silica gel column with dichloromethane/methanol (20:1). This resulted in 950 mg (73.04%) of 3-([3-amino-4-[(2S)-2-methyl-4-(2-methyloxan-4-yl)piperazin-1-yl]phenyl]amino)-5-bromo-1-methylpyrazin-2-one as a light yellow solid. LC-MS: (ES, m/z): M+1: 491

Synthesis of N-[5-[(6-bromo-4-methyl-3-oxopyrazin-2-yl)amino]-2-[(2S)-2-methyl-4-[(2R,4R)-2-methyloxan-4-yl]piperazin-1-yl]phenyl]prop-2-enamide (cis) and N-[5-[(6-bromo-4-methyl-3-oxopyrazin-2-yl)amino]-2-[(2S)-2-methyl-4-[(2R,4S)-2-methyloxan-4-yl]piperazin-1-yl]phenyl]prop-2-enamide (trans): Into a 100-mL round-bottom flask, was placed 3-([3-amino-4-[(2S)-2-methyl-4-(2-methyloxan-4-yl)piperazin-1-yl]phenyl]amino)-5-bromo-1-methylpyrazin-2-one (950.00 mg, 1.933 mmol, 1.00 equiv), DCM (10.00 mL), DIEA (501.00 mg, 3.876 mmol, 2.01 equiv), acryloyl chloride (174.00 mg, 1.922 mmol, 0.99 equiv). The resulting solution was stirred for 2 hr at 25 degrees C. The resulting mixture was concentrated under vacuum. The residue was applied onto a silica gel column with dichloromethane/methanol (20:1). The crude product was purified by Prep-HPLC with the following conditions (Prep-HPLC-006): Column, XBridge Shield RP18 OBD Column, Sum, 19*150 mm; mobile phase, Water (0.05% $NH_3 \cdot H_2O$) and ACN (40% Phase B up to 90% in 7 min); Detector, UV 254/220 nm. This resulted in 420 mg (39.83%) of N-[5-[(6-bromo-4-methyl-3-oxopyrazin-2-yl)amino]-2-[(2S)-2-methyl-4-[(2R,4R)-2-methyloxan-4-yl]piperazin-1-yl]phenyl]prop-2-enamide (cis) as a yellow solid and 140 mg (13.28%) of N-[5-[(6-bromo-4-methyl-3-oxopyrazin-2-yl)amino]-2-[(2S)-2-methyl-4-[(2R,4S)-2-methyloxan-4-yl]piperazin-1-yl]phenyl]prop-2-enamide (trans) as a yellow solid. LC-MS: (ES, m/z): M+1: 545; H-NMR (300 MHz, Chloroform-d, ppm) δ 9.19 (s, 1H), 8.61 (d, J=2.5 Hz, 1H), 8.38 (s, 1H), 7.98 (dd, J=8.7, 2.6 Hz, 1H), 7.29 (s, 1H), 6.77 (s, 1H), 6.48-6.21 (m, 2H), 5.80 (dd, J=9.7, 1.7 Hz, 1H), 4.16-4.03 (m, 1H), 3.54 (s, 3H), 3.48 (dt, J=11.8, 5.8 Hz, 2H), 3.19-2.76 (m, 5H), 2.63-2.37 (m, 2H), 2.13 (t, J=10.1 Hz, 1H), 1.96-1.50 (m, 5H), 1.26 (d, J=6.1 Hz, 4H), 0.81 (d, J=6.1 Hz, 3H).

Synthesis of N-(5-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxopyrazin-2-yl]amino]-2-[(2S)-2-methyl-4-[(2R,4R)-2-methyloxan-4-yl]piperazin-1-yl]phenyl)prop-2-enamide hydrochloride (cis): Into a 40-mL vial purged and maintained with an inert atmosphere of nitrogen, was placed N-[5-[(6-bromo-4-methyl-3-oxopyrazin-2-yl)amino]-2-[(2S)-2-methyl-4-[(2R,4R)-2-methyloxan-4-yl]piperazin-1-yl]phenyl]prop-2-enamide (105.00 mg, 0.192 mmol, 1.00 equiv), dioxane (5.00 mL), $H_2O$ (0.5 mL), 10-[1-hydroxy-3H-[1,2]oxaborolo[4,3-c]pyridin-4-yl]-4,4-dimethyl-1,10-diazatricyclo[6.4.0.0^[2,6]]dodeca-2(6),7-dien-9-one (130.00 mg, 0.386 mmol, 2.00 equiv), $K_2CO_3$ (133.00 mg, 0.962 mmol, 5.00 equiv), Xphos Pd G3 (33.00 mg, 0.039 mmol, 0.20 equiv). The resulting solution was stirred for 1 hr at 90 degrees C. in an oil bath. The reaction mixture was cooled to room temperature. The resulting mixture was concentrated under vacuum. The crude product was purified by Prep-HPLC with the following conditions: Column, XBridge Shield RP18 OBD Column, Sum, 19*150 mm; mobile phase, Water (0.05% FA) and ACN (40% Phase B up to 70% in 7 min); Detector, UV 254/220 nm. The collected solution was concentrated under vacuum to remove $CH_3CN$ and the resulting solution was dried by lyophilization (added with Conc.HCl (1 drop)). This resulted in 40 mg (26.78%) of N-(5-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxopyrazin-2-yl]amino]-2-[(2S)-2-methyl-4-[(2R,4R)-2-methyloxan-4-yl]piperazin-1-yl]phenyl)prop-2-enamide hydrochloride (cis) as a yellow solid. LC-MS: (ES, m/z): M+1: 776; H-NMR (300 MHz, DMSO-$d_6$, ppm) δ 10.75 (s, 1H), 9.23 (d, J=14.3 Hz, 2H), 9.10 (s, 1H), 8.48 (d, J=5.2 Hz, 1H), 7.95 (d, J=5.2 Hz, 1H), 7.77 (s, 1H), 7.61 (d, J=8.5 Hz, 1H), 7.25 (d, J=8.7 Hz, 1H), 6.66-6.53 (m, 2H), 6.29 (d, J=17.0 Hz, 1H), 5.80 (dd, J=10.0, 1.8 Hz, 1H), 5.03 (s, 1H), 4.68-4.42 (m, 2H), 4.22 (s, 3H), 3.97-3.65 (m, 3H), 3.57 (s, 4H), 3.00 (dd, J=29.9, 17.9 Hz, 3H), 2.75 (d, J=11.5 Hz, 2H), 2.59 (d, J=4.7 Hz, 3H), 2.44 (s, 2H), 2.33-2.25 (m, 1H), 2.00 (s, 1H), 1.91-1.57 (m, 4H), 1.41 (d, J=11.1 Hz, 1H), 1.23 (s, 6H), 1.08 (t, J=6.2 Hz, 3H), 0.82-0.70 (m, 3H).

Synthesis of N-(5-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxopyrazin-2-yl]amino]-2-[(2S)-2-methyl-4-[(2R,4S)-2-methyloxan-4-yl]piperazin-1-yl]phenyl)prop-2-enamide (trans): Into a 40-mL vial purged and maintained with an inert atmosphere of nitrogen, was placed N-[5-[(6-bromo-4-methyl-3-oxopyrazin-2-yl)amino]-2-[(2S)-2-methyl-4-[(2R,4S)-2-methyloxan-4-yl]piperazin-1-yl]phenyl]prop-2-enamide (35.00 mg, 0.064 mmol, 1.00 equiv), dioxane (2.00 mL), $H_2O$ (0.20 mL), $K_2CO_3$ (44.00 mg, 0.318 mmol, 4.96 equiv), 10-[1-hydroxy-3H-[1,2]oxaborolo[4,3-c]pyridin-4-yl]-4,4-dimethyl-1,10-diazatricyclo[6.4.0.0^[2,6]]dodeca-2(6),7-dien-9-one (43.00 mg, 0.128 mmol, 1.99 equiv), Xphos Pd G3 (11.00 mg, 0.013 mmol, 0.20 equiv). The resulting solution was stirred for 1 hr at 90 degrees C. in an oil bath. The reaction mixture was cooled to room temperature. The resulting mixture was concentrated under vacuum. The crude product was purified by Prep-HPLC with the following conditions: Column, XBridge Shield RP18 OBD Column, Sum, 19*150 mm; mobile phase, Water (0.05% $NH_3 \cdot H_2O$) and ACN (20% Phase B up to 60% in 10 min); Detector, UV 254/220 nm. This resulted in 15 mg (30.13%) of N-(5-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxopyrazin-2-yl]amino]-2-[(2S)-2-methyl-4-[(2R,4S)-2-methyloxan-4-yl]piperazin-1-yl]phenyl)prop-2-enamide (trans) as a white solid. LC-MS: (ES, m/z): M+1: 776; H-NMR (300 MHz, DMSO-$d_6$, ppm) δ 9.23 (d, J=14.3 Hz, 2H), 9.10 (s, 1H), 8.48 (d, J=5.2 Hz, 1H), 7.95 (d, J=5.2 Hz, 1H), 7.77 (s, 1H), 7.61 (d, J=8.5 Hz, 1H), 7.25 (d, J=8.7 Hz, 1H), 6.66-6.53 (m, 2H), 6.29 (d, J=17.0 Hz, 1H), 5.80 (dd, J=10.0, 1.8 Hz, 1H), 5.03 (s, 1H), 4.68-4.42 (m, 2H), 4.22 (s, 3H), 3.97-3.65 (m, 3H), 3.57 (s, 4H), 3.00 (dd, J=29.9, 17.9 Hz, 3H), 2.75 (d, J=11.5 Hz, 2H), 2.59 (d, J=4.7 Hz, 3H), 2.44 (s, 2H), 2.33-2.25 (m, 1H), 2.00 (s, 1H), 1.91-1.57 (m, 4H), 1.41 (d, J=11.1 Hz, 1H), 1.23 (s, 6H), 1.08 (t, J=6.2 Hz, 3H), 0.82-0.70 (m, 3H).

Example 38: Preparation of N-(5-[[6-(2-[4,4-dimethyl-9-oxo-1,10-diazatricyclo[6.5.0.0^[2,6]]trideca-2(6),7-dien-10-yl]-3-(hydroxymethyl)pyridin-4-yl)-4-methyl-3-oxopyrazin-2-yl]amino]-2-[(2S)-2-methyl-4-[(2R,4r,6S)-2,6-dimethyloxan-4-yl]piperazin-1-yl]phenyl)prop-2-enamide (cis)

Synthesis of [(3,3-dimethylcyclopent-1-en-1-yl)oxy]trimethylsilane: Into a 10-L 4-necked round-bottom flask purged and maintained with an inert atmosphere of nitrogen, was placed CuCl (20.60 g, 208.083 mmol, 0.05 equiv), LiCl (17.64 g, 416.108 mmol, 0.10 equiv), THF (2.50 L). This was followed by the addition of 2-cyclopenten-1-one, 3-methyl-(400.00 g, 4161.075 mmol, 1.00 equiv) at −5 to 5 degrees C. To this was added TMSCl (474.67 g, 4369.129 mmol, 1.05 equiv) dropwise with stirring at −5 to 5 degrees C. To the mixture was added MeMgCl (1670.00 mL, 14495.069 mmol, 3.48 equiv) dropwise with stirring at −5 to 10 degrees C. The resulting solution was stirred for 2 h at −5 to 10 degrees C. in an ice/salt bath. The reaction was then quenched by the addition of 34 g of MeOH. The resulting solution was diluted with 5 L of $NH_4Cl$. The solids were filtered out. The resulting solution was extracted with 3×5 L of petroleum ether dried over anhydrous sodium sulfate and concentrated. This resulted in 780 g (crude) of [(3,3-dimethylcyclopent-1-en-1-yl)oxy]trimethylsilane as yellow oil. GC-MS: (ES, m/z): M 184

Synthesis of 3,3-dimethylcyclopentanone: Into a 20-L 4-necked round-bottom flask, was placed [(3,3-dimethylcyclopent-1-en-1-yl)oxy]trimethylsilane (780.00 g, 4230.990 mmol, 1.00 equiv), DCM (7.8 L), $H_2O$ (30.49 g, 1692.396 mmol, 0.4 equiv). This was followed by the addition of $POCl_3$ (214.09 g, 1396.251 mmol, 0.33 equiv) dropwise with stirring at 25 to 30 degrees C. The resulting solution was stirred for 0.5 hr at 25 degrees C. This solvent straight used for next step. GC-MS (ES, m/z): M: 112

Synthesis of 3,3-dimethylcyclopentanone: Into a 20-L 4-necked round-bottom flask, was placed 3,3-dimethylcyclopentan-1-one (crude) in DCM (7.80 L). This was followed by the addition of DMF (619 g, 2.0 equiv) dropwise with stirring at 25 degrees C. To this was added $POCl_3$ (1362 g, 2.1 equiv) dropwise with stirring at 40 degrees C. The resulting solution was stirred for overnight at 40 degrees C. in an oil bath. The reaction was then quenched by the addition of 2000 g of $K_3PO_4$. The resulting solution was extracted with 3×10 L of dichloromethane dried over anhydrous sodium sulfate and concentrated. This resulted in 530 g of 2-chloro-4,4-dimethylcyclopent-1-ene-1-carbaldehyde as a brown solid. GC-MS: (ES, m/z): M: 158

Synthesis of 4,4-dimethyl-1,10-diazatricyclo[6.5.0.0^[2,6]]trideca-2(6),7-dien-9-one: Into a 250-mL round-bottom flask, was placed 2-chloro-4,4-dimethylcyclopent-1-ene-1-carbaldehyde (21.35 g, 0.135 mmol, 1.2 equiv), DMF (100.00 mL), 1,4-diazepan-2-one (12.80 g, 112.135 mmol, 1.00 equiv), DIEA (28.99 g, 0.224 mmol, 2 equiv). The resulting solution was stirred for overnight at 115 degrees C. in an oil bath. The reaction mixture was cooled to room temperature with a water/ice bath. The reaction was then quenched by the addition of 200 mL of water. The resulting solution was extracted with 3×300 mL of ethyl acetate concentrated. The residue was applied onto a silica gel column and eluted with ethyl acetate/petroleum ether (1:1). The collected fractions were combined and concentrated. This resulted in 3.35 g (13.69%) of 4,4-dimethyl-1,10-diazatricyclo[6.5.0.0^[2,6]]trideca-2(6),7-dien-9-one as a grey solid. LC-MS: (ES, m/z): M+1: 219

Synthesis of 2,4-dibromopyridine-3-carbaldehyde: Into a 1000-mL 3-necked round-bottom flask, was placed 2,4-dibromopyridine (40.00 g, 168.852 mmol, 1.00 equiv), THF (400.00 mL). This was followed by the addition of LDA (2M in hexane, 126.60 mL, 1.5 equiv) dropwise with stirring at −78 degrees C. The resulting solution was stirred for 1 hr at −78 degrees C. Then DMF (16.04 g, 219.507 mmol, 1.3 equiv) was added dropwise with stirring at −78 degrees C. The resulting solution was stirred for 0.5 hr at −78 degrees C. The reaction was then quenched by the addition of 500 mL of $NH_4Cl$. The resulting solution was extracted with 3×500 mL of ethyl acetate and concentrated. The residue was applied onto a silica gel column and eluted with ethyl acetate/petroleum ether (0:1-1:1). This resulted in 24.4 g (54.55%) of 2,4-dibromopyridine-3-carbaldehyde as a white solid. LC-MS: (ES, m/z): M+1: 264

Synthesis of (2,4-dibromopyridin-3-yl)methanol: Into a 100-mL round-bottom flask, was placed 2,4-dibromopyridine-3-carbaldehyde (20.00 g, 75.50 mmol, 1.00 equiv), EtOH (300.00 mL). This was followed by the addition of $NaBH_4$ (2.86 g, 75.50 mmol, 1.00 equiv), in portions at 0 degrees C. The resulting solution was stirred for 3 h at room temperature. The reaction was then quenched by the addition of 300 mL of water. The resulting solution was extracted with 3×300 mL of ethyl acetate and concentrated. The residue was applied onto a silica gel column and eluted with ethyl acetate/petroleum ether (1:1). The collected fractions were combined and concentrated. This resulted in 14 g (69.47%) of (2,4-dibromopyridin-3-yl)methanol as a light yellow solid. LC-MS: (ES, m/z): M+1: 266

Synthesis of 2,4-dibromo-3-[(oxan-2-yloxy)methyl]pyridine: Into a 100-mL round-bottom flask, was placed (2,4-dibromopyridin-3-yl)methanol (14.0 g, 52.45 mmol, 1.00 equiv), DCM (300.00 mL), PPTS (1.32 g, 5.25 mmol, 0.10 equiv), DHP (6.62 g, 78.68 mmol, 1.50 equiv). The resulting solution was stirred overnight at 45 degrees C. in an oil bath. The reaction was then quenched by the addition of 300 mL of water. The resulting solution was extracted with 3×300 mL of dichloromethane and concentrated. The residue was applied onto a silica gel column and eluted with ethyl acetate/petroleum ether (1:1). The collected fractions were combined and concentrated. This resulted in 15 g (80%) of 2,4-dibromo-3-[(oxan-2-yloxy)methyl]pyridine as colorless oil. LC-MS: (ES, m/z): M+1: 350

Synthesis of 10-[4-bromo-3-[(oxan-2-yloxy)methyl]pyridin-2-yl]-4,4-dimethyl-1,10-diazatricyclo[6.5.0.0^[2,6]]trideca-2(6),7-dien-9-one: Into a 100-mL round-bottom flask purged and maintained with an inert atmosphere of nitrogen, was placed 2,4-dibromo-3-[(oxan-2-yloxy)methyl]pyridine (5.36 g, 15.269 mmol, 1.00 equiv), 4,4-dimethyl-1,10-diazatricyclo[6.5.0.0^[2,6]]trideca-2(6),7-dien-9-one (3.33 g, 0.015 mmol, 1 equiv), dioxane (40.00 mL), $Cs_2CO_3$ (9.95 g, 0.031 mmol), $Pd_2(dba)_3$ (1.40 g, 0.002 mmol, 0.1 equiv), Xantphos (883.49 mg, 1.527 mmol, 0.10 equiv). The resulting solution was stirred for 1.5 hr at 100 degrees C. in an oil bath. The solids were filtered out. The resulting mixture was concentrated. The residue was applied onto a silica gel and eluted column with ethyl acetate/petroleum ether (1:1). The collected fractions were combined and concentrated. This resulted in 3.65 g (48.94%) of 10-[4-bromo-3-[(oxan-2-yloxy)methyl]pyridin-2-yl]-4,4-dimethyl-1,10-diazatricyclo[6.5.0.0^[2,6]]trideca-2(6),7-dien-9-one as brown oil. LC-MS: (ES, m/z): M+1: 488

Synthesis of 2-[4,4-dimethyl-9-oxo-1,10-diazatricyclo[6.5.0.0^[2,6]]trideca-2(6),7-dien-10-yl]-3-[(oxan-2-yloxy)methyl]pyridin-4-ylboronic acid: Into a 100-mL round-bottom flask purged and maintained with an inert atmosphere of nitrogen, was placed 10-[4-bromo-3-[(oxan-2-yloxy)methyl]pyridin-2-yl]-4,4-dimethyl-1,10-diazatricyclo[6.5.0.0^[2,6]]trideca-2(6),7-dien-9-one (3.65 g, 7.473 mmol, 1.00 equiv), dioxane (50.00 mL), bis(pinacolato)diboron (2.85 g, 0.011 mmol, 1.5 equiv), KOAc (2.20 g, 0.022 mmol, 3 equiv), $Pd(dppf)Cl_2$ (546.80 mg, 0.747 mmol, 0.10 equiv). The resulting solution was stirred for 2 hr at 100 degrees C. in an oil bath. The solids were filtered out. The resulting mixture was concentrated. The resulting solution was diluted with 30 mL of $CH_3CN$. The solids were collected by filtration. This resulted in 1.95 g (57.56%) of 2-[4,4-dimethyl-9-oxo-1,10-diazatricyclo[6.5.0.0^[2,6]]trideca-2(6),7-dien-10-yl]-3-[(oxan-2-yloxy)methyl]pyridin-4-ylboronic acid as a yellow solid. LC-MS: (ES, m/z): M+1: 454

Synthesis of 10-[1-hydroxy-3H-[1,2]oxaborolo[4,3-c]pyridin-4-yl]-4,4-dimethyl-1,10-diazatricyclo[6.5.0.0^[2,6]]trideca-2(6),7-dien-9-one: Into a 50-mL round-bottom flask, was placed 2-[4,4-dimethyl-9-oxo-1,10-diazatricyclo[6.5.0.0^[2,6]]trideca-2(6),7-dien-10-yl]-3-[(oxan-2-yloxy)methyl]pyridin-4-ylboronic acid (1.95 g, 4.301 mmol, 1.00 equiv), HCl(gas) in 1,4-dioxane. The resulting solution was stirred for 1 hr at room temperature. The resulting mixture was concentrated. The resulting solution was diluted with 20 mL of $Et_2O$. The solids were collected by filtration. This resulted in 1.7 g (112.53%) of 10-[1-hydroxy-3H-[1,2]oxaborolo[4,3-c]pyridin-4-yl]-4,4-dimethyl-1,10-diazatricyclo[6.5.0.0^[2,6]]trideca-2(6),7-dien-9-one as a yellow solid. LC-MS: (ES, m/z): M+1: 352

Synthesis of tert-butyl (3S)-4-[4-[(6-bromo-4-methyl-3-oxopyrazin-2-yl)amino]-2-nitrophenyl]-3-methylpiperazine-1-carboxylate: Into a 50-mL round-bottom flask, was placed 5-bromo-3-[(4-fluoro-3-nitrophenyl)amino]-1-methylpyrazin-2-one (20.00 g, 58.29 mmol, 1.00 equiv), NMP (200.00 mL), tert-butyl (3S)-3-methylpiperazine-1-carboxylate (11.7 g, 58.42 mmol, 1.00 equiv), DIEA (22.6 g, 174.87 mmol, 3.00 equiv). The resulting solution was stirred for 48 h at 110° C. in an oil bath. The resulting solution was diluted with 1000 mL of $H_2O$. The resulting solution was extracted with 3×500 mL of dichloromethane/methanol (10:1). The resulting mixture was washed with 3×200 mL of brine. The resulting mixture was concentrated. The residue was applied onto a silica gel column with dichloromethane/methanol (10:1). This resulted in 30 g (59.00%) of tert-butyl (3S)-4-[4-[(6-bromo-4-methyl-3-oxopyrazin-2-yl)amino]-2-nitrophenyl]-3-methylpiperazine-1-carboxylate as a brown solid. LC-MS: (ES, m/z): M+1: 523

Synthesis of 5-bromo-1-methyl-3-([4-[(2S)-2-methylpiperazin-1-yl]-3-nitrophenyl]amino)pyrazin-2-one: Into a 100-mL round-bottom flask, was placed tert-butyl (3S)-4-[4-[(6-bromo-4-methyl-3-oxopyrazin-2-yl)amino]-2-nitrophenyl]-3-methylpiperazine-1-carboxylate (30.00 g, 1.00 equiv, 60%), HCl (2M) in 1,4-dioxane (300.00 mL). The resulting solution was stirred for 13 h at room temperature. The resulting mixture was concentrated. The resulting solution was diluted with 300 mL of $H_2O$. The pH value of the solution was adjusted to 8 with $NH_3{\cdot}H_2O$. The resulting solution was extracted with 3×150 mL of dichloromethane and concentrated. The residue was applied onto a silica gel column with dichloromethane/methanol (10:1). This resulted in 7.0 g (48.09%) of 5-bromo-1-methyl-3-([4-[(2S)-2-methylpiperazin-1-yl]-3-nitrophenyl]amino)pyrazin-2-one as a red solid. LC-MS: (ES, m/z): M+1: 423

Synthesis of (cis)-2,6-dimethyloxan-4-ol: Into a 2000-mL pressure tank reactor (10 atm), was placed gamma-2,6-dimethylpyrone (50.00 g, 402.774 mmol, 1.00 equiv), EtOH (800.00 mL), 10% Pd/C (4.00 g, 37.587 mmol, 0.09 equiv), to the above $H_2$ was introduced in. The resulting solution was stirred overnight at 35 degrees C. in an oil bath. The solids were filtered out. The resulting mixture was concentrated under vacuum. This resulted in 49.4 g (94.21%) of (cis)-2,6-dimethyloxan-4-ol as yellow oil. GC-MS: (ES, m/z): M: 130

Synthesis of (cis)-2,6-dimethyloxan-4-one: Into a 1000-mL round-bottom flask, was placed (cis)-2,6-dimethyloxan-4-ol (40.00 g, 307.250 mmol, 1.00 equiv), DCM (500.00 mL), $CH_3COONa$ (21.00 g, 256.098 mmol, 0.83 equiv), PCC (140.00 g, 649.486 mmol, 2.11 equiv). The resulting solution was stirred for 2 hr at 25 degrees C. The reaction was then quenched by the addition of 1000/1000 mL of $Na_2SO_3$/DCM. The solids were filtered out. The resulting solution was extracted with 3×500 mL of dichloromethane and the organic layers combined. The resulting mixture was washed with 1×2000 ml of brine. The mixture was dried over anhydrous sodium sulfate and concentrated under vacuum. The residue was applied onto a silica gel column with ethyl acetate/petroleum ether (1:9). This resulted in 9.88 g (25.09%) of (cis)-2,6-dimethyloxan-4-one as yellow oil. GC-MS: (ES, m/z): M: 128

Synthesis of 5-bromo-3-([4-[(2S)-4-[(2R,6S)-2,6-dimethyloxan-4-yl]-2-methylpiperazin-1-yl]-3-nitrophenyl]amino)-1-methylpyrazin-2-one: Into a 250-mL round-bottom flask, was placed 5-bromo-1-methyl-3-([4-[(2S)-2-methylpiperazin-1-yl]-3-nitrophenyl]amino)pyrazin-2-one hydrochloride (10.00 g, 21.752 mmol, 1.00 equiv), THF (100 mL), (cis)-2,6-dimethyloxan-4-one (3.60 g, 28.087 mmol, 1.29 equiv), HOAc (300.00 mg, 4.996 mmol, 0.23 equiv), $NaBH(OAc)_3$ (9.26 g, 43.691 mmol, 2.01 equiv). The resulting solution was stirred overnight at 30 degrees C. in an oil bath. The resulting mixture was concentrated under vacuum. The residue was applied onto a silica gel column with dichloromethane/methanol (10:1). This resulted in 6.3 g (54.09%) of 5-bromo-3-([4-[(2S)-4-[(2R,6S)-2,6-dimethyloxan-4-yl]-2-methylpiperazin-1-yl]-3-nitrophenyl]amino)-1-methylpyrazin-2-one as a red solid(cis and trans mixtures). LC-MS: (ES, m/z): M+1: 535

Synthesis of 3-([3-amino-4-[(2S)-2-methyl-4-[(2R,4r,6S)-2,6-dimethyloxan-4-yl]piperazin-1-yl]phenyl]amino)-5-bromo-1-methylpyrazin-2-one (cis) and 3-([3-amino-4-[(2S)-2-methyl-4-[(2R,4s,6S)-2,6-dimethyloxan-4-yl]piperazin-1-yl]phenyl]amino)-5-bromo-1-methylpyrazin-2-one (trans): Into a 250-mL round-bottom flask, was placed 5-bromo-1-methyl-3-([4-[(2S)-2-methyl-4-[(2R,4r,6S)-2,6-dimethyloxan-4-yl]piperazin-1-yl]-3-nitrophenyl]amino)pyrazin-2-one (6.30 g, 11.766 mmol, 1.00 equiv), EtOH (60.00 mL), $H_2O$ (20.00 mL), Fe (4.03 g, 72.164 mmol, 6.13 equiv), $NH_4Cl$ (3.82 g, 71.414 mmol, 6.07 equiv). The resulting solution was stirred for 2 hr at 70 degrees C. in an oil bath. The reaction mixture was cooled to room temperature. The resulting solution was diluted with 1000 mL of water. The resulting solution was extracted with 3×300 mL of dichloromethane and the organic layers combined. The resulting mixture was washed with 1×1000 ml of brine. The mixture was dried over anhydrous sodium sulfate and concentrated under vacuum. The residue was applied onto a silica gel column with dichloromethane/methanol (10:1). This resulted in 3 g (50.44%) of 3-([3-amino-4-[(2S)-2-methyl-4-[(2R,4r,6S)-2,6-dimethyloxan-4-yl]piperazin-1-yl]phenyl]amino)-5-bromo-1-methylpyrazin-2-one (cis) as a yellow solid and 150 mg (2.52%) of 3-([3-amino-4-[(2S)-2-methyl-4-[(2R,4s,6S)-2,6-dimethyloxan-4-yl]piperazin-1-yl]phenyl]amino)-5-bromo-1-methylpyrazin-2-one (trans) as a yellow solid. LC-MS: (ES, m/z): M+1: 504

Synthesis of N-[5-[(6-bromo-4-methyl-3-oxopyrazin-2-yl)amino]-2-[(2S)-2-methyl-4-[(2R,4r,6S)-2,6-dimethyloxan-4-yl]piperazin-1-yl]phenyl]prop-2-enamide (cis): Into a 250-mL round-bottom flask purged and maintained with an inert atmosphere of nitrogen, was placed 3-([3-amino-4-[(2S)-2-methyl-4-[(2R,4r,6S)-2,6-dimethyloxan-4-yl]piperazin-1-yl]phenyl]amino)-5-bromo-1-methylpyrazin-2-one (cis) (2.00 g, 3.957 mmol, 1.00 equiv), DCM (50.00 mL), DIEA (1.02 g, 7.892 mmol, 1.99 equiv), acryloyl chloride (357.00 mg, 3.944 mmol, 1.00 equiv). The resulting solution was stirred for 2 hr at 25 degrees C. The resulting mixture was concentrated under vacuum. The residue was applied onto a silica gel column with dichloromethane/methanol (20:1). This resulted in 1.8 g (81.31%) of N-[5-[(6-bromo-4-methyl-3-oxopyrazin-2-yl)amino]-2-[(2S)-2-methyl-4-[(2R,4r,6S)-2,6-dimethyloxan-4-yl]piperazin-1-yl]phenyl] prop-2-enamide (cis) as a yellow solid. LC-MS: (ES, m/z): M+1: 558

Synthesis of N-(5-[[6-(2-[4,4-dimethyl-9-oxo-1,10-diazatricyclo[6.5.0.0^[2,6]]trideca-2(6),7-dien-10-yl]-3-(hydroxymethyl)pyridin-4-yl)-4-methyl-3-oxopyrazin-2-yl] amino]-2-[(2S)-2-methyl-4-[(2R,4r,6S)-2,6-dimethyloxan-4-yl]piperazin-1-yl]phenyl)prop-2-enamide (cis): Into a 40-mL vial purged and maintained with an inert atmosphere of nitrogen, was placed N-[5-[(6-bromo-4-methyl-3-oxopyrazin-2-yl)amino]-2-[(2S)-2-methyl-4-[(2R,4r,6S)-2,6-dimethyloxan-4-yl]piperazin-1-yl]phenyl]prop-2-enamide (350.00 mg, 0.626 mmol, 1.00 equiv), 10-[1-hydroxy-3H-[1,2]oxaborolo[4,3-c]pyridin-4-yl]-4,4-dimethyl-1,10-diazatricyclo[6.5.0.0^[2,6]]trideca-2(6),7-dien-9-one (263.64 mg, 0.751 mmol, 1.20 equiv), dioxane (15.00 mL), $H_2O$ (1.50 mL), $K_2CO_3$ (216.14 mg, 1.564 mmol, 2.5 equiv), DTBPF $PdCl_2$ (40.72 mg, 0.063 mmol, 0.10 equiv). The resulting solution was stirred for 1.5 hr at 90 degrees C. in an oil bath. The solids were filtered out. The resulting solution was extracted with 3×30 mL of ethyl acetate concentrated. The residue was applied onto a silica gel column with dichloromethane/methanol (10:1). The collected fractions were combined and concentrated. This resulted in 115 mg (22.87%) of N-(5-[[6-(2-[4,4-dimethyl-9-oxo-1,10-diazatricyclo[6.5.0.0^[2,6]]trideca-2(6),7-dien-10-yl]-3-(hydroxymethyl)pyridin-4-yl)-4-methyl-3-oxopyrazin-2-yl]amino]-2-[(2S)-2-methyl-4-[(2R,4r,6S)-2,6-dimethyloxan-4-yl]piperazin-1-yl]phenyl)prop-2-enamide as a light yellow solid. LC-MS: (ES, m/z): M+1: 804. $^1$H NMR (300 MHz, DMSO-$d_6$, ppm) δ 8.98 (d, J=2.4 Hz, 1H), 8.46 (d, J=5.1 Hz, 1H), 7.81 (d, J=5.1 Hz, 1H), 7.63 (s, 1H), 7.56 (dd, J=8.7, 2.7 Hz, 1H), 7.24 (d, J=8.7 Hz, 1H), 6.56 (dd, J=16.8, 10.2 Hz, 1H), 6.49 (s, 1H), 6.25 (dd, J=16.8, 1.8 Hz, 1H), 5.85-5.69 (m, 1H), 4.51 (s, 2H), 4.15 (s, 3H), 3.55 (s, 3H), 3.40 (dd, J=11.1, 6.3 Hz, 2H), 3.00 (s, 1H), 2.86 (dd, J=22.5, 10.2 Hz, 2H), 2.77-2.65 (m, 2H), 2.54 (s, 3H), 2.41 (s, 2H), 2.11 (d, J=10.2 Hz, 3H), 1.79 (d, J=12.3 Hz, 2H), 1.20 (s, 6H), 1.11 (d, J=6.0 Hz, 6H), 1.06-0.91 (m, 2H), 0.69 (d, J=6.0 Hz, 3H).

Example 39: Preparation of N-(5-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxopyrazin-2-yl]amino]-2-[(2S)-2-methyl-4-(oxolan-3-yl)piperazin-1-yl]phenyl)prop-2-enamide Synthesis of [(3,3-dimethylcyclopent-1-en-1-yl)oxy]trimethylsilane: Into a 10-L 4-necked round-bottom flask purged and maintained with an inert atmosphere of nitrogen, was placed CuCl (20.60 g, 208.083 mmol, 0.05 equiv), LiCl (17.64 g, 416.108 mmol, 0.10 equiv), THF (2.50 L). This was followed by the addition of 2-cyclopenten-1-one, 3-methyl-(400.00 g, 4161.075 mmol, 1.00 equiv) at −5 to 5 degrees C. To this was added TMSCl (474.67 g, 4369.129 mmol, 1.05 equiv) dropwise with stirring at −5 to 5 degrees C. To the mixture was added MeMgCl (1670.00 mL, 14495.069 mmol, 3.48 equiv) dropwise with stirring at −5 to 10 degrees C. The resulting solution was stirred for 2 h at −5 to 10 degrees C. in an ice/salt bath. The reaction was then quenched by the addition of 34 g of MeOH. The resulting solution was diluted with 5 L of $NH_4Cl$. The solids were filtered out. The resulting solution was extracted with 3×5 L of petroleum ether dried over anhydrous sodium sulfate and concentrated. This resulted in 780 g (crude) of [(3,3-dimethylcyclopent-1-en-1-yl)oxy]trimethylsilane as yellow oil. GC-MS: (ES, m/z): M 184

Synthesis of 3,3-dimethylcyclopentanone: Into a 20-L 4-necked round-bottom flask, was placed [(3,3-dimethylcyclopent-1-en-1-yl)oxy]trimethylsilane (780.00 g, 4230.990 mmol, 1.00 equiv), DCM (7.8 L), $H_2O$ (30.49 g, 1692.396 mmol, 0.4 equiv). This was followed by the addition of $POCl_3$ (214.09 g, 1396.251 mmol, 0.33 equiv) dropwise with stirring at 25 to 30 degrees C. The resulting solution was stirred for 0.5 hr at 25 degrees C. This solvent straight used for next step. GC-MS (ES, m/z): M 112

Synthesis of 3,3-dimethylcyclopentanone: Into a 20-L 4-necked round-bottom flask, was placed 3,3-dimethylcyclopentan-1-one (crude) in DCM (7.80 L). This was followed by the addition of DMF (619 g, 2.0 equiv) dropwise with stirring at 25 degrees C. To this was added $POCl_3$ (1362 g, 2.1 equiv) dropwise with stirring at 40 degrees C. The resulting solution was stirred for overnight at 40 degrees C. in an oil bath. The reaction was then quenched by the addition of 2000 g of $K_3PO_4$. The resulting solution was extracted with 3×10 L of dichloromethane dried over anhydrous sodium sulfate and concentrated. This resulted in 530 g of 2-chloro-4,4-dimethylcyclopent-1-ene-1-carbaldehyde as a brown solid. GC-MS: (ES, m/z): M: 158

Synthesis of 4,4-dimethyl-1,10-diazatricyclo[6.4.0.0^[2,6]]dodeca-2(6),7-dien-9-one: Into a 5-L 4-necked round-bottom flask, was placed 2-chloro-4,4-dimethylcyclopent-1-ene-1-carbaldehyde (474.00 g, 2988.085 mmol, 1.00 equiv), DMF (3 L), piperazin-2-one (299.17 g, 2988.084 mmol, 1.00 equiv), DIEA (463.43 g, 3585.703 mmol, 1.2 equiv). The resulting solution was stirred overnight at 115 degrees C. in an oil bath. The reaction mixture was cooled to room temperature with a water/ice bath. The solids were collected by filtration and washed with 3×2 L of $H_2O$ and 3×2 L of PE. The solid was dried in an oven under reduced pressure. This resulted in 230 g (37.68%) of 4,4-dimethyl-1,10-diazatricyclo[6.4.0.0^[2,6]]dodeca-2(6),7-dien-9-one as a grey solid. LC-MS: (ES, m/z): M+1: 205

Synthesis of 2,4-dibromopyridine-3-carbaldehyde: Into a 1000-mL 3-necked round-bottom flask, was placed 2,4-dibromopyridine (40.00 g, 168.852 mmol, 1.00 equiv), THF (400.00 mL). This was followed by the addition of LDA (2M in hexane, 126.60 mL, 1.5 equiv) dropwise with stirring at −78 degrees C. The resulting solution was stirred for 1 hr at −78 degrees C. Then DMF (16.04 g, 219.507 mmol, 1.3 equiv) was added dropwise with stirring at −78 degrees C. The resulting solution was stirred for 0.5 hr at −78 degrees C. The reaction was then quenched by the addition of 500 mL of $NH_4Cl$. The resulting solution was extracted with 3×500 mL of ethyl acetate and concentrated. The residue was applied onto a silica gel column and eluted with ethyl acetate/petroleum ether (0:1-1:1). This resulted in 24.4 g (54.55%) of 2,4-dibromopyridine-3-carbaldehyde as a white solid. LC-MS: (ES, m/z): M+1: 264

Synthesis of (2,4-dibromopyridin-3-yl)methanol: Into a 100-mL round-bottom flask, was placed 2,4-dibromopyridine-3-carbaldehyde (20.00 g, 75.50 mmol, 1.00 equiv), EtOH (300.00 mL). This was followed by the addition of $NaBH_4$ (2.86 g, 75.50 mmol, 1.00 equiv), in portions at 0 degrees C. The resulting solution was stirred for 3 h at room temperature. The reaction was then quenched by the addition of 300 mL of water. The resulting solution was extracted with 3×300 mL of ethyl acetate and concentrated. The residue was applied onto a silica gel column and eluted with ethyl acetate/petroleum ether (1:1). The collected fractions were combined and concentrated. This resulted in 14 g (69.47%) of (2,4-dibromopyridin-3-yl)methanol as a light yellow solid. LC-MS: (ES, m/z): M+1: 266

Synthesis of 2,4-dibromo-3-[(oxan-2-yloxy)methyl]pyridine: Into a 100-mL round-bottom flask, was placed (2,4-dibromopyridin-3-yl)methanol (14.0 g, 52.45 mmol, 1.00 equiv), DCM (300.00 mL), PPTS (1.32 g, 5.25 mmol, 0.10 equiv), DHP (6.62 g, 78.68 mmol, 1.50 equiv). The resulting solution was stirred overnight at 45 degrees C. in an oil bath. The reaction was then quenched by the addition of 300 mL of water. The resulting solution was extracted with 3×300 mL of dichloromethane and concentrated. The residue was applied onto a silica gel column and eluted with ethyl acetate/petroleum ether (1:1). The collected fractions were combined and concentrated. This resulted in 15 g (80%) of 2,4-dibromo-3-[(oxan-2-yloxy)methyl]pyridine as colorless oil. LC-MS: (ES, m/z): M+1: 350

Synthesis of 10-[4-bromo-3-[(oxan-2-yloxy)methyl]pyridin-2-yl]-4,4-dimethyl-1,10-diazatricyclo[6.4.0.0^[2,6]]dodeca-2(6),7-dien-9-one: Into a 100-mL round-bottom flask purged and maintained with an inert atmosphere of nitrogen, was placed 4,4-dimethyl-1,10-diazatricyclo[6.4.0.0^[2,6]]dodeca-2(6),7-dien-9-one (10.00 g, 48.95 mmol, 1.00 equiv), dioxane (400.00 mL), $Cs_2CO_3$ (31.9 g, 97.91 mmol, 2.00 equiv), 2,4-dibromo-3-[(oxan-2-yloxy)methyl]pyridine (17.2 g, 49.0 mmol, 1.00 equiv), $Pd_2(dba)_3$ (4.48 g, 4.90 mmol, 0.1 equiv), XantPhos (2.83 g, 4.90 mmol, 0.1 equiv). The resulting solution was stirred for 1 h at 100 degrees C. in an oil bath. The reaction was then quenched by the addition of 400 mL of water. The resulting solution was extracted with 3×400 mL of ethyl acetate and concentrated. The residue was applied onto a silica gel column and eluted with ethyl acetate/petroleum ether (1:1). The collected fractions were combined and concentrated. This resulted in 9 g (38.75%) of 10-[4-bromo-3-[(oxan-2-yloxy)methyl]pyridin-2-yl]-4,4-dimethyl-1,10-diazatricyclo[6.4.0.0^[2,6]]dodeca-2(6),7-dien-9-one as a brown solid. LC-MS: (ES, m/z): M+1: 474

Synthesis of 2-[4,4-dimethyl-9-oxo-1,10-diazatricyclo[6.4.0.0^[2,6]]dodeca-2(6),7-dien-10-yl]-3-[(oxan-2-yloxy)methyl]pyridin-4-ylboronic acid: Into a 100-mL round-bottom flask purged and maintained with an inert atmosphere of nitrogen, was placed 10-[4-bromo-3-[(oxan-2-yloxy)methyl]pyridin-2-yl]-4,4-dimethyl-1,10-diazatricyclo[6.4.0.0^[2,6]]dodeca-2(6),7-dien-9-one (10.00 g, 21.08 mmol, 1.00 equiv), dioxane (100.00 mL), bis(pinacolato)diboron (13.4 g, 52.77 mmol, 2.50 equiv), KOAc (6.20 g, 63.17 mmol, 3.00 equiv), $Pd(dppf)Cl_2$ (1.72 g, 2.11 mmol, 0.10 equiv). The resulting solution was stirred for 2 h at 100 degrees C. in an oil bath. The reaction mixture was cooled to room temperature. The solids were filtered out. The resulting mixture was concentrated under vacuum. This resulted in 9.2 g (crude) of 2-[4,4-dimethyl-9-oxo-1,10-diazatricyclo[6.4.0.0^[2,6]]dodeca-2(6),7-dien-10-yl]-3-[(oxan-2-yloxy)methyl]pyridin-4-ylboronic acid as brown oil. LC-MS: (ES, m/z): M+1: 436

Synthesis of 10-[1-hydroxy-3H-[1,2]oxaborolo[4,3-c]pyridin-4-yl]-4,4-dimethyl-1,10-diazatricyclo[6.4.0.0^[2,6]]dodeca-2(6),7-dien-9-one: Into a 100-mL round-bottom flask, was placed 2-[4,4-dimethyl-9-oxo-1,10-diazatricyclo[6.4.0.0^[2,6]]dodeca-2(6),7-dien-10-yl]-3-[(oxan-2-yloxy)methyl]pyridin-4-ylboronic acid (9.2 g, 1.00 equiv, crude), dioxane (100 mL), HCl (6N, 100 mL). The resulting solution was stirred for 1 h at 25 degrees C. The resulting mixture was concentrated under vacuum. The crude product was purified by Flash-Prep-HPLC with the following conditions: Column, C18 reversed phase column; mobile phase, $H_2O$ (0.05% $NH_3 \cdot H_2O$) and $CH_3CN$ (5% $CH_3CN$ up to 30% in 15 min); Flow rate: 60 mL/min; Detector, 254/220 nm. This resulted in 3.5 g of 10-[1-hydroxy-3H-[1,2]oxaborolo[4,3-c]pyridin-4-yl]-4,4-dimethyl-1,10-diazatricyclo[6.4.0.0^[2,6]]dodeca-2(6),7-dien-9-one as a light yellow solid. LC-MS: (ES, m/z): M+1: 338

Synthesis of 5-bromo-3-[(4-fluoro-3-nitrophenyl)amino]-1-methylpyrazin-2-one: Into a 250-mL round-bottom flask, was placed 4-fluoro-3-nitroaniline (10.00 g, 64.055 mmol, 1.00 equiv), 3,5-dibromo-1-methylpyrazin-2-one (17.16 g, 64.052 mmol, 1.00 equiv), NMP (30 mL). The resulting solution was stirred for 1 h at 140 degrees C. in an oil bath. The resulting solution was diluted with 300 mL of EA. The solids were collected by filtration. This resulted in 13 g (59.15%) of 5-bromo-3-[(4-fluoro-3-nitrophenyl)amino]-1-methylpyrazin-2-one as a brown solid. LCMS (ES, m/z): M+1: 343/345

Synthesis of tert-butyl (3S)-4-[4-[(6-bromo-4-methyl-3-oxopyrazin-2-yl)amino]-2-nitrophenyl]-3-methylpiperazine-1-carboxylate: Into a 50-mL round-bottom flask, was placed 5-bromo-3-[(4-fluoro-3-nitrophenyl)amino]-1-methylpyrazin-2-one (10 g, 29.2 mmol, 1.00 equiv), NMP (40.00 mL), tert-butyl (3S)-3-methylpiperazine-1-carboxylate (5.8 g, 5.842 mmol, 1.00 equiv), DIEA (2.26 g, 17.487 mmol, 3.00 equiv). The resulting solution was stirred for 40 h at 120° C. in an oil bath. The resulting solution was diluted with 100 mL of $H_2O$. The resulting solution was extracted with 3×50 mL of dichloromethane/methanol (10:1). The resulting mixture was washed with 3×20 ml of brine. The resulting mixture was concentrated. The residue was applied onto a silica gel column with dichloromethane/methanol (10:1). This resulted in 10 g (57.00%) of tert-butyl (3S)-4-[4-[(6-bromo-4-methyl-3-oxopyrazin-2-yl)amino]-2-nitrophenyl]-3-methylpiperazine-1-carboxylate as a brown solid. LC-MS: (ES, m/z): M+1: 523

Synthesis of 5-bromo-1-methyl-3-([4-[(2S)-2-methylpiperazin-1-yl]-3-nitrophenyl]amino)pyrazin-2-one: Into a 100-mL round-bottom flask, was placed tert-butyl (3S)-4-[4-[(6-bromo-4-methyl-3-oxopyrazin-2-yl)amino]-2-nitrophenyl]-3-methylpiperazine-1-carboxylate (10.00 g, 1 equiv, 60%), HCl in 1,4-dioxane (2N, 100 mL). The resulting solution was stirred for 14 h at room temperature. The resulting mixture was concentrated. The resulting solution was diluted with 30 mL of $H_2O$. The pH value of the solution was adjusted to 8 with $NH_3 \cdot H_2O$. The resulting solution was extracted with 3×15 mL of dichloromethane and concentrated. The residue was applied onto a silica gel column with dichloromethane/methanol (10:1). This resulted in 5 g of 5-bromo-1-methyl-3-([4-[(2S)-2-methylpiperazin-1-yl]-3-nitrophenyl]amino)pyrazin-2-one as a red solid. LC-MS: (ES, m/z): M+1: 423

Synthesis of 5-bromo-1-methyl-3-([4-[(2S)-2-methyl-4-(oxolan-3-yl)piperazin-1-yl]-3-nitrophenyl]amino)pyrazin-2-one: Into a 250-mL round-bottom flask, was placed 5-bromo-1-methyl-3-([4-[(2S)-2-methylpiperazin-1-yl]-3-nitrophenyl]amino)pyrazin-2-one (2.00 g, 4.725 mmol, 1.00 equiv), THF (30.00 mL), dihydrofuran-3-one (500.00 mg, 5.808 mmol, 1.23 equiv), HOAc (50.00 mg, 0.833 mmol, 0.18 equiv), $NaBH(OAc)_3$ (1.90 g, 8.965 mmol, 1.90 equiv). The resulting solution was stirred overnight at 30 degrees C. in an oil bath. The resulting mixture was concentrated under vacuum. The residue was applied onto a silica gel column with dichloromethane/methanol (20:1). This resulted in 1.86 g (79.79%) of 5-bromo-1-methyl-3-([4-[(2S)-2-methyl-4-(oxolan-3-yl)piperazin-1-yl]-3-nitrophenyl]amino)pyrazin-2-one as red oil. LC-MS: (ES, m/z): M+1: 493

Synthesis of 3-([3-amino-4-[(2S)-2-methyl-4-(oxolan-3-yl)piperazin-1-yl]phenyl]amino)-5-bromo-1-methylpyrazin-2-one: Into a 250-mL round-bottom flask, was placed 5-bromo-1-methyl-3-([4-[(2S)-2-methyl-4-(oxolan-3-yl)piperazin-1-yl]-3-nitrophenyl]amino)pyrazin-2-one (1.80 g, 3.648 mmol, 1.00 equiv), EtOH (30.00 mL), $H_2O$ (10.00 mL), Fe (1.23 g, 22.025 mmol, 6.04 equiv), $NH_4Cl$ (1.18 g, 22.060 mmol, 6.05 equiv). The resulting solution was stirred for 2 hr at 70 degrees C. in an oil bath. The reaction mixture was cooled to room temperature. The resulting solution was diluted with 500 mL of water. The resulting solution was extracted with 3×300 mL of dichloromethane and the organic layers combined. The resulting mixture was washed with 1×1000 ml of brine. The mixture was dried over anhydrous sodium sulfate and concentrated under vacuum. The residue was applied onto a silica gel column with dichloromethane/methanol (20:1). This resulted in 1.5 g (88.73%) of 3-([3-amino-4-[(2S)-2-methyl-4-(oxolan-3-yl)piperazin-1-yl]phenyl]amino)-5-bromo-1-methylpyrazin-2-one as a yellow solid. LC-MS: (ES, m/z): M+1: 463

Synthesis of N-[5-[(6-bromo-4-methyl-3-oxopyrazin-2-yl)amino]-2-[(2S)-2-methyl-4-(oxolan-3-yl)piperazin-1-yl]phenyl]prop-2-enamide: Into a 100-mL round-bottom flask purged and maintained with an inert atmosphere of nitrogen, was placed 3-([3-amino-4-[(2S)-2-methyl-4-(oxolan-3-yl)piperazin-1-yl]phenyl]amino)-5-bromo-1-methylpyrazin-2-one (800.00 mg, 1.726 mmol, 1.00 equiv), DCM (10.00 mL), DIEA (446.00 mg, 3.451 mmol, 2.00 equiv), acryloyl chloride (156.00 mg, 1.724 mmol, 1.00 equiv). The resulting solution was stirred for 2 hr at room temperature. The resulting mixture was concentrated under vacuum. The residue was applied onto a silica gel column with dichloromethane/methanol (20:1). This resulted in 850 mg (95.15%) of N-[5-[(6-bromo-4-methyl-3-oxopyrazin-2-yl)amino]-2-[(2S)-2-methyl-4-(oxolan-3-yl)piperazin-1-yl]phenyl]prop-2-enamide as a yellow solid. LC-MS: (ES, m/z): M+1: 517

Synthesis of N-(5-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxopyrazin-2-yl]amino]-2-[(2S)-2-methyl-4-(oxolan-3-yl)piperazin-1-yl]phenyl)prop-2-enamide: Into a 40-mL vial purged and maintained with an inert atmosphere of nitrogen, was placed N-[5-[(6-bromo-4-methyl-3-oxopyrazin-2-yl)amino]-2-[(2S)-2-methyl-4-(oxolan-3-yl)piperazin-1-yl]phenyl]prop-2-enamide (400.00 mg, 0.773 mmol, 1.00 equiv), dioxane (10.00 mL), $H_2O$ (1.00 mL), 10-[1-hydroxy-3H-[1,2]oxaborolo[4,3-c]pyridin-4-yl]-4,4-dimethyl-1,10-diazatricyclo[6.4.0.0^[2,6]]dodeca-2(6),7-dien-9-one (522.00 mg, 1.548 mmol, 2.00 equiv), $K_2CO_3$ (535.00 mg, 3.871 mmol, 5.01 equiv), Xphos Pd G3 (130.00 mg, 0.154 mmol, 0.20 equiv). The resulting solution was stirred for 1 hr at 100 degrees C. in an oil bath. The reaction mixture was cooled to room temperature. The resulting mixture was concentrated under vacuum. The residue was applied onto a silica gel column with dichloromethane/methanol (20:1). The crude product was purified by Flash-Prep-HPLC with the following conditions (IntelFlash-1): Column, C18 reversed phase column; mobile phase, $H_2O$ (0.05% $NH_3 \cdot H_2O$) and $CH_3CN$ (30% $CH_3CN$ up to 80% in 15 min); Detector, 254/220 nm. This resulted in 250 mg (43.24%) of N-(5-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxopyrazin-2-yl]amino]-2-[(2S)-2-methyl-4-(oxolan-3-yl)piperazin-1-yl]phenyl)prop-2-enamide as a white solid. LC-MS: (ES, m/z): M+1: 748; H-NMR (300 MHz, DMSO-$d_6$, ppm) δ 9.24 (d, J=14.3 Hz, 2H), 9.12 (s, 1H), 8.48 (d, J=5.1 Hz, 1H), 7.95 (d, J=5.2 Hz, 1H), 7.77 (s, 1H), 7.60 (d, J=8.6 Hz, 1H), 7.24 (d, J=8.7 Hz, 1H), 6.74-6.53 (m, 2H), 6.30 (d, J=16.9 Hz, 1H), 5.81 (dd, J=10.1, 1.8 Hz, 1H), 5.02 (s, 1H), 4.57 (dd, J=22.2, 14.0 Hz, 2H), 4.21 (s, 3H), 3.92-3.74 (m, 3H), 3.67 (q, J=7.9 Hz, 1H), 3.57 (s, 4H), 3.06 (s, 1H), 3.01-2.63 (m, 5H), 2.58 (d, J=4.7 Hz, 2H), 2.43 (s, 3H), 2.17-1.93 (m, 2H), 1.90-1.70 (m, 1H), 1.23 (s, 6H), 0.72 (dd, J=6.2, 4.2 Hz, 3H).

Example 40: Preparation of N-(5-[[6-(2-[4,4-dimethyl-9-oxo-1,10-diazatricyclo[6.4.0.0^[2,6]]dodeca-2(6),7-dien-10-yl]-3-methylpyridin-4-yl)-4-methyl-3-oxopyrazin-2-yl]amino]-2-[(2S)-2-methyl-4-(oxan-4-yl)piperazin-1-yl]phenyl)prop-2-enamide Synthesis of 5-bromo-3-[(4-fluoro-3-nitrophenyl)amino]-1-methylpyrazin-2-one: Into a 250-mL round-bottom flask, was placed 4-fluoro-3-nitroaniline (10.00 g, 64.055 mmol, 1.00 equiv), 3, 5-dibromo-1-methylpyrazin-2-one (17.16 g, 64.052 mmol, 1.00 equiv), NMP (30 ml). The resulting solution was stirred for 1 h at 140 degrees C. in an oil bath. The resulting solution was diluted with 300 mL of EA. The solids were collected by filtration. This resulted in 13 g (59.15%) of 5-bromo-3-[(4-fluoro-3-nitrophenyl) amino]-1-methylpyrazin-2-one as a brown solid. LC-MS: (ES, m/z): M+1: 343/345

Synthesis of [(3,3-dimethylcyclopent-1-en-1-yl)oxy]trimethylsilane: Into a 10-L 4-necked round-bottom flask purged and maintained with an inert atmosphere of nitrogen, was placed CuCl (20.60 g, 208.083 mmol, 0.05 equiv), LiCl (17.64 g, 416.108 mmol, 0.10 equiv), THF (2.50 L). This was followed by the addition of 2-cyclopenten-1-one, 3-methyl-(400.00 g, 4161.075 mmol, 1.00 equiv) at −5 to 5 degrees C. To this was added TMSCl (474.67 g, 4369.129 mmol, 1.05 equiv) dropwise with stirring at −5 to 5 degrees C. To the mixture was added MeMgCl (1670.00 mL, 14495.069 mmol, 3.48 equiv) dropwise with stirring at −5 to 10 degrees C. The resulting solution was stirred for 2 h at −5 to 10 degrees C. in an ice/salt bath. The reaction was then quenched by the addition of 34 g of MeOH. The resulting solution was diluted with 5 L of $NH_4Cl$. The solids were filtered out. The resulting solution was extracted with 3×5 L of petroleum ether dried over anhydrous sodium sulfate and concentrated. This resulted in 780 g (crude) of [(3,3-dimethylcyclopent-1-en-1-yl)oxy]trimethylsilane as yellow oil. GC-MS: (ES, m/z): M: 184

Synthesis of 3,3-dimethylcyclopentanone: Into a 20-L 4-necked round-bottom flask, was placed [(3,3-dimethylcyclopent-1-en-1-yl)oxy]trimethylsilane (780.00 g, 4230.990 mmol, 1.00 equiv), DCM (7.8 L), $H_2O$ (30.49 g, 1692.396 mmol, 0.4 equiv). This was followed by the addition of $POCl_3$ (214.09 g, 1396.251 mmol, 0.33 equiv) dropwise with stirring at 25 to 30 degrees C. The resulting solution was stirred for 0.5 hr at 25 degrees C. This solvent straight used for next step. GC-MS: (ES, m/z): M+1: 112

Synthesis of 3,3-dimethylcyclopentanon: Into a 20-L 4-necked round-bottom flask, was placed 3,3-dimethylcyclopentan-1-one in DCM (7.80 L). This was followed by the addition of DMF (619 g, 2.0 equiv) dropwise with stirring at 25 degrees C. To this was added $POCl_3$ (1362 g, 2.1 equiv) dropwise with stirring at 40 degrees C. The resulting solution was stirred for overnight at 40 degrees C. in an oil bath. The reaction was then quenched by the addition of 2000 g of $K_3PO_4$. The resulting solution was extracted with 3×10 L of dichloromethane dried over anhydrous sodium sulfate and concentrated. This resulted in 530 g (crude) of 2-chloro-4, 4-dimethylcyclopent-1-ene-1-carbaldehyde as a brown solid. GC-MS: (ES, m/z): M+1: 158

Synthesis of 4,4-dimethyl-1,10-diazatricyclo[6.4.0.0^[2,6]]dodeca-2(6),7-dien-9-one: Into a 5-L 4-necked round-bottom flask, was placed 2-chloro-4,4-dimethylcyclopent-1-ene-1-carbaldehyde (474.00 g, 2988.085 mmol, 1.00 equiv), DMF (3 L), piperazin-2-one (299.17 g, 2988.084 mmol, 1.00 equiv), DIEA (463.43 g, 3585.703 mmol, 1.2 equiv). The resulting solution was stirred for overnight at 115 degrees C. in an oil bath. The reaction mixture was cooled to room temperature with a water/ice bath. The solids were collected by filtration. The resulting mixture was washed with 3×2 L of $H_2O$ and 3×2 L of PE. The solid was dried in an oven under reduced pressure. This resulted in 230 g (37.68%) of 4,4-dimethyl-1,10-diazatricyclo[6.4.0.0^[2,6]]dodeca-2(6),7-dien-9-one as a grey solid. LC-MS: (ES, m/z): M+1: 205

Synthesis of 2, 4-dibromo-3-methylpyridine: Into a 1000-mL 3-necked round-bottom flask purged and maintained with an inert atmosphere of nitrogen, was placed diisopropylamine (19.10 g, 189.959 mmol, 1.50 equiv), THF (300.00 mL). This was followed by the addition of butyllithium (12.30 g, 189.959 mmol, 1.50 equiv) at −30 degrees C. and the solution was stirred for 30 min. To this was added 2,4-dibromopyridine (30.00 g, 126.639 mmol, 1.00 equiv) at −70 degrees C. and stirred for other 30 min. To the mixture was added MeI (27.00 g, 189.959 mmol, 1.50 equiv) at −70 degrees C. and the solution was stirred for 0.5 h in a liquid nitrogen bath. The reaction was then quenched by the addition of 300 mL of $NH_4Cl$. The resulting solution was extracted with 3×200 mL of ethyl acetate and the organic layers combined. The resulting mixture was washed with 2×100 ml of water and 1×100 mL of brine. The mixture was dried over anhydrous sodium sulfate and concentrated. The residue was applied onto a silica gel column and eluted with ethyl acetate/petroleum ether (1:10). This resulted in 20 g of 2,4-dibromo-3-methylpyridine as a brown solid. LC-MS: (ES, m/z): M+1: 250

Synthesis of 10-(4-bromo-3-methylpyridin-2-yl)-4,4-dimethyl-1,10-diazatricyclo[6.4.0.0^[2,6]]dodeca-2(6),7-dien-9-one: Into a 100-mL round-bottom flask purged and maintained with an inert atmosphere of nitrogen, was placed 2,4-dibromo-3-methylpyridine (5.00 g, 19.927 mmol, 1.00 equiv), 4,4-dimethyl-1,10-diazatricyclo[6.4.0.0^[2,6]]dodeca-2(6),7-dien-9-one (4.07 g, 19.924 mmol, 1.00 equiv), XantPhos PD G2 (1.77 g, 1.995 mmol, 0.10 equiv), dioxane (50.00 mL, 590.204 mmol, 29.62 equiv), $Cs_2CO_3$ (19.48 g, 59.788 mmol, 3.00 equiv). The resulting solution was stirred for 3 hr at 100 degrees C. in an oil bath. The resulting mixture was concentrated. The residue was applied onto a silica gel column and eluted with ethyl acetate/petroleum ether (1:1). This resulted in 2.5 g (33.52%) of 10-(4-bromo-3-methylpyridin-2-yl)-4,4-dimethyl-1,10-diazatricyclo[6.4.0.0^[2,6]]dodeca-2(6),7-dien-9-one as a brown solid. LC-MS: (ES, m/z): M+1: 374

Synthesis of 2-[4,4-dimethyl-9-oxo-1,10-diazatricyclo[6.4.0.0^[2,6]]dodeca-2(6),7-dien-10-yl]-3-methylpyridin-4-ylboronic acid: Into a 50-mL round-bottom flask purged and maintained with an inert atmosphere of nitrogen, was placed 10-(4-bromo-3-methylpyridin-2-yl)-4,4-dimethyl-1,10-diazatricyclo[6.4.0.0^[2,6]]dodeca-2(6),7-dien-9-one (1.00 g, 2.672 mmol, 1.00 equiv), bis(pinacolato)diboron (1.02 g, 4.017 mmol, 1.50 equiv), dioxane (15.00 mL), KOAc (0.52 g, 5.298 mmol, 1.98 equiv), $Pd(dppf)Cl_2$ (195.49 mg, 0.267 mmol, 0.10 equiv). The resulting solution was stirred for 2 hr at 100 degrees C. in an oil bath. The resulting mixture was concentrated. The crude product was purified by Flash-Prep-HPLC with the following conditions (CombiFlash-1): Column, C18 silica gel; mobile phase, A: 0.1% $NH_3$—$H_2O$ in water; B: ACN; Gradient: 35%-70% B in 9 min; Detector, 220 nm. This resulted in 450 mg (49.65%) of 2-[4,4-dimethyl-9-oxo-1,10-diazatricyclo[6.4.0.0^[2,6]]dodeca-2(6),7-dien-10-yl]-3-methylpyridin-4-ylboronic acid as a white solid. LC-MS: (ES, m/z): M+1: 340

Synthesis of tert-butyl (3S)-4-[4-[(6-bromo-4-methyl-3-oxopyrazin-2-yl)amino]-2-nitrophenyl]-3-methylpiperazine-1-carboxylate: Into a 50-mL round-bottom flask, was placed 5-bromo-3-[(4-fluoro-3-nitrophenyl)amino]-1-methylpyrazin-2-one (2.00 g, 5.829 mmol, 1.00 equiv), NMP (20.00 mL), tert-butyl (3S)-3-methylpiperazine-1-carboxylate (1.17 g, 5.842 mmol, 1.00 equiv), DIEA (2.26 g, 17.487 mmol, 3.00 equiv). The resulting solution was stirred for 48 h at 110° C. in an oil bath. The resulting solution was diluted with 100 mL of $H_2O$. The resulting solution was extracted with 3×50 mL of dichloromethane/methanol (10:1). The resulting mixture was washed with 3×20 ml of NaCl. The resulting mixture was concentrated. The residue was applied onto a silica gel column with dichloromethane/methanol (10:1). This resulted in 3 g (59.00%) of tert-butyl (3S)-4-[4-[(6-bromo-4-methyl-3-oxopyrazin-2-yl)amino]-2-nitrophenyl]-3-methylpiperazine-1-carboxylate as a brown solid. LC-MS: (ES, m/z): M+1: 523

Synthesis of 5-bromo-1-methyl-3-([4-[(2S)-2-methylpiperazin-1-yl]-3-nitrophenyl]amino)pyrazin-2-one: Into a 100-mL round-bottom flask, was placed tert-butyl (3S)-4-[4-[(6-bromo-4-methyl-3-oxopyrazin-2-yl)amino]-2-nitrophenyl]-3-methylpiperazine-1-carboxylate (3.00 g, 1 equiv, 60%), HCl (2M) in 1,4-dioxane (30.00 mL). The resulting solution was stirred for 13 h at room temperature. The resulting mixture was concentrated. The resulting solution was diluted with 30 mL of $H_2O$. The pH value of the solution was adjusted to 8 with $NH_3$—$H_2O$. The resulting solution was extracted with 3×15 mL of dichloromethane concentrated. The residue was applied onto a silica gel column with dichloromethane/methanol (10:1). This resulted in 700 mg (48.09%) of 5-bromo-1-methyl-3-([4-[(2S)-2-methylpiperazin-1-yl]-3-nitrophenyl]amino)pyrazin-2-one as a red solid. LC-MS: (ES, m/z): M+1: 423

Synthesis of 5-bromo-1-methyl-3-([4-[(2S)-2-methyl-4-(oxan-4-yl)piperazin-1-yl]-3-nitrophenyl]amino)pyrazin-2-one: Into a 50-mL round-bottom flask, was placed 5-bromo-1-methyl-3-([4-[(2S)-2-methylpiperazin-1-yl]-3-nitrophenyl]amino)pyrazin-2-one (250 mg, 0.591 mmol, 1.00 equiv), 4H-pyran-4-one, tetrahydro-(70.96 mg, 0.709 mmol, 1.20 equiv), THF (5 ml), AcOH (5 drops), $NaBH(AcO)_3$ (250.36 mg, 1.181 mmol, 2.00 equiv). The resulting solution was stirred for 14 h at 30° C. in an oil bath. The resulting mixture was concentrated. The residue was applied onto a silica gel column with dichloromethane/methanol (10:1). This resulted in 220 mg (73.41%) of 5-bromo-1-methyl-3-([4-[(2S)-2-methyl-4-(oxan-4-yl)piperazin-1-yl]-3-nitrophenyl]amino)pyrazin-2-one as a white solid. LC-MS: (ES, m/z): M+1: 507

Synthesis of 3-([3-amino-4-[(2S)-2-methyl-4-(oxan-4-yl)piperazin-1-yl]phenyl]amino)-5-bromo-1-methylpyrazin-2-one: Into a 250-mL round-bottom flask, was placed 5-bromo-1-methyl-3-([4-[(2S)-2-methyl-4-(oxan-4-yl)piperazin-1-yl]-3-nitrophenyl]amino)pyrazin-2-one (10.00 g, 19.709 mmol, 1.00 equiv), EtOH (90.00 mL), $H_2O$ (30.00 mL), Fe (4.40 g, 0.079 mmol, 4.00 equiv), $NH_4Cl$ (8.43 g, 0.158 mmol, 8.00 equiv). The resulting solution was stirred for 1.5 hr at 80 degrees C. in an oil bath. The solids were filtered out. The resulting mixture was concentrated. This resulted in 7.7 g (81.84%) of 3-([3-amino-4-[(2S)-2-methyl-4-(oxan-4-yl)piperazin-1-yl]phenyl]amino)-5-bromo-1-methylpyrazin-2-one as a yellow solid. LC-MS: (ES, m/z): M+1: 477

Synthesis of N-[5-[(6-bromo-4-methyl-3-oxopyrazin-2-yl)amino]-2-[(2S)-2-methyl-4-(oxan-4-yl)piperazin-1-yl]phenyl]prop-2-enamide: Into a 250-mL round-bottom flask, was placed 3-([3-amino-4-[(2S)-2-methyl-4-(oxan-4-yl)piperazin-1-yl]phenyl]amino)-5-bromo-1-methylpyrazin-2-one (3.50 g, 7.331 mmol, 1.00 equiv), DCM (125.00 mL), DIEA (1.90 g, 0.015 mmol, 2.00 equiv). This was followed by the addition of acryloyl chloride (663.55 mg, 7.331 mmol, 1.00 equiv) dropwise with stirring at 0 degrees C. The resulting solution was stirred for 2 hr at room temperature. The resulting mixture was concentrated. The residue was applied onto a silica gel column with dichloromethane/methanol (10:1). The collected fractions were combined and concentrated. This resulted in 4.3 g (110.36%) of N-[5-[(6-bromo-4-methyl-3-oxopyrazin-2-yl)amino]-2-[(2S)-2-methyl-4-(oxan-4-yl)piperazin-1-yl]phenyl]prop-2-enamide as a yellow solid. LC-MS: (ES, m/z): M+1: 531

Synthesis of N-(5-[[6-(2-[4,4-dimethyl-9-oxo-1,10-diazatricyclo[6.4.0.0^[2,6]]dodeca-2(6),7-dien-10-yl]-3-methylpyridin-4-yl)-4-methyl-3-oxopyrazin-2-yl]amino]-2-[(2S)-2-methyl-4-(oxan-4-yl)piperazin-1-yl]phenyl)prop-2-enamide: Into a 50-mL round-bottom flask purged and maintained with an inert atmosphere of nitrogen, was placed N-[5-[(6-bromo-4-methyl-3-oxopyrazin-2-yl)amino]-24 (2S)-2-methyl-4-(oxan-4-yl)piperazin-1-yl]phenyl]prop-2-enamide (430.00 mg, 0.811 mmol, 1.00 equiv), 2-[4,4-dimethyl-9-oxo-1,10-diazatricyclo[6.4.0.0^[2,6]]dodeca-2(6),7-dien-10-yl]-3-methylpyridin-4-ylboronic acid (330.00 mg, 1.217 mmol, 1.20 equiv), $Pd(DTBPF)Cl_2$ (53.00 mg, 0.081 mmol, 0.10 equiv), $K_2CO_3$ (2808.00 mg, 2.028 mmol, 2.50 equiv), Dioxane (8.00 mL), $H_2O$ (0.80 mL). The resulting solution was stirred for 2h at 80 degrees C. in an oil bath. The resulting mixture was concentrated. The residue was applied onto a silica gel column with dichloromethane/methanol (1:10). The crude product (330 mg) was purified by Prep-HPLC with the following conditions: column, X-Bridge Prep C18 19*150 mm 5 um; mobile phase, A: water (it contains 10 mM $NH_4HCO_3$ 0.05% ammonia); B: ACN; Gradient: 20-45% B in 8 min; Flow rate: 20 mL/min; detector, UV 220 nm. The collected solution was concentrated under vacuum to remove $CH_3CN$ and the resulting solution was dried by lyophilization. This resulted in 230 mg of N-(5-[[6-(2-[4,4-dimethyl-9-oxo-1,10-diazatricyclo[6.4.0.0^[2,6]]dodeca-2(6),7-dien-10-yl]-3-methylpyridin-4-yl)-4-methyl-3-oxopyrazin-2-yl]amino]-2-[(2S)-2-methyl-4-(oxan-4-yl)piperazin-1-yl]phenyl)prop-2-enamide as a HCl salt light yellow solid. LC-MS (ES, m/z): M+1-4HCl: 746, $^1H$ NMR (300 MHz, DMSO-$d_6$) δ 11.27 (s, 1H), 9.23-9.28 (d, J=15.0 Hz, 2H), 9.06 (s, 1H), 8.38-8.40 (d, J=6.0 Hz, 1H), 7.74-7.76 (m, 2H), 7.46 (d, J=6.0 Hz, 2H), 7.28 (s, 2H), 7.17-7.19 (d, J=6.0 Hz, 1H), 7.11 (s, 2H), 6.76-6.85 (m, 1H), 6.56 (s, 1H), 6.27-6.33 (d, J=18.0 Hz, 1H), 5.77-5.81 (d, J=12.0 Hz, 1H), 4.11-4.39 (m, 2H), 4.00-4.02 (m, 2H), 3.89-3.92 (m, 1H), 3.59 (s, 3H), 3.51-3.55 (m, 2H), 3.31-3.46 (m, 4H), 3.01-3.05 (m, 2H), 2.89-2.91 (d, J=6.0 Hz, 1H), 2.56-2.58 (m, 2H), 2.43 (s, 1H), 2.30-2.32 (s, 2H), 1.99-2.11 (m, 2H), 1.76-1.83 (m, 2H), 1.22 (s, 6H), 0.77-0.79 (d, J=6.0 Hz, 3H).

Example 41: Preparation of N-(5-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxopyrazin-2-yl]amino]-2-[(2R)-4-methyl-1-(oxetan-3-yl)-3-oxopiperazin-2-yl]phenyl)prop-2-enamide (assumed) and N-(5-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxopyrazin-2-yl]amino]-2-[(2S)-4-methyl-1-(oxetan-3-yl)-3-oxopiperazin-2-yl]phenyl)prop-2-enamide (assumed)

Synthesis of [(3,3-dimethylcyclopent-1-en-1-yl)oxy]trimethylsilane: Into a 10-L 4-necked round-bottom flask purged and maintained with an inert atmosphere of nitrogen, was placed CuCl (20.60 g, 208.083 mmol, 0.05 equiv), LiCl (17.64 g, 416.108 mmol, 0.10 equiv), THF (2.50 L). This was followed by the addition of 2-cyclopenten-1-one, 3-methyl-(400.00 g, 4161.075 mmol, 1.00 equiv) at −5 to 5 degrees C. To this was added TMSCl (474.67 g, 4369.129 mmol, 1.05 equiv) dropwise with stirring at −5 to 5 degrees C. To the mixture was added MeMgCl (1670.00 mL, 14495.069 mmol, 3.48 equiv) dropwise with stirring at −5 to 10 degrees C. The resulting solution was stirred for 2 h at −5 to 10 degrees C. in an ice/salt bath. The reaction was then quenched by the addition of 34 g of MeOH. The resulting solution was diluted with 5 L of $NH_4Cl$. The solids were filtered out. The resulting solution was extracted with 3×5 L of petroleum ether dried over anhydrous sodium sulfate and concentrated. This resulted in 780 g (crude) of [(3,3-dimethylcyclopent-1-en-1-yl)oxy]trimethylsilane as yellow oil. GC-MS: (ES, m/z): M: 184

Synthesis of 3,3-dimethylcyclopentanone: Into a 20-L 4-necked round-bottom flask, was placed [(3,3-dimethylcyclopent-1-en-1-yl)oxy]trimethylsilane (780.00 g, 4230.990 mmol, 1.00 equiv), DCM (7.8 L), $H_2O$ (30.49 g, 1692.396 mmol, 0.4 equiv). This was followed by the addition of $POCl_3$ (214.09 g, 1396.251 mmol, 0.33 equiv) dropwise with stirring at 25 to 30 degrees C. The resulting solution was stirred for 0.5 hr at 25 degrees C. This solvent straight used for next step. GC-MS: (ES, m/z): M: 112

Synthesis of 3,3-dimethylcyclopentanon: Into a 20-L 4-necked round-bottom flask, was placed 3,3-dimethylcyclopentan-1-one (crude) in DCM (7.80 L). This was followed by the addition of DMF (619 g, 2.0 equiv) dropwise with stirring at 25 degrees C. To this was added $POCl_3$ (1362 g, 2.1 equiv) dropwise with stirring at 40 degrees C. The resulting solution was stirred for overnight at 40 degrees C. in an oil bath. The reaction was then quenched by the addition of 2000 g of $K_3PO_4$. The resulting solution was extracted with 3×10 L of dichloromethane dried over anhydrous sodium sulfate and concentrated. This resulted in 530 g of 2-chloro-4,4-dimethylcyclopent-1-ene-1-carbaldehyde as a brown solid. GC-MS: (ES, m/z): M: 158

Synthesis of 4,4-dimethyl-1,10-diazatricyclo[6.4.0.0^[2,6]]dodeca-2(6),7-dien-9-one: Into a 5-L 4-necked round-bottom flask, was placed 2-chloro-4,4-dimethylcyclopent-1-ene-1-carbaldehyde (474.00 g, 2988.085 mmol, 1.00 equiv), DMF (3 L), piperazin-2-one (299.17 g, 2988.084 mmol, 1.00 equiv), DIEA (463.43 g, 3585.703 mmol, 1.2 equiv). The resulting solution was stirred for overnight at 115 degrees C. in an oil bath. The reaction mixture was cooled to room temperature with a water/ice bath. The solids were collected by filtration. The resulting mixture was washed with 3×2 L of $H_2O$ and 3×2 L of PE. The solid was dried in an oven under reduced pressure. This resulted in 230 g (37.68%) of 4,4-dimethyl-1,10-diazatricyclo[6.4.0.0^[2,6]]dodeca-2(6),7-dien-9-one as a grey solid. LC-MS: (ES, m/z): M+1: 205

Synthesis of 2,4-dibromopyridine-3-carbaldehyde, Into a 1000-mL 3-necked round-bottom flask, was placed 2,4-dibromopyridine (40.00 g, 168.852 mmol, 1.00 equiv), THF (400.00 mL). This was followed by the addition of LDA (2M in hexane, 126.60 mL, 1.5 equiv) dropwise with stirring at −78 degrees C. The resulting solution was stirred for 1 h at −78 degrees C. Then added DMF (16.04 g, 219.507 mmol, 1.3 equiv) by dropwise with stirring at −78 degrees C. The resulting solution was stirred for 0.5 hr at −78 degrees C. The reaction was then quenched by the addition of 500 mL of $NH_4Cl$. The resulting solution was extracted with 3×500 mL of ethyl acetate concentrated. The residue was applied onto a silica gel column and eluted with ethyl acetate/petroleum ether (0:1-1:1). This resulted in 24.4 g (54.55%) of 2,4-dibromopyridine-3-carbaldehyde as a white solid. LC-MS: (ES, m/z): M+1: 264

Synthesis of (2,4-dibromopyridin-3-yl)methanol, Into a 100-mL round-bottom flask, was placed 2,4-dibromopyridine-3-carbaldehyde (2.00 g, 7.550 mmol, 1.00 equiv), EtOH (30.00 mL). This was followed by the addition of $NaBH_4$ (285.64 mg, 7.550 mmol, 1 equiv), in portions at 0 degrees C. The resulting solution was stirred for 3 h at room temperature. The reaction was then quenched by the addition of 30 mL of water. The resulting solution was extracted with 3×30 mL of ethyl acetate concentrated. The residue was applied onto a silica gel column and eluted with ethyl acetate/petroleum ether (1:1). The collected fractions were combined and concentrated. This resulted in 1.4 g (69.47%) of (2,4-dibromopyridin-3-yl)methanol as a light yellow solid. LC-MS: (ES, m/z): M+1: 266

Synthesis of 2,4-dibromo-3-[(oxan-2-yloxy)methyl]pyridine, Into a 100-mL round-bottom flask, was placed (2,4-dibromopyridin-3-yl)methanol (1.40 g, 5.245 mmol, 1.00 equiv), DCM (30.00 mL, 0.353 mmol, 0.07 equiv), PPTS (131.81 mg, 0.525 mmol, 0.10 equiv), DHP (661.79 mg, 7.868 mmol, 1.50 equiv). The resulting solution was stirred for overnight at 45 degrees C. in an oil bath. The reaction was then quenched by the addition of 30 mL of water. The resulting solution was extracted with 3×30 mL of dichloromethane concentrated. The residue was applied onto a silica gel column and eluted with ethyl acetate/petroleum ether (1:1). The collected fractions were combined and concentrated. This resulted in 1.5 g (80%) of 2,4-dibromo-3-[(oxan-2-yloxy)methyl]pyridine as colorless oil. LC-MS: (ES, m/z): M+1: 350

Synthesis of 10-[4-bromo-3-[(oxan-2-yloxy)methyl]pyridin-2-yl]-4,4-dimethyl-1,10-diazatricyclo[6.4.0.0^[2,6]]dodeca-2(6),7-dien-9-one, Into a 100-mL round-bottom flask purged and maintained with an inert atmosphere of nitrogen, was placed 4,4-dimethyl-1,10-diazatricyclo[6.4.0.0^[2,6]]dodeca-2(6),7-dien-9-one (1.00 g, 4.895 mmol, 1.00 equiv), dioxane (40.00 mL, 0.454 mmol, 0.09 equiv), $Cs_2CO_3$ (3.19 g, 9.791 mmol, 2 equiv), 2,4-dibromo-3-[(oxan-2-yloxy)methyl]pyridine (1.72 g, 4.900 mmol, 1.00 equiv), $Pd_2(dba)_3$ (448.28 mg, 0.490 mmol, 0.1 equiv), XantPhos (283.26 mg, 0.490 mmol, 0.1 equiv). The resulting solution was stirred for 1 h at 100 degrees C. in an oil bath. The reaction was then quenched by the addition of 40 mL of water. The resulting solution was extracted with 3×40 mL of ethyl acetate concentrated. The residue was applied onto a silica gel column and eluted with ethyl acetate/petroleum ether (1:1). The collected fractions were combined and concentrated. This resulted in 900 mg (38.75%) of 10-[4-bromo-3-[(oxan-2-yloxy)methyl]pyridin-2-yl]-4,4-dimethyl-1,10-diazatricyclo[6.4.0.0^[2,6]]dodeca-2(6),7-dien-9-one as a brown solid. LC-MS: (ES, m/z): M+1: 474

Synthesis of 2-[4,4-dimethyl-9-oxo-1,10-diazatricyclo[6.4.0.0^[2,6]]dodeca-2(6),7-dien-10-yl]-3-[(oxan-2-yloxy)methyl]pyridin-4-ylboronic acid, Into a 100-mL round-bottom flask purged and maintained with an inert atmosphere of nitrogen, was placed 10-[4-bromo-3-[(oxan-2-yloxy)methyl]pyridin-2-yl]-4,4-dimethyl-1,10-diazatricyclo[6.4.0.0^[2,6]]dodeca-2(6),7-dien-9-one (1.00 g, 2.108 mmol, 1.00 equiv), dioxane (10.00 mL), bis(pinacolato)diboron (1.34 g, 5.277 mmol, 2.50 equiv), KOAc (620.00 mg, 6.317 mmol, 3.00 equiv), $Pd(dppf)Cl_2$ (172.00 mg, 0.211 mmol, 0.10 equiv). The resulting solution was stirred for 2 h at 100 degrees C. in an oil bath. The reaction mixture was cooled to room temperature. The solids were filtered out. The resulting mixture was concentrated under vacuum. This resulted in 920 mg (crude) of 2-[4,4-dimethyl-9-oxo-1,10-diazatricyclo[6.4.0.0^[2,6]]dodeca-2(6),7-dien-10-yl]-3-[(oxan-2-yloxy)methyl]pyridin-4-ylboronic acid as brown oil. LC-MS: (ES, m/z): M+1: 436

Synthesis of 10-[1-hydroxy-3H-[1,2]oxaborolo[4,3-c]pyridin-4-yl]-4,4-dimethyl-1,10-diazatricyclo[6.4.0.0^[2,6]]dodeca-2(6),7-dien-9-one: Into a 100-mL round-bottom flask, was placed 2-[4,4-dimethyl-9-oxo-1,10-diazatricyclo[6.4.0.0^[2,6]]dodeca-2(6),7-dien-10-yl]-3-[(oxan-2-yloxy)methyl]pyridin-4-ylboronic acid (920 mg, 1.00 equiv, crude), dioxane (10 mL), HCl (6N, 10 mL). The resulting solution was stirred for 1 h at 25 degrees C. The resulting mixture was concentrated under vacuum. The crude product was purified by Flash-Prep-HPLC with the following conditions: Column, C18 reversed phase column; mobile phase, $H_2O$ (0.05% $NH_3 \cdot H_2O$) and $CH_3CN$ (5% $CH_3CN$ up to 30% in 15 min); Flow rate: 60 mL/min; Detector, 254/220 nm. This resulted in 350 mg of 10-[1-hydroxy-3H-[1,2]oxaborolo[4,3-c]pyridin-4-yl]-4,4-dimethyl-1,10-diazatricyclo[6.4.0.0^[2,6]]dodeca-2(6),7-dien-9-one as a light yellow solid. LC-MS: (ES, m/z): M+1: 338

Synthesis of tert-butyl N-(4-fluoro-3-nitrophenyl)carbamate: Into a 1-L round-bottom flask, was placed 4-fluoro-3-nitroaniline (50.00 g, 320.275 mmol, 1.00 equiv), DCM (500.00 mL), TEA (97.23 g, 0.961 mmol, 3 equiv), DMAP (3.91 g, 0.032 mmol, 0.1 equiv), $Boc_2O$ (104.85 g, 480.419 mmol, 1.50 equiv). The resulting solution was stirred overnight at 25 degrees C. The reaction was then quenched by the addition of 500 mL of water. The resulting solution was extracted with 3×500 mL of dichloromethane and the organic layers combined and concentrated under vacuum. The residue was applied onto a silica gel column with ethyl acetate/petroleum ether (1:3). This resulted in 60 g (73.11%) of tert-butyl N-(4-fluoro-3-nitrophenyl)carbamate as yellow oil. LC-MS: (ES, m/z): M+1: 257

Synthesis of 1,3-dimethyl 2-[4-[(tert-butoxycarbonyl)amino]-2-nitrophenyl]propanedioate: Into a 1-L 3-necked round-bottom flask, was placed dimethyl malonate (61.87 g, 468.324 mmol, 2.00 equiv), DMSO (300.00 mL), add NaH (18.73 g, 468.324 mmol, 2.00 equiv, 60%) at 10 degrees C. The resulting solution was stirred for 1 hr at 25 degrees C. Into the resulting solution was placed tert-butyl N-(4-fluoro-3-nitrophenyl)carbamate (60.00 g, 234.162 mmol, 1.00 equiv). The resulting solution was stirred for 2 hr at 90 degrees C. The reaction was then quenched by the addition of 500 mL of $NH_4Cl$. The resulting solution was extracted with 3×1000 mL of ethyl acetate and the organic layers combined. The resulting mixture was washed with 3×1000 ml of brine. The mixture was dried over anhydrous sodium sulfate and concentrated under vacuum. This resulted in 75 g (86.95%) of 1,3-dimethyl 2-[4-[(tert-butoxycarbonyl)

amino]-2-nitrophenyl]propanedioate as a yellow semi-solid. LC-MS: (ES, m/z): M+1: 369

Synthesis of methyl 2-[4-[(tert-butoxycarbonyl)amino]-2-nitrophenyl]acetate: Into a 1-L 3-necked round-bottom flask, was placed 1,3-dimethyl 2-[4-[(tert-butoxycarbonyl) amino]-2-nitrophenyl]propanedioate (75.00 g, 203.615 mmol, 1.00 equiv), DMSO (300.00 mL), NaCl (23.80 g, 407.230 mmol, 2 equiv), $H_2O$ (15.00 mL). The resulting solution was stirred for 6 hr at 140 degrees C. The reaction was then quenched by the addition of 500 mL of water. The resulting solution was extracted with 3×1000 mL of ethyl acetate and the organic layers combined. The resulting mixture was washed with 3×1000 ml of brine. The mixture was dried over anhydrous sodium sulfate and concentrated under vacuum. The residue was applied onto a silica gel column with ethyl acetate/petroleum ether (1:3). This resulted in 26 g (41.15%) of methyl 2-[4-[(tert-butoxycarbonyl)amino]-2-nitrophenyl]acetate as a yellow solid. LC-MS: (ES, m/z): M-1: 309

Synthesis of methyl 2-bromo-2-[4-[(tert-butoxycarbonyl) amino]-2-nitrophenyl]acetate: Into a 500-mL round-bottom flask, was placed methyl 2-[4-[(tert-butoxycarbonyl)amino]-2-nitrophenyl]acetate (12.00 g, 38.672 mmol, 1.00 equiv), CCL (200.00 mL, 2063.020 mmol, 53.35 equiv), AIBN (1.27 g, 7.744 mmol, 0.20 equiv), NBS (20.65 g, 116.022 mmol, 3.00 equiv). The resulting solution was stirred for 18 hr at 80 degrees C. The resulting mixture was concentrated under vacuum. The residue was applied onto a silica gel column with ethyl acetate/petroleum ether (1:5). This resulted in 8 g (53.15%) of methyl 2-bromo-2-[4-[(tert-butoxycarbonyl)amino]-2-nitrophenyl]acetate as a yellow solid. LC-MS: (ES, m/z): M+1: 389, 391

Synthesis of tert-butyl N-[3-nitro-4-(3-oxopiperazin-2-yl) phenyl]carbamate: Into a 1-L round-bottom flask, was placed methyl 2-bromo-2-[4-[(tert-butoxycarbonyl)amino]-2-nitrophenyl]acetate (8.00 g, 20.555 mmol, 1.00 equiv), 2-methoxyethanol (400 mL), DIEA (5.31 g, 41.110 mmol, 2.00 equiv), ethylenediamine (1.85 g, 30.782 mmol, 1.50 equiv). The resulting solution was stirred for 2 hr at 25 degrees C. The reaction was then quenched by the addition of 500 mL of water. The resulting solution was extracted with 3×500 mL of ethyl acetate and the organic layers combined and concentrated under vacuum. The residue was applied onto a silica gel column with dichloromethane/methanol (10:1). This resulted in 5.5 g (79.55%) of tert-butyl N-[3-nitro-4-(3-oxopiperazin-2-yl)phenyl]carbamate as a yellow solid. LC-MS: (ES, m/z): M+1: 337

Synthesis of tert-butyl N-[3-nitro-4-[1-(oxetan-3-yl)-3-oxopiperazin-2-yl]phenyl]carbamate: Into a 500-mL round-bottom flask, was placed tert-butyl N-[3-nitro-4-(3-oxopiperazin-2-yl)phenyl]carbamate (5.50 g, 16.352 mmol, 1.00 equiv), 3-oxetanone (5.89 g, 81.734 mmol, 5.00 equiv), DCE (500.00 mL), HOAc (5.00 mL, 87.258 mmol, 5.34 equiv). The resulting solution was stirred for 4 hr at 25 degrees C. Into the resulting solution was placed NaBH $(OAc)_3$ (34.66 g, 163.536 mmol, 10.00 equiv). The resulting solution was stirred for 4 hr at 25 degrees C. The reaction was then quenched by the addition of 200 mL of water. The resulting solution was extracted with 3×200 mL of DCM/MeOH=20:1 and the organic layers combined and concentrated under vacuum. The residue was applied onto a silica gel column with dichloromethane/methanol (10:1). The product was precipitated by the addition of PE/DCM=3:1. This resulted in 3.5 g (54.54%) of tert-butyl N-[3-nitro-4-[1-(oxetan-3-yl)-3-oxopiperazin-2-yl]phenyl]carbamate as a yellow solid. LC-MS: (ES, m/z): M+1: 393

Synthesis of tert-butyl N-[4-[4-methyl-1-(oxetan-3-yl)-3-oxopiperazin-2-yl]-3-nitrophenyl]carbamate: Into a 250-mL 3-necked round-bottom flask, was placed tert-butyl N-[3-nitro-4-[1-(oxetan-3-yl)-3-oxopiperazin-2-yl]phenyl]carbamate (2.30 g, 5.861 mmol, 1.00 equiv), THF (100.00 mL, 617.150 mmol), NaHMDS (8.80 mL), methyl iodide (1.00 g, 7.045 mmol, 1.20 equiv). The resulting solution was stirred for 4 hr at 0 degrees C. The reaction was then quenched by the addition of water. The resulting solution was extracted with 3×100 mL of ethyl acetate and the organic layers combined and concentrated under vacuum. The residue was applied onto a silica gel column with dichloromethane/methanol (10:1). The crude product was purified by Flash-Prep-HPLC with the following conditions (IntelFlash-1): Column, C18 reversed phase column; mobile phase, Water (0.05% $NH_3 \cdot H_2O$) and ACN (5% Phase B up to 50% in 10 min, 50% hold in 5 min); Flow rate: 80 mL/min. Detector, UV 220, 254 nm. This resulted in 640 mg (26.87%) of tert-butyl N-[4-[4-methyl-1-(oxetan-3-yl)-3-oxopiperazin-2-yl]-3-nitrophenyl]carbamate as yellow oil. LC-MS: (ES, m/z): M+1: 407; H-NMR (300 MHz, DMSO-$d_6$, ppm) δ 9.85 (s, 1H), 8.00 (d, J=2.2 Hz, 1H), 7.59 (dd, J=8.5, 2.3 Hz, 1H), 7.43 (d, J=8.5 Hz, 1H), 4.49 (t, J=6.6 Hz, 1H), 4.39 (t, J=6.6 Hz, 1H), 4.15 (s, 1H), 3.86 (t, J=6.6 Hz, 1H), 3.77 (t, J=6.5 Hz, 1H), 3.65 (p, J=7.0 Hz, 1H), 3.49 (td, J=11.3, 3.7 Hz, 1H), 2.93 (d, J=12.0 Hz, 1H), 2.86 (s, 3H), 1.49 (s, 9H).

Synthesis of 3-(4-amino-2-nitrophenyl)-1-methyl-4-(oxetan-3-yl)piperazin-2-one: Into a 100-mL round-bottom flask, was placed tert-butyl N-[4-[4-methyl-1-(oxetan-3-yl)-3-oxopiperazin-2-yl]-3-nitrophenyl]carbamate (640.00 mg, 1.575 mmol, 1.00 equiv), DCM (40.00 mL). This was followed by the addition of TFA (5.00 mL) dropwise with stirring at 0 degrees C. The resulting solution was stirred for 1 hr at room temperature. The pH value of the solution was adjusted to 8 with $NaHCO_3$. The resulting solution was extracted with 3×100 mL of DCM:MeOH=10:1 and the organic layers combined. The resulting mixture was washed with 1×500 ml of brine. The mixture was dried over anhydrous sodium sulfate and concentrated under vacuum. This resulted in 450 mg (69.97%) of 3-(4-amino-2-nitrophenyl)-1-methyl-4-(oxetan-3-yl)piperazin-2-one as a yellow solid. LC-MS: (ES, m/z): M+1: 307

Synthesis of 5-bromo-1-methyl-3-([4-[4-methyl-1-(oxetan-3-yl)-3-oxopiperazin-2-yl]-3-nitrophenyl]amino) pyrazin-2-one: Into a 40-mL vial purged and maintained with an inert atmosphere of nitrogen, was placed 3-(4-amino-2-nitrophenyl)-1-methyl-4-(oxetan-3-yl)piperazin-2-one (450.00 mg, 1.469 mmol, 1.00 equiv), toluene (10.00 mL), 3,5-dibromo-1-methylpyrazin-2-one (391.00 mg, 1.459 mmol, 0.99 equiv), $Pd(OAc)_2$ (66.00 mg, 0.294 mmol, 0.20 equiv), Xantphos (340.00 mg, 0.588 mmol, 0.40 equiv), $K_2CO_3$ (304.00 mg, 2.200 mmol, 1.50 equiv). The resulting solution was stirred for 2 hr at 100 degrees C. in an oil bath. The reaction mixture was cooled to room temperature. The resulting mixture was concentrated under vacuum. The residue was applied onto a silica gel column with dichloromethane/methanol (10:1). This resulted in 370 mg (34.21%) of 5-bromo-1-methyl-3-([4-[4-methyl-1-(oxetan-3-yl)-3-oxopiperazin-2-yl]-3-nitrophenyl]amino)pyrazin-2-one as a yellow solid. LC-MS: (ES, m/z): M+1: 493

Synthesis of 3-([3-amino-4-[4-methyl-1-(oxetan-3-yl)-3-oxopiperazin-2-yl]phenyl]amino)-5-bromo-1-methylpyrazin-2-one: Into a 40-mL vial, was placed 5-bromo-1-methyl-3-([4-[4-methyl-1-(oxetan-3-yl)-3-oxopiperazin-2-yl]-3-nitrophenyl]amino)pyrazin-2-one (350.00 mg, 0.709 mmol, 1.00 equiv), EtOH (12.00 mL), $H_2O$ (4.00 mL), Fe (238.00 mg, 4.262 mmol, 6.01 equiv), $NH_4Cl$ (228.00 mg, 4.262 mmol, 6.01 equiv). The resulting solution was stirred for 2 hr at 55 degrees C. in an oil bath. The reaction mixture was cooled to room temperature. The resulting solution was diluted with 200/200 mL of DCM and water. The solids were filtered out. The resulting solution was extracted with 2×100 mL of dichloromethane and the organic layers combined. The resulting mixture was washed with 1×500 ml of brine. The mixture was dried over anhydrous sodium sulfate and concentrated under vacuum. The residue was applied onto a silica gel column with dichloromethane/methanol (19:1). This resulted in 250 mg (76.05%) of 3-([3-amino-4-[4-methyl-1-(oxetan-3-yl)-3-oxopiperazin-2-yl]phenyl]amino)-5-bromo-1-methylpyrazin-2-one as yellow oil. LC-MS: (ES, m/z): M+1: 463

Synthesis of N-[5-[(6-bromo-4-methyl-3-oxopyrazin-2-yl)amino]-2-[4-methyl-1-(oxetan-3-yl)-3-oxopiperazin-2-yl]phenyl]prop-2-enamide: Into a 40-mL vial purged and maintained with an inert atmosphere of nitrogen, was placed 3-([3-amino-4-[4-methyl-1-(oxetan-3-yl)-3-oxopiperazin-2-yl]phenyl]amino)-5-bromo-1-methylpyrazin-2-one (250.00 mg, 0.540 mmol, 1.00 equiv), DCM (5.00 mL), DIEA (140.00 mg, 1.083 mmol, 2.01 equiv), acryloyl chloride (49.00 mg, 0.541 mmol, 1.00 equiv). The resulting solution was stirred for 2 hr at room temperature. The resulting mixture was concentrated under vacuum. The residue was applied onto a silica gel column with dichloromethane/methanol (19:1). This resulted in 250 mg (89.55%) of N-[5-[(6-bromo-4-methyl-3-oxopyrazin-2-yl)amino]-2-[4-methyl-1-(oxetan-3-yl)-3-oxopiperazin-2-yl]phenyl]prop-2-enamide as yellow oil. LC-MS: (ES, m/z): M+1: 517

Synthesis of N-(5-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxopyrazin-2-yl]amino]-2-[(2R)-4-methyl-1-(oxetan-3-yl)-3-oxopiperazin-2-yl]phenyl)prop-2-enamide (assumed): Into a 40-mL vial purged and maintained with an inert atmosphere of nitrogen, was placed N-[5-[(6-bromo-4-methyl-3-oxopyrazin-2-yl)amino]-2-[4-methyl-1-(oxetan-3-yl)-3-oxopiperazin-2-yl]phenyl]prop-2-enamide (250.00 mg, 0.483 mmol, 1.00 equiv), dioxane (10.00 mL), $H_2O$ (1.00 mL), 10-[1-hydroxy-3H-[1,2]oxaborolo[4,3-c]pyridin-4-yl]-4,4-dimethyl-1,10-diazatricyclo[6.4.0.0^[2,6]]dodeca-2(6),7-dien-9-one (326.00 mg, 0.967 mmol, 2.00 equiv), Xphos Pd G3 (81.00 mg, 0.096 mmol, 0.20 equiv), $K_2CO_3$ (331.00 mg, 2.395 mmol, 4.96 equiv). The resulting solution was stirred for 1 hr at 100 degrees C. in an oil bath. The reaction mixture was cooled to room temperature. The resulting mixture was concentrated under vacuum. The residue was applied onto a silica gel column with dichloromethane/methanol (10:1). The crude product was purified by Prep-HPLC with the following conditions: Column, XBridge Shield RP18 OBD Column, Sum, 19*150 mm; mobile phase, Water (0.05% $NH_3{\cdot}H_2O$) and ACN (26% Phase B up to 50% in 7 min); Detector, UV 254/220 nm. The crude product was purified by Chiral-Prep-HPLC with the following conditions: Column, CHIRALPAK IF; mobile phase, THF and EtOH (0.1% DEA); Flow rate: 12 mL/min. This resulted in 30 mg (Y=8.30%, RT=2.27 min) of N-(5-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxopyrazin-2-yl]amino]-2-[(2R)-4-methyl-1-(oxetan-3-yl)-3-oxopiperazin-2-yl]phenyl)prop-2-enamide (assumed) as a white solid. LC-MS: (ES, m/z): M+1: 748; H-NMR: (300 MHz, DMSO-$d_6$, ppm) δ 9.82 (s, 1H), 9.36 (d, J=3.2 Hz, 1H), 8.71 (d, J=15.3 Hz, 1H), 8.46 (d, J=5.1 Hz, 1H), 7.82 (d, J=14.4 Hz, 2H), 7.68 (s, 1H), 7.16 (d, J=8.4 Hz, 1H), 6.65-6.44 (m, 2H), 6.32 (dd, J=16.5, 6.1 Hz, 1H), 5.81 (d, J=10.1 Hz, 1H), 5.04 (d, J=26.4 Hz, 1H), 4.72-4.36 (m, 4H), 4.22 (s, 3H), 4.08 (s, 1H), 4.00-3.80 (m, 3H), 3.70 (t, J=6.9 Hz, 1H), 3.62 (s, 1H), 3.57 (s, 3H), 3.04 (d, J=12.0 Hz, 1H), 2.83 (s, 3H), 2.59 (d, J=5.0 Hz, 3H), 2.44 (s, 2H), 1.23 (s, 6H).

Synthesis of N-(5-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxopyrazin-2-yl]amino]-2-[(2S)-4-methyl-1-(oxetan-3-yl)-3-oxopiperazin-2-yl]phenyl)prop-2-enamide (assumed): Into a 40-mL vial purged and maintained with an inert atmosphere of nitrogen, was placed N-[5-[(6-bromo-4-methyl-3-oxopyrazin-2-yl)amino]-2-[4-methyl-1-(oxetan-3-yl)-3-oxopiperazin-2-yl]phenyl]prop-2-enamide (250.00 mg, 0.483 mmol, 1.00 equiv), dioxane (10.00 mL), $H_2O$ (1.00 mL), 10-[1-hydroxy-3H-[1,2]oxaborolo[4,3-c]pyridin-4-yl]-4,4-dimethyl-1,10-diazatricyclo[6.4.0.0^[2,6]]dodeca-2(6),7-dien-9-one (326.00 mg, 0.967 mmol, 2.00 equiv), Xphos Pd G3 (81.00 mg, 0.096 mmol, 0.20 equiv), $K_2CO_3$ (331.00 mg, 2.395 mmol, 4.96 equiv). The resulting solution was stirred for 1 hr at 100 degrees C. in an oil bath. The reaction mixture was cooled to room temperature. The resulting mixture was concentrated under vacuum. The residue was applied onto a silica gel column with dichloromethane/methanol (10:1). The crude product was purified by Prep-HPLC with the following conditions: Column, XBridge Shield RP18 OBD Column, Sum, 19*150 mm; mobile phase, Water (0.05% $NH_3{\cdot}H_2O$) and ACN (26% Phase B up to 50% in 7 min); Detector, UV 254/220 nm. The crude product was purified by Chiral-Prep-HPLC with the following conditions: Column, CHIRALPAK IF; mobile phase, THF and EtOH (0.1% DEA); Flow rate: 12 mL/min. This resulted in 30 mg (Y=8.30%, RT=2.80 min) of N-(5-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxopyrazin-2-yl]amino]-2-[(2S)-4-methyl-1-(oxetan-3-yl)-3-oxopiperazin-2-yl]phenyl)prop-2-enamide (assumed) as a white solid. LC-MS: (ES, m/z): M+1: 748; H-NMR: (300 MHz, DMSO-$d_6$, ppm) δ 9.82 (s, 1H), 9.36 (d, J=3.2 Hz, 1H), 8.71 (d, J=15.3 Hz, 1H), 8.46 (d, J=5.1 Hz, 1H), 7.82 (d, J=14.4 Hz, 2H), 7.68 (s, 1H), 7.16 (d, J=8.4 Hz, 1H), 6.65-6.44 (m, 2H), 6.32 (dd, J=16.5, 6.1 Hz, 1H), 5.81 (d, J=10.1 Hz, 1H), 5.04 (d, J=26.4 Hz, 1H), 4.72-4.36 (m, 4H), 4.22 (s, 3H), 4.08 (s, 1H), 4.00-3.80 (m, 3H), 3.70 (t, J=6.9 Hz, 1H), 3.62 (s, 1H), 3.57 (s, 3H), 3.04 (d, J=12.0 Hz, 1H), 2.83 (s, 3H), 2.59 (d, J=5.0 Hz, 3H), 2.44 (s, 2H), 1.23 (s, 6H).

Example 42: Preparation of N-(5-[[6-(2-[4,4-dimethyl-9-oxo-1,10-diazatricyclo[6.4.0.0^[2,6]]dodeca-2(6),7-dien-10-yl]-3-(hydroxymethyl)pyri-din-4-yl)-4-methyl-3-oxopyrazin-2-yl]amino]-2-[1-methyl-4-(oxetan-3-yl)-6-oxopiperazin-2-yl]phenyl)prop-2-enamide Synthesis of [(3,3-dimethylcyclopent-1-en-1-yl)oxy]trimethylsilane Into a 20-L 4-necked round-bottom flask purged and maintained with an inert atmosphere of nitrogen, was placed CuCl (49.5g, 500 mmol, 0.05 equiv), LiCl (42.4 g, 1000 mmol, 0.10 equiv), THF (6 L). This was followed by the addition of 2-cyclopenten-1-one, 3-methyl-(960.00 g, 10 mol, 1.00 equiv) at −5 to 5 degrees C. To this was added TMSCl (1140.3 g, 10.5 mol, 1.05 equiv) dropwise with stirring at −5 to 5 degrees C. To the mixture was added MeMgCl (4000 mL, 12 mol, 1.2 equiv) dropwise with stirring at −5 to 10 degrees C. The resulting solution was stirred for 2 h at −5 to 10 degrees C. in an ice/salt bath. The reaction was then quenched by the addition of 82 g of MeOH. The resulting solution was diluted with 10 L of $NH_4Cl$. The solids were filtered out. The resulting solution was extracted with 3×10 L of petroleum ether dried over anhydrous sodium sulfate and concentrated. This resulted in 1730 g (crude) of [(3,3-dimethylcyclopent-1-en-1-yl)oxy] trimethylsilane as yellow oil. GC-MS-1: (ES, m/z): M: 184

Synthesis of 3,3-dimethylcyclopentanone Into a 20-L 4-necked round-bottom flask, was placed [(3,3-dimethylcyclopent-1-en-1-yl)oxy]trimethylsilane (1730.00 g, 9.40 mol, 1.00 equiv), DCM (7.0 L), $H_2O$ (67.69g, 3.76 mol, 0.4 equiv). This was followed by the addition of $POCl_3$ (474.71 g, 3.10 mol, 0.33 equiv) dropwise with stirring at 25 to 30 degrees C. The resulting solution was stirred for 0.5 hr at 25 degrees C. This crude solvent straight used for next step. GC-MS-2: (ES, m/z): M: 112

Synthesis of 3,3-dimethylcyclopentanone Into a 20-L 4-necked round-bottom flask, was placed previous step solution 3,3-dimethylcyclopentan-1-one in DCM (7.0 L). This was followed by the addition of DMF (1372.4 g, 2.0 equiv) dropwise with stirring at 25 degrees C. To this was added $POCl_3$ (3020.22 g, 2.1 equiv) dropwise with stirring at 40 degrees C. The resulting solution was stirred for overnight at 40 degrees C. in an oil bath. The reaction was then quenched by the addition of 4000 g of $K_3PO_4$ in 30 L Water. The resulting solution was extracted with 3×20 L of dichloromethane dried over anhydrous sodium sulfate and concentrated. This resulted in 1700 g (Crude) of 2-chloro-4,4-dimethylcyclopent-1-ene-1-carbaldehyde as a brown solid. GC-MS-3: (ES, m/z): M: 158

Synthesis of 4,4-dimethyl-1,10-diazatricyclo[6.4.0.0^[2,6]]dodeca-2(6),7-dien-9-one Into a 10-L 4-necked round-bottom flask, was placed 2-chloro-4,4-dimethylcyclopent-1-ene-1-carbaldehyde (1700.00 g, 10.759 mol, 1.00 equiv), DMF (6 L), piperazin-2-one (1075.95 g, 10.759 mol, 1.00 equiv), DIEA (1665.49 g, 12.91 mol, 1.2 equiv). The resulting solution was stirred for overnight at 115 degrees C. in an oil bath. The reaction mixture was cooled to room temperature with a water/ice bath. The solids were collected by filtration. The resulting mixture was washed with 3×6 L of $H_2O$ and 3×4 L of PE. The solid was dried in an oven under reduced pressure. This resulted in 720 g (32.81%) of 4,4-dimethyl-1,10-diazatricyclo[6.4.0.0^[2,6]]dodeca-2(6),7-dien-9-one as a grey solid. LC-MS-4: (ES, m/z): M+1: 205

Synthesis of 2,4-dibromopyridine-3-carbaldehyde Into a 10000-mL 4-necked round-bottom flask, was placed 2,4-dibromopyridine (500.00 g, 2.11 mol, 1.00 equiv), THF (5000.00 mL). This was followed by the addition of LDA (2M in hexane, 1.58 L, 1.5 equiv) dropwise with stirring at −78 degrees C. The resulting solution was stirred for 1 h at −78 degrees C. Then add DMF (200 g, 2.74 mol, 1.3 equiv) by dropwise with stirring at −78 degrees C. The resulting solution was stirred for 1 h at −78 degrees C. The reaction was then quenched by the addition of 5000 mL of aq. $NH_4Cl$/HOAc(1:1). The resulting solution was extracted with 3×5000 mL of ethyl acetate concentrated. The residue was applied onto a silica gel column and eluted with ethyl acetate/petroleum ether (0:1-1:1). This resulted in 450 g (80%) of 2,4-dibromopyridine-3-carbaldehyde as a white solid. LC-MS-5: M+1: 264

Synthesis of (2,4-dibromopyridin-3-yl)methanol Into a 10000-mL 4-necked round-bottom flask, was placed 2,4-dibromopyridine-3-carbaldehyde (450 g, 1.7 mol, 1.00 equiv), EtOH (4500.00 mL). This was followed by the addition of $NaBH_4$ (65 g, 1.7 mol, 1 equiv), in portions at 0 degrees C. The resulting solution was stirred for 3 h at room temperature. The reaction was then quenched by the addition of 3000 mL of water. The resulting solution was extracted with 3×3000 mL of ethyl acetate concentrated. The residue was applied onto a silica gel column and eluted with ethyl acetate/petroleum ether (1:1). The collected fractions were combined and concentrated. This resulted in 500 g (crude, 90%) of (2,4-dibromopyridin-3-yl)methanol as a light yellow solid. LC-MS-6: (ES, m/z): M+1: 266

Synthesis of 2,4-dibromo-3-[(oxan-2-yloxy)methyl]pyridine Into a 10-L 4-necked round-bottom flask, was placed (2,4-dibromopyridin-3-yl)methanol (500 g, 1.89 mol, 1.00 equiv), DCM (5 L), PPTS (47.358 g, 188.68 mmol, 0.10 equiv), DHP (237.73g, 2.83 mol, 1.50 equiv). The resulting solution was stirred for overnight at 45 degrees C. in an oil bath. The reaction was then quenched by the addition of 3 L of water. The resulting solution was extracted with 3×5 L of dichloromethane concentrated. The residue was applied onto a silica gel column and eluted with ethyl acetate/petroleum ether (1:1). The collected fractions were combined and concentrated. This resulted in 560 g (97.4%) of 2,4-dibromo-3-[(oxan-2-yloxy)methyl]pyridine as colorless oil. LC-MS-7: (ES, m/z): M+1: 350

Synthesis of 10-[4-bromo-3-[(oxan-2-yloxy)methyl]pyridin-2-yl]-4,4-dimethyl-1,10-diazatricyclo[6.4.0.0^[2,6]]dodeca-2(6),7-dien-9-one Into a 5 L 4-necked round-bottom flask purged and maintained with an inert atmosphere of nitrogen, was placed 2,4-dibromo-3-[(oxan-2-yloxy)methyl] pyridine (400.00 g, 1139.478 mmol, 1.00 equiv), DMA (5.20 L), 4,4-dimethyl-1,10-diazatricyclo[6.4.0.0^[2,6]]dodeca-2(6),7-dien-9-one (256.04 g, 1253.426 mmol, 1.10 equiv), $K_2CO_3$ (472.44 g, 3418.388 mmol, 3.00 equiv), CuI (130.2 g, 683.686 mmol, 0.60 equiv), 1,10-phenanthroline (123.2g, 683.686 mmol, 0.60 equiv). The resulting solution was stirred for overnight at 110 degrees C. in an oil bath. The reaction mixture was cooled to room temperature with an ice/salt bath. The solids were filtered out. The resulting solution was concentrated. The residue was applied onto a silica gel column with dichloromethane/EA (1:1). The collected fractions were combined and concentrated. This resulted in 260 g (92%) and 165 g(36.8%) of 10-[4-bromo-3-[(oxan-2-yloxy)methyl]pyridin-2-yl]-4,4-dimethyl-1,10-diazatricyclo[6.4.0.0^[2,6]]dodeca-2(6),7-dien-9-one as a brown solid. LC-MS-8: (ES, m/z): M+1: 474.

Synthesis of 2-[4,4-dimethyl-9-oxo-1,10-diazatricyclo [6.4.0.0^[2,6]]dodeca-2(6),7-dien-10-yl]-3-[(oxan-2-yloxy) methyl]pyridin-4-ylboronic acid Into a 5 L 4-necked round-bottom flask purged and maintained with an inert atmosphere of nitrogen, was placed 10-[4-bromo-3-[(oxan-2-yloxy)methyl]pyridin-2-yl]-4,4-dimethyl-1,10-diazatricyclo[6.4.0.0^[2,6]]dodeca-2(6),7-dien-9-one (230 g, 486.25 mmol, 1.00 equiv), dioxane (2.3 L), bis(pinacolato)diboron (247.01 g, 972.51 mmol, 2.0 equiv), KOAc (142.96 g, 1458.75 mmol, 3.00 equiv), $Pd(dppf)Cl_2$ (35.54g, 48.62 mmol, 0.10 equiv). The resulting solution was stirred for overnight at 100 degrees C. in an oil bath. The reaction mixture was cooled to room temperature. The solids were filtered out. The resulting mixture was concentrated under vacuum. Then added $CH_3CN$ (300 mL) to residue, the solids were filtered out. This resulted in 170 g (95%) and 260g (19.1%) of 2-[4,4-dimethyl-9-oxo-1,10-diazatricyclo [6.4.0.0^[2,6]]dodeca-2(6),7-dien-10-yl]-3-[(oxan-2-yloxy) methyl]pyridin-4-ylboronic acid as brown oil. LC-MS-9(ES, m/z): M+1: 440

Synthesis of 2-[4,4-dimethyl-9-oxo-1,10-diazatricyclo [6.4.0.0^[2,6]]dodeca-2(6),7-dien-10-yl]-3-[(oxan-2-yloxy) methyl]pyridin-4-ylboronic acid Into a 1-L round-bottom flask, was placed 2-chloro-6-chloro-pyrazine (20.00 g, 134.255 mmol, 1.00 equiv), dioxane (120.00 mL, 1416.490 mmol, 10.55 equiv), $H_2O$ (50.000 mL), NaOH (10.74 g, 268.519 mmol, 2.00 equiv). The resulting solution was stirred for 4 hr at 110 degrees C. in an oil bath. The organic phase was concentrated. The pH value of the solution was adjusted to 4 with HCL (6M). The solids were collected by filtration. The solid was dried by baking. This resulted in 14 g (79.89%) of 6-chloro-1H-pyrazin-2-one as a white solid. $^1$H NMR (300 MHz, DMSO-$d_6$) δ 12.44 (s, 1H), 8.20 (s, 1H), 8.11 (s, 1H).

Synthesis of 6-chloro-1-methylpyrazin-2-one Into a 500-mL 3-necked round-bottom flask purged and maintained with an inert atmosphere of nitrogen, was placed Na (1.69 g, 73.511 mmol, 1.20 equiv), MeOH (200.00 mL), the resulting solution was stirred for 1 hr at room temperature. Then 6-chloro-1H-pyrazin-2-one (8.00 g, 61.289 mmol, 1.00 equiv) and $Me_2SO_4$ (9.27 g, 73.571 mmol, 1.20 equiv) were added. The resulting solution was allowed to react, with stirring, for an additional 2 hr while the temperature was maintained at 70 degrees C. in an oil bath. The resulting mixture was concentrated. The resulting solution was diluted with 200 mL of EA. The resulting mixture was washed with 2×20 ml of $H_2O$ and 1×20 mL of NaCl(aq). The mixture was dried over anhydrous sodium sulfate and concentrated. The residue was applied onto a silica gel column and eluted with ethyl acetate/petroleum ether (1:10). This resulted in 2.5 g (21.16%) of 6-chloro-1-methylpyrazin-2-one as a brown solid. $^1$H NMR (300 MHz, DMSO-$d_6$) δ 7.98 (s, 1H), 7.54 (s, 1H), 3.53 (s, 3H).

Synthesis of tert-butyl N-[4-(1-methyl-6-oxopyrazin-2-yl)-3-nitrophenyl]carbamate Into a 250-mL round-bottom flask purged and maintained with an inert atmosphere of nitrogen, was placed 6-chloro-1-methylpyrazin-2-one (2.50 g, 18.677 mmol, 1.00 equiv), tert-butyl N-[3-nitro-4-(4,4,5,5-tetramethyl-1,3,2-dioxaborolan-2-yl)phenyl]carbamate (8.84 g, 24.272 mmol, 1.30 equiv), t-BuOH (100.00 mL), $H_2O$ (10.00 mL), RuPhos Palladacycle Gen.3 (781.06 mg, 0.934 mmol, 0.05 equiv), $Na_2CO_3$ (5.94 g, 56.044 mmol, 3.00 equiv). The resulting solution was stirred for 1 hr at 90 degrees C. in an oil bath. The resulting mixture was concentrated. The residue was applied onto a silica gel column and eluted with ethyl acetate/petroleum ether (1:1). This resulted in 3.5 g (54.11%) of tert-butyl N-[4-(1-methyl-6-oxopyrazin-2-yl)-3-nitrophenyl]carbamate as a brown solid. $^1$H NMR (300 MHz, DMSO-$d_6$) δ 10.17 (s, 1H), 8.54 (d, J=2.1 Hz, 1H), 8.07 (s, 1H), 7.85 (dd, J=8.7, 2.1 Hz, 1H), 7.63 (d, J=8.7 Hz, 1H), 7.20 (s, 1H), 3.14 (s, 3H), 1.52 (s, 9H).

Synthesis of tert-butyl (3-amino-4-(1-methyl-6-oxopiperazin-2-yl)phenyl)carbamate Into a 50-mL pressure tank reactor, was placed tert-butyl N-[4-(1-methyl-6-oxopyrazin-2-yl)-3-nitrophenyl]carbamate (1.00 g), MeOH (50.00 mL), Pd/C (100.00 mg). To the above $H_2$ (gas, 30 atm) was introduced in. The resulting solution was stirred for 20 hr at 60 degrees C. in an oil bath. The solids were filtered out. This resulted in 900 mg of tert-butyl (3-amino-4-(1-methyl-6-oxopiperazin-2-yl)phenyl)carbamate as a brown solid. LC-MS-13: (ES, m/z): M+1: 321.

Synthesis of tert-butyl N-[3-amino-4-[1-methyl-4-(oxetan-3-yl)-6-oxopiperazin-2-yl]phenyl]carbamate Into a 100-mL round-bottom flask, was placed tert-butyl N-[3-amino-4-(1-methyl-6-oxopiperazin-2-yl)phenyl]carbamate (900 mg, 2.809 mmol, 1.00 equiv), 3-oxetanone (0.51 g, 7.079 mmol, 2.52 equiv), DCE (10.00 mL), HOAC (0.10 mL) and the resulting solution was stirred for 6 hr at room temperature. MeOH (10.00 mL) and $NaBH_3CN$ (1059.16 mg, 16.854 mmol, 6.00 equiv) were added. The resulting solution was allowed to react, with stirring, for an additional 14 hr while the temperature was maintained at 30 degrees C. in an oil bath. The resulting mixture was concentrated. The residue was applied onto a silica gel column with dichloromethane/methanol (10:1). This resulted in 700 mg of tert-butyl N-[3-amino-4-[1-methyl-4-(oxetan-3-yl)-6-oxopiperazin-2-yl]phenyl]carbamate as a brown solid. LC-MS-14: (ES, m/z): M+1: 377

Synthesis of tert-butyl N-[4-[1-methyl-4-(oxetan-3-yl)-6-oxopiperazin-2-yl]-3-(prop-2-enamido)phenyl]carbamate Into a 25-mL round-bottom flask, was placed tert-butyl N-[3-amino-4-[1-methyl-4-(oxetan-3-yl)-6-oxopiperazin-2-yl]phenyl]carbamate (700.00 mg, 70%), DCM (10.00 mL, 0.118 mmol, 0.06 equiv), TEA (564.47 mg, 5.578 mmol, 3.00 equiv), acryloyl chloride (336.60 mg, 3.719 mmol, 2.00 equiv). The resulting solution was stirred for 30 min at room temperature. The resulting mixture was concentrated. The residue was applied onto a silica gel column and eluted with dichloromethane/methanol (10:1). This resulted in 350 mg of tert-butyl N-[4-[1-methyl-4-(oxetan-3-yl)-6-oxopiperazin-2-yl]-3-(prop-2-enamido)phenyl]carbamate as a solid. LC-MS-15: (ES, m/z): M+1: 431.

Synthesis of N-[5-amino-2-[1-methyl-4-(oxetan-3-yl)-6-oxopiperazin-2-yl]phenyl]prop-2-enamide Into a 25-mL round-bottom flask, was placed tert-butyl N-[4-[1-methyl-4-(oxetan-3-yl)-6-oxopiperazin-2-yl]-3-(prop-2-enamido)phenyl]carbamate (350.00 mg, 0.813 mmol, 1.00 equiv), DCM (5 mL). This was followed by the addition of TFA (2 mL) at 0 degrees C. The resulting solution was stirred for 3 hr at room temperature. The resulting solution was diluted with 10 mL of DCM. The resulting mixture was washed with 3×5 ml of $NaHCO_3$. The mixture was dried over anhydrous sodium sulfate. The residue was applied onto a silica gel column and eluted with dichloromethane/methanol (10:1). This resulted in 160 mg (59.57%) of N-[5-amino-2-[1-methyl-4-(oxetan-3-yl)-6-oxopiperazin-2-yl]phenyl]prop-2-enamide as a red solid. LC-MS-16: (ES, m/z): M+1: 331.

Synthesis of N-[5-[(6-bromo-4-methyl-3-oxopyrazin-2-yl)amino]-2-[1-methyl-4-(oxetan-3-yl)-6-oxopiperazin-2-yl]phenyl]prop-2-enamide Into a 25-mL round-bottom flask purged and maintained with an inert atmosphere of nitrogen, was placed N-[5-amino-2-[1-methyl-4-(oxetan-3-yl)-6-oxopiperazin-2-yl]phenyl]prop-2-enamide (50.00 mg, 0.151 mmol, 1.00 equiv), 3,5-dibromo-1-methylpyrazin-2-one (48.65 mg, 0.182 mmol, 1.20 equiv), t-BuOH (3.00 mL), Pd(DtBPF)$Cl_2$ (9.86 mg, 0.015 mmol, 0.10 equiv), $K_2CO_3$ (62.75 mg, 0.454 mmol, 3.00 equiv). The resulting solution was stirred for 2 hr at 90 degrees C. in an oil bath. The resulting mixture was concentrated. The residue was applied onto a silica gel column and eluted with dichloromethane/methanol (10:1). This resulted in 35 mg (26.82%) of N-[5-[(6-bromo-4-methyl-3-oxopyrazin-2-yl)amino]-2-[1-methyl-4-(oxetan-3-yl)-6-oxopiperazin-2-yl]phenyl]prop-2-enamide as a brown solid. LC-MS-17: (ES, m/z): M+1: 517/519.

Synthesis of tert-butyl N-(4-bromo-3-nitrophenyl)carbamate Into a 250-mL round-bottom flask, was placed 4-bromo-3-nitroaniline (14.00 g, 64.510 mmol, 1.00 equiv), DCM (100.00 mL), TEA (19.58 g, 193.497 mmol, 3.00 equiv), DMAP (0.79 g, 6.451 mmol, 0.10 equiv), $Boc_2O$ (14.08 g, 64.510 mmol, 1.00 equiv). The resulting solution was stirred for 14 hr at room temperature. The resulting solution was concentrated. The residue was applied onto a silica gel column and eluted with ethyl acetate/petroleum ether (1:3). This resulted in 14 g (68.43%) of tert-butyl N-(4-bromo-3-nitrophenyl)carbamate as a white solid. $^1$H NMR (300 MHz, Chloroform-d) δ 8.06 (d, J=2.7 Hz, 1H), 7.63 (d, J=8.7 Hz, 1H), 7.40 (dd, J=8.7, 2.7 Hz, 1H), 6.64 (s, 1H), 1.55 (s, 9H).

Synthesis of tert-butyl N-[3-nitro-4-(4,4,5,5-tetramethyl-1,3,2-dioxaborolan-2-yl)phenyl]carbamate Into a 500-mL round-bottom flask purged and maintained with an inert atmosphere of nitrogen, was placed tert-butyl N-(4-bromo-3-nitrophenyl)carbamate (14.00 g, 44.145 mmol, 1.00 equiv), bis(pinacolato)diboron (16.82 g, 66.217 mmol, 1.50 equiv), dioxane (150 mL), AcOK (8.66 g, 88.289 mmol, 2.00 equiv), Pd(dppf)$Cl_2$ (1.62 g, 2.214 mmol, 0.05 equiv). The resulting solution was stirred for 2 hr at 100 degrees C. in an oil bath. The resulting mixture was concentrated. The residue was applied onto a silica gel column and eluted with ethyl acetate/petroleum ether (1:3). This resulted in 12 g (74.64%) of tert-butyl N-[3-nitro-4-(4,4,5,5-tetramethyl-1,3,2-dioxaborolan-2-yl)phenyl]carbamate as a light yellow solid. $^1$H NMR (300 MHz, Chloroform-d) δ 8.24 (d, J=2.1 Hz, 1H), 7.65 (dd, J=8.1, 2.1 Hz, 1H), 7.47 (d, J=8.1 Hz, 1H), 6.70 (s, 1H), 1.51 (s, 9H), 1.43 (s, 12H).

Synthesis of N-(5-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxopyrazin-2-yl]amino]-2-[1-methyl-4-(oxetan-3-yl)-6-oxopiperazin-2-yl]phenyl)prop-2-enamide Into a 8-mL vial purged and maintained with an inert atmosphere of nitrogen, was placed N-[5-[(6-bromo-4-methyl-3-oxopyrazin-2-yl)amino]-2-[1-methyl-4-(oxetan-3-yl)-6-oxopiperazin-2-yl]phenyl]prop-2-enamide (22.00 mg, 0.043 mmol, 1.00 equiv), 10-[1-hydroxy-3H-[1,2]oxaborolo[4,3-c]pyridin-4-yl]-4,4-dimethyl-1,10-diazatricyclo[6.4.0.0^[2,6]]dodeca-2(6),7-dien-9-one (14.34 mg, 0.043 mmol, 1.00 equiv), dioxane (3.00 mL), $H_2O$ (0.30 mL), Pd(DtBPF)$Cl_2$ (2.77 mg, 0.004 mmol, 0.10 equiv), $K_2CO_3$ (17.63 mg, 0.128 mmol, 3.00 equiv). The resulting solution was stirred for 1 hr at 90 degrees C. in an oil bath. The resulting mixture was concentrated. The residue was purified by Prep-TLC with dichloromethane/methanol (10:1). The crude product was purified by Prep-HPLC with the following conditions (Waters 2767): Column, X Bridge Prep C18 OBD 19*150 mm 5 um; mobile phase, A: 0.1% $NH_3$—$H_2O$ in water; B: ACN; Gradient: 40%-75% B in 7.9 min; Flow rate: 20 ml/min; Detector, 220 nm. This resulted in 7 mg (22.01%) of N-(5-[[6-(2-[4,4-dimethyl-9-oxo-1,10-diazatricyclo[6.4.0.0^[2,6]]dodeca-2(6),7-dien-10-yl]-3-(hydroxymethyl)pyri-din-4-yl)-4-methyl-3-oxopyrazin-2-yl]amino]-2-[1-methyl-4-(oxetan-3-yl)-6-oxopiperazin-2-yl]phenyl)prop-2-enamide as a white solid. LC-MS-100: (ES, m/z): M+1: 748. $^1$H NMR (300 MHz, Methanol-$d_4$) δ 8.50 (d, J=5.1 Hz, 1H), 8.21 (s, 1H), 7.82-7.57 (m, 3H), 7.39 (dd, J=13.8, 8.7 Hz, 1H), 6.74 (s, 1H), 6.55-6.24 (m, 2H), 5.87-5.71 (m, 1H), 4.82-4.48 (m, 5H), 4.38 (q, J=10.8, 9.3 Hz, 2H), 4.31-4.17 (m, 2H), 3.98 (d, J=12.3 Hz, 1H), 3.67 (s, 3H), 3.64-3.52 (m, 1H), 3.37 (s, 2H), 3.09 (d, J=16.5 Hz, 1H), 3.00-2.87 (m, 1H), 2.76 (d, J=12.6 Hz, 4H), 2.63 (d, J=3.1 Hz, 2H), 2.52 (s, 2H), 1.29 (s, 6H).

Example 43: Preparation of N-(5-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxopyrazin-2-yl]amino]-2-[(2R)-4-methyl-1-(oxetan-3-yl)-5-oxopiperazin-2-yl]phenyl)prop-2-enamide (assumed) and N-(5-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxopyrazin-2-yl]amino]-2-[(2S)-4-methyl-1-(oxetan-3-yl)-5-oxopiperazin-2-yl]phenyl)prop-2-enamide (assumed)

Synthesis of [(3,3-dimethylcyclopent-1-en-1-yl)oxy]trimethylsilane: Into a 10-L 4-necked round-bottom flask purged and maintained with an inert atmosphere of nitrogen, was placed CuCl (20.60 g, 208.083 mmol, 0.05 equiv), LiCl (17.64 g, 416.108 mmol, 0.10 equiv), THF (2.50 L). This was followed by the addition of 2-cyclopenten-1-one, 3-methyl-(400.00 g, 4161.075 mmol, 1.00 equiv) at −5 to 5 degrees C. To this was added TMSCl (474.67 g, 4369.129 mmol, 1.05 equiv) dropwise with stirring at −5 to 5 degrees C. To the mixture was added MeMgCl (1670.00 mL, 14495.069 mmol, 3.48 equiv) dropwise with stirring at −5 to 10 degrees C. The resulting solution was stirred for 2 h at −5 to 10 degrees C. in an ice/salt bath. The reaction was then quenched by the addition of 34 g of MeOH. The resulting solution was diluted with 5 L of $NH_4Cl$. The solids were filtered out. The resulting solution was extracted with 3×5 L of petroleum ether dried over anhydrous sodium sulfate and concentrated. This resulted in 780 g (crude) of [(3,3-dimethylcyclopent-1-en-1-yl)oxy]trimethylsilane as yellow oil. GC-MS: (ES, m/z): M: 184.

Synthesis of 3,3-dimethylcyclopentanone: Into a 20-L 4-necked round-bottom flask, was placed [(3,3-dimethylcyclopent-1-en-1-yl)oxy]trimethylsilane (780.00 g, 4230.990 mmol, 1.00 equiv), DCM (7.8 L), $H_2O$ (30.49 g, 1692.396 mmol, 0.4 equiv). This was followed by the addition of $POCl_3$ (214.09 g, 1396.251 mmol, 0.33 equiv) dropwise with stirring at 25 to 30 degrees C. The resulting solution was stirred for 0.5 hr at 25 degrees C. This solvent straight used for next step. GC-MS: (ES, m/z): M: 112

Synthesis of 3,3-dimethylcyclopentanon: Into a 20-L 4-necked round-bottom flask, was placed 3,3-dimethylcyclopentan-1-one (crude) in DCM (7.80 L). This was followed by the addition of DMF (619 g, 2.0 equiv) dropwise with stirring at 25 degrees C. To this was added $POCl_3$ (1362 g, 2.1 equiv) dropwise with stirring at 40 degrees C. The resulting solution was stirred for overnight at 40 degrees C. in an oil bath. The reaction was then quenched by the addition of 2000 g of $K_3PO_4$. The resulting solution was extracted with 3×10 L of dichloromethane dried over anhydrous sodium sulfate and concentrated. This resulted in 530 g of 2-chloro-4,4-dimethylcyclopent-1-ene-1-carbaldehyde as a brown solid. GC-MS: (ES, m/z): M: 158.

Synthesis of 4,4-dimethyl-1,10-diazatricyclo[6.4.0.0^[2,6]]dodeca-2(6),7-dien-9-one: Into a 5-L 4-necked round-bottom flask, was placed 2-chloro-4,4-dimethylcyclopent-1-ene-1-carbaldehyde (474.00 g, 2988.085 mmol, 1.00 equiv), DMF (3 L), piperazin-2-one (299.17 g, 2988.084 mmol, 1.00 equiv), DIEA (463.43 g, 3585.703 mmol, 1.2 equiv). The resulting solution was stirred for overnight at 115 degrees C. in an oil bath. The reaction mixture was cooled to room temperature with a water/ice bath. The solids were collected by filtration. The resulting mixture was washed with 3×2 L of $H_2O$ and 3×2 L of PE. The solid was dried in an oven under reduced pressure. This resulted in 230 g (37.68%) of 4,4-dimethyl-1,10-diazatricyclo[6.4.0.0^[2,6]]dodeca-2(6),7-dien-9-one as a grey solid. LC-MS: (ES, m/z): M+1: 205

Synthesis of 2,4-dibromopyridine-3-carbaldehyde, Into a 1000-mL 3-necked round-bottom flask, was placed 2,4-dibromopyridine (40.00 g, 168.852 mmol, 1.00 equiv), THF (400.00 mL). This was followed by the addition of LDA (2M in hexane, 126.60 mL, 1.5 equiv) dropwise with stirring at −78 degrees C. The resulting solution was stirred for 1 h at −78 degrees C. Then added DMF (16.04 g, 219.507 mmol, 1.3 equiv) by dropwise with stirring at −78 degrees C. The resulting solution was stirred for 0.5 hr at −78 degrees C. The reaction was then quenched by the addition of 500 mL of $NH_4Cl$. The resulting solution was extracted with 3×500 mL of ethyl acetate concentrated. The residue was applied onto a silica gel column and eluted with ethyl acetate/petroleum ether (0:1-1:1). This resulted in 24.4 g (54.55%) of 2,4-dibromopyridine-3-carbaldehyde as a white solid. LC-MS: (ES, m/z): M+1: 264

Synthesis of (2,4-dibromopyridin-3-yl)methanol, Into a 100-mL round-bottom flask, was placed 2,4-dibromopyridine-3-carbaldehyde (2.00 g, 7.550 mmol, 1.00 equiv), EtOH (30.00 mL). This was followed by the addition of $NaBH_4$ (285.64 mg, 7.550 mmol, 1 equiv), in portions at 0 degrees C. The resulting solution was stirred for 3 h at room temperature. The reaction was then quenched by the addition of 30 mL of water. The resulting solution was extracted with 3×30 mL of ethyl acetate concentrated. The residue was applied onto a silica gel column and eluted with ethyl acetate/petroleum ether (1:1). The collected fractions were combined and concentrated. This resulted in 1.4 g (69.47%) of (2,4-dibromopyridin-3-yl)methanol as a light yellow solid. LC-MS: (ES, m/z): M+1: 266

Synthesis of 2,4-dibromo-3-[(oxan-2-yloxy)methyl]pyridine, Into a 100-mL round-bottom flask, was placed (2,4-dibromopyridin-3-yl)methanol (1.40 g, 5.245 mmol, 1.00 equiv), DCM (30.00 mL, 0.353 mmol, 0.07 equiv), PPTS (131.81 mg, 0.525 mmol, 0.10 equiv), DHP (661.79 mg, 7.868 mmol, 1.50 equiv). The resulting solution was stirred for overnight at 45 degrees C. in an oil bath. The reaction was then quenched by the addition of 30 mL of water. The resulting solution was extracted with 3×30 mL of dichloromethane concentrated. The residue was applied onto a silica gel column and eluted with ethyl acetate/petroleum ether (1:1). The collected fractions were combined and concentrated. This resulted in 1.5 g (80%) of 2,4-dibromo-3-[(oxan-2-yloxy)methyl]pyridine as colorless oil. LC-MS: (ES, m/z): M+1: 350

Synthesis of 10-[4-bromo-3-[(oxan-2-yloxy)methyl]pyridin-2-yl]-4,4-dimethyl-1,10-diazatricyclo[6.4.0.0^[2,6]]dodeca-2(6),7-dien-9-one Into a 100-mL round-bottom flask purged and maintained with an inert atmosphere of nitrogen, was placed 4,4-dimethyl-1,10-diazatricyclo[6.4.0.0^[2,6]]dodeca-2(6),7-dien-9-one (1.00 g, 4.895 mmol, 1.00 equiv), dioxane (40.00 mL, 0.454 mmol, 0.09 equiv), $Cs_2CO_3$ (3.19 g, 9.791 mmol, 2 equiv), 2,4-dibromo-3-[(oxan-2-yloxy)methyl]pyridine (1.72 g, 4.900 mmol, 1.00 equiv), $Pd_2(dba)_3$ (448.28 mg, 0.490 mmol, 0.1 equiv), XantPhos (283.26 mg, 0.490 mmol, 0.1 equiv). The resulting solution was stirred for 1 h at 100 degrees C. in an oil bath. The reaction was then quenched by the addition of 40 mL of water. The resulting solution was extracted with 3×40 mL of ethyl acetate concentrated. The residue was applied onto a silica gel column and eluted with ethyl acetate/petroleum ether (1:1). The collected fractions were combined and concentrated. This resulted in 900 mg (38.75%) of 10-[4-bromo-3-[(oxan-2-yloxy)methyl]pyridin-2-yl]-4,4-dimethyl-1,10-diazatricyclo[6.4.0.0^[2,6]]dodeca-2(6),7-dien-9-one as a brown solid. LC-MS: (ES, m/z): M+1: 474

Synthesis of 2-[4,4-dimethyl-9-oxo-1,10-diazatricyclo[6.4.0.0^[2,6]]dodeca-2(6),7-dien-10-yl]-3-[(oxan-2-yloxy)methyl]pyridin-4-ylboronic acid, Into a 100-mL round-bottom flask purged and maintained with an inert atmosphere of nitrogen, was placed 10-[4-bromo-3-[(oxan-2-yloxy)methyl]pyridin-2-yl]-4,4-dimethyl-1,10-diazatricyclo[6.4.0.0^[2,6]]dodeca-2(6),7-dien-9-one (1.00 g, 2.108 mmol, 1.00 equiv), dioxane (10.00 mL), bis(pinacolato)diboron (1.34 g, 5.277 mmol, 2.50 equiv), KOAc (620.00 mg, 6.317 mmol, 3.00 equiv), $Pd(dppf)Cl_2$ (172.00 mg, 0.211 mmol, 0.10 equiv). The resulting solution was stirred for 2 h at 100 degrees C. in an oil bath. The reaction mixture was cooled to room temperature. The solids were filtered out. The resulting mixture was concentrated under vacuum. This resulted in 920 mg (crude) of 2-[4,4-dimethyl-9-oxo-1,10-diazatricyclo[6.4.0.0^[2,6]]dodeca-2(6),7-dien-10-yl]-3-[(oxan-2-yloxy)methyl]pyridin-4-ylboronic acid as brown oil. LC-MS: (ES, m/z): M+1: 436

Synthesis of 10-[1-hydroxy-3H-[1,2]oxaborolo[4,3-c]pyridin-4-yl]-4,4-dimethyl-1,10-diazatricyclo[6.4.0.0^[2,6]]dodeca-2(6),7-dien-9-one: Into a 100-mL round-bottom flask, was placed 2-[4,4-dimethyl-9-oxo-1,10-diazatricyclo[6.4.0.0^[2,6]]dodeca-2(6),7-dien-10-yl]-3-[(oxan-2-yloxy)methyl]pyridin-4-ylboronic acid (920 mg, 1.00 equiv, crude), dioxane (10 mL), HCl (6N, 10 mL). The resulting solution was stirred for 1 h at 25 degrees C. The resulting mixture was concentrated under vacuum. The crude product was purified by Flash-Prep-HPLC with the following conditions: Column, C18 reversed phase column; mobile phase, $H_2O$ (0.05% $NH_3 \cdot H_2O$) and $CH_3CN$ (5% $CH_3CN$ up to 30% in 15 min); Flow rate: 60 mL/min; Detector, 254/220 nm. This resulted in 350 mg of 10-[1-hydroxy-3H-[1,2]oxaborolo[4,3-c]pyridin-4-yl]-4,4-dimethyl-1,10-diazatricyclo[6.4.0.0^[2,6]]dodeca-2(6),7-dien-9-one as a light yellow solid. LC-MS: (ES, m/z): M+1: 338.

Synthesis of tert-butyl N-(4-bromo-3-nitrophenyl)carbamate: Into a 250-mL round-bottom flask, was placed 4-bromo-3-nitroaniline (15.00 g, 69.117 mmol, 1.00 equiv), $CH_3CN$ (150.00 mL), $Boc_2O$ (16.00 g, 73.311 mmol, 1.06 equiv), TEA (21.00 g, 207.530 mmol, 3.00 equiv), DMAP (844.00 mg, 6.909 mmol, 0.10 equiv). The resulting solution was stirred for 4 hr at room temperature. The resulting mixture was concentrated under vacuum. The residue was applied onto a silica gel column with ethyl acetate/petroleum ether (1:4). This resulted in 11 g (50.18%) of tert-butyl N-(4-bromo-3-nitrophenyl)carbamate as yellow oil. LC-MS: (ES, m/z): M+1: 317.

Synthesis of tert-butyl N-[3-nitro-4-(4,4,5,5-tetramethyl-1,3,2-dioxaborolan-2-yl)phenyl]carbamate: Into a 250-mL round-bottom flask purged and maintained with an inert atmosphere of nitrogen, was placed tert-butyl N-(4-bromo-3-nitrophenyl)carbamate (6.50 g, 20.496 mmol, 1.00 equiv), dioxane (100.00 mL), bis(pinacolato)diboron (7.80 g, 30.716 mmol, 1.50 equiv), AcOK (5.00 g, 50.946 mmol, 2.49 equiv), $Pd(dppf)Cl_2 \cdot CH_2Cl_2$ (1.67 g, 2.045 mmol, 0.10 equiv). The resulting solution was stirred for 2 hr at 100 degrees C. in an oil bath. The reaction mixture was cooled to room temperature. The solids were filtered out. The resulting mixture was concentrated under vacuum. The residue was applied onto a silica gel column with ethyl acetate/petroleum ether (1:5). This resulted in 6.68 g (89.49%) of tert-butyl N-[3-nitro-4-(4,4,5,5-tetramethyl-1,3,2-dioxaborolan-2-yl)phenyl]carbamate as yellow oil. LC-MS: (ES, m/z): M+1: 365

Synthesis of tert-butyl N-[4-(4-methyl-5-oxopyrazin-2-yl)-3-nitrophenyl]carbamate: Into a 250-mL round-bottom flask purged and maintained with an inert atmosphere of nitrogen, was placed tert-butyl N-[3-nitro-4-(4,4,5,5-tetramethyl-1,3,2-dioxaborolan-2-yl)phenyl]carbamate (6.64 g, 18.231 mmol, 1.30 equiv), dioxane (70.00 mL), $H_2O$ (7.00 mL), 5-bromo-1-methylpyrazin-2-one (2.65 g, 14.020 mmol, 1.00 equiv), $K_2CO_3$ (3.88 g, 28.041 mmol, 2.00 equiv), $Pd(dppf)Cl_2 \cdot CH_2Cl_2$ (1.14 g, 1.402 mmol, 0.10 equiv). The resulting solution was stirred for 1 hr at 90 degrees C. in an oil bath. The reaction mixture was cooled to room temperature. The resulting mixture was concentrated under vacuum. The residue was applied onto a silica gel column with ethyl acetate/DCM (1:3). This resulted in 4.5 g (92.67%) of tert-butyl N-[4-(4-methyl-5-oxopyrazin-2-yl)-3-nitrophenyl]carbamate as brown oil. LC-MS: (ES, m/z): M+1: 347; H-NMR (300 MHz, DMSO-$d_6$, ppm) δ 9.93 (s, 1H), 8.13 (d, J=1.2 Hz, 1H), 8.08 (d, J=2.2 Hz, 1H), 7.96 (d, J=1.1 Hz, 1H), 7.70 (dd, J=8.6, 2.2 Hz, 1H), 7.58 (d, J=8.5 Hz, 1H), 3.52 (s, 3H), 1.50 (s, 9H).

Synthesis of tert-butyl N-[3-amino-4-(4-methyl-5-oxopyrazin-2-yl)phenyl]carbamate: Into a 250-mL round-bottom flask, was placed tert-butyl N-[4-(4-methyl-5-oxopyrazin-2-yl)-3-nitrophenyl]carbamate (4.30 g, 12.415 mmol, 1.00 equiv), EtOH (75.00 mL), $H_2O$ (25.00 mL), Fe (4.16 g, 74.493 mmol, 6.00 equiv), $NH_4Cl$ (3.98 g, 74.405 mmol, 5.99 equiv). The resulting solution was stirred for 1.5 hr at 55 degrees C. in an oil bath. The reaction mixture was cooled to room temperature. The resulting solution was diluted with 200/200 mL of water and DCM. The solids were filtered out. The resulting solution was extracted with 3×200 mL of dichloromethane and the organic layers combined. The resulting mixture was washed with 1×500 ml of brine. The mixture was dried over anhydrous sodium sulfate and concentrated under vacuum. The residue was applied onto a silica gel column with dichloromethane/ethyl acetate (1:1). This resulted in 2.65 g (67.47%) of tert-butyl N-[3-amino-4-(4-methyl-5-oxopyrazin-2-yl)phenyl]carbamate as a yellow solid. LC-MS: (ES, m/z): M+1: 317; H-NMR (300 MHz, DMSO-$d_6$, ppm) δ 9.16 (s, 1H), 8.03 (d, J=1.2 Hz, 1H), 7.88 (d, J=1.3 Hz, 1H), 7.11 (d, J=8.4 Hz, 1H), 6.97 (d, J=2.1 Hz, 1H), 6.65 (dd, J=8.4, 2.1 Hz, 1H), 5.61 (s, 2H), 3.50 (s, 3H), 1.48 (s, 9H)

Synthesis of tert-butyl N-[4-(4-methyl-5-oxopyrazin-2-yl)-3-(4-methylbenzenesulfonamido)phenyl]carbamate: Into a 100-mL round-bottom flask purged and maintained with an inert atmosphere of nitrogen, was placed tert-butyl N-[3-amino-4-(4-methyl-5-oxopyrazin-2-yl)phenyl]carbamate (1.83 g, 5.785 mmol, 1.00 equiv), DCM (30.00 mL), Pyridine (1.37 g, 17.320 mmol, 2.99 equiv), TsCl (1.10 g, 5.785 mmol, 1.00 equiv). The resulting solution was stirred for 3 hr at room temperature. The resulting mixture was concentrated under vacuum. The residue was applied onto a silica gel column with dichloromethane/ethyl acetate (1:1). This resulted in 2.08 g (76.42%) of tert-butyl N-[4-(4-methyl-5-oxopyrazin-2-yl)-3-(4-methylbenzenesulfonamido)phenyl]carbamate as a yellow solid. LC-MS: (ES, m/z): M+1: 471

Synthesis of tert-butyl N-[4-(4-methyl-5-oxopiperazin-2-yl)-3-(4-methylbenzenesulfonamido)phenyl]carbamate: Into a 250-mL pressure tank reactor, was placed tert-butyl N-[4-(4-methyl-5-oxopyrazin-2-yl)-3-(4-methylbenzenesulfonamido)phenyl]carbamate (2.00 g, 4.250 mmol, 1.00 equiv), EtOAc (80.00 mL), Pd/C (701.11 mg, 6.588 mmol, 1.55 equiv), to the above $H_2$ (gas) was introduced in. The resulting solution was stirred overnight at 50 degrees C. in an oil bath. The reaction mixture was cooled to room temperature. The solids were filtered out. The resulting mixture was concentrated under vacuum. This resulted in 1.37 g (67.92%) of tert-butyl N-[4-(4-methyl-5-oxopiperazin-2-yl)-3-(4-methylbenzenesulfonamido)phenyl]carbamate as a yellow solid. LC-MS: (ES, m/z): M+1: 475

Synthesis of tert-butyl N-[4-[4-methyl-1-(oxetan-3-yl)-5-oxopiperazin-2-yl]-3-(4-methylbenzenesulfonamido)phenyl]carbamate: Into a 100-mL round-bottom flask, was placed tert-butyl N-[4-(4-methyl-5-oxopiperazin-2-yl)-3-(4-methylbenzenesulfonamido)phenyl]carbamate (1.00 g, 2.107 mmol, 1.00 equiv), DCE (20.00 mL), 3-oxetanone (1.06 g, 14.709 mmol, 6.98 equiv), $NaBH(OAc)_3$ (3.13 g, 14.768 mmol, 7.01 equiv). The resulting solution was stirred overnight at room temperature. The resulting mixture was concentrated under vacuum. The residue was applied onto a silica gel column with dichloromethane/methanol (20:1) to give the imine INT. To the INT was placed THF (20.00 mL), $NaBH_3CN$ (1.06 g, 16.868 mmol, 8.01 equiv). The resulting solution was stirred for 4 h at 60 degrees C. The resulting mixture was concentrated under vacuum. The residue was applied onto a silica gel column with dichloromethane/methanol (20:1). This resulted in 950 mg (84.96%) of tert-butyl N-[4-[4-methyl-1-(oxetan-3-yl)-5-oxopiperazin-2-yl]-3-(4-methylbenzenesulfonamido)phenyl]carbamate as a yellow solid. LC-MS: (ES, m/z): M+1: 531; H-NMR (300 MHz, DMSO-$d_6$, ppm) δ 9.79 (s, 1H), 9.45 (s, 1H), 7.67-7.60 (m, 2H), 7.42-7.32 (m, 3H), 7.24 (d, J=1.6 Hz, 2H), 5.33 (dd, J=5.5, 4.2 Hz, 1H), 4.41 (t, J=6.6 Hz, 1H), 4.23 (d, J=6.8 Hz, 1H), 3.96 (t, J=6.2 Hz, 1H), 3.85 (dd, J=9.7, 4.1 Hz, 1H), 2.77 (d, J=2.3 Hz, 3H), 2.37 (s, 3H), 2.05-1.95 (m, 2H), 1.46 (s, 9H).

Synthesis of tert-butyl N-[3-amino-4-[4-methyl-1-(oxetan-3-yl)-5-oxopiperazin-2-yl]phenyl]carbamate: Into a 40-mL vial purged and maintained with an inert atmosphere of nitrogen, was placed Na (494.00 mg, 21.488 mmol, 12.00 equiv), Naphthalene (2.75 g, 21.456 mmol, 11.98 equiv), DME (10.00 mL). The mixture was stirred at room temperature for 40 min until the formation of Na/naphthalene was complete. Another 100-mL round-bottom flask purged and maintained with an inert atmosphere of nitrogen, was placed tert-butyl N-[4-[4-methyl-1-(oxetan-3-yl)-5-oxopiperazin-2-yl]-3-(4-methylbenzenesulfonamido)phenyl]carbamate (950.00 mg, 1.790 mmol, 1.00 equiv), THF (20.00 mL). This was followed by the addition of above solution at −78 degrees C. The resulting solution was stirred for 3 hr at room temperature. The reaction was then quenched by the addition of 100 mL of $NH_4Cl$. The resulting solution was extracted with 2×200 mL of DCM:MeOH=10:1 and the organic layers combined. The resulting mixture was washed with 1×300 ml of brine. The mixture was dried over anhydrous sodium sulfate and concentrated under vacuum. The residue was applied onto a silica gel column with dichloromethane/methanol (10:1). This resulted in 660 mg (97.93%) of tert-butyl N-[3-amino-4-[4-methyl-1-(oxetan-3-yl)-5-oxopiperazin-2-yl]phenyl]carbamate as a yellow solid. LC-MS: (ES, m/z): M+1: 377; H-NMR (300 MHz, DMSO-$d_6$, ppm) δ 9.11 (s, 1H), 6.95-6.80 (m, 2H), 6.56 (dd, J=8.3, 2.1 Hz, 1H), 5.30 (s, 2H), 4.48 (t, J=6.6 Hz, 1H), 4.28 (q, J=6.8 Hz, 2H), 3.85-3.61 (m, 4H), 3.26 (d, J=16.3 Hz, 1H), 3.20-3.10 (m, 1H), 2.93 (d, J=16.2 Hz, 1H), 2.84 (s, 3H), 1.46 (s, 9H).

Synthesis of tert-butyl N-[4-[4-methyl-1-(oxetan-3-yl)-5-oxopiperazin-2-yl]-3-(prop-2-enamido)phenyl]carbamate: Into a 100-mL round-bottom flask purged and maintained with an inert atmosphere of nitrogen, was placed tert-butyl N-[3-amino-4-[4-methyl-1-(oxetan-3-yl)-5-oxopiperazin-2-yl]phenyl]carbamate (660.00 mg, 1.753 mmol, 1.00 equiv), DCM (10.00 mL), DIEA (453.00 mg, 3.505 mmol, 2.00 equiv), acryloyl chloride (159.00 mg, 1.757 mmol, 1.00 equiv). The resulting solution was stirred for 2 hr at room temperature. The resulting mixture was concentrated under vacuum. The residue was applied onto a silica gel column with dichloromethane/methanol (20:1). This resulted in 590 mg (78.17%) of tert-butyl N-[4-[4-methyl-1-(oxetan-3-yl)-5-oxopiperazin-2-yl]-3-(prop-2-enamido)phenyl]carbamate as a yellow solid. LC-MS: (ES, m/z): M+1: 431; H-NMR (300 MHz, DMSO-$d_6$, ppm) δ 9.95 (s, 1H), 9.48 (s, 1H), 7.72 (d, J=1.9 Hz, 1H), 7.41-7.20 (m, 2H), 6.46 (dd, J=17.0, 10.1 Hz, 1H), 6.25 (dd, J=17.0, 2.0 Hz, 1H), 5.79 (dd, J=10.1, 2.0 Hz, 1H), 4.44 (t, J=6.6 Hz, 1H), 4.29 (t, J=6.6 Hz, 1H), 4.10-3.97 (m, 1H), 3.86-3.67 (m, 2H), 3.64-3.49 (m, 2H), 3.30 (dd, J=12.6, 4.4 Hz, 2H), 2.86 (s, 3H), 1.47 (s, 9H).

Synthesis of N-[5-amino-2-[4-methyl-1-(oxetan-3-yl)-5-oxopiperazin-2-yl]phenyl]prop-2-enamide: Into a 100-mL round-bottom flask, was placed tert-butyl N-[4-[4-methyl-1-(oxetan-3-yl)-5-oxopiperazin-2-yl]-3-(prop-2-enamido) phenyl]carbamate (590.00 mg, 1.370 mmol, 1.00 equiv), DCM (10.00 mL), TFA (2.00 mL). The resulting solution was stirred for 2 hr at room temperature. The pH value of the solution was adjusted to 6 with aqueous $NaHCO_3$. The resulting mixture was concentrated under vacuum. The residue was applied onto a silica gel column with dichloromethane/methanol (10:1). This resulted in 290 mg (64.05%) of N-[5-amino-2-[4-methyl-1-(oxetan-3-yl)-5-oxopiperazin-2-yl]phenyl]prop-2-enamide as a yellow solid. LC-MS: (ES, m/z): M+1: 331; H-NMR (300 MHz, DMSO-$d_6$, ppm) δ 9.78 (s, 1H), 7.02 (d, J=8.4 Hz, 1H), 6.80 (d, J=2.1 Hz, 1H), 6.51-6.35 (m, 2H), 6.22 (dd, J=17.0, 2.0 Hz, 1H), 5.79 (dd, J=10.1, 2.0 Hz, 1H), 5.25 (s, 2H), 4.43 (t, J=6.7 Hz, 1H), 4.29 (t, J=6.6 Hz, 1H), 4.06 (t, J=6.7 Hz, 1H), 3.82-3.65 (m, 2H), 3.53 (qd, J=9.6, 4.8 Hz, 2H), 3.28-3.18 (m, 2H), 2.85 (d, J=3.9 Hz, 4H).

Synthesis of N-[5-[(6-bromo-4-methyl-3-oxopyrazin-2-yl)amino]-2-[4-methyl-1-(oxetan-3-yl)-5-oxopiperazin-2-yl]phenyl]prop-2-enamide: Into a 40-mL vial purged and maintained with an inert atmosphere of nitrogen, was placed N-[5-amino-2-[4-methyl-1-(oxetan-3-yl)-5-oxopiperazin-2-yl]phenyl]prop-2-enamide (250.00 mg, 0.757 mmol, 1.00 equiv), toluene (5.00 mL), 3,5-dibromo-1-methylpyrazin-2-one (223.00 mg, 0.832 mmol, 1.10 equiv), $Cs_2CO_3$ (740.00 mg, 2.271 mmol, 3.00 equiv), Xantphos (88.00 mg, 0.152 mmol, 0.20 equiv), $Pd_2(dba)_3{\cdot}CHCl_3$ (78.00 mg, 0.075 mmol, 0.10 equiv). The resulting solution was stirred for 1.5 hr at 100 degrees C. in an oil bath. The reaction mixture was cooled to room temperature. The resulting mixture was concentrated under vacuum. The residue was applied onto a silica gel column with dichloromethane/methanol (10:1). This resulted in 193 mg (49.30%) of N-[5-[(6-bromo-4-methyl-3-oxopyrazin-2-yl)amino]-2-[4-methyl-1-(oxetan-3-yl)-5-oxopiperazin-2-yl]phenyl]prop-2-enamide as a yellow solid. LC-MS: (ES, m/z): M+1: 517

Synthesis of N-(5-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxopyrazin-2-yl]amino]-2-[(2R)-4-methyl-1-(oxetan-3-yl)-5-oxopiperazin-2-yl]phenyl)prop-2-enamide (assumed): Into a 40-mL vial purged and maintained with an inert atmosphere of nitrogen, was placed N-[5-[(6-bromo-4-methyl-3-oxopyrazin-2-yl)amino]-2-[4-methyl-1-(oxetan-3-yl)-5-oxopiperazin-2-yl]phenyl]prop-2-enamide (100.00 mg, 0.193 mmol, 1.00 equiv), dioxane (2.00 mL), $H_2O$ (0.20 mL), 10-[1-hydroxy-3H-[1,2]oxaborolo[4,3-c]pyridin-4-yl]-4,4-dimethyl-1,10-diazatricyclo[6.4.0.0^[2,6]]dodeca-2(6),7-dien-9-one (130.00 mg, 0.386 mmol, 1.99 equiv), $K_2CO_3$ (134.00 mg, 0.970 mmol, 5.02 equiv), Xphos Pd G3 (33.00 mg, 0.039 mmol, 0.20 equiv). The resulting solution was stirred for 1 hr at 100 degrees C. in an oil bath. The reaction mixture was cooled to room temperature. The resulting mixture was concentrated under vacuum. The residue was applied onto a silica gel column with dichloromethane/methanol (10:1). The crude product was purified by Prep-HPLC with the following conditions: Column, X Bridge Shield RP18 OBD Column, Sum, 19*150 mm; mobile phase, Water (0.05% $NH_3{\cdot}H_2O$) and ACN (26% Phase B up to 50% in 7 min); Detector, UV 254/220 nm. The crude product was purified by Chiral-Prep-HPLC with the following conditions: Column, CHIRALPAK ID-3; mobile phase, DCM and EtOH (0.1% DEA); Flow rate: 12 mL/min. This resulted in 25 mg (17.30%) of N-(5-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxopyrazin-2-yl]amino]-2-[(2R)-4-methyl-1-(oxetan-3-yl)-5-oxopiperazin-2-yl]phenyl)prop-2-enamide (assumed) as a white solid. LC-MS: (ES, m/z): M+1: 748; H-NMR (300 MHz, DMSO-$d_6$, ppm) δ 9.98 (d, J=5.4 Hz, 1H), 9.46 (d, J=4.0 Hz, 1H), 8.53 (s, 1H), 8.46 (d, J=5.1 Hz, 1H), 7.86-7.66 (m, 3H), 7.34 (d, J=8.6 Hz, 1H), 6.59 (d, J=4.8 Hz, 1H), 6.49 (dd, J=17.0, 10.1 Hz, 1H), 6.31 (dd, J=17.0, 2.0 Hz, 1H), 5.80 (d, J=10.1 Hz, 1H), 5.13-4.91 (m, 1H), 4.68-4.41 (m, 3H), 4.36-4.17 (m, 4H), 4.08 (dt, J=13.3, 6.6 Hz, 1H), 3.83 (ddd, J=27.0, 13.6, 6.4 Hz, 3H), 3.57 (s, 5H), 3.36 (s, 1H), 3.29 (d, J=4.5 Hz, 1H), 2.87 (s, 4H), 2.59 (d, J=4.7 Hz, 2H), 2.44 (s, 2H), 1.23 (s, 6H).

Synthesis of N-(5-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxopyrazin-2-yl]amino]-2-[(2S)-4-methyl-1-(oxetan-3-yl)-5-oxopiperazin-2-yl]phenyl)prop-2-enamide (assumed): Into a 40-mL vial purged and maintained with an inert atmosphere of nitrogen, was placed N-[5-[(6-bromo-4-methyl-3-oxopyrazin-2-yl)amino]-2-[4-methyl-1-(oxetan-3-yl)-5-oxopiperazin-2-yl]phenyl]prop-2-enamide (100.00 mg, 0.193 mmol, 1.00 equiv), dioxane (2.00 mL), $H_2O$ (0.20 mL), 10-[1-hydroxy-3H-[1,2]oxaborolo[4,3-c]pyridin-4-yl]-4,4-dimethyl-1,10-diazatricyclo[6.4.0.0^[2,6]]dodeca-2(6),7-dien-9-one (130.00 mg, 0.386 mmol, 1.99 equiv), $K_2CO_3$ (134.00 mg, 0.970 mmol, 5.02 equiv), Xphos Pd G3 (33.00 mg, 0.039 mmol, 0.20 equiv). The resulting solution was stirred for 1 hr at 100 degrees C. in an oil bath. The reaction mixture was cooled to room temperature. The resulting mixture was concentrated under vacuum. The residue was applied onto a silica gel column with dichloromethane/methanol (10:1). The crude product was purified by Prep-HPLC with the following conditions: Column, X Bridge Shield RP18 OBD Column, 5 um, 19*150 mm; mobile phase, Water (0.05% $NH_3{\cdot}H_2O$) and ACN (26% Phase B up to 50% in 7 min); Detector, UV 254/220 nm. The crude product was purified by Chiral-Prep-HPLC with the following conditions: Column, CHIRALPAK ID-3; mobile phase, DCM and EtOH (0.1% DEA); Flow rate: 12 mL/min. This resulted in 25 mg (17.30%) of N-(5-[[6-(2-[4,4-dimethyl-9-oxo-1,10-diazatricyclo[6.4.0.0^[2,6]]dodeca-2(6),7-dien-10-yl]-3-(hydroxymethyl)pyridin-4-yl)-4-methyl-3-oxopyrazin-2-yl]amino]-2-[(2S)-4-methyl-1-(oxetan-3-yl)-5-oxopiperazin-2-yl]phenyl)prop-2-enamide (assumed) as a white solid. LC-MS: (ES, m/z): M+1: 748; H-NMR (300 MHz, DMSO-$d_6$, ppm) δ 9.98 (d, J=5.4 Hz, 1H), 9.46 (d, J=4.0 Hz, 1H), 8.53 (s, 1H), 8.46 (d, J=5.1 Hz, 1H), 7.86-7.66 (m, 3H), 7.34 (d, J=8.6 Hz, 1H), 6.59 (d, J=4.8 Hz, 1H), 6.49 (dd, J=17.0, 10.1 Hz, 1H), 6.31 (dd, J=17.0, 2.0 Hz, 1H), 5.80 (d, J=10.1 Hz, 1H), 5.13-4.91 (m, 1H), 4.68-4.41 (m, 3H), 4.36-4.17 (m, 4H), 4.08 (dt, J=13.3, 6.6 Hz, 1H), 3.83 (ddd, J=27.0, 13.6, 6.4 Hz, 3H), 3.57 (s, 5H), 3.36 (s, 1H), 3.29 (d, J=4.5 Hz, 1H), 2.87 (s, 4H), 2.59 (d, J=4.7 Hz, 2H), 2.44 (s, 2H), 1.23 (s, 6H).

Example 44: Preparation of (S)—N-(2-(2-methyl-4-(oxetan-3-yl)piperazin-1-yl)-5-((4-methyl-6-(3-methyl-2-(1-oxo-3, 4, 5, 6, 7, 8-hexahydrobenzo [4, 5]thieno[2, 3-c]pyridin-2(1H)-yl) pyridin-4-yl)-3-oxo-3, 4-dihydropyrazin-2-yl) amino) phenyl) acrylamide Synthesis of 2, 4-dibromo-3-methylpyridine Into a 1000-mL 3-necked round-bottom flask purged and maintained with an inert atmosphere of nitrogen, was placed diisopropylamine (19.10 g, 189.959 mmol, 1.50 equiv), THF (300.00 mL). This was followed by the addition of n-butyllithium (12.30 g, 189.959 mmol, 1.50 equiv) at −70 degrees C. and the solution was stirred for 30 min. To this was added 2,4-dibromopyridine (30.00 g, 126.639 mmol, 1.00 equiv) at −70 degrees C. and stirred for other 30 min. To the mixture was added MeI (27.00 g, 189.959 mmol, 1.50 equiv) at −70 degrees C. and the solution was stirred for 2h at −70 degrees C. The reaction was then quenched by the addition of 300 mL of $NH_4Cl$. The resulting solution was extracted with 3×200 mL of ethyl acetate and the organic layers combined. The resulting mixture was washed with 2×100 ml of water and 1×100 mL of brine. The mixture was dried over anhydrous sodium sulfate and concentrated. The residue was applied onto a silica gel column and eluted with ethyl acetate/petroleum ether (1:10). This resulted in 20 g of 2, 4-dibromo-3-methylpyridine as a brown solid. LC-MS-1 (ES, m/z): M+1: 250.

Synthesis of 5-bromo-3-[(4-fluoro-3-nitrophenyl) amino]-1-methylpyrazin-2-one Into a 10 L round-bottom flask, was placed 4-fluoro-3-nitroaniline (586.47 g, 3.759 mol, 1.00 equiv), 3, 5-dibromo-1-methylpyrazin-2-one (1000 g, 3.759 mol, 1.00 equiv), NMP (3000 ml). The resulting solution was stirred for 1 h at 135-140 degrees C. in an oil bath. The resulting solution was cooled and diluted with 3 L of H2O. The solids were collected by filtration. The solids washed by EA (2×1 L). This resulted in 980 g (90% purity) of 5-bromo-3-[(4-fluoro-3-nitrophenyl) amino]-1-methylpyrazin-2-one as a brown solid. LC-MS-2 (ES, m/z): M+1: 343/345

Synthesis of tert-butyl (3S)-4-[4-[(6-bromo-4-methyl-3-oxopyrazin-2-yl) amino]-2-nitrophenyl]-3-methylpiperazine-1-carboxylate Into a 10 L round-bottom flask, was placed 5-bromo-3-[(4-fluoro-3-nitrophenyl) amino]-1-methylpyrazin-2-one (1000 g, 2923.9 mmol, 1.00 equiv), NMP (4000.00 mL), tert-butyl (3S)-3-methylpiperazine-1-carboxylate (701.7 g, 3508.7 mmol, 1.20 equiv), DIEA (1131.55 g, 8771.7 mmol, 3.00 equiv). The resulting solution was stirred for 48-64 h at 115-125° C. in an oil bath. The resulting solution was diluted with 10000 mL of H2O. The solids were collected by filtration. This resulted in 1200 g of tert-butyl (3S)-4-[4-[(6-bromo-4-methyl-3-oxopyrazin-2-yl) amino]-2-nitrophenyl]-3-methylpiperazine-1-carboxylate as a brown crude solid. LC-MS-3 (ES, m/z): M+1: 523/525.

Synthesis of 5-bromo-1-methyl-3-([4-[(2S)-2-methylpiperazin-1-yl]-3-nitrophenyl]amino) pyrazin-2-one Into a 10 L round-bottom flask, was placed tert-butyl (3S)-4-[4-[(6-bromo-4-methyl-3-oxopyrazin-2-yl) amino]-2-nitrophenyl]-3-methylpiperazine-1-carboxylate (1200 g, 1 equiv), dioxane(3000 ml), HCl (4M) in 1,4-dioxane (3000.00 mL). The resulting solution was stirred for 13h at room temperature. The solids were collected by filtration. Filter cake was washed by EA. The filter cake was diluted with 300 mL of $H_2O$. The pH value of the solution was adjusted to 8 with $NaHCO_3$. The solids were collected by filtration. This resulted in 900 g (87.8% purity) of 5-bromo-1-methyl-3-([4-[(2S)-2-methylpiperazin-1-yl]-3-nitrophenyl] amino) pyrazin-2-one as a red solid. LC-MS-4 (ES, m/z): M+1: 423/425.

Synthesis of 5-bromo-1-methyl-3-([4-[(2S)-2-methyl-4-(oxetan-3-yl) piperazin-1-yl]-3-nitrophenyl] amino) pyrazin-2-one Into a 250-mL round-bottom flask, was placed 5-bromo-1-methyl-3-([4-[(2S)-2-methylpiperazin-1-yl]-3-nitrophenyl] amino) pyrazin-2-one (4.00 g, 9.450 mmol, 1.00 equiv), 3-oxetanone (0.89 g, 12.350 mmol, 1.31 equiv), THF (40.00 mL), AcOH (0.80 mL). This was followed by the addition of $NaBH(AcO)_3$ (3.00 g, 14.155 mmol, 1.50 equiv) dropwise with stirring at room temperature. The resulting solution was stirred for 4 h at room temperature. The reaction was then quenched by the addition of 10 mL of water. The resulting mixture was concentrated. The resulting solution was diluted with 40 mL of DCM. The resulting mixture was washed with 1×10 ml $Na_2CO_3$(aq). The mixture was dried over anhydrous sodium sulfate and concentrated. The residue was applied onto a silica gel column with and eluted with dichloromethane/methanol (10:1). This resulted in 3 g (66.23%) of 5-bromo-1-methyl-3-([4-[(2S)-2-methyl-4-(oxetan-3-yl) piperazin-1-yl]-3-nitrophenyl] amino) pyrazin-2-one as a brown solid. LC-MS-5 (ES, m/z): M+1: 479/481.

Synthesis of 3-([3-amino-4-[(2S)-2-methyl-4-(oxetan-3-yl) piperazin-1-yl]phenyl] amino)-5-bromo-1-methylpyrazin-2-one Into a 250-mL round-bottom flask, was placed 5-bromo-1-methyl-3-([4-[(2S)-2-methyl-4-(oxetan-3-yl) piperazin-1-yl]-3-nitrophenyl]amino)pyrazin-2-one (3.00 g, 6.259 mmol, 1.00 equiv), Fe (1.40 g, 25.035 mmol, 4.00 equiv), $NH_4Cl$ (2.01 g, 37.576 mmol, 6.00 equiv), EtOH (30.00 mL), $H_2O$ (30.00 mL). The resulting solution was stirred for 2h at 80 degrees C. in an oil bath. The reaction mixture was cooled to room temperature with a water/ice bath. The solids were filtered out. The resulting mixture was concentrated. The resulting solution was diluted with 200 mL of DCM. The pH value of the solution was adjusted to 8 with $NH_3 \cdot H_2O$. The resulting mixture was washed with 1×20 ml of $H_2O$. The resulting mixture was washed with 1×20 mL of NaCl(aq). The mixture was dried over anhydrous sodium sulfate. The residue was applied onto a silica gel column and eluted with dichloromethane/methanol (10:1). This resulted in 2.5 g (88.89%) of 3-([3-amino-4-[(2S)-2-methyl-4-(oxetan-3-yl) piperazin-1-yl] phenyl] amino)-5-bromo-1-methylpyrazin-2-one as a brown solid. LC-MS-6 (ES, m/z): M+1: 479/481

Synthesis of N-[5-[(6-bromo-4-methyl-3-oxopyrazin-2-yl) amino]-2-[(2S)-2-methyl-4-(oxetan-3-yl) piperazin-1-yl] phenyl] prop-2-enamide Into a 100-mL round-bottom flask, was placed 3-([3-amino-4-[(2S)-2-methyl-4-(oxetan-3-yl) piperazin-1-yl]phenyl] amino)-5-bromo-1-methylpyrazin-2-one (2.50 g, 5.564 mmol, 1.00 equiv), DCM (30.00 mL, 471.901 mmol, 84.82 equiv), DIEA (1.44 g, 11.142 mmol, 2.00 equiv). This was followed by the addition of acryloyl chloride (0.65 g, 7.182 mmol, 1.29 equiv) in portions at 0 degrees C. The resulting solution was stirred for 1 h at 0 degrees C. in a water/ice bath. The reaction was then quenched by the addition of 1 mL of MeOH. The resulting mixture was concentrated. The residue was applied onto a silica gel column and eluted with dichloromethane/methanol (10:1). This resulted in 2.8 g (80.98%) of N-[5-[(6-bromo-4-methyl-3-oxopyrazin-2-yl) amino]-2-[(2S)-2-methyl-4-(oxetan-3-yl) piperazin-1-yl]phenyl] prop-2-enamide as a yellow solid. LC-MS-7 (ES, m/z): M+1: 503/505.

Synthesis of N-(methoxymethyl)-N-methyl-4, 5, 6, 7-tetrahydro-1-benzothiophene-2-carboxamide Into a 250-mL 3-necked round-bottom flask purged and maintained with an inert atmosphere of nitrogen, was placed 4,5,6,7-tetrahydro-1-benzothiophene-2-carboxylic acid (8.0 g, 43.95 mmol, 1.0 equiv), DMF (193 mg, 2.197 mmol, 0.05 equiv), DCM (150 ml). This was followed by the addition of oxalyl chloride (6.1 g, 48.35 mmol, 1.1 equiv) dropwise with stirring at 0 degrees C. The resulting solution was stirred for 1 h in a water/ice bath. To this was added TEA (13.3 g, 131.85 mmol, 3.0 equiv) and N,O-dimethylhydroxylamine HCl salt (4.3 g, 43.95 mmol, 1.0 equiv) at 0 degrees C. The resulting solution was stirred for 2h at room temperature. The resulting solution was diluted with 100 mL of water. The resulting solution was extracted with 3×150 mL of dichloromethane and the organic layers combined. The resulting mixture was washed with 2×100 ml of water and 1×100 mL of brine. The mixture was dried over anhydrous sodium sulfate and concentrated. The residue was applied onto a silica gel column with ethyl acetate/petroleum ether (1:10). This resulted in 9.0 g of N-(methoxymethyl)-N-methyl-4, 5, 6, 7-tetrahydro-1-benzothiophene-2-carboxamide as a white solid. LC-MS-8 (ES, m/z): M+1: 226.

Synthesis of 3-chloro-1-(4, 5, 6, 7-tetrahydro-1-benzothiophen-2-yl) propan-1-one Into a 250-mL 3-necked round-bottom flask purged and maintained with an inert atmosphere of nitrogen, was placed N-methoxy-N-methyl-4,5,6,7-tetrahydro-1-benzothiophene-2-carboxamide (8.00 g, 35.560 mmol, 1.00 equiv), THF (40.00 mL). This was followed by the addition of bromo(ethenyl)magnesium(1M in THF) (160.00 mL, 142.220 mmol, 4.00 equiv) dropwise with stirring at −10 degrees C. The resulting solution was stirred for 3h at 0 degrees C. in an ice/salt bath. The reaction was then quenched by the addition of 40 mL of 2M HCl (aq). The resulting solution was extracted with 2×100 mL of ethyl acetate and the organic layers combined. The resulting mixture was washed with 2×100 ml of water and 1×100 mL of brine. The mixture was dried over anhydrous sodium sulfate and concentrated. The resulting solution was diluted with 80 mL of DCM. The residue was dissolved in 40 mL of 2M HCl(gas) in $Et_2O$. The resulting mixture was stirred for 3h at R.T. Then the solution was concentrated. The residue was applied onto a silica gel column with ethyl acetate/petroleum ether (1:5). This resulted in 2.3 g of 3-chloro-1-(4, 5, 6, 7-tetrahydro-1-benzothiophen-2-yl) propan-1-one as yellow oil. LC-MS-9 (ES, m/z): M+1: 229.

Synthesis of 1, 2, 5, 6, 7, 8-hexahydro-3H-benzo[b] cyclopenta[d]thiophen-3-one Into a 100-mL round-bottom flask, was placed 3-chloro-1-(4, 5, 6, 7-tetrahydro-1-benzothiophen-2-yl) propan-1-one (2.30 g, 10.090 mmol, 1.00 equiv), $H_2SO_4$ (20.00 mL). The resulting solution was stirred for 16h at 95 degrees C. in an oil bath. The reaction mixture was cooled to room temperature with a water/ice bath. The resulting solution was diluted with 50 mL of water. The resulting solution was extracted with 2×50 mL of ethyl acetate and the organic layers combined. The resulting mixture was washed with 1×50 ml of brine. The mixture was dried over anhydrous sodium sulfate and concentrated. The residue was applied onto a silica gel column with ethyl acetate/petroleum ether (1:5). This resulted in 0.8 g of 1, 2, 5, 6, 7, 8-hexahydro-3H-benzo[b]cyclopenta[d]thiophen-3-one as brown oil. LC-MS-10 (ES, m/z): M+1: 193.

Synthesis of (Z)-1, 2, 5, 6, 7, 8-hexahydro-3H-benzo[b] cyclopenta[d]thiophen-3-one oxime Into a 100-mL 3-necked round-bottom flask purged and maintained with an inert atmosphere of nitrogen, was placed $NH_2OH{\cdot}HCl$ (1.41 g, 20.313 mmol, 5.00 equiv), MeOH (30.00 mL). This was followed by the addition of NaOAc (1.66 g, 20.313 mmol, 5.00 equiv) at 0 degrees C. and the solution was stirred for 30 min at 0 degrees C. To this was added 1, 2, 5, 6, 7, 8-hexahydro-3H-benzo[b]cyclopenta[d]thiophen-3-one (780.00 mg, 4.063 mmol, 1.00 equiv) at 0 degrees C. The resulting solution was stirred for 18h at room temperature. The resulting mixture was concentrated. This resulted in 300 mg of (Z)-1, 2, 5, 6, 7, 8-hexahydro-3H-benzo[b]cyclopenta [d]thiophen-3-one oxime as brown oil. LC-MS-11(ES, m/z): M+1: 208.

Synthesis of 3, 4, 5, 6, 7, 8-hexahydrobenzo [4, 5] thieno[2, 3-c]pyridin-1(2H)-one Into a 50-mL round-bottom flask purged and maintained with an inert atmosphere of nitrogen, was placed (Z)-1, 2, 5, 6, 7, 8-hexahydro-3H-benzo[b]cyclopenta[d]thiophen-3-one oxime (295.00 mg, 1.425 mmol, 1.00 equiv), PPA (6.00 mL). The resulting solution was stirred for 18h at 80 degrees C. in an oil bath. The reaction mixture was cooled to room temperature with a water bath. The resulting solution was diluted with 20 mL of water. The solids were collected by filtration. This resulted in 260 mg of 3, 4, 5, 6, 7, 8-hexahydrobenzo [4, 5]thieno[2, 3-c]pyridin-1(2H)-one as an off-white solid. LC-MS-12 (ES, m/z): M+1: 208

Synthesis of 2-(4-bromo-3-methylpyridin-2-yl)-3, 5, 6, 7, 8-hexahydrobenzo [4, 5]thieno[2, 3-c]pyridin-1(2H)-one Into a 50-mL round-bottom flask purged and maintained with an inert atmosphere of nitrogen, was placed 2,4-dibromo-3-methylpyridine (219.00 mg, 0.879 mmol, 1.30 equiv), 8-thia-5-azatricyclo[7.4.0.0^[2,7]]trideca-1(9), 2(7)-dien-6-one 3, 4, 5, 6, 7, 8-hexahydrobenzo [4, 5]thieno[2, 3-c]pyridin-1(2H)-one (140.00 mg, 0.676 mmol, 1.00 equiv), CuI (77.00 mg, 0.405 mmol, 0.60 equiv), $Cs_2CO_3$ (440.00 mg, 1.352 mmol, 2.00 equiv), DMA (10.00 mL), 1,10-phenanthroline (73.00 mg, 0.405 mmol, 0.60 equiv). The resulting solution was stirred for 4h at 110 degrees C. in an oil bath. The reaction mixture was cooled to room temperature with a water bath. The resulting solution was diluted with 50 mL of EA. The solids were filtered out. The mixture was dried over anhydrous sodium sulfate and concentrated. The residue was applied onto a silica gel column with ethyl acetate/petroleum ether (3:1). This resulted in 270 mg of 2-(4-bromo-3-methylpyridin-2-yl)-3, 4, 5, 6, 7, 8-hexahydrobenzo [4, 5] thieno[2, 3-c]pyridin-1(2H)-one as brown oil. LC-MS-13 (ES, m/z): M+1: 377.

Synthesis of (3-methyl-2-(1-oxo-3, 4, 5, 6, 7, 8-hexahydrobenzo [4, 5]thieno[2, 3-c] pyridin-2(1H)-yl) pyridin-4-yl) boronic acid Into a 50-mL round-bottom flask purged and maintained with an inert atmosphere of nitrogen, was placed 2-(4-bromo-3-methylpyridin-2-yl)-3, 4, 5, 6, 7, 8-hexahydrobenzo [4, 5] thieno[2, 3-c]pyridin-1(2H)-one (270.00 mg, 0.718 mmol, 1.00 equiv), bis(pinacolato)diboron (254.00 mg, 1.795 mmol, 2.50 equiv), KOAc (98.00 mg, 2.154 mmol, 3.00 equiv), $Pd(dppf)Cl_2$ (52.00 mg, 0.072 mmol, 0.10 equiv), Dioxane (10.00 mL). The resulting solution was stirred for 2h at 100 degrees C. in an oil bath. The reaction mixture was cooled to room temperature with a water bath. The reaction was then quenched by the addition of 30 mL of water. The resulting solution was extracted with 2×30 mL of ethyl acetate and the organic layers combined. The resulting mixture was washed with 1×30 mL of brine. The mixture was dried over anhydrous sodium sulfate and concentrated. The residue was applied onto a silica gel column with dichloromethane/methanol (20:1). This resulted in 80 mg of (3-methyl-2-(1-oxo-3, 4, 5, 6, 7, 8-hexahydrobenzo [4, 5] thieno[2, 3-c]pyridin-2(1H)-yl) pyridin-4-yl) boronic acid as an off-white solid. LC-MS-14 (ES, m/z): M+1: 343.

Synthesis of (S)—N-(2-(2-methyl-4-(oxetan-3-yl)piperazin-1-yl)-5-((4-methyl-6-(3-methyl-2-(1-oxo-3, 4, 5, 6, 7, 8-hexahydrobenzo [4, 5] thieno[2, 3-c]pyridin-2(1H)-yl) pyridin-4-yl)-3-oxo-3, 4-dihydropyrazin-2-yl) amino) phenyl) acrylamide Into a 50-mL round-bottom flask purged and maintained with an inert atmosphere of nitrogen, was placed (S)—N-(5-((6-bromo-4-methyl-3-oxo-3, 4-dihydropyrazin-2-yl) amino)-2-(2-methyl-4-(oxetan-3-yl) piperazin-1-yl) phenyl) acrylamide (120.00 mg, 0.239 mmol, 1.00 equiv), (3-methyl-2-(1-oxo-3, 4, 5, 6, 7, 8-hexahydrobenzo [4, 5] thieno[2, 3-c]pyridin-2(1H)-yl) pyridin-4-yl) boronic acid (80.00 mg, 0.239 mmol, 1.00 equiv), $K_3PO_4$ (149.00 mg, 0.478 mmol, 2.00 equiv), Toluene (5.00 mg), $H_2O$ (0.10 mg), BrettPhos Pd G3 (20.00 mg, 0.024 mmol, 0.10 equiv). The resulting solution was stirred for 2h at 90 degrees C. in an oil bath. The reaction mixture was cooled to room temperature with a water/ice bath. The solids were filtered out. The resulting solution was diluted with 50 mL of EA. The resulting mixture was washed with 3×20 ml of water and 1×20 mL of brine. The solid was dried in an oven under reduced pressure. The residue was applied onto a silica gel column with dichloromethane/methanol (10:1). The crude product (80 mg) was purified by Prep-HPLC with the following conditions: column, X-Bridge Prep C18 19*150 mm 5 um; mobile phase, A: water (it contains 10 mM $NH_4HCO_3$ 0.05% ammonia); B: ACN; Gradient: 20-45% B in 8 min; Flow rate: 20 mL/min; detector, UV 220 nm. The collected solution was concentrated under vacuum to remove $CH_3CN$ and the resulting solution was dried by lyophilization. This resulted in 10 mg of (S)—N-(2-(2-methyl-4-(oxetan-3-yl)piperazin-1-yl)-5-((4-methyl-6-(3-methyl-2-(1-oxo-3,4,5,6,7,8-hexahydrobenzo[4,5]thieno[2,3-c]pyridin-2(1H)-yl)pyridin-4-yl)-3-oxo-3,4-dihydropyrazin-2-yl)amino)phenyl)acrylamide as an off-white solid. LC-MS-0 (ES, m/z): M+1: 721. $^1H$ NMR (300 MHz, DMSO-$d_6$, ppm) δ 6 9.18-9.22 (d, J=12.0 Hz, 2H), 8.98-9.02 (d, J=12.0 Hz, 1H), 8.35-8.37 (d, J=6.0 Hz, 1H), 7.62-7.70 (m, 2H), 7.42 (s, 1H), 7.24-7.26 (d, J=6.0 Hz, 1H), 6.53-6.62 (m, 1H), 6.26-6.28 (d, J=6.0 Hz, 1H), 5.76-5.80 (d, J=12.0 Hz, 1H), 4.52-4.59 (m, 2H), 4.45-4.50 (m, 2H), 4.11-4.20 (m, 1H), 3.81-3.85 (d, J=12.0 Hz, 1H), 3.58 (s, 3H), 3.49-3.51 (m, 1H), 3.07-3.13 (m, 1H), 2.87-2.90 (m, 2H), 2.67-2.80 (m, 7H), 2.56-2.58 (m, 1H), 2.30 (s, 3H), 2.20-2.28 (m, 1H), 1.90-1.96 (m, 1H), 1.78-1.83 (m, 4H), 0.71-0.74 (m, 3H).

Example 45: Preparation of N-[2-[2,2-dimethyl-4-(oxetan-3-yl)piperazin-1-yl]-5-[[6-(2-[4,4-dimethyl-9-oxo-1,10-diazatricyclo[6.4.0.0^[2,6]]dodeca-2(6),7-dien-10-yl]-3-methylpyridin-4-yl)-4-methyl-3-oxopyrazin-2-yl]amino]phenyl]prop-2-enamide Synthesis of [(3,3-dimethylcyclopent-1-en-1-yl)oxy]trimethylsilane: Into a 10 L 4-necked round-bottom flask purged and maintained with an inert atmosphere of nitrogen, was placed CuCl (20.60 g, 208.083 mmol, 0.05 equiv), LiCl (17.64 g, 416.108 mmol, 0.10 equiv), THF (2.50 L). This was followed by the addition of 2-cyclopenten-1-one, 3-methyl-(400.00 g, 4161.075 mmol, 1.00 equiv) at −5 to 5 degrees C. To this was added TMSCl (474.67 g, 4369.129 mmol, 1.05 equiv) dropwise with stirring at −5 to 5 degrees C. To the mixture was added MeMgCl (1670.00 mL, 14495.069 mmol, 3.48 equiv) dropwise with stirring at −5 to 10 degrees C. The resulting solution was stirred for 2 h at −5 to 10 degrees C. in an ice/salt bath. The reaction was then quenched by the addition of 34 g of MeOH. The resulting solution was diluted with 5 L of $NH_4Cl$. The solids were filtered out. The resulting solution was extracted with 3×5 L of petroleum ether dried over anhydrous sodium sulfate and concentrated. This resulted in 780 g (crude) of [(3,3-dimethylcyclopent-1-en-1-yl)oxy]trimethylsilane as yellow oil. GCMS: (ES, m/z): M+1: 184

Synthesis of 3,3-dimethylcyclopentanone: Into a 20-L 4-necked round-bottom flask, was placed [(3,3-dimethylcyclopent-1-en-1-yl)oxy]trimethylsilane (780.00 g, 4230.990 mmol, 1.00 equiv), DCM (7.8 L), $H_2O$ (30.49 g, 1692.396 mmol, 0.4 equiv). This was followed by the addition of $POCl_3$ (214.09 g, 1396.251 mmol, 0.33 equiv) dropwise with stirring at 25 to 30 degrees C. The resulting solution was stirred for 0.5 h at 25 degrees C. This solvent straight used for next step. GCMS (ES, m/z): M+1: 112

Synthesis of 3,3-dimethylcyclopentanone: Into a 20-L 4-necked round-bottom flask, was placed 3,3-dimethylcyclopentan-1-one in DCM (7.80 L). This was followed by the addition of DMF (619 g, 2.0 equiv) dropwise with stirring at 25 degrees C. To this was added $POCl_3$ (1362 g, 2.1 equiv) dropwise with stirring at 40 degrees C. The resulting solution was stirred for overnight at 40 degrees C. in an oil bath. The reaction was then quenched by the addition of 2000 g of $K_3PO_4$. The resulting solution was extracted with 3×10 L of dichloromethane dried over anhydrous sodium sulfate and concentrated. This resulted in 530 g (4804.86%) of 2-chloro-4,4-dimethylcyclopent-1-ene-1-carbaldehyde as a brown solid. GCMS: (ES, m/z): M+1: 15.

Synthesis of 4,4-dimethyl-1,10-diazatricyclo[6.4.0.0^[2,6]]dodeca-2(6),7-dien-9-one: Into a 5-L 4-necked round-bottom flask, was placed 2-chloro-4,4-dimethylcyclopent-1-ene-1-carbaldehyde (474.00 g, 2988.085 mmol, 1.00 equiv), DMF (3 L), piperazin-2-one (299.17 g, 2988.084 mmol, 1.00 equiv), DIEA (463.43 g, 3585.703 mmol, 1.2 equiv). The resulting solution was stirred for overnight at 115 degrees C. in an oil bath. The reaction mixture was cooled to room temperature with a water/ice bath. The solids were collected by filtration. The resulting mixture was washed with 3×2 L of $H_2O$ and 3×2 L of PE. The solid was dried in an oven under reduced pressure. This resulted in 230 g (37.68%) of 4,4-dimethyl-1,10-diazatricyclo[6.4.0.0^[2,6]]dodeca-2(6),7-dien-9-one as a grey solid. LCMS: (ES, m/z): M+1: 205.

Synthesis of 2, 4-dibromo-3-methylpyridine: Into a 1000-mL 3-necked round-bottom flask purged and maintained with an inert atmosphere of nitrogen, was placed diisopropylamine (19.10 g, 189.959 mmol, 1.50 equiv), THF (300.00 mL). This was followed by the addition of n-butyllithium (12.30 g, 189.959 mmol, 1.50 equiv) at −30 degrees C. and the solution was stirred for 30 min. To this was added 2,4-dibromopyridine (30.00 g, 126.639 mmol, 1.00 equiv) at −70 degrees C. and stirred for other 30 min. To the mixture was added MeI (27.00 g, 189.959 mmol, 1.50 equiv) at −70 degrees C. and the solution was stirred for 0.5 h in a liquid nitrogen bath. The reaction was then quenched by the addition of 300 mL of $NH_4Cl$. The resulting solution was extracted with 3×200 mL of ethyl acetate and the organic layers combined. The resulting mixture was washed with 2×100 ml of water and 1×100 mL of brine. The mixture was dried over anhydrous sodium sulfate and concentrated. The residue was applied onto a silica gel column and eluted with ethyl acetate/petroleum ether (1:10). This resulted in 20 g of 2,4-dibromo-3-methylpyridine as a brown solid. LCMS: (ES, m/z): M+1: 250.

Synthesis of 10-(4-bromo-3-methylpyridin-2-yl)-4,4-dimethyl-1,10-diazatricyclo[6.4.0.0^[2,6]] dodeca-2(6),7-dien-9-one: Into a 100-mL round-bottom flask purged and maintained with an inert atmosphere of nitrogen, was placed 2,4-dibromo-3-methylpyridine (20.00 g, 79.696 mmol, 1.00 equiv), 4,4-dimethyl-1,10-diazatricyclo[6.4.0.0^[2,6]]dodeca-2(6),7-dien-9-one (4.07 g, 19.924 mmol, 1.00 equiv), XantPhos PD G2 (7.08 g, 4.980 mmol, 0.10 equiv), dioxane (200.00 mL), $Cs_2CO_3$ (77.92 g, 239.152 mmol, 3.00 equiv). The resulting solution was stirred for 3h at 100 degrees C. in an oil bath. The resulting mixture was concentrated. The residue was applied onto a silica gel column and eluted with ethyl acetate/petroleum ether (1:1). This resulted in 10 g (33.52%) of 10-(4-bromo-3-methylpyridin-2-yl)-4,4-dimethyl-1,10-diazatricyclo[6.4.0.0^[2,6]]dodeca-2(6),7-dien-9-one as a brown solid. LCMS (ES, m/z): M+1: 374.

Synthesis of 2-[4,4-dimethyl-9-oxo-1,10-diazatricyclo[6.4.0.0^[2,6]]dodeca-2(6),7-dien-10-yl]-3-methylpyridin- 4-ylboronic acid: Into a 50-mL round-bottom flask purged and maintained with an inert atmosphere of nitrogen, was placed 10-(4-bromo-3-methylpyridin-2-yl)-4,4-dimethyl-1,10-diazatricyclo[6.4.0.0^[2,6]]dodeca-2(6),7-dien-9-one (8.00 g, 20.788 mmol, 1.00 equiv), bis(pinacolato)diboron (7.936 g, 31.252 mmol, 1.50 equiv), Dioxane (110.00 mL), KOAc (4.046 g, 41.218 mmol, 1.98 equiv), $Pd(dppf)Cl_2$ (1.521 g, 2.077 mmol, 0.10 equiv). The resulting solution was stirred for 2h at 100 degrees C. in an oil bath. The resulting mixture was concentrated. The crude product was purified by Flash-Prep-HPLC with the following conditions (CombiFlash-1): Column, C18 silica gel; mobile phase, A: 0.1% $NH_3 \cdot H_2O$ in water; B: ACN; Gradient: 35%-70% B in 9 min; Detector, 220 nm. This resulted in 3.5 g (49.65%) of 2-[4,4-dimethyl-9-oxo-1,10-diazatricyclo[6.4.0.0^[2,6]]dodeca-2(6),7-dien-10-yl]-3-methylpyridin-4-ylboronic acid as a white solid. LCMS (ES, m/z): M+1: 340.

Synthesis of 5-bromo-3-[(4-fluoro-3-nitrophenyl)amino]-1-methylpyrazin-2-one: Into a 10 L round-bottom flask, was placed 4-fluoro-3-nitroaniline (586.47 g, 3.759 mol, 1.00 equiv), 3,5-dibromo-1-methylpyrazin-2-one (1000 g, 3.759 mol, 1.00 equiv), NMP (3000 mL). The resulting solution was stirred for 1 h at 135-140 degrees C. in an oil bath. The resulting solution was cooled and diluted with 3 L of $H_2O$. The solids were collected by filtration. The solids washed by EA (2×1 L). This resulted in 980 g (90% purity) of 5-bromo-3-[(4-fluoro-3-nitrophenyl) amino]-1-methylpyrazin-2-one as a brown solid. LC-MS: (ES, m/z): M+1: 343/345

Synthesis of tert-butyl 4-[4-[(6-bromo-4-methyl-3-oxopyrazin-2-yl)amino]-2-nitrophenyl]-3,3-dimethylpiperazine-1-carboxylate: Into a 100-mL round-bottom flask, was placed 5-bromo-3-[(4-fluoro-3-nitrophenyl)amino]-1-methylpyrazin-2-one (3.20 g, 9.326 mmol, 1.00 equiv), NMP (15.00 mL), tert-butyl 3,3-dimethylpiperazine-1-carboxylate (2.00 g, 9.332 mmol, 1.00 equiv), DIEA (3.62 g, 28.009 mmol, 3.00 equiv). The resulting solution was stirred for 5 days at 138 degrees C. in an oil bath. The reaction mixture was cooled to room temperature. The resulting solution was diluted with 100 mL of water. The solids were collected by filtration. The residue was applied onto a silica gel column with ethyl acetate/petroleum ether (1:1). This resulted in 1.48 g (crude, 9% purity, Y=2.66%) of tert-butyl 4-[4-[(6-bromo-4-methyl-3-oxopyrazin-2-yl)amino]-2-nitrophenyl]-3,3-dimethylpiperazine-1-carboxylate as a red solid. LC-MS: (ES, m/z): M+1: 536.

Synthesis of 5-bromo-3-[[4-(2,2-dimethylpiperazin-1-yl)-3-nitrophenyl]amino]-1-methylpyrazin-2-one: Into a 100-mL round-bottom flask, was placed tert-butyl 4-[4-[(6-bromo-4-methyl-3-oxopyrazin-2-yl)amino]-2-nitrophenyl]-3,3-dimethylpiperazine-1-carboxylate (1.48 g, 0.248 mmol, 1.00 equiv, 9% purity), HCl(gas) in 1,4-dioxane (2M, 20.00 mL). The resulting solution was stirred for 1 hr at room temperature. The resulting mixture was concentrated under vacuum. This resulted in 1.37 g (crude) of 5-bromo-3[[4-(2,2-dimethylpiperazin-1-yl)-3-nitrophenyl]amino]-1-methylpyrazin-2-one as a brown solid. LC-MS: (ES, m/z): M+1: 436.

Synthesis of 5-bromo-3-([4-[2,2-dimethyl-4-(oxetan-3-yl)piperazin-1-yl]-3-nitrophenyl]amino)-1-methylpyrazin-2-one: Into a 100-mL round-bottom flask, was placed 5-bromo-3-[[4-(2,2-dimethylpiperazin-1-yl)-3-nitrophenyl] amino]-1-methylpyrazin-2-one (1.27 g, 0.508 mmol, 1.00 equiv, 17.5%), DCM (15.00 mL), 3-oxetanone (92.00 mg, 1.277 mmol, 2.51 equiv), HOAc (3.00 mg, 0.050 mmol, 0.10 equiv), $NaBH(OAc)_3$ (270.00 mg, 1.274 mmol, 2.51 equiv). The resulting solution was stirred overnight at room temperature. The resulting mixture was concentrated under vacuum. The residue was applied onto a silica gel column with dichloromethane/methanol (20:1). This resulted in 290 mg (61.30%) of 5-bromo-3-([4-[2,2-dimethyl-4-(oxetan-3-yl)piperazin-1-yl]-3-nitrophenyl]amino)-1-methylpyrazin-2-one as a red solid. LC-MS: (ES, m/z): M+1: 493

Synthesis of 3-([3-amino-4-[2,2-dimethyl-4-(oxetan-3-yl) piperazin-1-yl]phenyl]amino)-5-bromo-1-methylpyrazin-2-one: Into a 100-mL round-bottom flask, was placed 5-bromo-3-([4-[2,2-dimethyl-4-(oxetan-3-yl)piperazin-1-yl]-3-nitrophenyl]amino)-1-methylpyrazin-2-one (290.00 mg, 0.312 mmol, 1.00 equiv, 53%), EtOH (10.00 mL), $H_2O$ (3.00 mL), Fe (104.00 mg, 1.862 mmol, 5.98 equiv), $NH_4Cl$ (100.00 mg, 1.869 mmol, 6.00 equiv). The resulting solution was stirred for 2 hr at 55 degrees C. in an oil bath. The reaction mixture was cooled to room temperature. The resulting solution was diluted with 100/100 mL of water and DCM. The solids were filtered out. The resulting solution was extracted with 3×50 mL of dichloromethane and the organic layers combined. The resulting mixture was washed with 1×200 ml of brine. The mixture was dried over anhydrous sodium sulfate and concentrated under vacuum. The residue was applied onto a silica gel column with dichloromethane/methanol (20:1). This resulted in 135 mg (50.50%) of 3-([3-amino-4-[2,2-dimethyl-4-(oxetan-3-yl) piperazin-1-yl]phenyl]amino)-5-bromo-1-methylpyrazin-2-one as a yellow solid. LC-MS: (ES, m/z): M+1: 463

Synthesis of N-[5-[(6-bromo-4-methyl-3-oxopyrazin-2-yl)amino]-2-[2,2-dimethyl-4-(oxetan-3-yl)piperazin-1-yl] phenyl]prop-2-enamide: Into a 40-mL round-bottom flask purged and maintained with an inert atmosphere of nitrogen, was placed 3-([3-amino-4-[2,2-dimethyl-4-(oxetan-3-yl) piperazin-1-yl]phenyl]amino)-5-bromo-1-methylpyrazin-2-one (135.00 mg, 0.157 mmol, 1.00 equiv, 54%), DCM (5.00 mL), DIEA (41.00 mg, 0.317 mmol, 2.02 equiv), acryloyl chloride (14.00 mg, 0.155 mmol, 0.98 equiv). The resulting solution was stirred for 2 hr at room temperature. The resulting mixture was concentrated under vacuum. The residue was applied onto a silica gel column with dichloromethane/methanol (20:1). This resulted in 150 mg (crude) of N-[5-[(6-bromo-4-methyl-3-oxopyrazin-2-yl)amino]-2-[2,2-dimethyl-4-(oxetan-3-yl)piperazin-1-yl]phenyl]prop-2-enamide as a yellow solid. LC-MS: (ES, m/z): M+1: 517.

Synthesis of N-[2-[2,2-dimethyl-4-(oxetan-3-yl)piperazin-1-yl]-5-[[6-(2-[4,4-dimethyl-9-oxo-1,10-diazatricyclo [6.4.0.0^[2,6]]dodeca-2(6),7-dien-10-yl]-3-methylpyridin-4-yl)-4-methyl-3-oxopyrazin-2-yl]amino]phenyl]prop-2-enamide: Into a 40-mL vial purged and maintained with an inert atmosphere of nitrogen, was placed N-[5-[(6-bromo-4-methyl-3-oxopyrazin-2-yl)amino]-2-[2,2-dimethyl-4-(oxetan-3-yl)piperazin-1-yl]phenyl]prop-2-enamide (150.00 mg, 0.290 mmol, 1.00 equiv), dioxane (5.00 mL), $H_2O$ (0.50 mL), 2-[4,4-dimethyl-9-oxo-1,10-diazatricyclo[6.4.0.0^[2,6]]dodeca-2(6),7-dien-10-yl]-3-methylpyridin-4-ylboronic acid (148.00 mg, 0.436 mmol, 1.51 equiv), $K_2CO_3$ (100.00 mg, 0.724 mmol, 2.50 equiv), $Pd(DTBPF)Cl_2$ (19.00 mg, 0.029 mmol, 0.10 equiv). The resulting solution was stirred for 2 hr at 90 degrees C. in an oil bath. The reaction mixture was cooled to room temperature. The resulting mixture was concentrated under vacuum. The residue was applied onto a silica gel column with dichloromethane/methanol (20:1). The crude product was purified by Prep-HPLC with the following conditions: Column, X ridge Shield RP18 OBD Column, 5 um, 19*150 mm; mobile phase, Water (0.05% $NH_3 \cdot H_2O$) and ACN (26% Phase B up to 50% in 7 min); Detector, UV 254/220 nm. This resulted in 35 mg (16.50%) of N-[2-[2,2-dimethyl-4-(oxetan-3-yl)piperazin-1-yl]-5-[[6-(2-[4,4-dimethyl-9-oxo-1,10-diazatricyclo[6.4.0.0^[2,6]]dodeca-2(6),7-dien-10-yl]-3-methylpyridin-4-yl)-4-methyl-3-oxopyrazin-2-yl]amino]phenyl]prop-2-enamide as a white solid. LC-MS: (ES, m/z): M+1: 732; $^1H$ NMR (300 MHz, DMSO-$d_6$, ppm) δ 9.30-9.16 (m, 2H), 9.07-8.95 (m, 1H), 8.35 (d, J=5.1 Hz, 1H), 7.65 (dd, J=15.3, 6.9 Hz, 2H), 7.42 (s, 1H), 7.25 (d, J=8.7 Hz, 1H), 6.56 (q, J=5.8, 4.8 Hz, 2H), 6.25 (d, J=16.9 Hz, 1H), 5.80 (d, J=10.4 Hz, 1H), 4.67-4.37 (m, 4H), 4.19 (q, J=13.2, 12.6 Hz, 3H), 3.85 (d, J=12.5 Hz, 1H), 3.58 (s, 3H), 3.52-3.32 (m, 3H), 2.74 (d, J=10.1 Hz, 1H), 2.57 (d, J=5.8 Hz, 2H), 2.45 (d, J=12.2 Hz, 3H), 2.30 (s, 3H), 2.20-2.08 (m, 1H), 1.99 (d, J=10.4 Hz, 1H), 1.22 (s, 9H), 0.74 (s, 3H).

Example 46: Preparation of N-(5-[[6-(2-[4,4-dimethyl-9-oxo-1,10-diazatricyclo[6.4.0.0^[2,6]]dodeca-2(6),7-dien-10-yl]-3-methylpyridin-4-yl)-4-methyl-3-oxopyrazin-2-yl]amino]-2-[(2S)-2-methyl-4-(oxetan-3-yl)piperazin-1-yl]pyridin-3-yl)prop-2-enamide Synthesis of [(3,3-dimethylcyclopent-1-en-1-yl)oxy]trimethylsilane: Into a 10 L 4-necked round-bottom flask purged and maintained with an inert atmosphere of nitrogen, was placed CuCl (20.60 g, 208.083 mmol, 0.05 equiv), LiCl (17.64 g, 416.108 mmol, 0.10 equiv), THF (2.50 L). This was followed by the addition of 2-cyclopenten-1-one, 3-methyl-(400.00 g, 4161.075 mmol, 1.00 equiv) at −5 to 5 degrees C. To this was added TMSCl (474.67 g, 4369.129 mmol, 1.05 equiv) dropwise with stirring at −5 to 5 degrees C. To the mixture was added MeMgCl (1670.00 mL, 14495.069 mmol, 3.48 equiv) dropwise with stirring at −5 to 10 degrees C. The resulting solution was stirred for 2 h at −5 to 10 degrees C. in an ice/salt bath. The reaction was then quenched by the addition of 34 g of MeOH. The resulting solution was diluted with 5 L of $NH_4Cl$. The solids were filtered out. The resulting solution was extracted with 3×5 L of petroleum ether dried over anhydrous sodium sulfate and concentrated. This resulted in 780 g (crude) of [(3,3-dimethylcyclopent-1-en-1-yl)oxy]trimethylsilane as yellow oil. GCMS: (ES, m/z): M+1: 184

Synthesis of 3,3-dimethylcyclopentanone: Into a 20-L 4-necked round-bottom flask, was placed [(3,3-dimethylcyclopent-1-en-1-yl)oxy]trimethylsilane (780.00 g, 4230.990 mmol, 1.00 equiv), DCM (7.8 L), $H_2O$ (30.49 g, 1692.396 mmol, 0.4 equiv). This was followed by the addition of $POCl_3$ (214.09 g, 1396.251 mmol, 0.33 equiv) dropwise with stirring at 25 to 30 degrees C. The resulting solution was stirred for 0.5 h at 25 degrees C. This solvent straight used for next step. GCMS (ES, m/z): M+1: 112

Synthesis of 3,3-dimethylcyclopentanone: Into a 20-L 4-necked round-bottom flask, was placed 3,3-dimethylcyclopentan-1-one in DCM (7.80 L). This was followed by the addition of DMF (619 g, 2.0 equiv) dropwise with stirring at 25 degrees C. To this was added $POCl_3$ (1362 g, 2.1 equiv) dropwise with stirring at 40 degrees C. The resulting solution was stirred for overnight at 40 degrees C. in an oil bath. The reaction was then quenched by the addition of 2000 g of $K_3PO_4$. The resulting solution was extracted with 3×10 L of dichloromethane dried over anhydrous sodium sulfate and concentrated. This resulted in 530 g (4804.86%) of 2-chloro-4,4-dimethylcyclopent-1-ene-1-carbaldehyde as a brown solid. GCMS: (ES, m/z): M+1: 15

Synthesis of 4,4-dimethyl-1,10-diazatricyclo[6.4.0.0^[2,6]]dodeca-2(6),7-dien-9-one: Into a 5-L 4-necked round-bottom flask, was placed 2-chloro-4,4-dimethylcyclopent-1-ene-1-carbaldehyde (474.00 g, 2988.085 mmol, 1.00 equiv), DMF (3 L), piperazin-2-one (299.17 g, 2988.084 mmol, 1.00 equiv), DIEA (463.43 g, 3585.703 mmol, 1.2 equiv). The resulting solution was stirred for overnight at 115 degrees C. in an oil bath. The reaction mixture was cooled to room temperature with a water/ice bath. The solids were collected by filtration. The resulting mixture was washed with 3×2 L of $H_2O$ and 3×2 L of PE. The solid was dried in an oven under reduced pressure. This resulted in 230 g (37.68%) of 4,4-dimethyl-1,10-diazatricyclo[6.4.0.0^[2,6]]dodeca-2(6),7-dien-9-one as a grey solid. LCMS: (ES, m/z): M+1: 205

Synthesis of 2, 4-dibromo-3-methylpyridine: Into a 1000-mL 3-necked round-bottom flask purged and maintained with an inert atmosphere of nitrogen, was placed diisopropylamine (19.10 g, 189.959 mmol, 1.50 equiv), THF (300.00 mL). This was followed by the addition of n-butyllithium (12.30 g, 189.959 mmol, 1.50 equiv) at −30 degrees C. and the solution was stirred for 30 min. To this was added 2,4-dibromopyridine (30.00 g, 126.639 mmol, 1.00 equiv) at −70 degrees C. and stirred for other 30 min. To the mixture was added MeI (27.00 g, 189.959 mmol, 1.50 equiv) at −70 degrees C. and the solution was stirred for 0.5 h in a liquid nitrogen bath. The reaction was then quenched by the addition of 300 mL of $NH_4Cl$. The resulting solution was extracted with 3×200 mL of ethyl acetate and the organic layers combined. The resulting mixture was washed with 2×100 ml of water and 1×100 mL of brine. The mixture was dried over anhydrous sodium sulfate and concentrated. The residue was applied onto a silica gel column and eluted with ethyl acetate/petroleum ether (1:10). This resulted in 20 g of 2,4-dibromo-3-methylpyridine as a brown solid. LCMS: (ES, m/z): M+1: 250.

Synthesis of 10-(4-bromo-3-methylpyridin-2-yl)-4,4-dimethyl-1,10-diazatricyclo[6.4.0.0^[2,6]] dodeca-2(6),7-dien-9-one Into a 100-mL round-bottom flask purged and maintained with an inert atmosphere of nitrogen, was placed 2,4-dibromo-3-methylpyridine (20.00 g, 79.696 mmol, 1.00 equiv), 4,4-dimethyl-1,10-diazatricyclo[6.4.0.0^[2,6]]dodeca-2(6),7-dien-9-one (4.07 g, 19.924 mmol, 1.00 equiv), XantPhos PD G2 (7.08 g, 4.980 mmol, 0.10 equiv), dioxane (200.00 mL), $Cs_2CO_3$ (77.92 g, 239.152 mmol, 3.00 equiv). The resulting solution was stirred for 3h at 100 degrees C. in an oil bath. The resulting mixture was concentrated. The residue was applied onto a silica gel column and eluted with ethyl acetate/petroleum ether (1:1). This resulted in 10 g (33.52%) of 10-(4-bromo-3-methylpyridin-2-yl)-4,4-dimethyl-1,10-diazatricyclo[6.4.0.0^[2,6]]dodeca-2(6),7-dien-9-one as a brown solid. LCMS (ES, m/z): M+1: 374

Synthesis of 2-[4,4-dimethyl-9-oxo-1,10-diazatricyclo[6.4.0.0^[2,6]]dodeca-2(6),7-dien-10-yl]-3-methylpyridin-4-ylboronic acid Into a 50-mL round-bottom flask purged and maintained with an inert atmosphere of nitrogen, was placed 10-(4-bromo-3-methylpyridin-2-yl)-4,4-dimethyl-1,10-diazatricyclo[6.4.0.0^[2,6]]dodeca-2(6),7-dien-9-one (8.00 g, 20.788 mmol, 1.00 equiv), bis(pinacolato)diboron (7.936 g, 31.252 mmol, 1.50 equiv), Dioxane (110.00 mL), KOAc (4.046 g, 41.218 mmol, 1.98 equiv), $Pd(dppf)Cl_2$ (1.521 g, 2.077 mmol, 0.10 equiv). The resulting solution was stirred for 2h at 100 degrees C. in an oil bath. The resulting mixture was concentrated. The crude product was purified by Flash-Prep-HPLC with the following conditions (CombiFlash-1): Column, C18 silica gel; mobile phase, A: 0.1% $NH_3 \cdot H_2O$ in water; B: ACN; Gradient: 35%-70% B in 9 min; Detector, 220 nm. This resulted in 3.5 g (49.65%) of 2-[4,4-dimethyl-9-oxo-1,10-diazatricyclo[6.4.0.0^[2,6]]dodeca-2(6),7-dien-10-yl]-3-methylpyridin-4-ylboronic acid as a white solid. LCMS (ES, m/z): M+1: 340

Synthesis of tert-butyl (3S)-4-(5-bromo-3-nitropyridin-2-yl)-3-methylpiperazine-1-carboxylat, Into a 100-mL round-bottom flask, was placed tert-butyl (3S)-3-methylpiperazine-1-carboxylate (1.69 g, 8.438 mmol, 1.00 equiv), $CH_3CN$ (30.00 mL), 5-bromo-2-chloro-3-nitropyridine (2.00 g, 8.423 mmol, 1.00 equiv), $K_2CO_3$ (2.92 g, 21.128 mmol, 2.50 equiv). The resulting solution was stirred for 1 overnight at 80 degrees C. in an oil bath. The reaction mixture was cooled to room temperature. The resulting solution was diluted with 500 mL of water. The resulting solution was extracted with 3×200 mL of ethyl acetate and the organic layers combined. The resulting mixture was washed with 1×1000 ml of brine. The mixture was dried over anhydrous sodium sulfate and concentrated under vacuum. The residue was applied onto a silica gel column with ethyl acetate/petroleum ether (1:7). This resulted in 3.2 g (94.51%) of tert-butyl (3S)-4-(5-bromo-3-nitropyridin-2-yl)-3-methylpiperazine-1-carboxylate as yellow oil. LC-MS: (ES, m/z): M+1: 401

Synthesis of (2S)-1-(5-bromo-3-nitropyridin-2-yl)-2-methylpiperazine hydrochloride, Into a 100-mL round-bottom flask, was placed tert-butyl (3S)-4-(5-bromo-3-nitropyridin-2-yl)-3-methylpiperazine-1-carboxylate (3.00 g, 7.476 mmol, 1.00 equiv), HCl(gas)/1,4-dioxane (2M, 30.00 mL). The resulting solution was stirred for 2 hr at room temperature. The resulting mixture was concentrated under vacuum. This resulted in 2.32 g (91.92%) of (2S)-1-(5-bromo-3-nitropyridin-2-yl)-2-methylpiperazine hydrochloride as a yellow solid. LC-MS: (ES, m/z): M+1: 301

Synthesis of (2S)-1-(5-bromo-3-nitropyridin-2-yl)-2-methyl-4-(oxetan-3-yl)piperazine, Into a 250-mL round-bottom flask, was placed (2S)-1-(5-bromo-3-nitropyridin-2-yl)-2-methylpiperazine hydrochloride (2.32 g, 6.872 mmol, 1.00 equiv), THF (30.00 mL), 3-oxetanone (746.00 mg, 10.352 mmol, 1.51 equiv), HOAc (100.00 mg, 1.665 mmol, 0.24 equiv), $NaBH(OAc)_3$ (2.93 g, 13.825 mmol, 2.01 equiv). The resulting solution was stirred for 1 overnight at 30 degrees C. in an oil bath. The resulting mixture was concentrated under vacuum. The residue was applied onto a silica gel column with ethyl acetate/petroleum ether (1:3). This resulted in 2.4 g (97.77%) of (2S)-1-(5-bromo-3-nitropyridin-2-yl)-2-methyl-4-(oxetan-3-yl)piperazine as yellow oil. LC-MS: (ES, m/z): M+1: 357; H-NMR (300 MHz, $CDCl_3$-d, ppm) δ 8.35 (d, J=2.3 Hz, 1H), 8.24 (d, J=2.3 Hz, 1H), 4.77-4.36 (m, 5H), 3.51 (td, J=12.2, 11.3, 3.6 Hz, 2H), 3.13 (d, J=13.3 Hz, 1H), 2.69 (d, J=10.9 Hz, 1H), 2.56 (d, J=11.1 Hz, 1H), 2.26 (d, J=11.2 Hz, 1H), 2.10 (q, J=11.6, 8.3 Hz, 1H), 1.42 (d, J=6.7 Hz, 3H).

Synthesis of N-[6-[(2S)-2-methyl-4-(oxetan-3-yl)piperazin-1-yl]-5-nitropyridin-3-yl]-1,1-diphenylmethanimine, Into a 250-mL round-bottom flask purged and maintained with an inert atmosphere of nitrogen, was placed (2S)-1-(5-bromo-3-nitropyridin-2-yl)-2-methyl-4-(oxetan-3-yl)piperazine (2.20 g, 6.159 mmol, 1.00 equiv), toluene (30.00 mL), diphenylmethanimine (1.34 g, 7.394 mmol, 1.20 equiv), $Cs_2CO_3$ (6.03 g, 18.507 mmol, 3.00 equiv), $Pd_2(dba)_3 \cdot CHCl_3$ (1.28 g, 1.237 mmol, 0.20 equiv), Xantphos (1.43 g, 2.471 mmol, 0.40 equiv). The resulting solution was stirred for 2 hr at 100 degrees C. in an oil bath. The reaction mixture was cooled to room temperature. The resulting mixture was concentrated under vacuum. The residue was applied onto a silica gel column with ethyl acetate/petroleum ether (1:1). This resulted in 2.54 g (90.14%) of N[6-[(2S)-2-methyl-4-(oxetan-3-yl)piperazin-1-yl]-5-nitropyridin-3-yl]-1,1-diphenylmethanimine as red oil. LC-MS: (ES, m/z): M+1: 458

Synthesis of 6-[(2S)-2-methyl-4-(oxetan-3-yl)piperazin-1-yl]-5-nitropyridin-3-amine, Into a 100-mL round-bottom flask, was placed N[6-[(2S)-2-methyl-4-(oxetan-3-yl)piperazin-1-yl]-5-nitropyridin-3-yl]-1,1-diphenylmethanimine (2.00 g, 4.371 mmol, 1.00 equiv), EtOH (15.00 mL), THF (15.00 mL), HCl (3.00 mL). The resulting solution was stirred for 1.5 hr at room temperature. The pH value of the solution was adjusted to 8 with aqueous $NaHCO_3$. The resulting solution was extracted with 3×100 mL of ethyl acetate and the organic layers combined. The resulting mixture was washed with 1×500 ml of brine. The mixture was dried over anhydrous sodium sulfate and concentrated under vacuum. The residue was applied onto a silica gel column with dichloromethane/methanol (10:1). This resulted in 1.26 g (98.27%) of 6-[(2S)-2-methyl-4-(oxetan-3-yl)piperazin-1-yl]-5-nitropyridin-3-amine as a red solid. LC-MS: (ES, m/z): M+1: 294; H NMR (300 MHz, DMSO-$d_6$, ppm) δ 8.01 (d, J=2.7 Hz, 1H), 7.32 (d, J=2.8 Hz, 1H), 5.63 (s, 2H), 4.69-4.29 (m, 4H), 3.43 (ddd, J=12.7, 8.5, 4.8 Hz, 2H), 3.05 (ddd, J=11.7, 5.3, 3.0 Hz, 1H), 2.89 (ddd, J=11.6, 8.5, 2.9 Hz, 1H), 2.45 (d, J=7.6 Hz, 1H), 2.27-2.08 (m, 1H), 1.89 (dd, J=10.8, 7.7 Hz, 1H), 0.79 (d, J=6.3 Hz, 3H).

Synthesis of 5-bromo-1-methyl-3-([6-[(2S)-2-methyl-4-(oxetan-3-yl)piperazin-1-yl]-5-nitropyridin-3-yl]amino)pyrazin-2-one: Into a 40-mL vial purged and maintained with an inert atmosphere of nitrogen, was placed 6-[(2S)-2-methyl-4-(oxetan-3-yl)piperazin-1-yl]-5-nitropyridin-3-amine (516.00 mg, 1.759 mmol, 1.00 equiv), toluene (5.00 mL), 3,5-dibromo-1-methylpyrazin-2-one (468.00 mg, 1.747 mmol, 0.99 equiv), $K_2CO_3$ (364.00 mg, 2.634 mmol, 1.50 equiv), Xantphos (407.00 mg, 0.703 mmol, 0.40 equiv), $Pd(OAc)_2$ (86.00 mg, 0.383 mmol, 0.22 equiv). The resulting solution was stirred for 2 hr at 100 degrees C. in an oil bath. The reaction mixture was cooled to room temperature. The resulting mixture was concentrated under vacuum. The residue was applied onto a silica gel column with ethyl acetate. This resulted in 650 mg (76.93%) of 5-bromo-1-methyl-3-([6-[4(2S)-2-methyl-4-(oxetan-3-yl)piperazin-1-yl]-5-nitropyridin-3-yl]amino)pyrazin-2-one as a red solid. LC-MS: (ES, m/z): M+1: 480; $^1$H NMR (300 MHz, DMSO-$d_6$, ppm) δ 9.98 (s, 1H), 8.94 (q, J=2.5 Hz, 2H), 7.39 (s, 1H), 4.66-4.15 (m, 6H), 3.45 (s, 3H), 3.42-3.32 (m, 2H), 3.08 (d, J=13.1 Hz, 1H), 2.64 (d, J=11.0 Hz, 1H), 2.16 (dd, J=11.0, 3.6 Hz, 1H), 2.10-1.95 (m, 1H), 1.22 (d, J=6.6 Hz, 3H).

Synthesis of 3-([5-amino-6-[(2S)-2-methyl-4-(oxetan-3-yl)piperazin-1-yl]pyridin-3-yl]amino)-5-bromo-1-methylpyrazin-2-one: Into a 100-mL round-bottom flask, was placed 5-bromo-1-methyl-3-([6-[(2S)-2-methyl-4-(oxetan-3-yl)piperazin-1-yl]-5-nitropyridin-3-yl]amino)pyrazin-2-one (870.00 mg, 1.811 mmol, 1.00 equiv), EtOH (15.00 mL), $H_2O$ (5.00 mL), Fe (610.00 mg, 10.923 mmol, 6.03 equiv), $NH_4Cl$ (578.00 mg, 10.806 mmol, 5.97 equiv). The resulting solution was stirred for 2 hr at 50 degrees C. in an oil bath. The reaction mixture was cooled to room temperature. The resulting solution was diluted with 200/200 mL of water/DCM. The solids were filtered out. The resulting solution was extracted with 3×100 mL of dichloromethane and the organic layers combined. The resulting mixture was washed with 1×500 ml of brine. The mixture was dried over anhydrous sodium sulfate and concentrated under vacuum. The residue was purified by Prep-TLC with dichloromethane/methanol (10:1). This resulted in 430 mg (41.65%) of 3-([5-amino-6-[(2S)-2-methyl-4-(oxetan-3-yl)piperazin-1-yl]pyridin-3-yl]amino)-5-bromo-1-methylpyrazin-2-one as a yellow solid. LC-MS: (ES, m/z): M+1: 450

Synthesis of N-[5-[(6-bromo-4-methyl-3-oxopyrazin-2-yl)amino]-2-[(2S)-2-methyl-4-(oxetan-3-yl)piperazin-1-yl] pyridin-3-yl]prop-2-enamide: Into a 100-mL round-bottom flask purged and maintained with an inert atmosphere of nitrogen, was placed 3-([5-amino-6-[(2S)-2-methyl-4-(oxetan-3-yl)piperazin-1-yl]pyridin-3-yl]amino)-5-bromo-1-methylpyrazin-2-one (340.00 mg, 0.755 mmol, 1.00 equiv), DCM (5.00 mL), DIEA (195.00 mg, 1.509 mmol, 2.00 equiv), acryloyl chloride (68.00 mg, 0.751 mmol, 1.00 equiv). The resulting solution was stirred for 2 hr at 25 degrees C. The resulting mixture was concentrated under vacuum. The residue was applied onto a silica gel column with dichloromethane/methanol (20:1). This resulted in 300 mg (78.78%) of N-[5-[(6-bromo-4-methyl-3-oxopyrazin-2-yl)amino]-2-[(2S)-2-methyl-4-(oxetan-3-yl)piperazin-1-yl] pyridin-3-yl]prop-2-enamide as a yellow solid. LC-MS: (ES, m/z): M+1: 504

Synthesis of N-(5-[[6-(2-[4,4-dimethyl-9-oxo-1,10-diazatricyclo[6.4.0.0^[2,6]]dodeca-2(6),7-dien-10-yl]-3-methylpyridin-4-yl)-4-methyl-3-oxopyrazin-2-yl]amino]-2-[(2S)-2-methyl-4-(oxetan-3-yl)piperazin-1-yl]pyridin-3-yl) prop-2-enamide: Into a 40-mL vial purged and maintained with an inert atmosphere of nitrogen, was placed N-[5-[(6-bromo-4-methyl-3-oxopyrazin-2-yl)amino]-2-[(2S)-2-methyl-4-(oxetan-3-yl)piperazin-1-yl]pyridin-3-yl]prop-2-enamide (150.00 mg, 0.297 mmol, 1.00 equiv), dioxane (5.00 mL), $H_2O$ (0.50 mL), 2-[4,4-dimethyl-9-oxo-1,10-diazatricyclo[6.4.0.0^[2,6]]dodeca-2(6),7-dien-10-yl]-3-methylpyridin-4-ylboronic acid (152.00 mg, 0.448 mmol, 1.51 equiv), $K_2CO_3$ (103.00 mg, 0.745 mmol, 2.51 equiv), Pd(DTBPF)$Cl_2$ (20.00 mg, 0.031 mmol, 0.10 equiv). The resulting solution was stirred for 2 hr at 100 degrees C. in an oil bath. The reaction mixture was cooled to room temperature. The resulting mixture was concentrated under vacuum. The residue was applied onto a silica gel column with dichloromethane/methanol (20:1). The crude product was purified by Prep-HPLC with the following conditions: Column, XBridge Shield RP18 OBD Column, 5 um, 19*150 mm; mobile phase, Water (0.05% $NH_3 \cdot H_2O$) and ACN (26% Phase B up to 50% in 7 min); Detector, UV 254/220 nm. This resulted in 35 mg (16.37%) of N-(5-[[6-(2-[4,4-dimethyl-9-oxo-1,10-diazatricyclo[6.4.0.0^[2,6]]dodeca-2(6),7-dien-10-yl]-3-methylpyridin-4-yl)-4-methyl-3-oxopyrazin-2-yl]amino]-2-[(2S)-2-methyl-4-(oxetan-3-yl)piperazin-1-yl]pyridin-3-yl)prop-2-enamide as a white solid. LC-MS: (ES, m/z): M+1: 719; $^1$H NMR (300 MHz, DMSO-$d_6$, ppm) δ 9.55 (d, J=3.7 Hz, 1H), 9.23 (d, J=16.4 Hz, 1H), 9.11 (s, 1H), 8.67 (dd, J=8.1, 2.6 Hz, 1H), 8.35 (d, J=5.1 Hz, 1H), 7.62 (dd, J=8.1, 5.1 Hz, 1H), 7.44 (s, 1H), 6.74-6.60 (m, 1H), 6.55 (s, 1H), 6.27 (ddd, J=17.0, 6.7, 1.9 Hz, 1H), 5.78 (dd, J=10.2, 1.9 Hz, 1H), 4.62-4.42 (m, 4H), 4.20 (d, J=22.9 Hz, 3H), 3.84 (d, J=11.9 Hz, 1H), 3.58 (s, 3H), 3.52-3.36 (m, 2H), 2.97-2.76 (m, 2H), 2.61 (dd, J=22.5, 7.7 Hz, 4H), 2.43 (s, 2H), 2.29 (d, J=1.8 Hz, 4H), 2.03 (t, J=10.0 Hz, 1H), 1.22 (s, 6H), 0.82 (d, J=6.2 Hz, 3H).

Example A: The compounds below are prepared by methods substantially identical, similar, or analogous to those disclosed in the General Scheme and above Examples.

| ID | Chemical Structure | m/z |
|---|---|---|
| A-1 | (R)-N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(4-(tetrahydro-2H-pyran-4-yl)-2-(trifluoromethyl)piperazin-1-yl)phenyl)acrylamide, | 800 |
| A-2 | (S)-N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(4-(tetrahydro-2H-pyran-4-yl)-2-(trifluoromethyl)piperazin-1-yl)phenyl)acrylamide, | 800 |
| A-3 | (S)-N-(2-(2-methyl-4-(tetrahydro-2H-pyran-4-yl)piperazin-1-yl)-5-((4-methyl-6-(3-methyl-2-(1-oxo-3,4,5,6,7,8-hexahydrobenzo[4,5]thieno[2,3-c]pyridin-2(1H)-yl)pyridin-4-yl)-3-oxo-3,4-dihydropyrazin-2-yl)amino)phenyl)acrylamide, | 749 |
| A-4 | (R)-N-(5-((4-methyl-6-(3-methyl-2-(1-oxo-3,4,5,6,7,8-hexahydrobenzo[4,5]thieno[2,3-c]pyridin-2(1H)-yl)pyridin-4-yl)-3-oxo-3,4-dihydropyrazin-2-yl)amino)-2-(4-(tetrahydro-2H-pyran-4-yl)-2-(trifluoromethyl)piperazin-1-yl)phenyl)acrylamide, | 803 |
| A-5 | (S)-N-(5-((4-methyl-6-(3-methyl-2-(1-oxo-3,4,5,6,7,8-hexahydrobenzo[4,5]thieno[2,3-c]pyridin-2(1H)-yl)pyridin-4-yl)-3-oxo-3,4-dihydropyrazin-2-yl)amino)-2-(4-(tetrahydro-2H-pyran-4-yl)-2-(trifluoromethyl)piperazin-1-yl)phenyl)acrylamide, | 803 |
| A-6 | (R)-N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(4-(tetrahydro-2H-pyran-4-yl)-2-(trifluoromethyl)piperazin-1-yl)phenyl)acrylamide, | 816 |
| A-7 | (S)-N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(4-(tetrahydro-2H-pyran-4-yl)-2-(trifluoromethyl)piperazin-1-yl)phenyl)acrylamide | 816 |

Biological Example 1: Binding Constant ($K_d$) Determination

The $K_d$ of the compounds were determined by KINOMEscan™ assay, the industry's most comprehensive high-throughput system for screening compounds against large numbers of human kinases. KINOMEscan™ assay is based on a competition binding assay that quantitatively measures the ability of a compound to compete with an immobilized, active-site directed ligand. The assay is performed by combining three components: DNA-tagged kinase; immobilized ligand; and a test compound. The ability of the test compound to compete with the immobilized ligand is measured via quantitative PCR of the DNA tag. The kinase-tagged T7 phage strains were prepared in an *E. coli* host derived from the BL21 strain. *E. coli* were grown to log-phase and infected with T7 phage and incubated with shaking at 32° C. until lysis. The lysates were centrifuged and filtered to remove cell debris. The remaining kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce non-specific binding. Binding reactions were assembled by combining kinases, liganded affinity beads, and test compounds in 1× binding buffer (20% SeaBlock, 0.17×PBS, 0.05% Tween 20, 6 mM DTT). All reactions were performed in polystyrene 96-well plates in a final volume of 0.135 nil. The assay plates were incubated at room temperature with shaking for 1 hour and the affinity beads were washed with wash buffer (lx PBS, 0.05% Tween 20). The beads were then re-suspended in elution buffer (lx PBS, 0.05% Tween 20, 0.5 μM nonbiotinylated affinity ligand) and incubated at room temperature with shaking for 30 minutes. The kinase concentration in the eluates was measured by qPCR. An 11-point 3-fold serial dilution of each test compound was prepared in 100% DMSO at 100× final test concentration and subsequently diluted to 1× in the assay (final DMSO concentration=1%). Most $K_d$ were determined using a compound top concentration=30,000 nM. If the initial Kd determined was <0.5 nM (the lowest concentration tested), the measurement was repeated with a serial dilution starting at a lower top concentration. A $K_d$ value reported as 40,000 nM indicates that the $K_d$ was determined to be >30,000 nM. Binding constants ($K_d$s) were calculated with a standard dose-response curve using the Hill equation: Response=Background+(Signal−Background)/[1+ $(K_d^{Hill\ Slope}/Dose^{Hill\ Slope})$]. The Hill Slope was set to −1. Curves were fitted using a non-linear least square fit with the Levenberg-Marquardt algorithm. Such assays, carried out with a range of doses of test compounds, allow the determination of an approximate $K_d$ value. Although the $K_d$ of the compounds of the present invention vary with structural change as expected, the activity generally exhibited by these agents is in the range of $K_d$=0.1-1000 nM.

Biological Example 2: In Vitro Dialysis Assay (Irreversibility Assay)

IC50 of the test compound, was determined in the presence of 0.1 nM Enzyme and 40 mM ATP. 0.003 mM Compound (39×IC50 @40 mM ATP) was pre-incubated with 2 nM BTK for 2 hr in assay buffer without ATP. The compound-enzyme complex was dialyzed against the same buffer supplemented with 40 mM ATP for 24 hr. Cumulative dialysis factor >160,000×. After dialysis, the BTK activity was measured in the presence 40 mM ATP and 1 mM substrate peptide and compared to that in non-dialyzed samples. Assay buffer: 100 mM HEPES, pH7.5; 0.1% BSA, 0.01% Triton-X 100; 5 mM $MgCl_2$; 1 mM DTT. In this study, Ibrutinib (a FDA approved irreversible BTK inhibitor) was used as a positive control and Saurosporine (a reversible BTK inhibitor) was used as a negative control. The following table shows the recovery after 24 hr dialysis.

In this assay, GDC-0853, a reversible BTK inhibitor, was used as a reference compound. GDC-0853, disclosure in WO 2013067274, is an orally bioavailable, selective, and reversible Bruton's tyrosine kinase (BTK) inhibitor with IC50s ranging from 2-9 nM for basophil activation, B cell receptor activation, and constitutive p-BTK activity in whole blood lysates. 1,2 In rats, treatment for longer than 7 days leads to pancreatic toxicity but it does not occur in mice or dogs, even at higher doses. Formulations containing GDC-0853 were well-tolerated in Phase I clinical trials and are in additional clinical trials for rheumatoid arthritis, lupus erythematosus and other autoimmune diseases.

The data of the WT BTK dialysis assay clearly shows that Ibrutnib, Example 2, Example 3, Example 11, Example 12 are irreversible inhibitors of WT BTK, while GDC-0853 is a reversible WT BTK inhibitor.

| | Recovery after 24 h dialysis | Conclusion (WT BTK) |
|---|---|---|
| GDC-0853 | ~100% | Reversible |
| Ibrutninb | ~1% | Irreversible/covalent inhibition |
| Example 2 | ~1% | Irreversible/covalent inhibition |
| Example 3 | ~1% | Irreversible/covalent inhibition |
| Example 11 | ~1% | Irreversible/covalent inhibition |
| Example 12 | ~1% | Irreversible/covalent inhibition |
| Example 17 | ~1% | Irreversible/covalent inhibition |
| Example 18 | ~1% | Irreversible/covalent inhibition |
| Example 19 | ~1% | Irreversible/covalent inhibition |
| Example 20 | ~1% | Irreversible/covalent inhibition |
| Example 21 | ~1% | Irreversible/covalent inhibition |
| Example 22 | ~1% | Irreversible/covalent inhibition |
| Example 23 | ~1% | Irreversible/covalent inhibition |
| Example 24 | ~1% | Irreversible/covalent inhibition |
| Example 25 | ~1% | Irreversible/covalent inhibition |
| Example 27 | ~1% | Irreversible/covalent inhibition |
| Example 29 | ~1% | Irreversible/covalent inhibition |
| Example 34 | ~1% | Irreversible/covalent inhibition |
| Example 35 | ~1% | Irreversible/covalent inhibition |
| Example 36 | ~1% | Irreversible/covalent inhibition |
| Example 37 | ~1% | Irreversible/covalent inhibition |
| Example 38 | ~1% | Irreversible/covalent inhibition |
| Example 39 | ~1% | Irreversible/covalent inhibition |
| Example 40 | ~1% | Irreversible/covalent inhibition |
| Example 41 | ~1% | Irreversible/covalent inhibition |
| Example 42 | ~1% | Irreversible/covalent inhibition |
| Example 43 | ~1% | Irreversible/covalent inhibition |
| Example 44 | ~1% | Irreversible/covalent inhibition |
| Example 45 | ~1% | Irreversible/covalent inhibition |
| Example 46 | ~1% | Irreversible/covalent inhibition |

For the C481S BTK enzyme, Ibrutinib, and our compounds such as Example 2 reversibly bind to the C481S BTK since the Cysteine residue is not available any more for covalent binding.

Biological Example 3: Biochemical Enzymatic Assay (IC50) Against WT and C481S BTK A Caliper-based kinase assay (Caliper Life Sciences, Hopkinton, MA) was used to measure inhibition of WT and C481S Btk kinase activity of a compound of the present disclosure. Ibrutinib and ACP=196 was used as control compounds. Serial dilutions of test compounds were incubated with human recombinant WT BTK or C481S Btk (0.5 nM), ATP (16 μM) and a phosphoacceptor peptide substrate FAM-GEEPLYWSFPAKKK-NH2 (1 μM) at room temperature for 3 h. The reaction was then terminated with EDTA, final concentration 20 mM and the phosphorylated reaction product was quantified on a Caliper Desktop Profiler (Caliper LabChip 3000). Percent inhibition was calculated for each compound dilution and the concentration that produced 50% inhibition was calculated.

The following table shows the IC50 of WT BTK, C481S BTK, and the IC50 ratio of C481S vs WT BTK for Ibrunitib, ACP-196, certain compounds of the disclosure. As expected, both Ibrutinib and ACP-196 dramatically lost binding affinity to the C481S BTK enzyme: Ibrutinib is X990 fold weaker in C481S BTK than that of WT BTK, and ACP-196 is X483 fold weaker in C481S BTK than that of WT BTK. On the contrary, the inventor unexpectedly find that our compounds still potently inhibits the C481S BTK as compared to that of WT BTK. Example 2 is X64 more potent than Ibrutinib and X477 more potent than the ACT-196 in C481S BTK assay. Example 22 is X2,333 fold more potent than the ACT-196 in C481S BTK assay. These data suggest that our compounds such as Example 22 reversibly binds to BTK by a different mechanism from the conventional covalent BTK inhibitors such as Ibrutinib and ACP-196, and so might be an important option for those patients that become resistant to Ibrutinib and ACP-196 due to a mutation in the C481 binding site.

| Covalent BTKi | WT BTK IC50 (nM) (irreversible inhibition) | C481S BTK IC50 (nM) (reversible inhibition) |
|---|---|---|
| ACP-196 | 2.20 | 1,120 |
| Example 3 | 0.14 | 0.72 |
| Example 11 | 0.25 | 15.9 |
| Example 12 | 0.046 | 0.25 |
| Example 17 | 0.1 | 7.1 |
| Example 18 | 0.18 | 11.4 |
| Example 19 | 0.12 | 0.97 |
| Example 20 | 0.053 | 0.4 |
| Example 21 | 0.040 | 0.4 |
| Example 22 | 0.046 | 0.48 |
| Example 23 | 0.048 | 0.49 |
| Example 24 | 0.058 | 0.40 |
| Example 25 | 0.065 | 0.60 |
| Example 27 | 0.068 | 0.22 |
| Example 28 | >100 | >1000 |
| Example 29 | 0.076 | 0.32 |
| Example 30 | 1.58 | 1.6 |
| Example 31 | >100 | |
| Example 32 | >100 | |
| Example 33 | >100 | |
| Example 34 | 0.073 | 0.46 |
| Example 35 | 0.13 | 17.9 |
| Example 36 | 0.1 | 1.1 |
| Example 37 | 0.042 | 0.35 |
| Example 38 | 0.073 | 0.26 |
| Example 39 | 0.06 | 0.34 |
| Example 40 | 0.083 | |
| Example 41 | 0.27 | 0.61 |
| Example 42 | 0.24 | 0.30 |
| Example 43 | 0.35 | 0.50 |
| Example 44 | 0.98 | |
| Example 45 | 0.36 | |
| Example 46 | 0.16 | |

Biological Example 4: Calcium Flux Fluorescence-Based Assay

Calcium flux fluorescence-based assays were performed in a FlexStation 11384 fluorometric imaging plate reader (Molecular Devices) according to manufacturer instructions. In brief, actively growing Ramos cells (ATCC) in RPMl medium supplemented with 10% FBS (Invitrogen) were washed and re-plated in low serum medium at approximately $5\times10^5$ cells per 100 µl per well in a 96-well plate. Compounds to be assayed were dissolved in DMSO and then diluted in low serum medium to final concentrations ranging from 0 to 10 µM (at a dilution factor of 0.3). The diluted compounds were then added to each well (final DMSO concentration was 0.01%) and incubated at 37 degree in 5% $CO_2$ incubator for one hour. Afterwards, 100 µl of a calcium-sensitive dye (from the Calcium 3 assay kit, Molecular Devices) was added to each well and incubated for an additional hour. The compound-treated cells were stimulated with a goat anti-human IgM antibody (80 ug/ml; Jackson ImmunoResearch) and read in the FlexStation II384 using a $\lambda_{Ex}$=485 nm and $\lambda_{Em}$=538 nm for 200 seconds. The relative fluorescence unit (RFU) and the $IC_{50}$ were recorded and analyzed using a built-in SoftMax program (Molecular devices).

Biological Example 5: Inhibition of B-Cell Activation—B Cell FLIPR Assay in Ramos Cells Inhibition of B-cell activation by compounds of the present invention is demonstrated by determining the effect of the test compounds on anti-IgM stimulated B cell responses. The B cell FLIPR assay is a cell based functional method of determining the effect of potential inhibitors of the intracellular calcium increase from stimulation by an anti-IgM antibody. Ramos cells (human Burkitt's lymphoma cell line. ATCC-No. CRL-1596) were cultivated in Growth Media (described below). One day prior to assay, Ramos cells were resuspended in fresh growth media (same as above) and set at a concentration of $0.5\times10^6$/mL in tissue culture flasks. On day of assay, cells are counted and set at a concentration of $1\times10^6$/mLl in growth media supplemented with IµM FLUO-3AM (TefLabs Cat-No. 0116, prepared in anhydrous DMSO and 10% Pluronic acid) in a tissue culture flask, and incubated at 37° C. (5% $C0_2$) for one h. To remove extracellular dye, cells were collected by centrifugation (5 min, 1000 rpm), resuspended in FLIPR buffer (described below) at $1\times10^6$ cells/mL and then dispensed into 96-well poly-D-lysine coated black/clear plates (BD Cat-No. 356692) at $1\times10^5$ cells per well. Test compounds were added at various concentrations ranging from 100 µM to 0.03 µM (7 concentrations, details below), and allowed to incubate with cells for 30 min at RT. Ramos cell $Ca^{2+}$ signaling was stimulated by the addition of 10 µg/mL anti-IgM (Southern Biotech, Cat-No. 2020-01) and measured on a FLIPR (Molecular Devices, captures images of 96 well plates using a CCD camera with an argon laser at 480 nM excitation).

Growth Medium: RPMI 1640 medium with L-glutamine (Invitrogen, Cat-No. 61870-010), 10% Fetal Bovine Serum (FBS, Summit Biotechnology Cat-No. FP-100-05); ImM Sodium Pyruvate (Invitrogen Cat. No. 11360-070).

FLIPR buffer: HBSS (Invitrogen, Cat-No. 141175-079), 2 mM $CaCl_2$ (Sigma Cat-No. C-4901), HEPES (Invitrogen, Cat-No. 15630-080), 2.5 mM Probenecid (Sigma, Cat-No. P-8761), 0.1% BSA (Sigma, Cat-No. A-7906), 11 mM Glucose (Sigma, Cat-No. G-7528);

Assay and Analysis: Intracellular increases in calcium were reported using a max–min statistic (subtracting the resting baseline from the peak caused by addition of the stimulatory antibody using a Molecular Devices FLIPR control and statistic exporting software. The $IC_{50}$ was determined using a nonlinear curve fit (GraphPad Prism).

Biological Example 6: In Vitro Anti-Proliferation Assay

Cell antiproliferation is assayed by PerkinElmer ATPlite™ Luminescence Assay System. Briefly, the various test cancer cell lines are plated at a density of about $1\times10^4$ cells per well in Costar 96-well plates, and are incubated with different concentrations of compounds for about 72 hours in medium supplemented with 5% FBS. One lyophilized substrate solution vial is then reconstituted by adding 5 mL of substrate buffer solution, and is agitated gently until the solution is homogeneous. About 50 μL of mammalian cell lysis solution is added to 100 μL of cell suspension per well of a microplate, and the plate is shaken for about five minutes in an orbital shaker at ~700 rpm. This procedure is used to lyse the cells and to stabilize the ATP. Next, 50 μL substrate solution is added to the wells and microplate is shaken for five minutes in an orbital shaker at ~700 rpm. Finally, the luminescence is measured by a PerkinElmer TopCount® Microplate Scintillation Counter. Such assays, carried out with a range of doses of test compounds, allow the determination of the cellular anti-antiproliferative $IC_{50}$ of the compounds of the present invention.

Biological Example 7: In Vivo Xenograft Studies

Typically, athymic nude mice (CD-1 nu/nu) or SCID mice are obtained at age 6-8 weeks from vendors and acclimated for a minimum 7-day period. The cancer cells are then implanted into the nude mice. Depending on the specific tumor type, tumors are typically detectable about two weeks following implantation. When tumor sizes reach ~100-200 $mm^3$, the animals with appreciable tumor size and shape are randomly assigned into groups of 8 mice each, including one vehicle control group and treatment groups. Dosing varies depending on the purpose and length of each study, which typically proceeds for about 3-4 weeks. Tumor sizes and body weight are typically measured three times per week. In addition to the determination of tumor size changes, the last tumor measurement is used to generate the tumor size change ratio (T/C value), a standard metric developed by the National Cancer Institute for xenograft tumor evaluation. In most cases, % T/C values are calculated using the following formula: % $T/C=100\times\Delta T/\Delta C$ if $\Delta T>0$. When tumor regression occurred ($\Delta T<0$), however, the following formula is used: % $T/T0=100\times\Delta T/T0$. Values of <42% are considered significant.

As shown below, Example 22 produced dose-dependent reduction of tumor growth in the REC-1 xenograft model at day 28 of the study.

| Group | mice | Agent | mg/kg | Dosing | Tumor volume |
|---|---|---|---|---|---|
| 1 | 7 | vehicle | Vehicle | po, BIDX28 | 1720 $mm^3$ |
| 2 | 7 | Acalabrutinib | 50 | po, BIDX28 | 108 $mm^3$ |
| 3 | 7 | Example 22 | 12.5 | po, BIDX28 | 201 $mm^3$ |
| 4 | 7 | Example 22 | 25 | po, BIDX28 | 58 $mm^3$ |
| 5 | 7 | Example 22 | 50 | po, BIDX28 | 56 $mm^3$ |

As shown below, Example 22 has better efficacy than Acalabrutinib in the REC-1 xenograft model at day 26 of the study.

| Group | mice | Agent | mg/kg | Dosing | Tumor volume |
|---|---|---|---|---|---|
| 1 | 7 | vehicle | Vehicle | po, BIDX28 | 1019 $mm^3$ |
| 2 | 7 | Acalabrutinib | 10 | po, BIDX28 | 672 $mm^3$ |
| 3 | 7 | Example 22 | 10 | po, BIDX28 | 450 $mm^3$ |

Biological Example 8: Mouse Collagen-Induced Arthritis (mCIA)

On day 0 mice are injected at the base of the tail or several spots on the back with an emulsion of Type II Collagen (i.d.) in Complete Freund's adjuvant (CFA). Following collagen immunization, animals will develop arthritis at around 21 to 35 days. The onset of arthritis is synchronized (boosted) by systemic administration of collagen in Incomplete Freund's adjuvant (IFA; i.d.) at day 21. Animals are examined daily after day 20 for any onset of mild arthritis (score of 1 or 2; see score description below) which is the signal to boost. Following boost, mice are scored and dosed with candidate therapeutic agents for the prescribed time (typically 2-3 weeks) and dosing frequency, daily (QD) or twice-daily (BID). The developing inflammation of the paws and limb joints is quantified using a scoring system that involves the assessment of the 4 paws following the criteria described below:

Scoring:

1=swelling and/or redness of paw or one digit.

2=swelling in two or more joints.

3=gross swelling of the paw with more than two joints involved.

4=severe arthritis of the entire paw and digits.

Evaluations are made on day 0 for baseline measurement and starting again at the first signs or swelling for up to three times per week until the end of the experiment. The arthritic index for each mouse is obtained by adding the four scores of the individual paws, giving a maximum score of 16 per animal.

Biological Example 9: Rat Collagen-Induced Arthritis (rCIA)

On day 0, rats are injected with an emulsion of Bovine Type II Collagen in Incomplete Freund's adjuvant (IFA) is injected intradermally (i.d.) on several locations on the back. A booster injection of collagen emulsion is given around day 7, (i.d.) at the base of the tail or alternative sites on the back. Arthritis is generally observed 12-14 days after the initial collagen injection. Animals may be evaluated for the development of arthritis as described below (Evaluation of arthritis) from day 14 onwards. Animals are dosed with candidate therapeutic agents in a preventive fashion starting at the time of secondary challenge and for the prescribed time (typically 2-3 weeks) and dosing frequency, daily (QD) or twice-daily (BID). The developing inflammation of the paws and limb joints is quantified using a scoring system that involves the assessment of the 4 paws following the criteria as described above. Evaluation are made on day 0 for baseline measurement and starting again at the first signs or swelling for up to three times per week until the end of the experiment. The arthritic index for each mouse is obtained by adding the four scores of the individual paws, giving a maximum score of 16 per animal.

Biological Example 10: Rat In Vivo Asthma Model

Male Brown-Norway rats are sensitized i.p. with 100 μg of OA (ovalbumin) in 0.2 ml alum once every week for three weeks (day 0, 7, and 14). On day 21 (one week following last sensitization), the rats are dosed q.d. with either vehicle or compound formulation subcutaneously 0.5 hour before OA aerosol challenge (1% OA for 45 minutes) and terminated 4 or 24 hours after challenge. At time of sacrifice, serum and plasma are collected from all animals for serology and PK, respectively. A tracheal cannula is inserted and the lungs are lavaged 3× with PBS. The BAL fluid is analyzed for total leukocyte number and differential leukocyte counts. Total leukocyte number in an aliquot of the cells (20-100μï) is determined by Coulter Counter. For differential leukocyte counts, 50-200μï of the sample is centrifuged in a Cyto spin and the slide stained with Diff-Quik. The proportions of monocytes, eosinophils, neutrophils and lymphocytes are counted under light microscopy using standard morphological criteria and expressed as a percentage. Representative inhibitors of Btk show decreased total leucocyte count in the BAL of OA sensitized and challenged rats as compared to control levels.

What is claimed is:

1. A compound of Formula (III), or an N-oxide thereof, or a pharmaceutically acceptable salt, solvate, polymorph, tautomer, stereoisomer, or an isotopic form of said compound of Formula (III) or N-oxide thereof:

Formula (III)

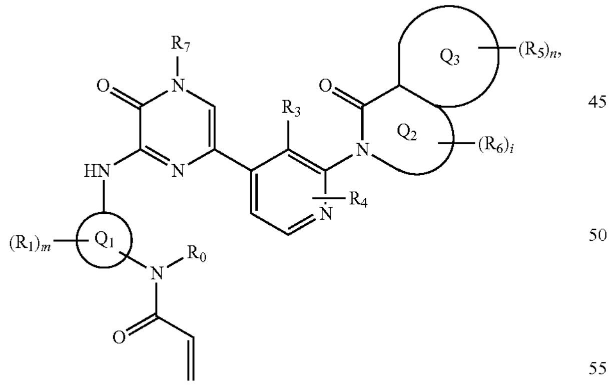

wherein $Q_1$ is a phenyl, pyridyl, or thiophenyl;

$Q_2$ is a piperazinyl, piperidinyl, thiadiazinanyl, or diazepanyl;

$Q_3$ is a imidazolyl, furanyl, or pyrrolyl;

each of $R_0$, $R_1$, $R_5$, $R_6$, and $R_7$, independently, is H, D, alkyl, spiroalkyl, alkenyl, alkynyl, cycloalkyl, cycloalkenyl, heterocycloalkyl, spiroheterocycloalkyl, heterocycloalkenyl, aryl, heteroaryl, halo, nitro, oxo, cyano, $OR_a$, $SR_a$, alkyl-$R_a$, $NH(CH_2)_pR_a$, $C(O)R_a$, $S(O)R_a$, $SO_2R_a$, $C(O)OR_a$, $OC(O)R_a$, $NR_bR_c$, $C(O)N(R_b)R_c$, $N(R_b)C(O)R_c$, $—P(O)R_bR_c$, -alkyl-$P(O)R_bR_c$, $—S(O)(=N(R_b))R_c$, $—N=S(O)R_bR_c$, $=NR_b$, $SO_2N(R_b)R_c$, or $N(R_b)SO_2R_c$, in which said cycloalkyl, cycloalkenyl, heterocycloalkyl, heterocycloalkenyl, aryl, heteroaryl is optionally substituted with one or more $R_d$;

$R_3$ is hydroxymethyl, methyl, or trifluoromethyl;

$R_4$ is H, halo, or low alkyl;

$R_0$ and $R_1$ groups, taken together with the atom to which they are attached, may optionally form a cycloalkyl or heterocycloalkyl optionally substituted with one or more $R_d$;

two of $R_1$ groups, taken together with the atom to which they are attached, may optionally form a cycloalkyl or heterocycloalkyl optionally substituted with one or more $R_d$;

two of $R_5$ groups, taken together with the atom to which they are attached, may optionally form a cycloalkyl or heterocycloalkyl optionally substituted with one or more $R_d$;

two of $R_6$ groups, taken together with the atom to which they are attached, may optionally form a cycloalkyl or heterocycloalkyl optionally substituted with one or more $R_d$;

$R_a$, $R_b$, $R_c$ and $R_d$, independently, is H, D, alkyl, spiroalkyl, alkenyl, alkynyl, halo, cyano, amine, nitro, hydroxy, =O, C(O)NHOH, C(O)OH, $C(O)NH_2$, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, spiroheterocycloalkyl, heterocycloalkenyl, aryl, or heteroaryl, in which said alkyl, cycloalkyl, cycloalkenyl, heterocycloalkyl, heterocycloalkenyl, aryl, heteroaryl is optionally substituted with one or more Re;

$R_e$ is H, D, alkyl, spiroalkyl, alkenyl, alkynyl, halo, cyano, amine, nitro, hydroxy, =O, C(O)NHOH, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, spiroheterocycloalkyl, heterocycloalkenyl, aryl, or heteroaryl;

two of $R_d$ groups, taken together with the atom to which they are attached, may optionally form a cycloalkyl or heterocycloalkyl optionally substituted with one or more $R_e$; and each of i, m, n, p, and q, independently, is 0, 1, 2, 3, or 4.

2. The compound according to claim 1 or an N-oxide thereof, or a pharmaceutically acceptable salt, solvate, polymorph, tautomer, stereoisomer, or an isotopic form thereof, wherein the compound is represented by Formula (IV) wherein:

Formula (IV)

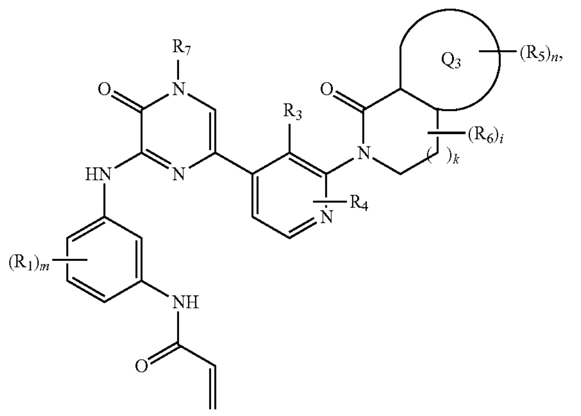

wherein k is 0, 1 or 2.

3. The compound according to claim 1 or an N-oxide thereof, or a pharmaceutically acceptable salt, solvate, polymorph, tautomer, stereoisomer, or an isotopic form, or a prodrug thereof, wherein the compound is (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(4-methyl-1-(oxetan-3-yl)-3-oxopiperazin-2-yl)phenyl)acrylamide, (R)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(4-methyl-1-(oxetan-3-yl)-5-oxopiperazin-2-yl)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(4-methyl-1-(oxetan-3-yl)-5-oxopiperazin-2-yl)phenyl)acrylamide, (R)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(1-methyl-4-(oxetan-3-yl)-6-oxopiperazin-2-yl)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(1-methyl-4-(oxetan-3-yl)-6-oxopiperazin-2-yl)phenyl)acrylamide, (R)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(1-isopropyl-4-(oxetan-3-yl)-6-oxopiperazin-2-yl)phenyl)acrylamide, (R)—N-(2-(1-cyclopropyl-4-(oxetan-3-yl)-6-oxopiperazin-2-yl)-5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)phenyl)acrylamide, (R)—N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(4-(tetrahydro-2H-pyran-4-yl)-2-(trifluoromethyl)piperazin-1-yl)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-methylpyridin-4-yl)-4-methyl-3-oxo-3,4-dihydropyrazin-2-yl)amino)-2-(4-(tetrahydro-2H-pyran-4-yl)-2-(trifluoromethyl)piperazin-1-yl)phenyl)acrylamide, (S)—N-(2-(2-methyl-4-(tetrahydro-2H-pyran-4-yl)piperazin-1-yl)-5-((4-methyl-6-(3-methyl-2-(1-oxo-3,4,5,6,7,8-hexahydrobenzo[4,5]thieno[2,3-c]pyridin-2 (1H)-yl)pyridin-4-yl)-3-oxo-3,4-dihydropyrazin-2-yl)amino)phenyl)acrylamide, (R)—N-(5-((4-methyl-6-(3-methyl-2-(1-oxo-3,4,5,6,7,8-hexahydrobenzo[4,5]thieno[2,3-c]pyridin-2 (1H)-yl)pyridin-4-yl)-3-oxo-3,4-dihydropyrazin-2-yl)amino)-2-(4-(tetrahydro-2H-pyran-4-yl)-2-(trifluoromethyl)piperazin-1-yl)phenyl)acrylamide, (S)—N-(5-((4-methyl-6-(3-methyl-2-(1-oxo-3,4,5,6,7,8-hexahydrobenzo[4,5]thieno[2,3-c]pyridin-2 (1H)-yl)pyridin-4-yl)-3-oxo-3,4-dihydropyrazin-2-yl)amino)-2-(4-(tetrahydro-2H-pyran-4-yl)-2-(trifluoromethyl)piperazin-1-yl)phenyl)acrylamide, (R)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(4-(tetrahydro-2H-pyran-4-yl)-2-(trifluoromethyl)piperazin-1-yl)phenyl)acrylamide, (S)—N-(5-((6-(2-(7,7-dimethyl-1-oxo-1,3,4,6,7,8-hexahydro-2H-cyclopenta[4,5]pyrrolo[1,2-a]pyrazin-2-yl)-3-(hydroxymethyl)pyridin-4-yl)-4-methyl-3-oxo-3,4-dihydropyrazin-2-yl)amino)-2-(4-(tetrahydro-2H-pyran-4-yl)-2-(trifluoromethyl)piperazin-1-yl)phenyl)acrylamide.

4. A pharmaceutical composition comprising a compound of Formula (III) or an N-oxide thereof as defined in claim 1, or a pharmaceutically acceptable salt, solvate, polymorph, tautomer, stereoisomer, or an isotopic form of said compound of Formula (III) or an N-oxide thereof, and a pharmaceutically acceptable diluent or carrier.

* * * * *